United States Patent
Takahashi et al.

(10) Patent No.: US 10,230,058 B2
(45) Date of Patent: Mar. 12, 2019

(54) COMPOUND, ORGANIC ELECTROLUMINESCENCE DEVICE AND ELECTRONIC DEVICE

(71) Applicant: IDEMITSU KOSAN CO., LTD., Chiyoda-ku (JP)

(72) Inventors: Ryota Takahashi, Ichihara (JP); Tomoki Kato, Ichihara (JP); Hidetsugu Ikeda, Ichihara (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 0 days.

(21) Appl. No.: 15/912,123

(22) Filed: Mar. 5, 2018

(65) Prior Publication Data

US 2018/0198076 A1    Jul. 12, 2018

Related U.S. Application Data

(63) Continuation of application No. 15/476,682, filed on Mar. 31, 2017, now Pat. No. 9,954,187.

(Continued)

(30) Foreign Application Priority Data

Apr. 8, 2016  (JP) .................... 2016-078344

(51) Int. Cl.
*C09K 11/06* (2006.01)
*H01L 51/00* (2006.01)
(Continued)

(52) U.S. Cl.
CPC ........ *H01L 51/0072* (2013.01); *C07D 487/06* (2013.01); *C07D 487/16* (2013.01);
(Continued)

(58) Field of Classification Search
CPC ............. H01L 51/0072; H01L 51/0061; H01L 51/0073; H01L 51/5016; H01L 51/5012;
(Continued)

(56) References Cited

U.S. PATENT DOCUMENTS 9,954,187 B2 *  4/2018  Takahashi ........... H01L 51/0072
2004/0076853 A1  4/2004  Jarikov
(Continued)

FOREIGN PATENT DOCUMENTS

CN    104119347    10/2014
JP    2014-073965    4/2014
(Continued)

OTHER PUBLICATIONS

Office Action dated Jul. 18, 2017 in the corresponding Japanese Patent Application.

(Continued)

*Primary Examiner* — Dawn L Garrett
(74) *Attorney, Agent, or Firm* — Oblon, McClelland, Maier & Neustadt, L.L.P.

(57) ABSTRACT

A novel compound capable of producing an organic electroluminescence (EL) device with excellent properties, an organic EL device comprising the compound, and an electronic device comprising the organic EL device are provided.

A compound represented by formula (1), an organic EL device comprising the compound, an organic EL device comprising an organic thin film layer between a cathode and an anode, wherein the organic thin film layer comprises one or more layers and a light emitting layer and at least one layer of the organic thin film layer comprises the compound, and an electronic device comprising the organic EL device:

(Continued)

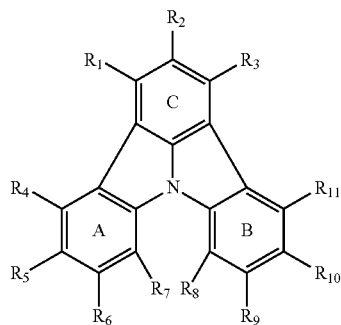

(1)

wherein A, B, C, and $R_1$ to $R_{11}$ are as defined in the description.

20 Claims, 2 Drawing Sheets

Related U.S. Application Data

(60) Provisional application No. 62/458,804, filed on Feb. 14, 2017.

(51) Int. Cl.
    *H01L 51/50*          (2006.01)
    *C07D 487/06*      (2006.01)
    *C07D 487/16*      (2006.01)

(52) U.S. Cl.
CPC .......... *C09K 11/06* (2013.01); *H01L 51/0052* (2013.01); *H01L 51/0058* (2013.01); *H01L 51/0061* (2013.01); *H01L 51/0073* (2013.01); *C09K 2211/1007* (2013.01); *C09K 2211/1011* (2013.01); *C09K 2211/1014* (2013.01); *C09K 2211/1029* (2013.01); *C09K 2211/1033* (2013.01); *C09K 2211/1037* (2013.01); *C09K 2211/1044* (2013.01); *C09K 2211/1088* (2013.01); *C09K 2211/1092* (2013.01); *H01L 51/5012* (2013.01); *H01L 51/5016* (2013.01)

(58) Field of Classification Search
CPC .... C07D 487/16; C07D 487/06; C09K 11/06; C09K 2211/1014; C09K 2211/1088; C09K 2211/1029; C09K 2211/1007
See application file for complete search history.

(56) References Cited

U.S. PATENT DOCUMENTS

| | | |
|---|---|---|
| 2013/0026422 A1 | 1/2013 | Parham et al. |
| 2014/0319507 A1 | 10/2014 | Yamamoto et al. |
| 2015/0179949 A1 | 6/2015 | Miyata |
| 2017/0213984 A1 | 7/2017 | Kim et al. |
| 2017/0324045 A1* | 11/2017 | Takahashi ........... H01L 51/0072 |

FOREIGN PATENT DOCUMENTS

| | | |
|---|---|---|
| KR | 10-2015-0135125 | 12/2015 |
| WO | 2011/128017 | 10/2011 |
| WO | 2013/077344 | 5/2013 |
| WO | 2016-006925 | 1/2016 |
| WO | 2016-195441 | 12/2016 |
| WO | 2017-014460 A1 | 1/2017 |

OTHER PUBLICATIONS

Communication dated Dec. 18, 2018, in European Patent Application No. 17 777 472.6, filed Mar. 31, 2017.

\* cited by examiner

COMPOUND, ORGANIC ELECTROLUMINESCENCE DEVICE AND ELECTRONIC DEVICE

CROSS-REFERENCE TO RELATED APPLICATIONS

This application is a Continuation of U.S. application Ser. No. 15/476,682, which was filed on Mar. 31, 2017. U.S. application Ser. No. 15/476,682 is based upon and claims the benefit of priority to U.S. Provisional Application No. 62/458,804, which was filed on Feb. 14, 2017, and to Japanese Application No. 2016-078344, which was filed on Apr. 8, 2016.

TECHNICAL FIELD

The present invention relates to novel compounds and material for organic electroluminescence devices comprising the novel compound. The present invention further relates to organic electroluminescence devices comprising the novel compound and electronic devices comprising the organic electroluminescence device.

BACKGROUND ART

An organic electroluminescence (EL) device generally comprises an anode, a cathode, and one or more organic thin film layers sandwiched between the anode and the cathode. When a voltage is applied between the electrodes, electrons are injected from the cathode and holes are injected from the anode into a light emitting region. The injected electrons recombine with the injected holes in the light emitting region to form excited state. When the excited state returns to the ground state, the energy is released as light.

Many researches have been made on the applications of organic EL device to display, etc. because of its possibility of wide selection of emission colors by using various emitting materials in a light emitting layer. Particularly, the research on the emitting materials which emit three primary red, green, and blue colors has been made actively, and the intensive research has been made to improve their properties.

The material for organic EL devices has been proposed, for example, in Patent Literatures 1 to 6.

CITATION LIST

Patent Literature

Patent Literature 1: JP 2014-73965A
Patent Literature 1: WO 2016/006925
Patent Literature 1: CN 104119347B
Patent Literature 1: WO 2011/128017
Patent Literature 1: KR 10-2015-0135125B
Patent Literature 1: WO 2013/077344

SUMMARY OF INVENTION

Technical Problem

As a result of further research, the inventors have found that the compounds disclosed in Patent Literatures 1 to 6 are still required to further improve the performance when used in an organic EL device.

Objects of the present invention are to provide a novel compound for producing an organic EL device with excellent performance and a material for organic EL devices which comprises the novel compound. Other objects are to provide an organic EL device comprising the compound and an electronic device comprising the organic EL device.

Solution to Problem

As a result of extensive research to solve the above problems, the inventors have found that the problems are solved by using a compound represented by formula (1), wherein two or more benzene rings of the indolo[3,2,1-jk]carbazole structure have fused rings, as a material for organic EL devices.

The present invention includes the following aspects (1) to (4).

(1) In an aspect of the invention, a compound represented by formula (1) is provided:

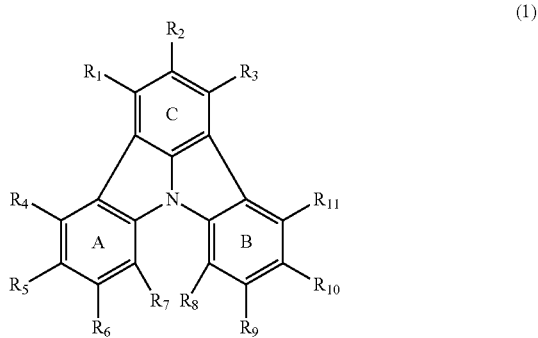

(1)

wherein:

in two or more pairs selected from $R_1$ and $R_2$, $R_2$ and $R_3$, $R_4$ and $R_5$, $R_5$ and $R_6$, $R_6$ and $R_7$, $R_8$ and $R_9$, $R_9$ and $R_{10}$, and $R_{10}$ and $R_{11}$, $R_n$ and $R_{n+1}$, wherein n is an integer selected from 1, 2, 4 to 6, and 8 to 10, are bonded to each other to form a ring structure together with two ring atoms to which $R_n$ and $R_{n+1}$ are bonded, wherein the ring structure has 3 or more atoms composed of a carbon atom, an oxygen atom, a sulfur atom, and a nitrogen atom;

when the atom composing the ring structure has a hydrogen atom, the atom may have a substituent, wherein the substituent is independently selected from a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalky group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by —Si($R_{101}$)($R_{102}$)($R_{103}$), a group represented by —N($R_{104}$)($R_{105}$), a substituted or unsubstituted aryl group having 6 to 50 ring carbon atoms, and a substituted or unsubstituted heteroaryl group having 5 to 50 ring atoms;

the substituents may be bonded to each other to form a ring structure;

the number of ring atoms of the ring having 3 or more atoms does not include the atom in the substituent;

provided that a pair of $R_1$ and $R_2$ and a pair of $R_2$ and $R_3$; a pair of $R_4$ and $R_5$ and a pair of $R_5$ and $R_6$; a pair of $R_5$ and $R_6$ and a pair of $R_6$ and $R_7$; a pair of $R_8$ and $R_9$ and a pair of $R_9$ and $R_{10}$; and a pair of $R_9$ and $R_{10}$ and a pair of $R_{10}$ and $R_{11}$ do not form the ring structure at the same time;

the two or more pairs are selected such that each of two or three rings selected from a ring A, a ring B, and a ring C has the ring structure having 3 or more atoms composed of a carbon atom, an oxygen atom, a sulfur atom, and a nitrogen atom;

two or more ring structures on the two or three rings may be the same or different;

$R_1$ to $R_{11}$ not forming the ring structure having 3 or more atoms is a hydrogen atom or a substituent, and the substituent represented by $R_1$ to $R_{11}$ is independently a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalky group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by —Si($R_{101}$)($R_{102}$)($R_{103}$), a group represented by —N($R_{104}$)($R_{105}$), a substituted or unsubstituted aryl group having 6 to 50 ring carbon atoms, or a substituted or unsubstituted heteroaryl group having 5 to 50 ring atoms; and each of $R_{101}$ to $R_{105}$ is independently a hydrogen atom, a substituted or unsubstituted alkyl group having 1 to 20 carbon atoms, a substituted or unsubstituted cycloalky group having 3 to 20 ring carbon atoms, a substituted or unsubstituted aryl group having 6 to 50 ring carbon atoms, or a substituted or unsubstituted heteroaryl group having 5 to 50 ring atoms.

(2) In an aspect of the invention, a material for organic electroluminescence devices comprising the compound described in (1) is provided.

(3) In an aspect of the invention, an organic electroluminescence device is provided, which comprises an organic thin film layer between a cathode and an anode, wherein the organic thin film layer comprises one or more layers and at least one light emitting layer, and at least one layer of the organic thin film layer comprises the compound described in (1).

(4) In an aspect of the invention, an electronic device comprising the organic electroluminescence device described in (3) is provided.

Advantageous Effects of Invention

The organic EL device comprising the compound of the invention as a material for organic EL device has excellent properties and is useful for use in an electronic device.

DESCRIPTION OF EMBODIMENTS

Figure 1:
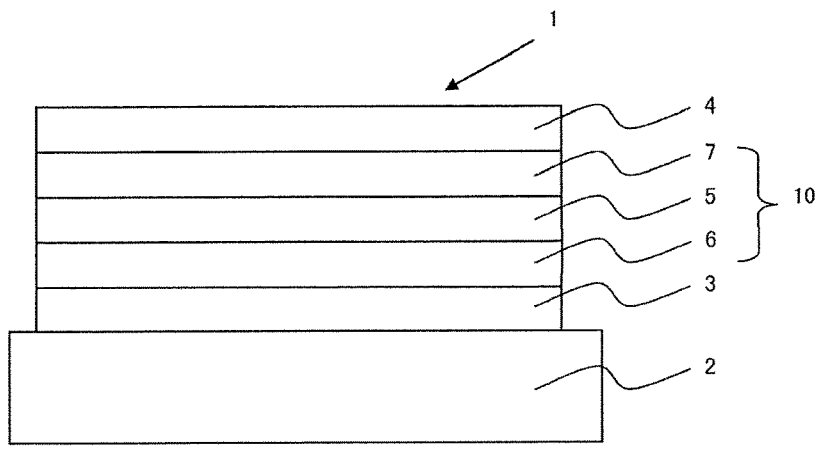
FIG. 1 is a schematic illustration showing an example of the structure of an organic electroluminescence device according to an embodiment of the invention.

The term of "XX to YY carbon atoms" referred to by "a substituted or unsubstituted group ZZ having XX to YY carbon atoms" used herein is the number of carbon atoms of the unsubstituted group ZZ and does not include any carbon atom in the substituent of the substituted group ZZ.

The term of "XX to YY atoms" referred to by "a substituted or unsubstituted group ZZ having XX to YY atoms" used herein is the number of atoms of the unsubstituted group ZZ and does not include any atom in the substituent of the substituted group ZZ.

The number of "ring carbon atoms" referred to herein means the number of the carbon atoms included in the atoms which are members forming the ring itself of a compound in which a series of atoms is bonded to form the ring (for example, a monocyclic compound, a fused ring compound, a cross-linked compound, a carbocyclic compound, and a heterocyclic compound). If the ring has a substituent, the carbon atom in the substituent is not included in the ring carbon atom. The same applies to the number of "ring carbon atom" described below, unless otherwise noted. For example, a benzene ring has 6 ring carbon atoms, a naphthalene ring has 10 ring carbon atoms, a pyridinyl group has 5 ring carbon atoms, and a furanyl group has 4 ring carbon atoms. If a benzene ring or a naphthalene ring has, for example, an alkyl substituent, the carbon atom in the alkyl substituent is not counted as the ring carbon atom of the benzene or naphthalene ring. In case of a fluorene ring to which a fluorene substituent is bonded (inclusive of a spirofluorene ring), the carbon atom in the fluorene substituent is not counted as the ring carbon atom of the fluorene ring.

The number of "ring atom" referred to herein means the number of the atoms which are members forming the ring itself (for example, a monocyclic ring, a fused ring, and a ring assembly) of a compound in which a series of atoms is bonded to form the ring (for example, a monocyclic compound, a fused ring compound, a cross-linked compound, a carbocyclic compound, and a heterocyclic compound). The atom not forming the ring (for example, hydrogen atom(s) for saturating the valence of the atom which forms the ring) and the atom in a substituent, if the ring is substituted, are not counted as the ring atom. The same applies to the number of "ring atoms" described below, unless otherwise noted. For example, a pyridine ring has 6 ring atoms, a quinazoline ring has 10 ring atoms, and a furan ring has 5 ring atoms. The hydrogen atom on the ring carbon atom of a pyridine ring or a quinazoline ring and the atom in a substituent are not counted as the ring atom. In case of a fluorene ring to which a fluorene substituent is bonded (inclusive of a spirofluorene ring), the atom in the fluorene substituent is not counted as the ring atom of the fluorene ring.

The definition of "hydrogen atom" used herein includes isotopes different in the neutron numbers, i.e., light hydrogen (protium), heavy hydrogen (deuterium), and tritium.

The terms of "heteroaryl group", "heteroarylene group", and "heterocyclic group" used herein means a group having at least one ring hetero atom, which is preferably at least one selected from a nitrogen atom, an oxygen atom, a sulfur atom, a silicon atom, and a selenium atom.

The term of "a substituted or unsubstituted carbazolyl group" referred to herein includes the following carbazolyl groups:

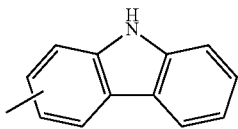

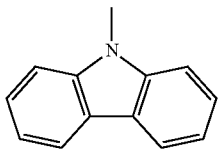

and a substituted carbazolyl group, wherein each of the above groups has a substituent.

The substituents of the substituted carbazolyl group may be bonded to each other to form a fused ring structure, may include a hetero atom, such as a nitrogen atom, an oxygen atom, a silicon atom, and selenium atom, and may be bonded to any of 1- to 9-positions. Examples of such substituted carbazolyl groups are shown below.

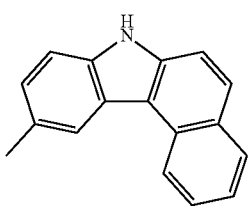

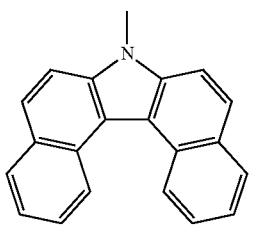

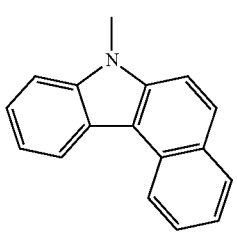

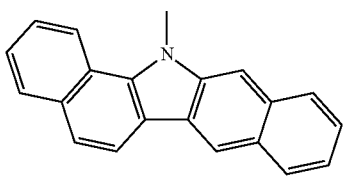

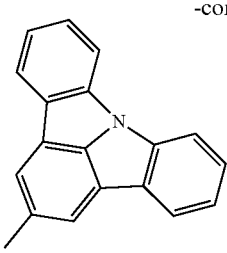

The terms of "a substituted or unsubstituted dibenzofuranyl group" and "a substituted or unsubstituted dibenzothiophenyl group" referred to herein include the following dibenzofuranyl group and the following dibenzothiophenyl group:

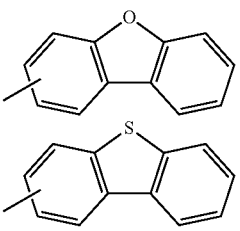

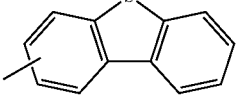

and a substituted dibenzofuranyl group and a substituted dibenzothiophenyl group, wherein each of the above groups has a substituent.

The substituents of the substituted dibenzofuranyl group and the substituted dibenzothiophenyl group may be bonded to each other to form a fused ring structure, may include a hetero atom, such as a nitrogen atom, an oxygen atom, a silicon atom, and selenium atom, and may be bonded to any of 1- to 8-positions. Examples of such substituted dibenzofuranyl groups and substituted dibenzothiophenyl groups are shown below:

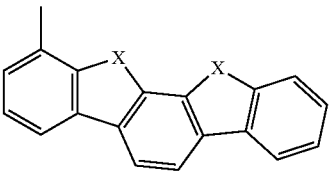

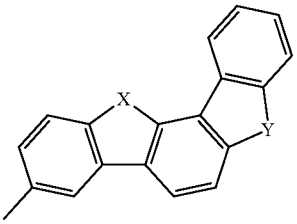

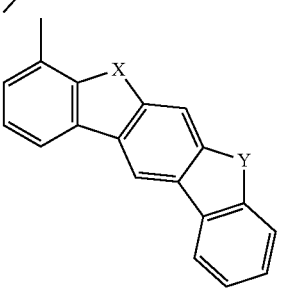

-continued

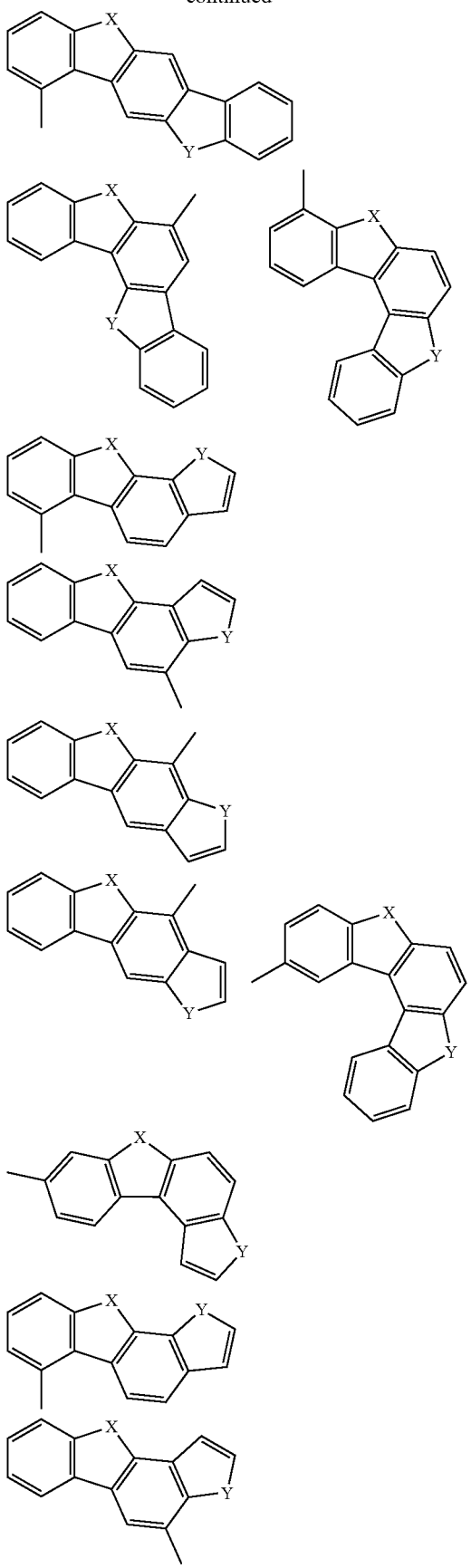

-continued

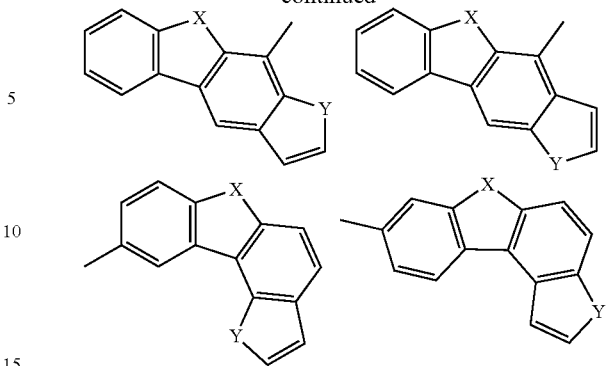

wherein X represents an oxygen atom or a sulfur atom and Y represents an oxygen atom, a sulfur atom, NH, $NR^a$ wherein $R^a$ represents an alkyl group or an aryl group, $CH_2$, or $CR^b{}_2$ wherein $R^b$ represents an alkyl group or an aryl group.

The substituent referred to by "a substituent" or "a substituted or unsubstituted" used herein is preferably, unless otherwise noted, at least one selected from the group consisting of an alkyl group having 1 to 50, preferably 1 to 18, more preferably 1 to 8 carbon atoms; a cycloalkyl group having 3 to 50, preferably 3 to 10, more preferably 3 to 8, still more preferably 5 or 6 ring carbon atoms; an aryl group having 6 to 50, preferably 6 to 25, more preferably 6 to 18 ring carbon atoms; an aralkyl group having 7 to 51, preferably 7 to 30, more preferably 7 to 20 carbon atoms which includes an aryl group having 6 to 50, preferably 6 to 25, more preferably 6 to 18 ring carbon atoms; an amino group; a mono- or di-substituted amino group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; an alkoxy group having an alkyl group having 1 to 50, preferably 1 to 18, more preferably 1 to 8 carbon atoms; an aryloxy group having an aryl group having 6 to 50, preferably 6 to 25, more preferably 6 to 18 ring carbon atoms; a mono-, di- or tri-substituted silyl group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; a heteroaryl group having 5 to 50, preferably 5 to 24, more preferably 5 to 13 ring atoms; a haloalkyl group having 1 to 50, preferably 1 to 18, more preferably 1 to 8 carbon atoms; a halogen atom selected from a fluorine atom, a chlorine atom, a bromine atom and an iodine atom; a cyano group; a nitro group; a substituted sulfonyl group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; a di-substituted phosphoryl group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; an alkylsulfonyloxy group; an arylsulfonyloxy group; an alkylcarbonyloxy group; an arylcarbonyloxy group; a boron-containing group; a zinc-containing group; a tin-containing group; a silicon-containing group; a magnesium-containing group; a lithium-containing group; a hydroxyl group; an alkyl-substituted or aryl-substituted carbonyl group; a carboxyl group; a vinyl group; a (meth) acryloyl group; an epoxy group; and an oxetanyl group, although not particularly limited thereto.

These substituents may be further substituted with the substituent mentioned above. The substituents may be bonded to each other to form a ring.

The term "unsubstituted" referred to by "a substituted or unsubstituted" means that a hydrogen atom is not substituted by the substituent mentioned above.

Of the above substituents, preferred are an alkyl group having 1 to 50, preferably 1 to 18, more preferably 1 to 8 carbon atoms; a cycloalkyl group having 3 to 50, preferably 3 to 10, more preferably 3 to 8, still more preferably 5 or 6 ring carbon atoms; an aryl group having 6 to 50, preferably 6 to 25, more preferably 6 to 18 ring carbon atoms; a mono- or di-substituted amino group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; a heteroaryl group having 5 to 50, preferably 5 to 24, more preferably 5 to 13 ring atoms; a halogen atom; and a cyano group.

Examples of the alkyl group having 1 to 50 carbon atoms include a methyl group, an ethyl group, a n-propyl group, an isopropyl group, a n-butyl group, an isobutyl group, a s-butyl group, a t-butyl group, a pentyl group (inclusive of isomeric groups), a hexyl group (inclusive of isomeric groups), a heptyl group (inclusive of isomeric groups), an octyl group (inclusive of isomeric groups), a nonyl group (inclusive of isomeric groups), a decyl group (inclusive of isomeric groups), an undecyl group (inclusive of isomeric groups), and a dodecyl group (inclusive of isomeric groups). Preferred are a methyl group, an ethyl group, a n-propyl group, an isopropyl group, a n-butyl group, an isobutyl group, a s-butyl group, a t-butyl group, and a pentyl group (inclusive of isomeric groups), with a methyl group, an ethyl group, a n-propyl group, an isopropyl group, a n-butyl group, an isobutyl group, a s-butyl group, and a t-butyl group being more preferred, and a methyl group, an ethyl group, an isopropyl group, and a t-butyl group being particularly preferred.

Examples of the cycloalkyl group having 3 to 50 ring carbon atoms include a cyclopropyl group, a cyclobutyl group, a cyclopentyl group, a cyclohexyl group, a cycloheptyl group, a cyclooctyl group, and an adamantyl group, with a cyclopentyl group and a cyclohexyl group being preferred.

Examples of the aryl group having 6 to 50 ring carbon atoms include a phenyl group, a biphenylyl group, a terphenylyl group, a naphthyl group, an acenaphthylenyl group, an anthryl group, a benzanthryl group, an aceanthryl group, a phenanthryl group, a benzo[c]phenanthryl group, a phenalenyl group, a fluorenyl group, a picenyl group, a pentaphenyl group, a pyrenyl group, a chrysenyl group, a benzo[g]chrysenyl group, a s-indacenyl group, an as-indacenyl group, a fluoranthenyl group, a benzo[k]fluoranthenyl group, a triphenylenyl group, a benzo[b]triphenylenyl group, and a perylenyl group, with a phenyl group, a biphenylyl group, a terphenylyl group, a naphthyl group, an anthryl group, a pyrenyl group, and a fluoranthenyl group being preferred, and a phenyl group, a biphenylyl group, and a terphenylyl group being more preferred, and a phenyl group being still more preferred.

In the aralkyl group having 7 to 51 carbon atoms which includes an aryl group having 6 to 50, the aryl portion is selected from the examples of the above aryl group having 6 to 50 ring carbon atoms and the alkyl portion is selected from the examples of the above alkyl group having 1 to 50 carbon atoms. Preferred examples thereof include those having an aryl portion selected from the preferred examples of the above aryl group having 6 to 50 ring carbon atoms and an alkyl portion selected from the preferred examples of the above alkyl group having 1 to 50 carbon atoms. The same applies to more preferred examples and still more preferred examples thereof.

In the mono- or di-substituted amino group, wherein the substituent is selected from an alkyl group having 1 to 50 and an aryl group having 6 to 50, the aryl substituent is selected from the examples of the above aryl group having 6 to 50 ring carbon atoms and the alkyl substituent is selected from the examples of the above alkyl group having 1 to 50 carbon atoms. Preferred examples thereof include those having an aryl substituent selected from the preferred examples of the above aryl group having 6 to 50 ring carbon atoms and an alkyl substituent selected from the preferred examples of the above alkyl group having 1 to 50 carbon atoms. The same applies to more preferred examples, still more preferred examples, and particularly preferred examples thereof.

In the alkoxy group having an alkyl group having 1 to 50 carbon atoms, the alkyl portion is selected from the examples of the above alkyl group having 1 to 50 carbon atoms. Preferred examples thereof include those having an alkyl portion selected from the preferred examples of the above alkyl group having 1 to 50 carbon atoms. The same applies to more preferred examples, still more preferred examples, and particularly preferred examples thereof.

In the aryloxy group having an aryl group having 6 to 50 ring carbon atoms, the aryl portion is selected from the examples of the above aryl group having 6 to 50 ring carbon atoms. Preferred examples thereof include those having an aryl portion selected from the preferred examples of the above aryl group having 6 to 50 ring carbon atoms. The same applies to more preferred examples and still more preferred examples thereof.

Examples of the mono-, di- or tri-substituted silyl group, wherein the substituent is selected from an alkyl group having 1 to 50 and an aryl group having 6 to 50, includes a monoalkylsilyl group, a dialkylsilyl group, a trialkylsilyl group, a monoarylsilyl group, a diarylsilyl group, a triarylsilyl group, a monoalkyldiarylsilyl group, and a dialkylmonoarylsilyl group, wherein the alkyl substituent is selected from the examples of the above alkyl group having 1 to 50 carbon atoms and the aryl substituent is selected from the examples of the above aryl group having 6 to 50 ring carbon atoms. Preferred examples thereof include a monoalkylsilyl group, a dialkylsilyl group, a trialkylsilyl group, a monoarylsilyl group, a diarylsilyl group, a triarylsilyl group, a monoalkyldiarylsilyl group, and a dialkylmonoarylsilyl group, wherein the alkyl substituent is selected from the preferred examples of the above alkyl group having 1 to 50 carbon atoms and the aryl substituent is selected from the preferred examples of the above aryl group having 6 to 50 ring carbon atoms. The same applies to more preferred examples, still more preferred examples, and particularly preferred examples thereof.

Examples of the heteroaryl group having 5 to 50 ring atoms include a pyrrolyl group, a furyl group, a thienyl group, a pyridyl group, an imidazopyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, a tetrazolyl group, an indolyl group, an isoindolyl group, a benzofuranyl group, an isobenzofuranyl group, a benzothiophenyl group, an isobenzothiophenyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a dibenzothiophenyl group, a carbazolyl group, a 9-phenylcarbazolyl group, a phenanthridinyl group, an acridinyl group, a phenanthrolinyl group, a phenazinyl group, a phenothiazinyl group, a phenoxazinyl group, and a xanthenyl group. Preferred are a pyridyl group, an imidazopyridyl group, a pyridazinyl group, a pyrimidinyl group, a pyrazinyl group, a triazinyl group, a benzimidazolyl group, a dibenzofuranyl group, a dibenzothiophenyl group, a carbazolyl group, a 9-phenylcarbazolyl group, a phenanthrolinyl group, and a quinazolinyl group.

The halogen atom include a fluorine atom, a chlorine atom, a bromine atom, and an iodine atom.

Examples of the haloalkyl group having 1 to 50 carbon atoms include the above alkyl group having 1 to 50 carbon atoms wherein a hydrogen atom is substituted by the above halogen atom. Preferred examples thereof include the above preferred alkyl group having 1 to 50 carbon atoms wherein a hydrogen atom is substituted by the above halogen atom. The same applies to more preferred examples, still more preferred examples, and particularly preferred examples thereof.

In each of the substituted sulfonyl group, wherein the substituent is selected from an alkyl group having 1 to 50 and an aryl group having 6 to 50, the di-substituted phosphoryl group, wherein the substituent is selected from an alkyl group having 1 to 50 and an aryl group having 6 to 50, the alkylsulfonyloxy group, the arylsulfonyloxy group, the alkylcarbonyloxy group, the arylcarbonyloxy group, and the alkyl-substituted or aryl-substituted carbonyl group, the aryl substituent is selected from the examples of the above aryl group having 6 to 50 ring carbon atoms and the alkyl substituent is selected from the examples of the above alkyl group having 1 to 50 carbon atoms. In each of the preferred examples thereof, the aryl substituent is selected from the preferred examples of the above aryl group having 6 to 50 ring carbon atoms and the alkyl substituent is selected from the preferred examples of the above alkyl group having 1 to 50 carbon atoms. The same applies to more preferred examples, still more preferred examples, and particularly preferred examples thereof.

A preferred embodiment, for example, for the compounds, the groups, and the numerical ranges described herein may be combined with any of other preferred embodiments, for example, for the compounds, the groups, and the numerical ranges. A combination of preferred embodiments (inclusive of more preferred embodiments, still more preferred embodiments, and particularly preferred embodiments) is a more preferred embodiment.

Compound

The compound in an aspect of the invention is represented by formula (1):

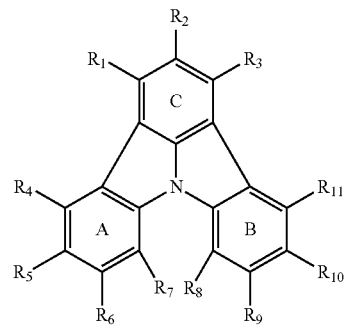

(1)

wherein:

in two or more pairs selected from $R_1$ and $R_2$, $R_2$ and $R_3$, $R_4$ and $R_5$, $R_5$ and $R_6$, $R_6$ and $R_7$, $R_8$ and $R_9$, $R_9$ and $R_{10}$, and $R_{10}$ and $R_{11}$, $R_n$ and $R_{n+1}$, wherein n is an integer selected from 1, 2, 4 to 6, and 8 to 10, are bonded to each other to form a ring structure together with two ring atoms to which $R_n$ and $R_{n+1}$ are bonded, wherein the ring structure has 3 or more atoms composed of a carbon atom, an oxygen atom, a sulfur atom, and a nitrogen atom;

when the atom composing the ring structure has a hydrogen atom, the atom may have a substituent, wherein the substituent is independently selected from a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalky group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by —Si($R_{101}$)($R_{102}$)($R_{103}$), a group represented by —N($R_{104}$)($R_{105}$), a substituted or unsubstituted aryl group having 6 to 50 ring carbon atoms, and a substituted or unsubstituted heteroaryl group having 5 to 50 ring atoms;

the substituents may be bonded to each other to form a ring structure;

the number of ring atoms of the ring having 3 or more atoms does not include the atom in the substituent;

provided that a pair of $R_1$ and $R_2$ and a pair of $R_2$ and $R_3$; a pair of $R_4$ and $R_5$ and a pair of $R_5$ and $R_6$; a pair of $R_5$ and $R_6$ and a pair of $R_6$ and $R_7$; a pair of $R_8$ and $R_9$ and a pair of $R_9$ and $R_{10}$; and a pair of $R_9$ and $R_{10}$ and a pair of $R_{10}$ and $R_{11}$ do not form the ring structure at the same time;

the two or more pairs are selected such that each of two or three rings selected from a ring A, a ring B, and a ring C has the ring structure having 3 or more atoms composed of a carbon atom, an oxygen atom, a sulfur atom, and a nitrogen atom; and two or more ring structures on the two or three rings may be the same or different;

$R_1$ to $R_{11}$ not forming the ring structure having 3 or more atoms is a hydrogen atom or a substituent, and the substituent represented by $R_1$ to $R_{11}$ is independently a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalky group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by —Si($R_{101}$)($R_{102}$)($R_{103}$), a group represented by —N($R_{104}$)($R_{105}$), a substituted or unsubstituted aryl group having 6 to 50 ring carbon atoms, or a substituted or unsubstituted heteroaryl group having 5 to 50 ring atoms; and each of $R_{101}$ to $R_{105}$ is independently a hydrogen atom, a substituted or unsubstituted alkyl group having 1 to 20 carbon atoms, a substituted or unsubstituted cycloalky group having 3 to 20 ring carbon atoms, a substituted or unsubstituted aryl group having 6 to 50 ring carbon atoms, or a substituted or unsubstituted heteroaryl group having 5 to 50 ring atoms.

The ring structure having 3 or more atoms composed of a carbon atom, an oxygen atom, a sulfur atom, and a nitrogen atom, which is formed by $R_n$ and $R_{n+1}$, wherein n is an integer selected from 1, 2, 4 to 6, and 8 to 10, bonded to each other together with two ring atoms to which $R_n$ and $R_{n+1}$ are bonded is described below in more detail.

Each of $R_1$ to $R_{11}$ is a hydrogen atom, a substituent, one atom selected from a carbon atom, an oxygen atom, a sulfur atom, and a nitrogen atom, or a group of atoms wherein atoms selected from a carbon atom, an oxygen atom, a sulfur atom, and a nitrogen atom are bonded to each other.

When each of $R_1$ to $R_{11}$ is one atom selected from a carbon atom, an oxygen atom, a sulfur atom, and a nitrogen atom, or a group of atoms wherein atoms selected from a carbon atom, an oxygen atom, a sulfur atom, and a nitrogen atom are bonded to each other, in each of two more pairs selected from $R_1$ and $R_2$, $R_2$ and $R_3$, $R_4$ and $R_5$, $R_5$ and $R_6$, $R_6$ and $R_7$, $R_8$ and $R_9$, $R_9$ and $R_{10}$, and $R_{10}$ and $R_{11}$, $R_n$ and $R_{n+1}$, wherein n is an integer selected from 1, 2, 4 to 6, and 8 to 10, are bonded to each other to form a ring structure together with two ring atoms to which $R_n$ and $R_{n+1}$ are bonded, wherein the ring structure has 3 or more atoms selected from a carbon atom, an oxygen atom, a sulfur atom, and a nitrogen atom.

When $R_n$ and $R_{n+1}$, wherein n is an integer selected from 1, 2, 4 to 6, and 8 to 10, are bonded to each other, an atom in $R_n$ and an atom in $R_{n+1}$ are bonded to each other. If $R_n$ includes one atom, "an atom in $R_n$" means said one atom. If $R_n$ is a group of atoms which are bonded to each other, "an atom in $R_n$" means a terminal atom or another atom. The same applies to "an atom in $R_{n+1}$."

The bond between $R_n$ and $R_{n+1}$ may be either a single bond, a double bond, or a bond with a bond order between 1 and 2. The same applies to the bond between atoms when each of $R_n$ and $R_{n+1}$ is a group of atoms which are bonded to each other.

In an embodiment of the invention, the compound of formula (1) has preferably two ring structures, i.e., in two pairs selected from $R_1$ and $R_2$, $R_2$ and $R_3$, $R_4$ and $R_5$, $R_5$ and $R_6$, $R_6$ and $R_7$, $R_8$ and $R_9$, $R_9$ and $R_{10}$, and $R_{10}$ and $R_{11}$, $R_n$ and $R_{n+1}$, wherein n is an integer selected from 1, 2, 4 to 6, and 8 to 10, are bonded to each other to form a ring structure together with two ring atoms to which $R_n$ and $R_{n+1}$ are bonded, wherein the ring structure has 3 or more atoms composed of a carbon atom, an oxygen atom, a sulfur atom, and a nitrogen atom. For example, in two or more pairs selected from $R_4$ and $R_5$, $R_5$ and $R_6$, $R_6$ and $R_7$, $R_8$ and $R_9$, $R_9$ and $R_{10}$, and $R_{10}$ and $R_{11}$, $R_n$ and $R_{n+1}$, wherein n is an integer selected from 4 to 6 and 8 to 10, are bonded to each other to form a ring structure together with two ring atoms to which $R_n$ and $R_{n+1}$ are bonded, wherein the ring structure has 3 or more atoms composed of a carbon atom, an oxygen atom, a sulfur atom, and a nitrogen atom. In an embodiment of the invention, two pairs selected from $R_4$ and $R_5$, $R_5$ and $R_6$, $R_6$ and $R_7$, $R_8$ and $R_9$, $R_9$ and $R_{10}$, and $R_{10}$ and $R_{11}$ form the ring structures.

In an embodiment of the invention, the compound of formula (1) has preferably three ring structures. Particularly preferably, each of the benzene rings in the main skeleton of formula (1), i.e., each of the ring A, the ring B, and the ring C has one ring structure.

In an embodiment of the invention, the compound of formula (1) has preferably four ring structures.

In an embodiment of the invention, $R_1$ to $R_3$ of formula (1) is preferably a hydrogen atom or a substituent, and the substituent represented by $R_1$ to $R_3$ is independently a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalky group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by —Si($R_{101}$)($R_{102}$)($R_{103}$), a group represented by —N($R_{104}$)($R_{105}$), a substituted or unsubstituted aryl group having 6 to 50 ring carbon atoms, or a substituted or unsubstituted heteroaryl group having 5 to 50 ring atoms.

In formula (1), the halogen atom for $R_1$ to $R_{11}$ includes a fluorine atom, a chlorine atom, a bromine atom, and an iodine atom.

Examples of the alkyl group having 1 to 20, preferably 1 to 10, and more preferably 1 to 6 carbon atoms for $R_1$ to $R_{11}$ include a methyl group, an ethyl group, a n-propyl group, an isopropyl group, a n-butyl group, an isobutyl group, a s-butyl group, a t-butyl group, a pentyl group (inclusive of isomeric groups), a hexyl group (inclusive of isomeric groups), a heptyl group (inclusive of isomeric groups), an octyl group (inclusive of isomeric groups), a nonyl group (inclusive of isomeric groups), a decyl group (inclusive of isomeric groups), an undecyl group (inclusive of isomeric groups), and a dodecyl group (inclusive of isomeric groups). Preferred are a methyl group, an ethyl group, a n-propyl group, an isopropyl group, a n-butyl group, an isobutyl group, a s-butyl group, a t-butyl group, and a pentyl group (inclusive of isomeric groups), more preferred are a methyl group, an ethyl group, a n-propyl group, an isopropyl group, a n-butyl group, an isobutyl group, a s-butyl group, and a t-butyl group, and still more preferred are a methyl group, an ethyl group, an isopropyl group, and a t-butyl group.

Examples of the alkenyl group having 1 to 20, preferably 1 to 10, and more preferably 1 to 6 carbon atoms for $R_1$ to $R_{11}$ include a vinyl group, a 2-propenyl group, a 2-butenyl group, a 3-butenyl group, a 4-pentenyl group, a 2-methyl-2-propenyl group, a 2-methyl-2-butenyl group, and a 3-methyl-2-butenyl group.

Examples of the alkynyl group having 1 to 20, preferably 1 to 10, and more preferably 1 to 6 carbon atoms for $R_1$ to $R_{11}$ include a 2-propynyl group, a 2-butynyl group, a 3-butynyl group, a 4-pentynyl group, a 5-hexynyl group, a 1-methyl-2-propynyl group, a 1-methyl-2-butynyl group, and a 1,1-dimethyl-2-propynyl group.

Examples of the cycloalkyl group having 3 to 20, preferably 3 to 6, and more preferably 5 or 6 ring carbon atoms for $R_1$ to $R_{11}$ include a cyclopropyl group, a cyclobutyl group, a cyclopentyl group, a cyclohexyl group, a cycloheptyl group, a cyclooctyl group, and an adamantyl group, with a cyclopentyl group and a cyclohexyl group being preferred.

In the alkoxy group having 1 to 20, preferably 1 to 10, and more preferably 1 to 6 carbon atoms for $R_1$ to $R_{11}$, the alkyl portion is selected from the above alkyl group having 1 to 20 carbon atoms. Preferred examples thereof include those having an alkyl portion selected from the preferred examples of the above alkyl group having 1 to 50 carbon atoms. The same applies to more preferred examples and still more preferred examples thereof.

Examples of the fluoroalkyl group having 1 to 20, preferably 1 to 10, and more preferably 1 to 6 carbon atoms for $R_1$ to $R_{11}$ include the above alkyl group wherein a hydrogen atom is substituted by a fluorine atom. Preferred examples thereof include the above preferred alkyl group wherein a hydrogen atom is substituted by a fluorine atom. The same applies to more preferred examples and still more preferred examples thereof.

Examples of the fluoroalkoxy group having 1 to 20, preferably 1 to 10, and more preferably 1 to 6 carbon atoms for $R_1$ to $R_{11}$ include the above alkoxy group wherein a hydrogen atom is substituted by a fluorine atom. Preferred examples thereof include the above preferred alkoxy group wherein a hydrogen atom is substituted by a fluorine atom. The same applies to more preferred examples and still more preferred examples thereof.

In the aryloxy group having 6 to 50, preferably 6 to 30, more preferably 6 to 24, and still more preferably 6 to 18 ring carbon atoms for $R_1$ to $R_{11}$, the aryl portion is selected from the aryl group having 6 to 50 ring carbon atoms for $R_1$ to $R_{11}$ which is described below. Preferred examples thereof include those having an aryl portion selected from the preferred examples of the aryl group having 6 to 50 ring carbon atoms which is described below. The same applies to more preferred examples and still more preferred examples thereof.

In the alkylthio group having 1 to 20, preferably 1 to 10, and more preferably 1 to 6 carbon atoms for $R_1$ to $R_{11}$, the alkyl portion is selected from the above alkyl group having 1 to 20 carbon atoms. Preferred examples thereof include those having an alkyl portion selected from the preferred examples of the above alkyl group. The same applies to more preferred examples and still more preferred examples thereof.

In the arylthio group having 6 to 50, preferably 6 to 30, more preferably 6 to 24, and still more preferably 6 to 18 ring carbon atoms for $R_1$ to $R_{11}$, the aryl portion is selected from the aryl group having 6 to 50 ring carbon atoms for $R_1$ to $R_{11}$ which is described below. Preferred examples thereof include those having an aryl portion selected from the preferred examples of the aryl group having 6 to 50 ring carbon atoms which is described below. The same applies to more preferred examples and still more preferred examples thereof.

Examples of the group represented by $-Si(R_{101})(R_{102})(R_{103})$ for $R_1$ to $R_{11}$ include a monoalkylsilyl group, a dialkylsilyl group, a trialkylsilyl group, a monoarylsilyl group, a diarylsilyl group, a triarylsilyl group, a monoalkyldiarylsilyl group, and a dialkylmonoarylsilyl group.

The alkyl portion of the above substituted silyl groups has preferably 1 to 20, more preferably 1 to 10, and still more preferably 1 to 6 carbon atoms. The aryl portion has preferably 6 to 50, more preferably 6 to 30, still more preferably 6 to 24, and particularly preferably 6 to 18 ring carbon atoms.

Preferred are a trialkylsilyl group and a triarylsilyl group and more preferred are a trimethylsilyl group, a triethylsilyl group, a triisopropylsilyl group, a t-butyldimethylsilyl group, a triphenylsilyl group, and a tritolylsilyl group.

Examples of the group represented by $-N(R_{104})(R_{105})$ for $R_1$ to $R_{11}$ include a monoalkylamino group, a dialkylamino group, a monoarylamino group, a diarylamino group, a monoheteroarylamino group, a diheteroarylamino group, a monoalkylmonoarylamino group, a monoalkylmonoheteroarylamino group, and a monoarylmonoheteroarylamino group. The aryl portion of these substituted amino groups may have an alkyl substituent having 1 to 20, preferably 1 to 10, and more preferably 1 to 6 carbon atoms.

The alkyl portion of these substituted amino groups has preferably 1 to 20, more preferably 1 to 10, and still more preferably 1 to 6 carbon atoms. The aryl portion has preferably 6 to 50, more preferably 6 to 30, still more preferably 6 to 24, and particularly preferably 6 to 18 ring carbon atoms. The heteroaryl portion has preferably 5 to 50, more preferably 5 to 30, still more preferably 5 to 18, and particularly preferably 5 to 13 ring atoms.

Preferred are a dialkylamino group, a diarylamino group, a diheteroarylamino group, and a monoarylmonoheteroarylamino group and more preferred are a dimethylamino group, a diethylamino group, a diisopropylamino group, a diphenylamino group, a bis(alkyl-substituted phenyl)amino group, and a bis(aryl-substituted phenyl)amino group.

The alkyl portion is selected from the above alkyl group having 1 to 20 carbon atoms. The preferred alkyl portion is selected from the preferred examples of the above alkyl group having 1 to 20 carbon atoms. The same applies to more preferred examples and still more preferred examples thereof.

The aryl portion is selected from the examples of the aryl group having 6 to 50 ring carbon atoms which is described below. Preferred examples of the aryl portion are selected from the preferred examples of the aryl group having 6 to 50 ring carbon atoms which is described below. The same applies to more preferred examples and still more preferred examples thereof.

The heteroaryl portion is selected from the examples of the heteroaryl group having 5 to 50 ring atoms which is described below. Preferred examples of the heteroaryl portion are selected from the preferred examples of the heteroaryl group having 5 to 50 ring atoms which is described below. The same applies to more preferred examples and still more preferred examples thereof.

Two or more groups represented by $-Si(R_{101})(R_{102})(R_{103})$ in formula (1), if any, may be the same or different. Two or more groups represented by $-N(R_{104})(R_{105})$ in formula (1), if any, may be the same or different.

The aryl group having 6 to 50, preferably 6 to 30, more preferably 6 to 24, and still more preferably 6 to 18 ring carbon atoms for $R_1$ to $R_{11}$ may be a fused ring group or a non-fused ring group. Examples of the aryl group include a phenyl group, a biphenylyl group, a terphenylyl group, a naphthyl group, an acenaphthylenyl group, an anthryl group, a benzanthryl group, an aceanthryl group, a phenanthryl group, a benzo[c]phenanthryl group, a phenalenyl group, a fluorenyl group, a picenyl group, a pentaphenyl group, a pyrenyl group, a chrysenyl group, a benzo[g]chrysenyl group, a s-indanyl group, an as-indanyl group, a fluoranthenyl group, a benzo[k]fluoranthenyl group, a triphenylenyl group, a benzo[b]triphenylenyl group, and a perylenyl group. Preferred are a phenyl group, a biphenylyl group, a terphenylyl group, a naphthyl group, an anthryl group, a pyrenyl group, and a fluoranthenyl group, more preferred are a phenyl group, a biphenylyl group, and a terphenylyl group, and still more preferred is a phenyl group.

The heteroaryl group having 5 to 50, preferably 5 to 30, more preferably 5 to 18, and particularly preferably 5 to 13 ring atoms for $R_1$ to $R_{11}$ includes at least one, preferably 1 to 5, more preferably 1 to 4, and still more preferably 1 to 3 hetero atoms, which is selected from, for example, a nitrogen atom, a sulfur atom and an oxygen atom and preferably a nitrogen atom and an oxygen atom.

Examples of the heteroaryl group include a pyrrolyl group, a furyl group, a thienyl group, a pyridyl group, an imidazopyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, a tetrazolyl group, an indolyl group, an isoindolyl group, a benzofuranyl group, an isobenzofuranyl group, a benzothiophenyl group, an isobenzothiophenyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a dibenzothiophenyl group, a carbazolyl group, a 9-phenylcarbazolyl group, a phenanthridinyl group, an acridinyl group, a phenanthrolinyl group, a phenazinyl group, a phenothiazinyl group, a phenoxazinyl group, and a xanthenyl group. Preferred are a pyridyl group, an imidazopyridyl group, a pyridazinyl group, a pyrimidinyl group, a pyrazinyl group, a triazinyl group, a benzimidazolyl group, a dibenzofuranyl group, a dibenzothiophenyl group, a carbazolyl group, a 9-phenylcarbazolyl group, a phenanthrolinyl group, and a quinazolinyl group.

Examples of the substituent of the ring structure having 3 or more atoms in formula (1) composed of a carbon atom, an oxygen atom, a sulfur atom, and a nitrogen atom together with two ring atoms to which $R_n$ and $R_{n+1}$ are bonded, i.e., examples of the halogen atom, the cyano group, the substituted or unsubstituted alkyl group having 1 to 20 carbon atoms, the substituted or unsubstituted alkenyl group having 1 to 20 carbon atoms, the substituted or unsubstituted alkynyl group having 1 to 20 carbon atoms, the substituted or unsubstituted cycloalky group having 3 to 20 ring carbon atoms, the amino group, the substituted or unsubstituted alkoxy group having 1 to 20 carbon atoms, the substituted or unsubstituted fluoroalkyl group having 1 to 20 carbon atoms, the substituted or unsubstituted fluoroalkoxy group having 1 to 20 carbon atoms, the substituted or unsubstituted aryloxy group having 6 to 50 ring carbon atoms, the substituted or unsubstituted alkylthio group having 1 to 20 carbon atoms, the substituted or unsubstituted arylthio group having 6 to 50 ring carbon atoms, the group represented by —Si($R_{101}$)($R_{102}$)($R_{103}$), the group represented by —N($R_{104}$)($R_{105}$), the substituted or unsubstituted aryl group having 6 to 50 ring carbon atoms, and the substituted or unsubstituted heteroaryl group having 5 to 50 ring atoms are the same as the examples of the corresponding groups which are described above with respect to $R_1$ to $R_{11}$. The same applies to the preferred number of carbon atoms, the preferred number of atoms, and the preferred examples of the groups. The substituent is preferably substituted or unsubstituted alkyl group having 1 to 20 carbon atoms or a substituted or unsubstituted aryl group having 6 to 50 ring carbon atoms.

The ring structure having 3 or more atoms in formula (1) composed of a carbon atom, an oxygen atom, a sulfur atom, and a nitrogen atom together with two ring atoms to which $R_n$ and $R_{n+1}$ are bonded has preferably 3 to 7 atoms and particularly preferably 5 or 6 atoms, although not particularly limited thereto.

The ring structure having 3 or more atoms in formula (1) composed of a carbon atom, an oxygen atom, a sulfur atom, and a nitrogen atom together with two ring atoms to which $R_n$ and $R_{n+1}$ are bonded is preferably a ring selected from formulae (2) to (8), or preferably a ring selected from formulae (9) to (11).

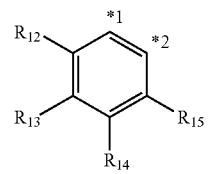

(2)

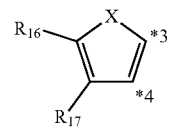

(3)

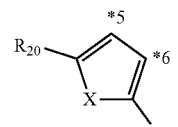

(4)

(5)

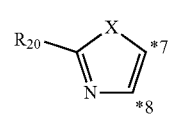

(6)

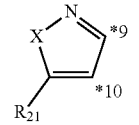

(7)

(8)

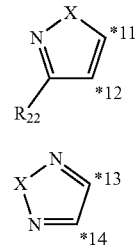

In formulae (2) to (8), each pair selected from *1 and *2, *3 and *4, *5 and *6, *7 and *8, *9 and *10, *11 and *12, and *13 and *14 represents two ring carbon atoms to which $R_n$ and $R_{n+1}$ are bonded;

$R_n$ may be bonded to either of two ring carbon atoms represented by *1 and *2, *3 and *4, *5 and *6, *7 and *8, *9 and *10, *11 and *12, or *13 and *14;

X is selected from $C(R_{23})(R_{24})$, $NR_{25}$, O, and S;

$R_{12}$ to $R_{25}$ are the same as $R_1$ to $R_{11}$ described above; and adjacent groups selected from $R_{12}$ to $R_{17}$ and $R_{23}$ to $R_{24}$ may be bonded to each other to form a ring structure.

Examples and preferred examples of $R_{12}$ to $R_{25}$ are the same as those described above with respect to $R_1$ to $R_{11}$ of formula (1).

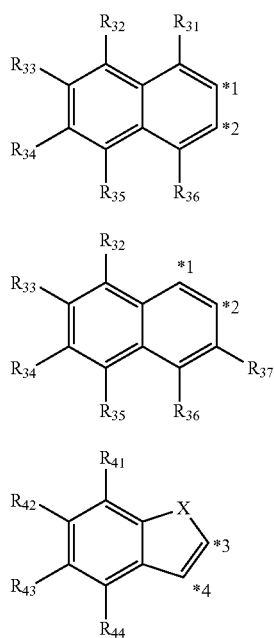

In formulae (9) to (11), each pair selected from *1 and *2, and *3 and *4 represents two ring carbon atoms to which $R_n$ and $R_{n+1}$ are bonded;

$R_n$ may be bonded to either of two ring carbon atoms represented by *1 and *2, or *3 and *4;

$R_{31}$ to $R_{37}$ and $R_{41}$ to $R_{44}$ are the same as $R_{12}$ to $R_{25}$ described above;

X is as defined above; and adjacent groups selected from $R_{31}$ to $R_{37}$ and $R_{41}$ to $R_{44}$ may be bonded to each other to form a ring structure.

Examples and preferred examples of $R_{23}$ to $R_{25}$ in X, $R_{31}$ to $R_{37}$, and $R_{41}$ to $R_{44}$ are the same as those described above with respect to $R_1$ to $R_{11}$ of formula (1).

In formula (1), at least one selected from $R_2$, $R_4$, $R_5$, $R_{10}$, and $R_{11}$, preferably at least one selected from $R_2$, $R_5$, and $R_{10}$, and still more preferably $R_2$ preferably does not form the ring structure and is a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalky group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by $—Si(R_{101})(R_{102})(R_{103})$ wherein $R_{101}$ to $R_{103}$ are as defined above, a group represented by $—N(R_{104})(R_{105})$ wherein $R_{104}$ and $R_{105}$ are as defined above, a substituted or unsubstituted aryl group having 6 to 50 ring carbon atoms, or a substituted or unsubstituted heteroaryl group having 5 to 50 ring atoms.

Examples, preferred numbers of carbon atoms, and preferred numbers of atoms of the above groups are the same as those described above with respect to $R_1$ to $R_{11}$.

Preferably, each of (i) the substituent of the ring structure having 3 or more atoms in formula (1) composed of a carbon atom, an oxygen atom, a sulfur atom, and a nitrogen atom together with two ring atoms to which $R_n$ and $R_{n+1}$ are bonded;

(ii) $R_1$ to $R_{11}$ in formula (1) not forming the ring structure; and (iii) $R_{12}$ to $R_{22}$, $R_{31}$ to $R_{37}$, and $R_{41}$ to $R_{44}$ in formulae (2) to (11) is independently a hydrogen atom, a substituted or unsubstituted alkyl group having 1 to 20 carbon atoms, a group represented by $—N(R_{104})(R_{105})$, a substituted or unsubstituted aryl group having 6 to 50 ring carbon atoms, a substituted or unsubstituted heteroaryl group having 5 to 50 ring atoms, or any of the following groups:

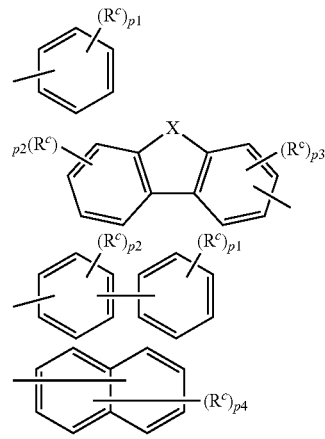

wherein:

$R^c$ is independently the same as $R_1$ to $R_{11}$ described above;

X is as defined above; and p1 is an integer of 0 to 5, p2 is an integer of 0 to 4, p3 is an integer of 0 to 3, and p4 is an integer of 0 to 7.

Examples and preferred examples of $R_{23}$ to $R_{25}$ in X and $R^c$ are the same as those described above with respect to $R_1$ to $R_{11}$.

The compound of formula (1) is represented preferably by any of formulae (1-1) to (1-6), more preferably by any of formulae (1-1) to (1-3) and (1-5), and still more preferably by formula (1-1) or (1-5).

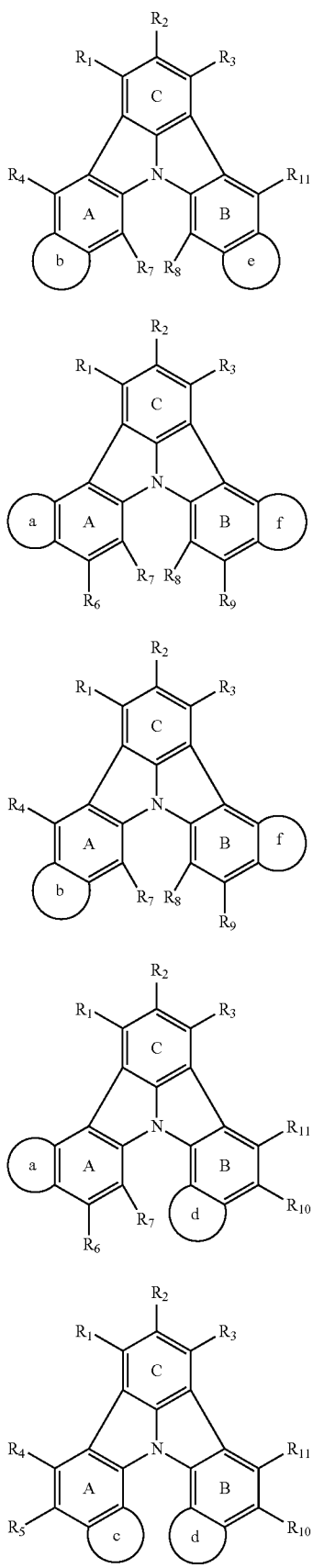

(1-1)
(1-2)
(1-3)
(1-4)
(1-5)

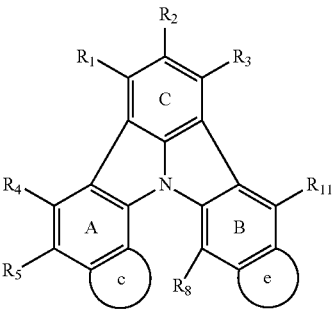

(1-6)

In formulae (1-1) to (1-6), $R_1$ to $R_{11}$ are as defined above and examples, preferred number of carbon atoms, preferred number of atoms, and preferred examples thereof are as described above;

each of the rings a to f is independently the ring structure having 3 or more atoms composed of a carbon atom, an oxygen atom, a sulfur atom, and a nitrogen atom;

the ring structure may have a substituent and the substituents may be bonded to each other to form a ring structure;

the substituent is the same as defined with respect to the substituent represented by $R_1$ to $R_{11}$; and the number of atoms of the ring structure having 3 or more atoms does not include the atom in the substituent.

In formulae (1-1) to (1-6), the ring structure having 3 or more atoms composed of a carbon atom, an oxygen atom, a sulfur atom, and a nitrogen atom which is represented by any of the rings a to f preferably has 3 to 7 atoms and particularly preferably has 5 or 6 atoms, although not particularly limited thereto. Each of the rings a to f is preferably a ring represented by any of formulae (2) to (8), or preferably a ring represented by any of formulae (9) to (11).

In formulae (1-1) to (1-6), examples, preferred number of carbon atoms, preferred number of atoms, and preferred examples of the substituent are the same as those of the corresponding groups described above with respect to $R_1$ to $R_{11}$.

The compound of formula (1) is preferably represented by any of formulae (2-1) to (2-6), more preferably represented by formula (2-2) or (2-5).

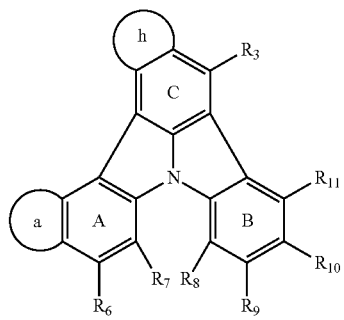

(2-1)

(2-2)
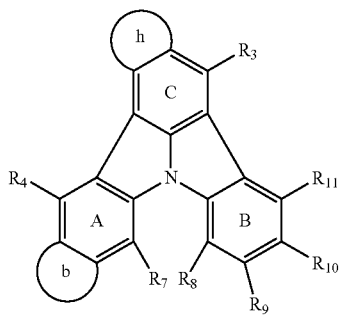

(2-3)
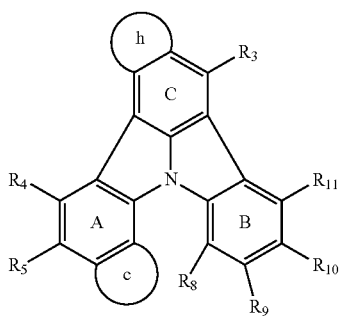

(2-4)
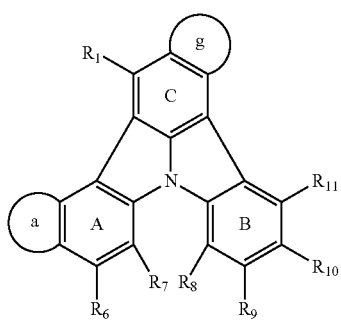

(2-5)
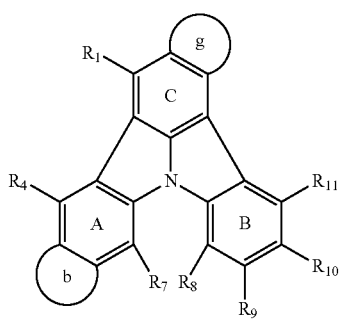

(2-6)
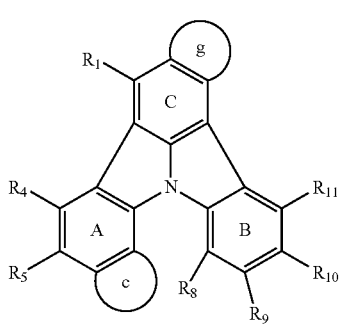

In formulae (2-1) to (2-6), $R_1$ and $R_3$ to $R_{11}$ are as defined above and examples, preferred number of carbon atoms, preferred number of atoms, and preferred examples thereof are as described above;

each of the rings a to c and g to h is independently the ring structure having 3 or more atoms composed of a carbon atom, an oxygen atom, a sulfur atom, and a nitrogen atom;

the ring structure may have a substituent and the substituents may be bonded to each other to form a ring structure;

the substituent is the same as defined with respect to the substituent represented by $R_1$ to $R_{11}$; and the number of atoms of the ring structure having 3 or more atoms does not include the atom in the substituent.

In formulae (2-1) to (2-6), the ring structure having 3 or more atoms composed of a carbon atom, an oxygen atom, a sulfur atom, and a nitrogen atom which is represented by any of the rings a to c and g to h preferably has 3 to 7 atoms and particularly preferably has 5 or 6 atoms, although not particularly limited thereto. Each of the rings a to c and g to h is preferably a ring represented by any of formulae (2) to (8), or preferably a ring represented by any of formulae (9) to (11).

In formulae (2-1) to (2-6), examples, preferred number of carbon atoms, preferred number of atoms, and preferred examples of the optional substituent are the same as those of the corresponding groups described above with respect to $R_1$ to $R_{11}$.

The compound of formula (1) is preferably represented by any of formulae (3-1) to (3-9) and more preferably represented by formula (3-1).

(3-1)
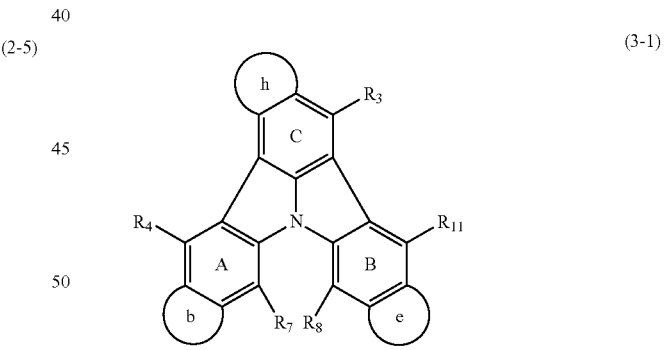

(3-2)
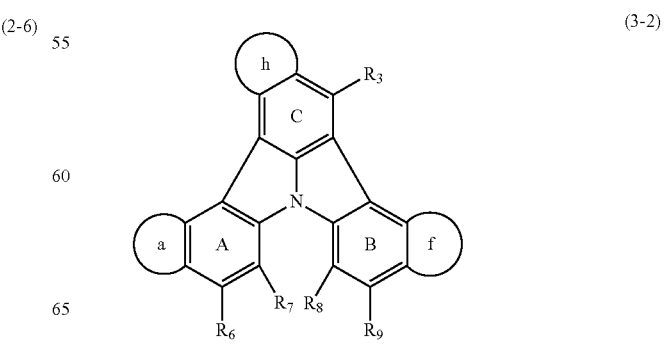

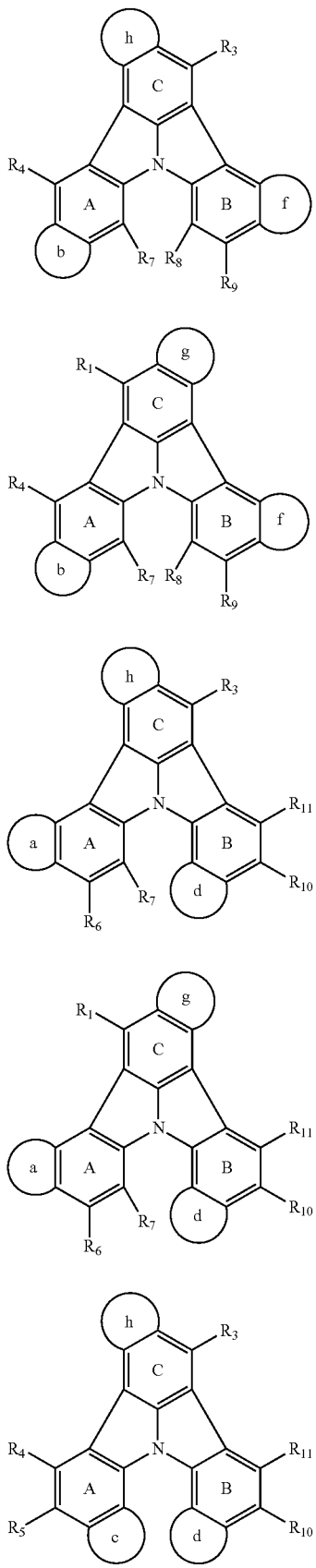

(3-3)
(3-4)
(3-5)
(3-6)
(3-7)

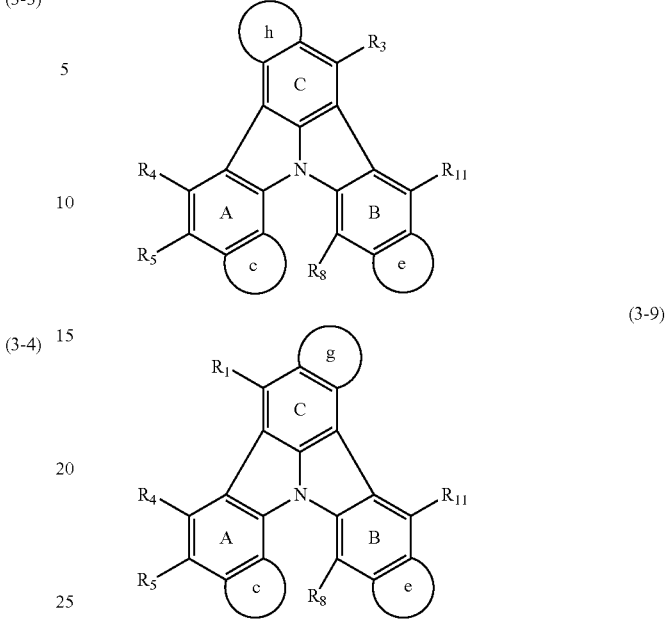

(3-8)
(3-9)

In formulae (3-1) to (3-9), $R_1$ and $R_3$ to $R_{11}$ are as defined above and examples, preferred number of carbon atoms, preferred number of atoms, and preferred examples thereof are as described above;

each of the rings a to h is independently the ring structure having 3 or more atoms composed of a carbon atom, an oxygen atom, a sulfur atom, and a nitrogen atom;

the ring structure may have a substituent and the substituents may be bonded to each other to form a ring structure;

the substituent is the same as defined above with respect to the substituent represented by $R_1$ to $R_{11}$; and the number of atoms of the ring structure having 3 or more atoms does not include the atom in the substituent.

In formulae (3-1) to (3-9), the ring structure having 3 or more atoms composed of a carbon atom, an oxygen atom, a sulfur atom, and a nitrogen atom which is represented by any of the rings a to h preferably has 3 to 7 atoms and particularly preferably has 5 or 6 atoms, although not particularly limited thereto Each of the rings a to h is preferably a ring represented by any of formulae (2) to (8), or preferably a ring represented by any of formulae (9) to (11).

In formulae (3-1) to (3-9), the ring structure having 3 or more atoms composed of a carbon atom, an oxygen atom, a sulfur atom, and a nitrogen atom which is represented by any of the rings a to h is preferably a ring structure having 3 or more atoms composed of a carbon atom, an oxygen atom, and a sulfur atom. The hetero atom of the heteroaryl group as the substituent of the ring g or h is preferably a sulfur and/or an oxygen atom.

In formulae (3-1) to (3-9), examples, preferred number of carbon atoms, preferred number of atoms, and preferred examples of the substituent are the same as those of the corresponding groups described above with respect to $R_1$ to $R_{11}$.

Preferably, in formulae (1-1) to (1-6), (2-1) to (2-6), and (3-1) to (3-9), the substituent for the rings a to h and $R_1$ to $R_{11}$ not forming the rings a to h is independently a hydrogen atom, a substituted or unsubstituted alkyl group having 1 to 20 carbon atoms, a group represented by —N(R$_{104}$)(R$_{105}$), a substituted or unsubstituted aryl group having 6 to 50 ring carbon atoms, a substituted or unsubstituted heteroaryl group having 5 to 50 ring atoms, or any one of the following groups:

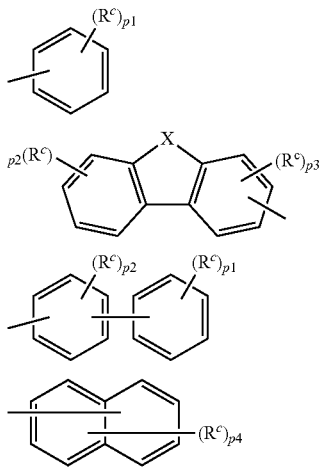

wherein:

R$^c$ is independently the same as R$_1$ to R$_{11}$ described above;

X is as defined above; and p1 is an integer of 0 to 5, p2 is an integer of 0 to 4, p3 is an integer of 0 to 3, and p4 is an integer of 0 to 7.

Examples and preferred examples of R$_{23}$ to R$_{25}$ in X and R$^c$ are the same as those described above with respect to R$_1$ to R$_{11}$.

The substituent of the rings g and h is preferably a substituted or unsubstituted alkyl group having 1 to 20 carbon atoms, a substituted or unsubstituted aryl group having 6 to 50 ring carbon atoms, or any of the following groups:

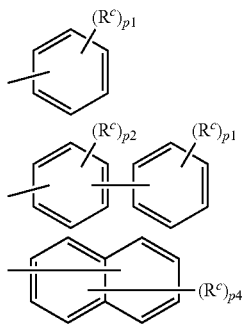

wherein:

R$^c$ is independently the same as R$_1$ to R$_{11}$ described above; and p1 is an integer of 0 to 5, p2 is an integer of 0 to 4, p3 is an integer of 0 to 3, and p4 is an integer of 0 to 7.

The compound of formula (1) is preferably represented by any of formulae (4-1) to (4-4):

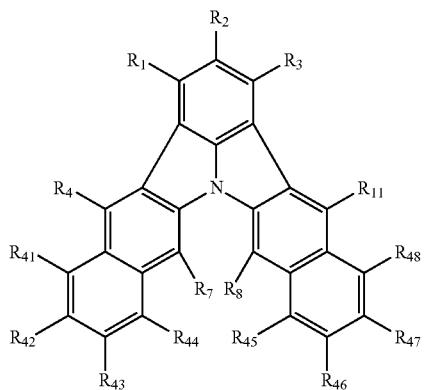
(4-1)

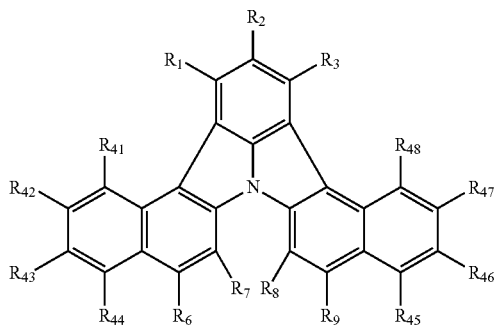
(4-2)

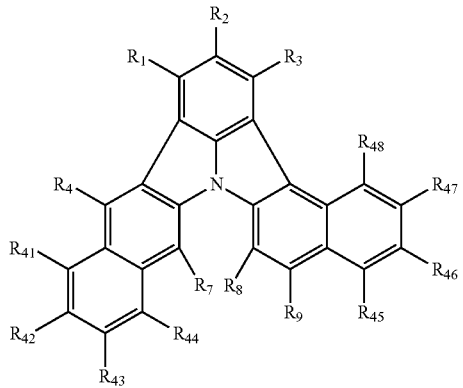
(4-3)

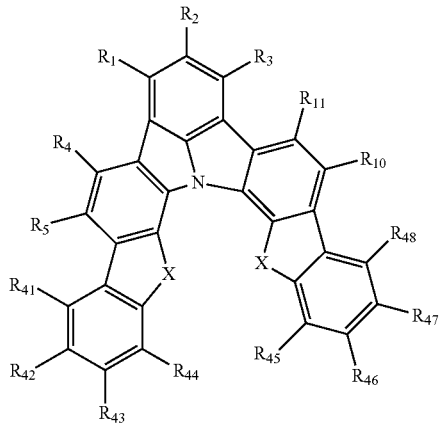
(4-4)

wherein:

X is selected from C(R$_{23}$)(R$_{24}$), NR$_{25}$, O, and S; and

R$_1$ to R$_5$, R$_7$ to R$_{11}$, R$_{41}$ to R$_{48}$, and R$_{23}$ to R$_{25}$ are the same as R$_1$ to R$_{11}$ described above.

Examples and preferred examples of $R_1$ to $R_5$, $R_7$ to $R_{11}$, $R_{41}$ to $R_{48}$, and $R_{23}$ to $R_{25}$ are the same as those described above with respect to $R_1$ to $R_{11}$.

The compound of formula (1) is preferably represented by formula (5-1):

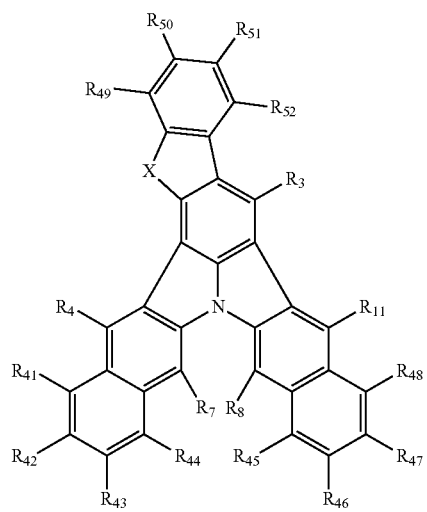

(5-1)

wherein:
X is selected from $C(R_{23})(R_{24})$, $NR_{25}$, O, and S; and $R_3$, $R_4$, $R_7$, $R_8$, $R_{11}$, $R_{41}$ to $R_{52}$, and $R_{23}$ to $R_{25}$ are the same as $R_1$ to $R_{11}$ described above.

Examples and preferred examples of $R_3$, $R_4$, $R_7$, $R_8$, $R_{11}$, $R_{41}$ to $R_{52}$, and $R_{23}$ to $R_{25}$ are the same as those described above with respect to $R_1$ to $R_{11}$. $R_{25}$ is preferably a substituted or unsubstituted aryl group having 6 to 50 ring carbon atoms.

Examples of the compound of the invention are described below, although not particularly limited thereto.

In the following examples, Ph is a phenyl group and D is a heavy hydrogen atom.

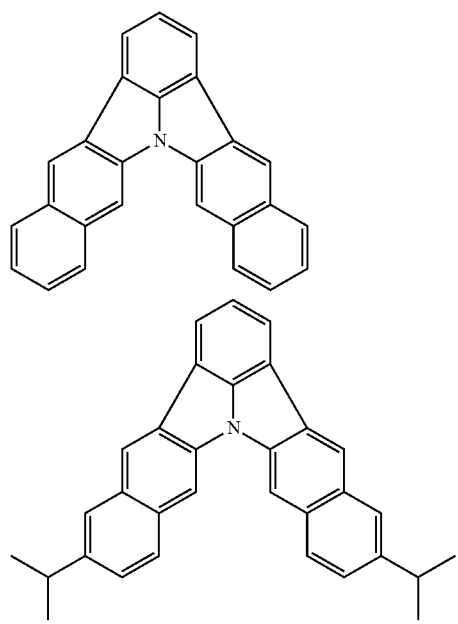

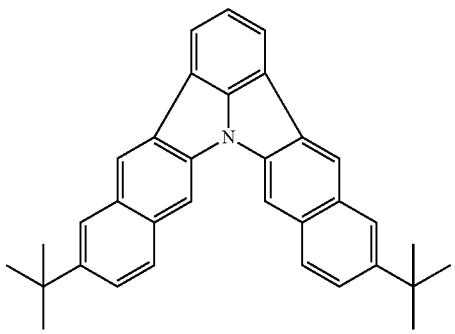

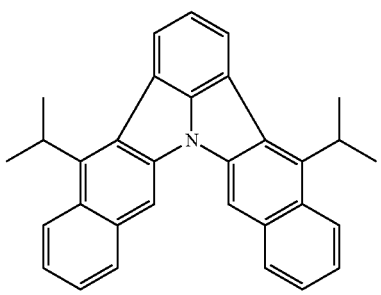

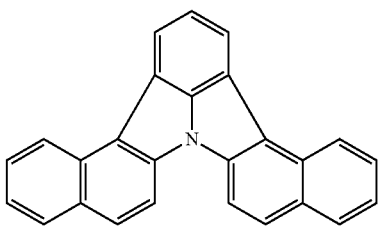

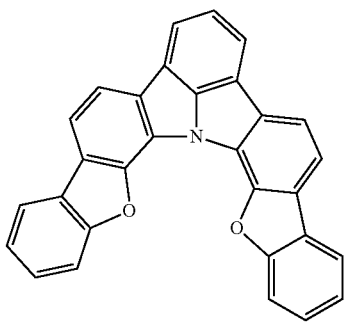

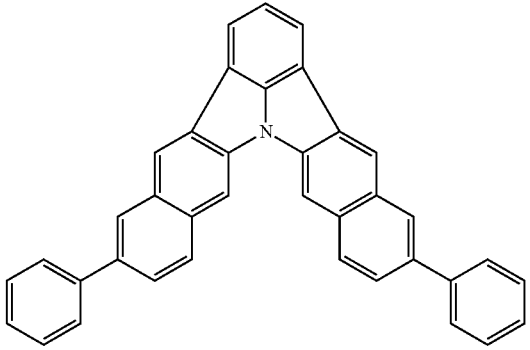

31
-continued
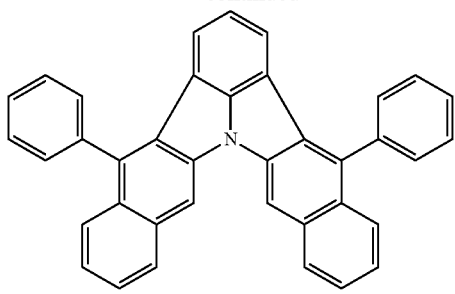
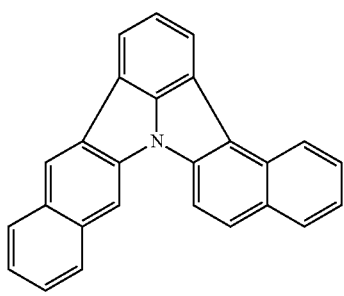
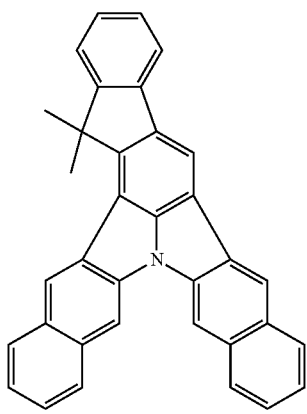
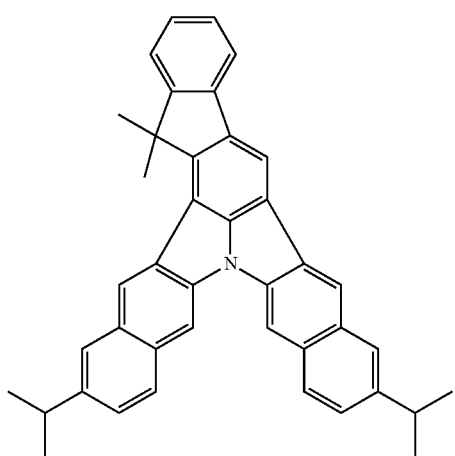
32
-continued
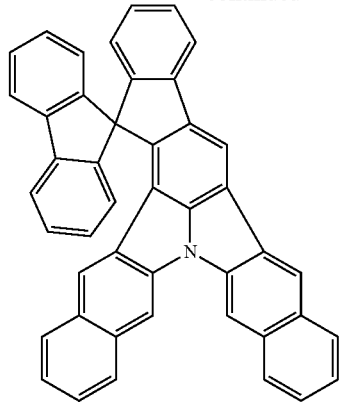
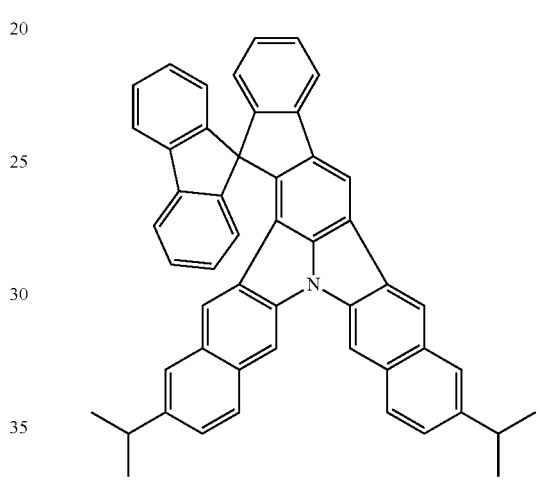
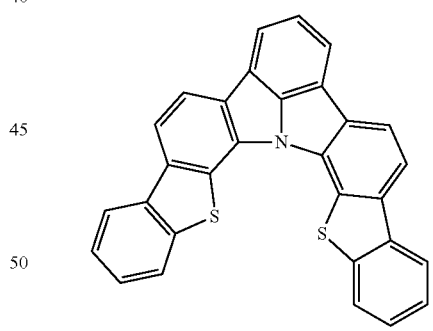
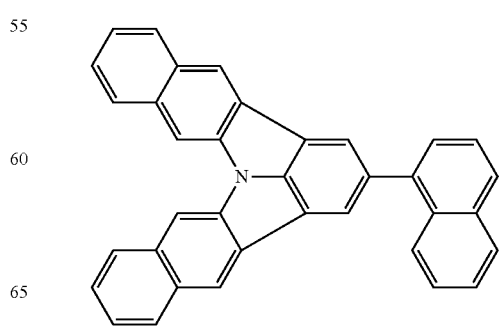

33
-continued
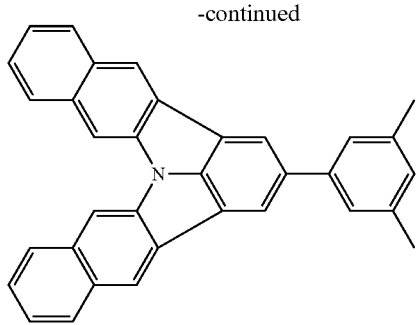
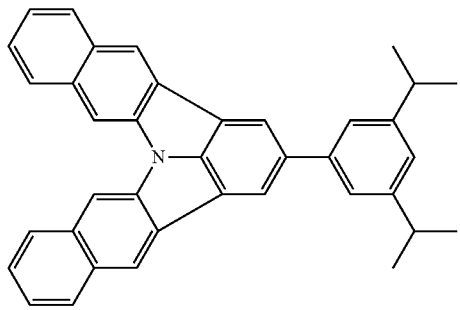
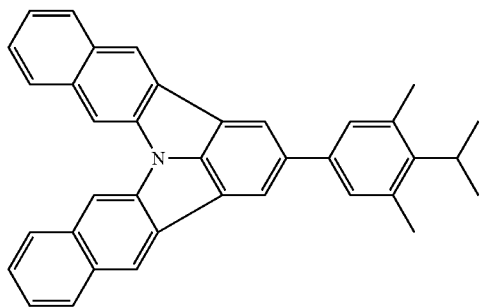
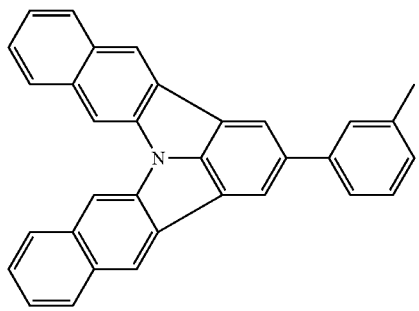
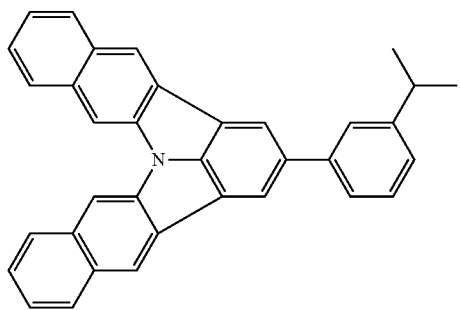
34
-continued
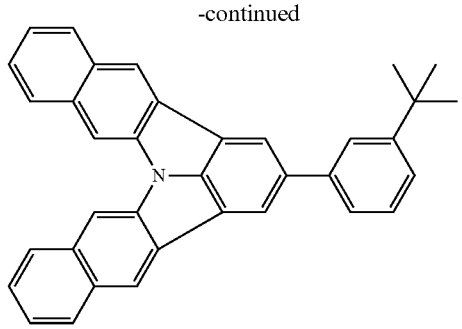
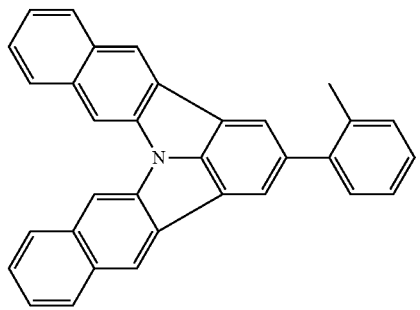
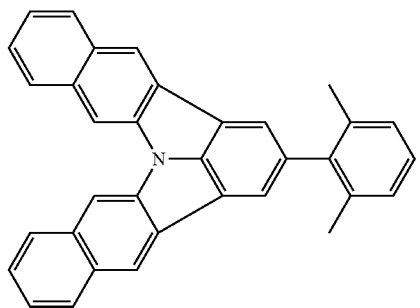
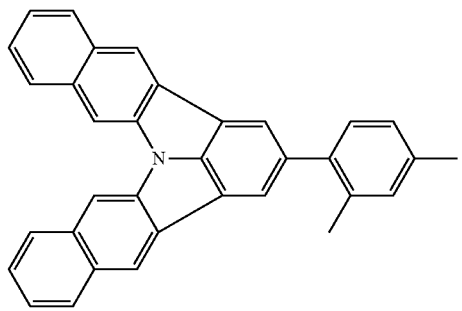
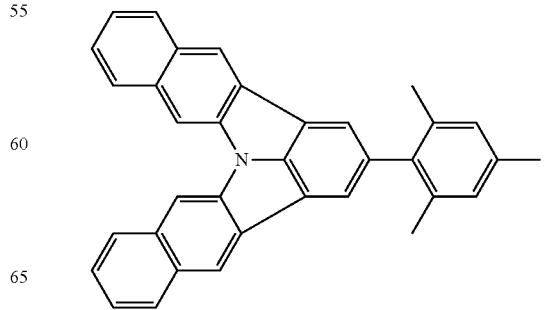

-continued
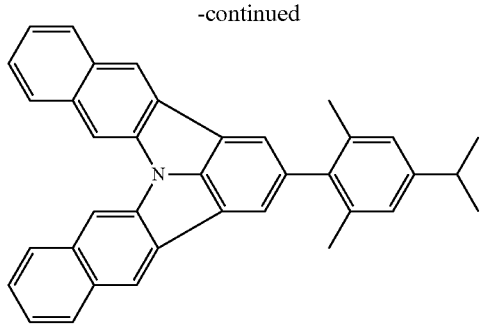
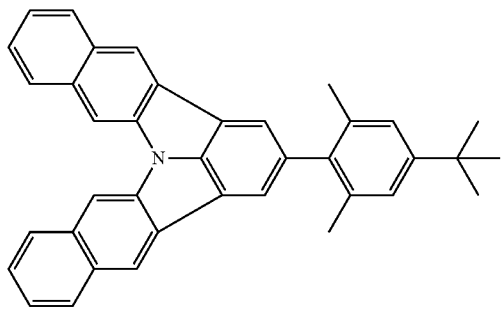
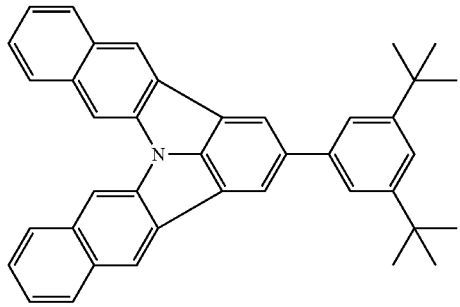
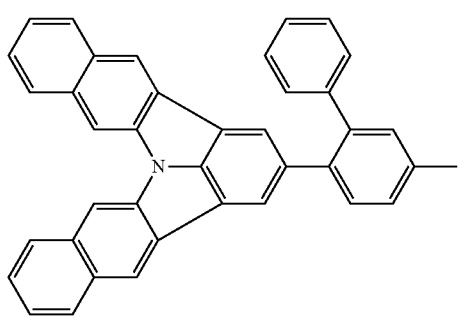
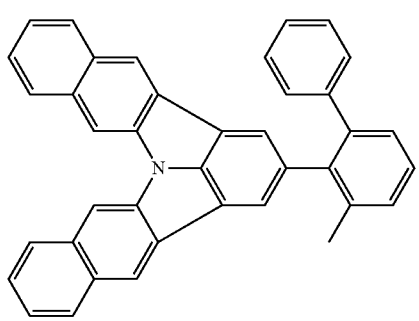
-continued
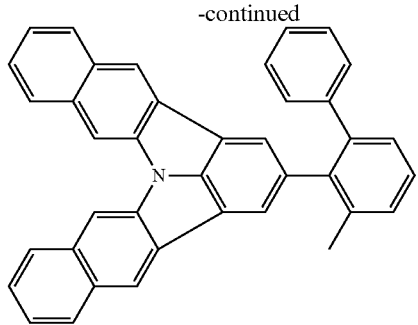
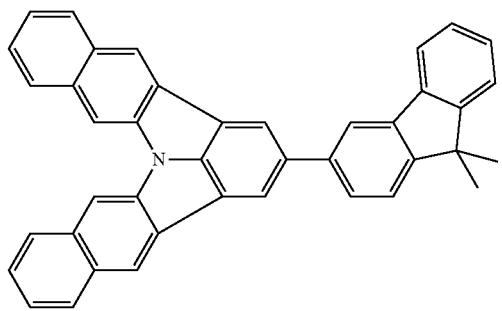
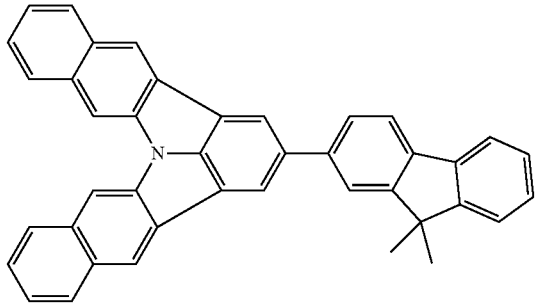
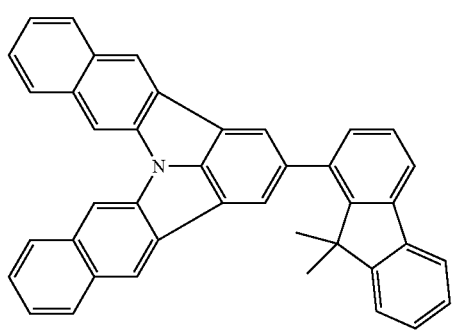
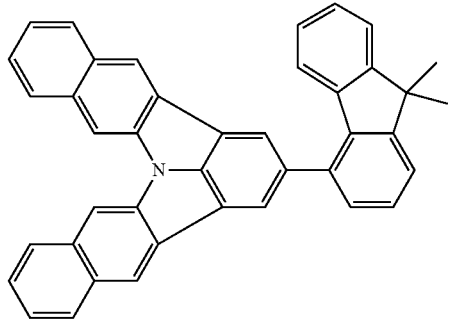

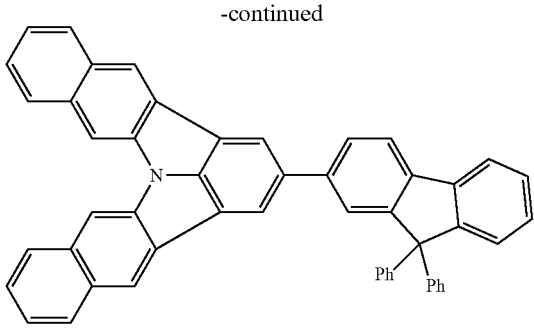
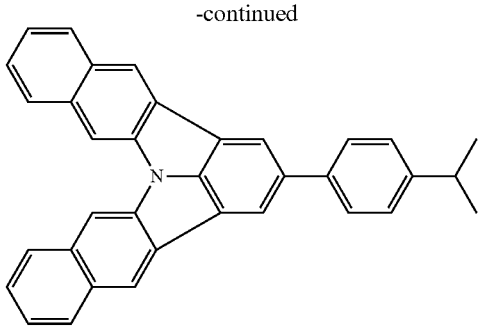
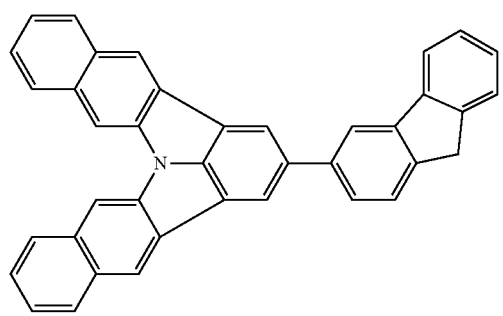
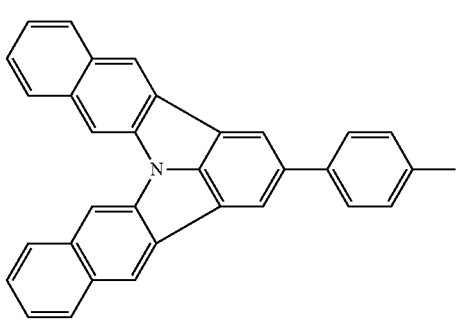
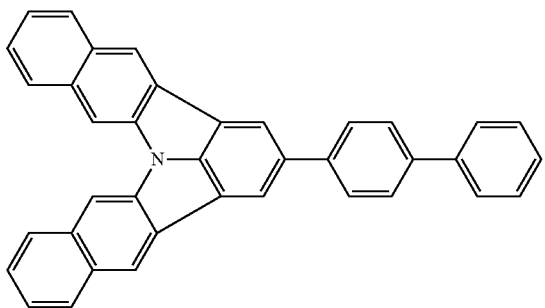
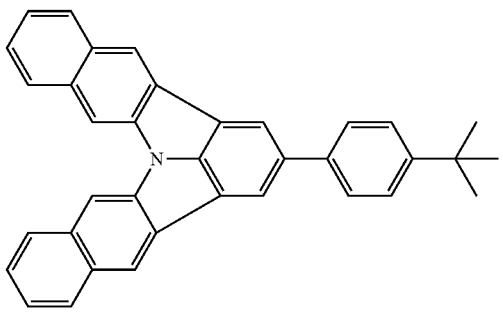
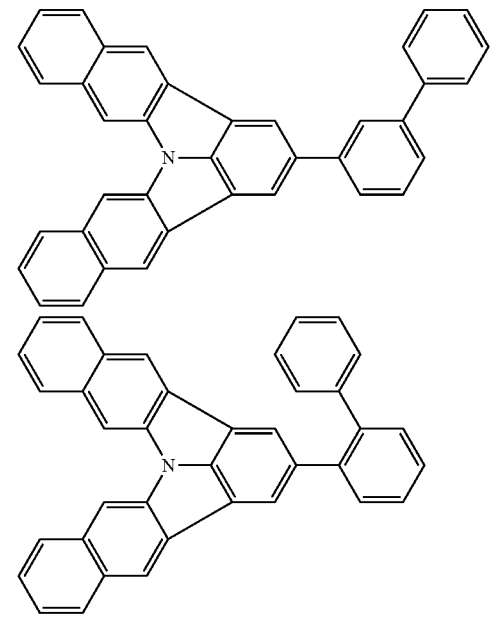
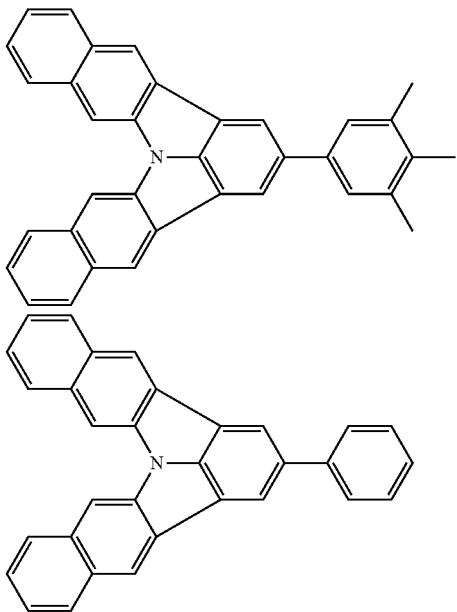

-continued
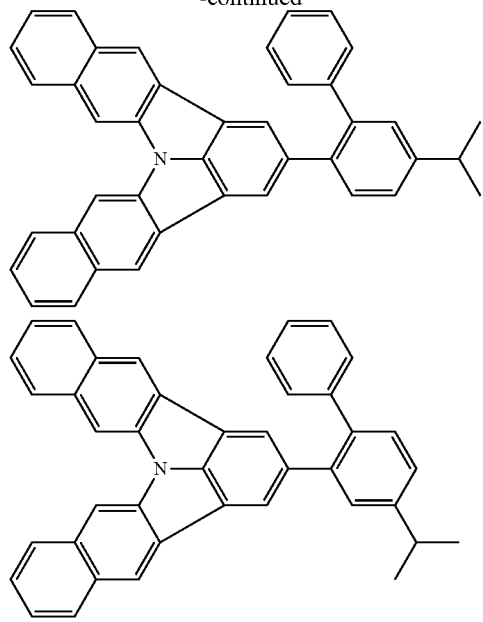
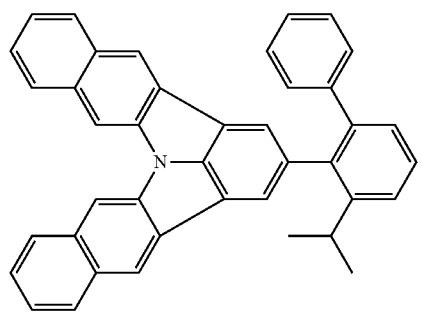
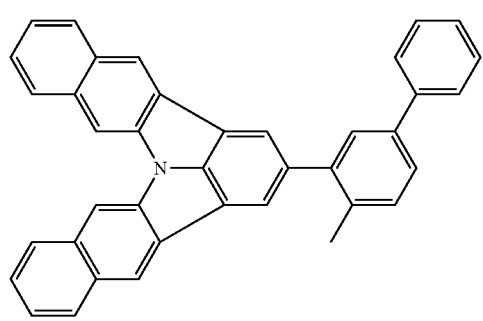
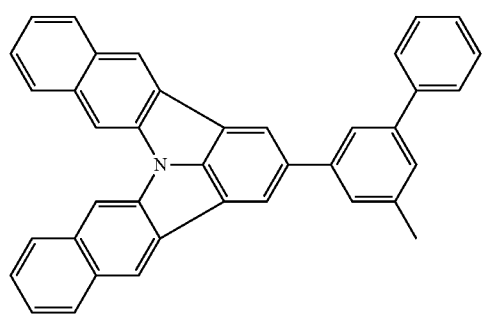
-continued
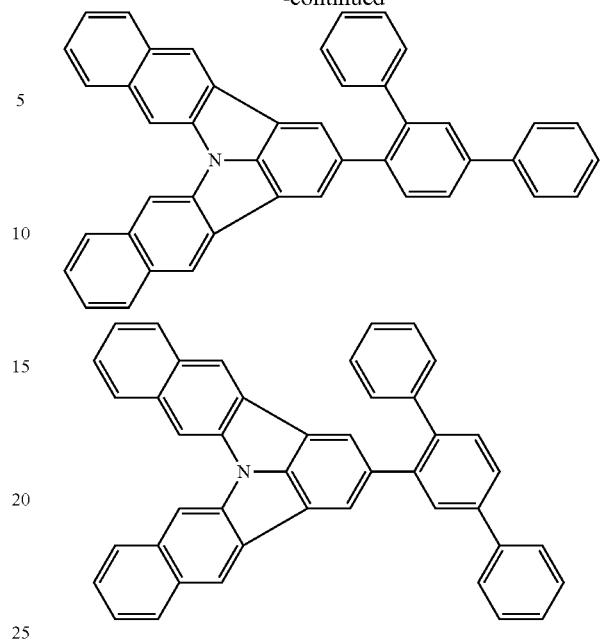
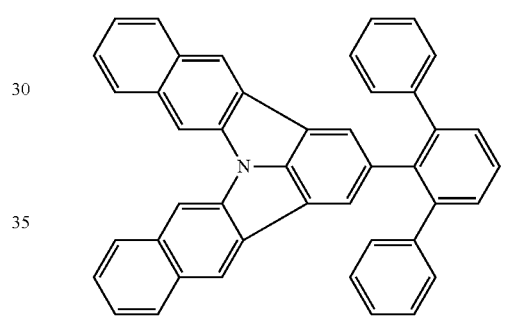
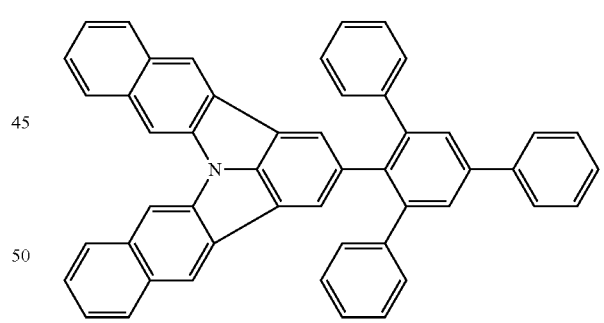
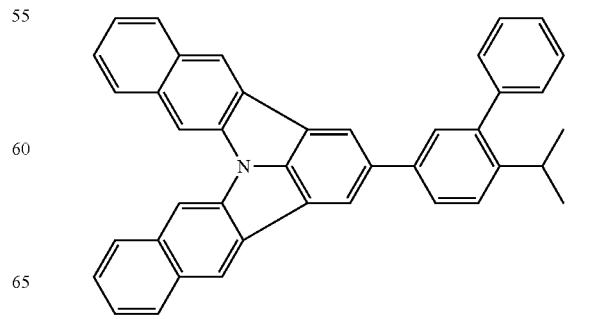

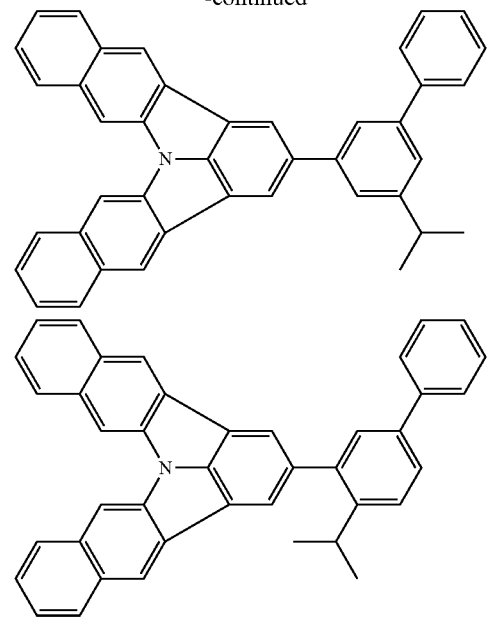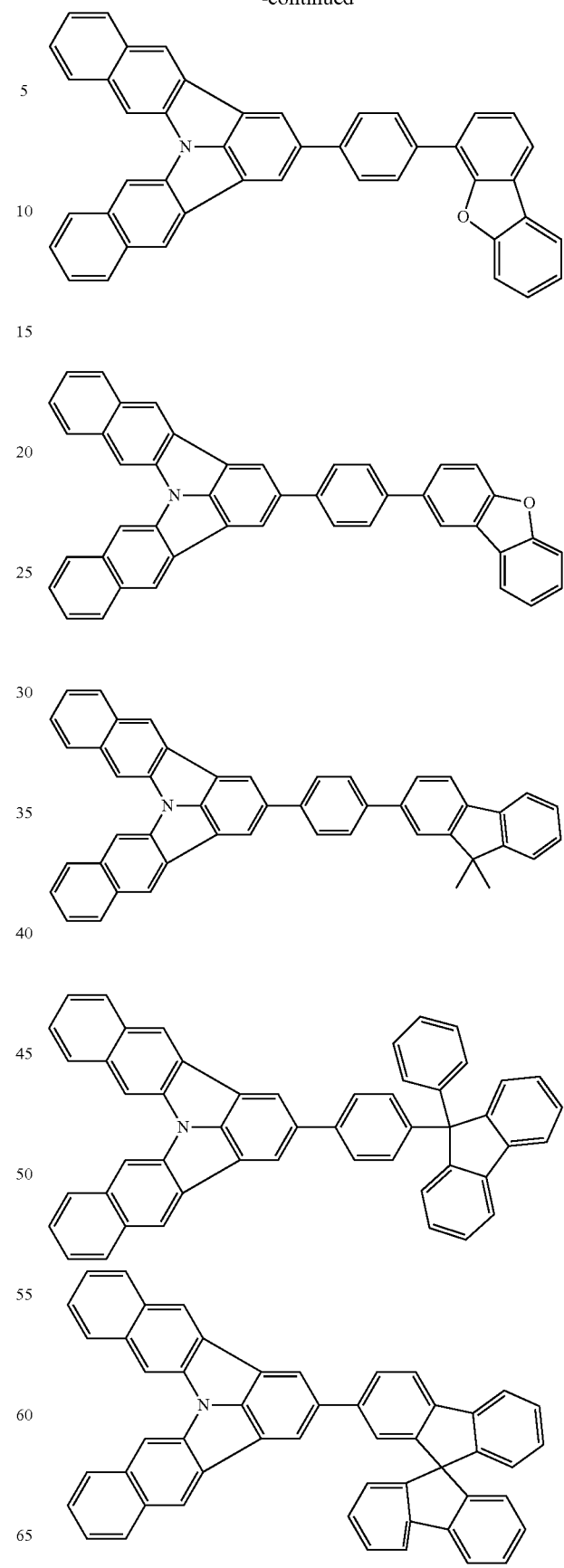

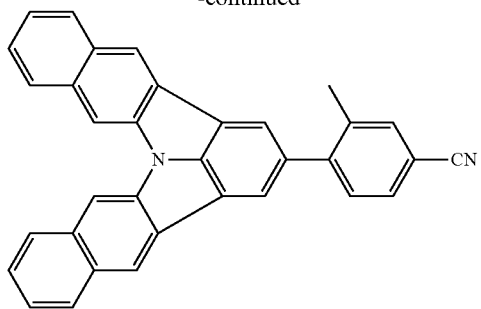
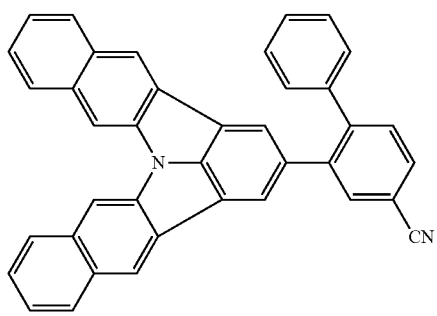
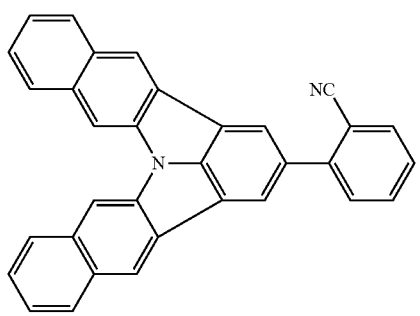
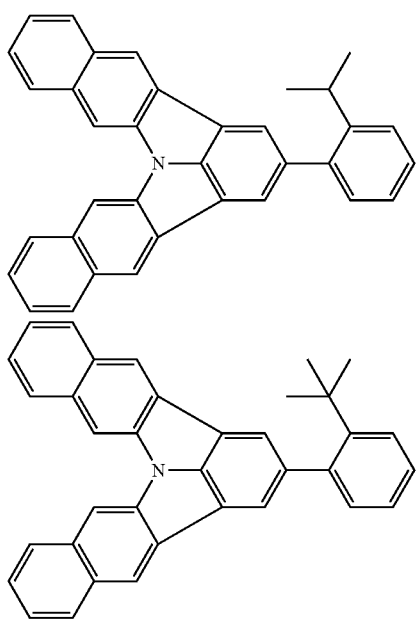
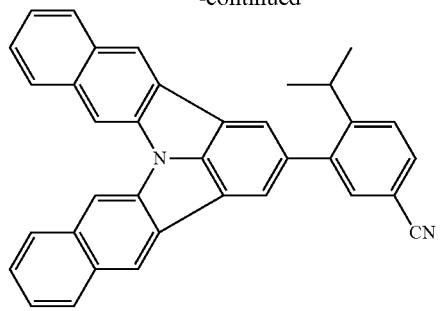
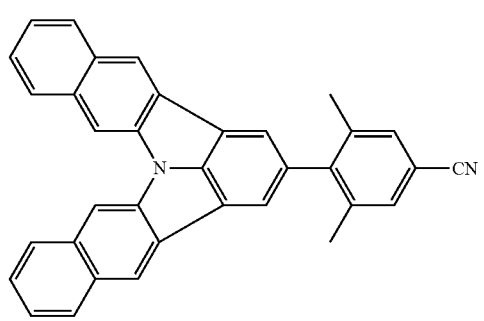
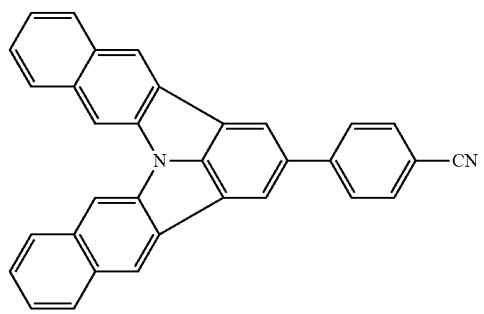
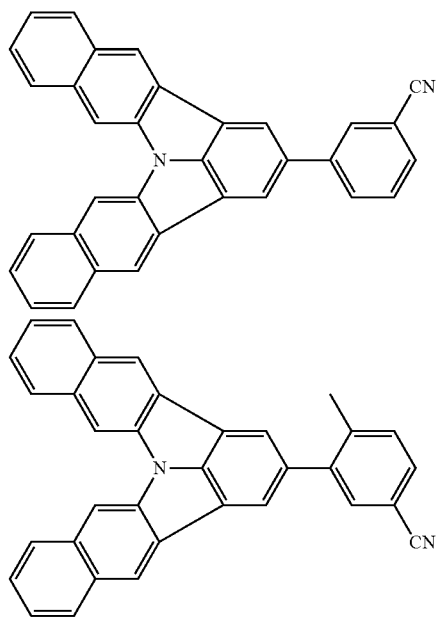

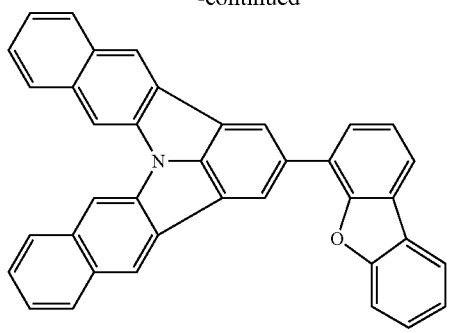
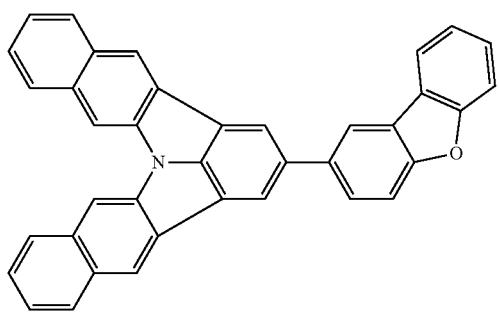
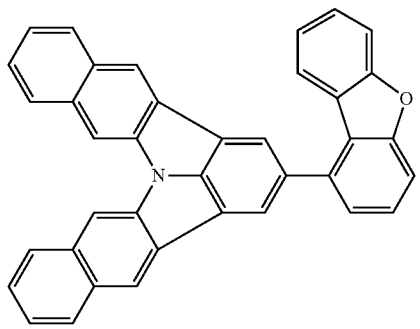
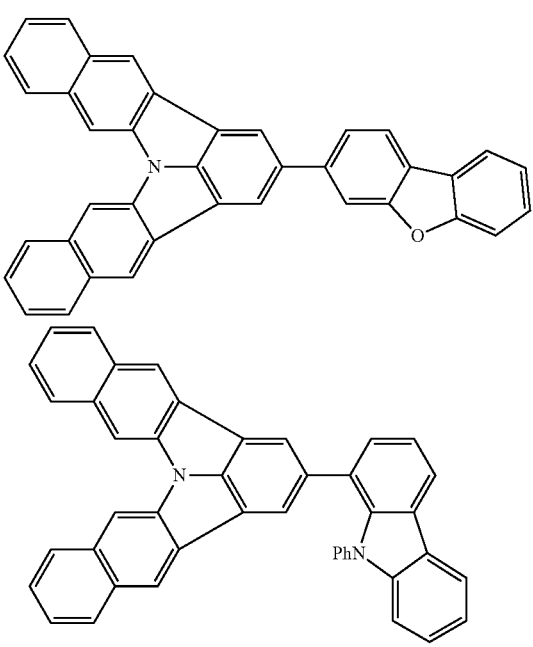
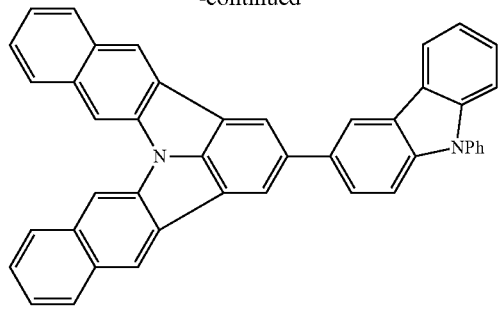
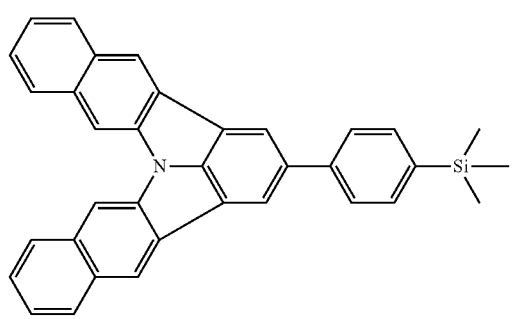
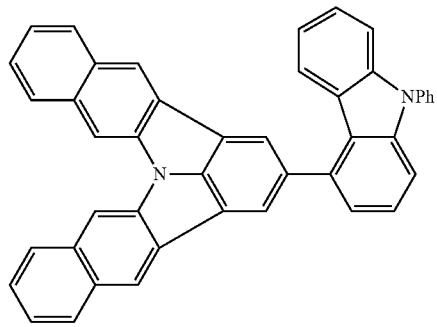
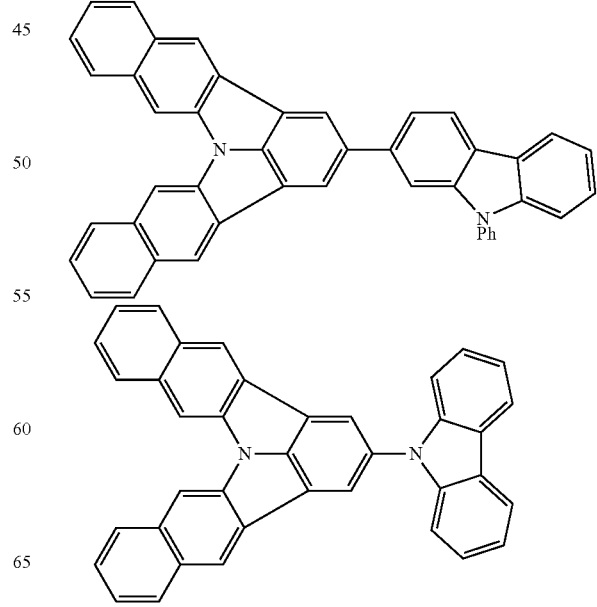

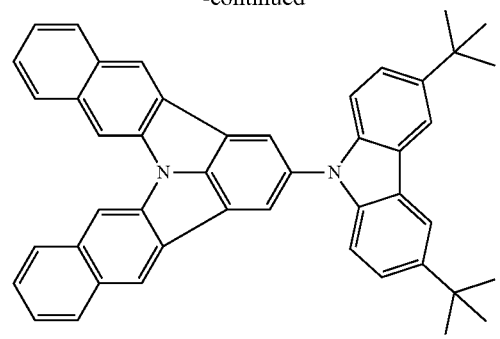
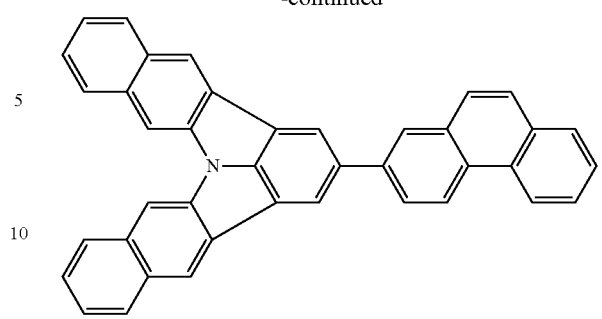
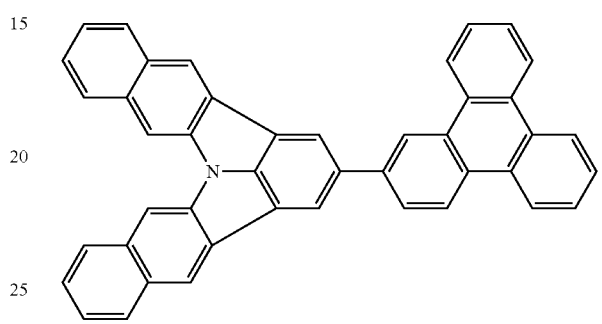
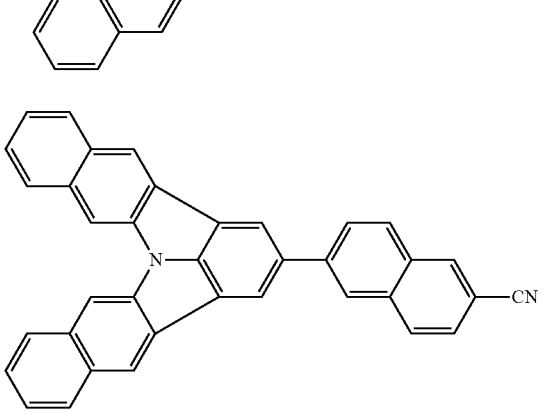
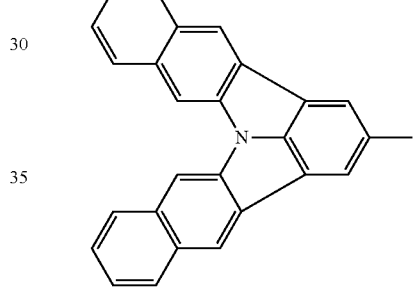
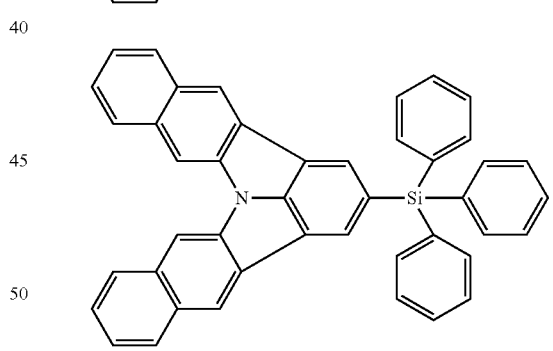
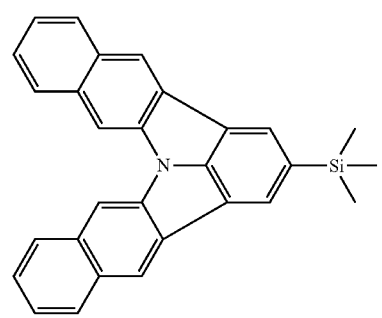
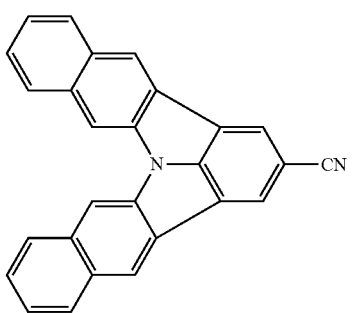

-continued
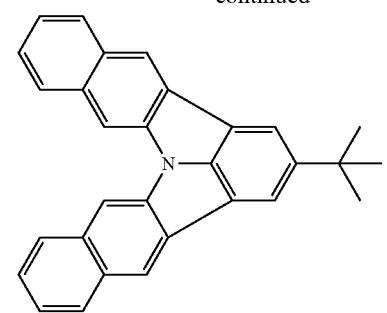
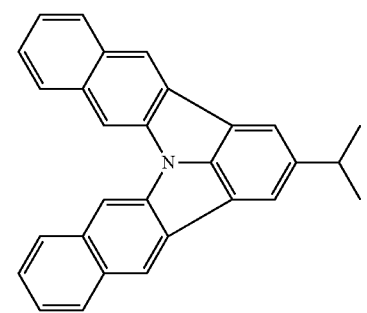
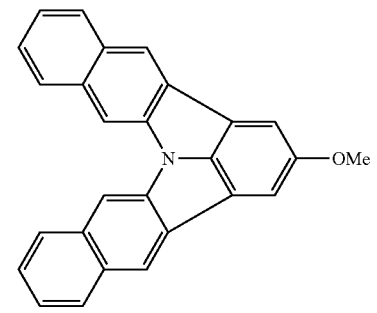
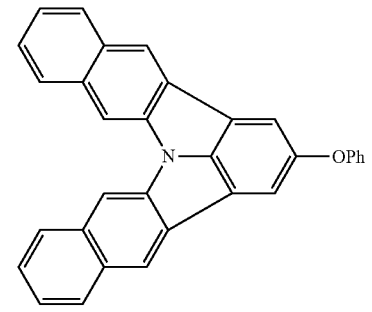
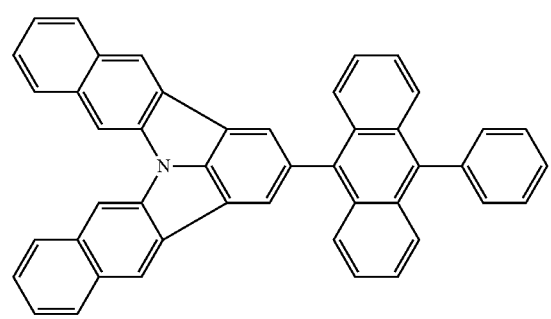
-continued
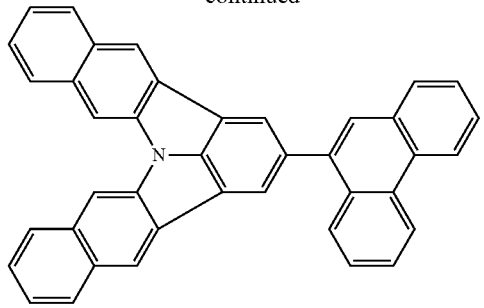
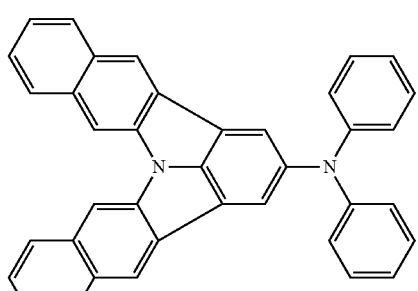
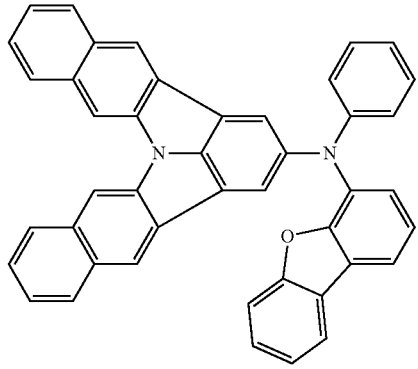
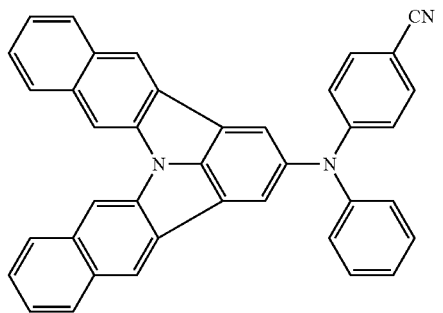
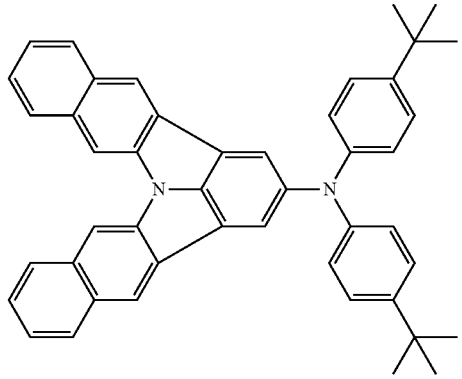

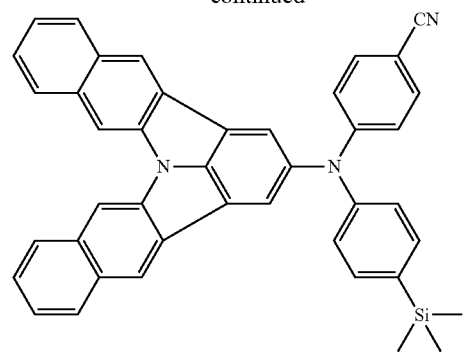
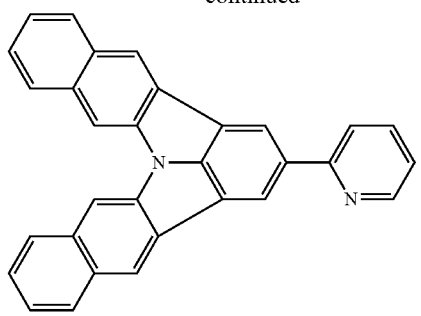
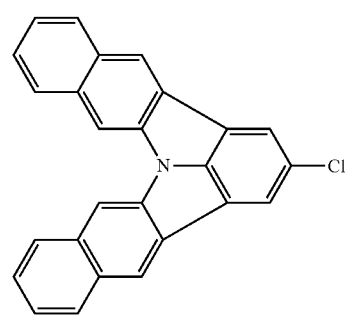
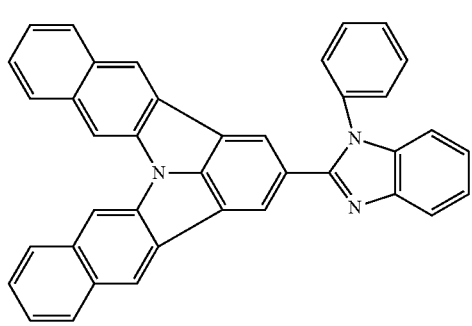
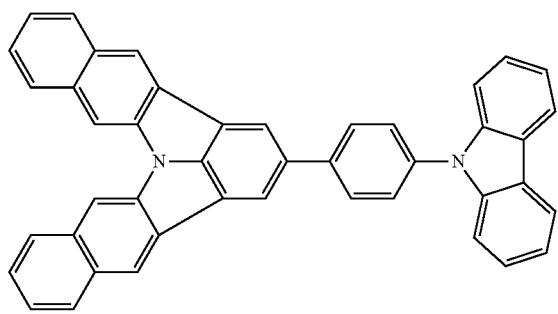
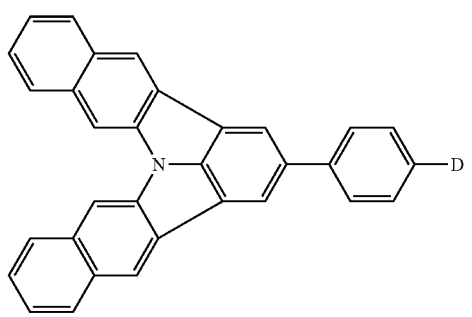
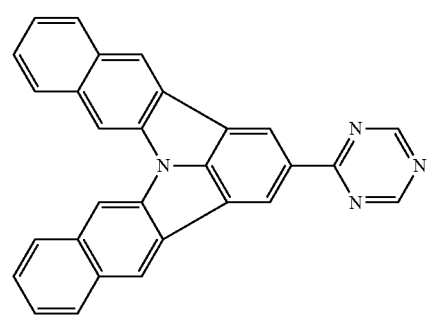
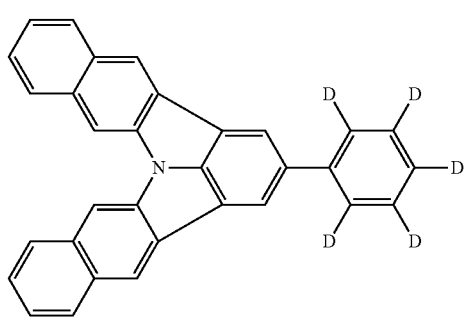
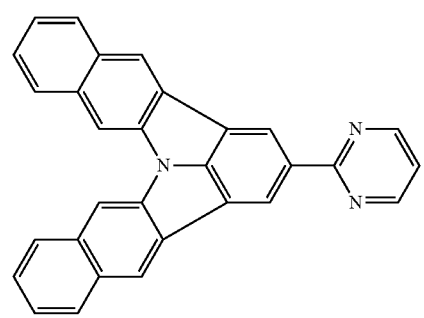
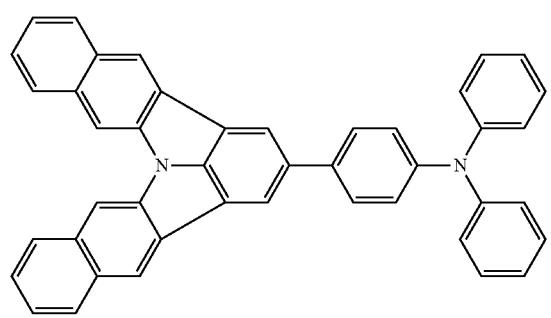

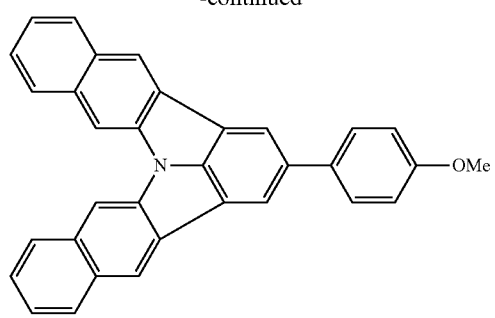
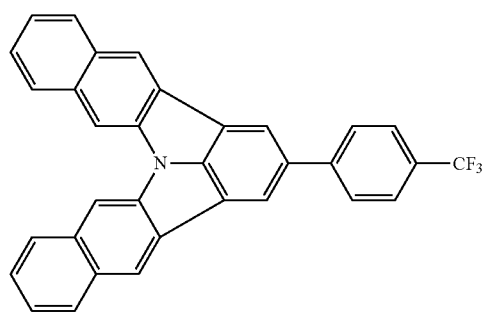
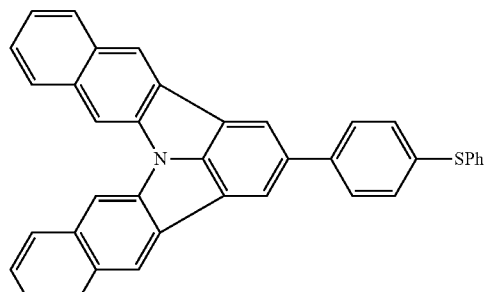
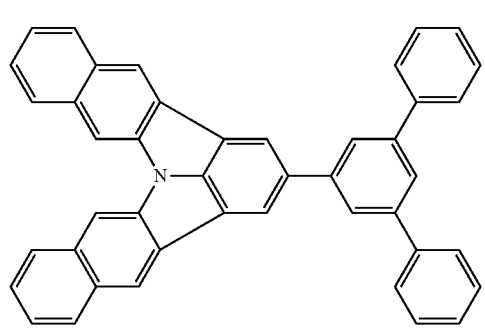
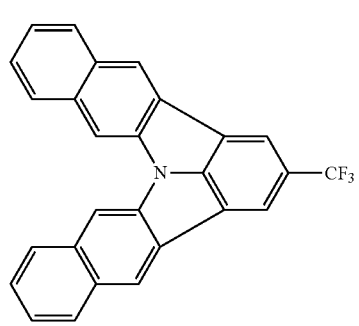
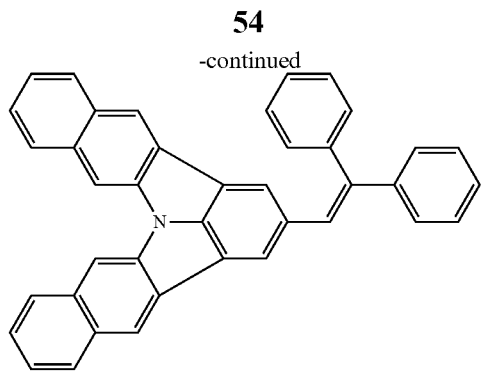
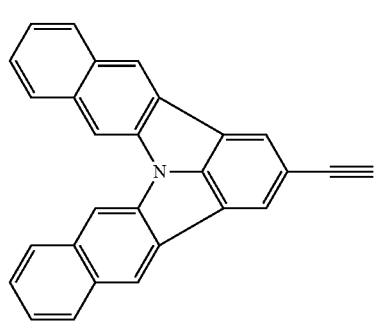
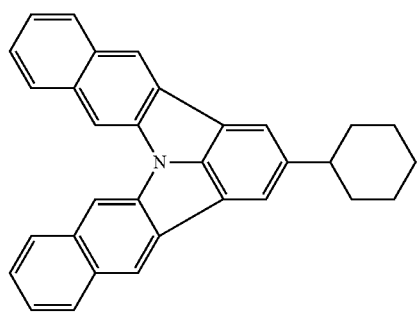
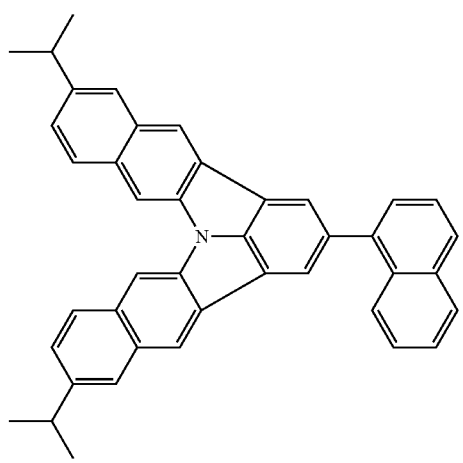

55
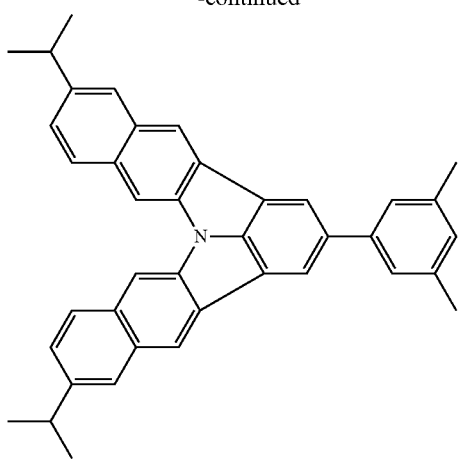
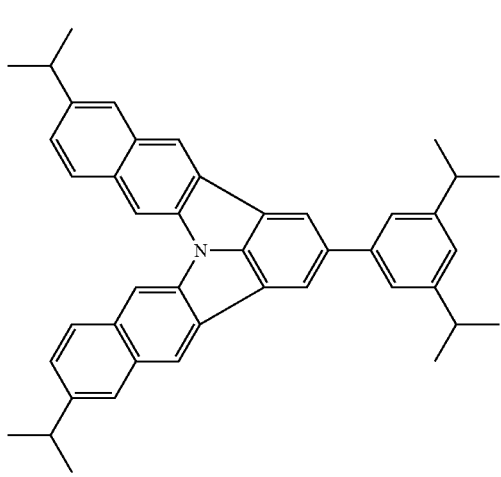
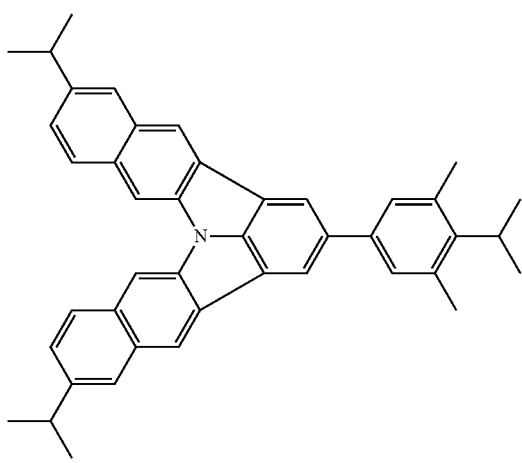
56
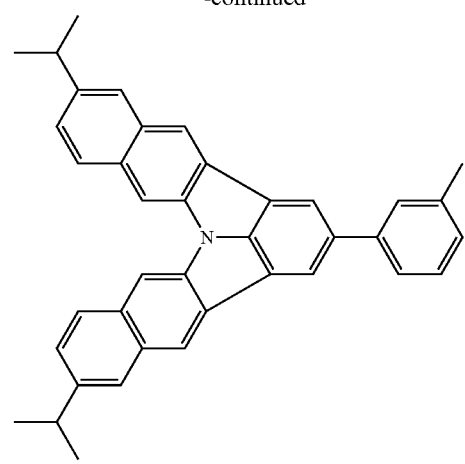
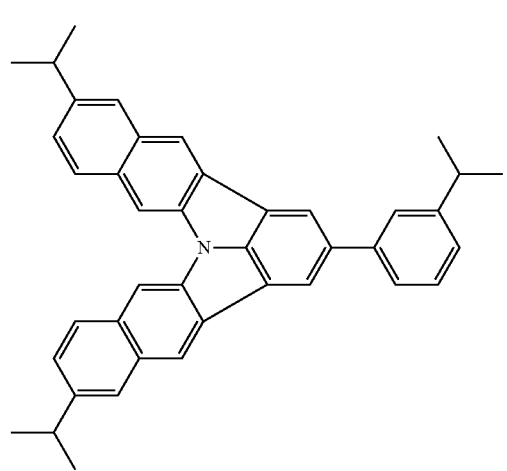
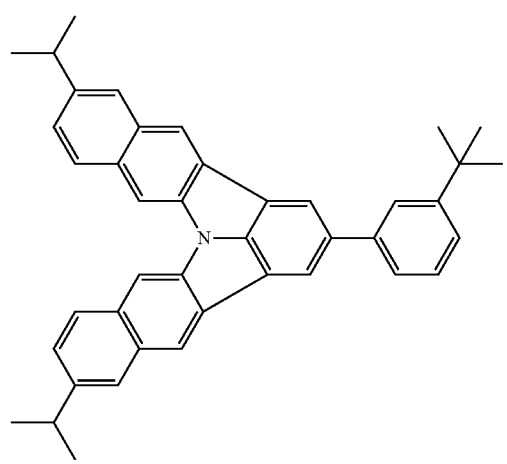

57
-continued
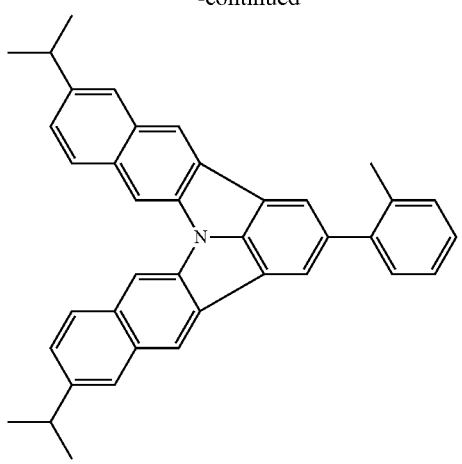
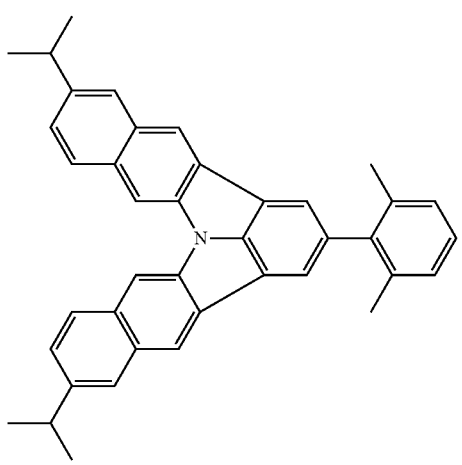
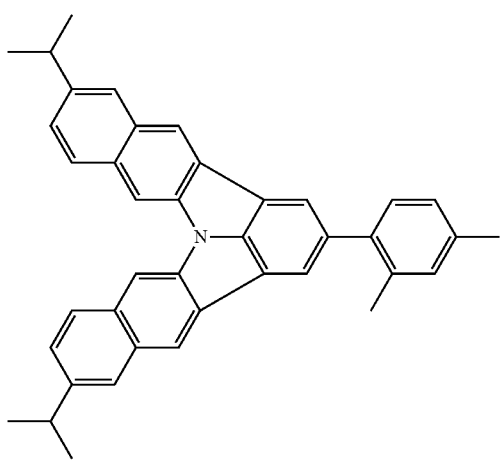
58
-continued
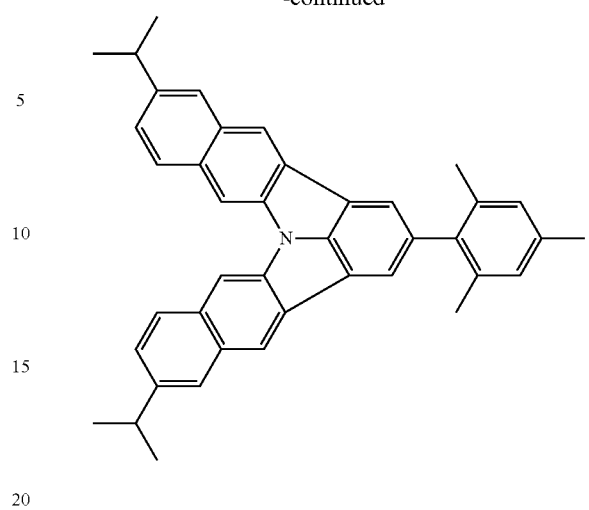
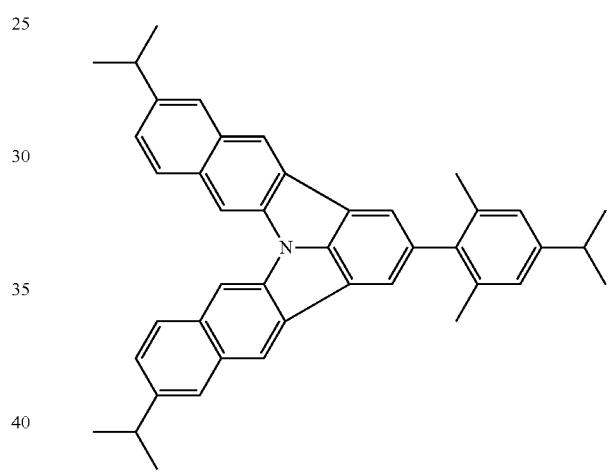
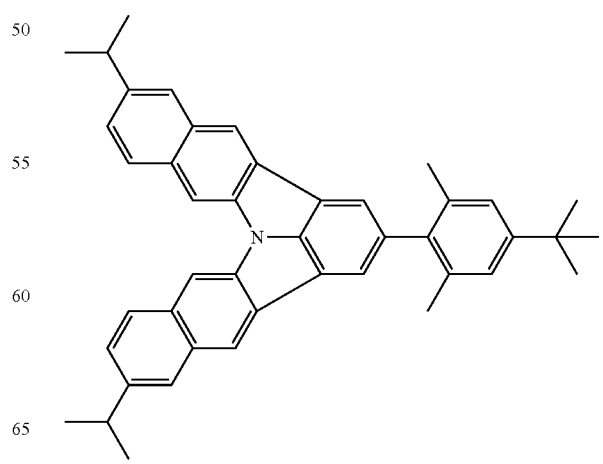

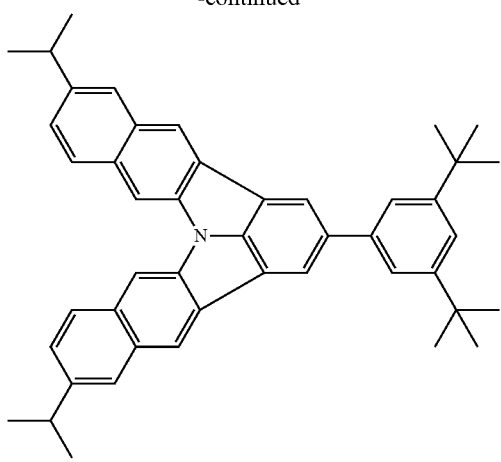
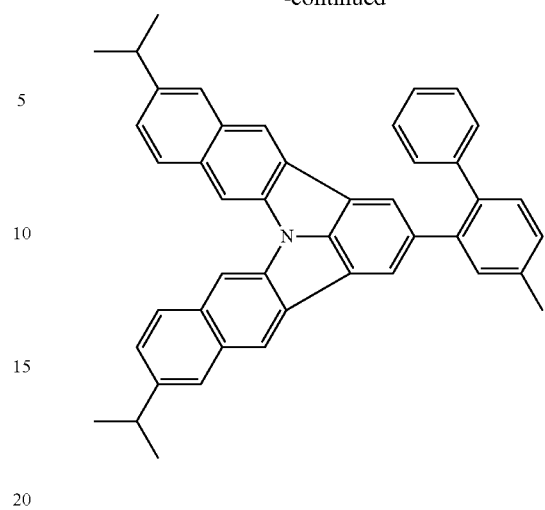
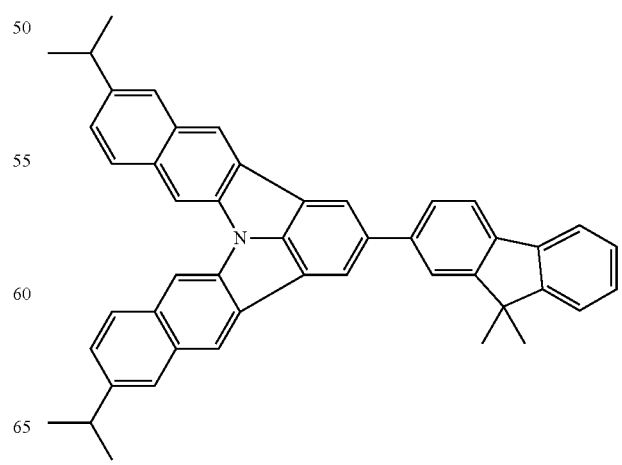

61
-continued
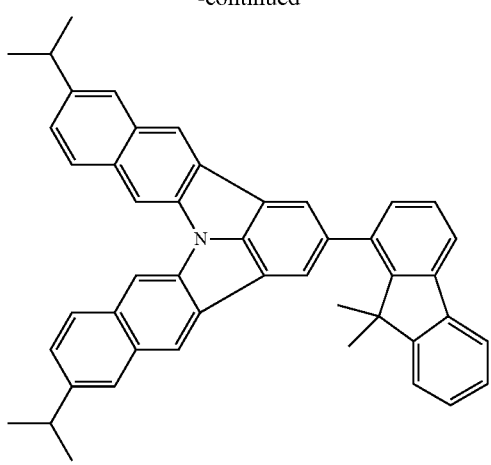
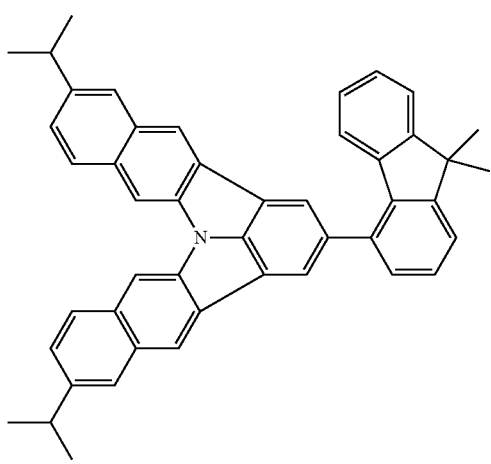
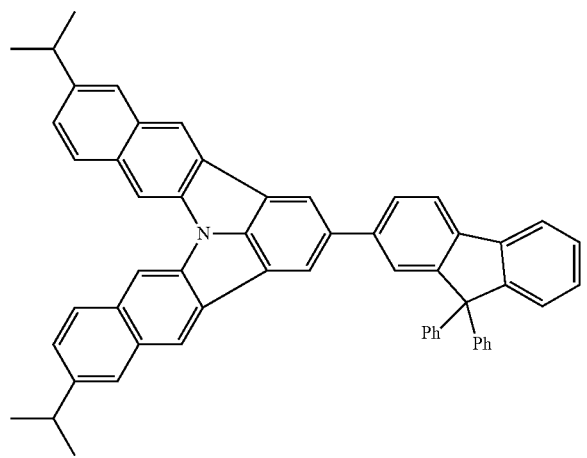
62
-continued
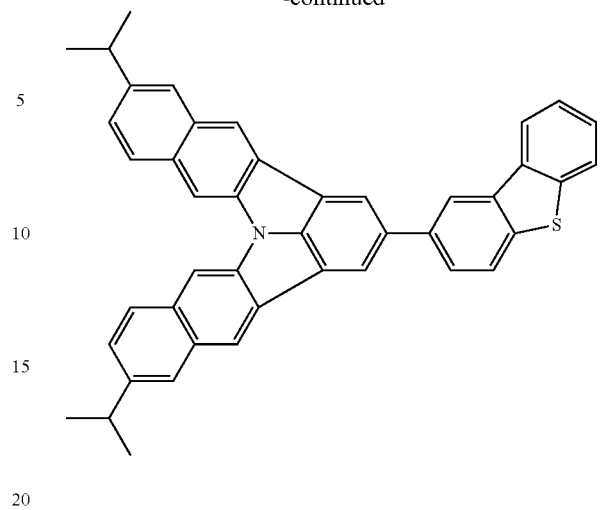
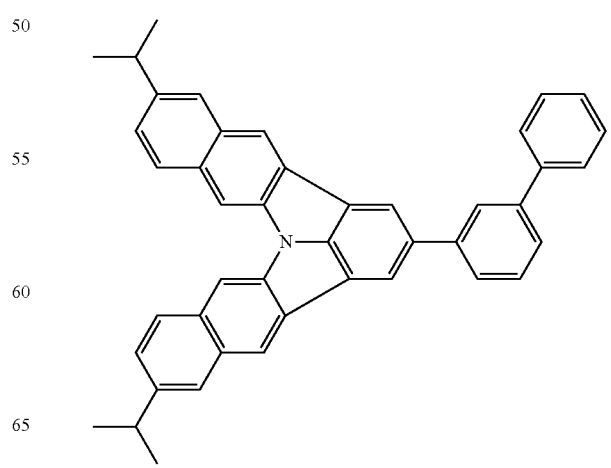

63
-continued
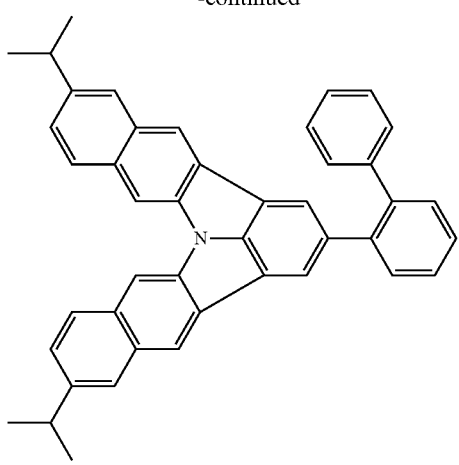
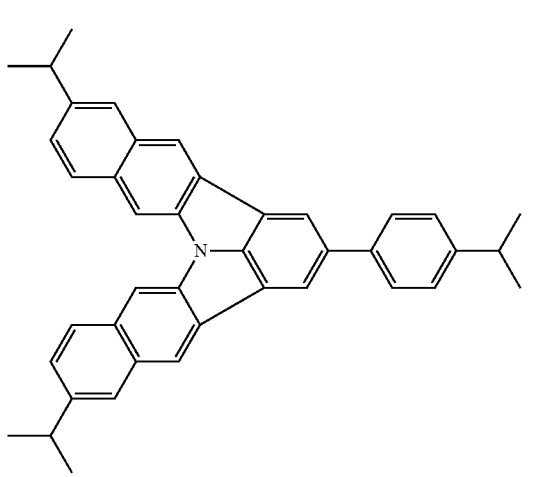
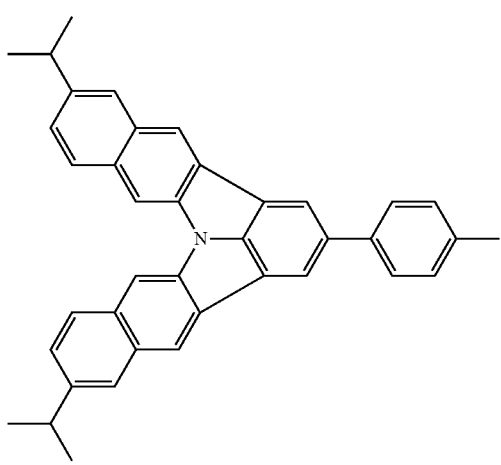
64
-continued
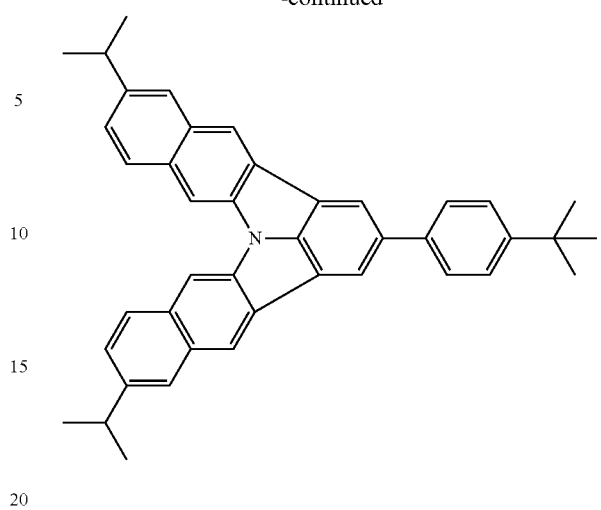
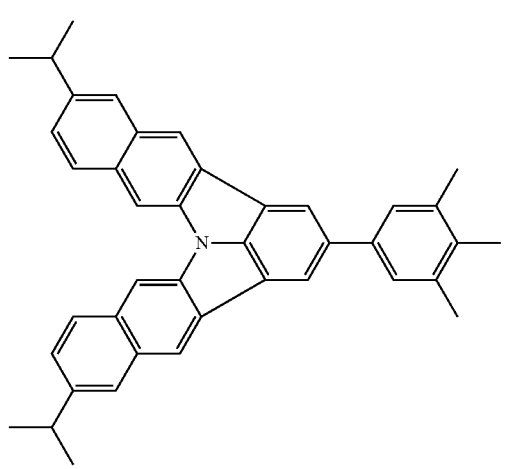
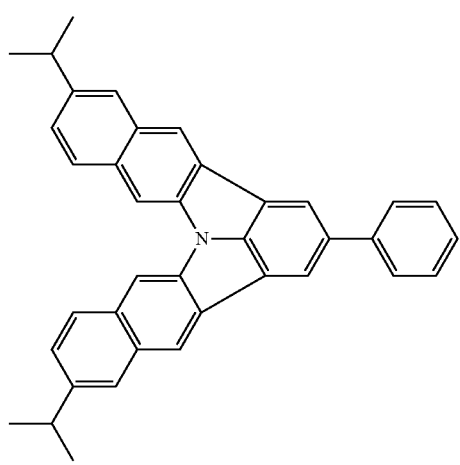

65
-continued
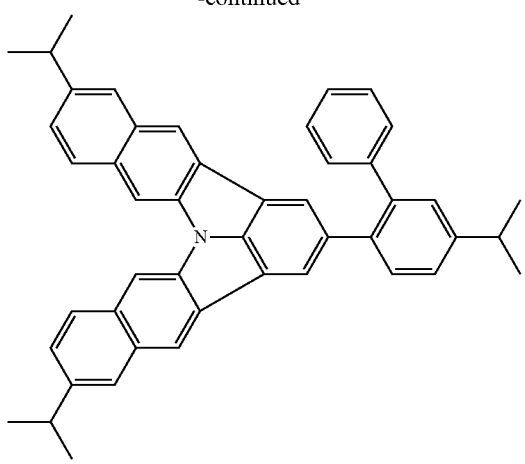
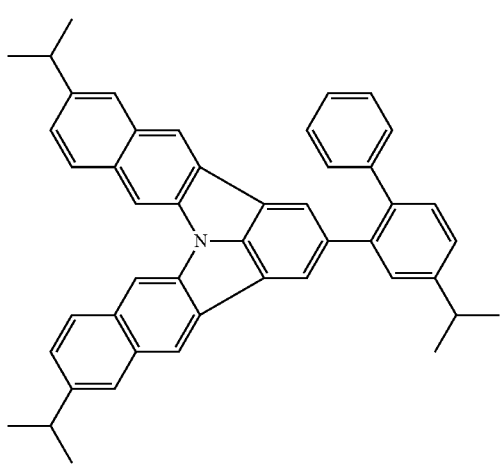
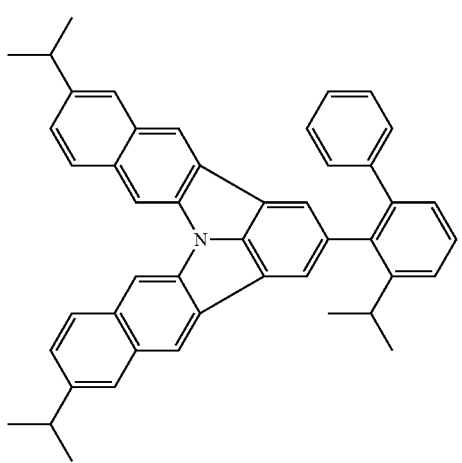
66
-continued
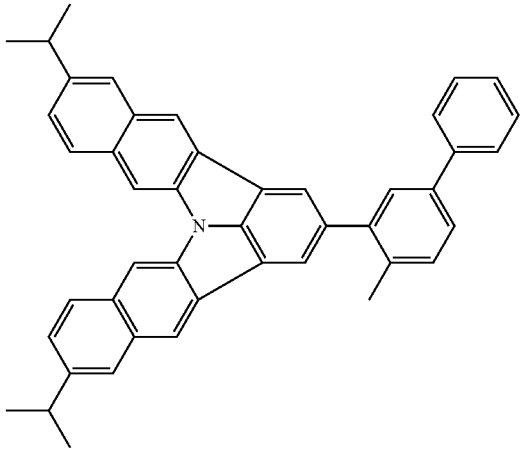
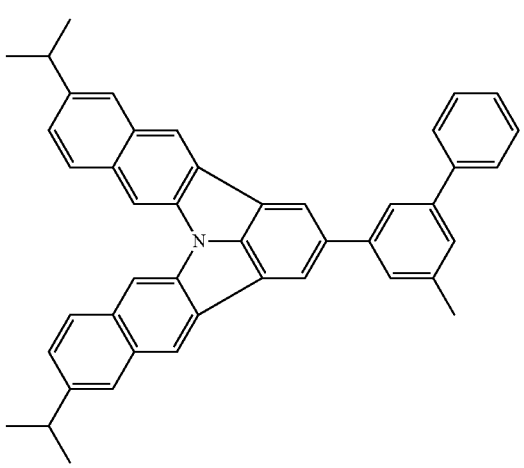
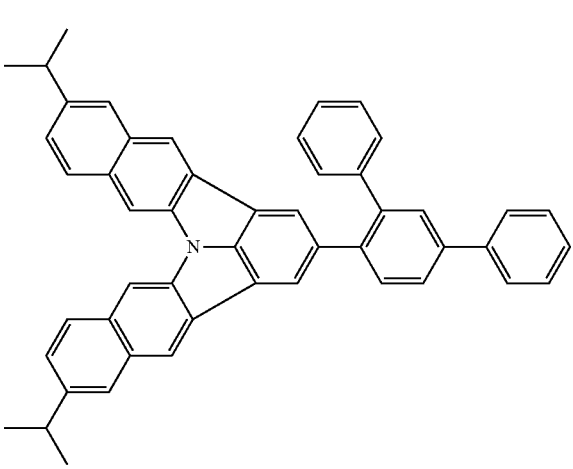

67
-continued
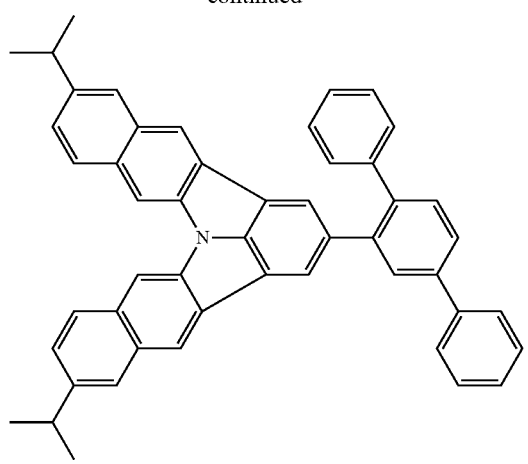
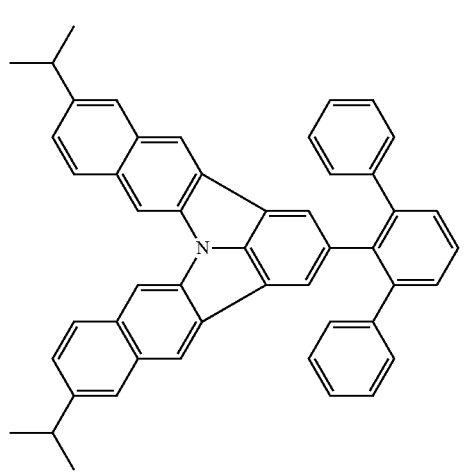
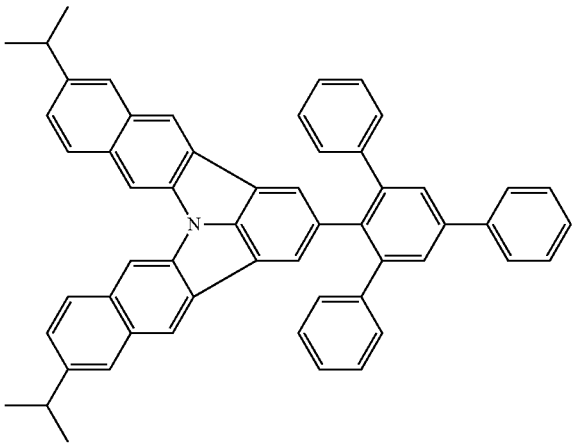
68
-continued
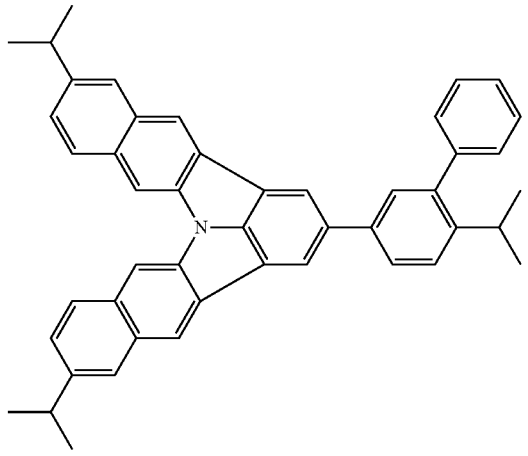
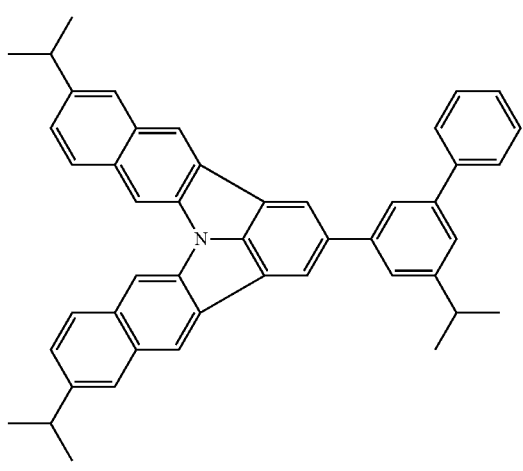
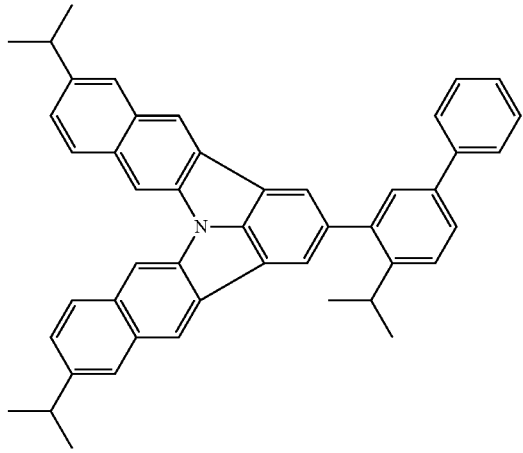

69
-continued
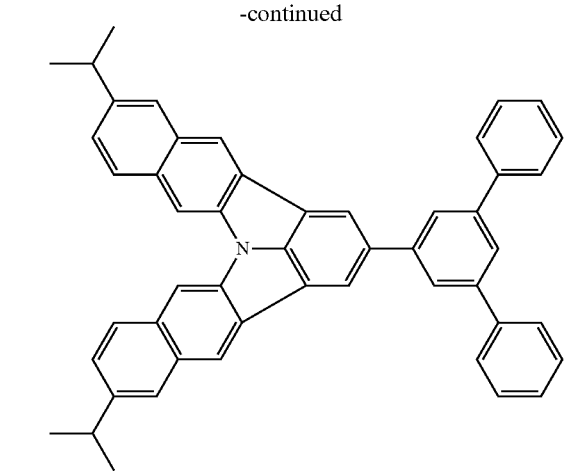
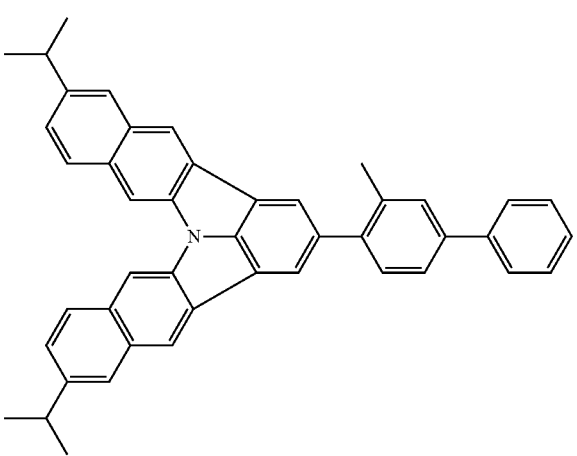
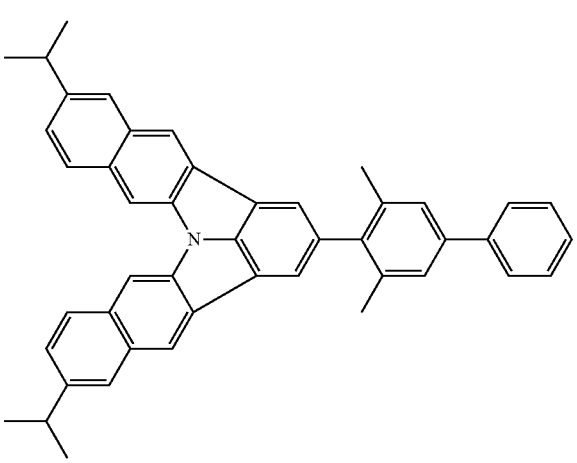
70
-continued
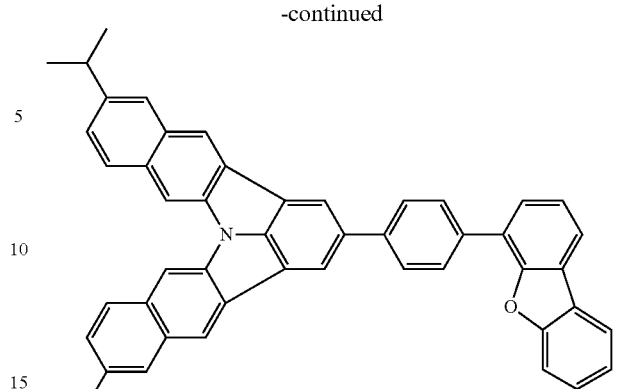
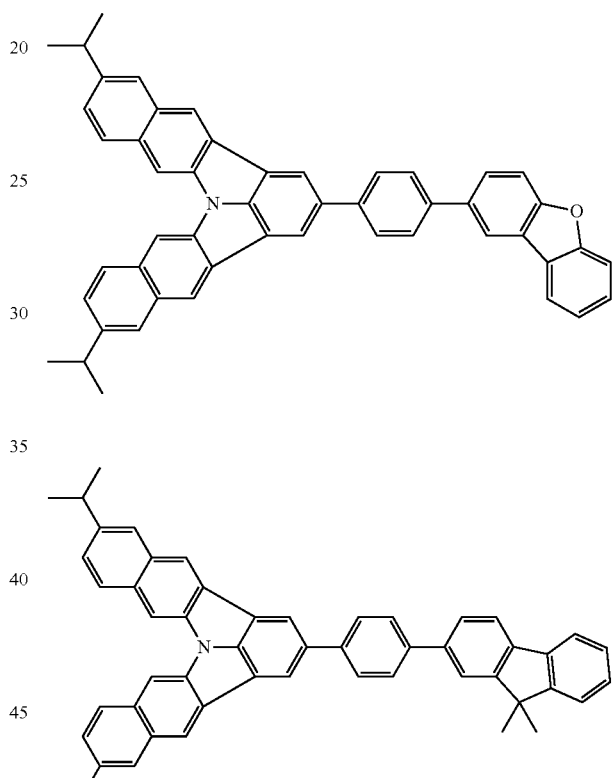
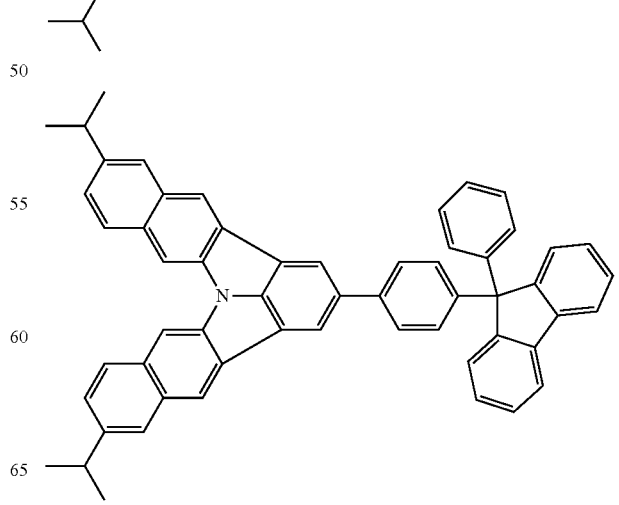

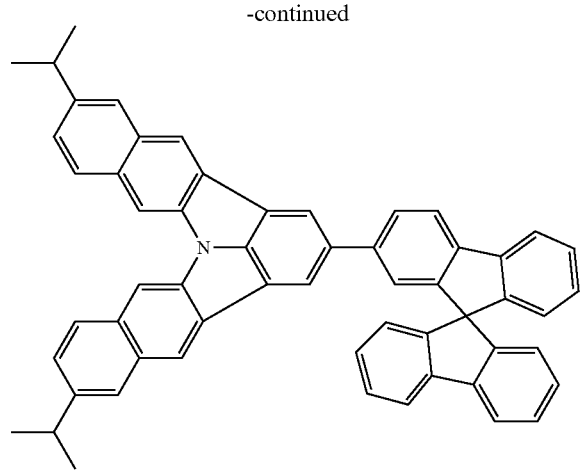
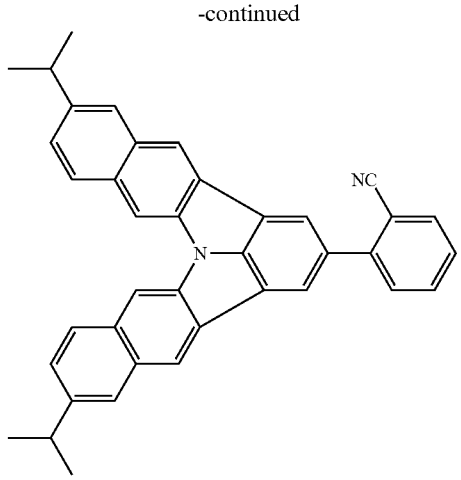
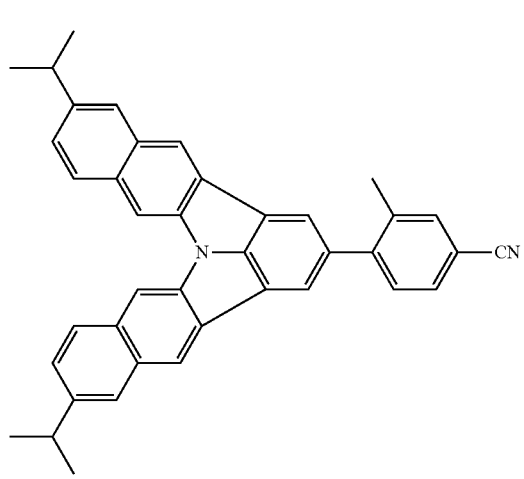
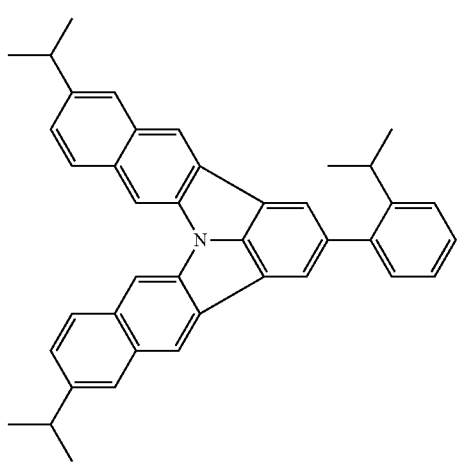
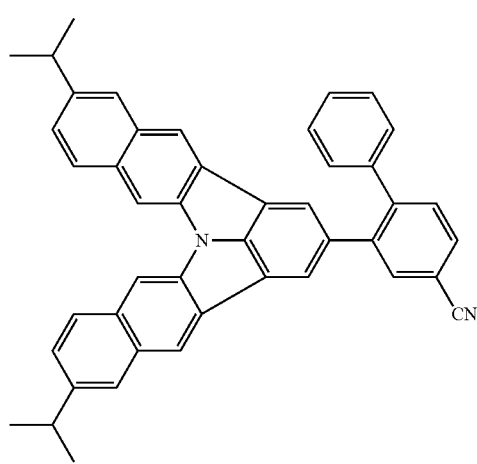
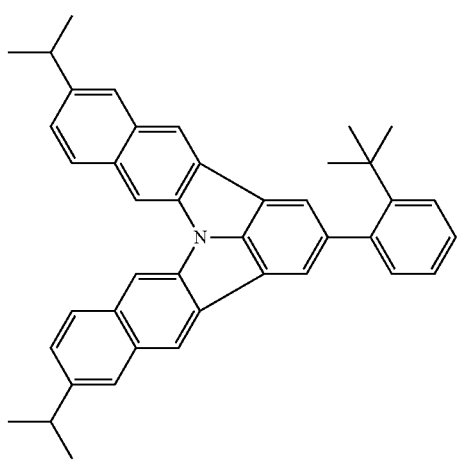

-continued
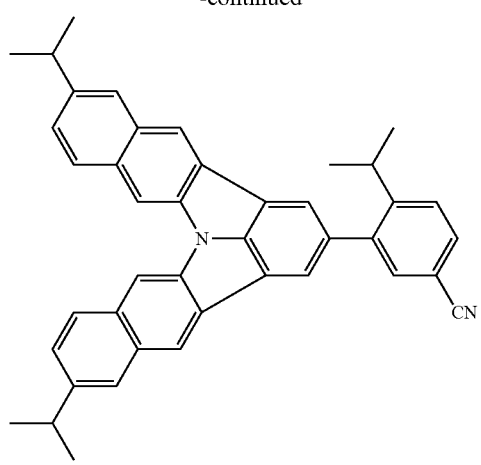
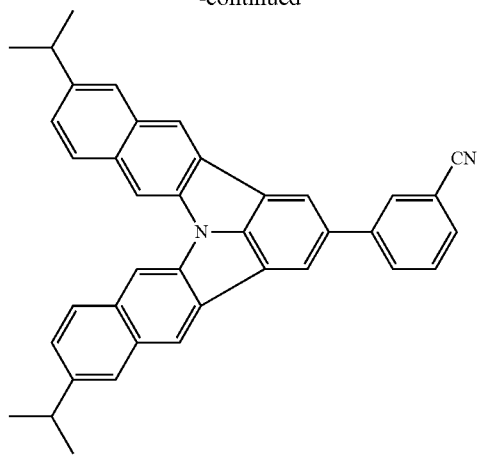
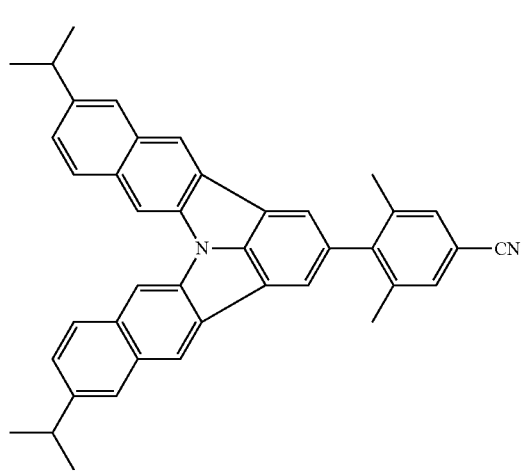
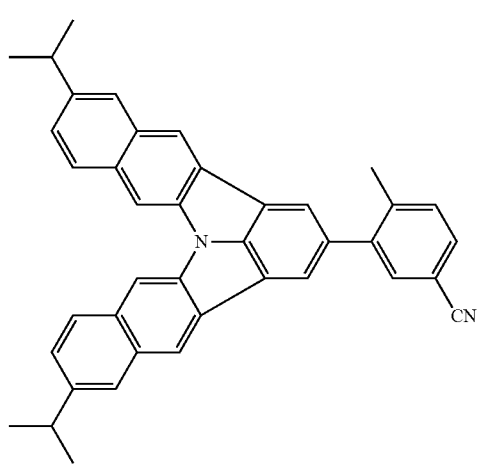
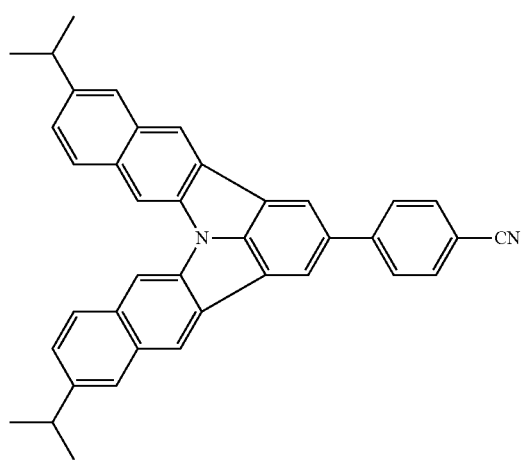
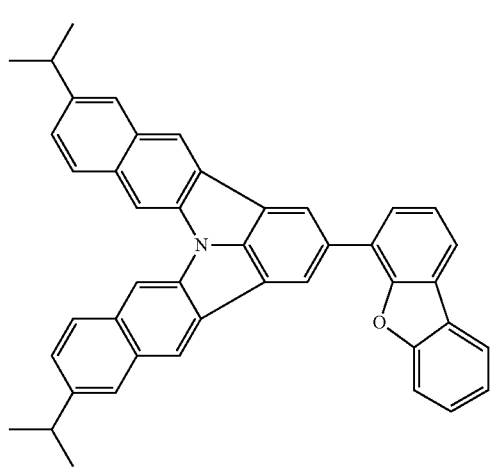

75
-continued
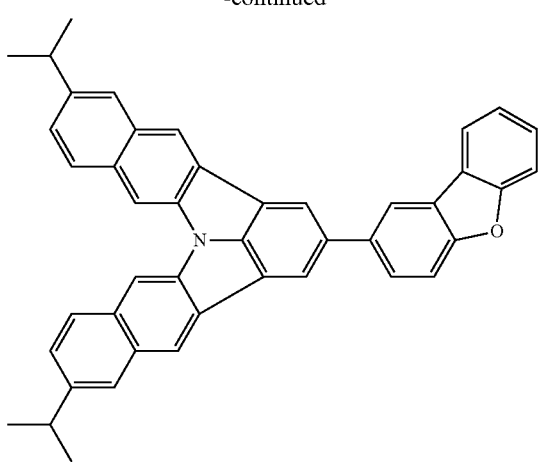
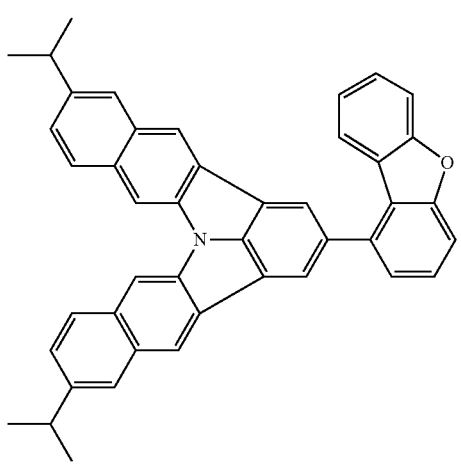
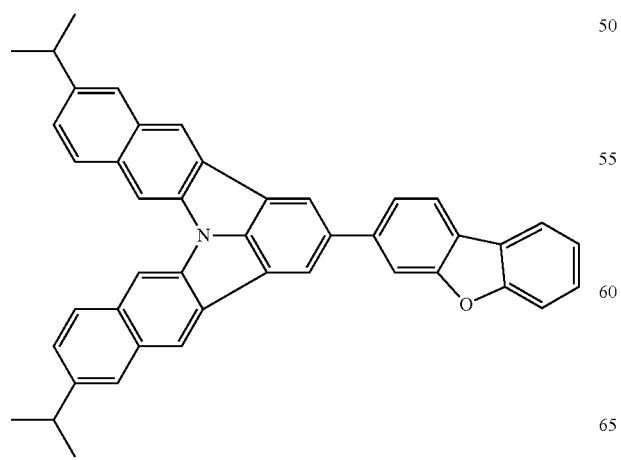
76
-continued
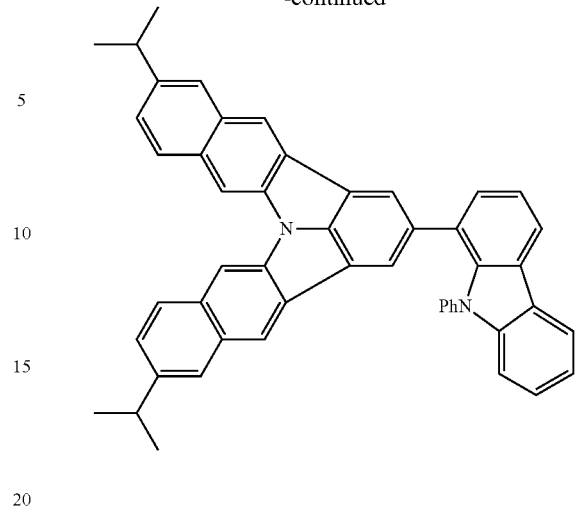
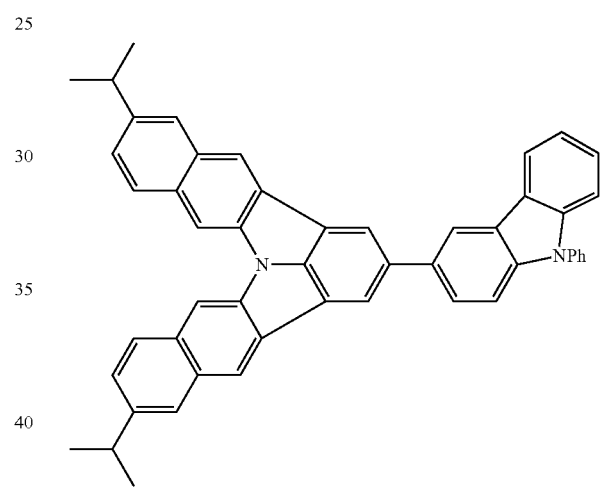
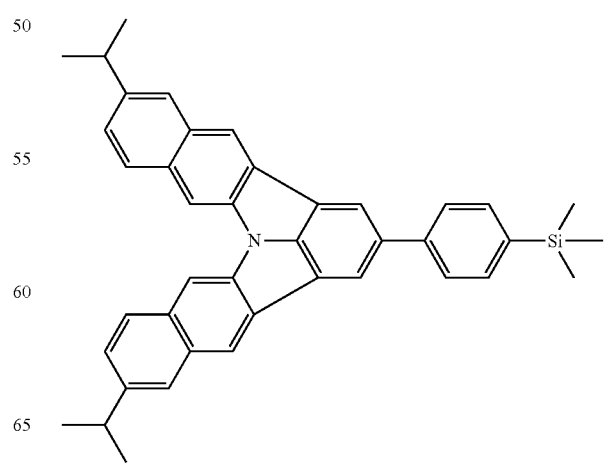

77
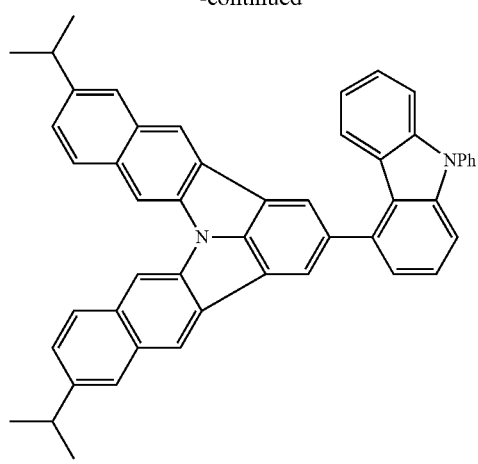
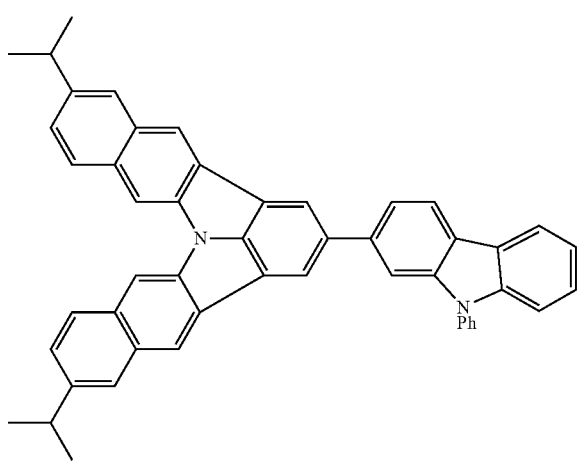
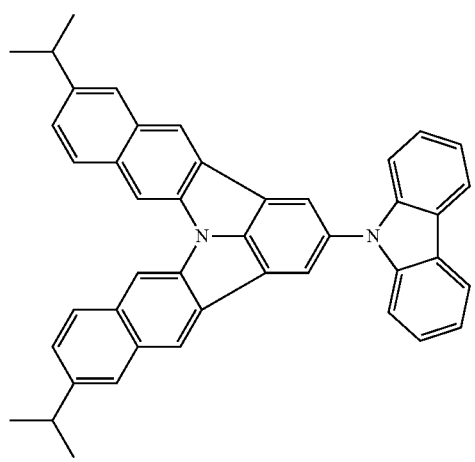
78
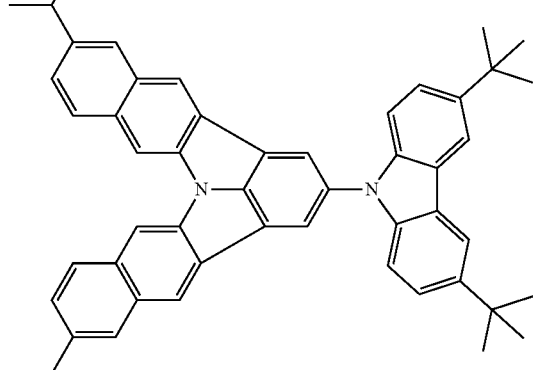
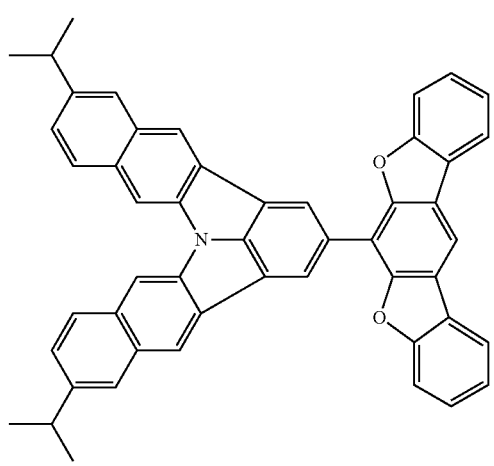
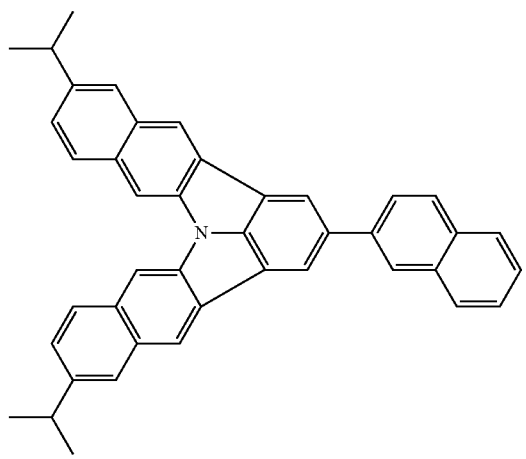

79
-continued
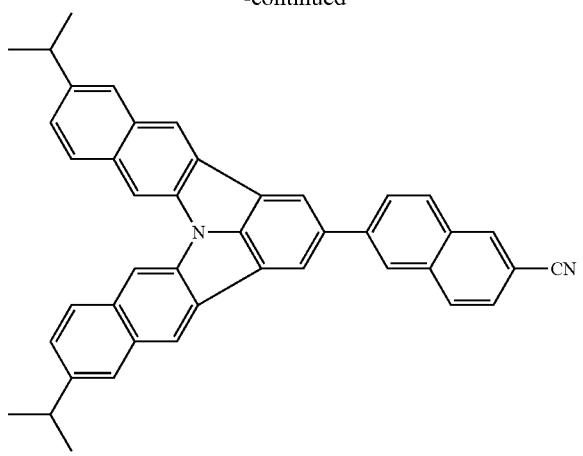
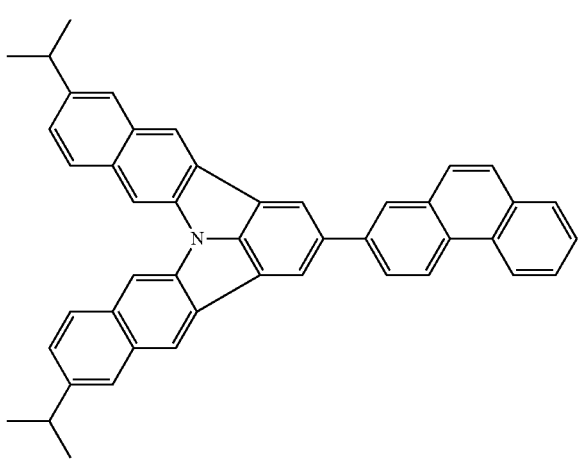
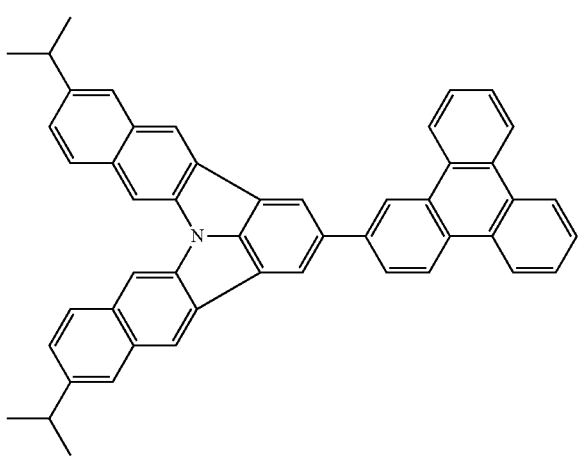
80
-continued
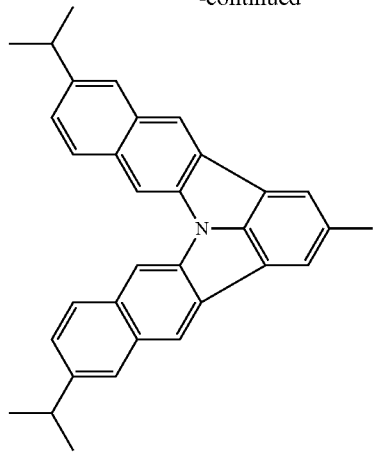
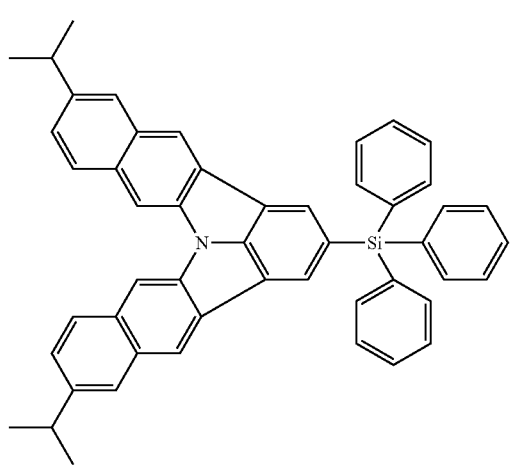
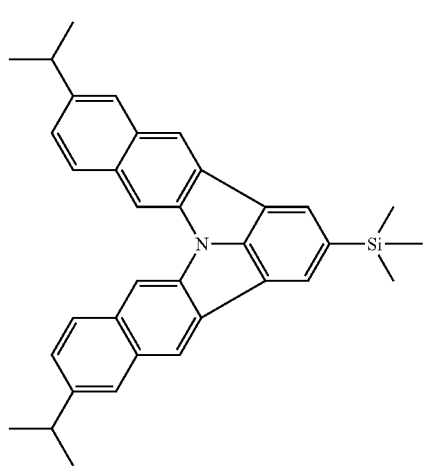

81
-continued
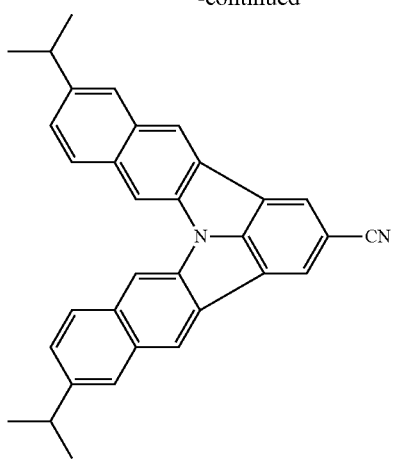
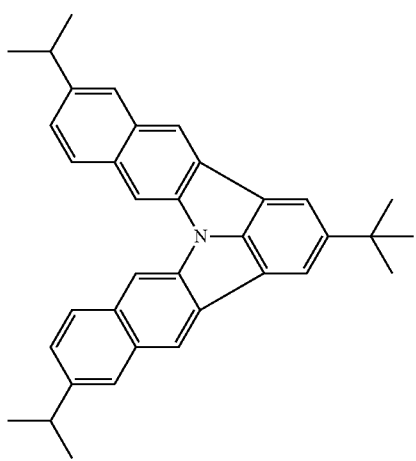
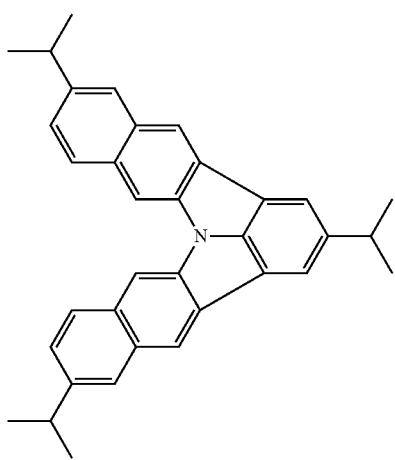
82
-continued
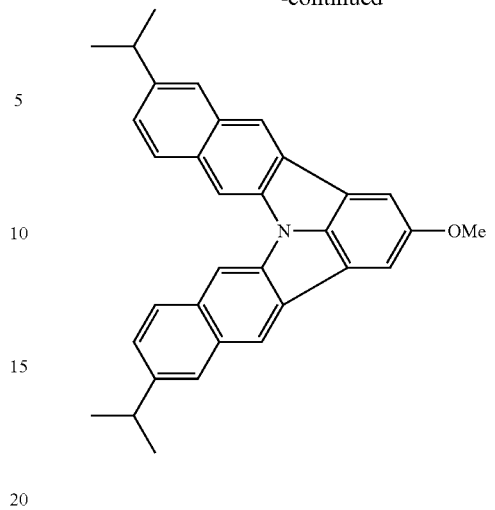
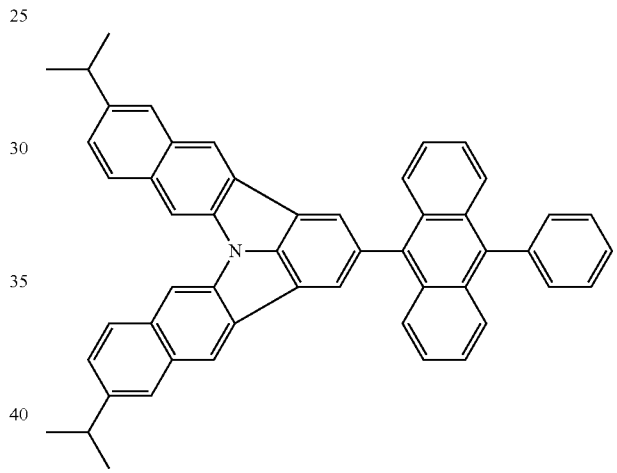
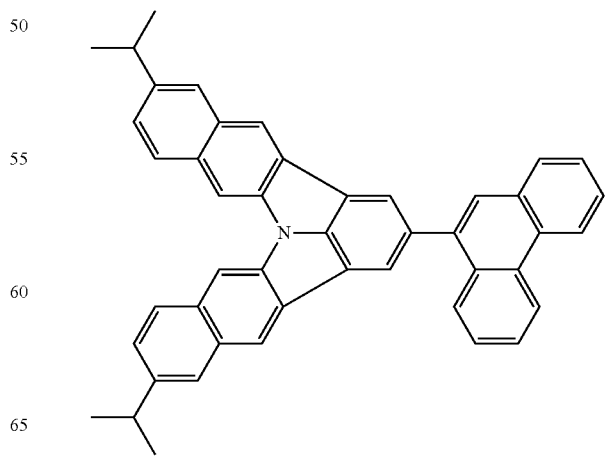

83
-continued
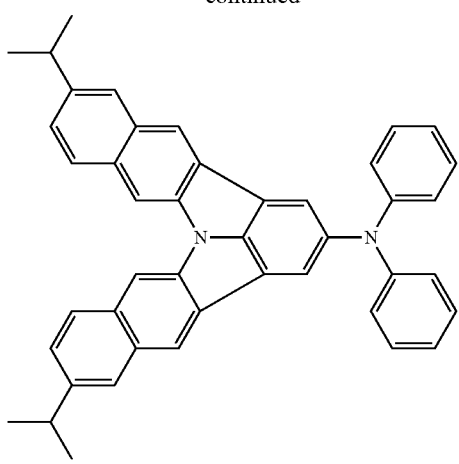
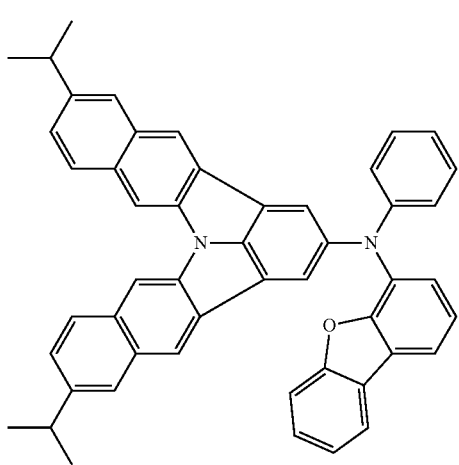
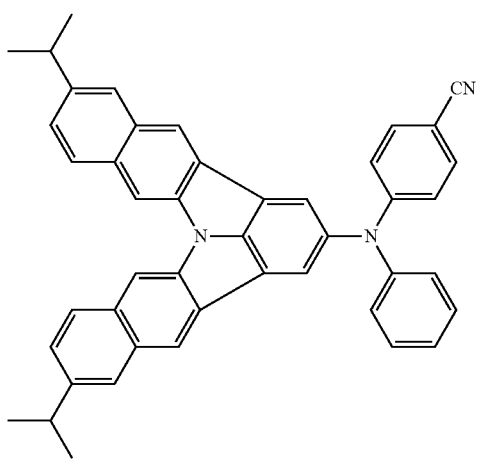
84
-continued
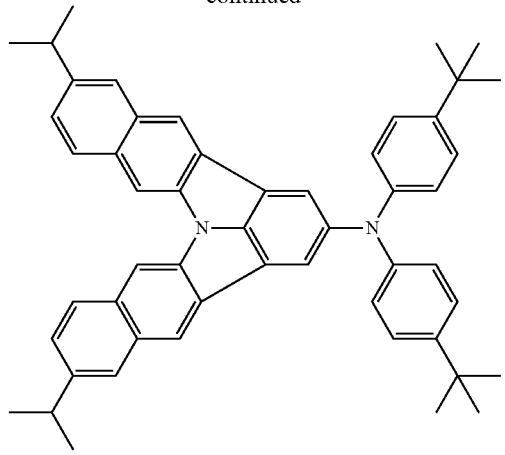
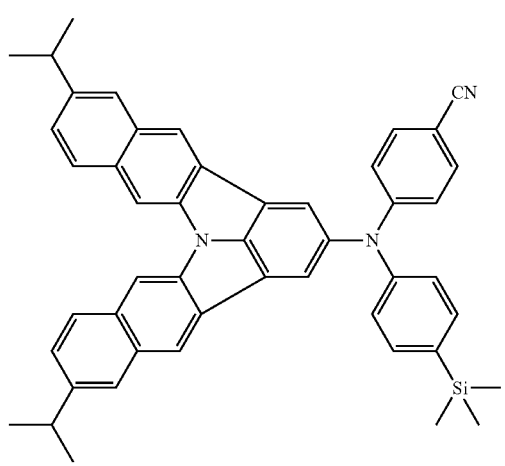
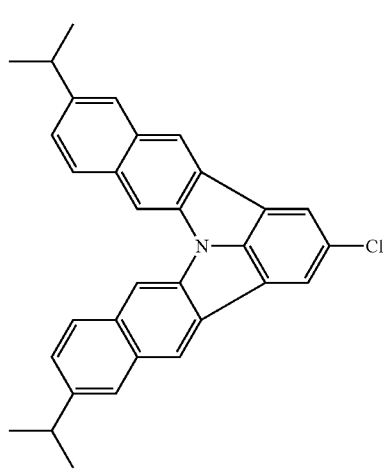

85
-continued
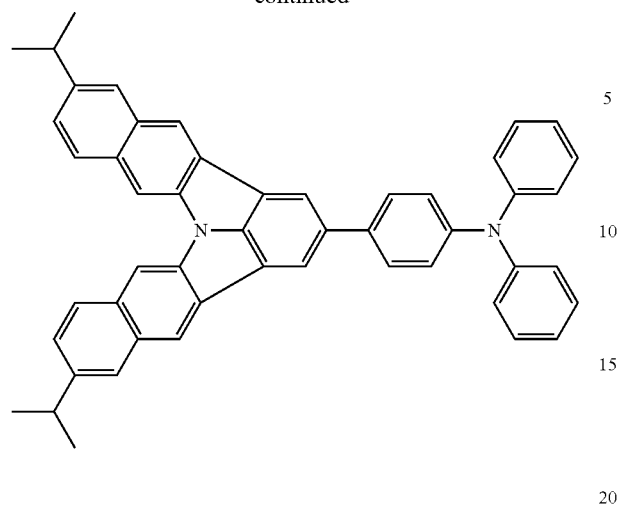
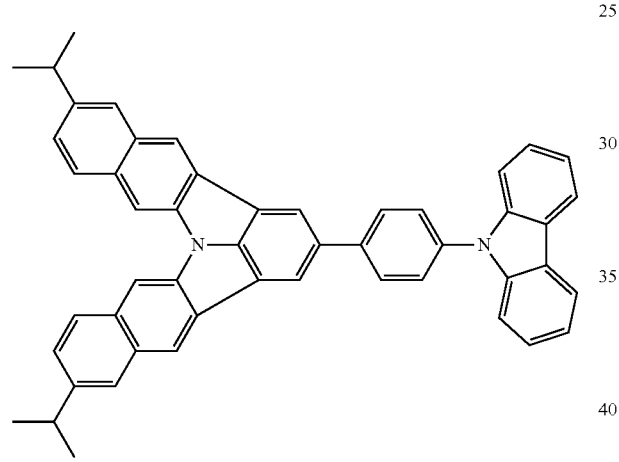
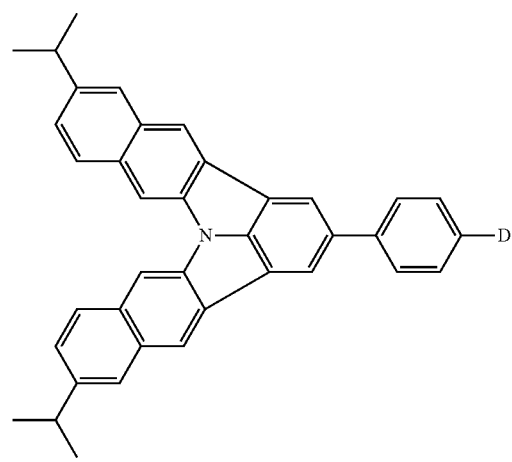
86
-continued
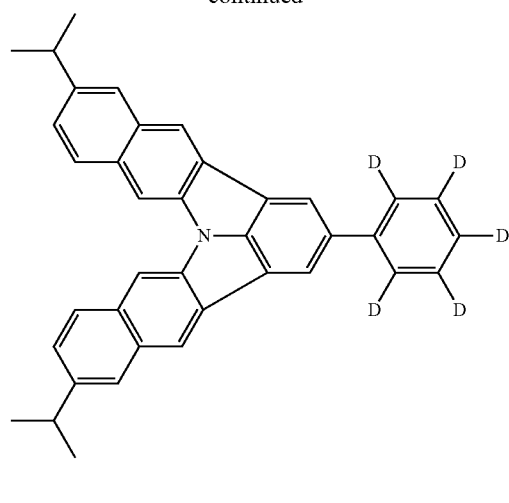
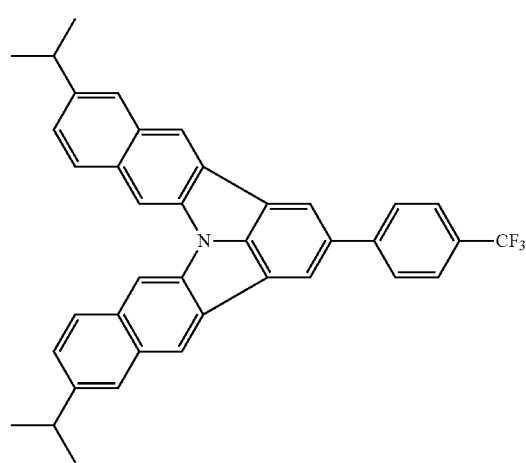
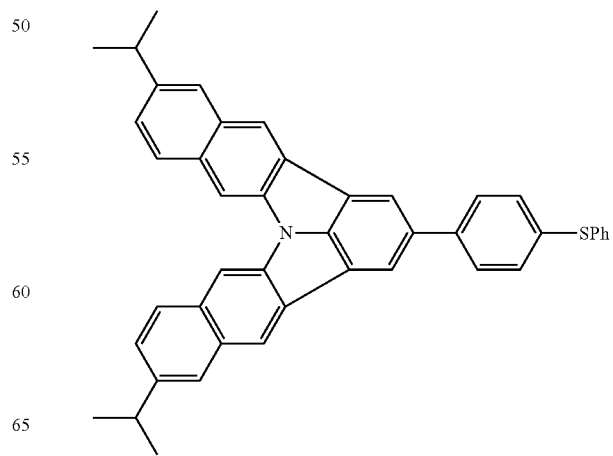

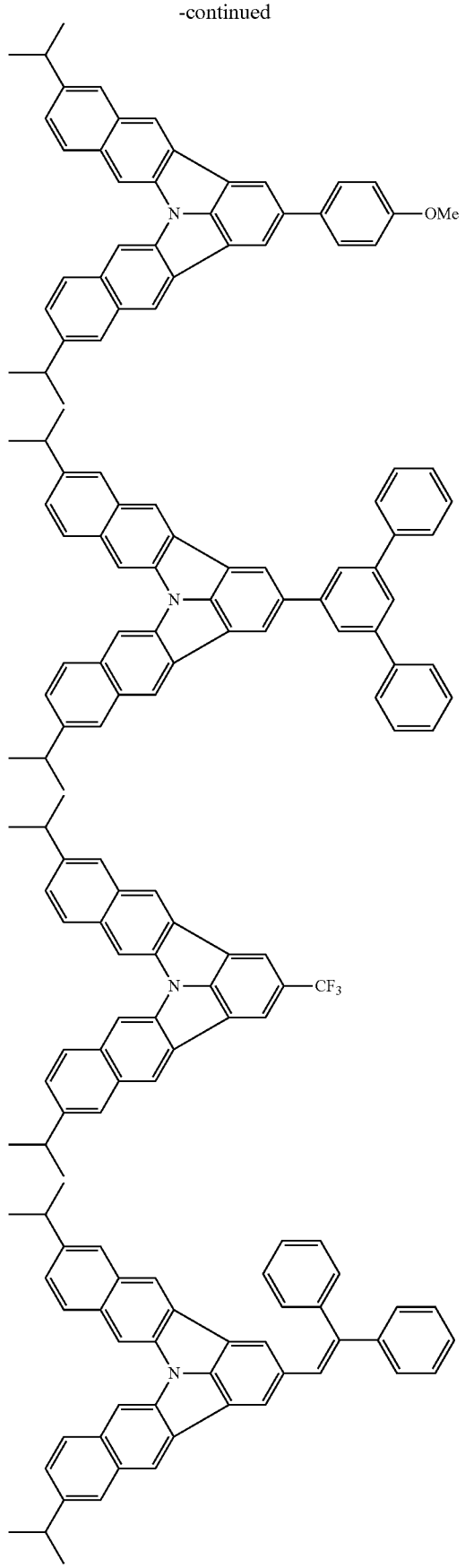
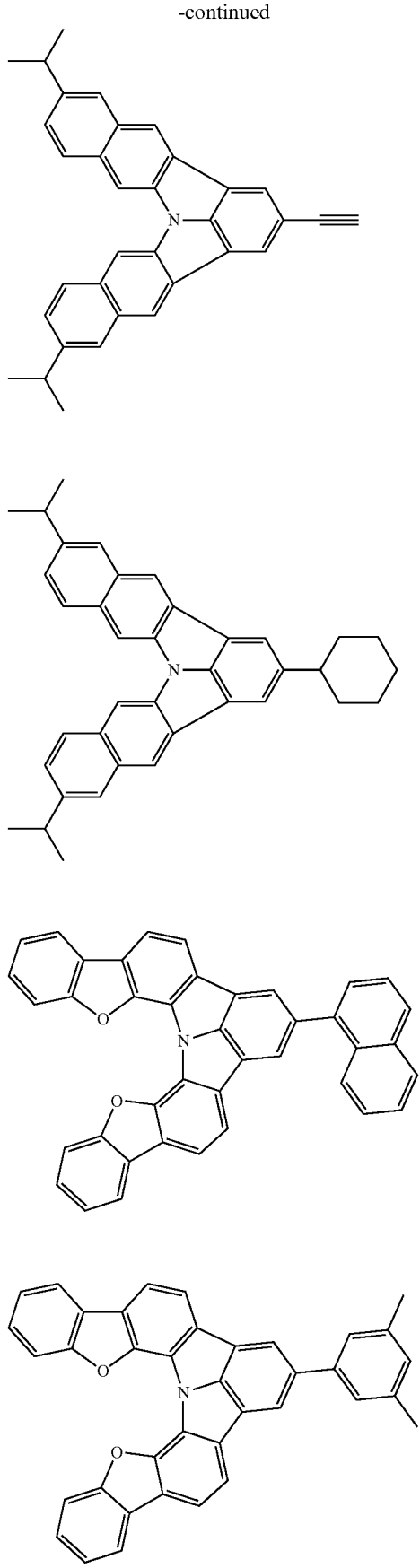

89
-continued
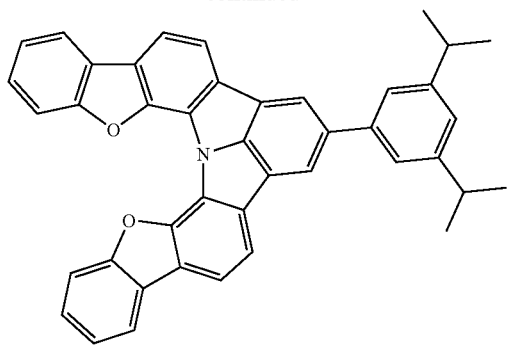
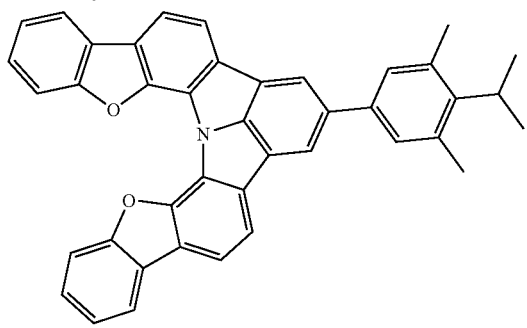
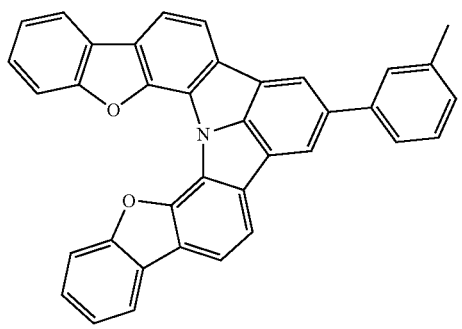
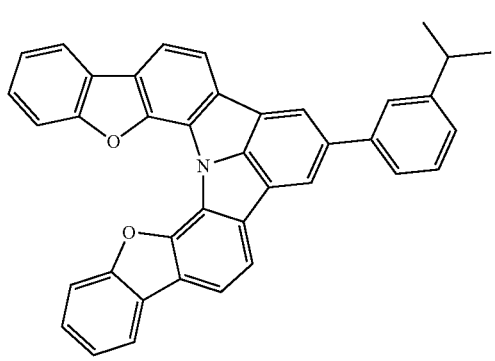
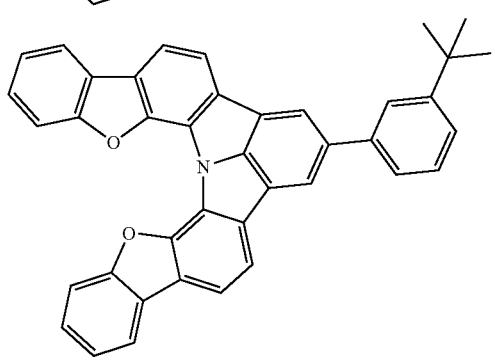
90
-continued
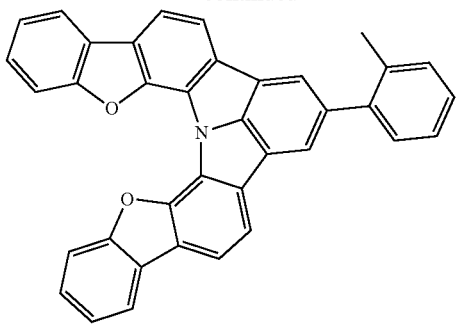
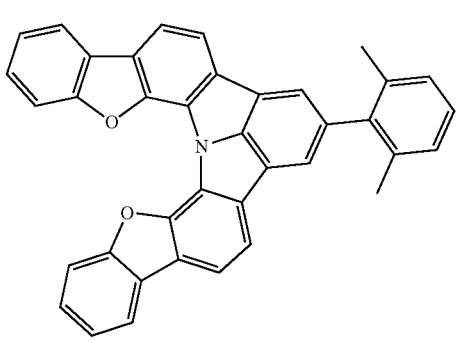
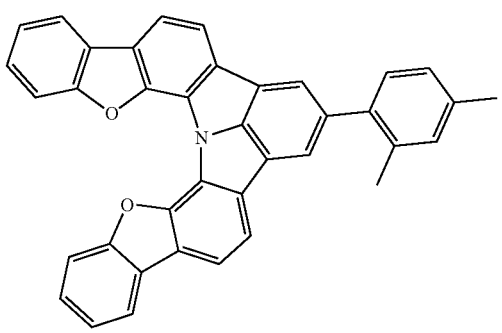
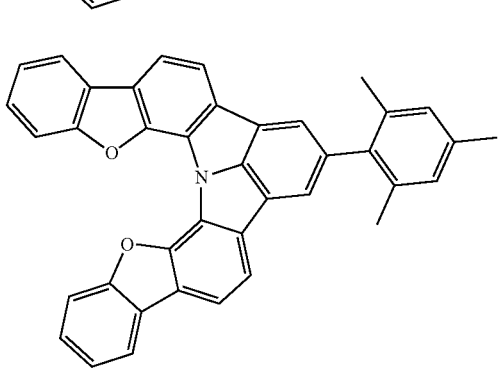
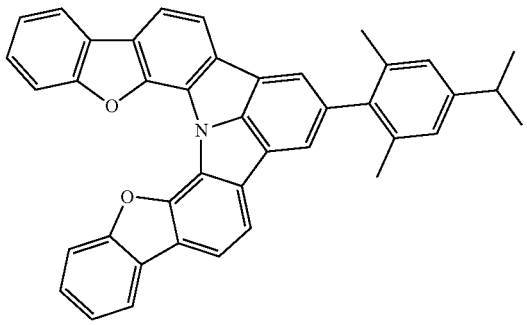

91
-continued
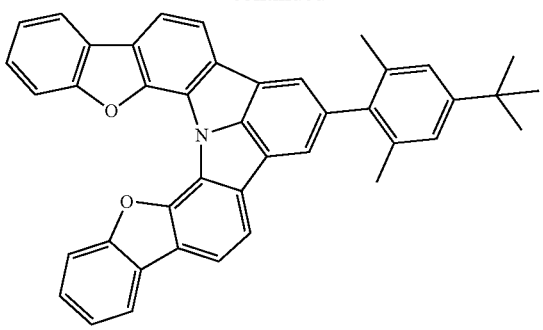
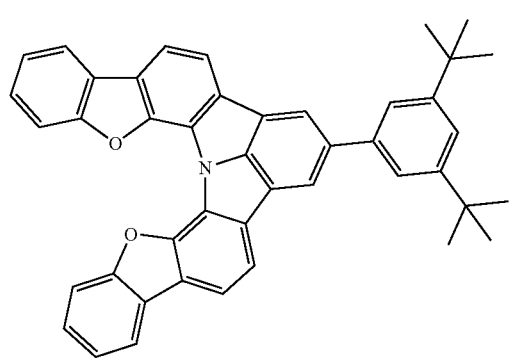
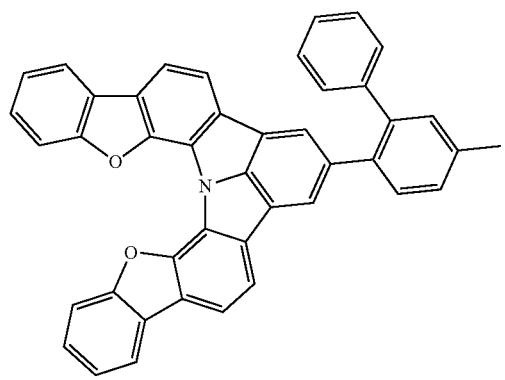
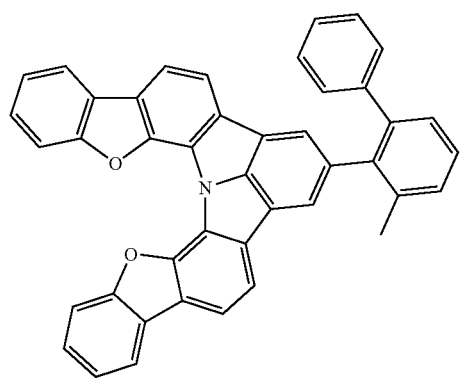
92
-continued
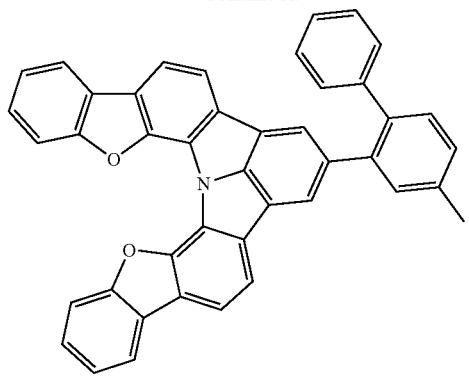
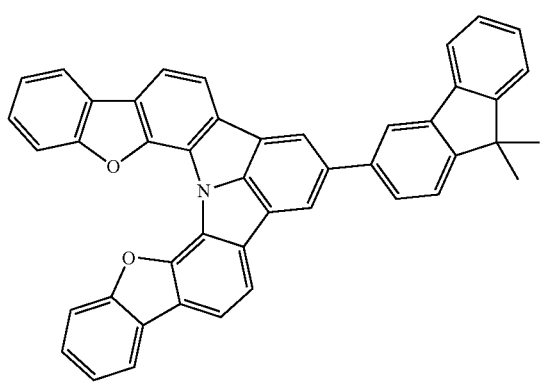
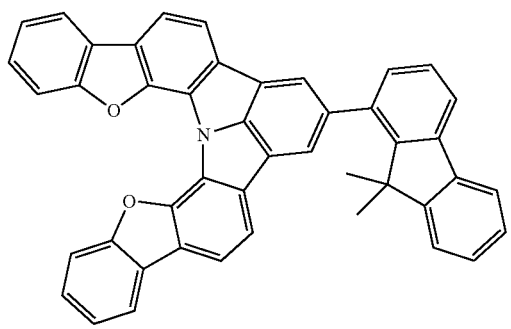

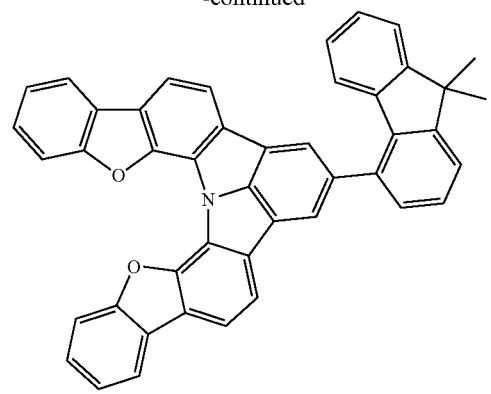
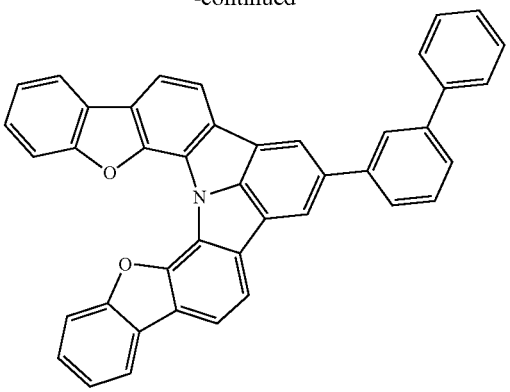
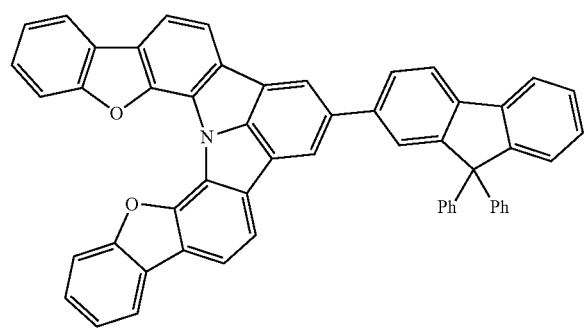
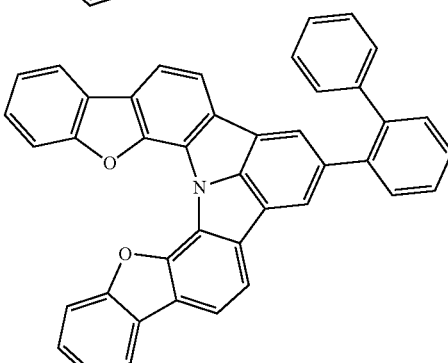
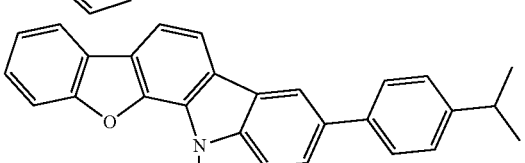
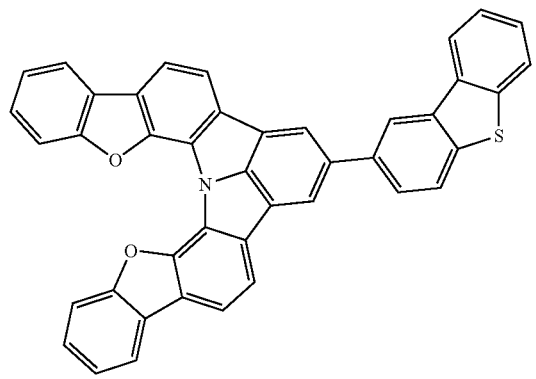
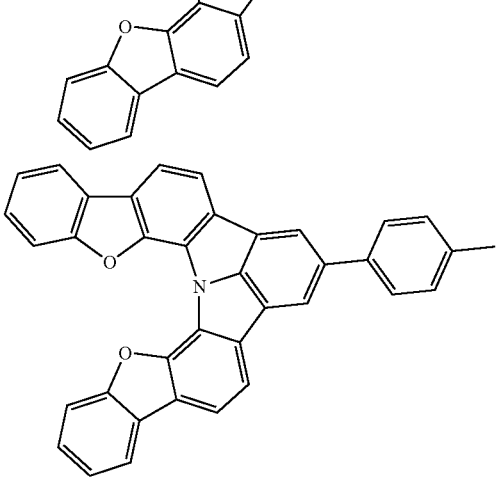
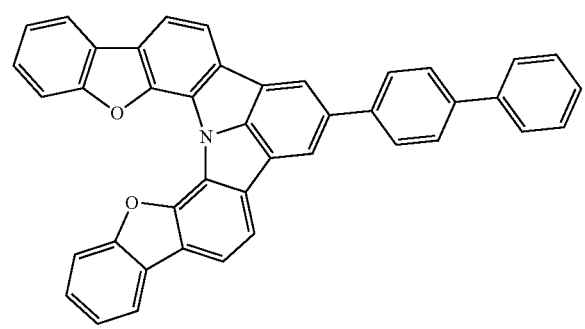
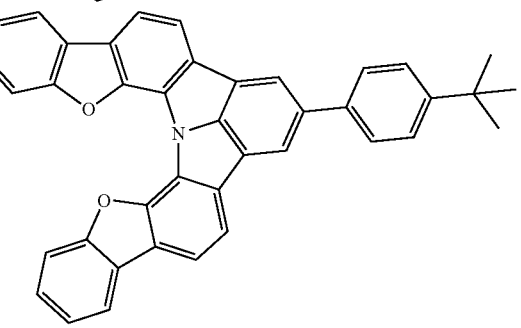

95
-continued
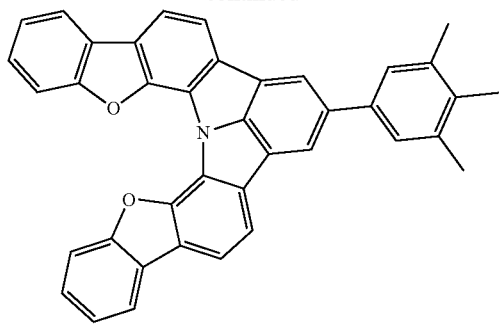
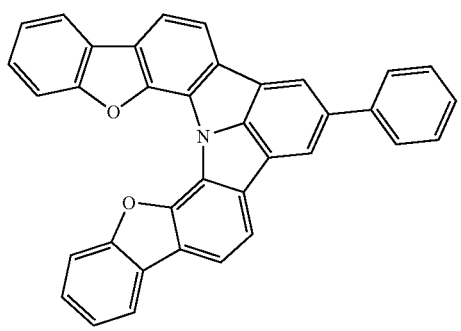
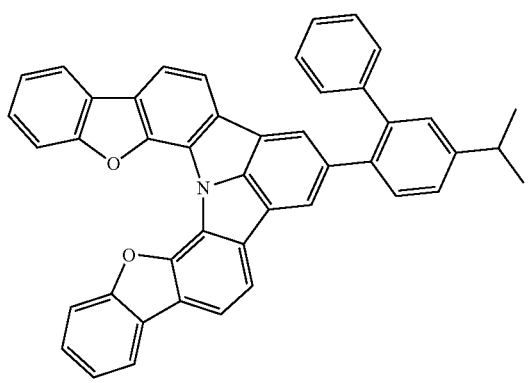
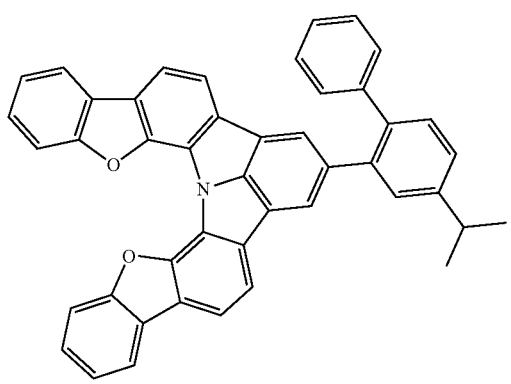
96
-continued
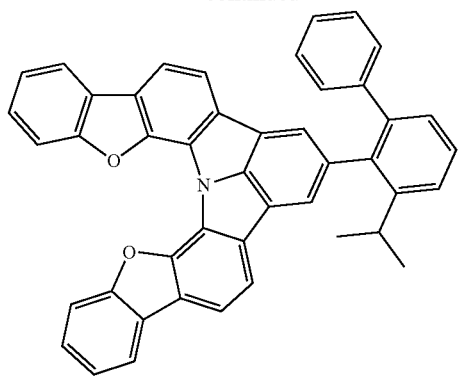
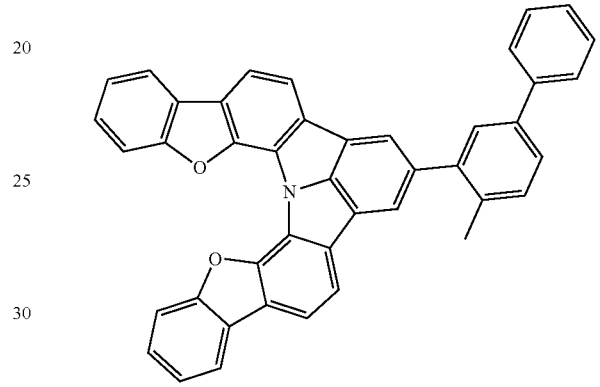
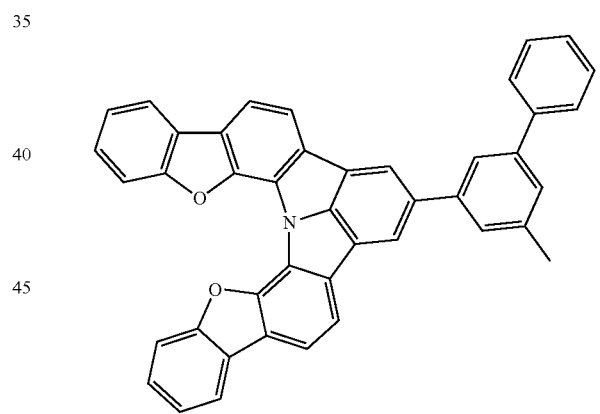
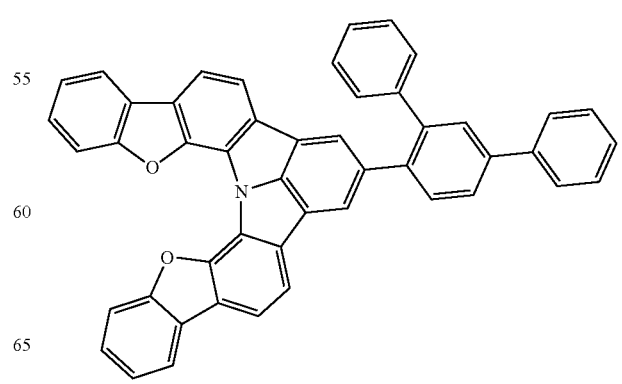

97
-continued
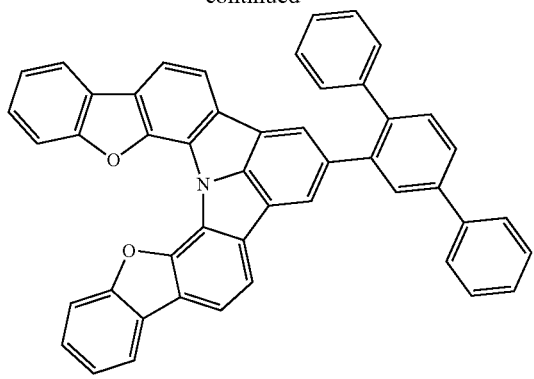
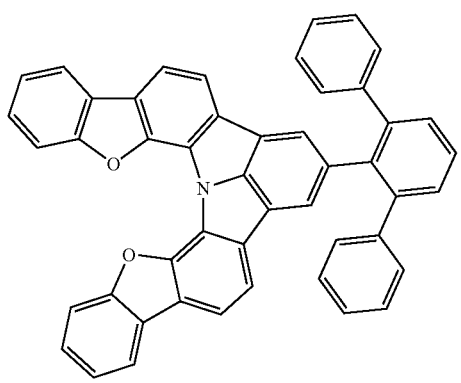
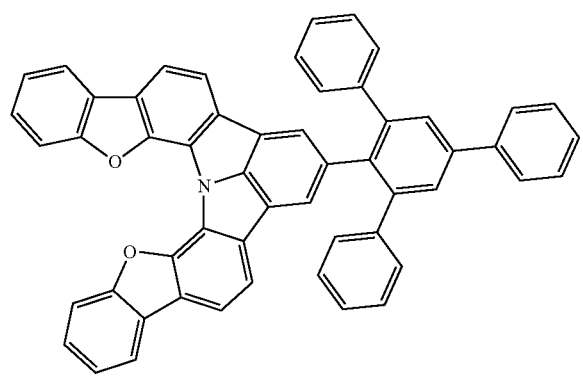
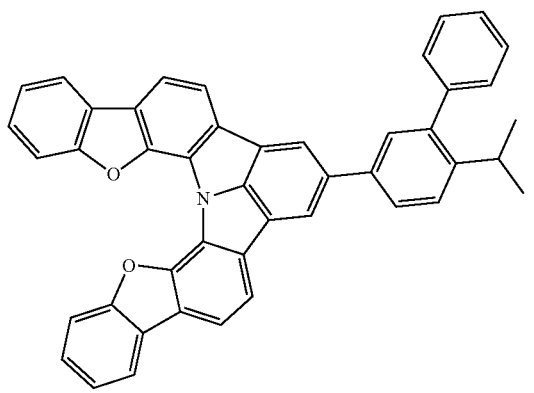
98
-continued
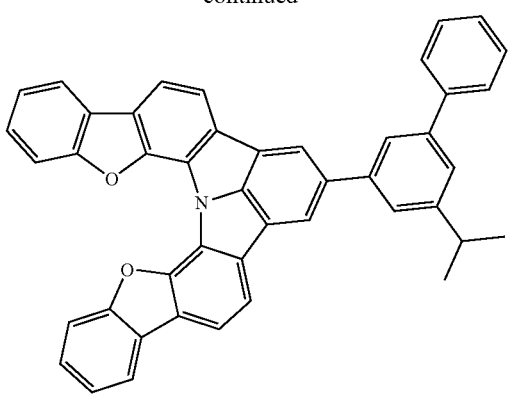
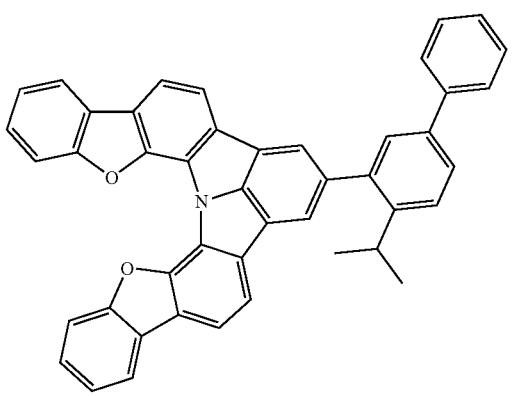
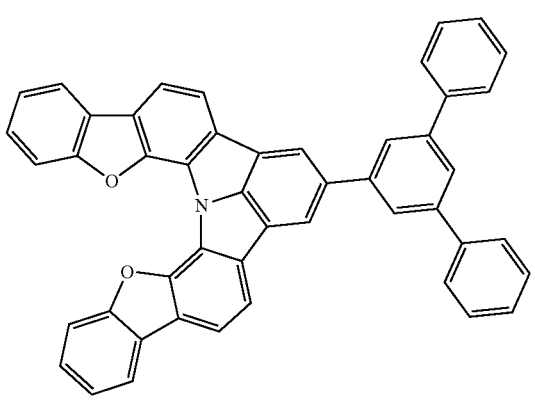

99
-continued
100
-continued
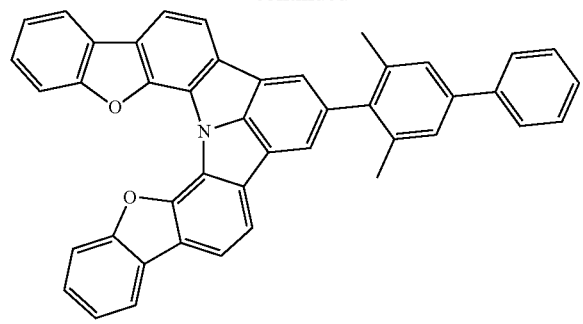
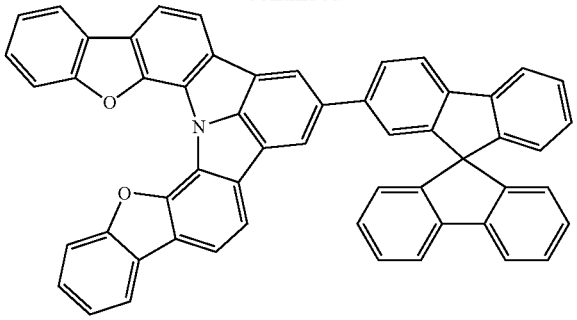
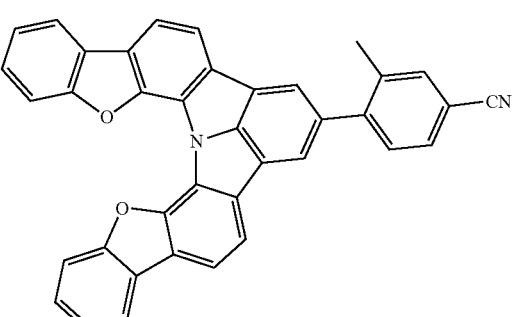
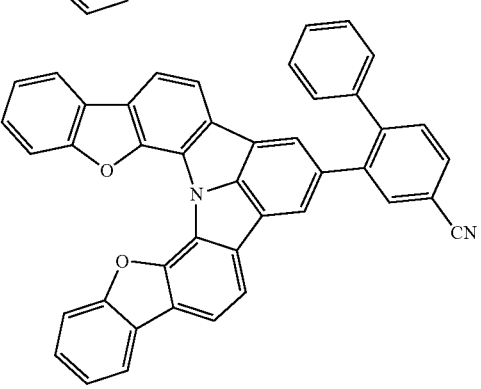
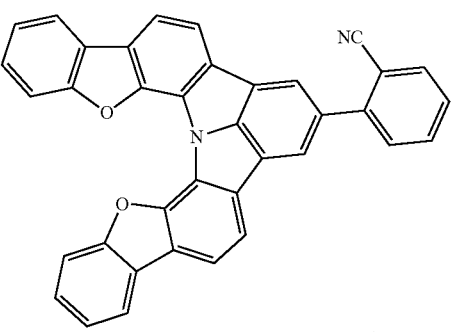
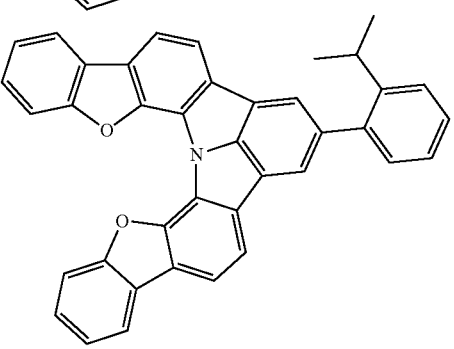

101
-continued
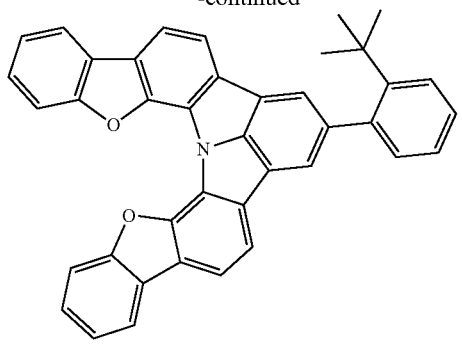
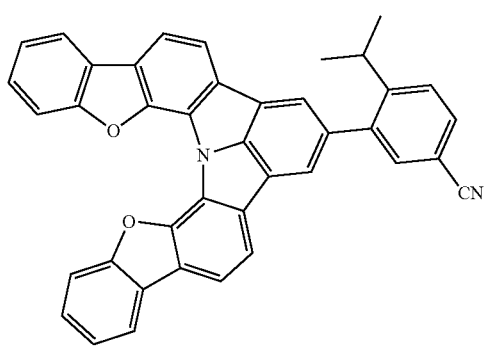
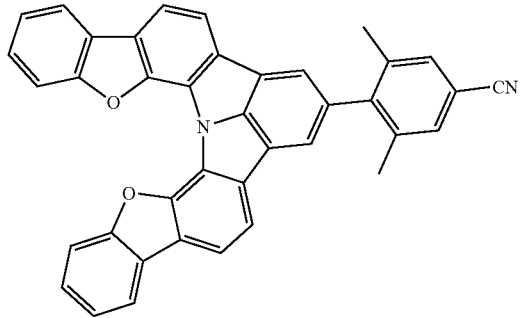
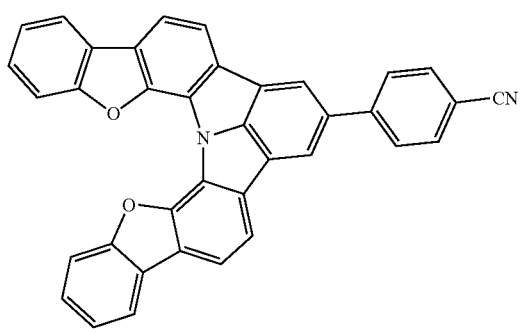
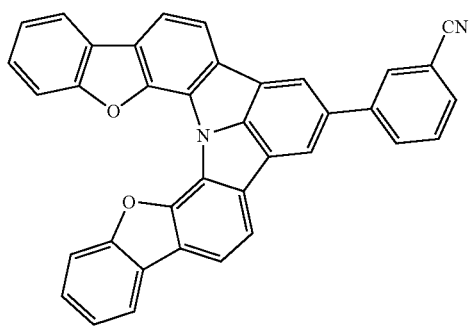
102
-continued
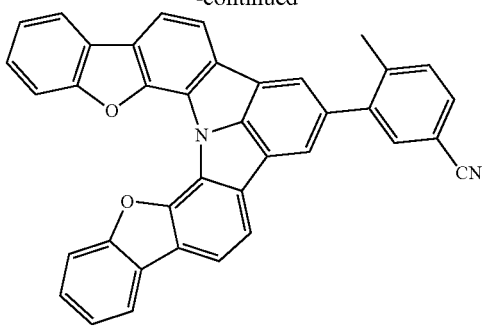
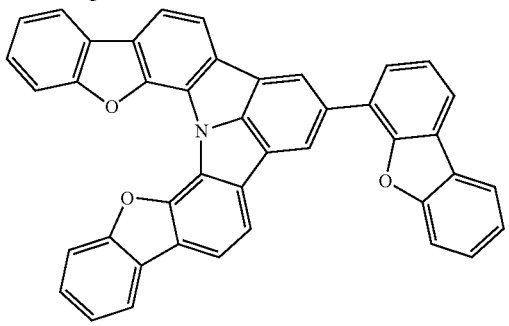
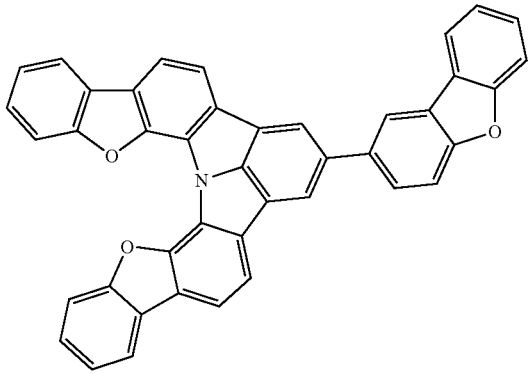
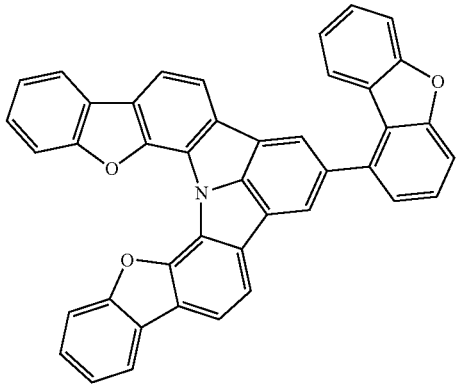
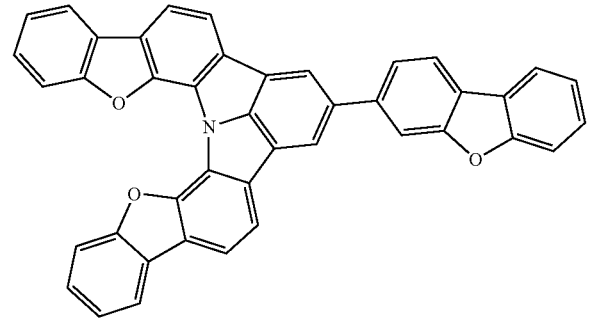

103
-continued
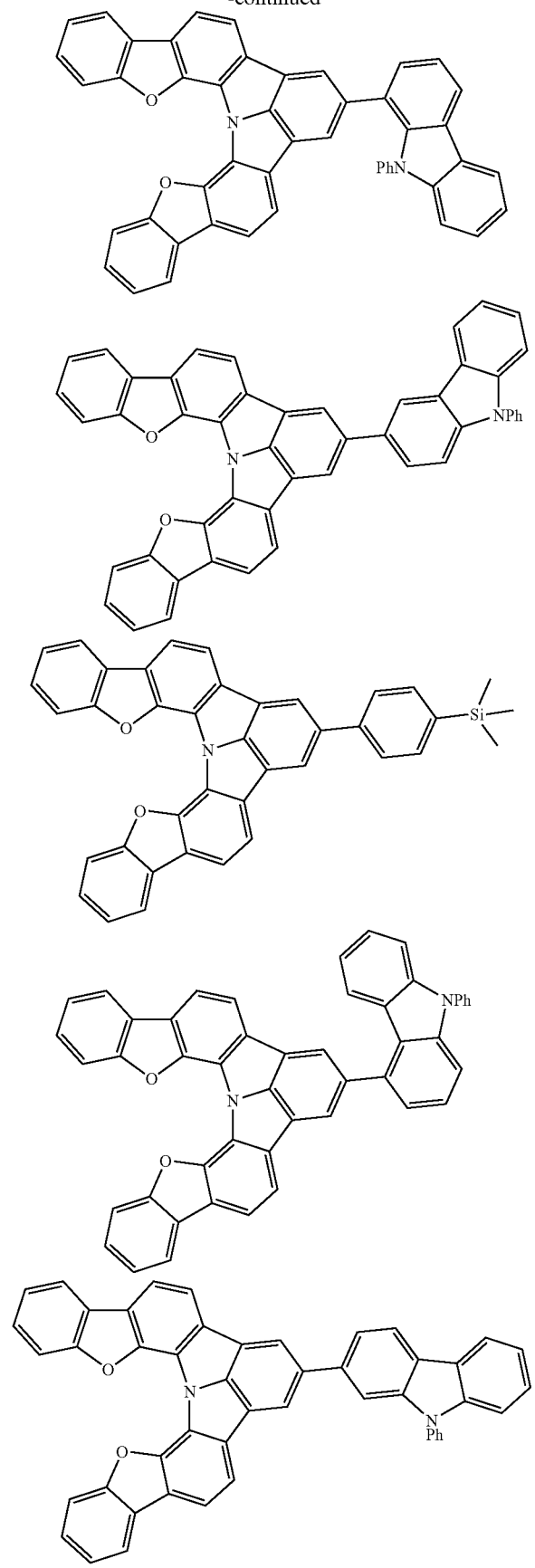
104
-continued
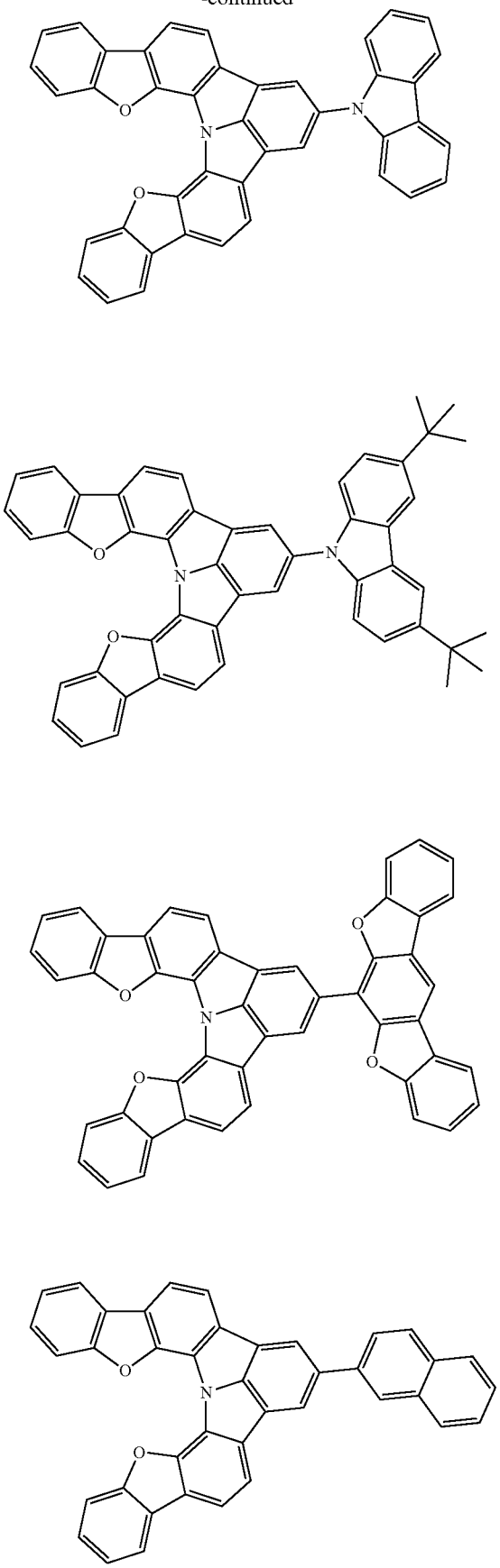

105
-continued
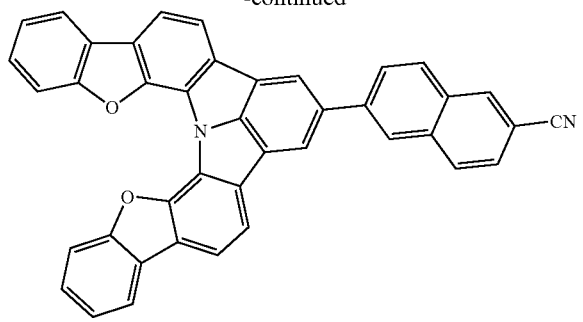
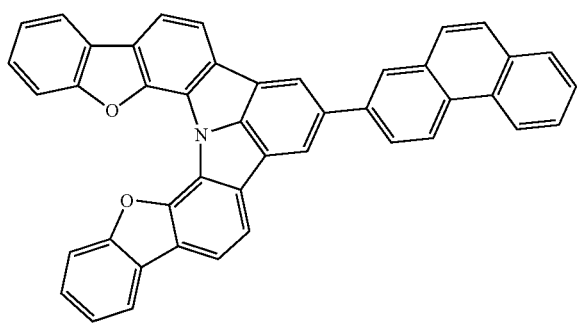
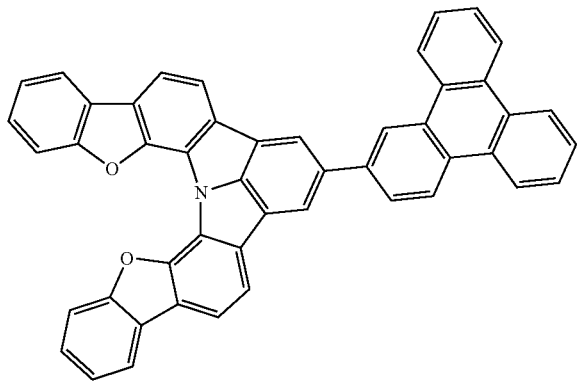
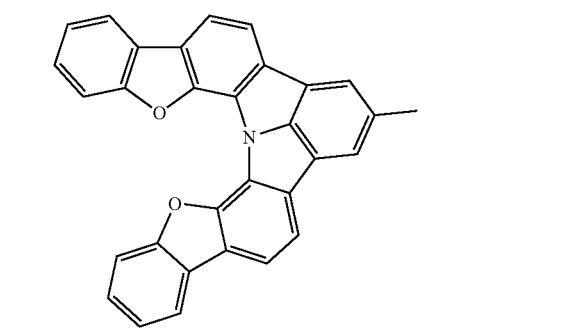
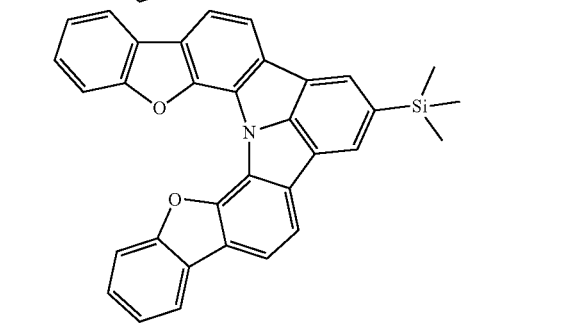
106
-continued
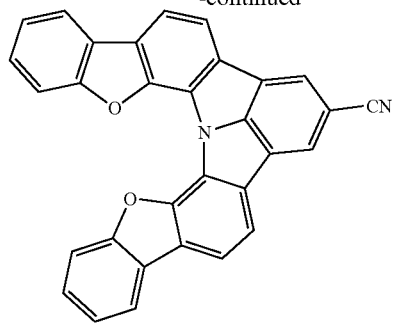
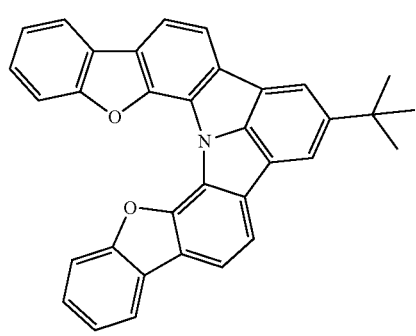
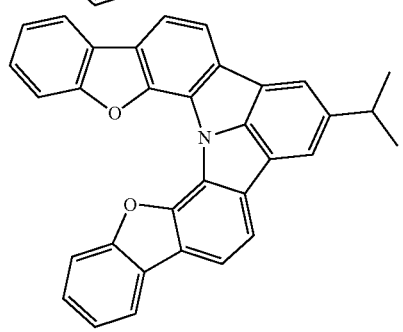
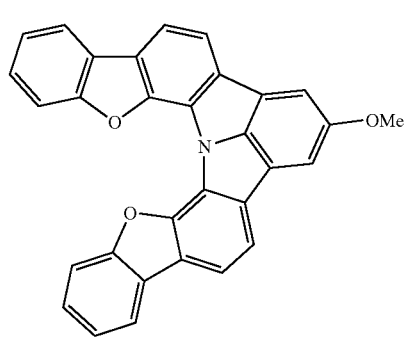
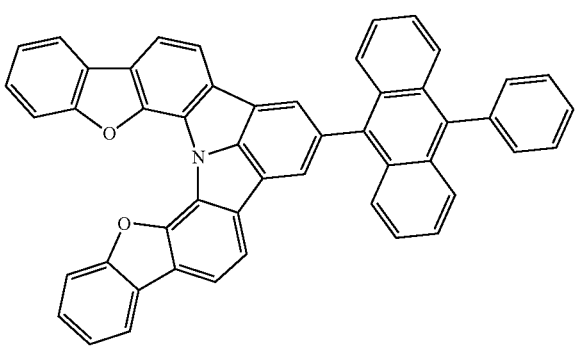

107
-continued
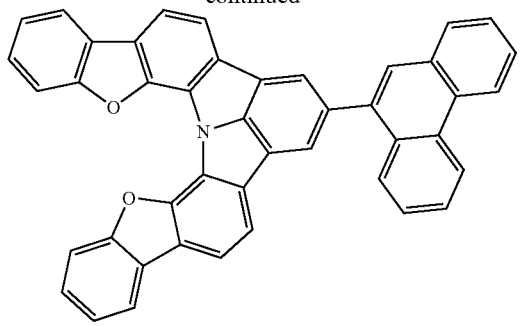
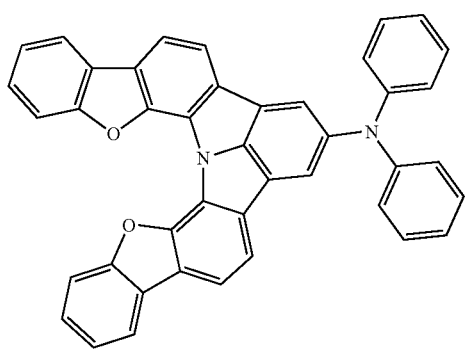
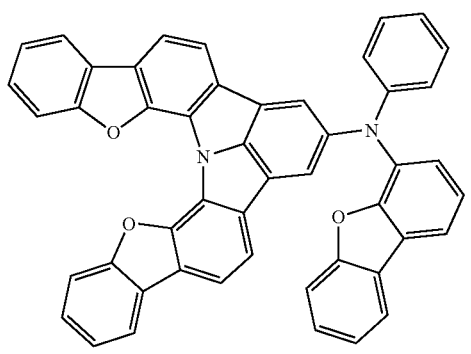
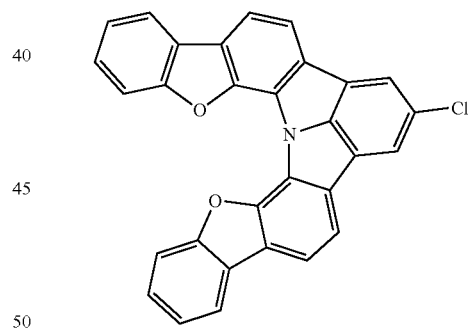
108
-continued
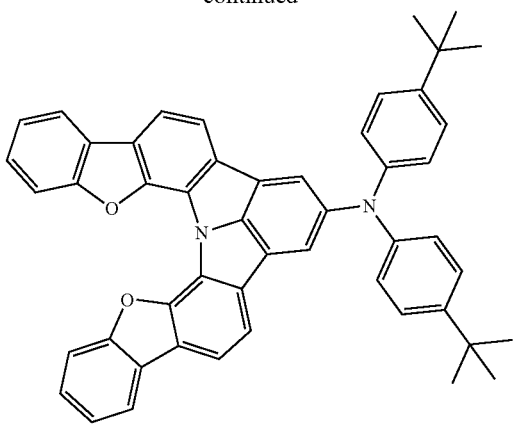
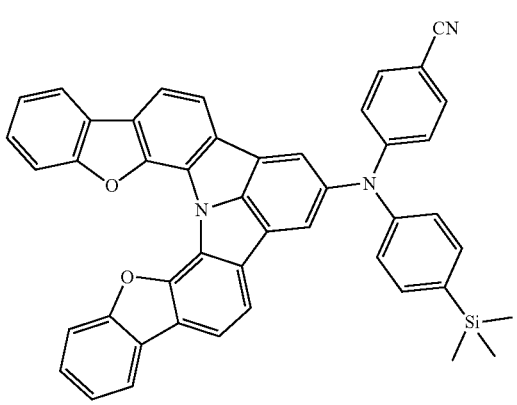
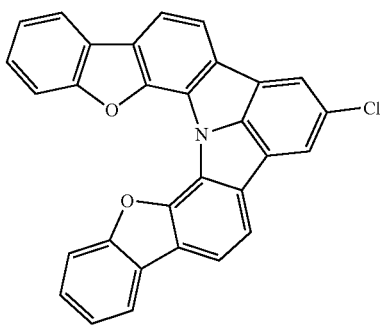
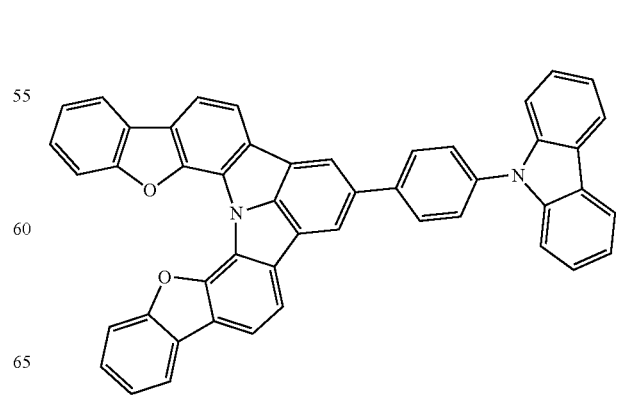

109
-continued
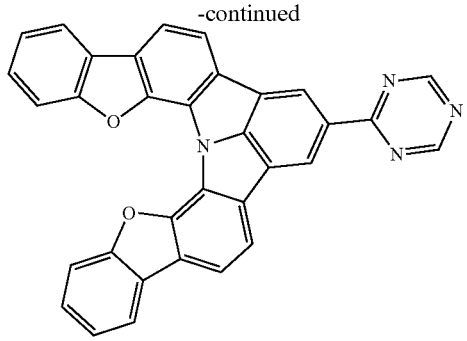
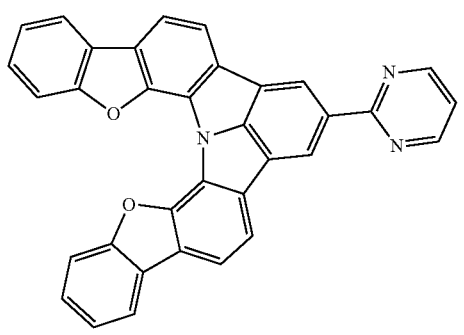
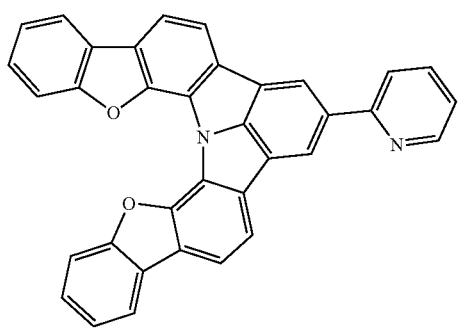
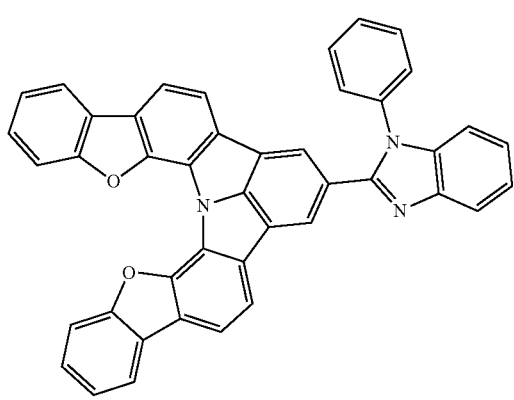
110
-continued
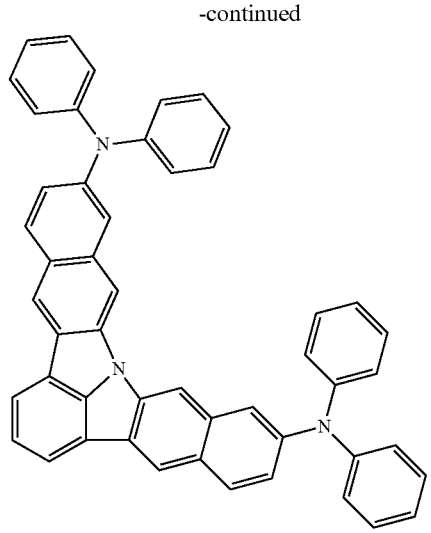
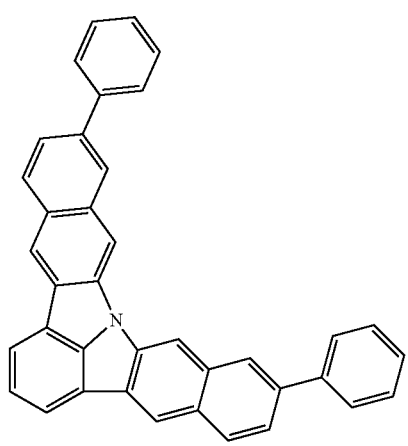
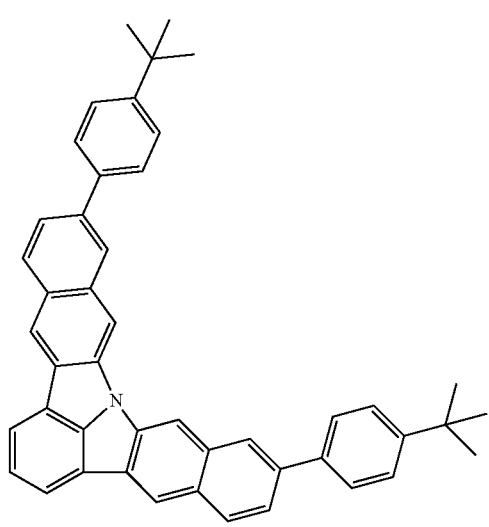

111
-continued
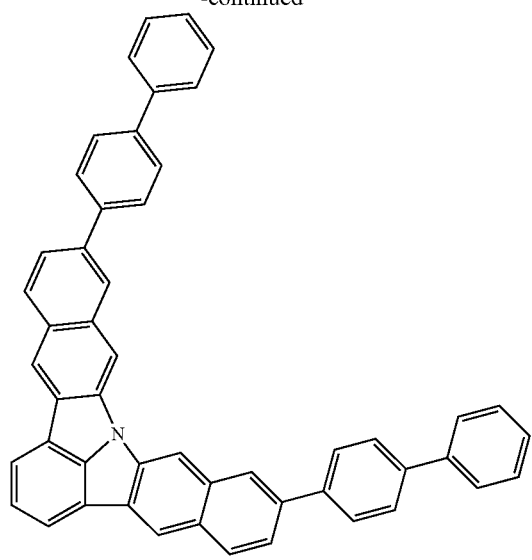
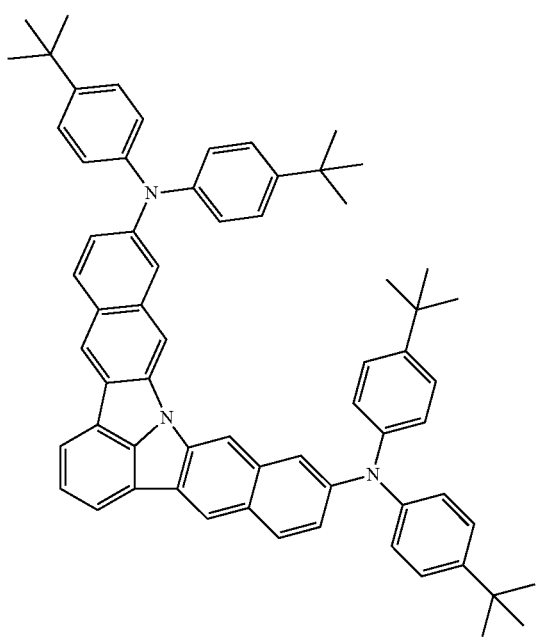
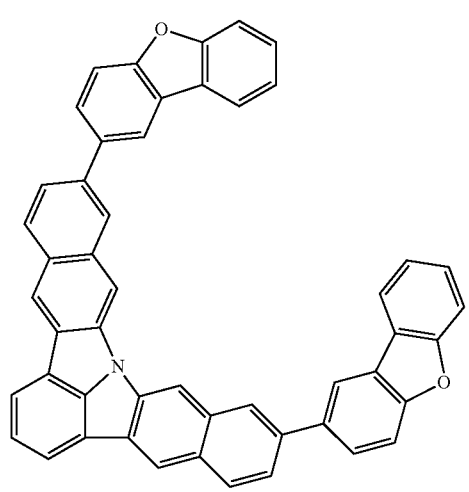
112
-continued
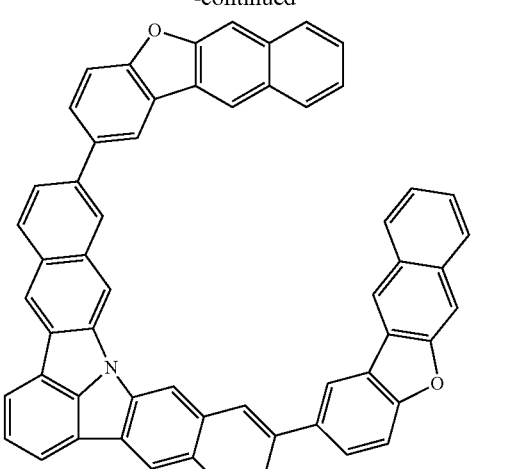
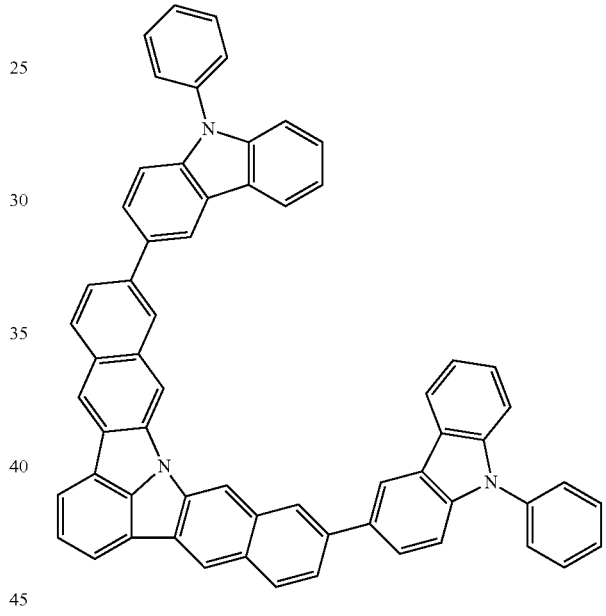
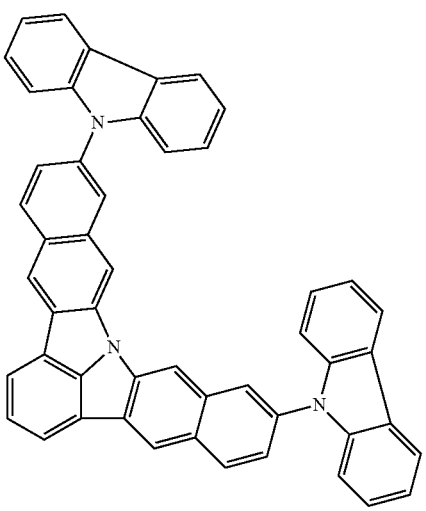

113
-continued
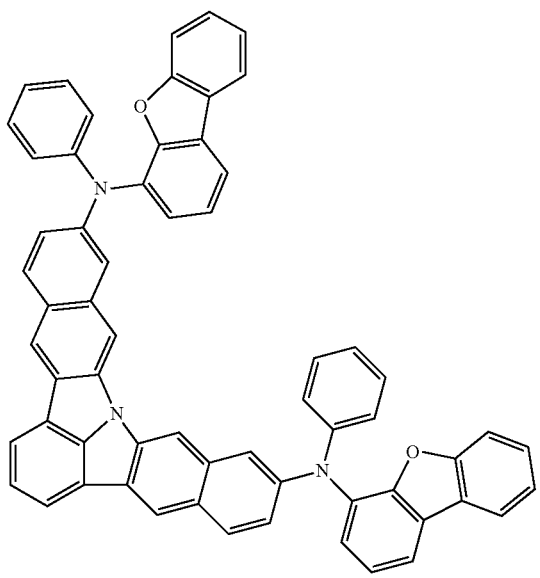
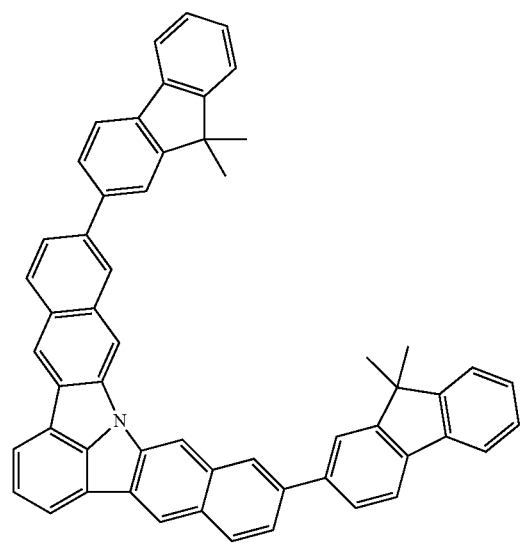
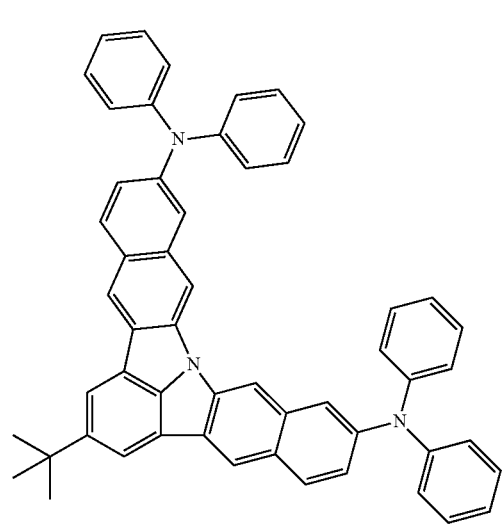
114
-continued
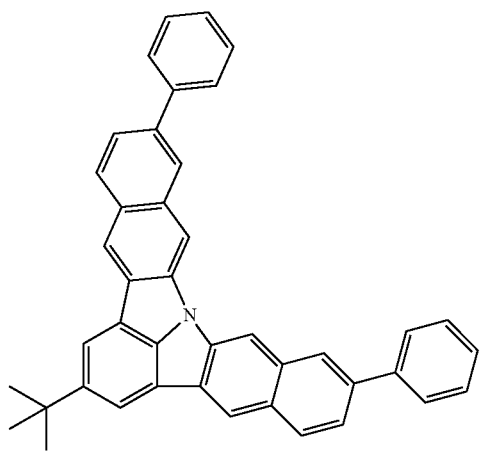
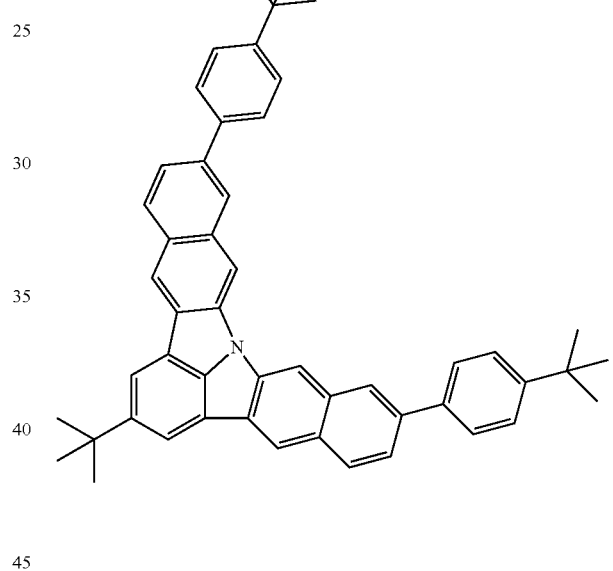
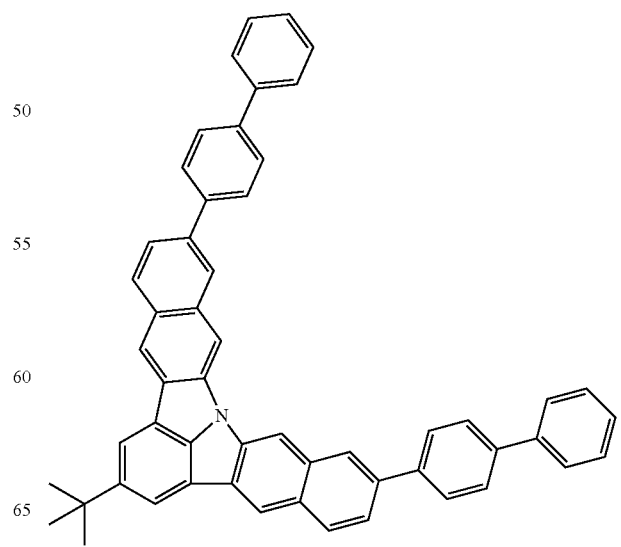

115
-continued
116
-continued
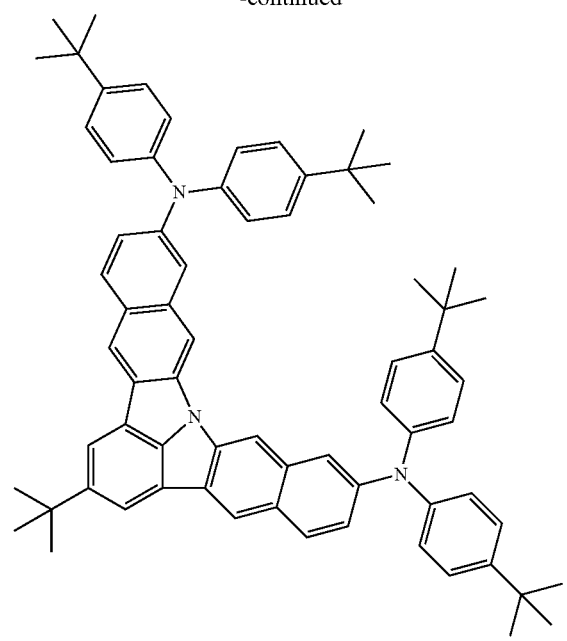
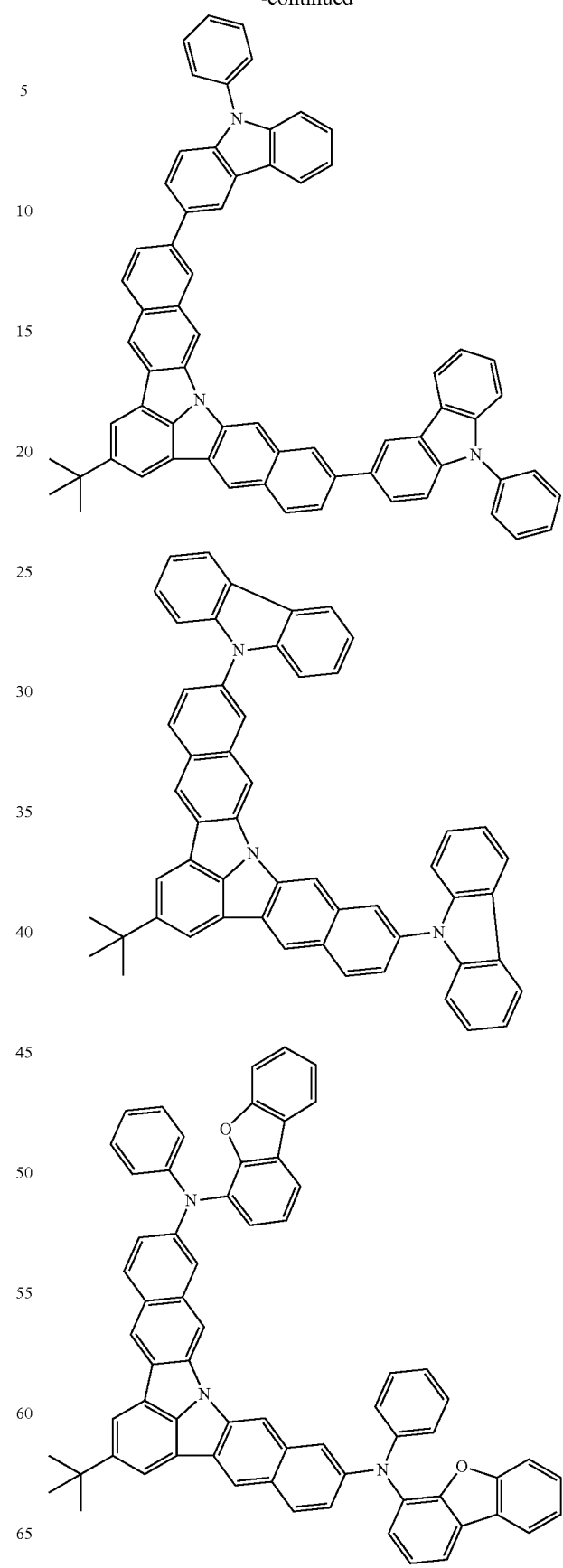

117
-continued
118
-continued
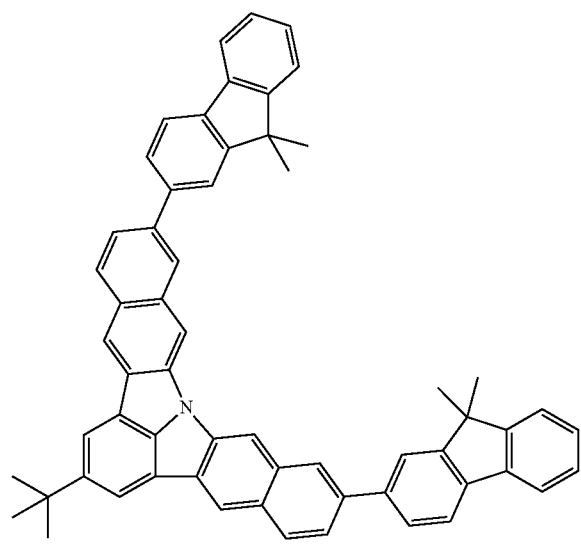
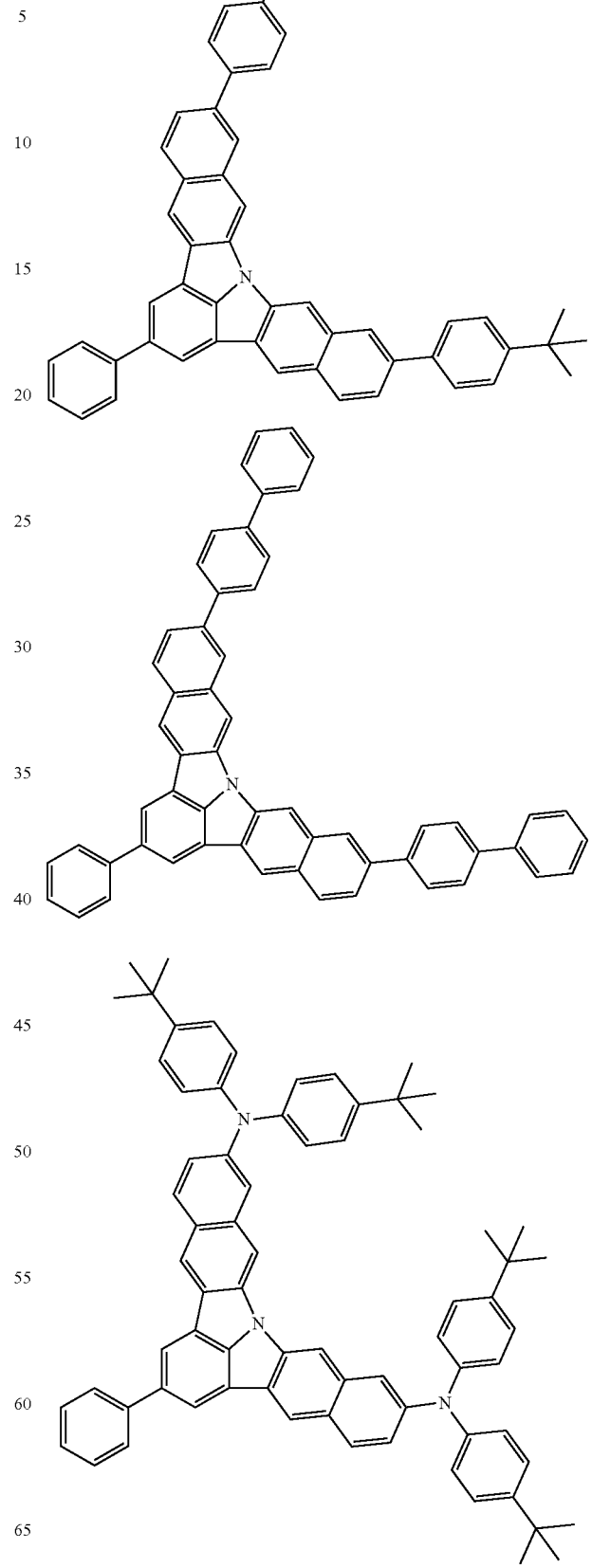

119
-continued
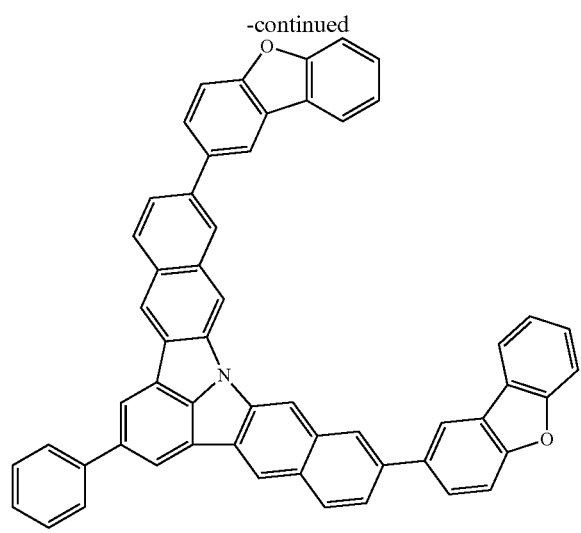
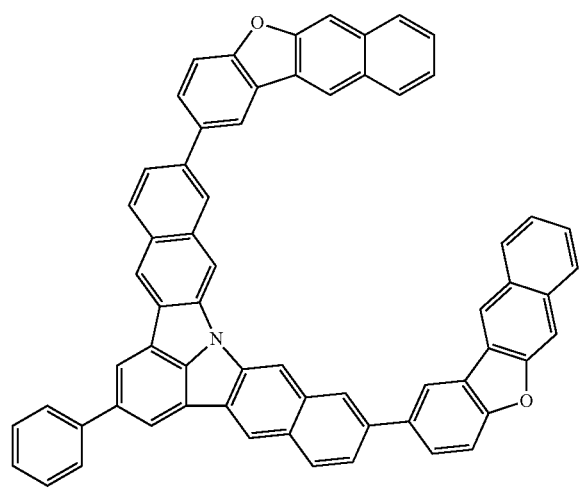
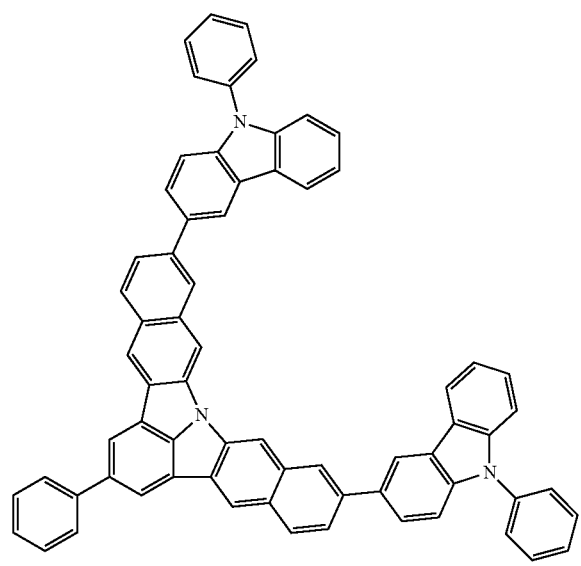
120
-continued
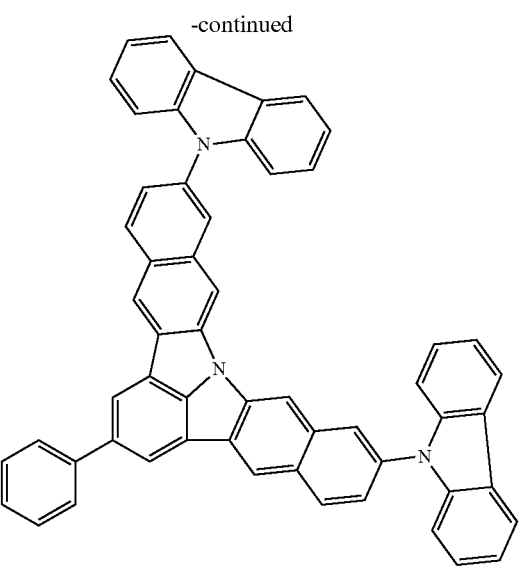
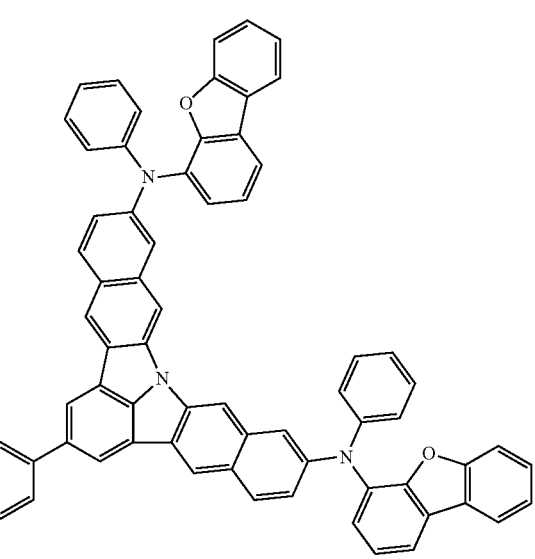
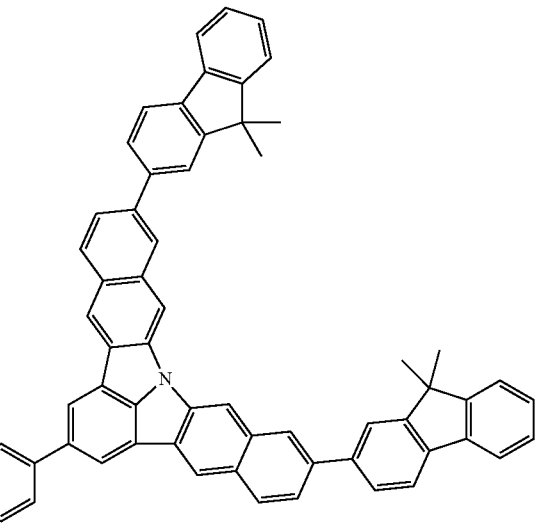

121
-continued
122
-continued
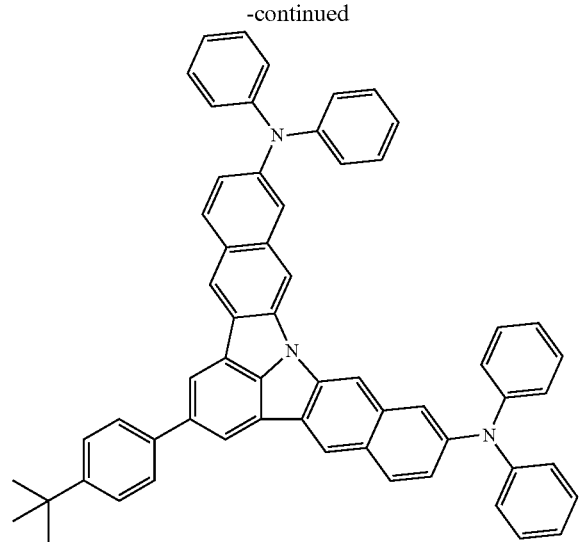
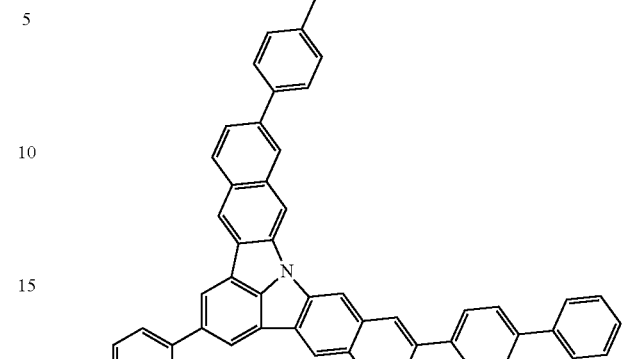
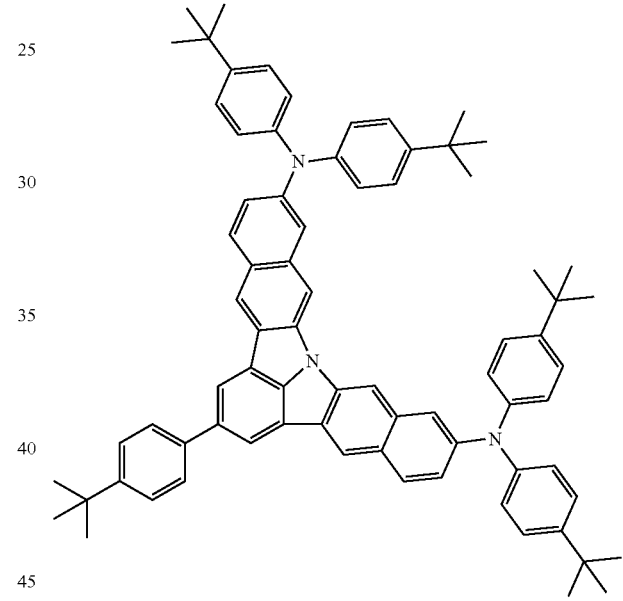
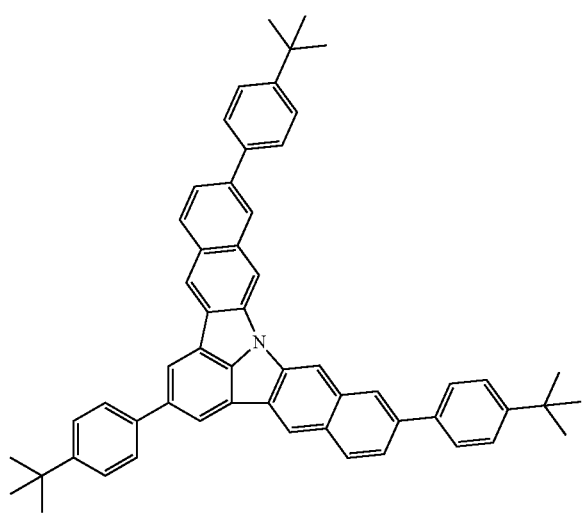
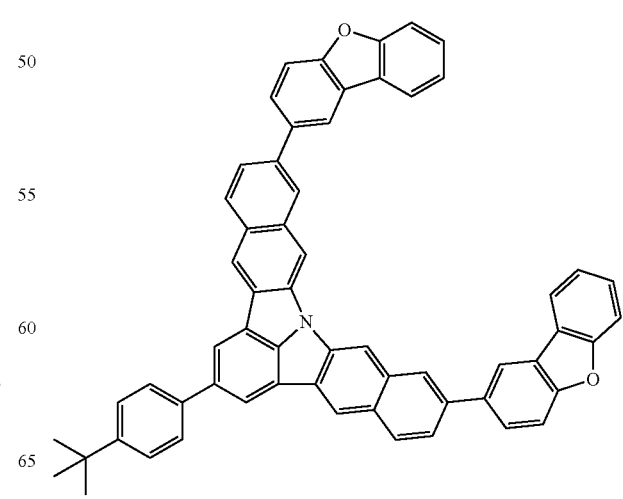

-continued
123
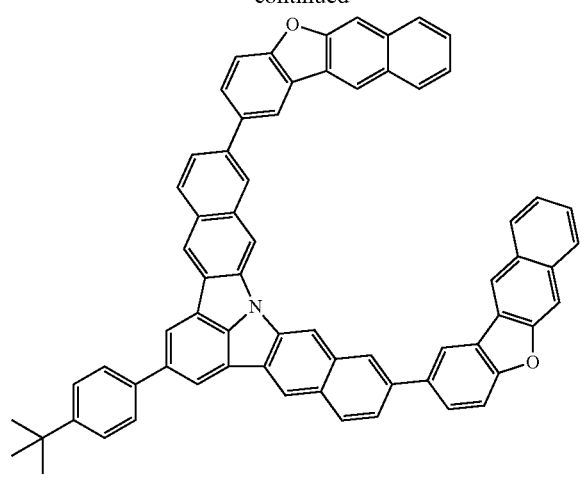
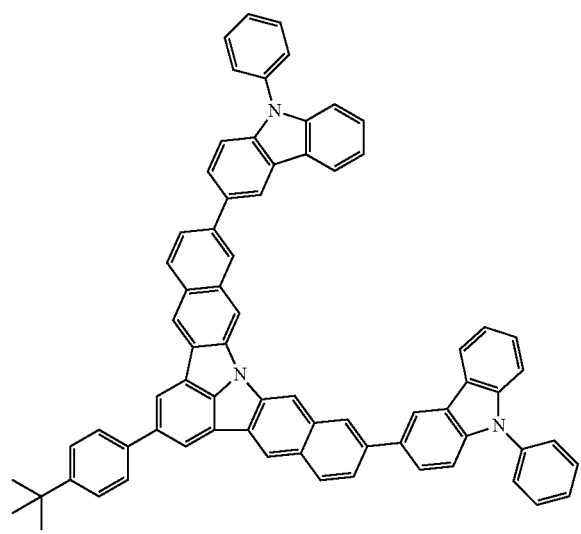
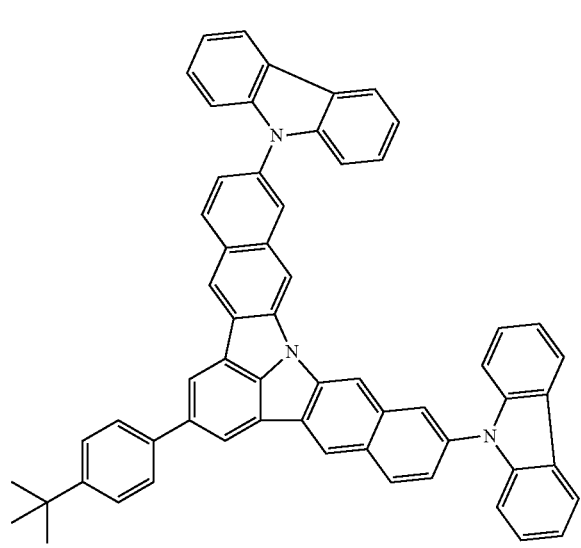
124
-continued
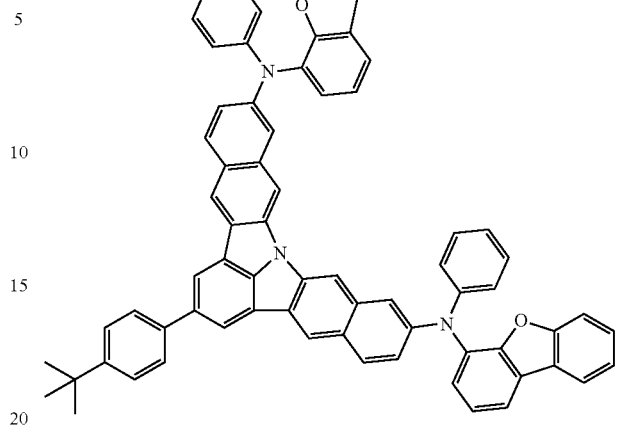
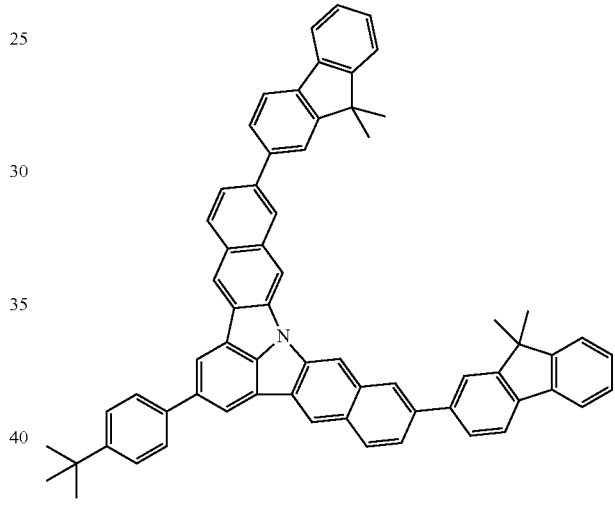
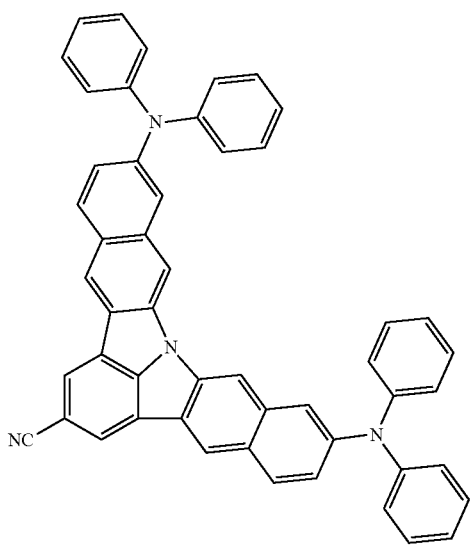

125
-continued
126
-continued
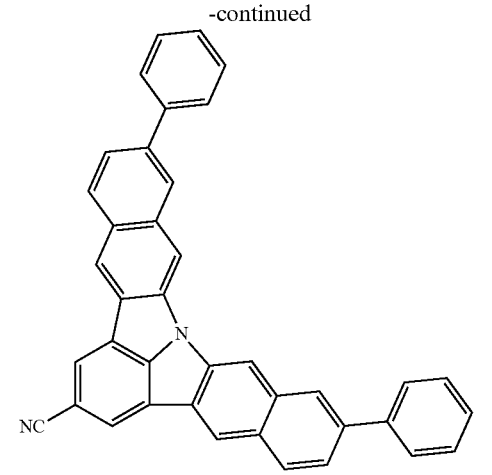
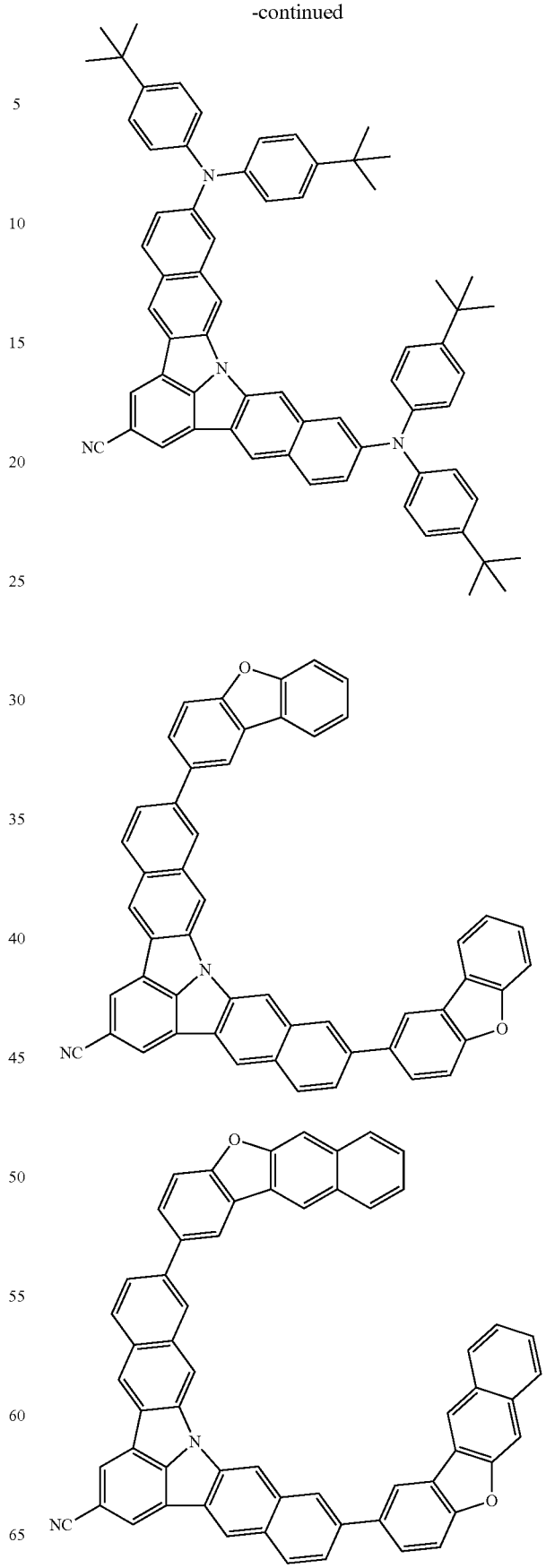

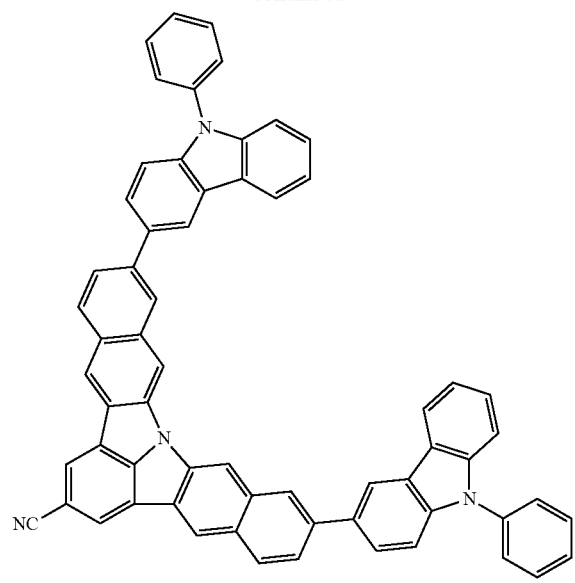
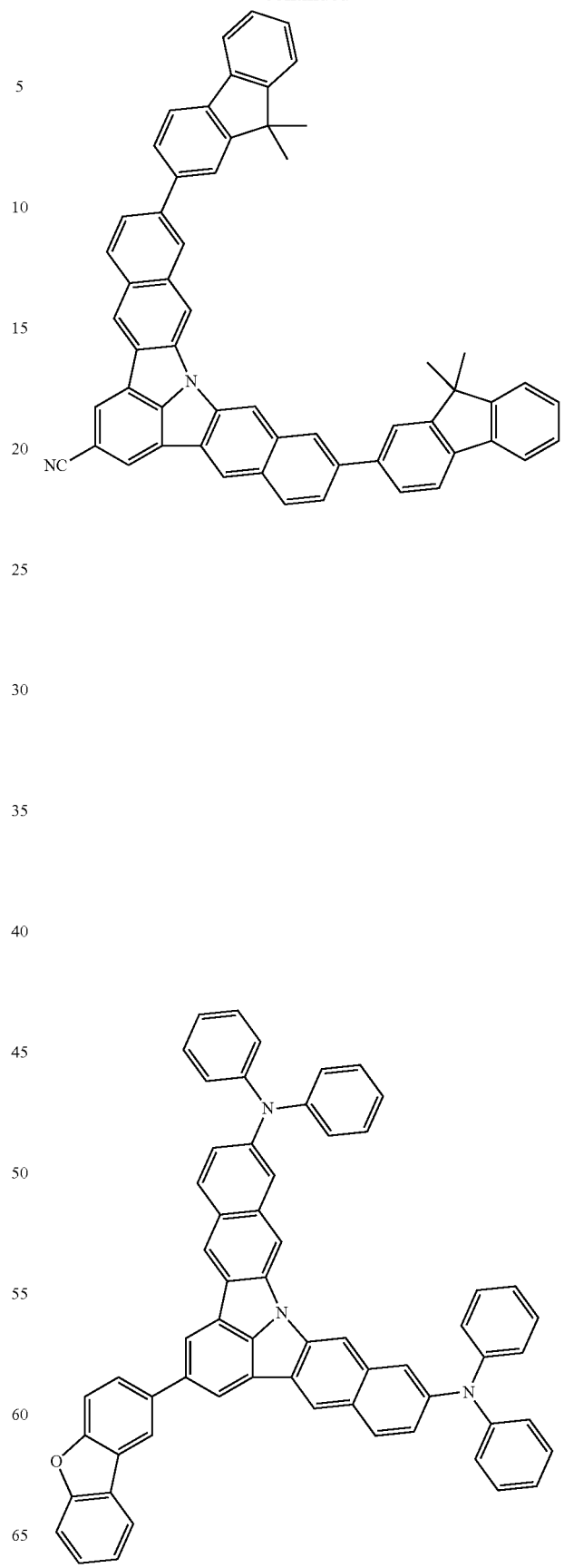

129
-continued
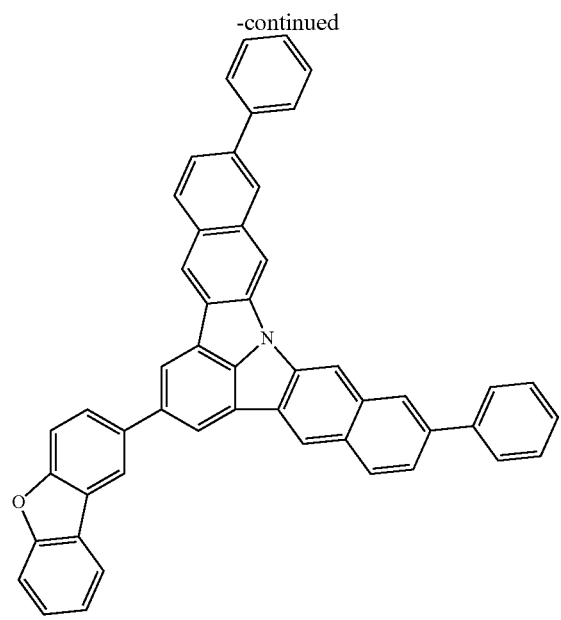
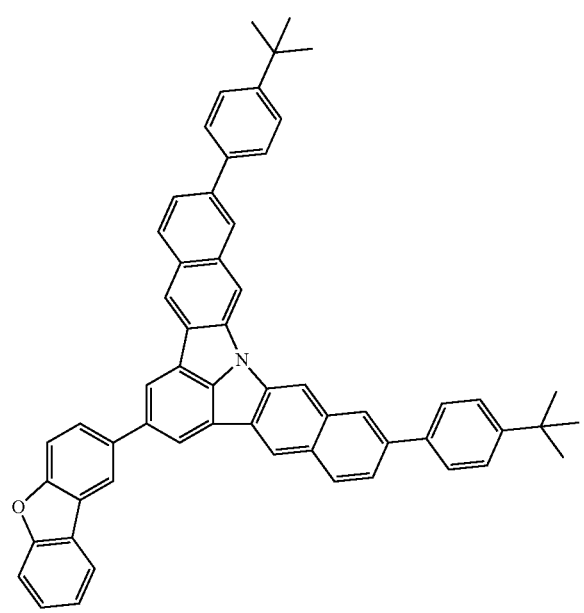
130
-continued
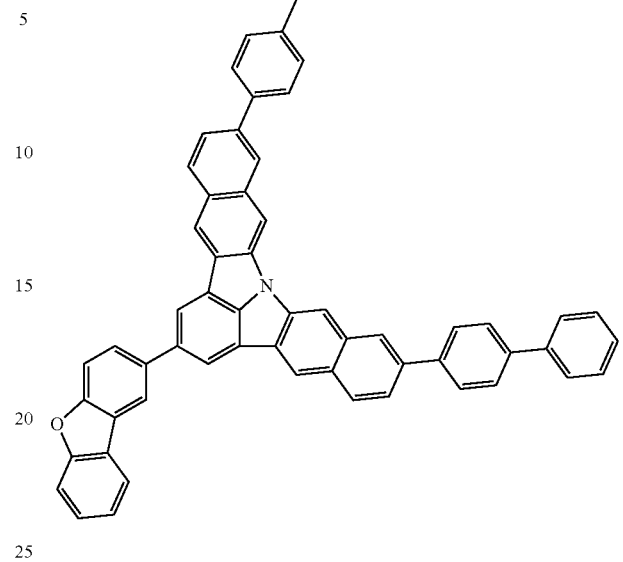
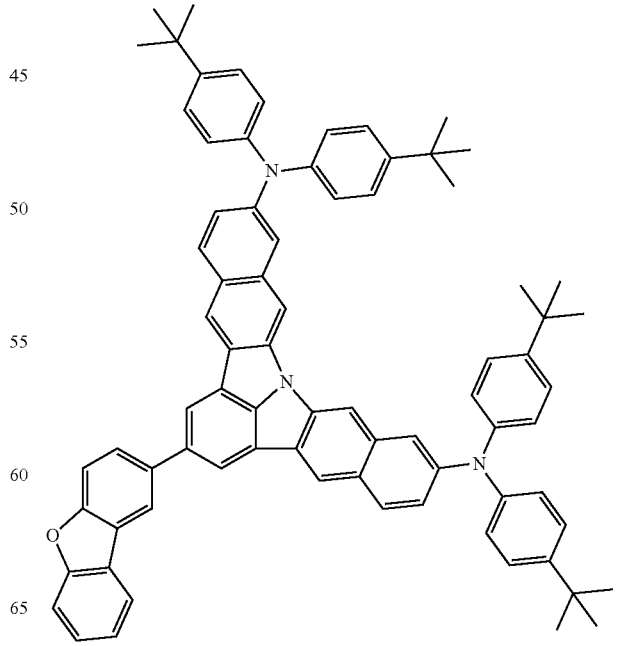

131
-continued
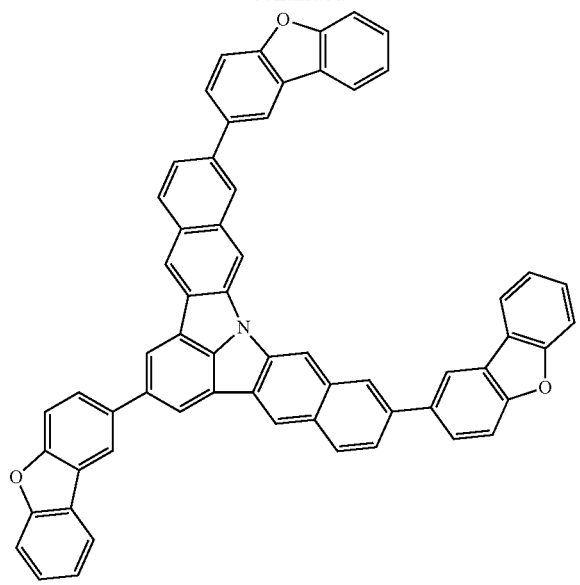
132
-continued
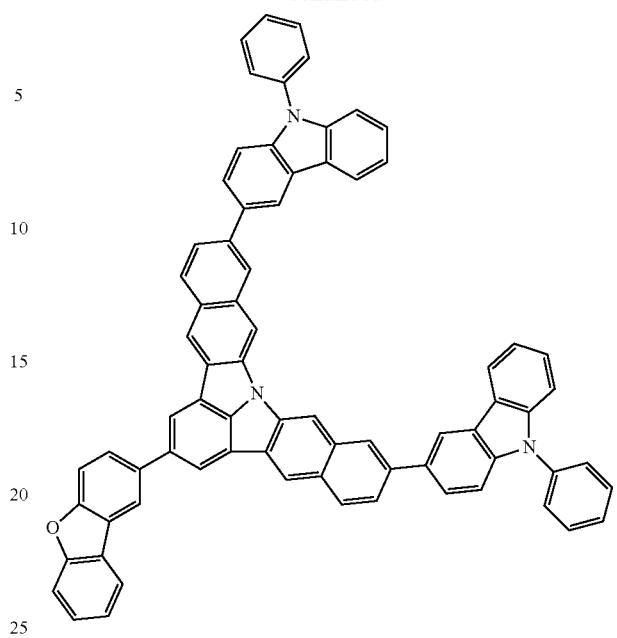
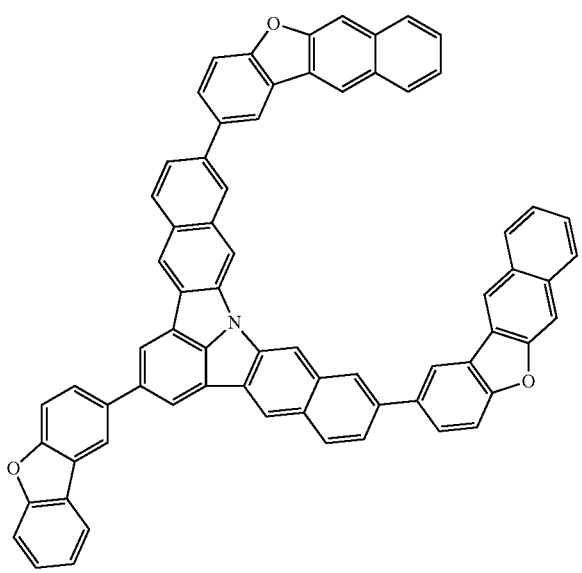
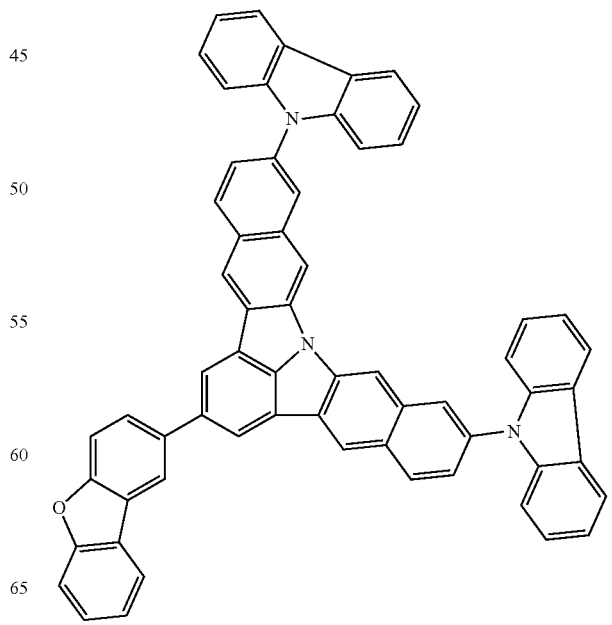

133
-continued
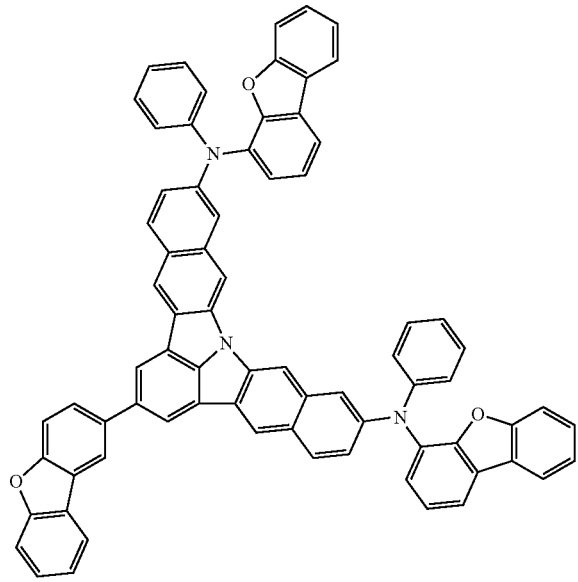
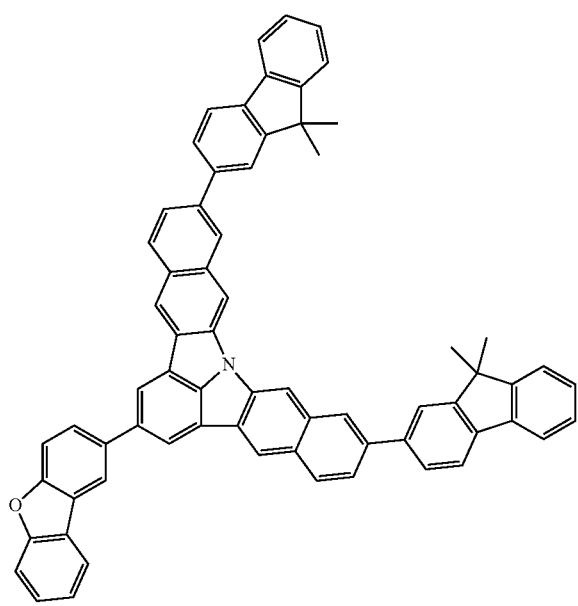
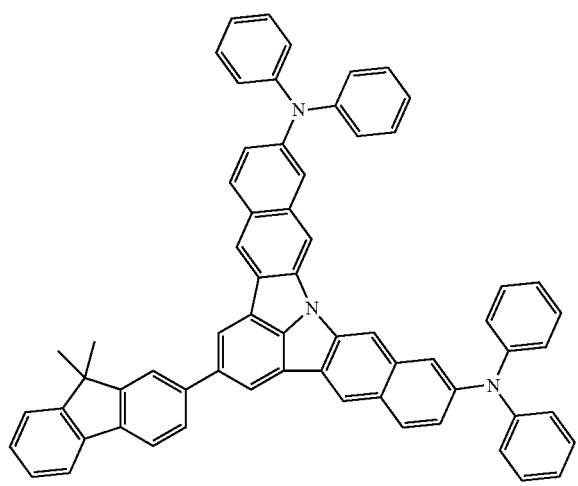
134
-continued
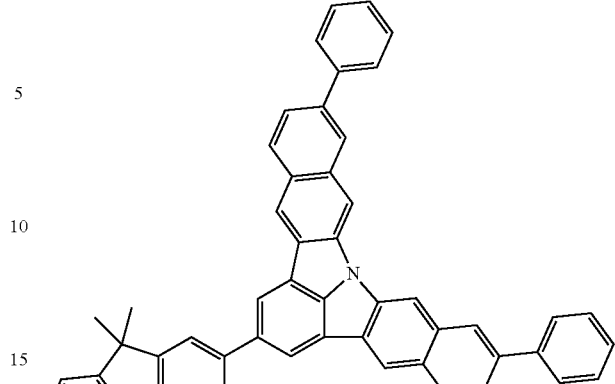
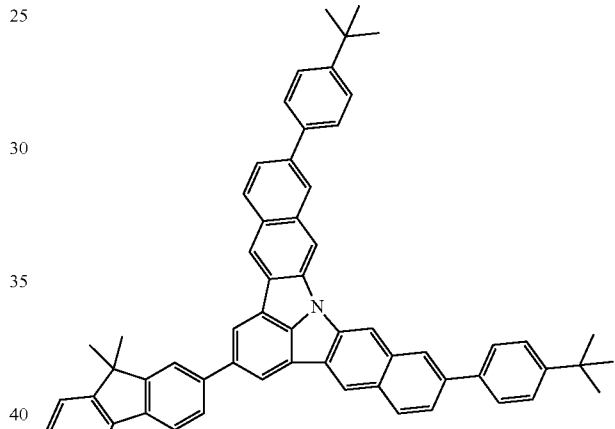
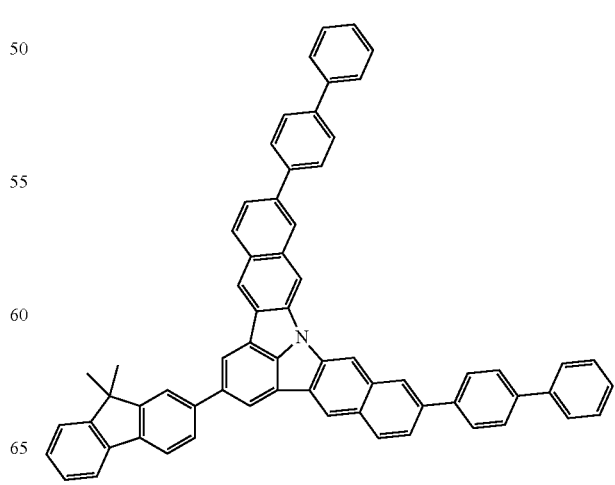

135 -continued
136 -continued
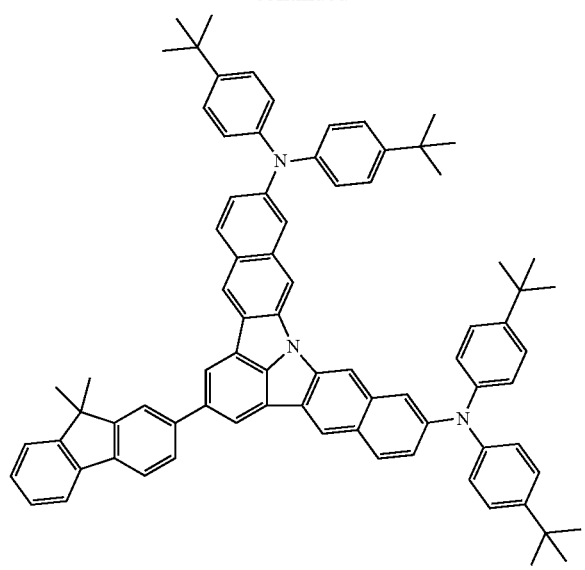
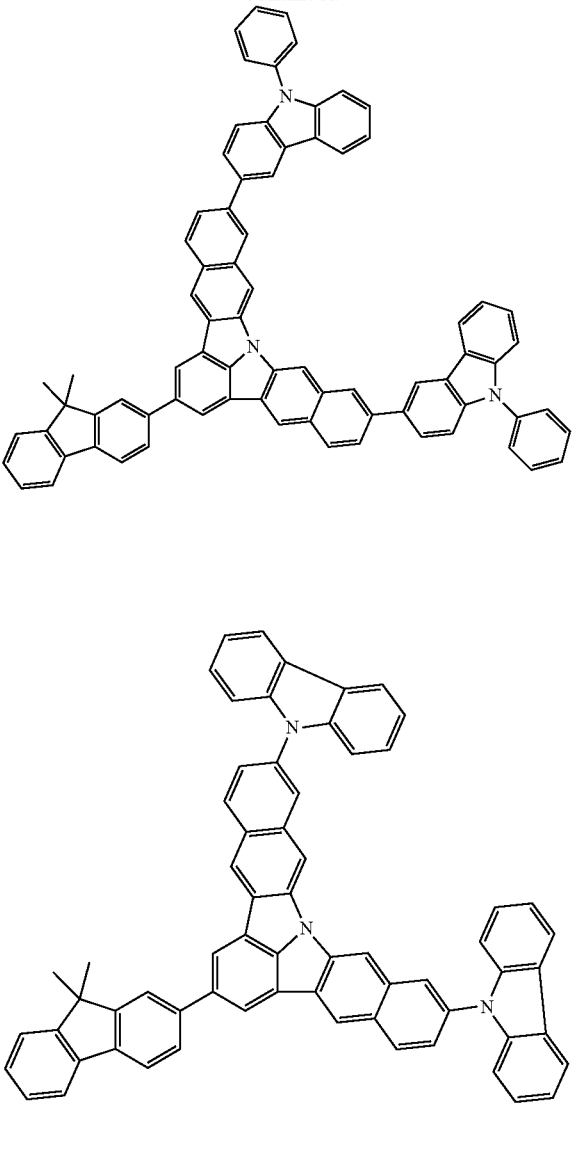
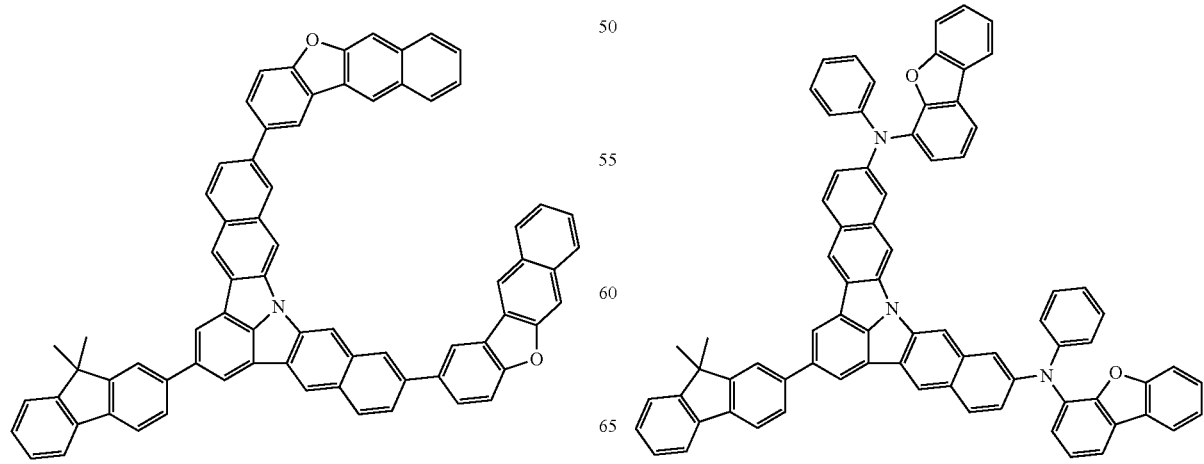

137
-continued
138
-continued
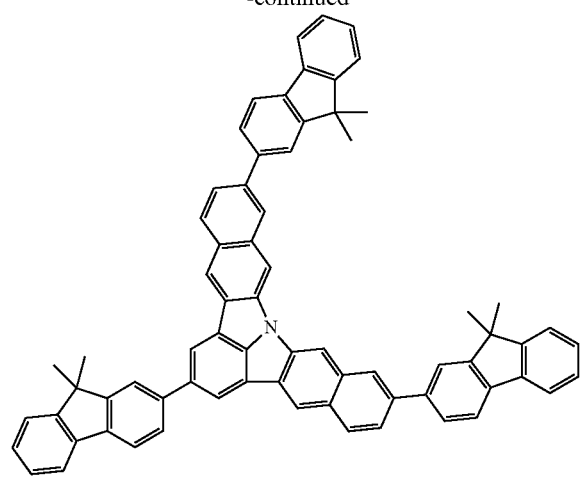
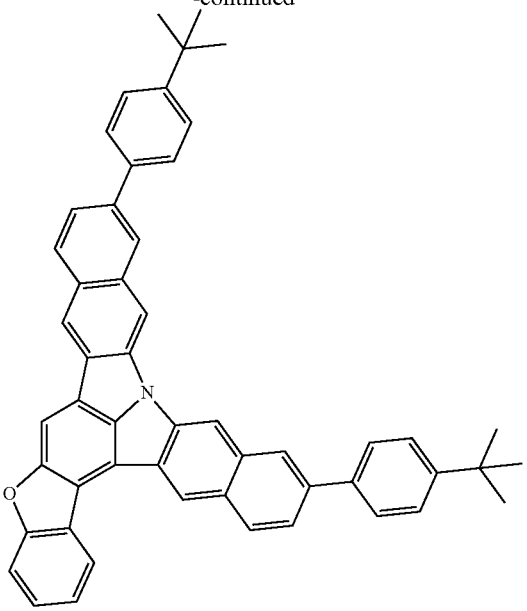
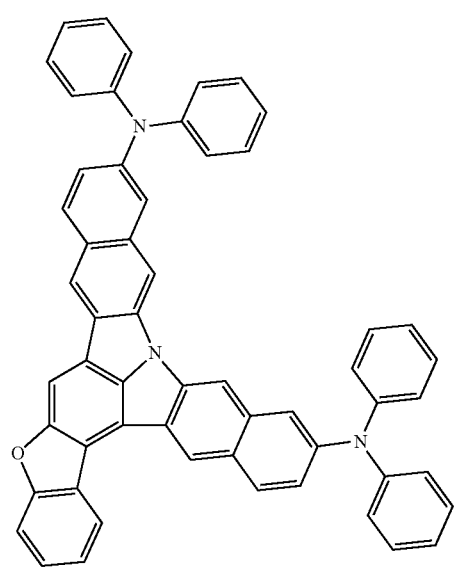
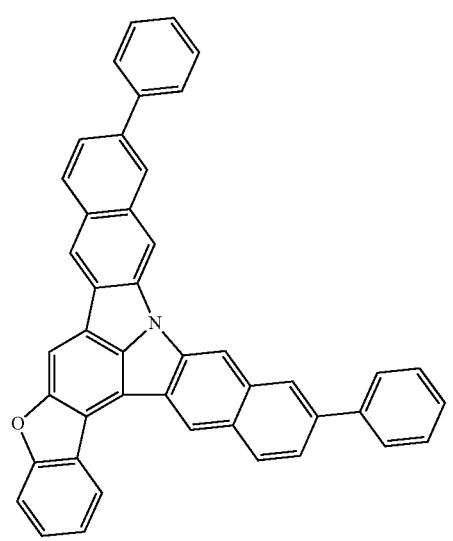
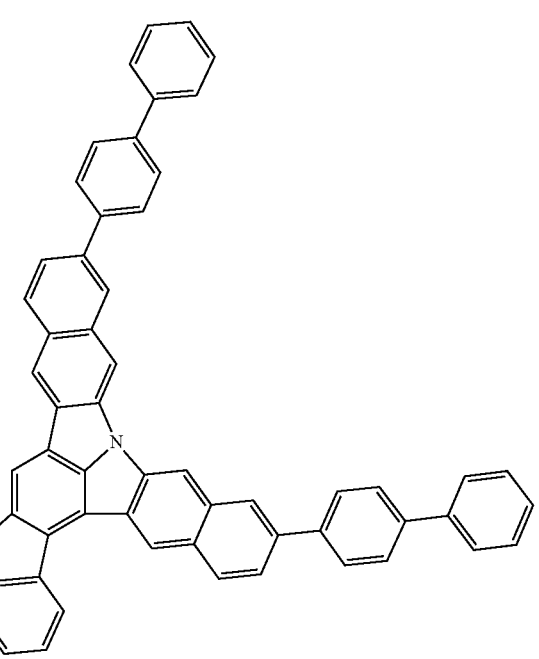

139
-continued
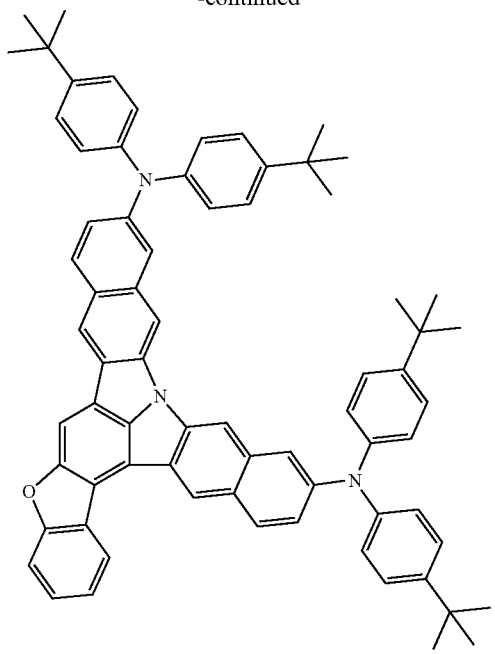
140
-continued
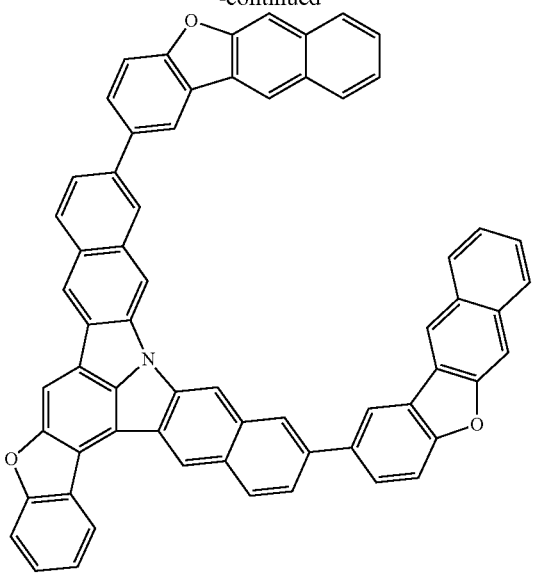
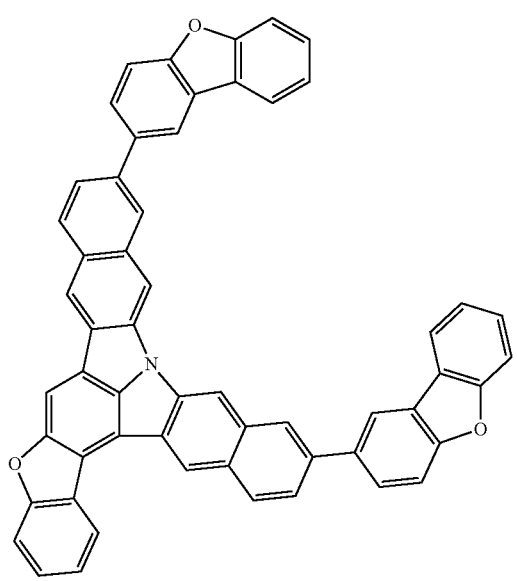
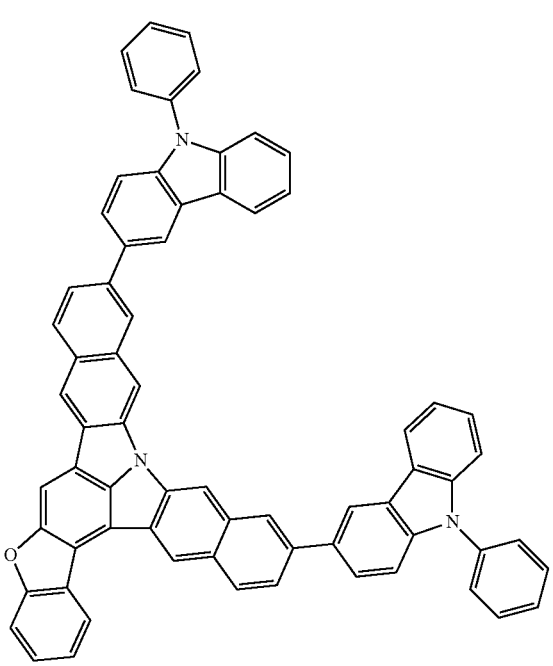

141
-continued
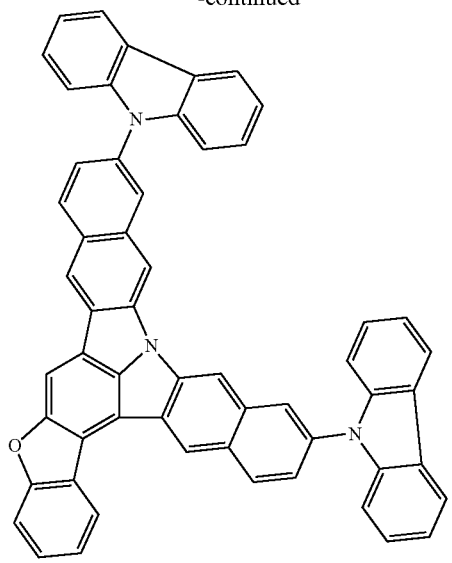
142
-continued
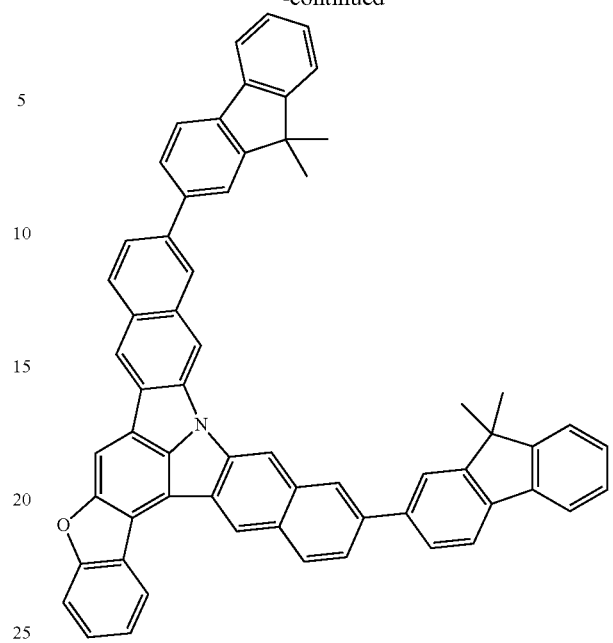
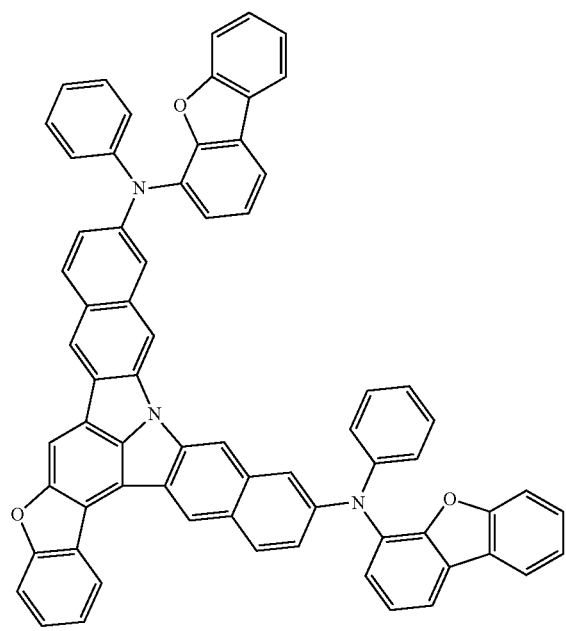
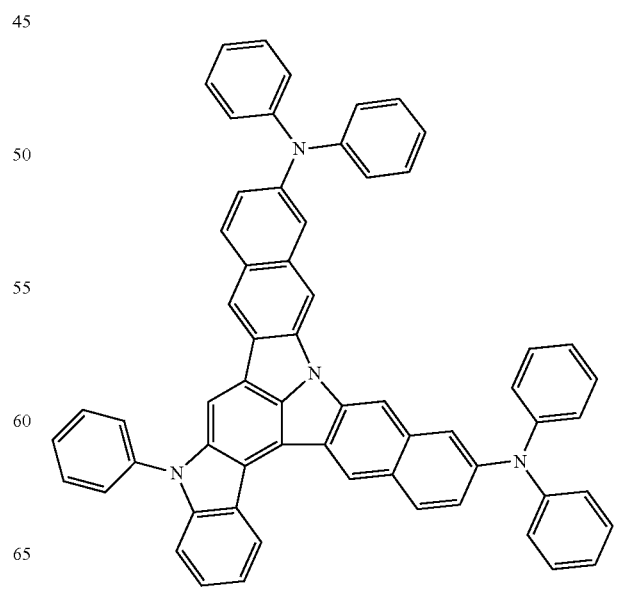

143
-continued
144
-continued
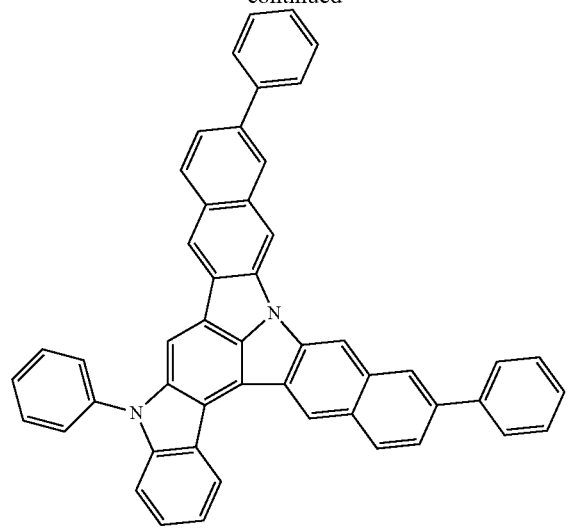
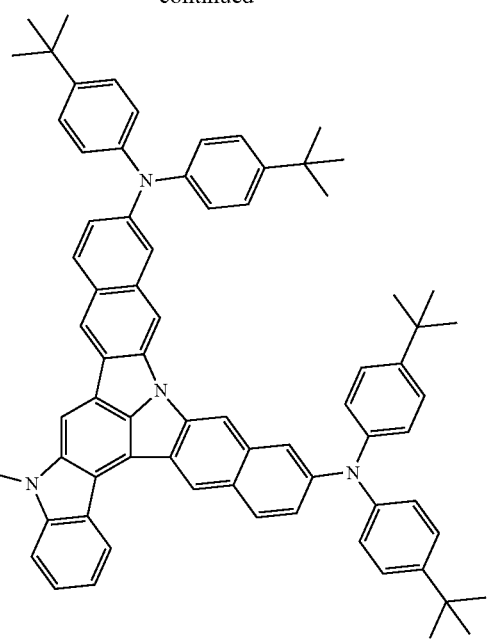
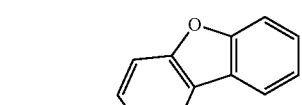
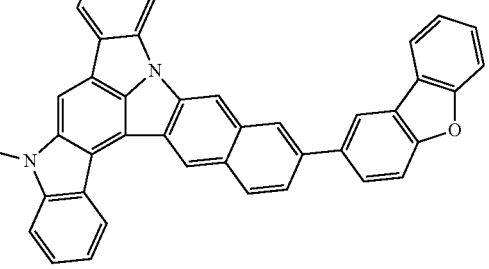
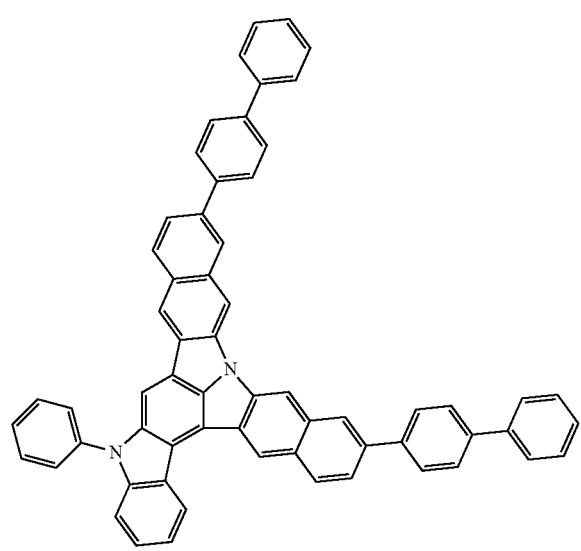
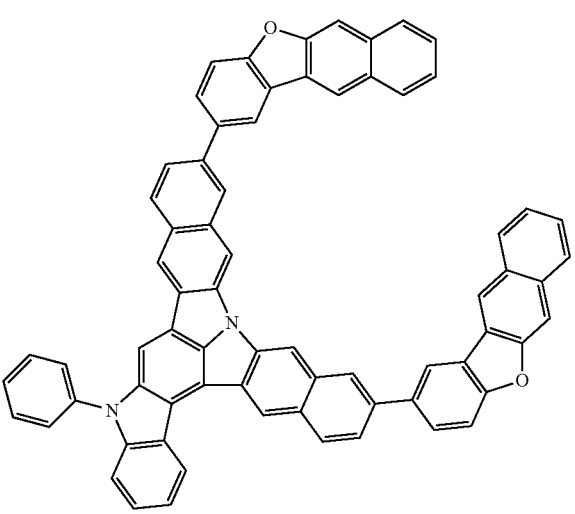

145
-continued
146
-continued
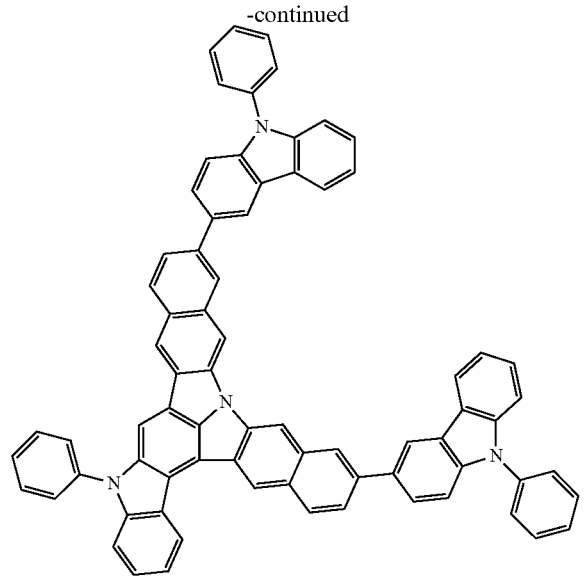
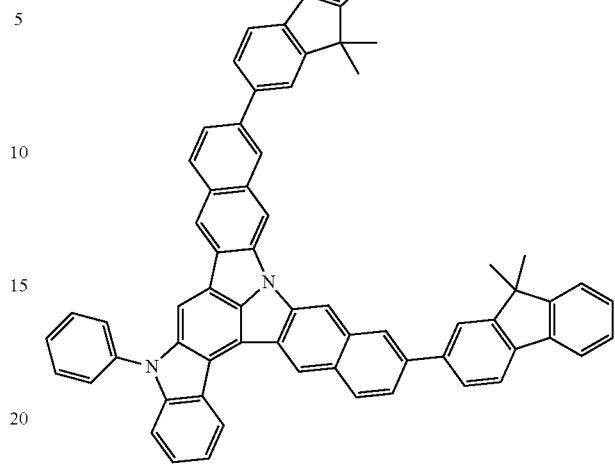
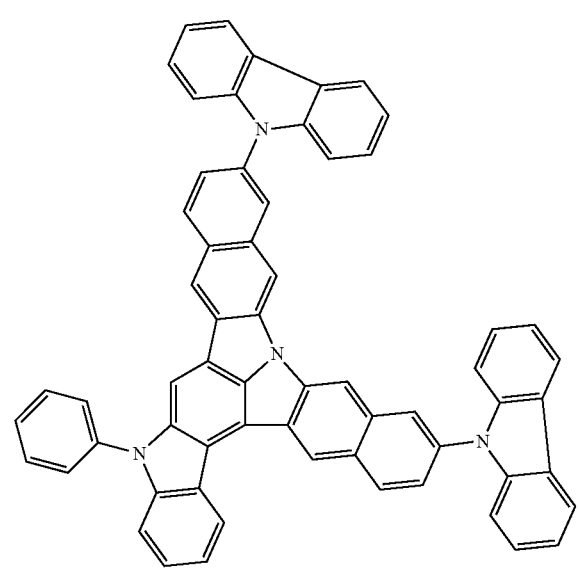
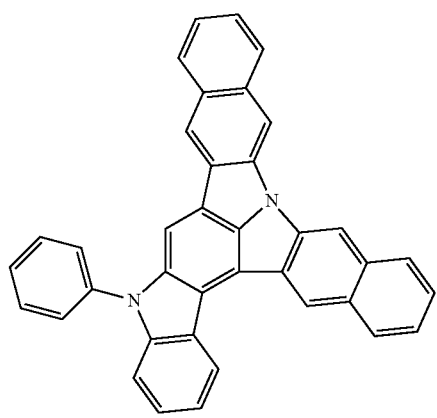
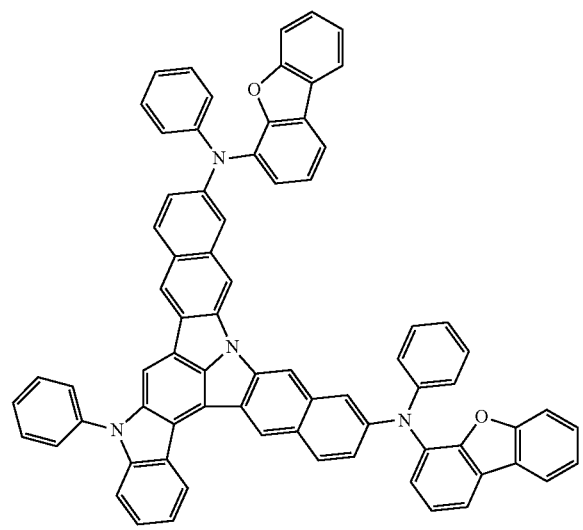
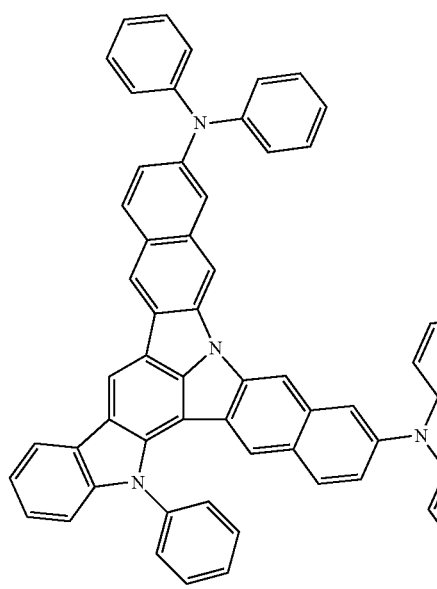

147
-continued
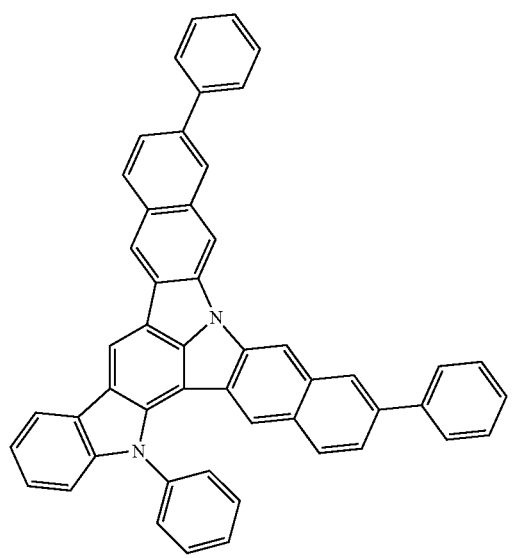
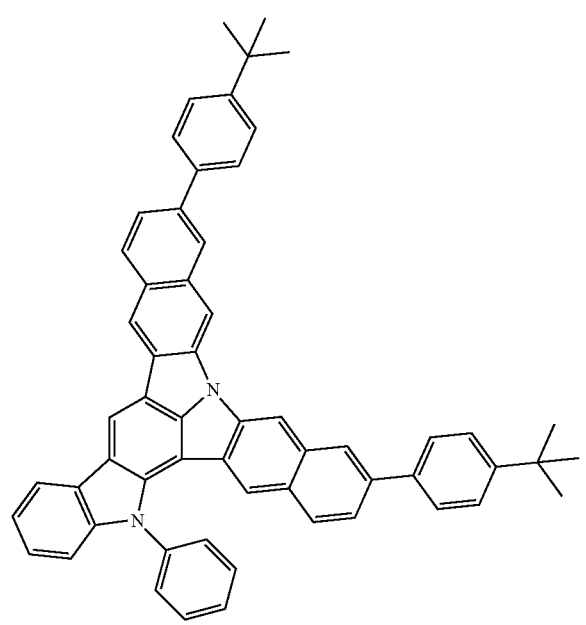
148
-continued
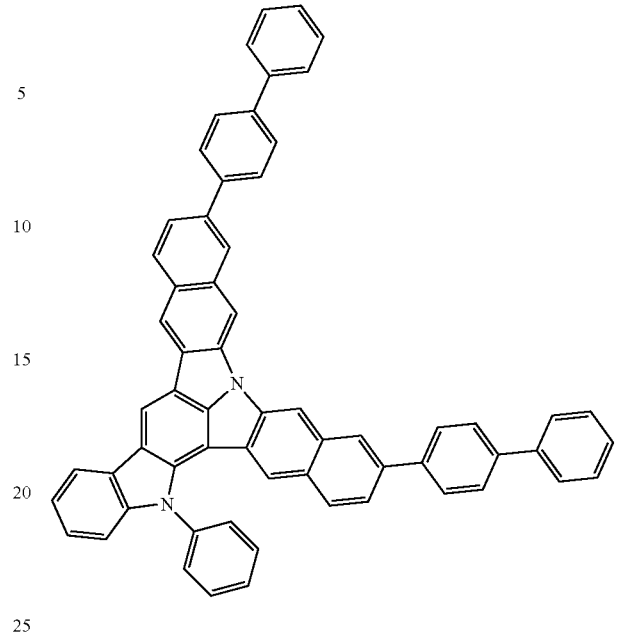
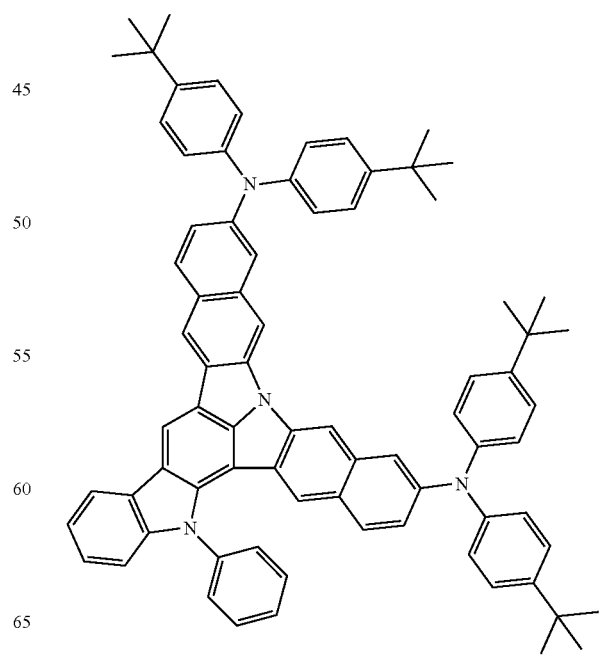

149
-continued
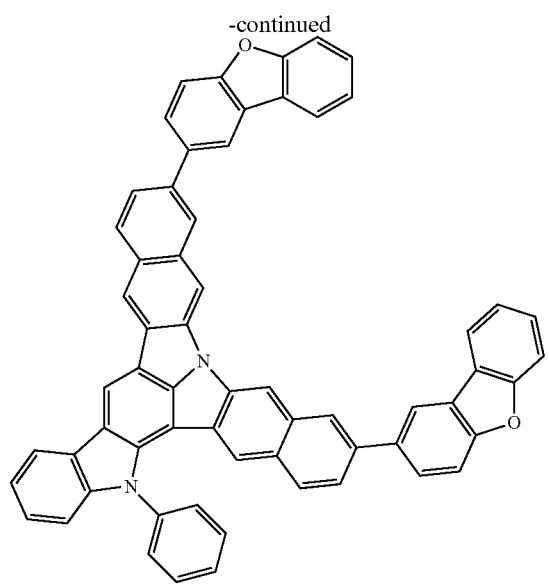
150
-continued
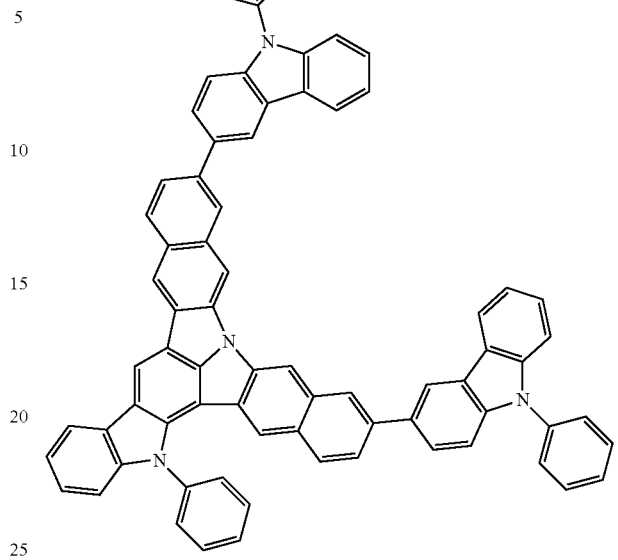
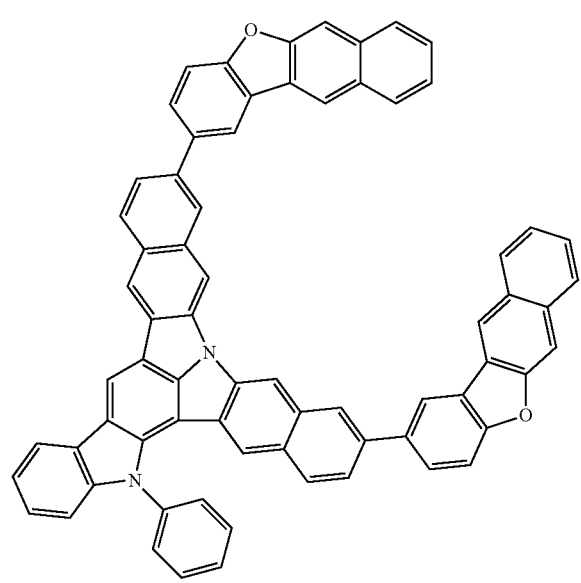
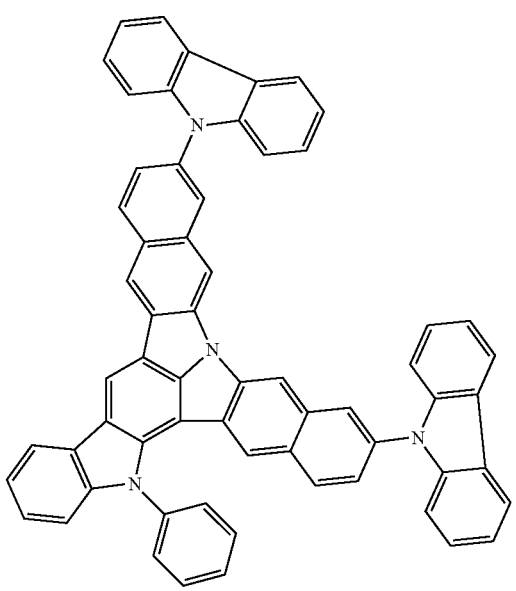

151
-continued
152
-continued
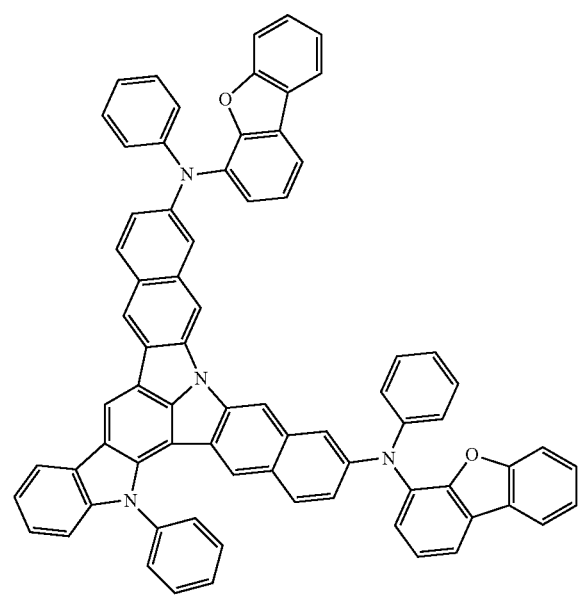
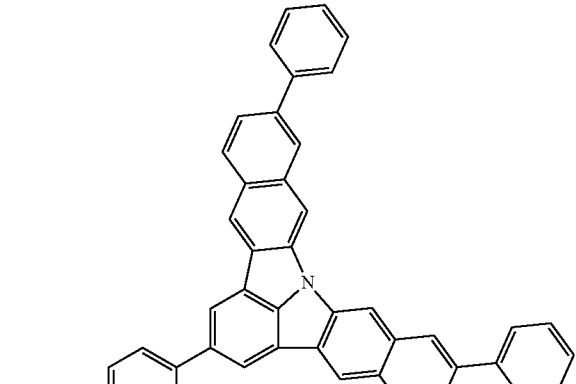
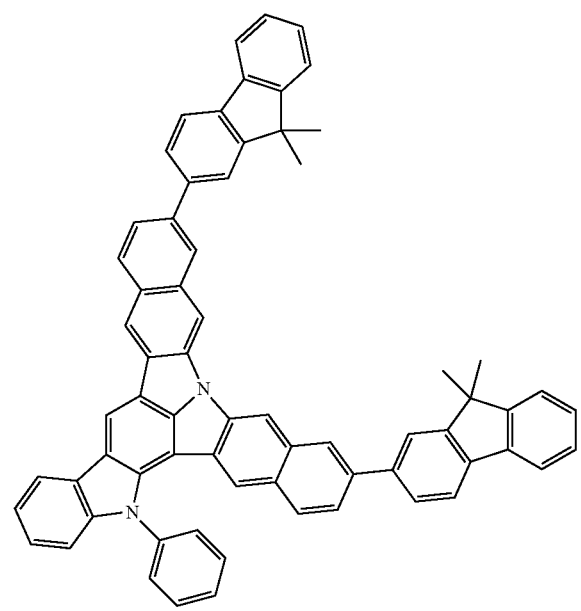
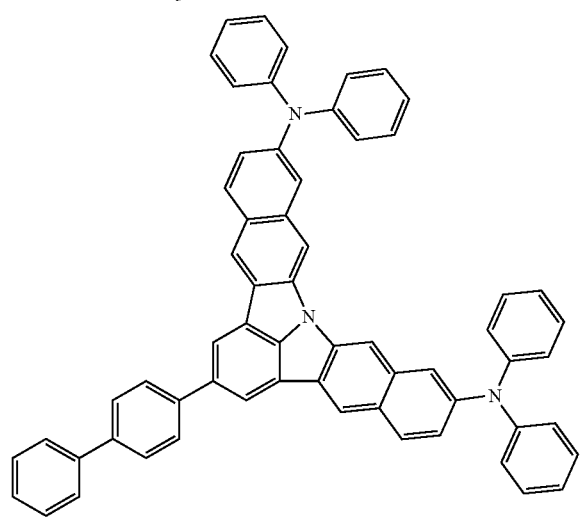
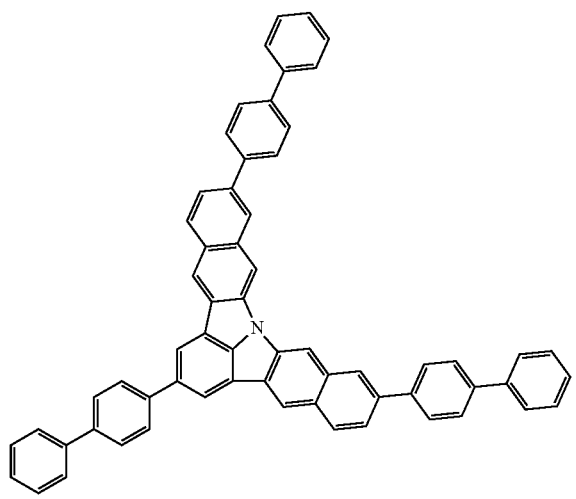

153
-continued
154
-continued
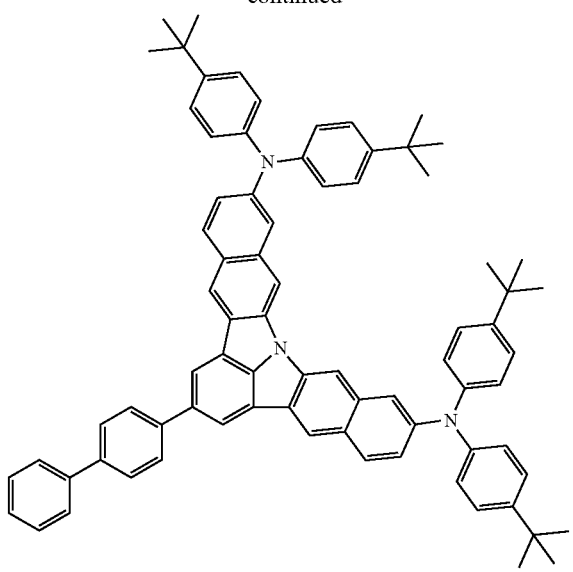
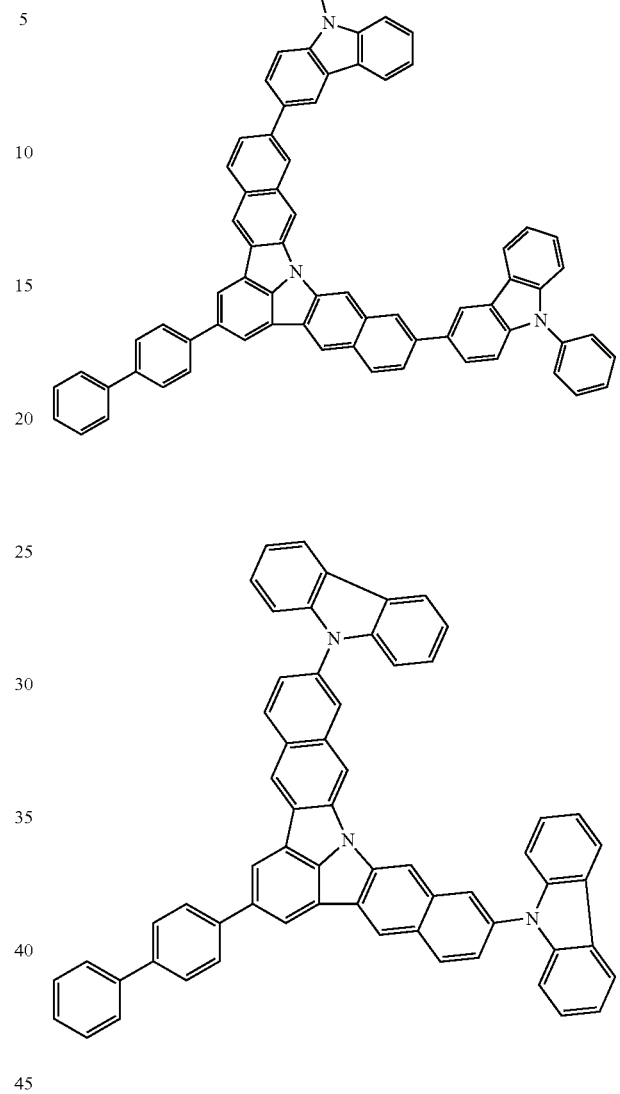
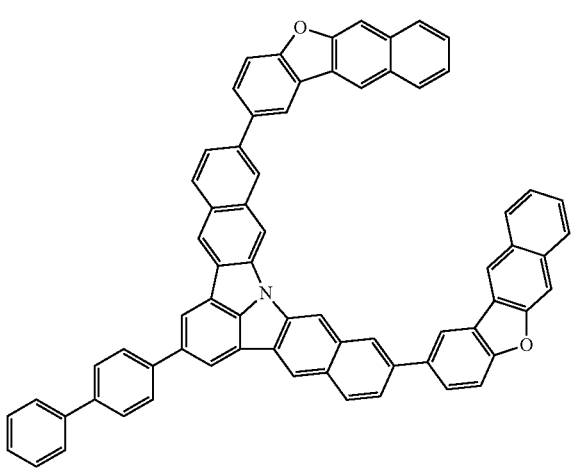
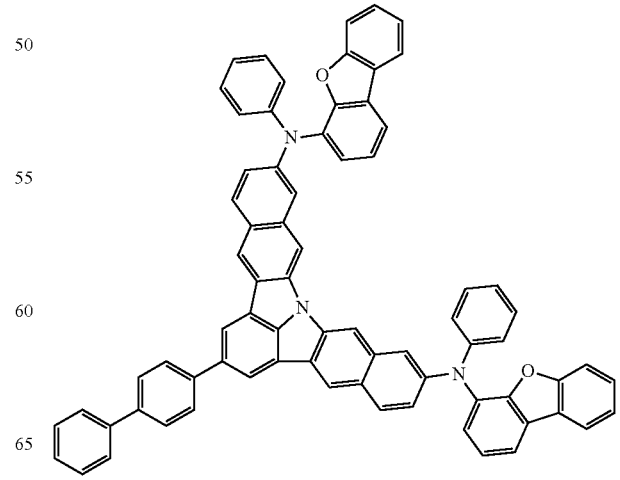

155
-continued
156
-continued
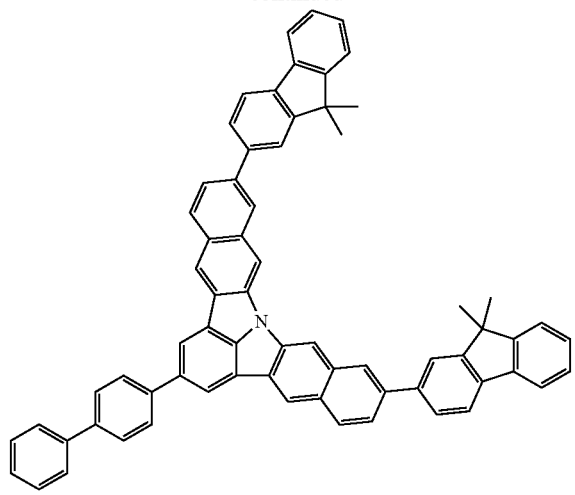
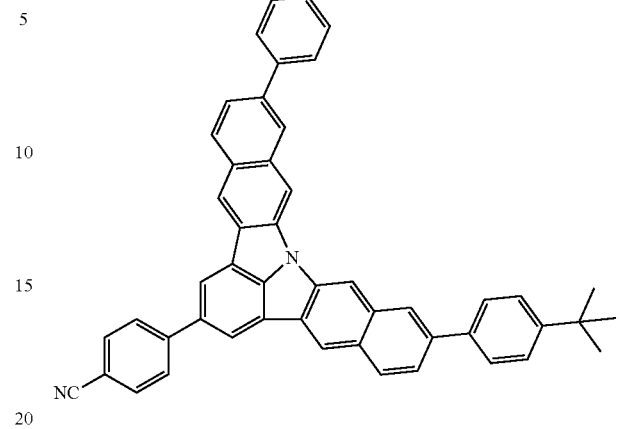
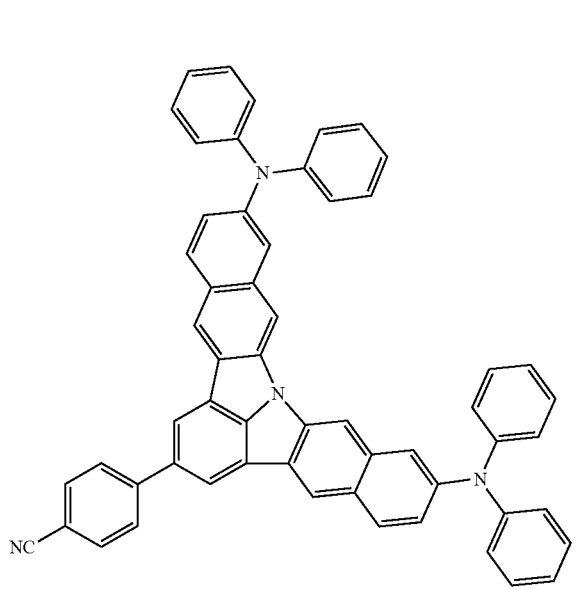
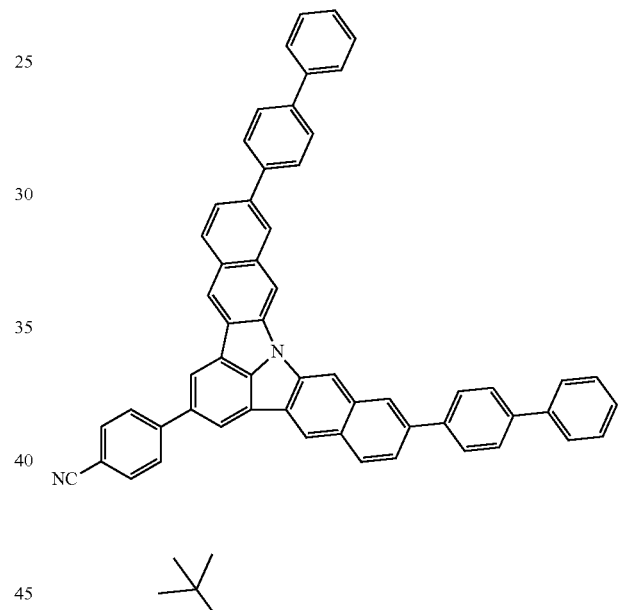
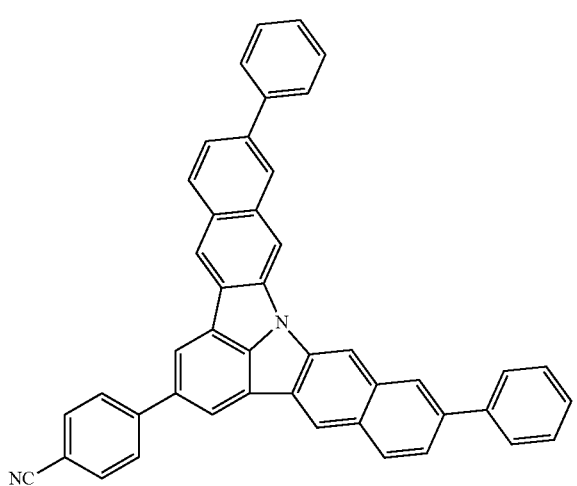
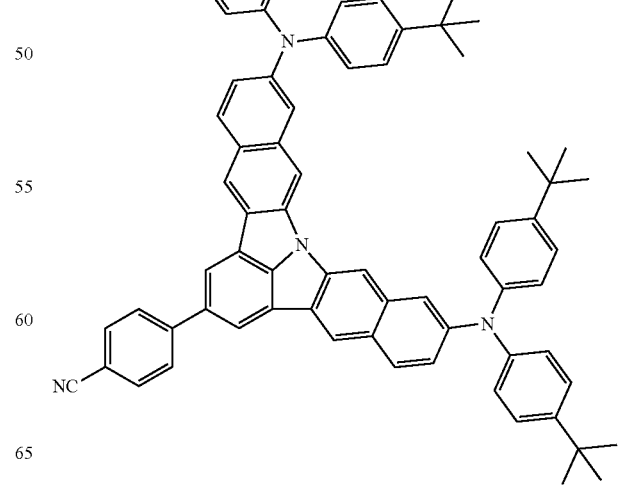

-continued
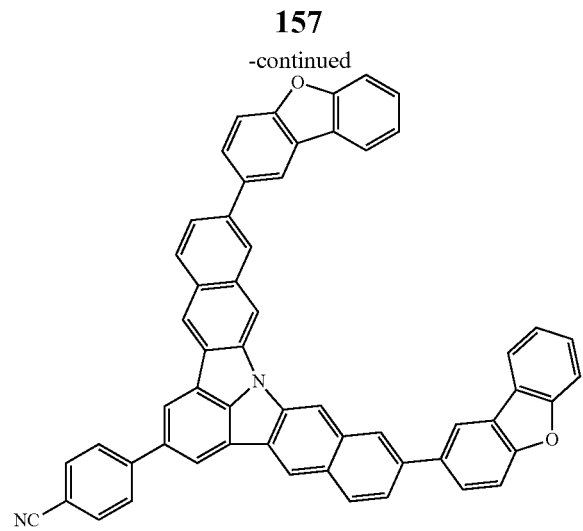
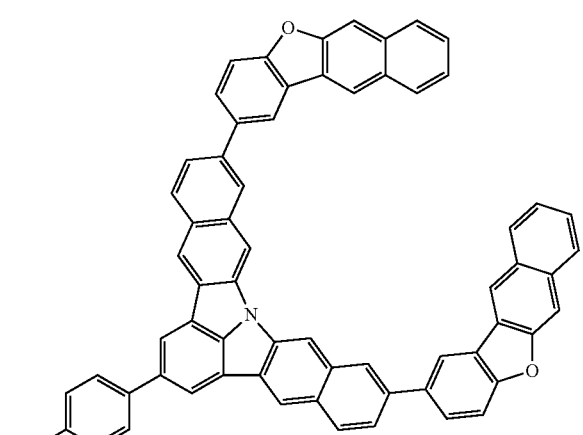
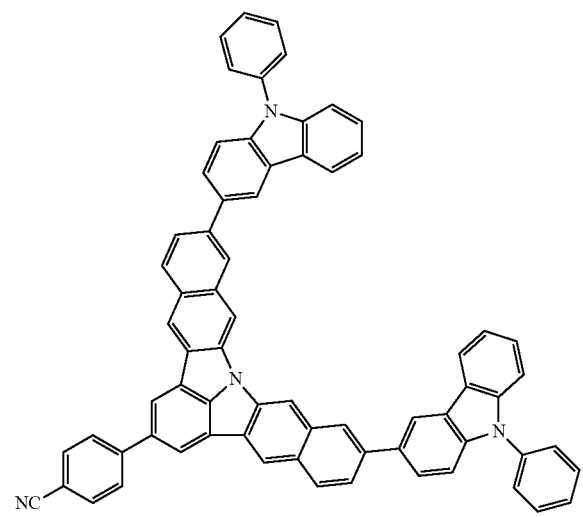
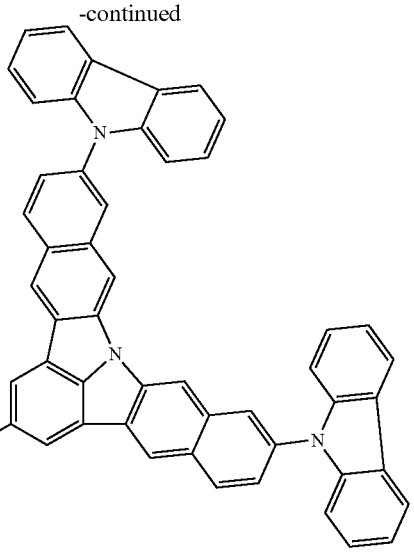
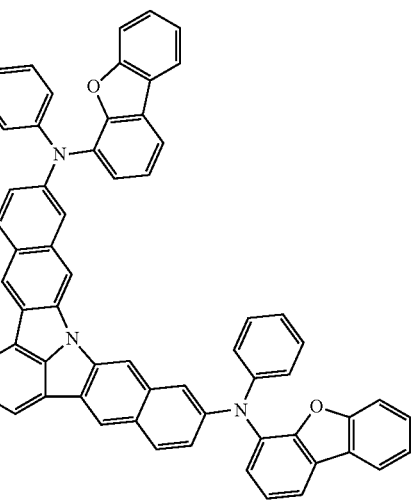
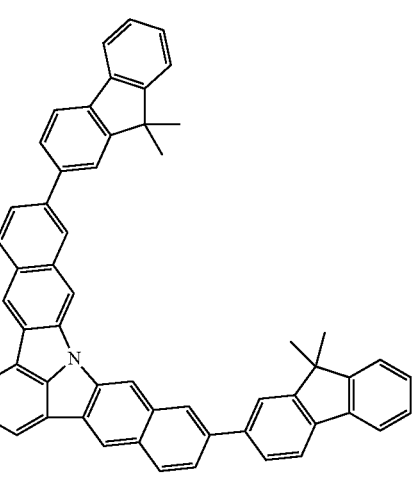

159
-continued
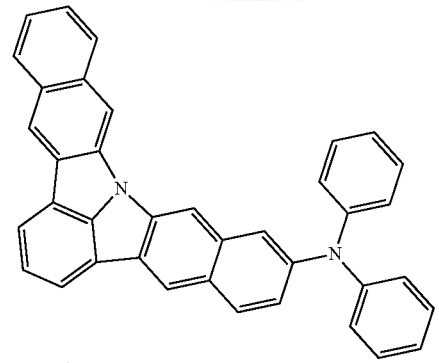
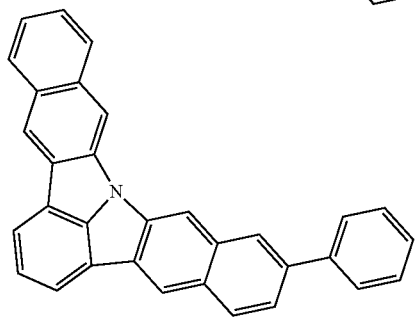
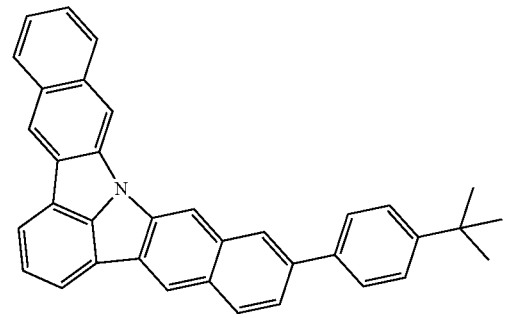
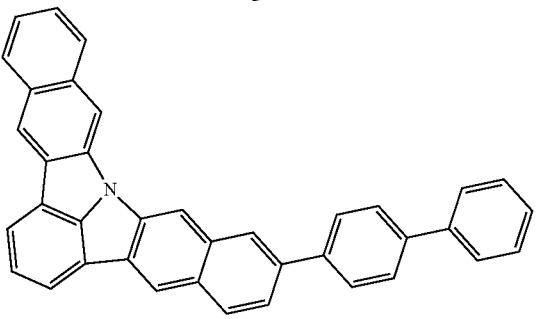
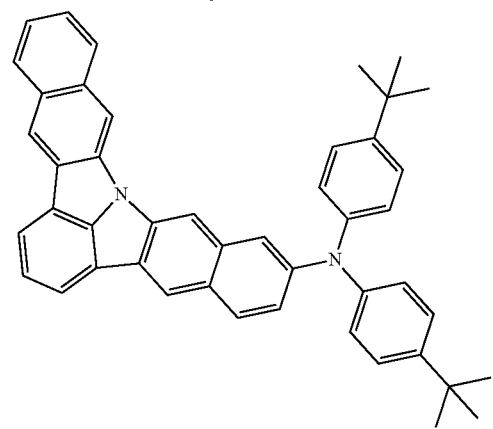
160
-continued
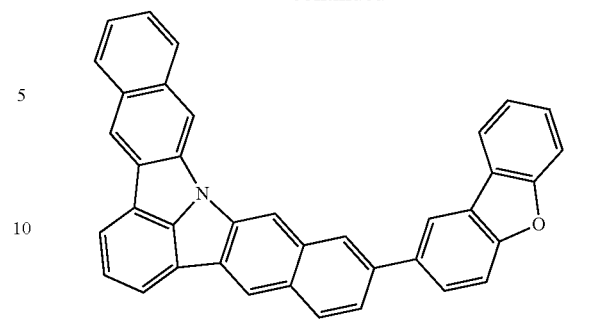
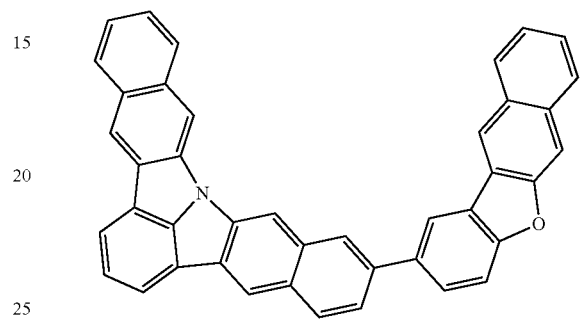
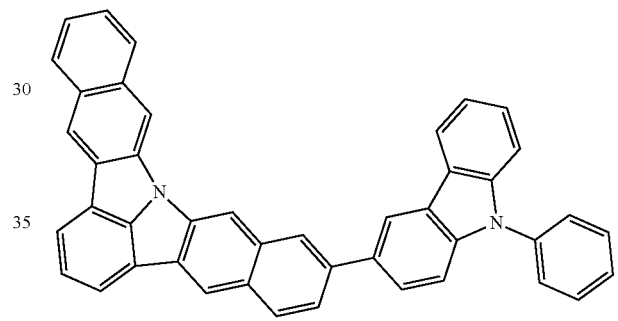
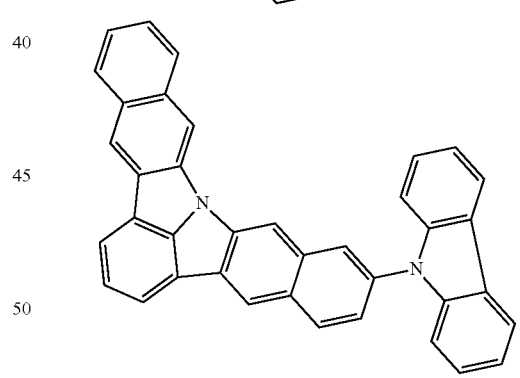
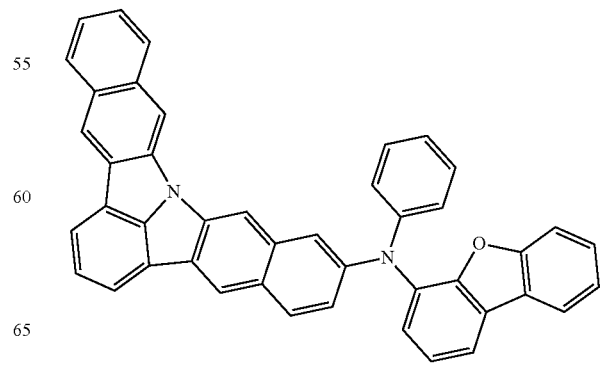

161
-continued
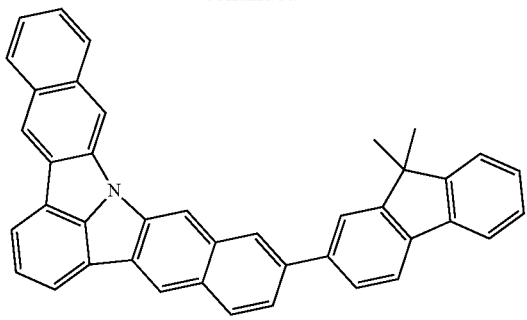
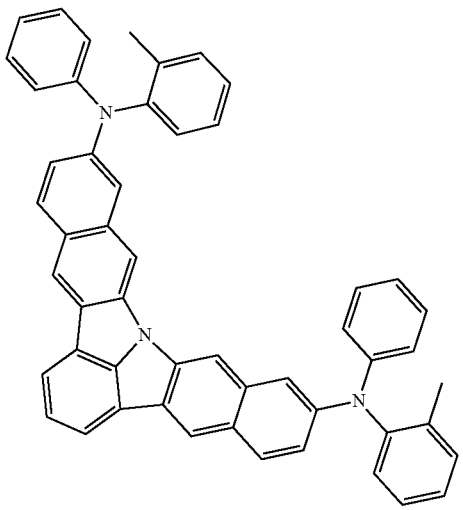
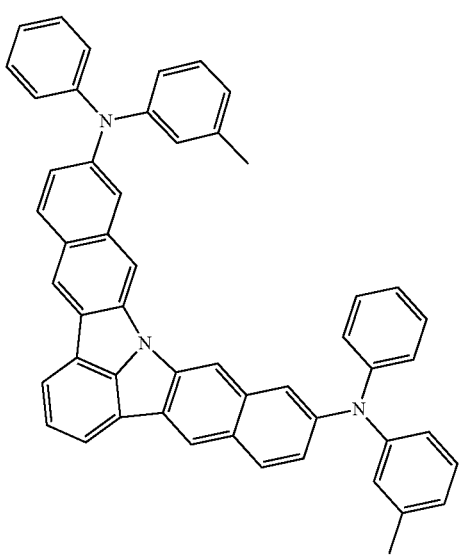
162
-continued
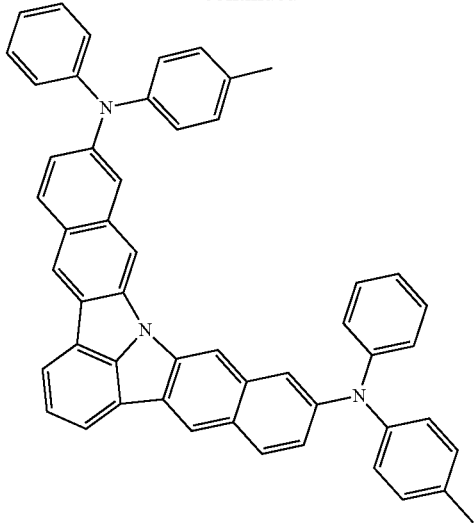
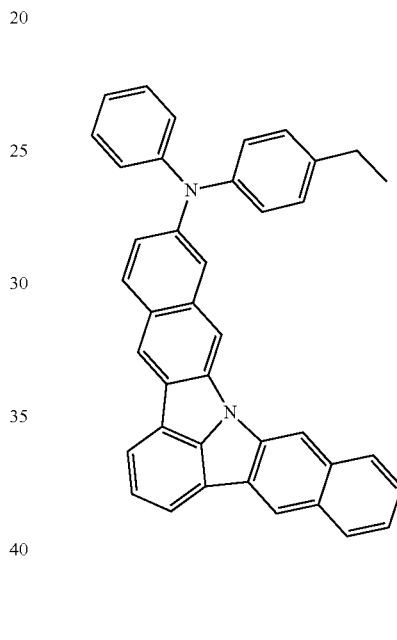
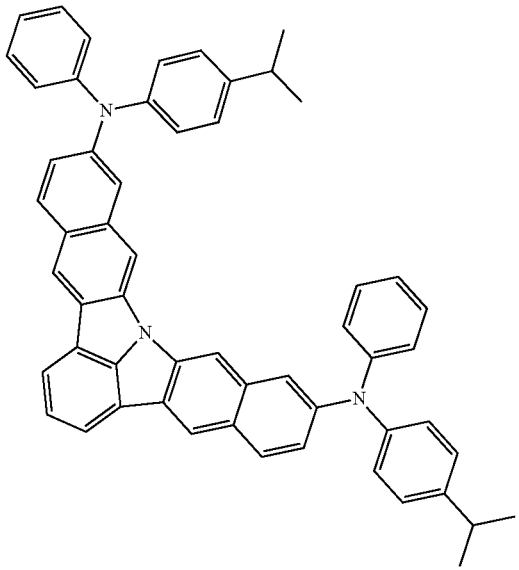

163
-continued
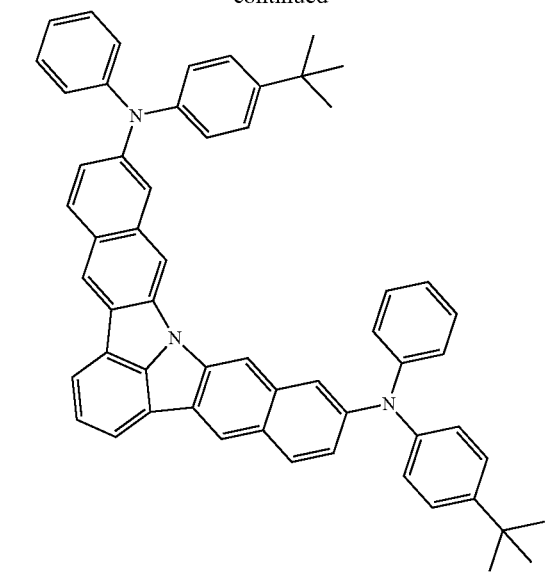
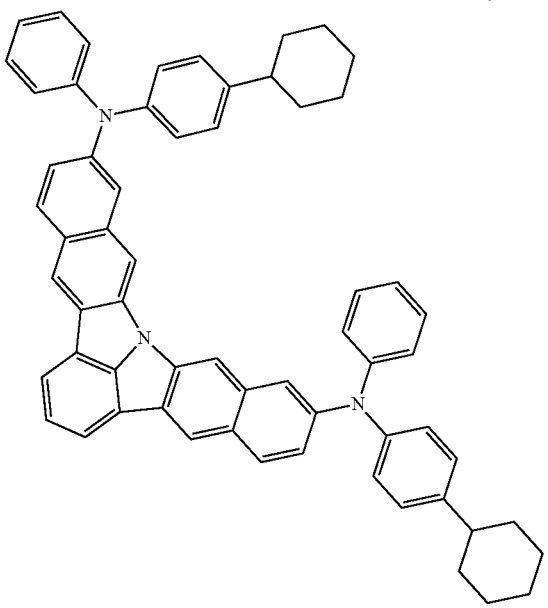
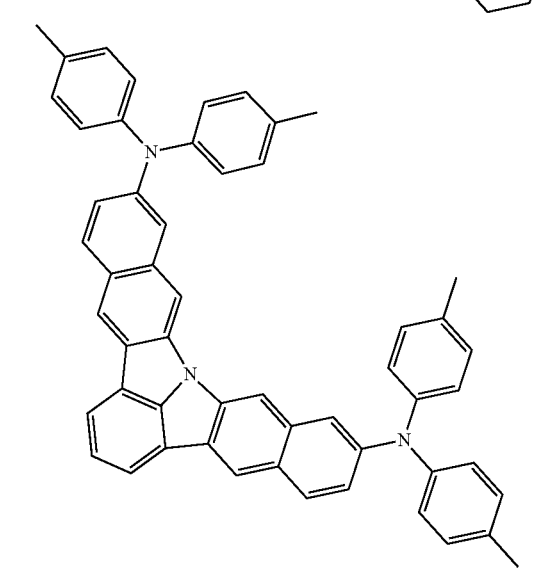
164
-continued
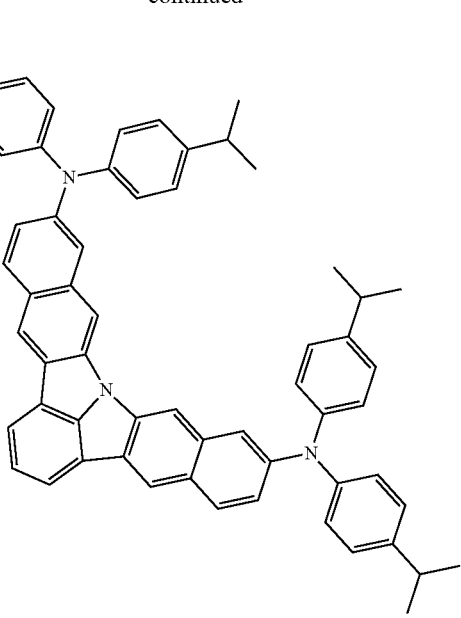
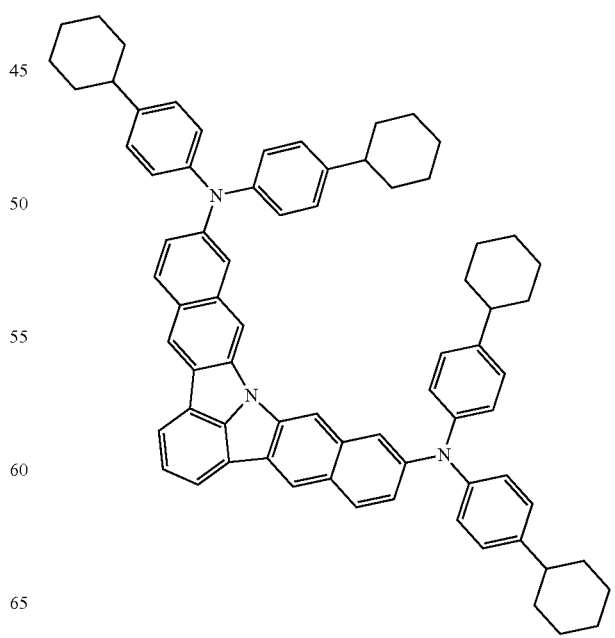

-continued
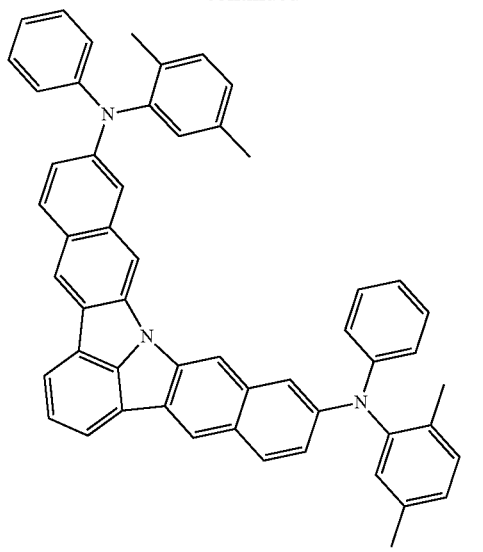
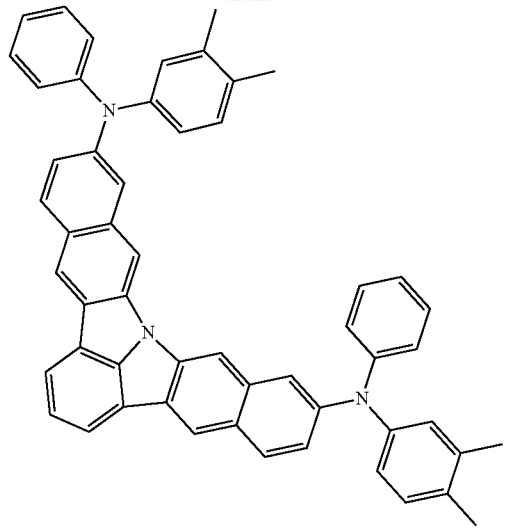
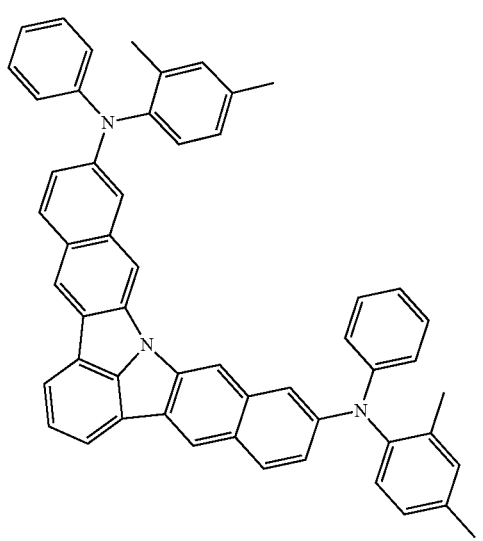
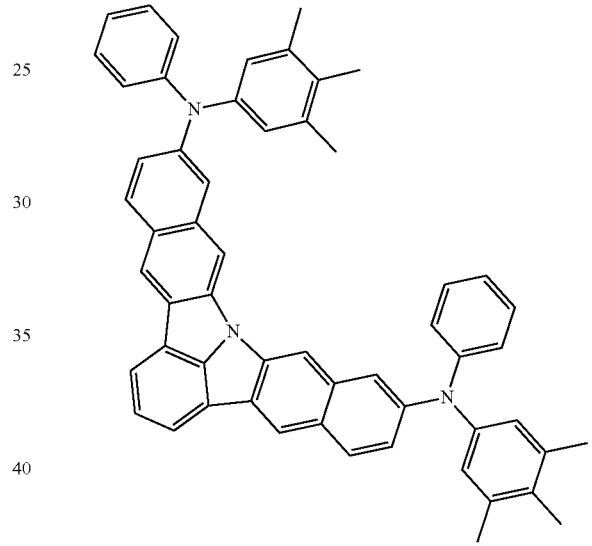
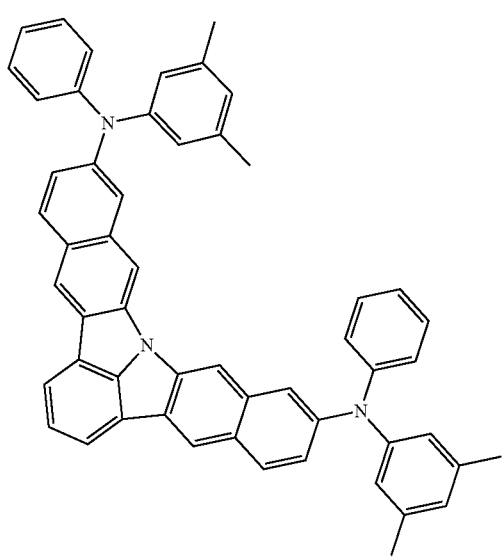
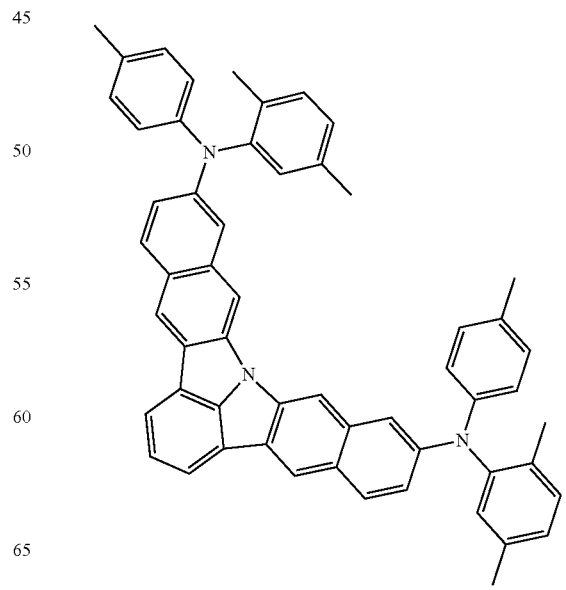

167
-continued
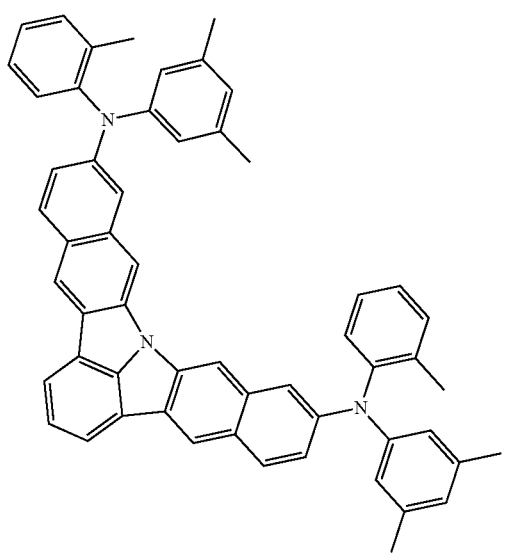
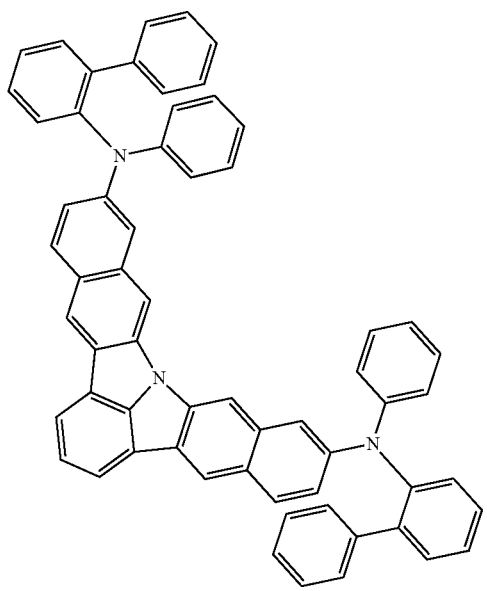
168
-continued
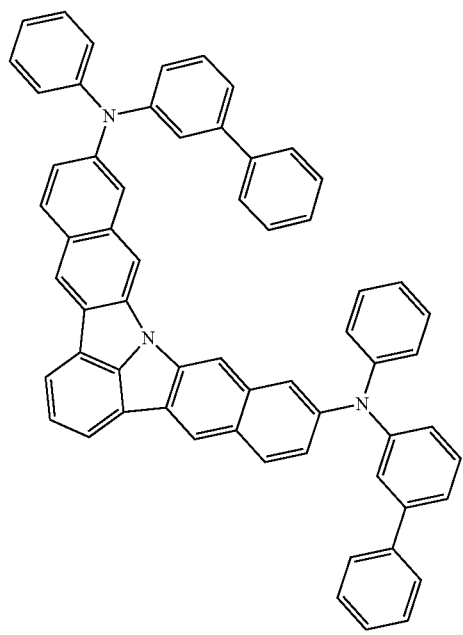
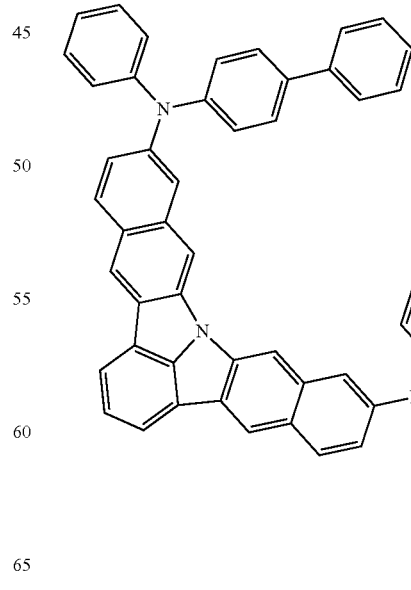

169
-continued
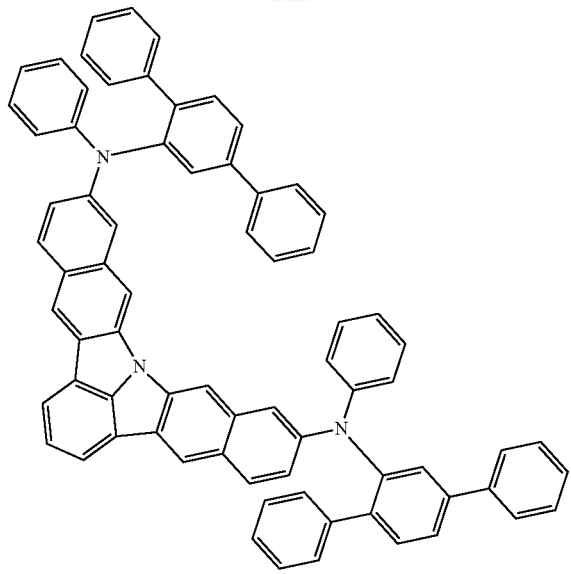
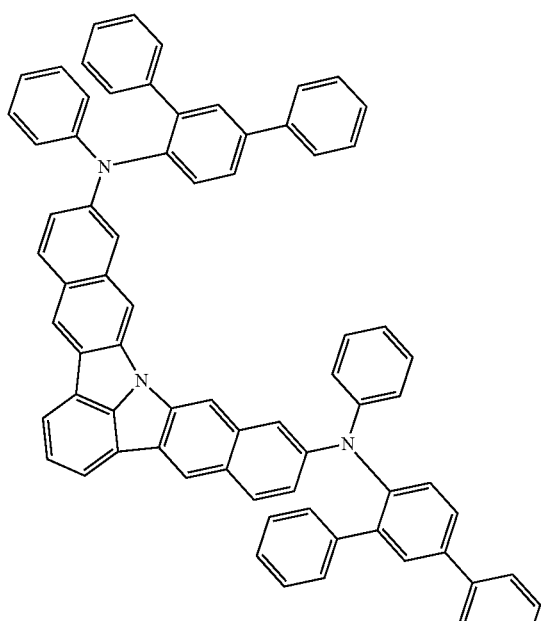
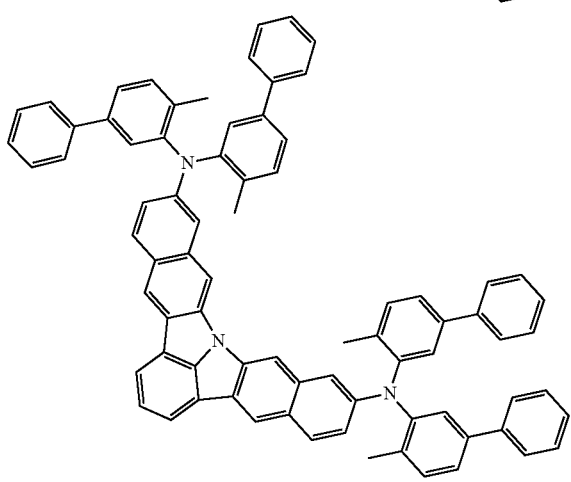
170
-continued
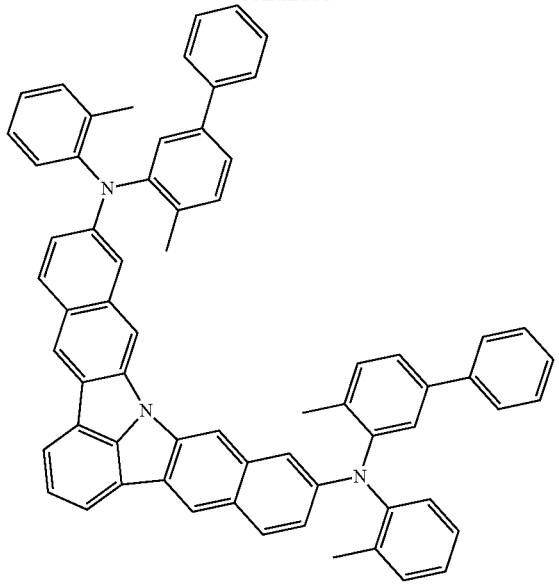
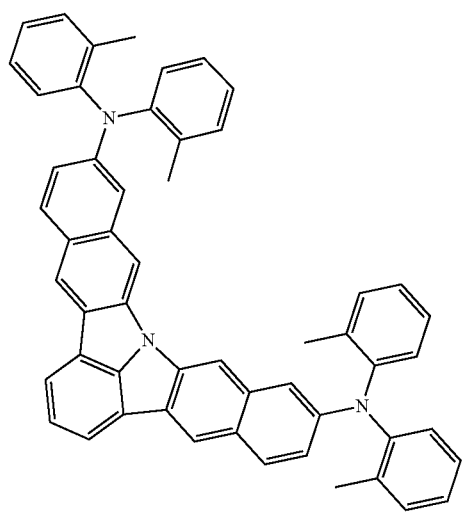
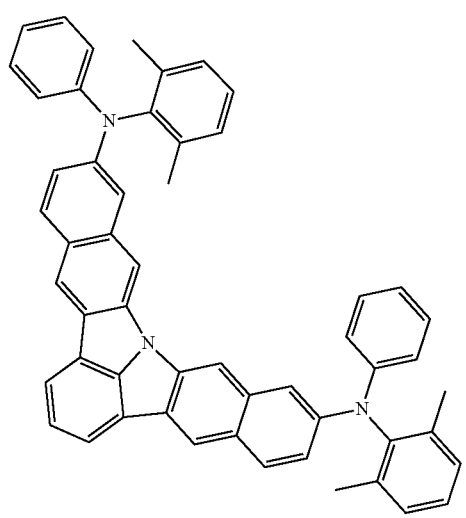

171 -continued
172 -continued
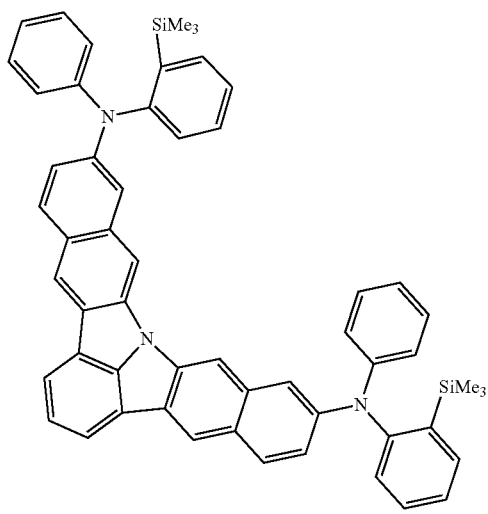
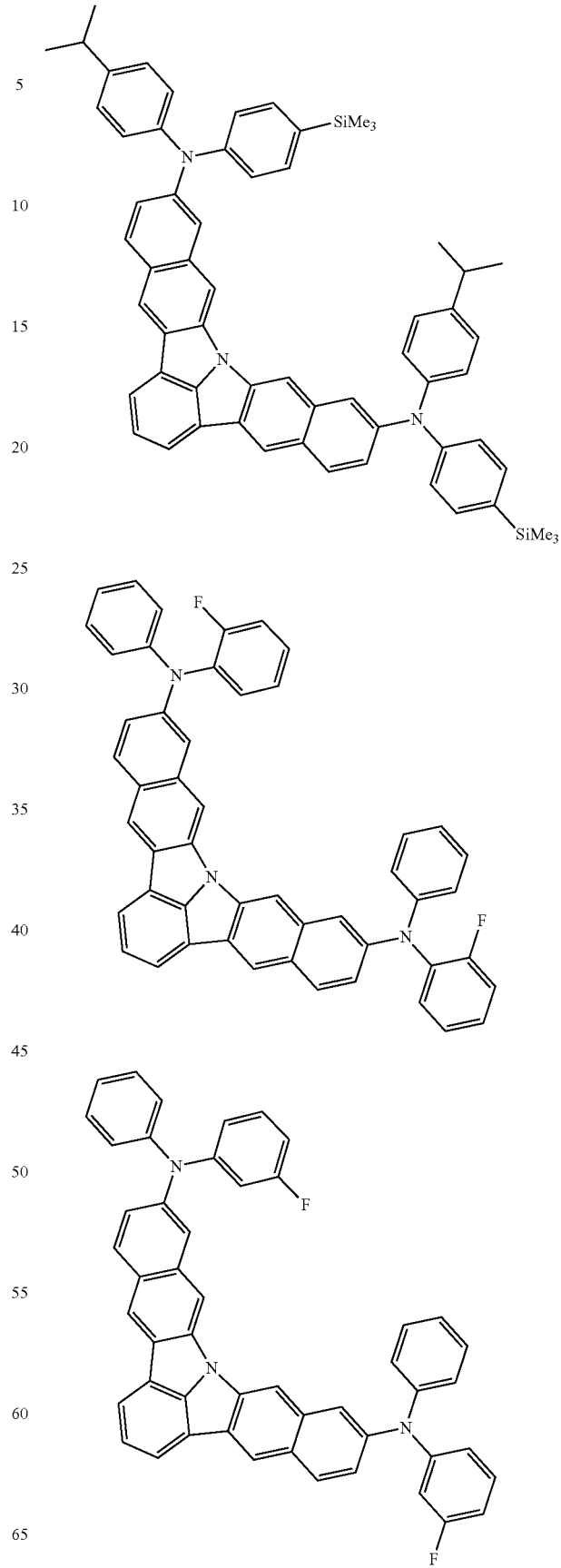

173
-continued
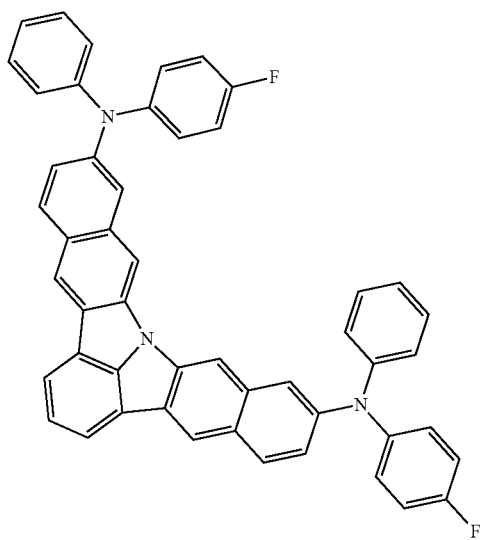
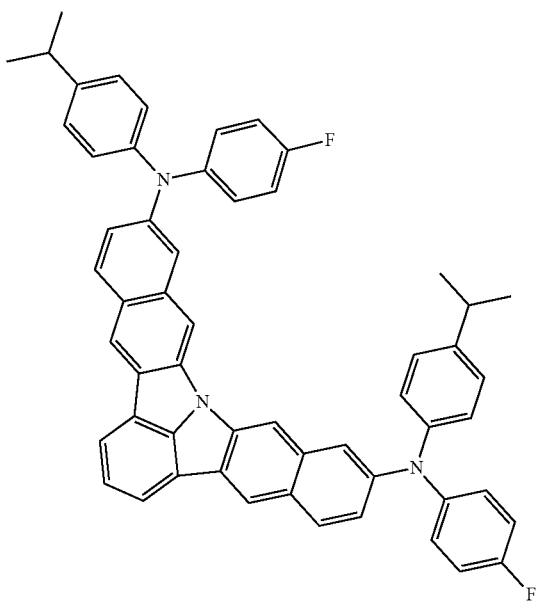
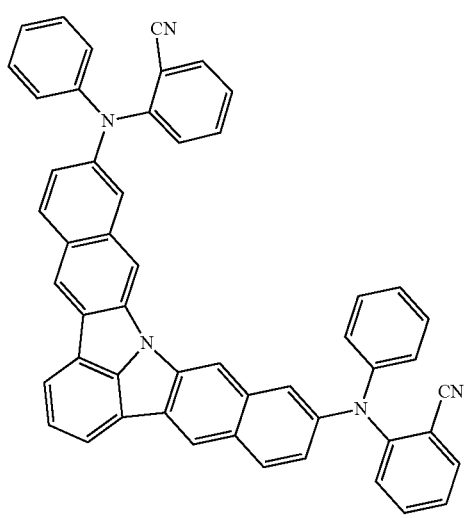
174
-continued
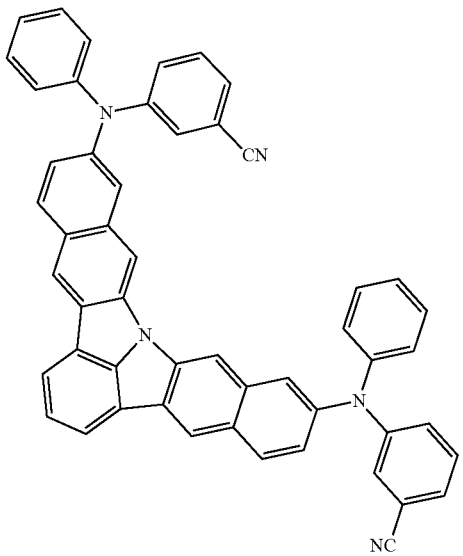
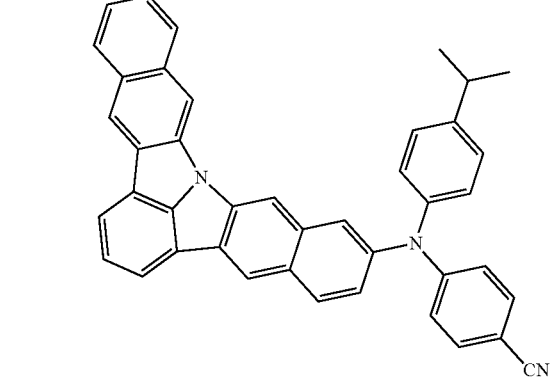

175
-continued
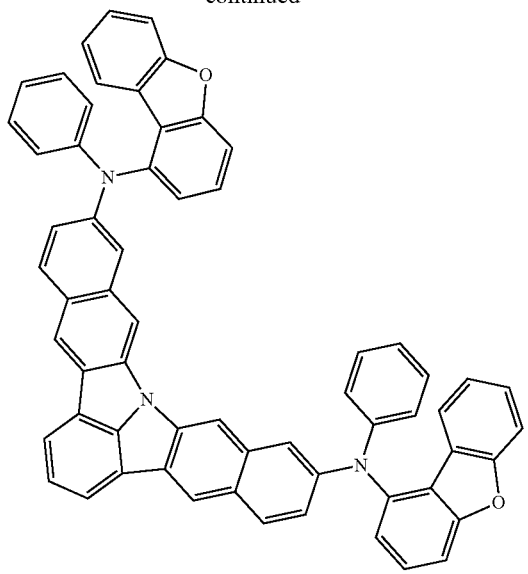
176
-continued
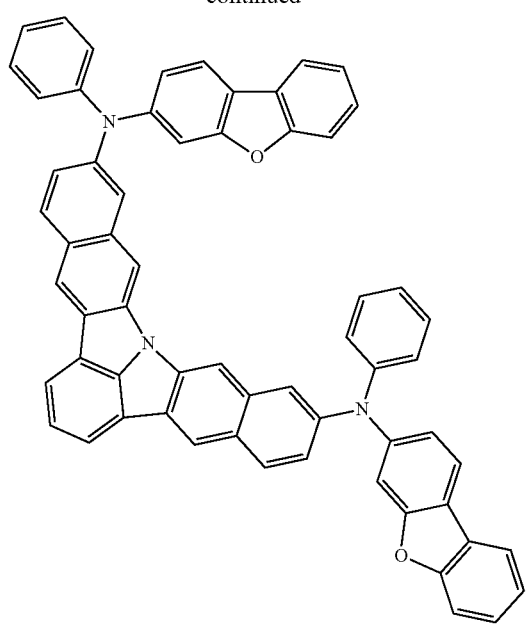
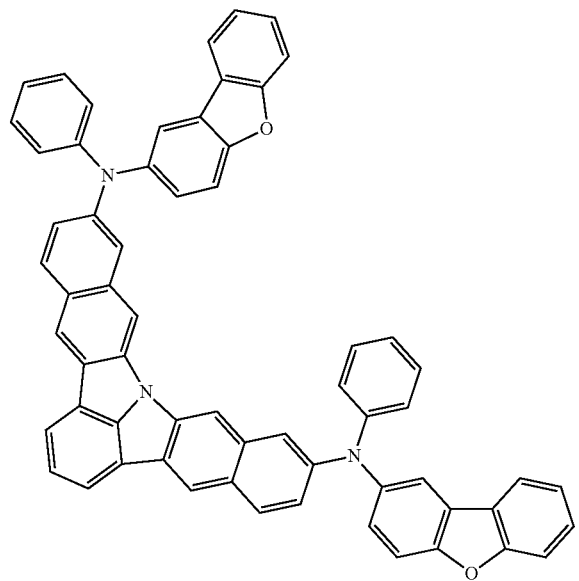
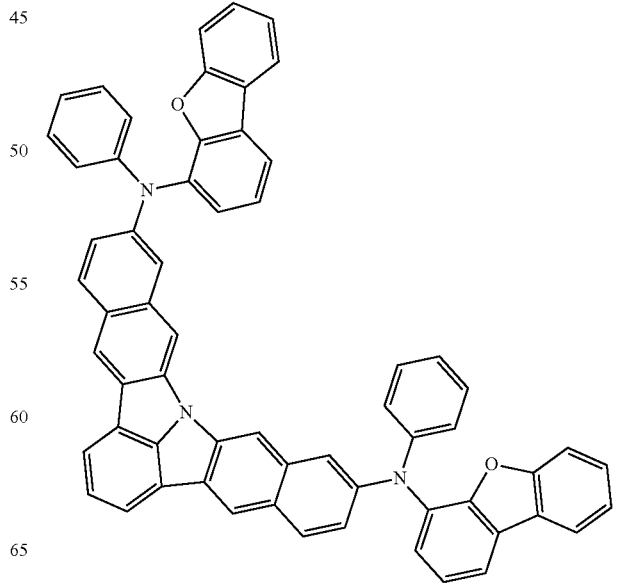

177
-continued
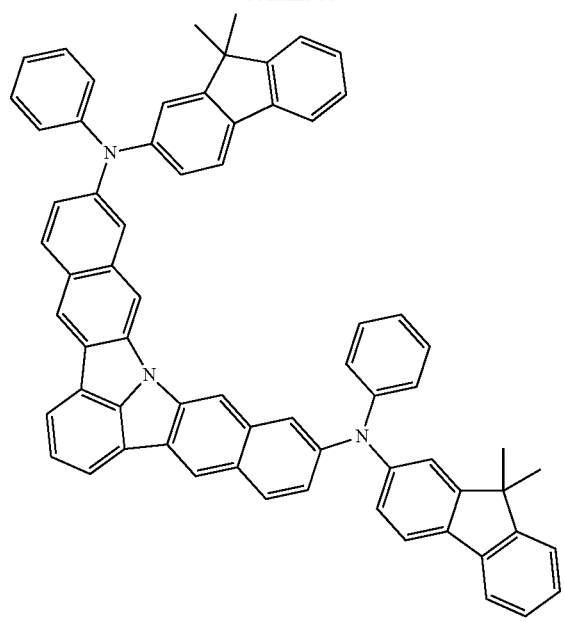
178
-continued
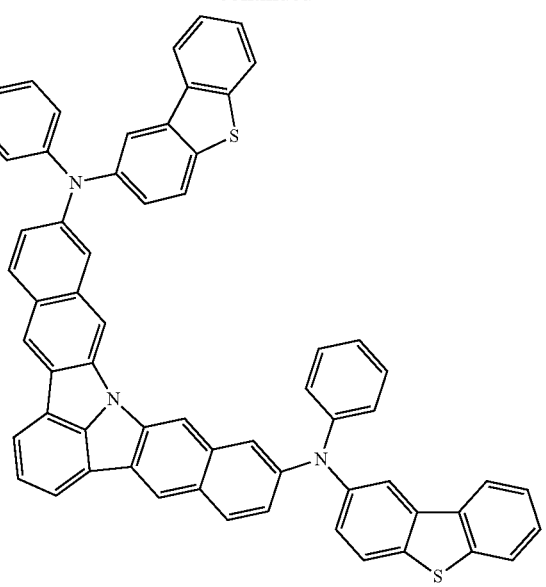
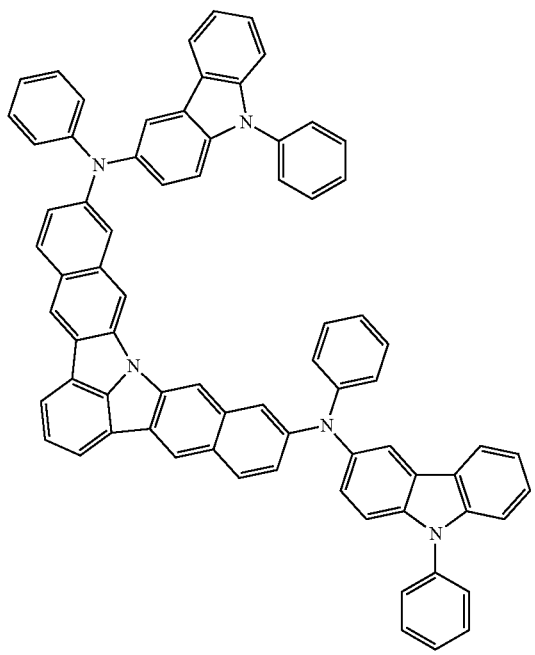
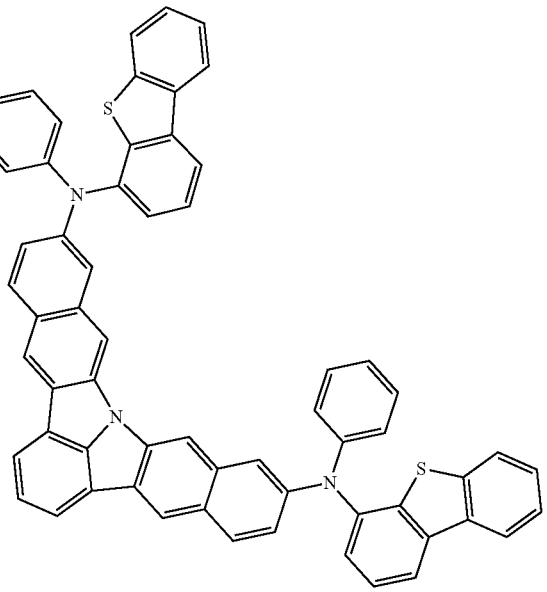

179
-continued
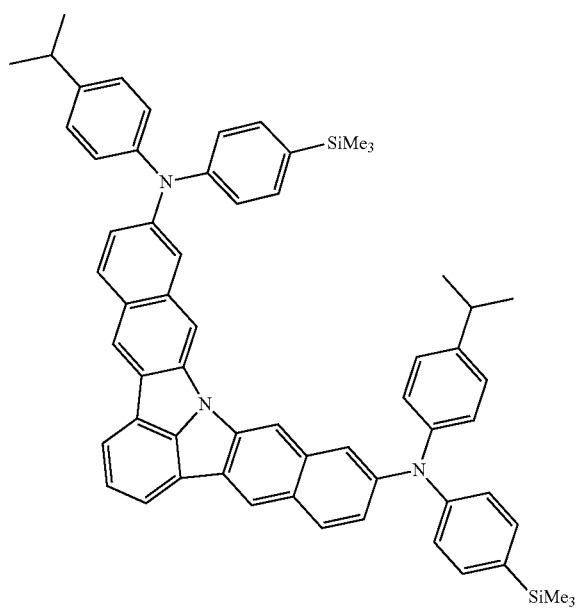
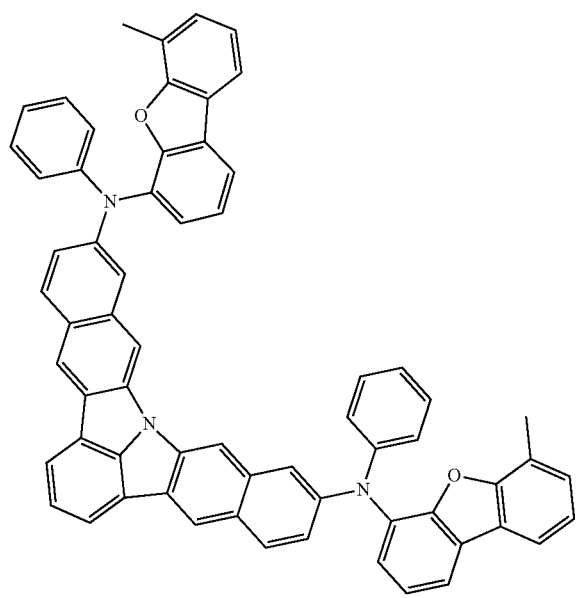
180
-continued
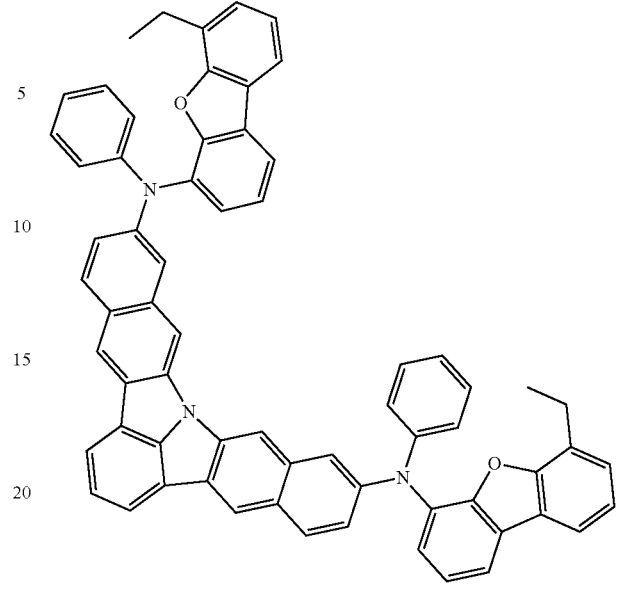
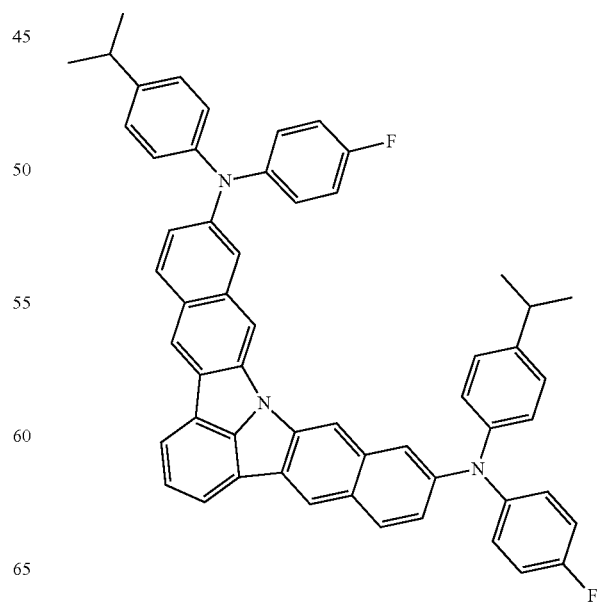

181
-continued
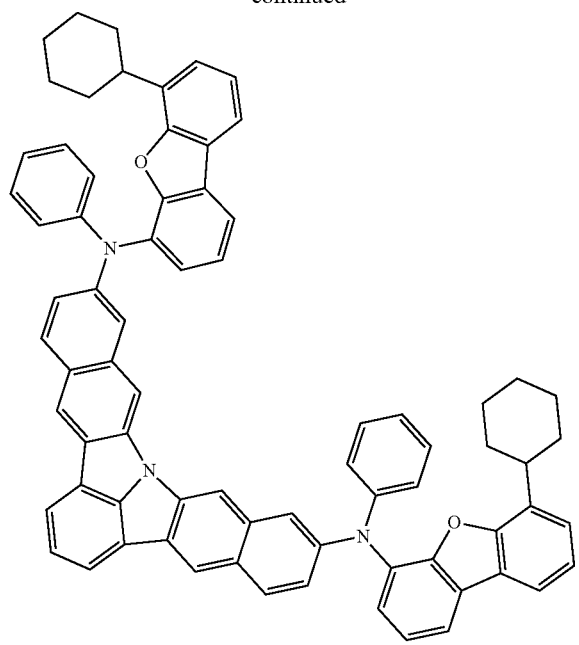
182
-continued
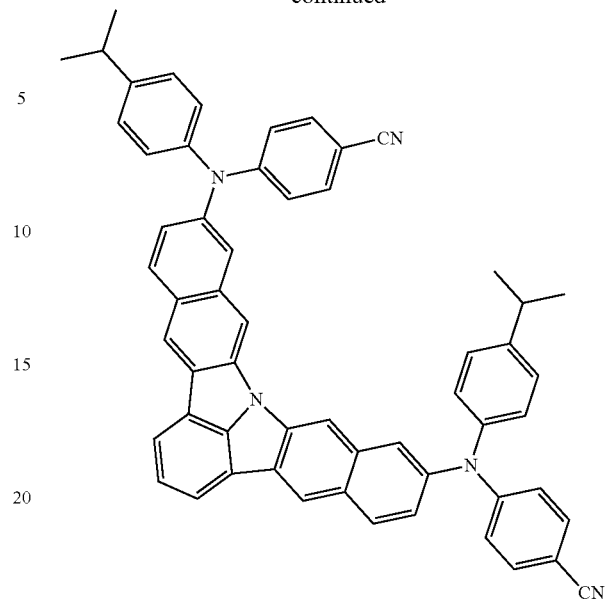
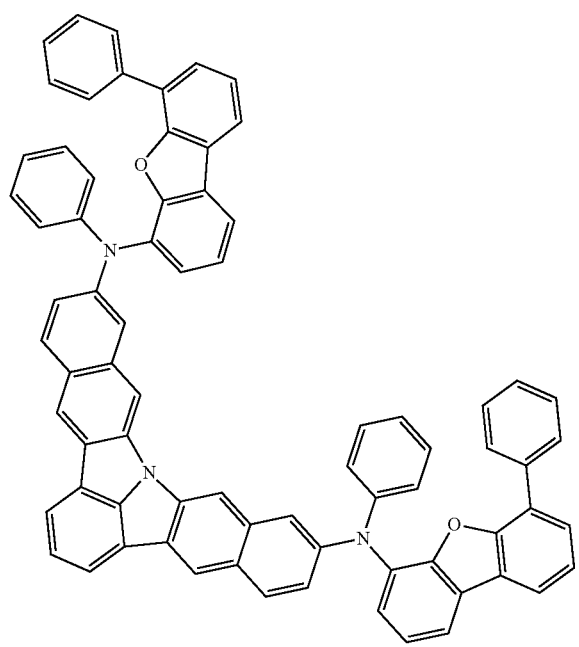
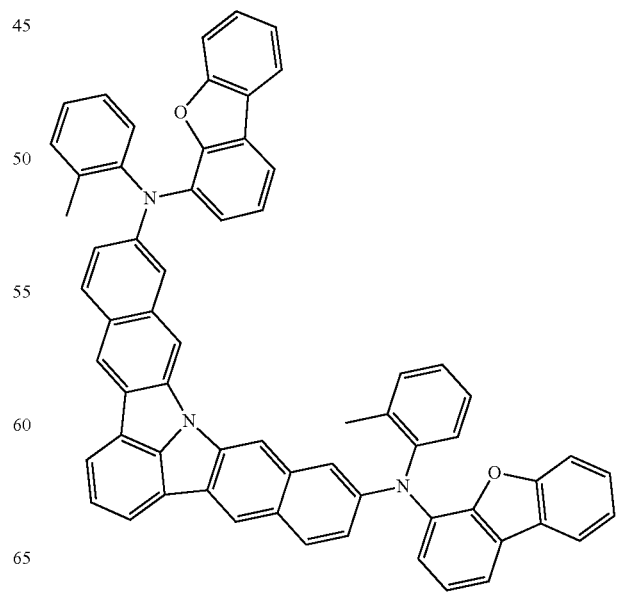

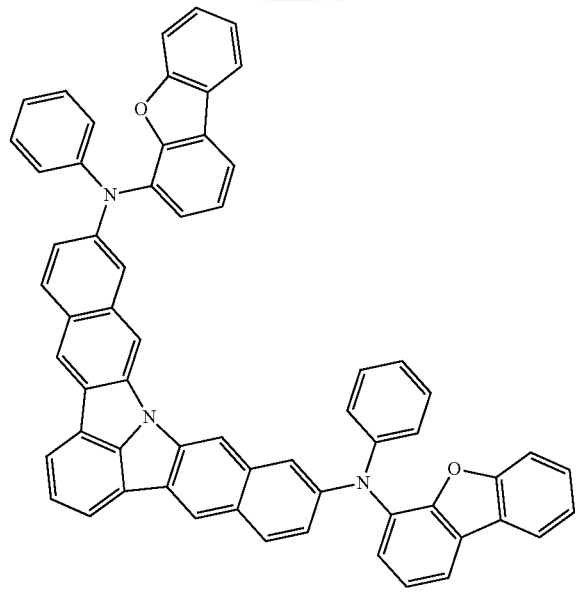
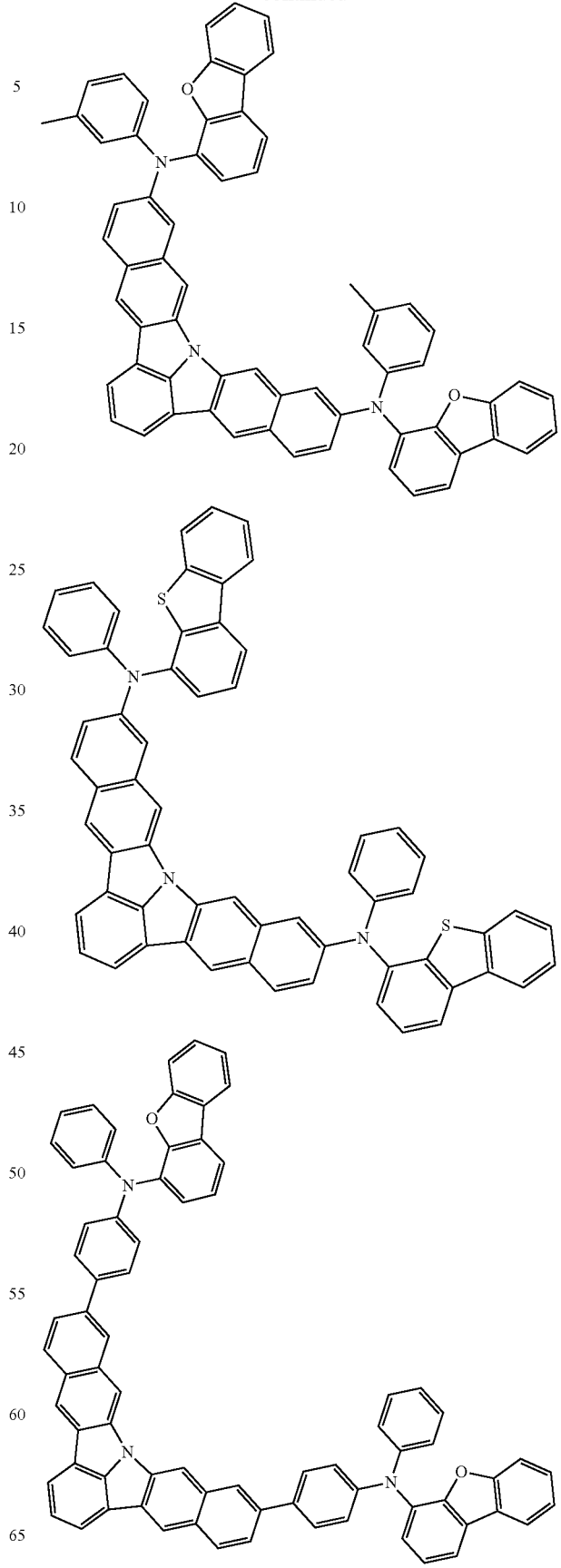

185
-continued
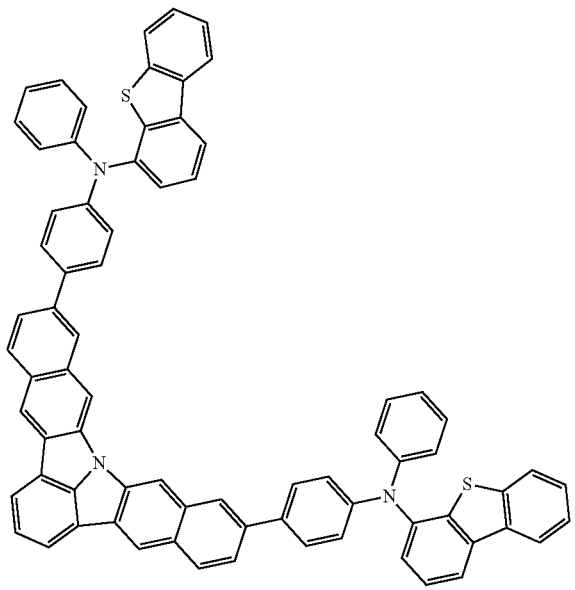
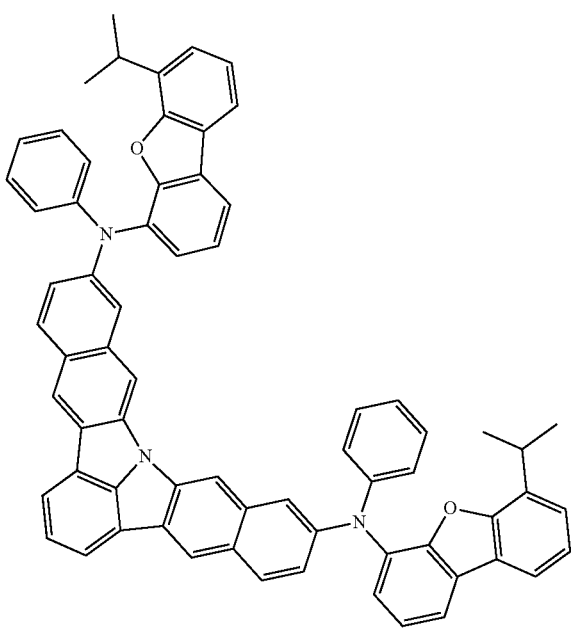
186
-continued
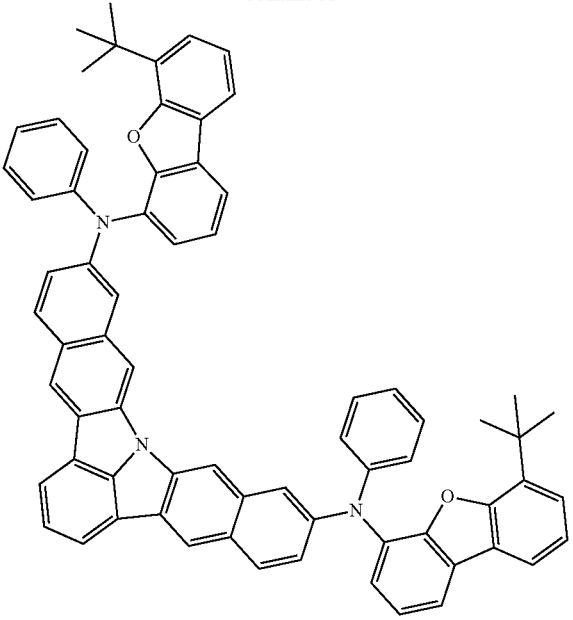
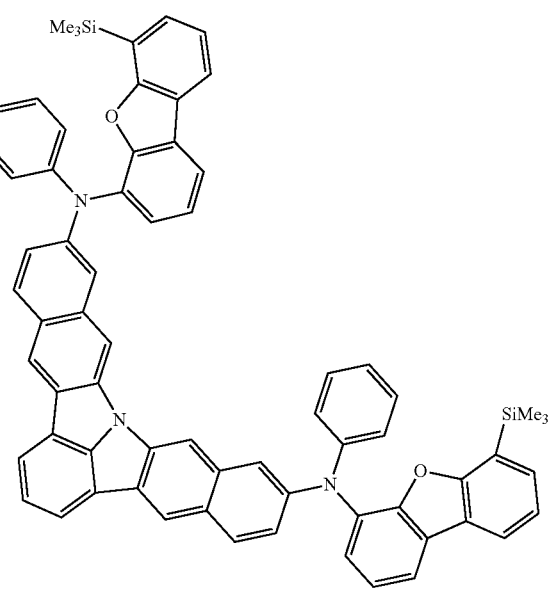

187
-continued
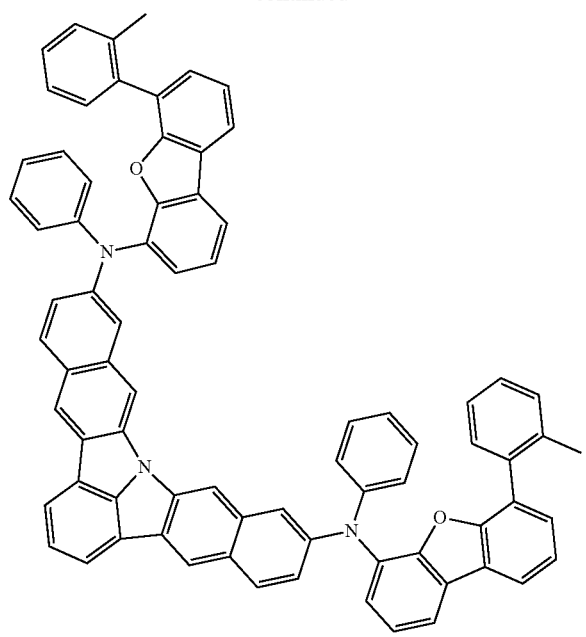
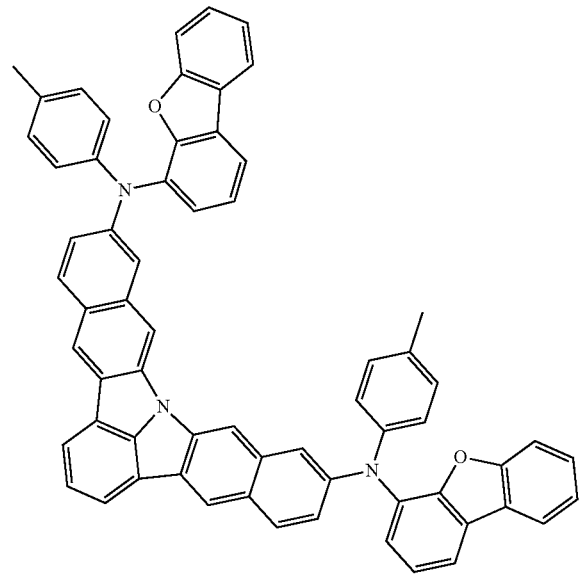
188
-continued
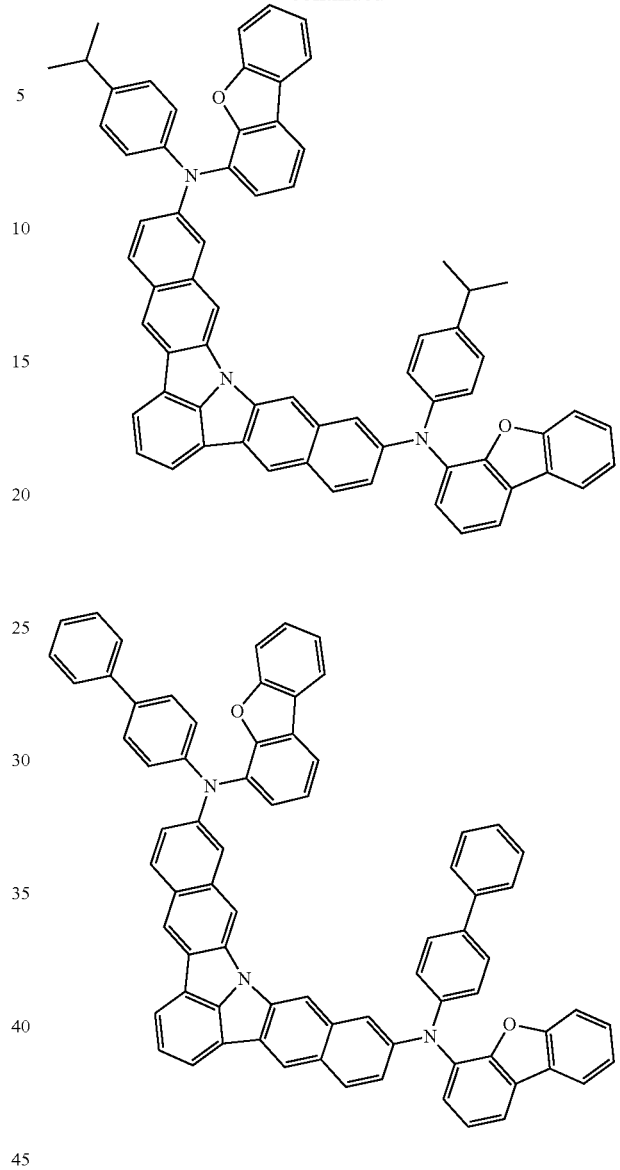
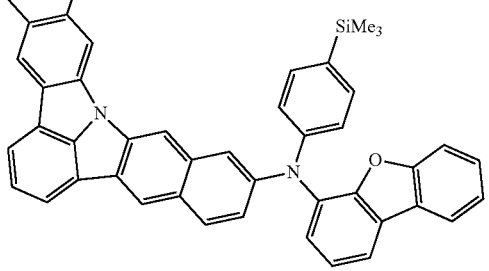

189
-continued
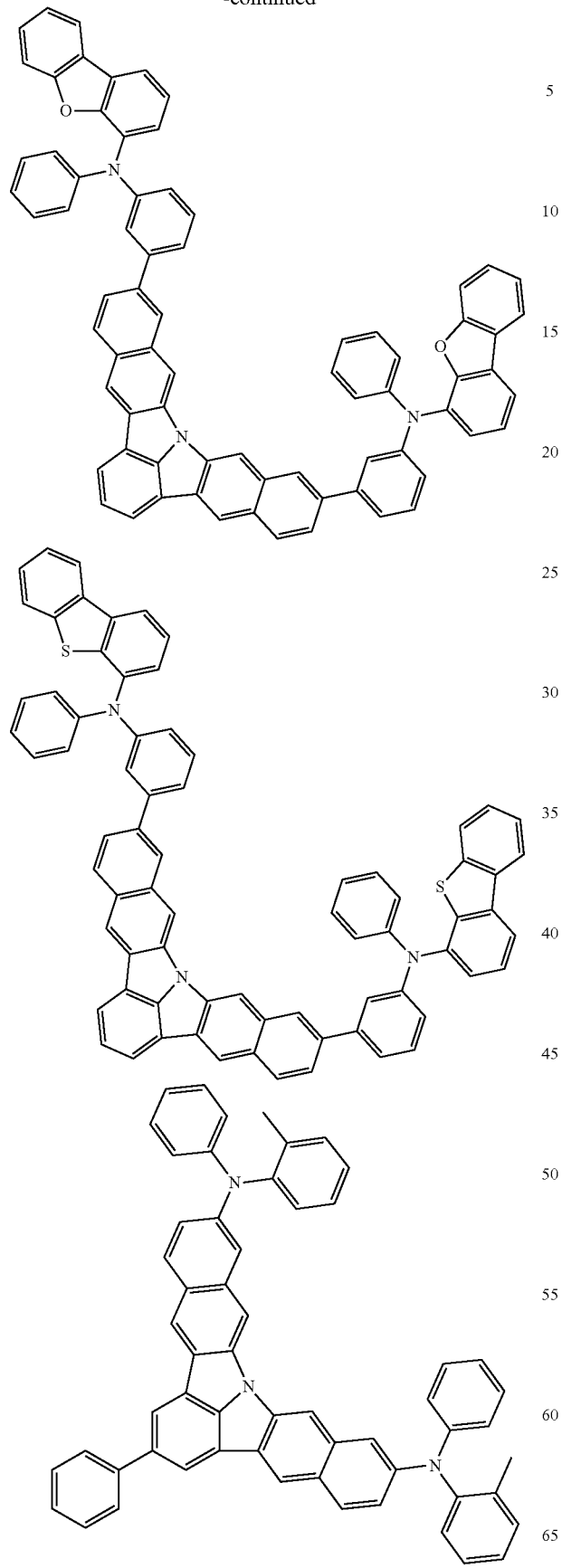
190
-continued

191
-continued
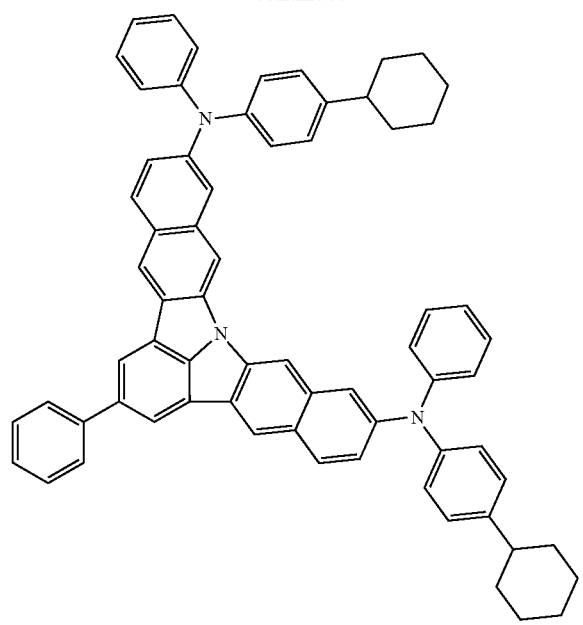
192
-continued
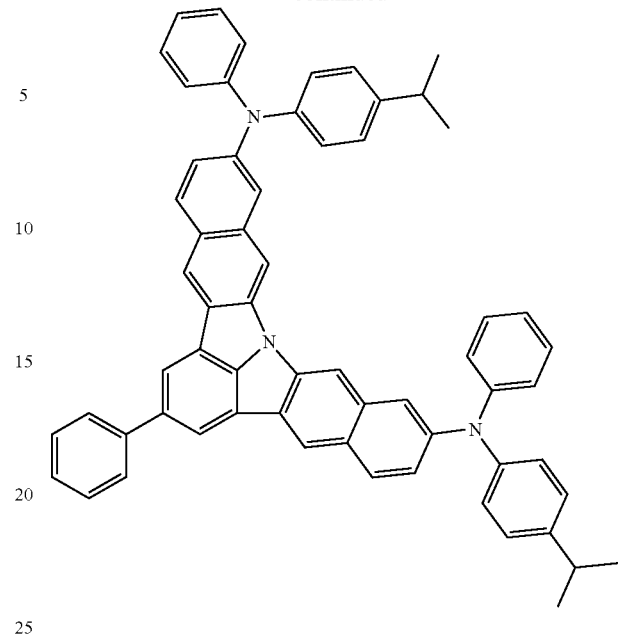
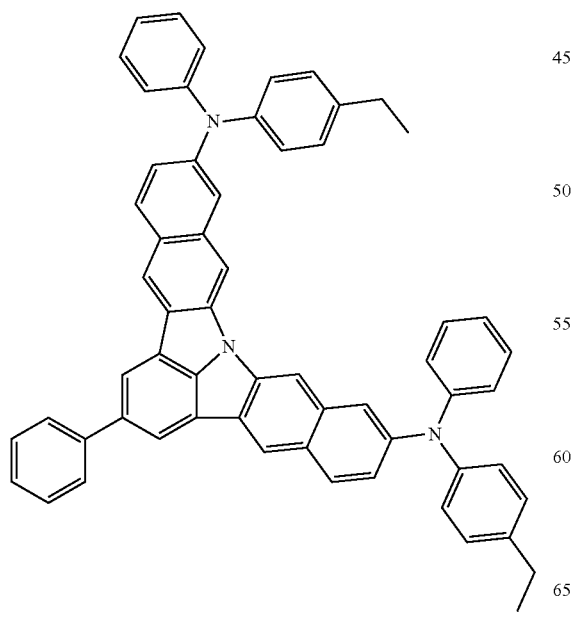
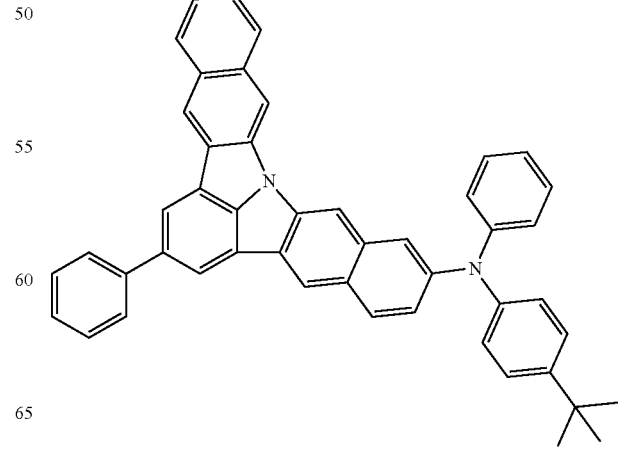

193
-continued
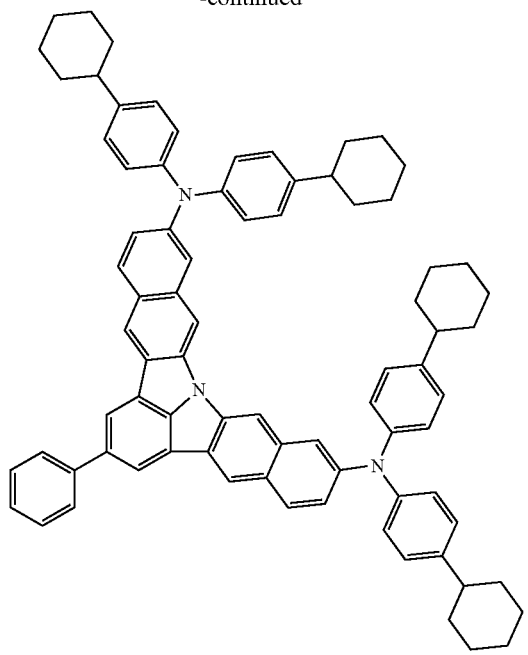
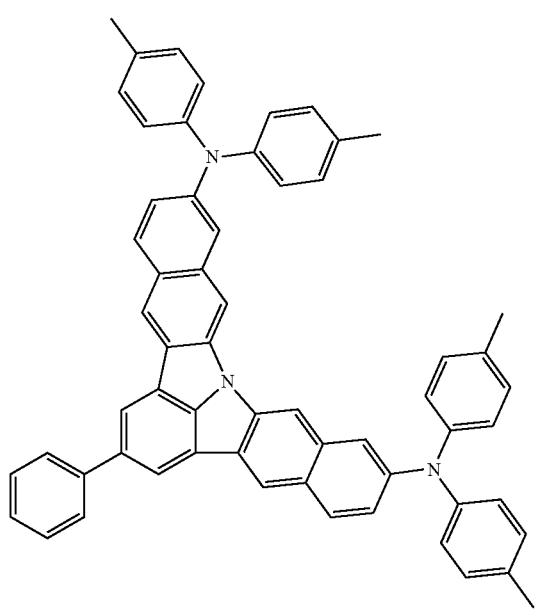
194
-continued
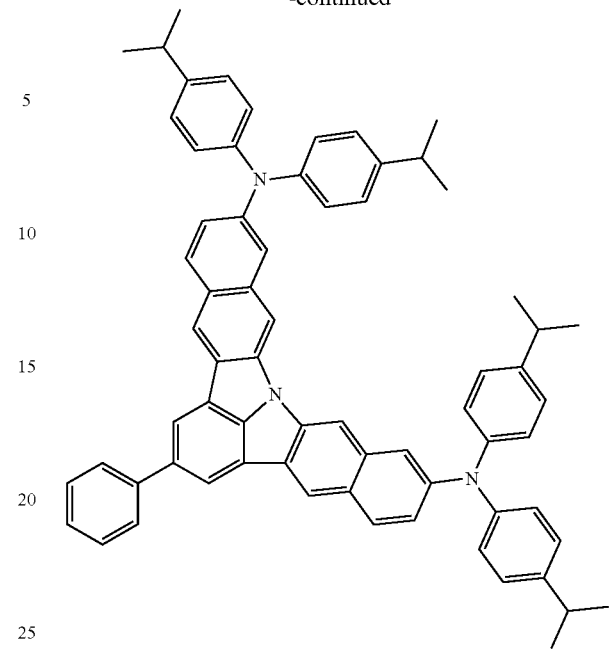
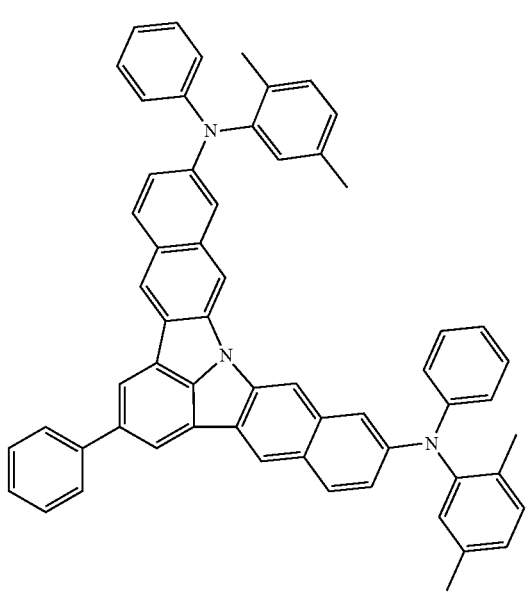

195
-continued
196
-continued
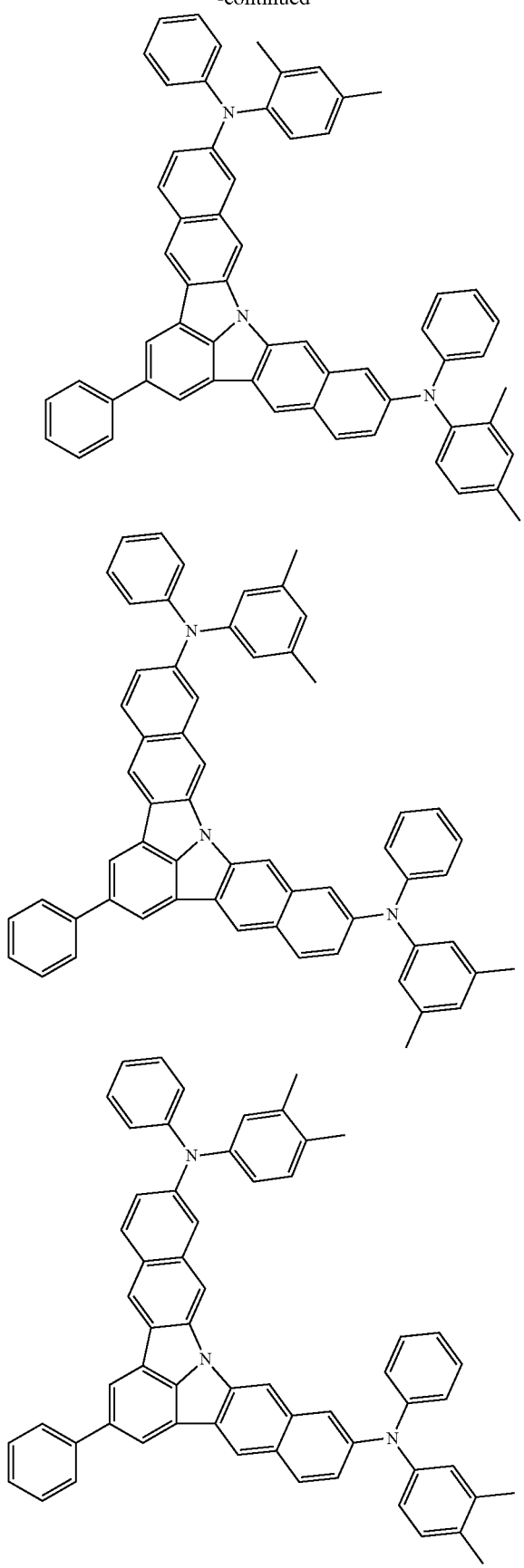
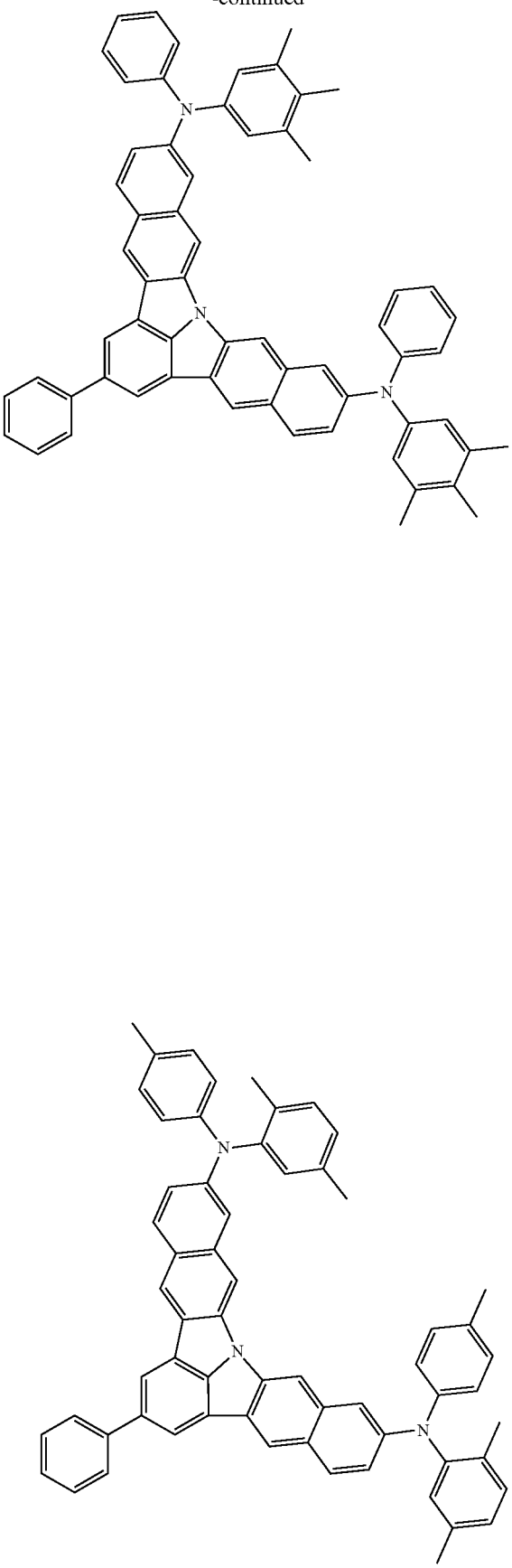

197
-continued
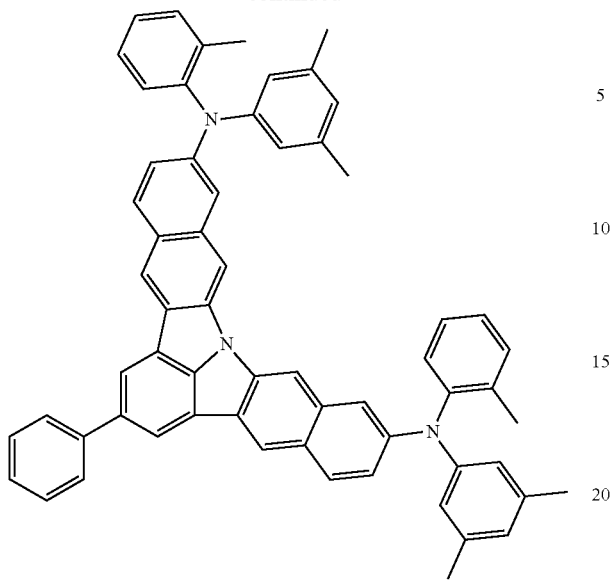
198
-continued
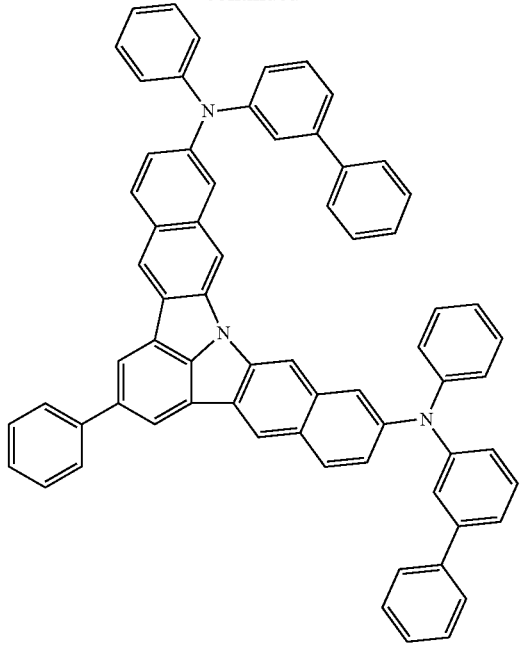
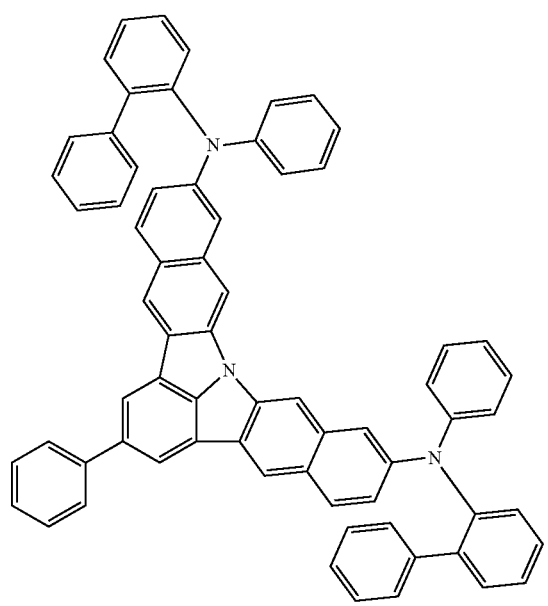
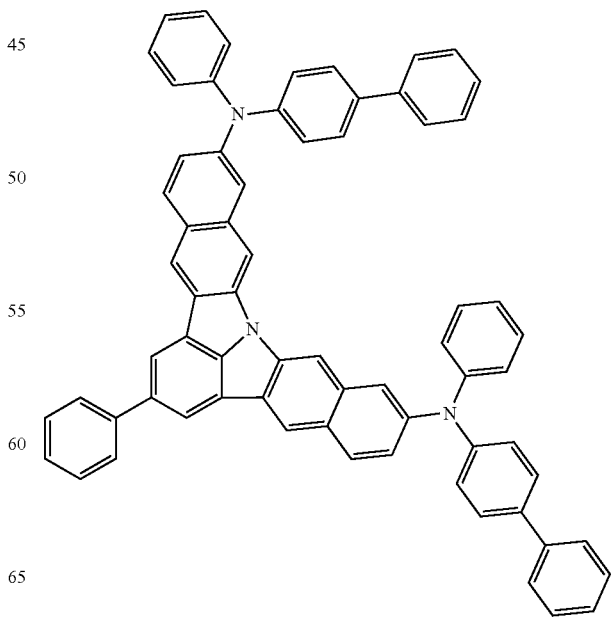

199
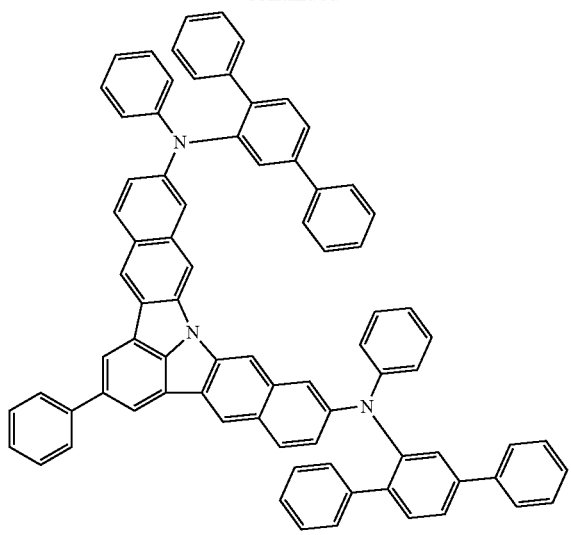
200
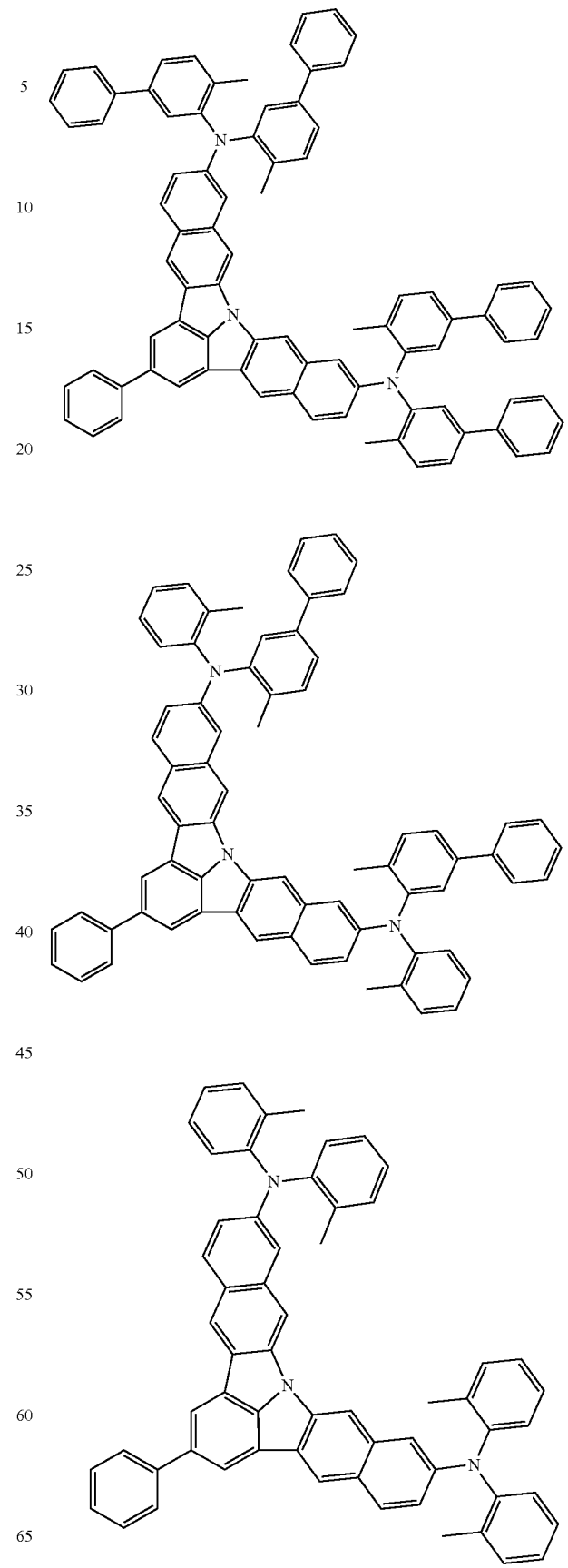

201
-continued
202
-continued
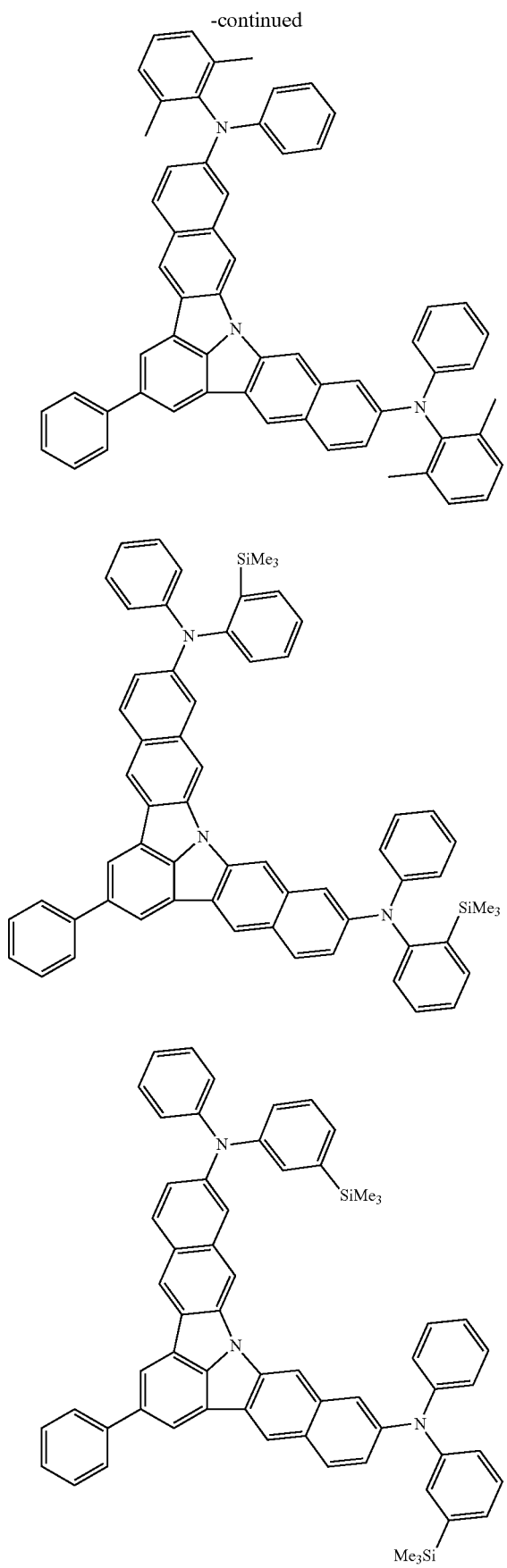
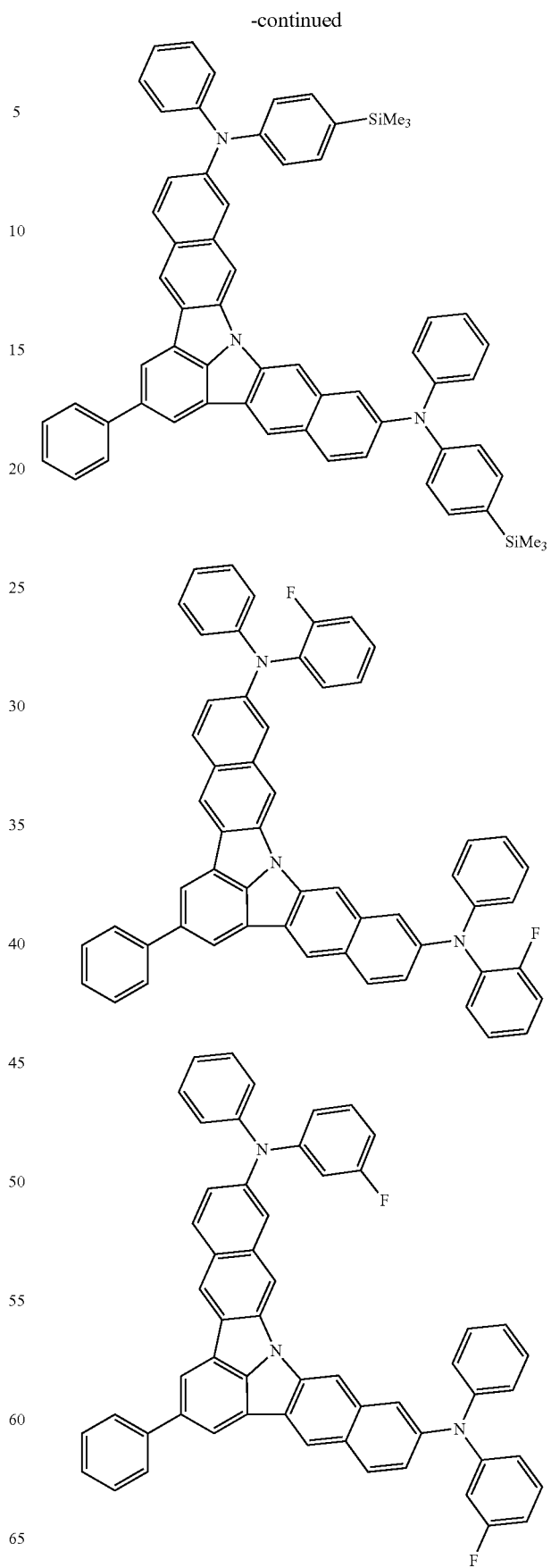

203
-continued
204
-continued
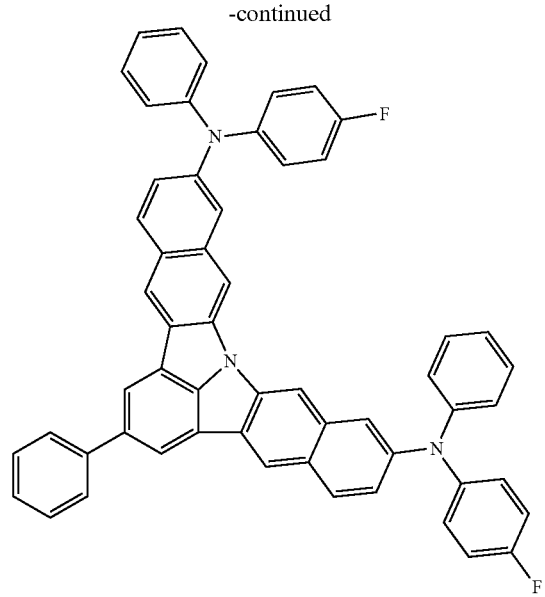
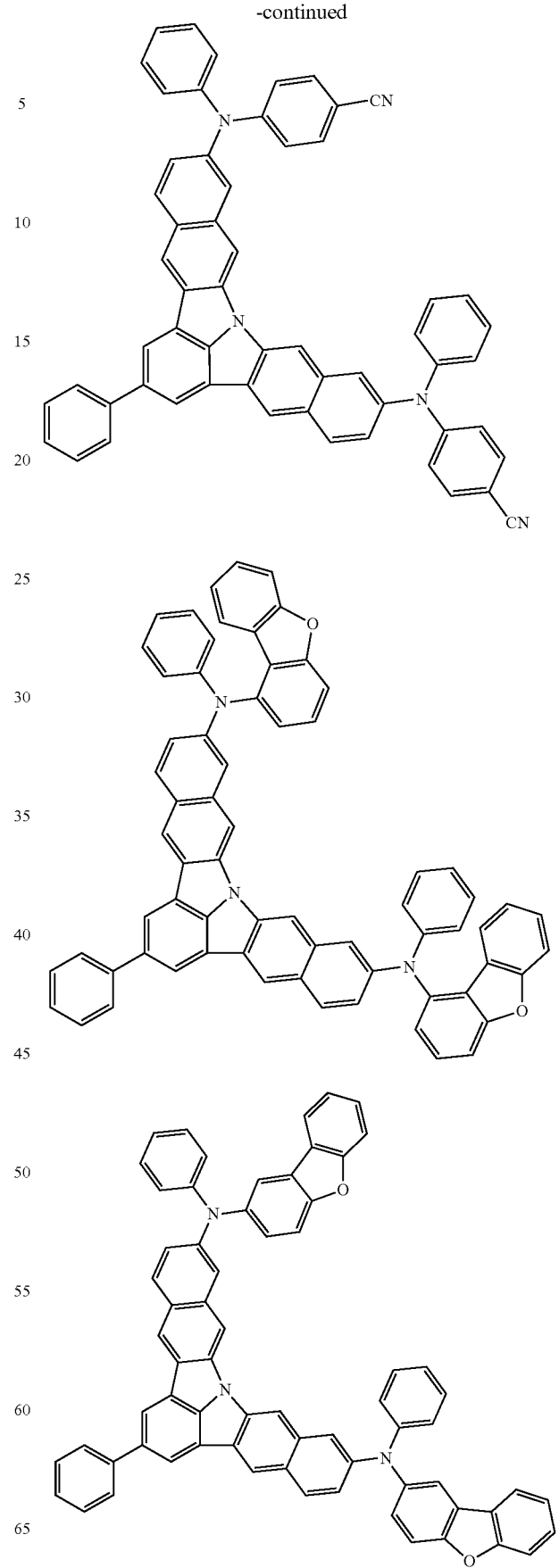

205
-continued
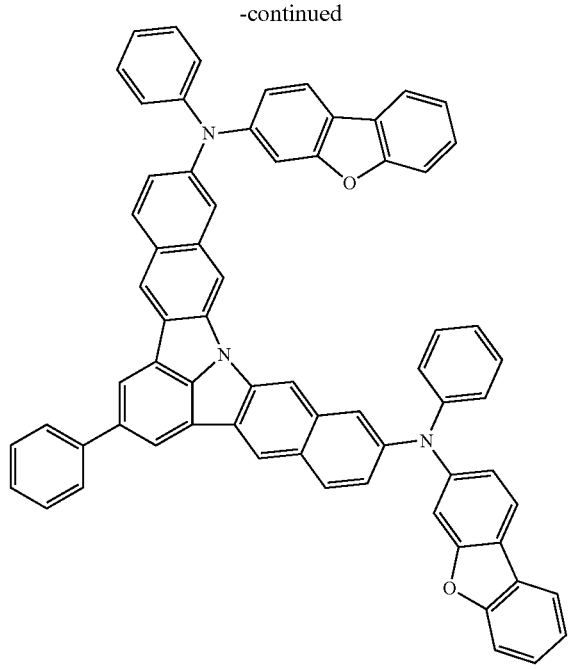
206
-continued
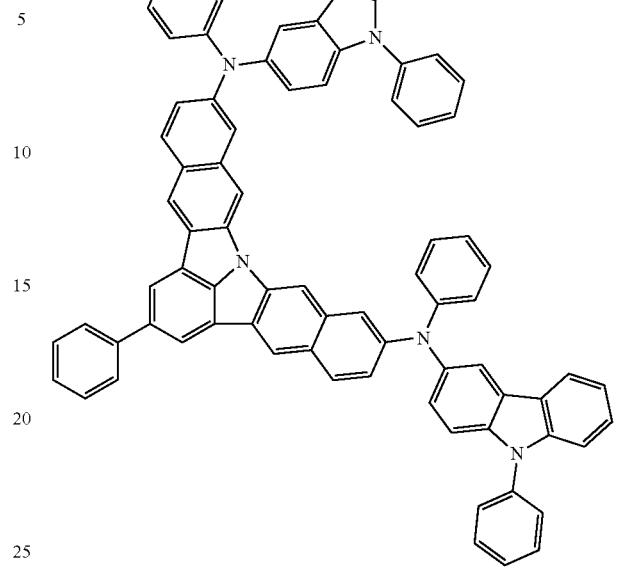
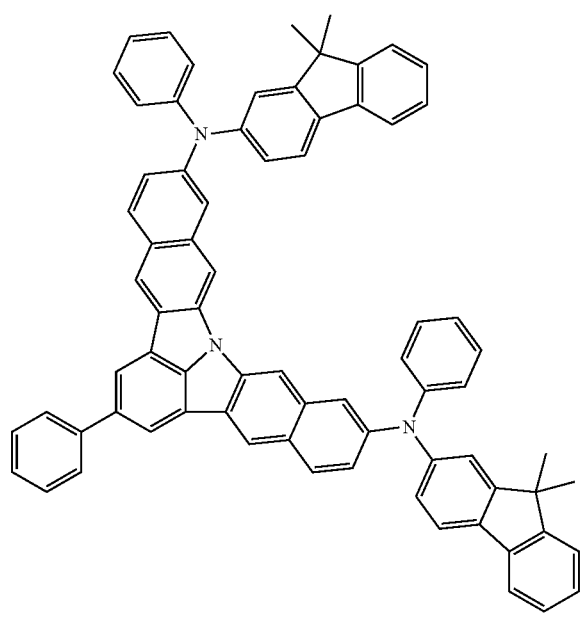
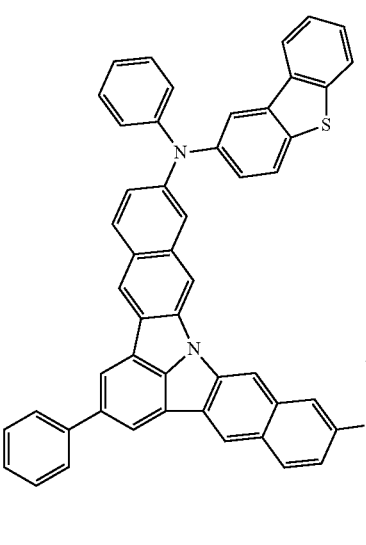

207
-continued
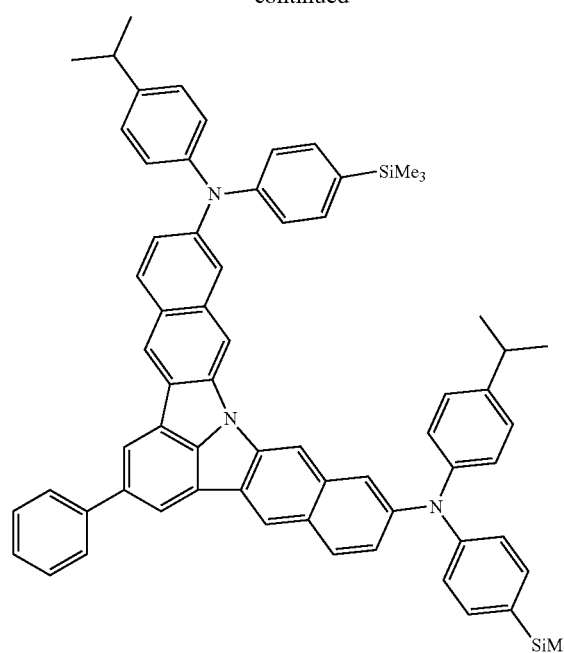
208
-continued
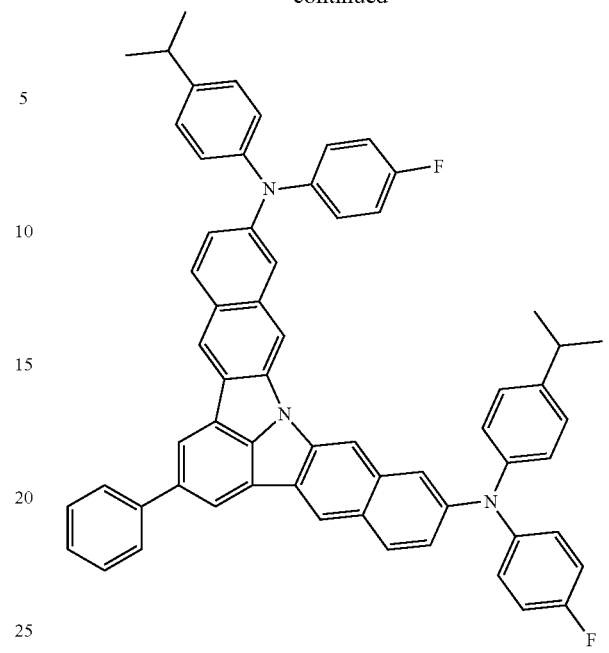
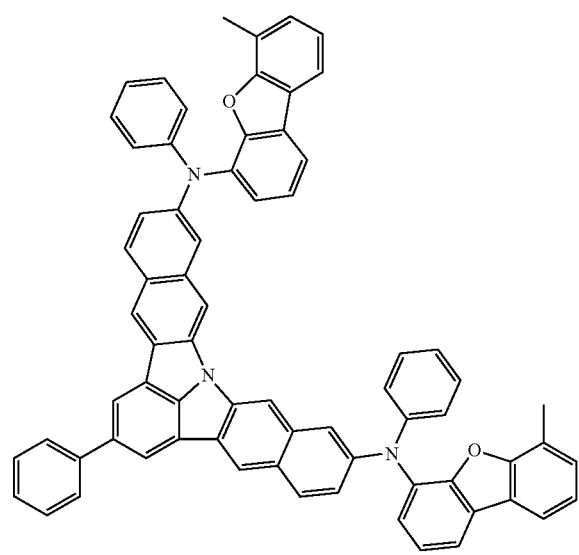
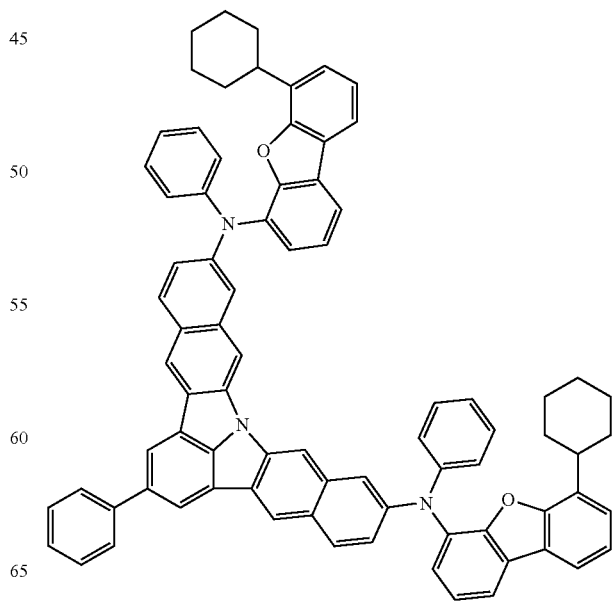

209
-continued
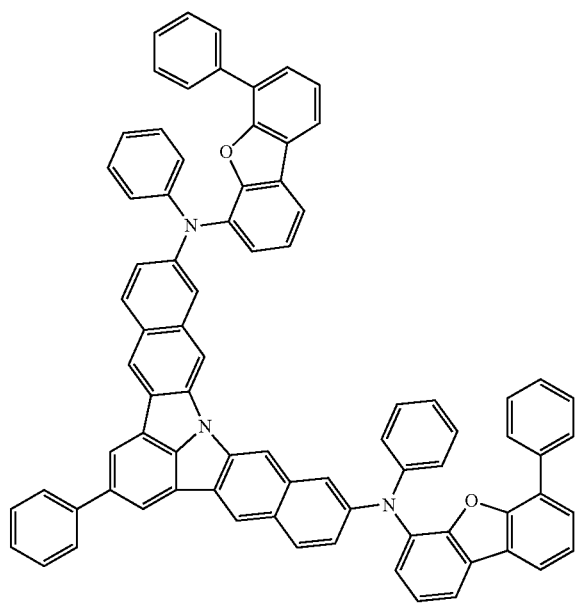
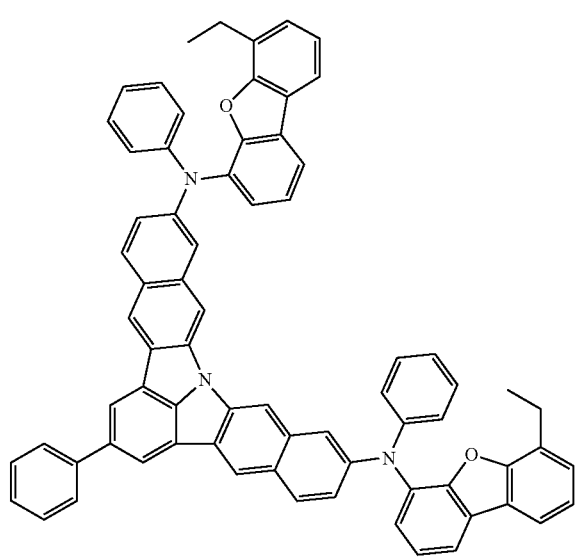
210
-continued
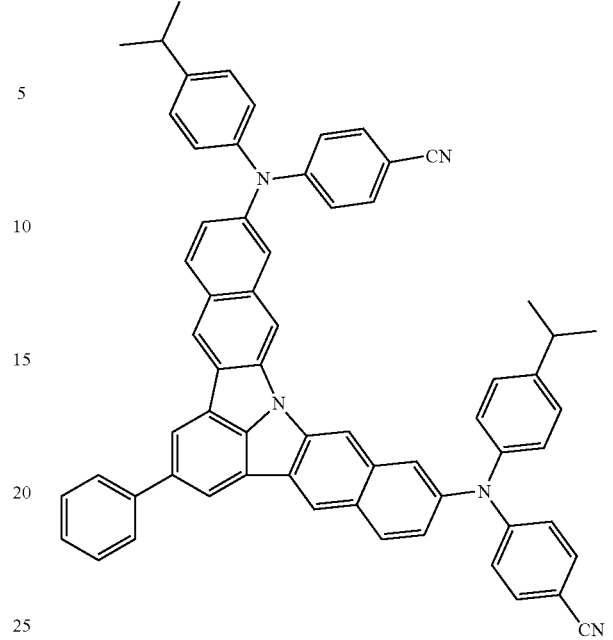
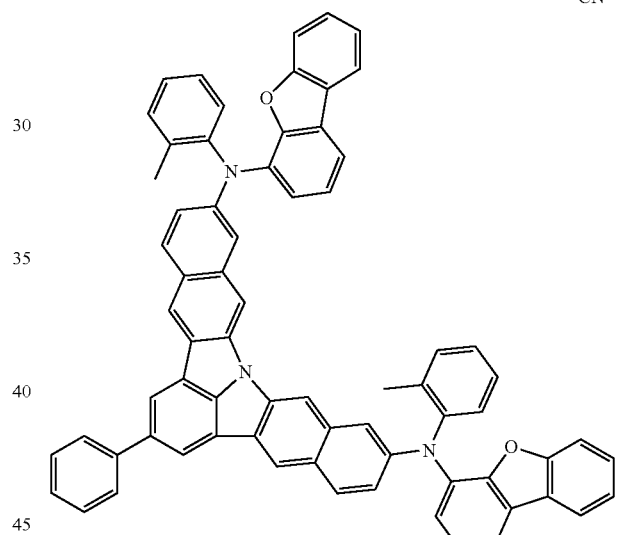
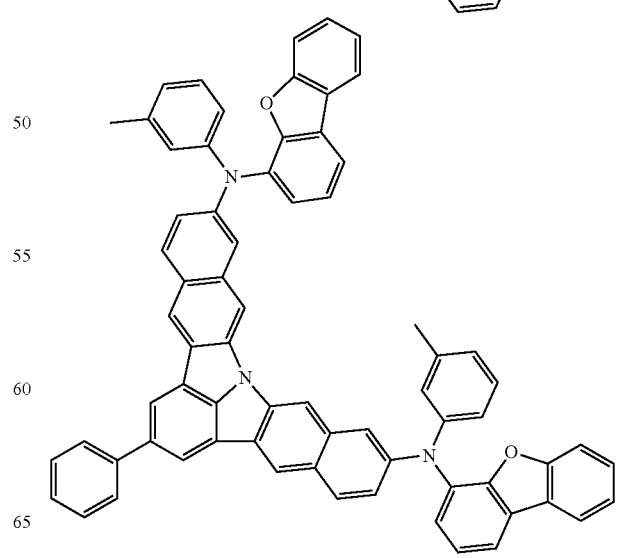

211
-continued
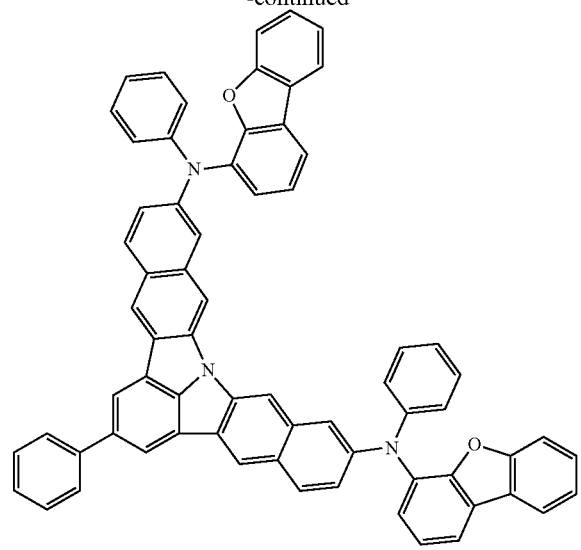
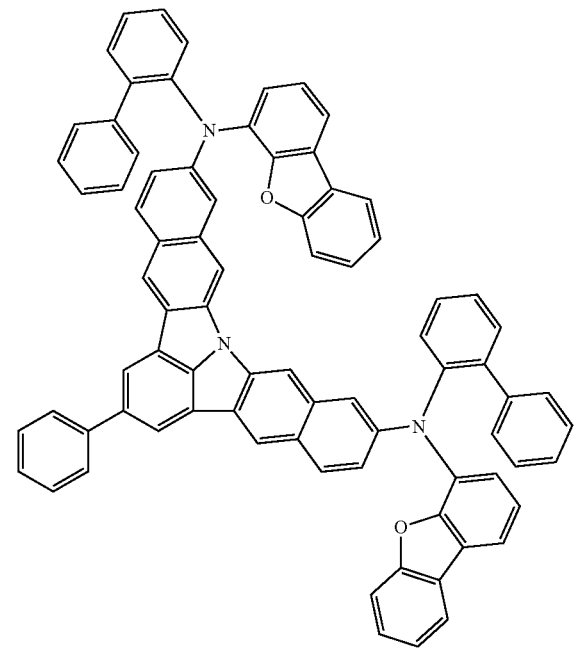
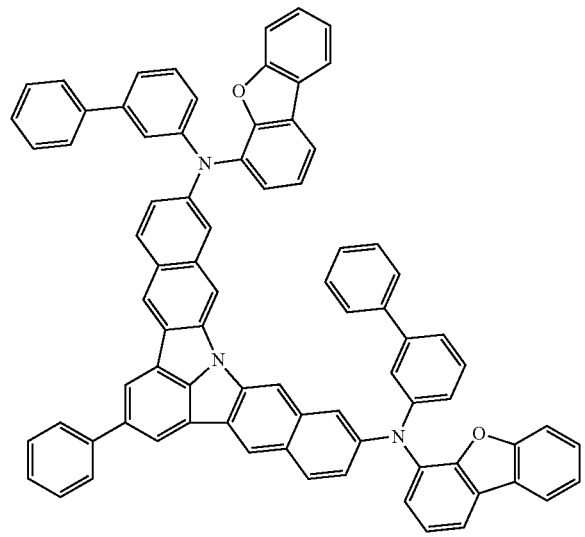
212
-continued
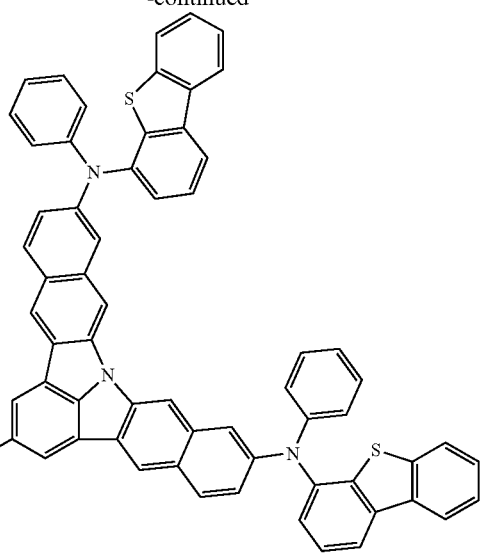
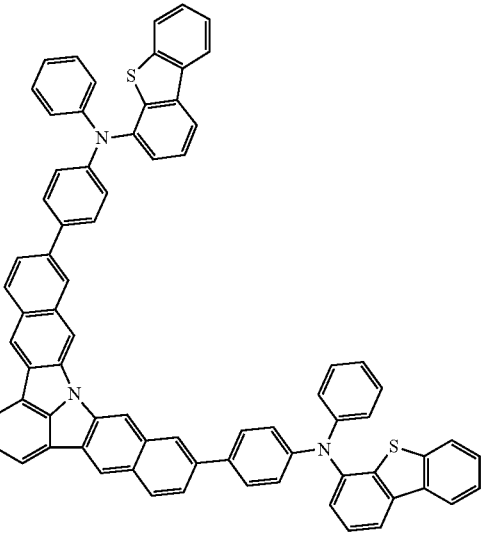

213
-continued
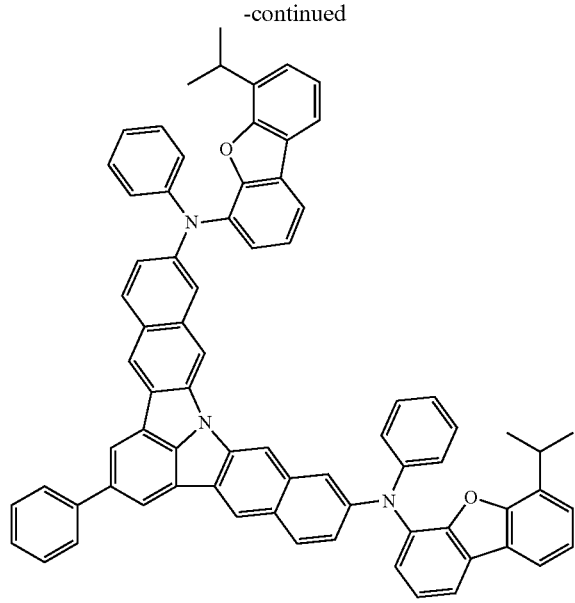
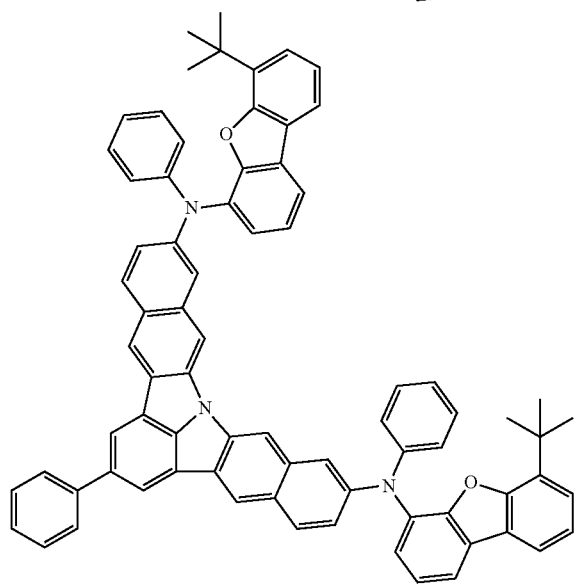
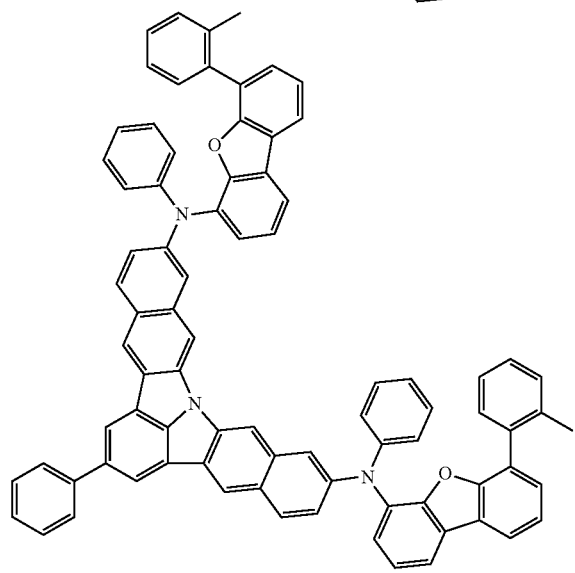
214
-continued
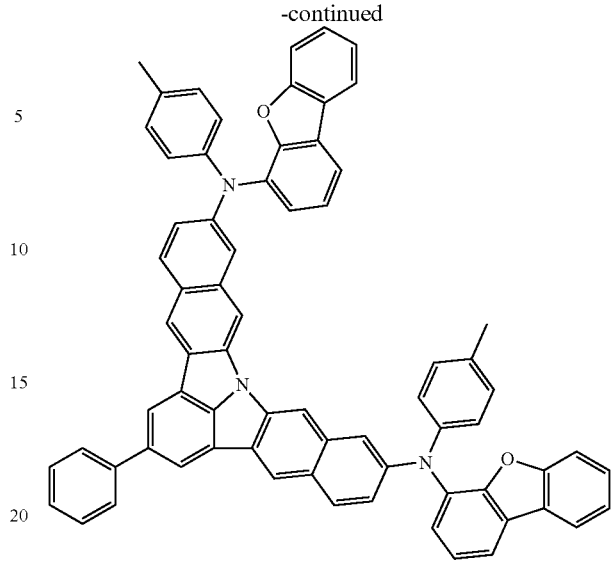
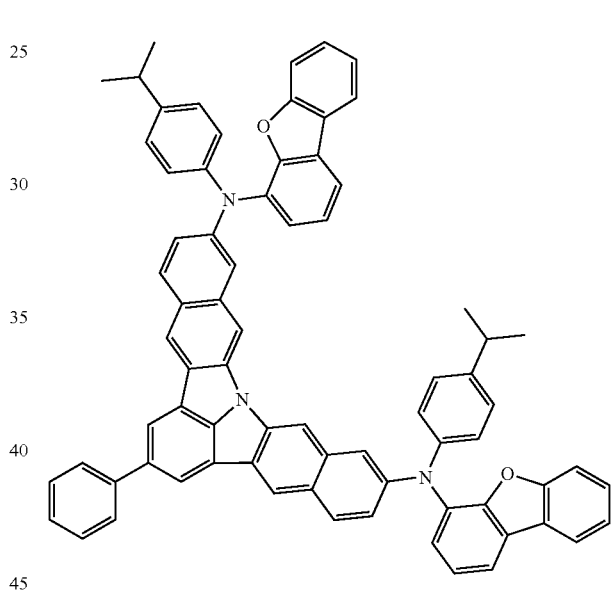
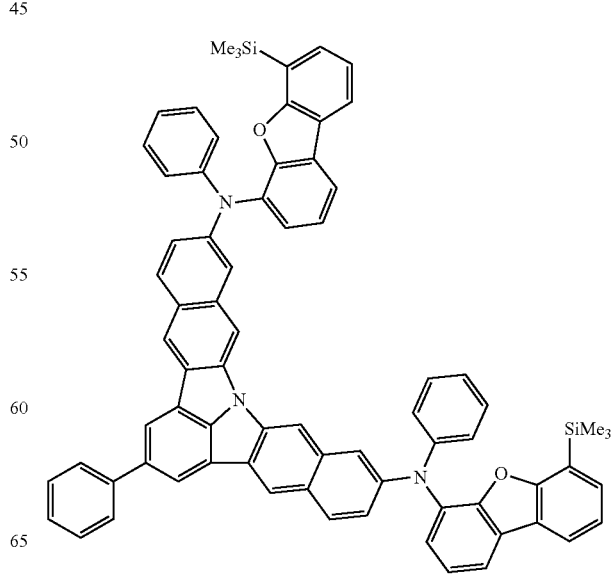

215
-continued
216
-continued
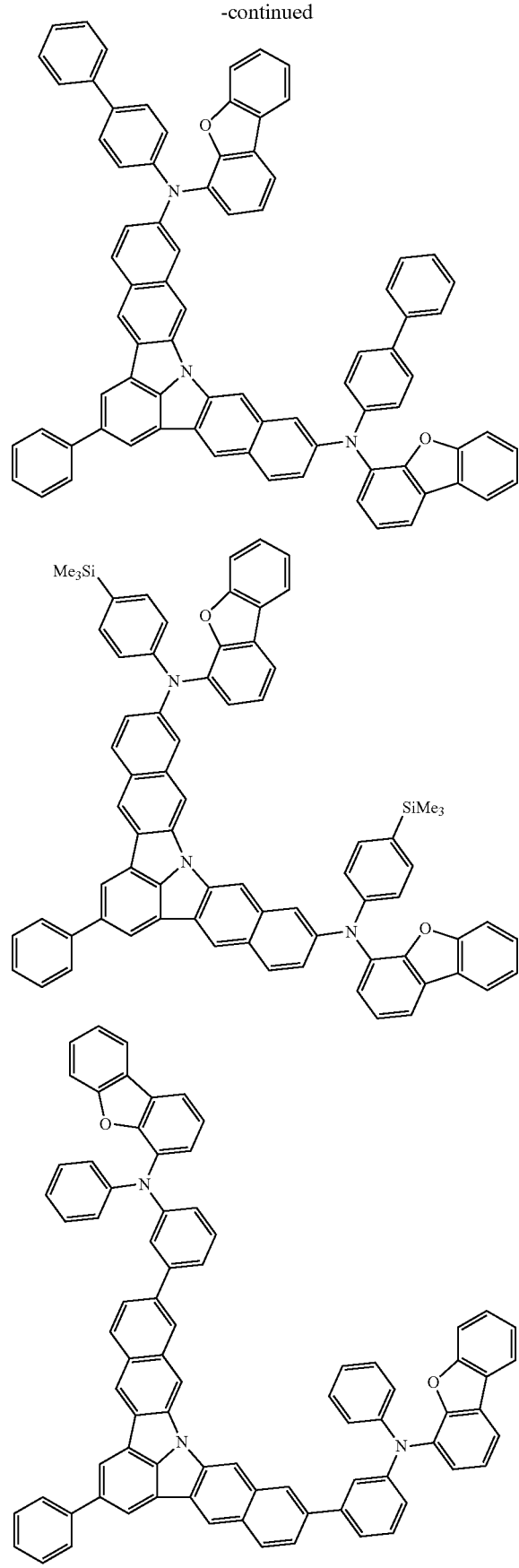
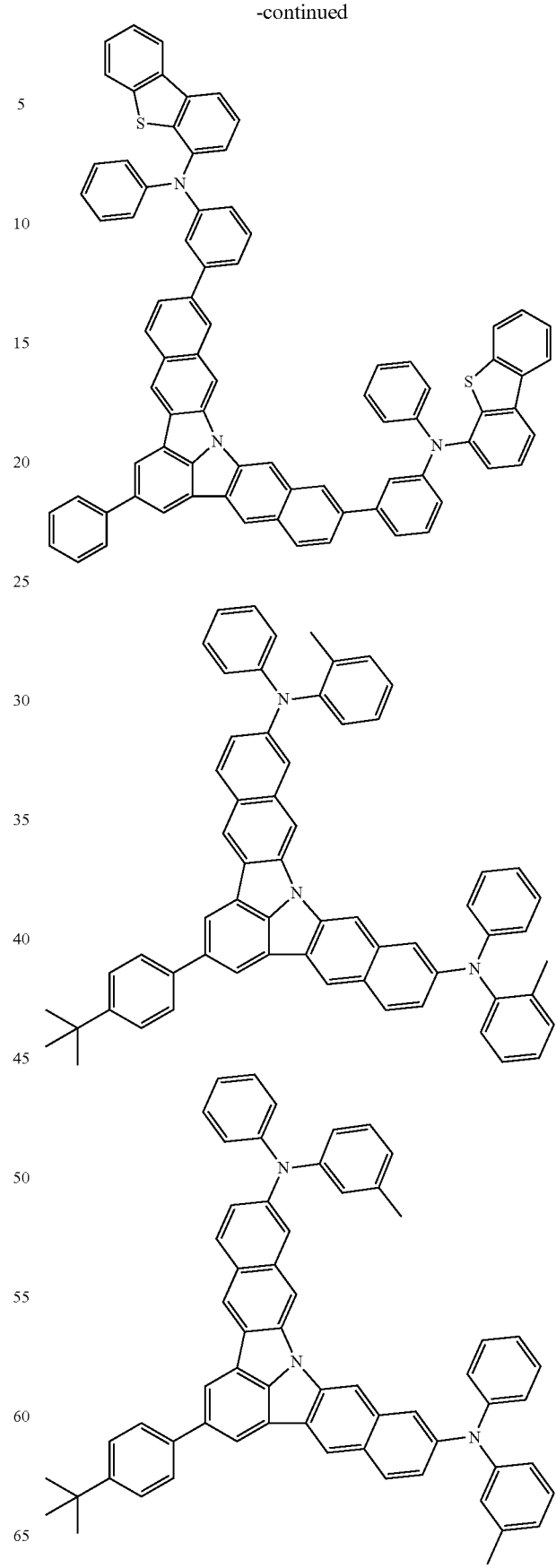

217
-continued
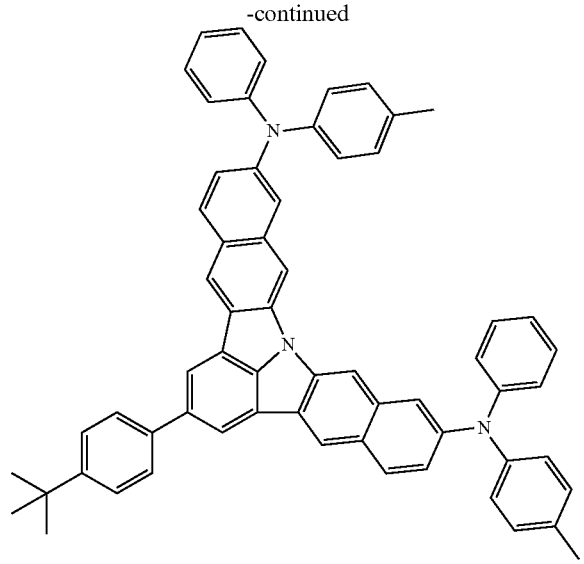
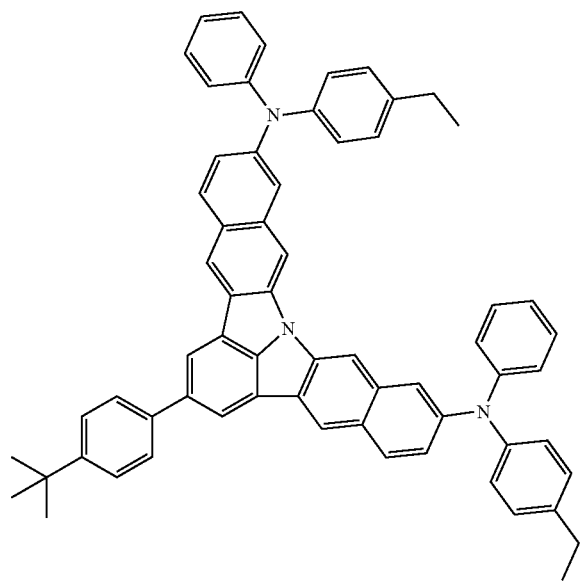
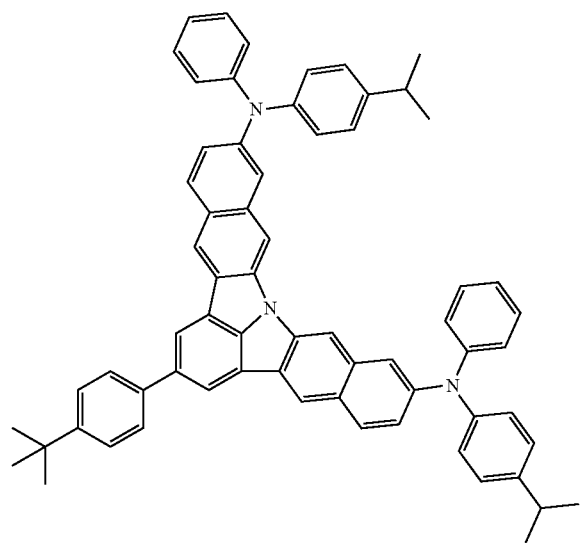
218
-continued
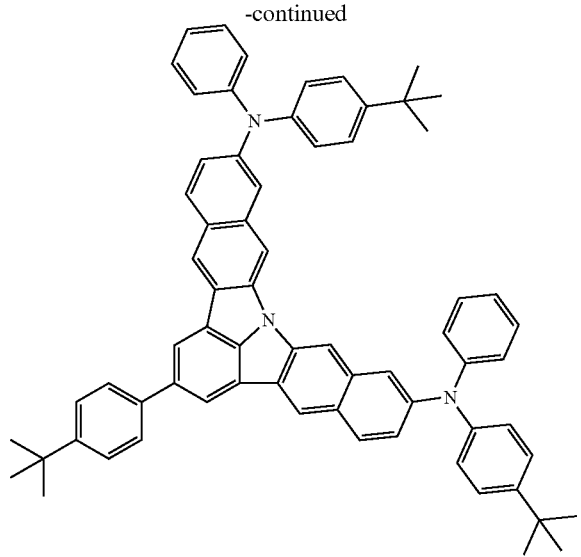
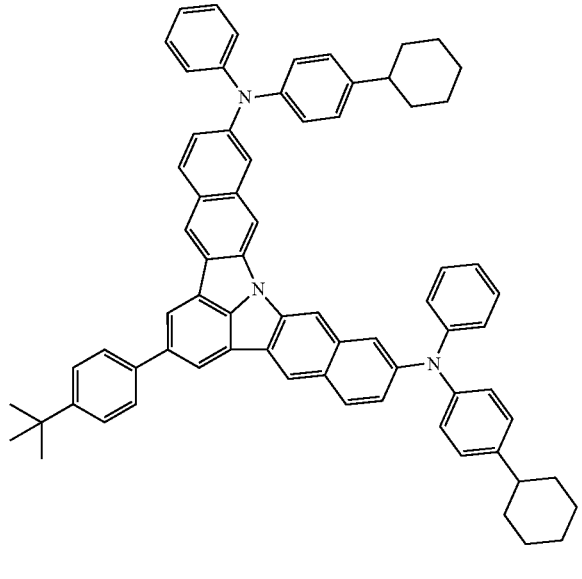
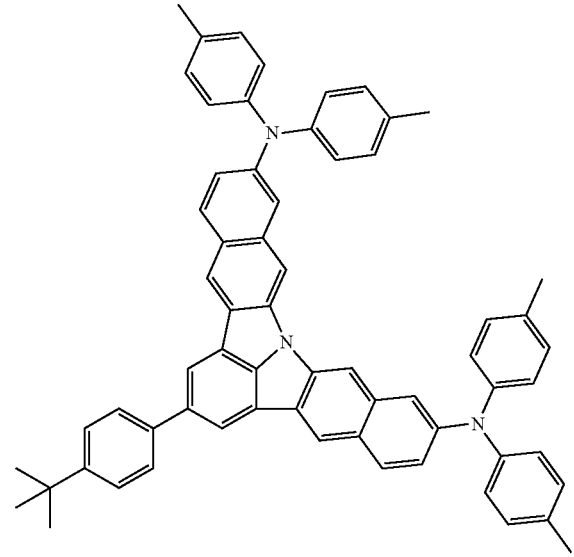

219
-continued
220
-continued
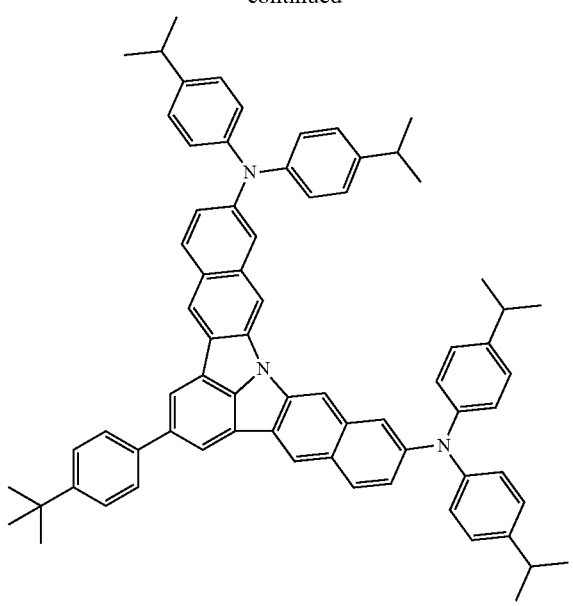
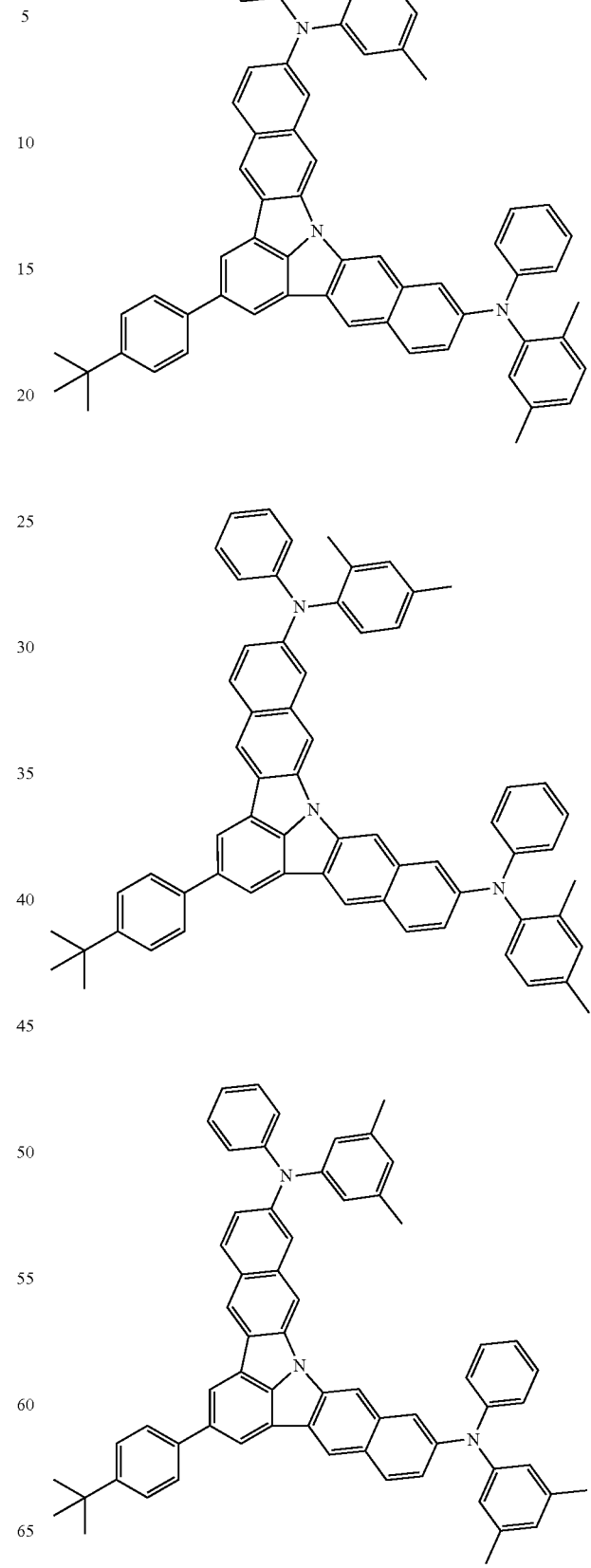

221
-continued
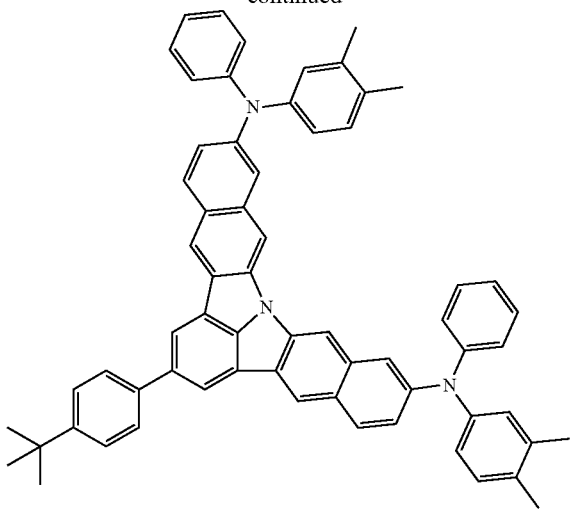
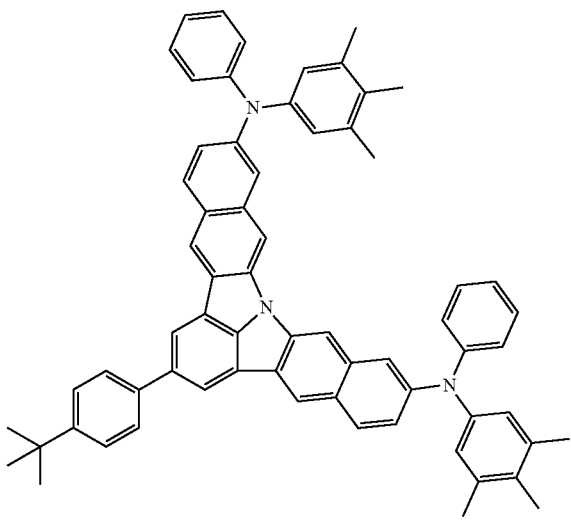
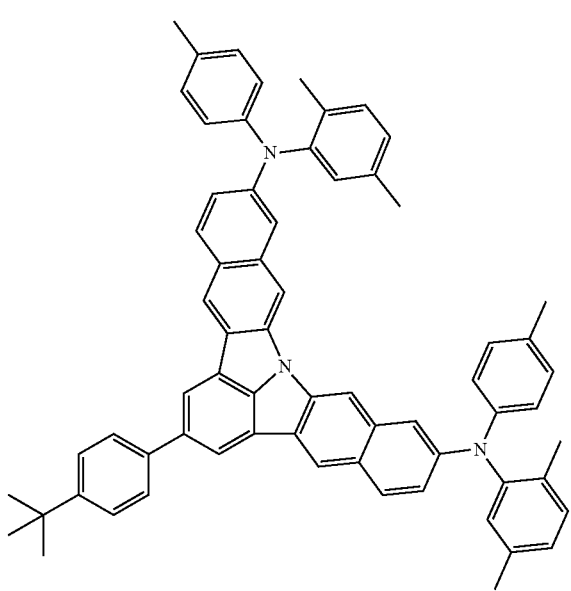
222
-continued
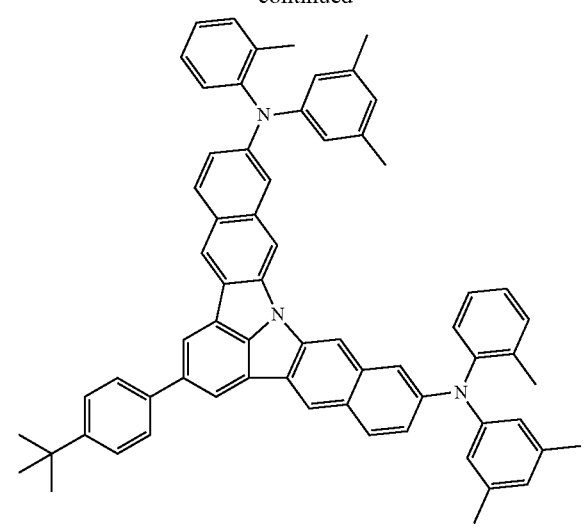
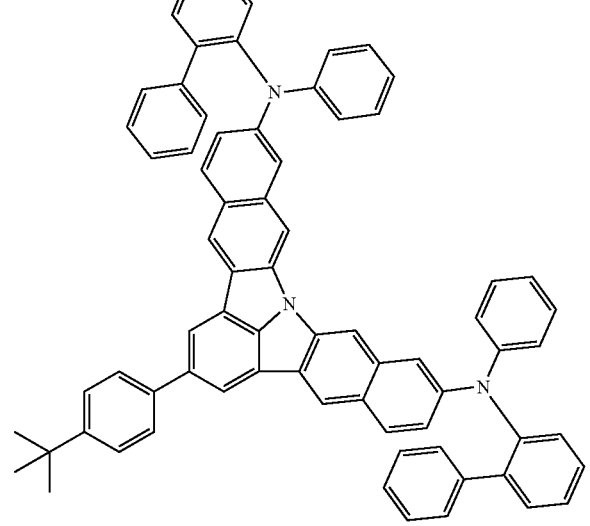
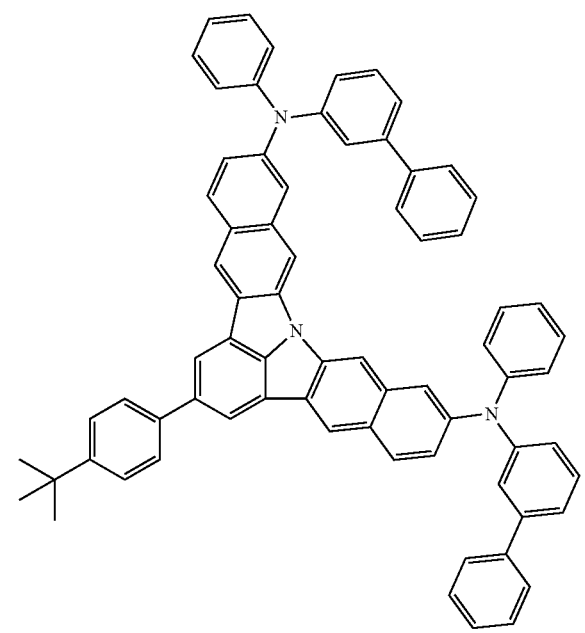

223
-continued
224
-continued
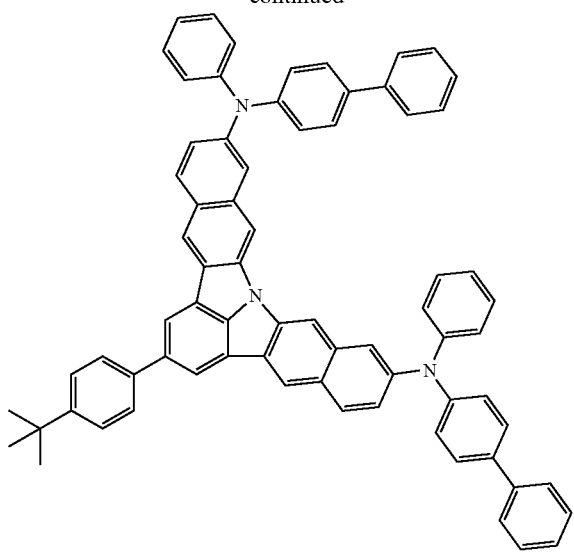
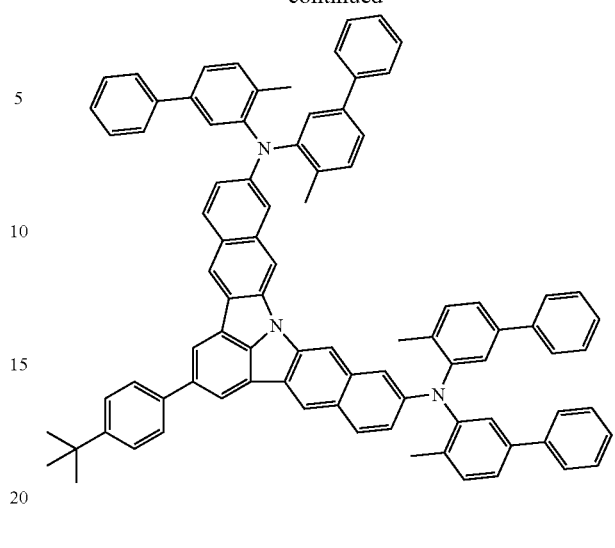
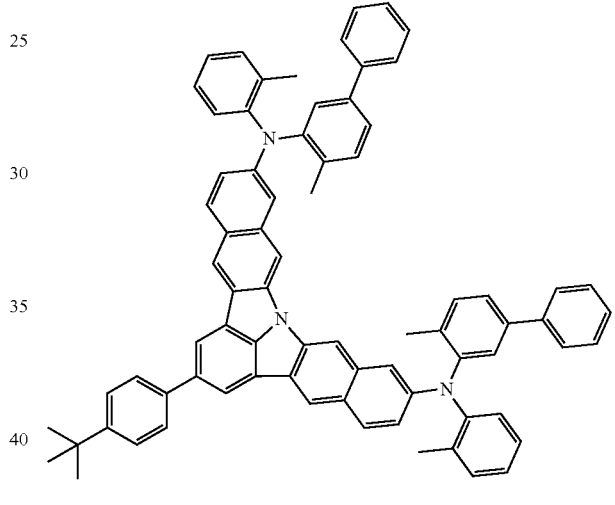
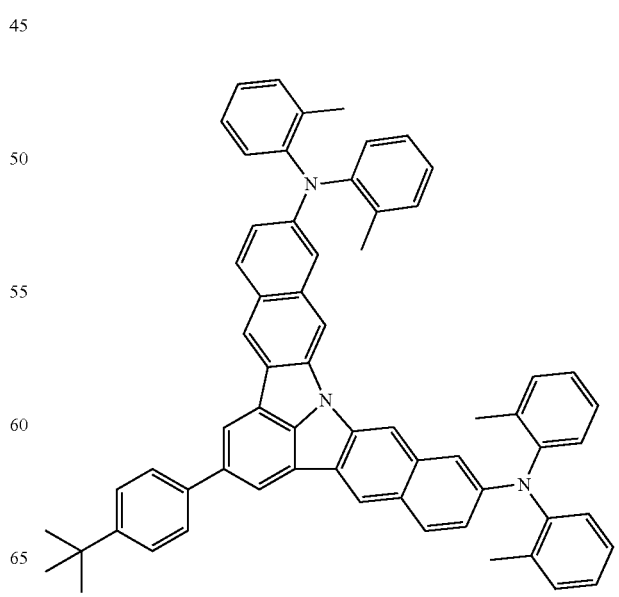

225
-continued
226
-continued
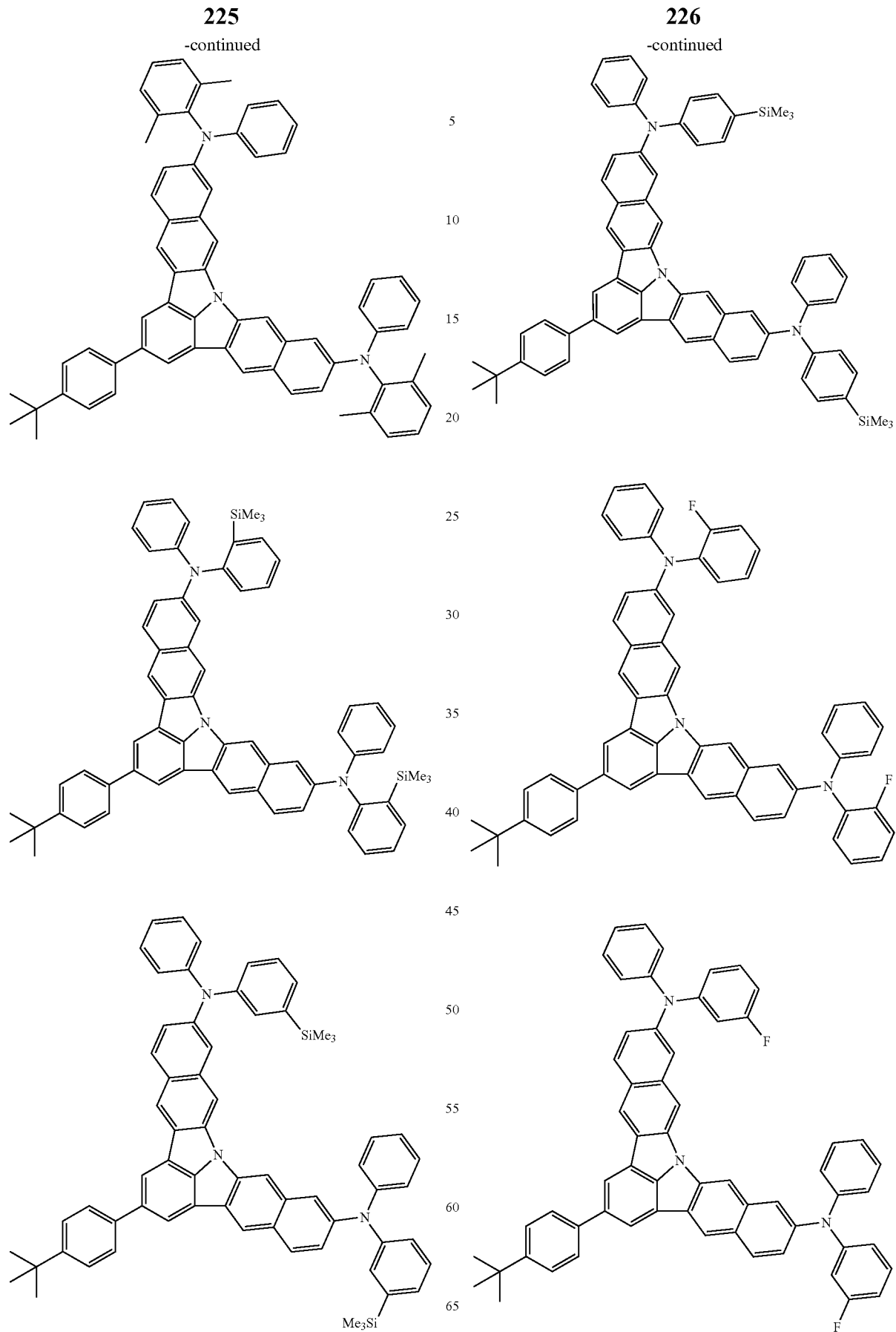

227
-continued
228
-continued
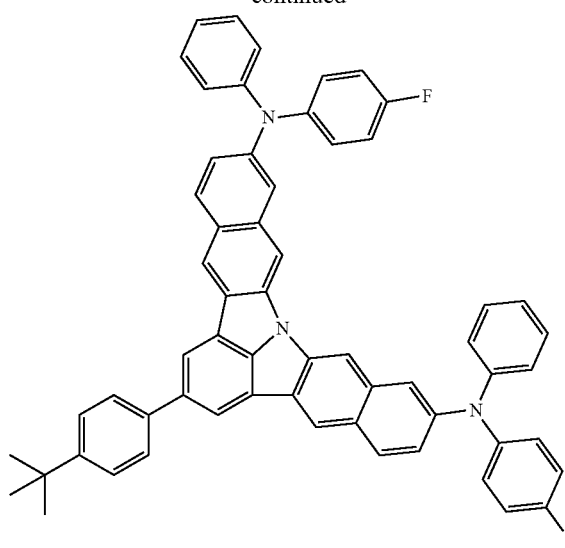
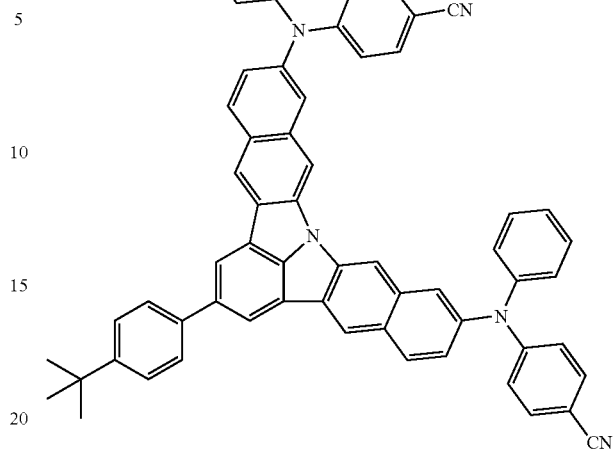
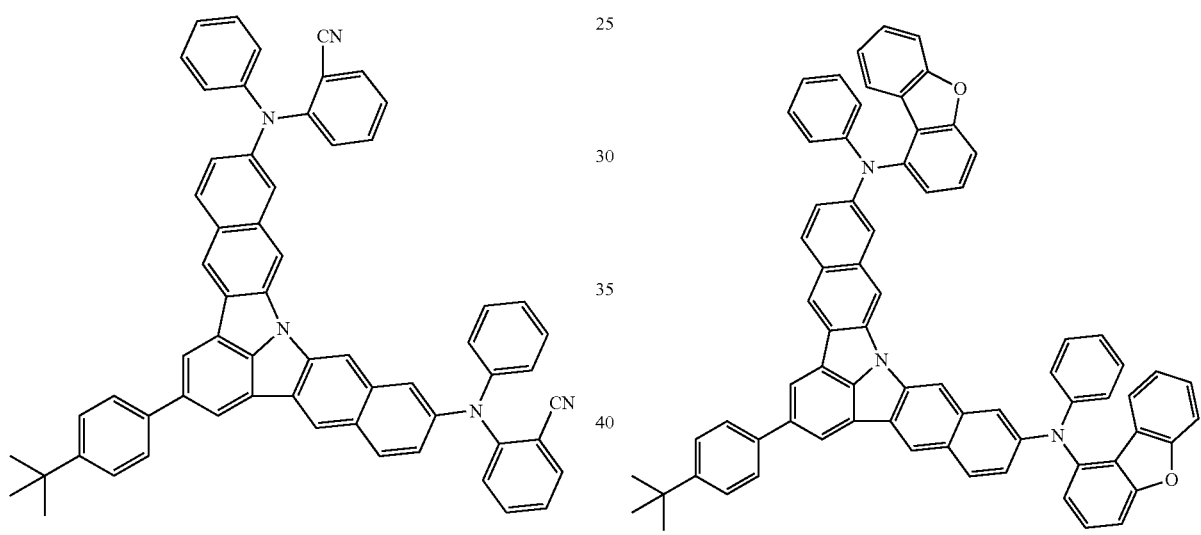
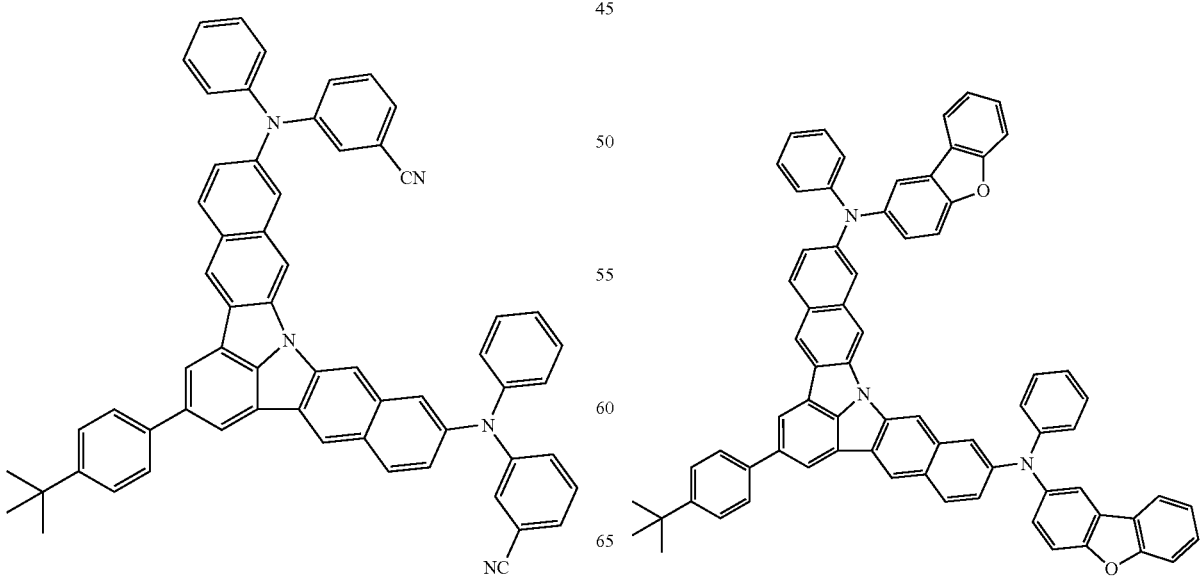

229
-continued
230
-continued
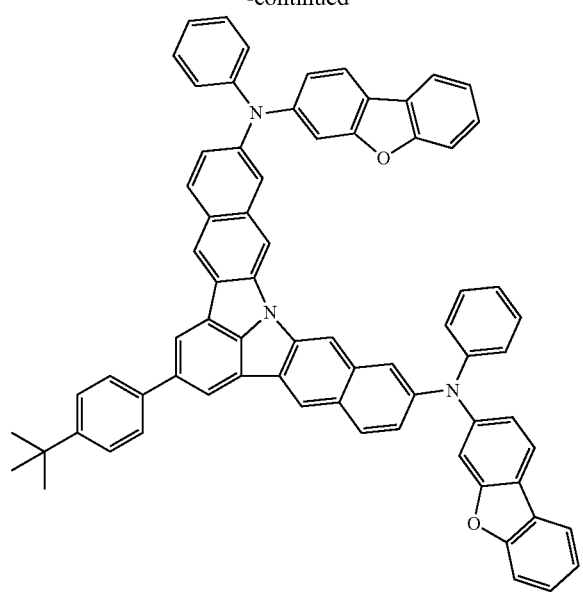
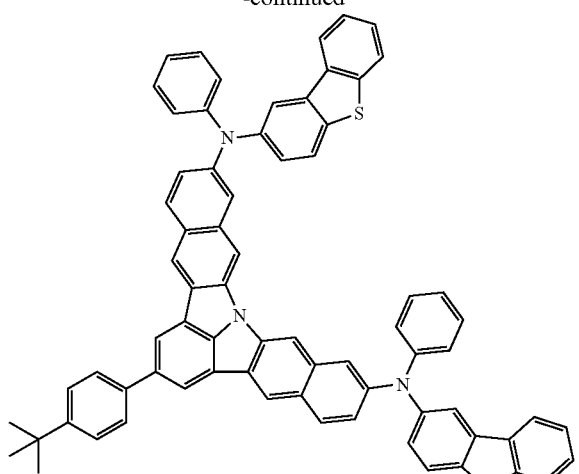
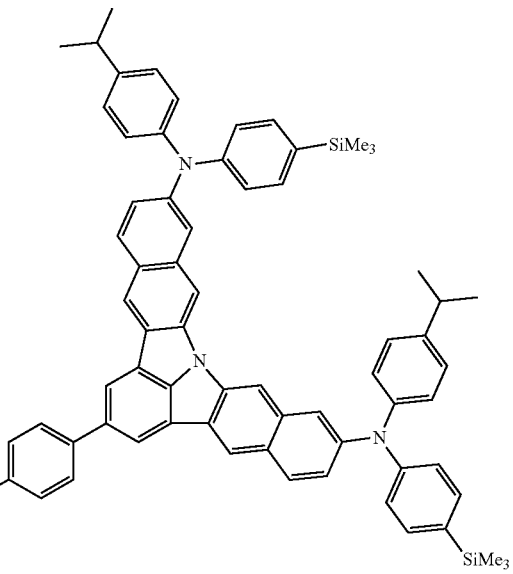
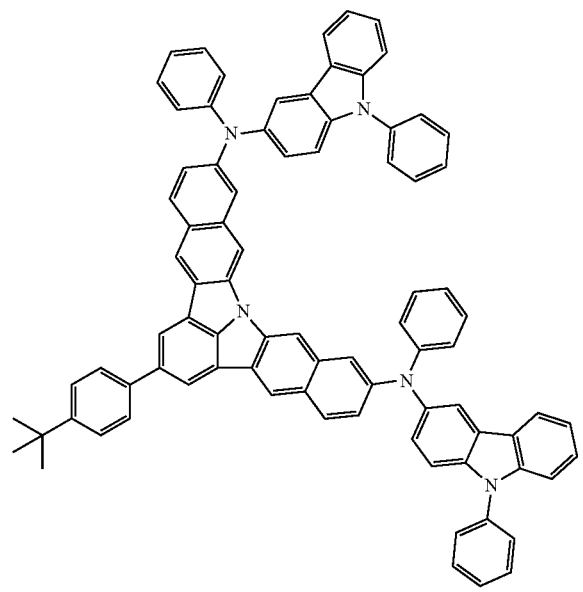
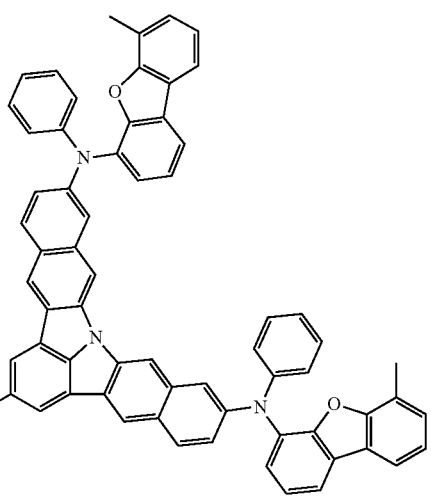

231
-continued
232
-continued
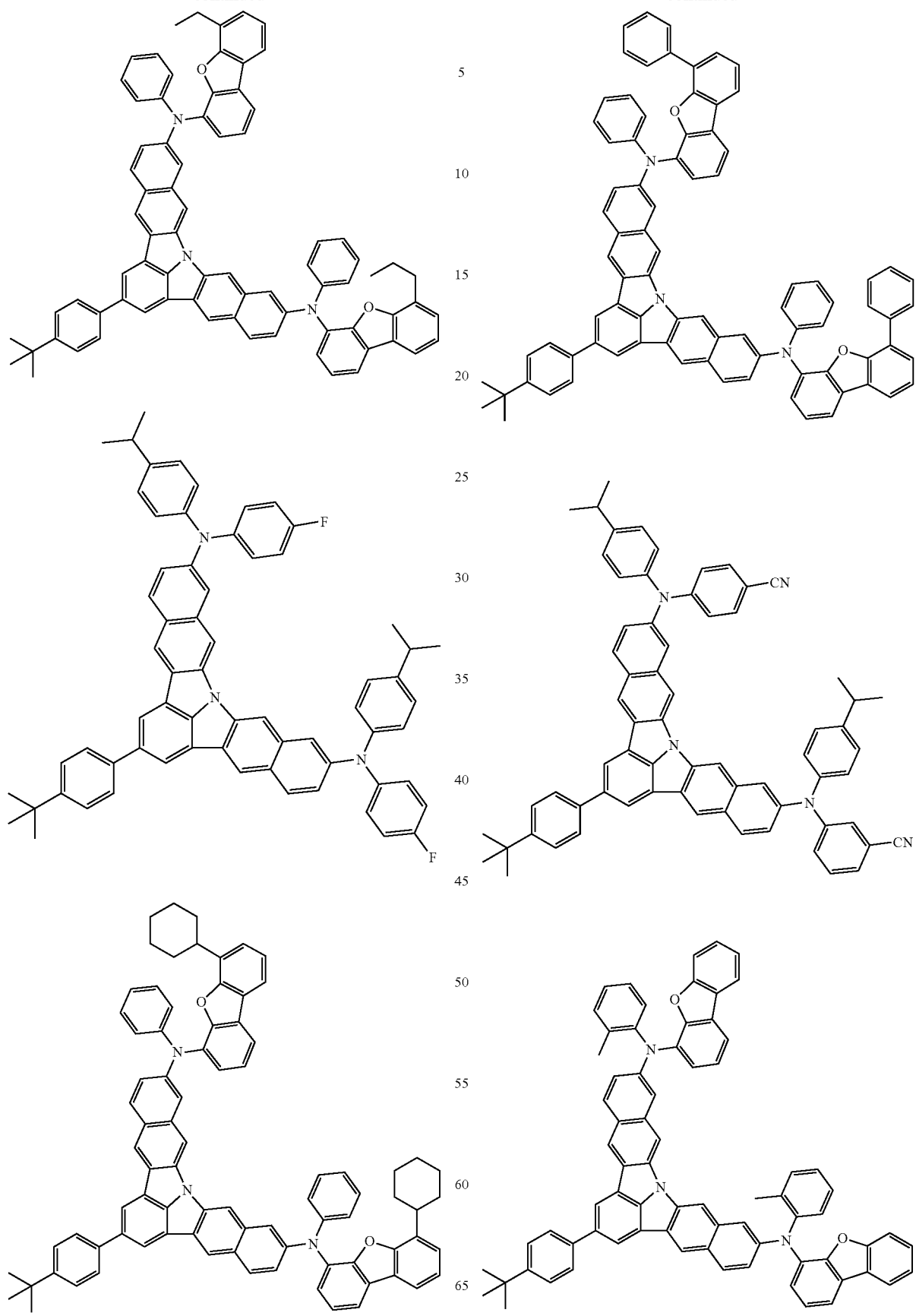

233
-continued
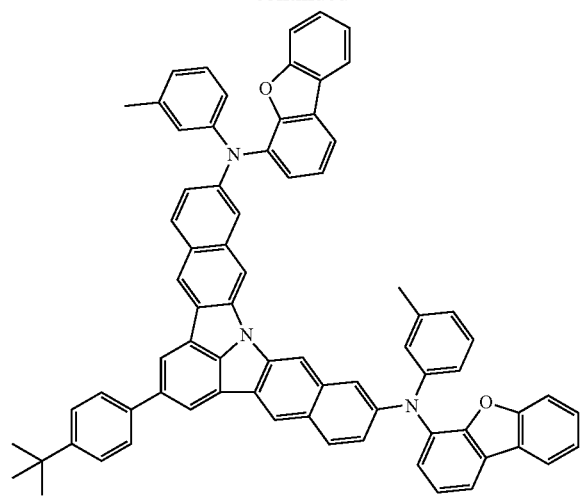
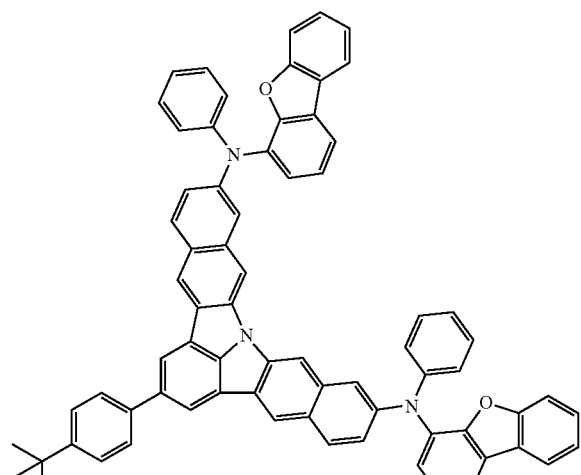
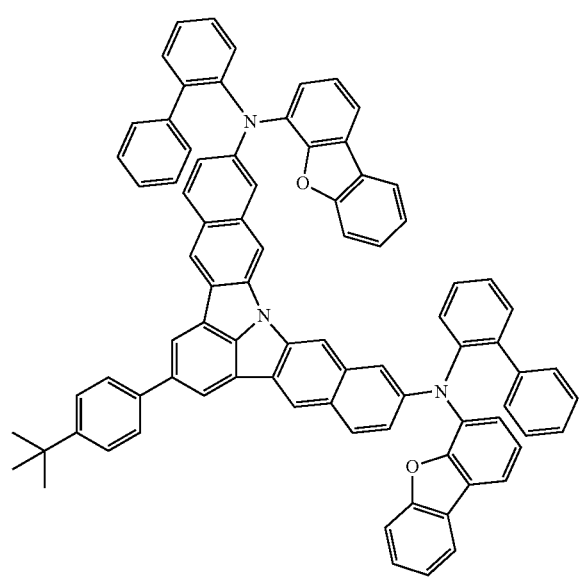
234
-continued
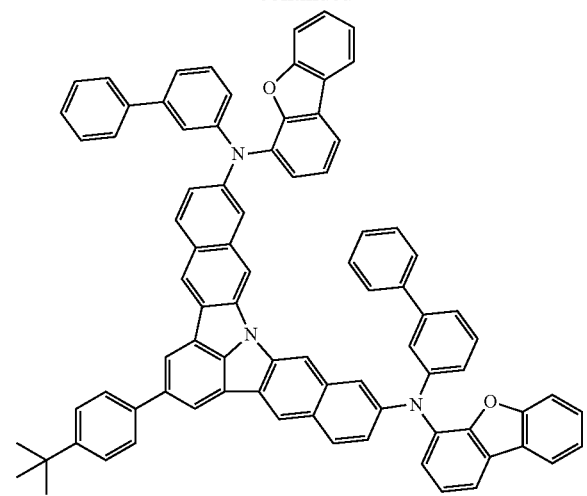
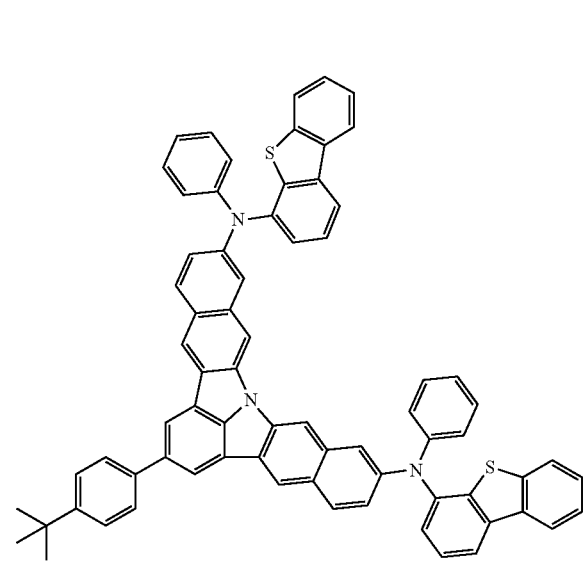
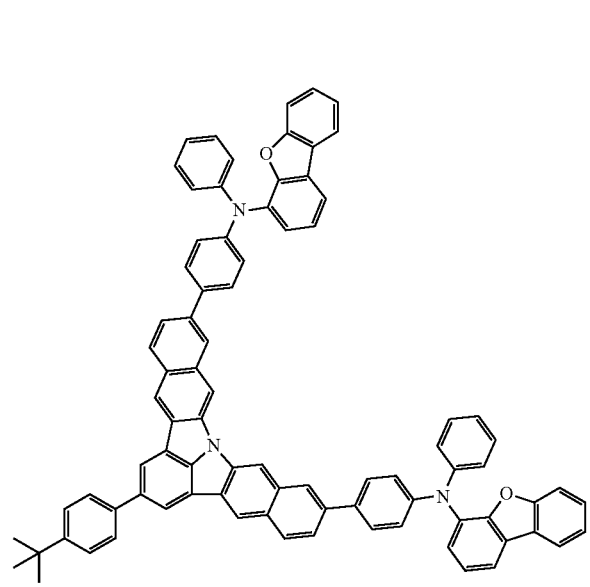

235
-continued
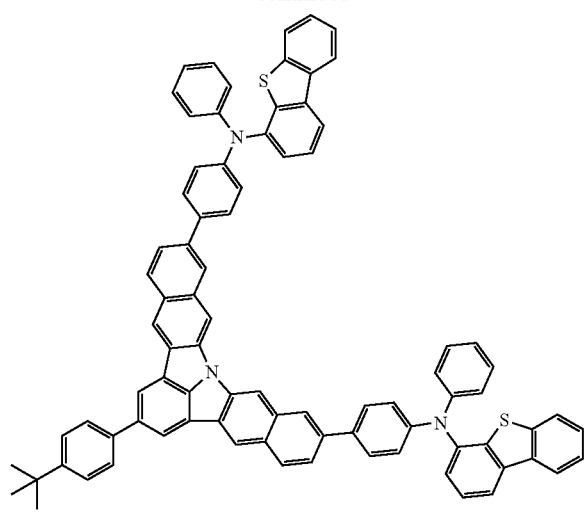
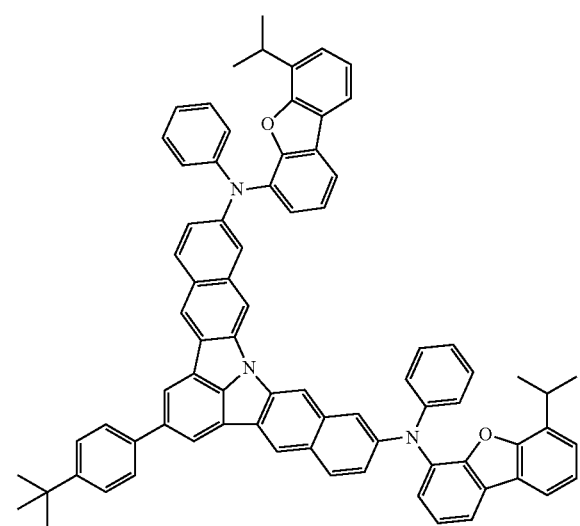
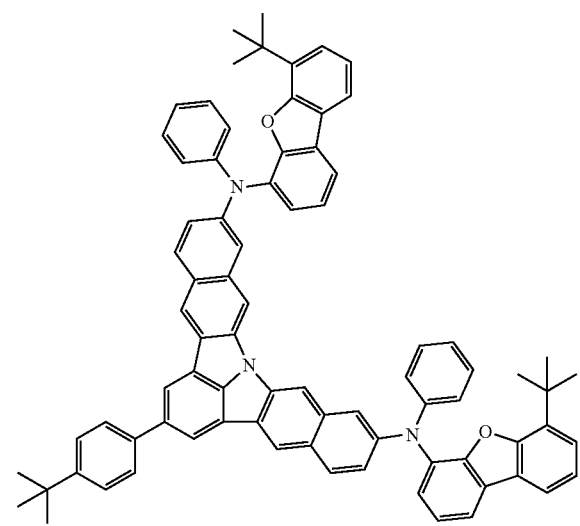
236
-continued
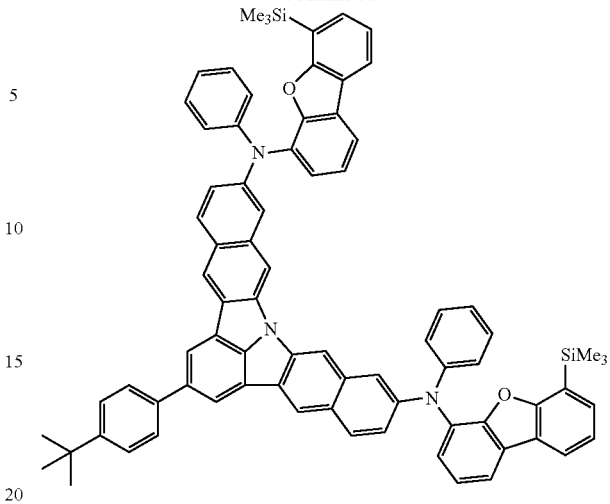
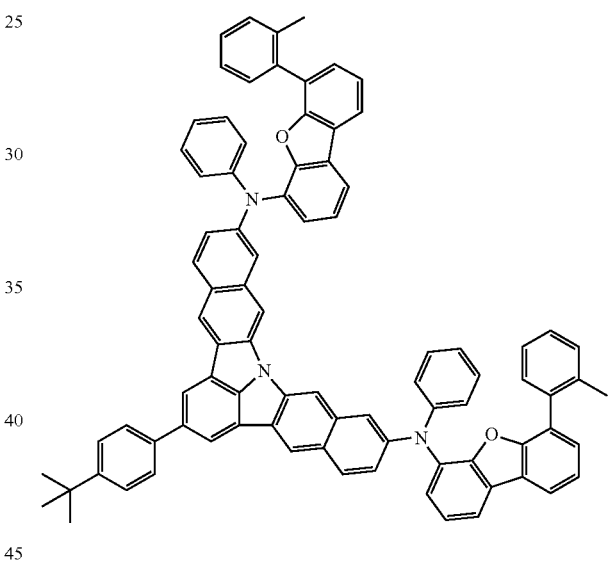
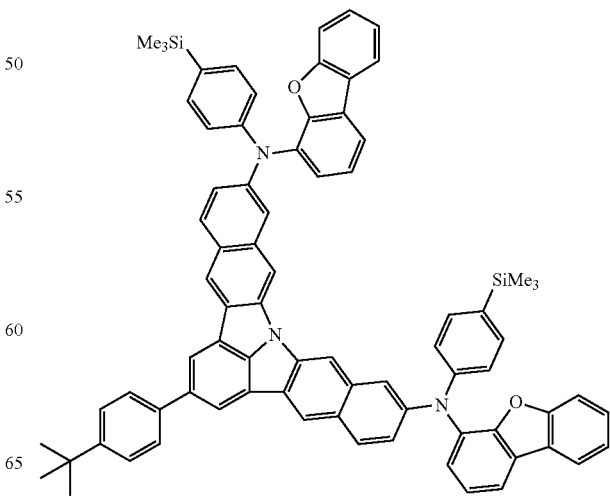

237
-continued

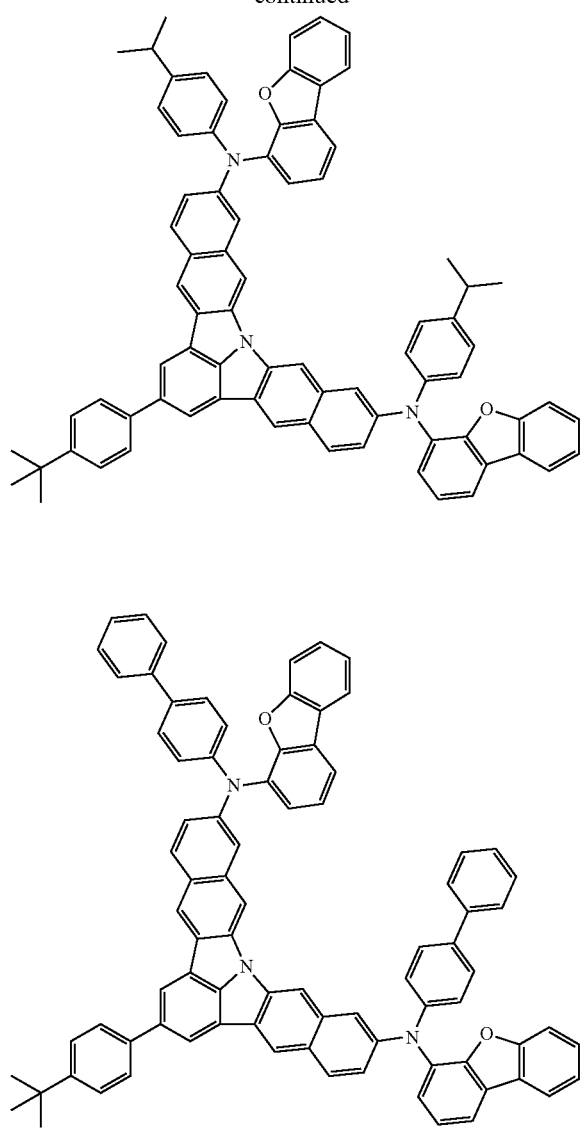

238
-continued

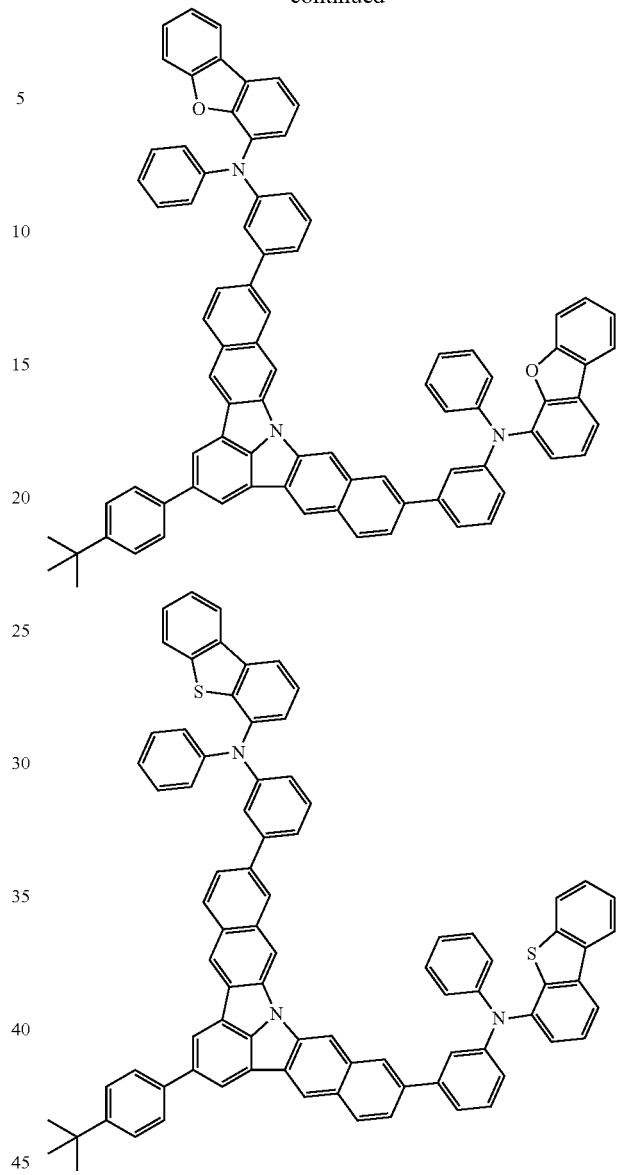

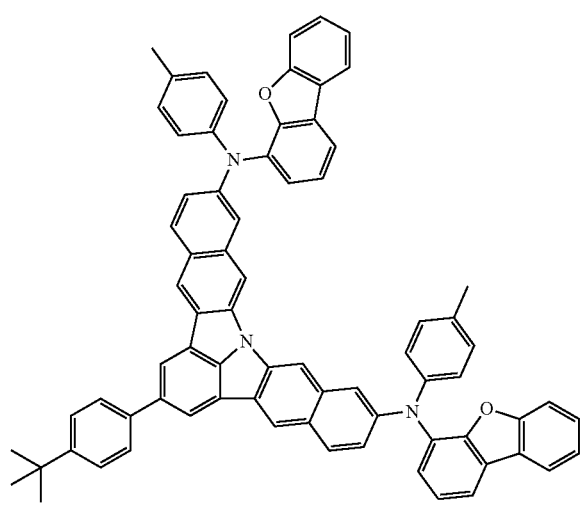

The compound in an aspect of the invention is useful as a material for organic EL devices.

The production method of the compound of the invention is not particularly limited, and the compound can be easily produced by using or modifying a known synthetic reaction while referring to the examples described herein.

In an embodiment, the compound of the invention can be used as a fluorescent dopant material in a light emitting layer of an organic EL device.

In view of the emission efficiency, the fluorescence quantum yield (PLQY) and the shape of fluorescence emission spectrum (half width) are important for the dopant material for use in the light emitting layer of organic EL device.

In a full-color display, to obtain an optimum color gamut, the three primary colors, i.e., red, green and blue light or four or more colors, for example, yellow in addition to the three primary colors are taken out after cutting off through a color filter or after amplifying a light with the intended wavelength and attenuating light with other wavelengths. Thus, the light with a wavelength other than required is removed, this leading to a loss of energy. Therefore, a material showing an emission spectrum with a sharp shape is advantageous for the efficiency, because the range of wavelength to be cut off is small to reduce the loss of energy.

A material little changing its structure between the ground state and the excited state is considered suitable as a dopant material showing an emission spectrum with a sharp shape.

The compound of the invention little changes its structure between the ground state and the excited state because of its rigid structure of the main fused aromatic ring structure.

As a result of extensive study, the inventors have found that the compound of the invention has a high PLQY even when the basic skeleton has no substituent. Generally, a substituent introduced increases the number of vibrational levels to broaden the spectrum. Therefore, in view of obtaining a sharp emission spectrum, it is better to reduce the number of the substituents introduced. Thus, a trade-off generally occurs between the improvement in PLQY by introducing a substituent and the broadening of the emission spectrum. Since the compound of the invention can have a high PLQY even when introducing no substituent to the basic skeleton, a high PLQY and a sharp emission spectrum can be achieved simultaneously in the present invention by minimizing the increase in the number of vibrational levels which is caused by introducing a substituent.

When the compound of the invention is of a highly symmetric fused ring structure, a sharper emission spectrum may be obtained because the vibrational levels are degenerated. The highly symmetric fused ring structure used herein is, for example, a fused ring structure which is symmetric with respect to a line connecting the nitrogen atom and $R_2$ of formula (1).

The compound of the invention having an asymmetric fused ring structure is effective particularly in controlling the wavelength without introducing a substituent. The asymmetric fused ring structure used herein is, for example, a fused ring structure which is asymmetric with respect to a line connecting the nitrogen atom and $R_2$ of formula (1).

A blue-emitting fluorescent dopant is required to emit a fluorescent light within a proper wavelength range, for example, within a blue visible light range, particularly within a deep blue range. The inventors have found that the above requirement can be met by fusing two or more rings to different rings of the indolo[3,2,1-jk]carbazole ring, as in the compound of the invention.

Organic EL Device

The organic EL device of the invention will be described below.

The organic EL device comprises an organic thin film layer between a cathode and an anode. The organic thin film layer comprises a light emitting layer and at least one layer of the organic thin film layer comprises the compound of the invention. The organic EL device of the invention includes one capable of operating at low driving voltage, one having a long lifetime, and one capable of emitting blue light with high color purity.

Examples of the organic thin film layer comprising the compound of the invention include a hole transporting layer, a light emitting layer, an electron transporting layer, a space layer, and a blocking layer, although not particularly limited thereto.

The compound of the invention is preferably used in a light emitting layer, particularly as a dopant material, and particularly preferably used in a fluorescent emitting layer as a dopant material. The compound of the invention is also preferably used as a dopant material in a light emitting layer using thermally activated delayed fluorescence.

The content of the compound of the invention in a light emitting layer when used as a dopant material is not particularly limited and can be suitably selected depending on the purpose. The content is preferably 0.1 to 70% by mass, more preferably 0.1 to 30% by mass, still more preferably 1 to 30% by mass, still further more preferably 1 to 20% by mass, and particularly preferably 1 to 10% by mass. If being 0.1% by mass or more, the emission is sufficient and the concentration quenching can be avoided if being 70% by mass or less.

The organic EL device of the invention may be any of a single color emitting device using fluorescence, phosphorescence, or thermally activated delayed fluorescence; a white-emitting hybrid device comprising the above single color emitting devices; an emitting device of a simple type having a single emission unit; and an emitting device of a tandem type having two or more emission units. The "emission unit" referred to herein is the smallest unit for emitting light by the recombination of injected holes and injected electrons, which comprises one or more organic layers wherein at least one layer is a light emitting layer.

Representative device structures of the simple-type organic EL device are shown below.

(1) Anode/Emission Unit/Cathode

The emission unit may be a laminate comprising two or more light emitting layers selected from a phosphorescent light emitting layer, a fluorescent light emitting layer, and a light emitting layer using thermally activated delayed fluorescence. A space layer may be disposed between the light emitting layers to prevent the diffusion of excitons generated in the phosphorescent emitting layer into the fluorescent emitting layer. Representative layered structures of the emission unit are shown below:

(a) hole transporting layer/light emitting layer(/electron transporting layer);
(b) hole transporting layer/first fluorescent emitting layer/second fluorescent emitting layer(/electron transporting layer);
(c) hole transporting layer/phosphorescent emitting layer/space layer/fluorescent emitting layer(/electron transporting layer);
(d) hole transporting layer/first phosphorescent emitting layer/second phosphorescent emitting layer/space layer/fluorescent emitting layer(/electron transporting layer);
(e) hole transporting layer/first phosphorescent emitting layer/space layer/second phosphorescent emitting layer/space layer/fluorescent emitting layer(/electron transporting layer); and
(f) hole transporting layer/phosphorescent emitting layer/space layer/first fluorescent emitting layer/second fluorescent emitting layer(/electron transporting layer).

The emission colors of the phosphorescent emitting layers and the fluorescent emitting layer may be different. For example, the layered structure (d) may be hole transporting layer/first phosphorescent emitting layer (red)/second phosphorescent emitting layer (green)/space layer/fluorescent emitting layer (blue)/electron transporting layer.

An electron blocking layer may be disposed between the light emitting layer and the hole transporting layer or between the light emitting layer and the space layer, if necessary. Also, a hole blocking layer may be disposed between the light emitting layer and the electron transporting layer, if necessary. With such an electron blocking layer or a hole blocking layer, electrons and holes are confined in the light emitting layer to facilitate the charge recombination in the light emitting layer, thereby improving the emission efficiency.

Representative device structure of the tandem-type organic EL device is shown below.

(2) Anode/First Emission Unit/Intermediate Layer/Second Emission Unit/Cathode

The layered structure of the first emission unit and the second emission unit may be selected from those described above with respect to the emission unit.

Generally, the intermediate layer is also called an intermediate electrode, an intermediate conductive layer, a charge generation layer, an electron withdrawing layer, a connecting layer, or an intermediate insulating layer. The intermediate layer may be formed by known materials so as to supply electrons to the first emission unit and holes to the second emission unit.

A schematic structure of an example of the organic EL device of the invention is shown in FIG. 1 wherein the organic EL device 1 comprises a substrate 2, an anode 3, a cathode 4, and an emission unit (organic thin film layer) 10 disposed between the anode 3 and the cathode 4. The emission unit 10 comprises a light emitting layer 5 which comprises at least one fluorescent emitting layer comprising a fluorescent host material and a fluorescent dopant material. A hole injecting layer/hole transporting layer 6 may be disposed between the light emitting layer 5 and the anode 3, and an electron injecting layer/electron transporting layer 7 may be disposed between the light emitting layer 5 and the cathode 4. An electron blocking layer may be disposed on the anode 3 side of the light emitting layer 5, and a hole blocking layer may be disposed on the cathode 4 side of the light emitting layer 5. With these blocking layers, electrons and holes are confined in the light emitting layer 5 to facilitate the exciton generation in the light emitting layer 5.

In the present invention, a host material is referred to as a fluorescent host material when combinedly used with a fluorescent dopant material and as a phosphorescent host material when combinedly used with a phosphorescent dopant material. Therefore, the fluorescent host material and the phosphorescent host material are not distinguished from each other merely by the difference in their molecular structures. Namely, in the present invention, the term "fluorescent host material" means a material for constituting a fluorescent emitting layer which contains a fluorescent dopant material and does not mean a material that cannot be used as a material for a phosphorescent emitting layer. The same applies to the phosphorescent host material.

Substrate

The organic EL device of the invention is formed on a light-transmissive substrate. The light-transmissive substrate serves as a support for the organic EL device and preferably a flat substrate having a transmittance of 50% or more to 400 to 700 nm visible light. Examples of the substrate include a glass plate and a polymer plate. The glass plate may include a plate made of soda-lime glass, barium-strontium-containing glass, lead glass, aluminosilicate glass, borosilicate glass, barium borosilicate glass, or quartz. The polymer plate may include a plate made of polycarbonate, acryl, polyethylene terephthalate, polyether sulfide, or polysulfone.

Anode

The anode of the organic EL device injects holes to the hole transporting layer or the light emitting layer, and an anode having a work function of 4.5 eV or more is effective. Examples of the material for anode include an indium tin oxide alloy (ITO), tin oxide (NESA), an indium zinc oxide alloy, gold, silver, platinum, and cupper. The anode is formed by making the electrode material into a thin film by a method, such as a vapor deposition method or a sputtering method. When getting the light emitted from the light emitting layer through the anode, the transmittance of anode to visible light is preferably 10% or more. The sheet resistance of anode is preferably several hundreds Ω or less. The film thickness of anode depends upon the kind of material and generally 10 nm to 1 μm, preferably 10 to 200 nm.

Cathode

The cathode injects electrons to the electron injecting layer, the electron transporting layer or the light emitting layer, and is formed preferably by a material having a small work function. Examples of the material for cathode include, but not limited to, indium, aluminum, magnesium, a magnesium-indium alloy, a magnesium-aluminum alloy, an aluminum-lithium alloy, an aluminum-scandium-lithium alloy, and a magnesium-silver alloy. Like the anode, the cathode is formed by making the material into a thin film by a method, such as the vapor deposition method and the sputtering method. The emitted light may be taken through the cathode, if necessary.

The material other than the compound of the invention usable in each layer will be described below.

Light Emitting Layer

The light emitting layer is an organic layer having a light emitting function and contains a host material and a dopant material when a doping system is employed. The major function of the host material is to promote the recombination of electrons and holes and confine excitons in the light emitting layer. The dopant material causes the excitons generated by recombination to emit light efficiently.

In case of a phosphorescent device, the major function of the host material is to confine the excitons generated on the dopant in the light emitting layer.

To control the carrier balance in the light emitting layer, the light emitting layer may be made into a double host (host/co-host) layer, for example, by combinedly using an electron transporting host material and a hole transporting host material.

The light emitting layer may be made into a double dopant layer, in which two or more kinds of dopant materials having high quantum yield are combinedly used and each dopant material emits light with its own color. For example, a yellow-emitting layer is obtained by co-depositing a host material, a red-emitting dopant material and a green-emitting dopant material into a single emitting layer.

In a laminated layer of two or more light emitting layers, electrons and holes are accumulated in the interface between the light emitting layers, and therefore, the recombination region is localized in the interface between the light emitting layers to improve the quantum efficiency.

The easiness of hole injection to the light emitting layer and the easiness of electron injection to the light emitting layer may be different from each other. Also, the hole transporting ability and the electron transporting ability in the light emitting layer, each expressed by hole mobility and electron mobility, may be different from each other.

The light emitting layer is formed, for example, by a known method, such as a vapor deposition method, a spin coating method, and LB method. The light emitting layer can be formed also by making a solution of a binder, such as resin, and a material for the light emitting layer in a solvent into a thin film by a method such as spin coating.

The light emitting layer is preferably a molecular deposit film. The molecular deposit film is a thin film formed by depositing a vaporized material or a film formed by solidifying a material in the form of solution or liquid. The molecular deposit film can be distinguished from a thin film formed by LB method (molecular build-up film) by the differences in the assembly structures and higher order structures and the functional difference due to the structural differences.

The thickness of the light emitting layer is preferably 5 to 50 nm, more preferably 7 to 50 nm, and still more preferably 10 to 50 nm. If being 5 nm or more, the light emitting layer is formed easily. If being 50 nm or less, the driving voltage is prevented from increasing.

Dopant Material

The fluorescent dopant material (fluorescent emitting material) for forming the light emitting layer is not particularly limited as long as emitting light by releasing the energy of excited singlet state. Examples thereof include a fluoranthene derivative, a styrylarylene derivative, a pyrene derivative, an arylacetylene derivative, a fluorene derivative, a boron complex, a perylene derivative, an oxadiazole derivative, an anthracene derivative, a styrylamine derivative, and an arylamine derivative, with an anthracene derivative, a fluoranthene derivative, a styrylamine derivative, an arylamine derivative, a styrylarylene derivative, a pyrene derivative, and a boron complex being preferred, and an anthracene derivative, a fluoranthene derivative, a styrylamine derivative, an arylamine derivative, and a boron complex compound being more preferred.

The content of the fluorescent dopant in the light emitting layer is not particularly limited and selected according to the use of the device, and preferably 0.1 to 70% by mass, more preferably 1 to 30% by mass, still more preferably 1 to 20% by mass, and particularly preferably 1 to 10% by mass. If being 0.1% by mass or more, the amount of light emission is sufficient. If being 70% by mass or less, the concentration quenching is avoided.

Host Material

Example of the host material for the light emitting layer includes an anthracene derivative and a compound comprising a polycyclic aromatic skeleton, with the anthracene derivative being preferred.

For example, an anthracene derivative represented by formula (20) is usable as a host material for a blue emitting layer:

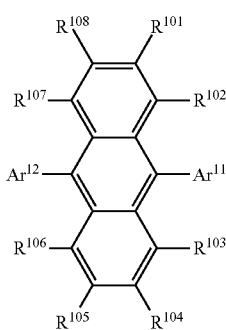

(20)

wherein:

each of $Ar^{11}$ and $Ar^{12}$ is independently a substituted or unsubstituted single ring group having 5 to 50 ring atoms or a substituted or unsubstituted fused ring group having 8 to 50 ring atoms; and each of $R^{101}$ to $R^{108}$ is independently selected from a hydrogen atom, a substituted or unsubstituted single ring group having 5 to 50, preferably 5 to 30, more preferably 5 to 20, and still more preferably 5 to 12 ring atoms, a substituted or unsubstituted fused ring group having 8 to 50, preferably 8 to 30, more preferably 8 to 20, and still more preferably 8 to 14 ring atoms, a group comprising the single ring group and the used ring group, a substituted or unsubstituted alkyl group having 1 to 50, preferably 1 to 20, more preferably 1 to 10, still more preferably 1 to 6 carbon atoms, a substituted or unsubstituted cycloalkyl group having 3 to 50, preferably 3 to 20, more preferably 3 to 10, and still more preferably 5 to 8 ring carbon atoms, a substituted or unsubstituted alkoxy group having 1 to 50, preferably 1 to 20, more preferably 1 to 10, and still more preferably 1 to 6 carbon atoms, a substituted or unsubstituted aralkyl group having 7 to 50, preferably 7 to 20, and more preferably 7 to 14 carbon atoms, a substituted or unsubstituted aryloxy group having 6 to 50, preferably 6 to 20, and more preferably 6 to 12 ring carbon atoms, a substituted or unsubstituted silyl group, a halogen atom, and a cyano group.

In a preferred embodiment, $R^{101}$ to $R^{108}$ may be all hydrogen atoms, or one of $R^{101}$ and $R^{108}$, one of $R^{104}$ and $R^{105}$, both of $R^{101}$ and $R^{105}$, or both of $R^{108}$ and $R^{104}$ may be a group selected from a single ring group having 5 to 50 ring atoms, preferably a phenyl group, a biphenylyl group, or a terphenylyl group; a substituted or unsubstituted alkyl group having 1 to 50 carbon atoms, preferably a methyl group, an ethyl group, a n-propyl group, an isopropyl group, a n-butyl group, an isobutyl group, a s-butyl group, or a t-butyl group; and a substituted silyl group, preferably a trimethylsilyl group. In a more preferred embodiment, $R^{101}$ to $R^{108}$ are all hydrogen atoms.

The single ring group of formula (20) is a group composed of only a ring structure having no fused ring structure.

The single ring group having 5 to 50 ring atoms is preferably an aromatic group, such as a phenyl group, a biphenylyl group, a terphenylyl group, and a quaterphenylyl group, and a heterocyclic group, such as a pyridyl group, a pyrazyl group, a pyrimidyl group, a triazinyl group, a furyl group, and a thienyl group, with a phenyl group, a biphenylyl group, and a terphenylyl group being more preferred.

The fused ring group of formula (20) is a group wherein two or more ring structures are fused together.

The fused ring group having 8 to 50 ring atoms is preferably a fused aromatic ring group, such as a naphthyl group, a phenanthryl group, an anthryl group, a chrysenyl group, a benzanthryl group, a benzophenanthryl group, a triphenylenyl group, a benzochrysenyl group, an indenyl group, a fluorenyl group, a 9,9-dimethylfluorenyl group, a benzofluorenyl group, a dibenzofluorenyl group, a fluoranthenyl group, and a benzofluoranthenyl group, and a fused heterocyclic group, such as a benzofuranyl group, a benzothiophenyl group, an indolyl group, a dibenzofuranyl group, a dibenzothiophenyl group, a carbazolyl group, a quinolyl group, and a phenanthrolinyl group, with a naphthyl group, a phenanthryl group, an anthryl group, a 9,9-dimethylfluorenyl group, a fluoranthenyl group, a benzanthryl group, a dibenzothiophenyl group, a dibenzofuranyl group, and a carbazolyl group being more preferred.

The substituent of $Ar^{11}$ and $Ar^{12}$ is preferably selected from the single ring group and the fused ring group each mentioned above, for example, the substituted or unsubstituted single ring group having 5 to 50 ring atoms and the substituted or unsubstituted fused ring group having 8 to 50 ring atoms.

In formula (20), the details of the alkyl group, the cycloalkyl group, the alkoxy group, the alkyl portion and the aryl portion of the aralkyl group, the aryloxy group, and the substituted silyl group, such as the alkylsilyl group and the arylsilyl group, are the same as those described above with respect to $R_1$ to $R_{11}$ of formula (1). Example of the halogen atom includes a fluorine atom, a chlorine atom, a bromine atom, and an iodine atom.

In formula (20), $R^{101}$ to $R^{108}$ are all preferably hydrogen atoms, or one of $R^{101}$ and $R^{108}$, one of $R^{104}$ and $R^{105}$, each of $R^{101}$ and $R^{105}$, or each of $R^{108}$ and $R^{104}$ is preferably a group selected from a single ring group having 5 to 50 ring atoms, such as a phenyl group, a biphenylyl group, and a terphenylyl group; a substituted or unsubstituted alkyl group having 1 to 50 carbon atoms, such as a methyl group, an ethyl group, a n-propyl group, an isopropyl group, a n-butyl group, an isobutyl group, a s-butyl group, and a t-butyl group; or a substituted silyl group, such as a trimethylsilyl group. More preferably $R^{101}$ to $R^{108}$ are all hydrogen atoms.

The anthracene derivative represented by formula (20) is preferably any of the following anthracene derivatives (A), (B), and (C), which are selected depending upon the construction of the organic EL device and the required properties.

Anthracene Derivative (A)

The anthracene derivative (A) is a compound represented by formula (20), wherein each of $Ar^{11}$ and $Ar^{12}$ is independently a substituted or unsubstituted fused ring group having 8 to 50 ring atoms. $Ar^{11}$ and $Ar^{12}$ may be the same or different.

Particularly preferably, $Ar^{11}$ and $Ar^{12}$ are different substituted or unsubstituted fused ring groups (inclusive of the difference in the bonding positions of the anthracene ring). The preferred example of the fused ring group is as described above, and preferably a naphthyl group, a phenanthryl group, a benzanthryl group, a 9,9-dimethylfluorenyl group, or a dibenzofuranyl group.

Anthracene Derivative (B)

The anthracene derivative (B) is a compound represented by formula (20), wherein one of $Ar^{11}$ and $Ar^{12}$ is a substituted or unsubstituted single ring group having 5 to 50 ring atoms and the other is a substituted or unsubstituted fused ring group having 8 to 50 ring atoms.

In a preferred embodiment, $Ar^{12}$ is a naphthyl group, a phenanthryl group, a benzanthryl group, a 9,9-dimethylfluorenyl group, or a dibenzofuranyl group, and $Ar^{11}$ is an unsubstituted phenyl group or a substituted phenyl group having a substituent selected from a single ring group and a fused ring group, for example, a phenyl group, a biphenyl group, a naphthyl group, a phenanthryl group, a 9,9-dimethylfluorenyl group, and a dibenzofuranyl group.

Preferred examples of the single ring group and the fused ring group are as describe above.

In another preferred embodiment, $Ar^{12}$ is a substituted or unsubstituted fused ring group having 8 to 50 ring atoms, and $Ar^{11}$ is an unsubstituted phenyl group. The fused ring group is particularly preferably a phenanthryl group, a 9,9-dimethylfluorenyl group, a dibenzofuranyl group, or a benzanthryl group.

Anthracene Derivative (C)

The anthracene derivative (C) is a compound represented by formula (20), wherein each of $Ar^{11}$ and $Ar^{12}$ is independently a substituted or unsubstituted single ring group having 5 to 50 ring atoms.

In a preferred embodiment, each of $Ar^{11}$ and $Ar^{12}$ is a substituted or unsubstituted phenyl group.

In a more preferred embodiment, $Ar^{11}$ is an unsubstituted phenyl group and $Ar^{12}$ is a substituted phenyl group having a substituent selected from the single ring group and the fused ring group, or each of $Ar^{11}$ and $Ar^{12}$ is independently a substituted phenyl group having a substituent selected from the single ring group and the fused ring group.

Preferred example of the single ring group and the fused ring group as the substituent is as describe above. The single ring group as the substituent is more preferably a phenyl group or a biphenyl group, and the fused ring group as the substituent is more preferably a naphthyl group, a phenanthryl group, a 9,9-dimethylfluorenyl group, a dibenzofuranyl group, or a benzanthryl group.

Examples of the anthracene derivative represented by formula (20) are shown below.

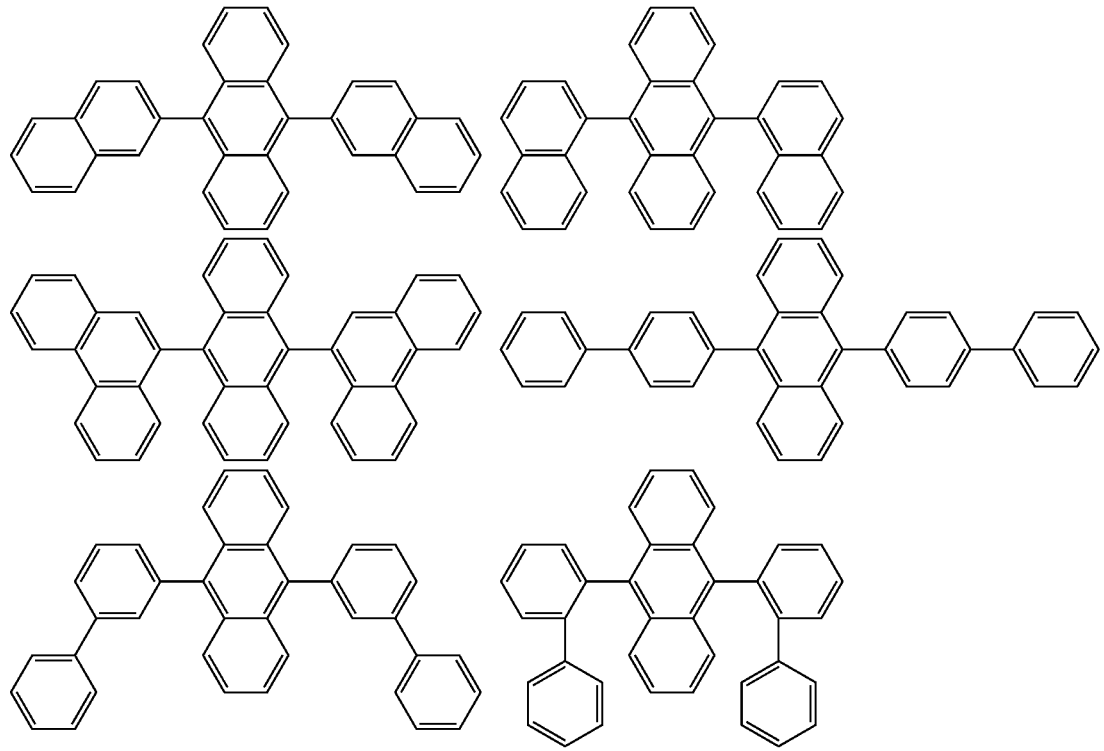

-continued
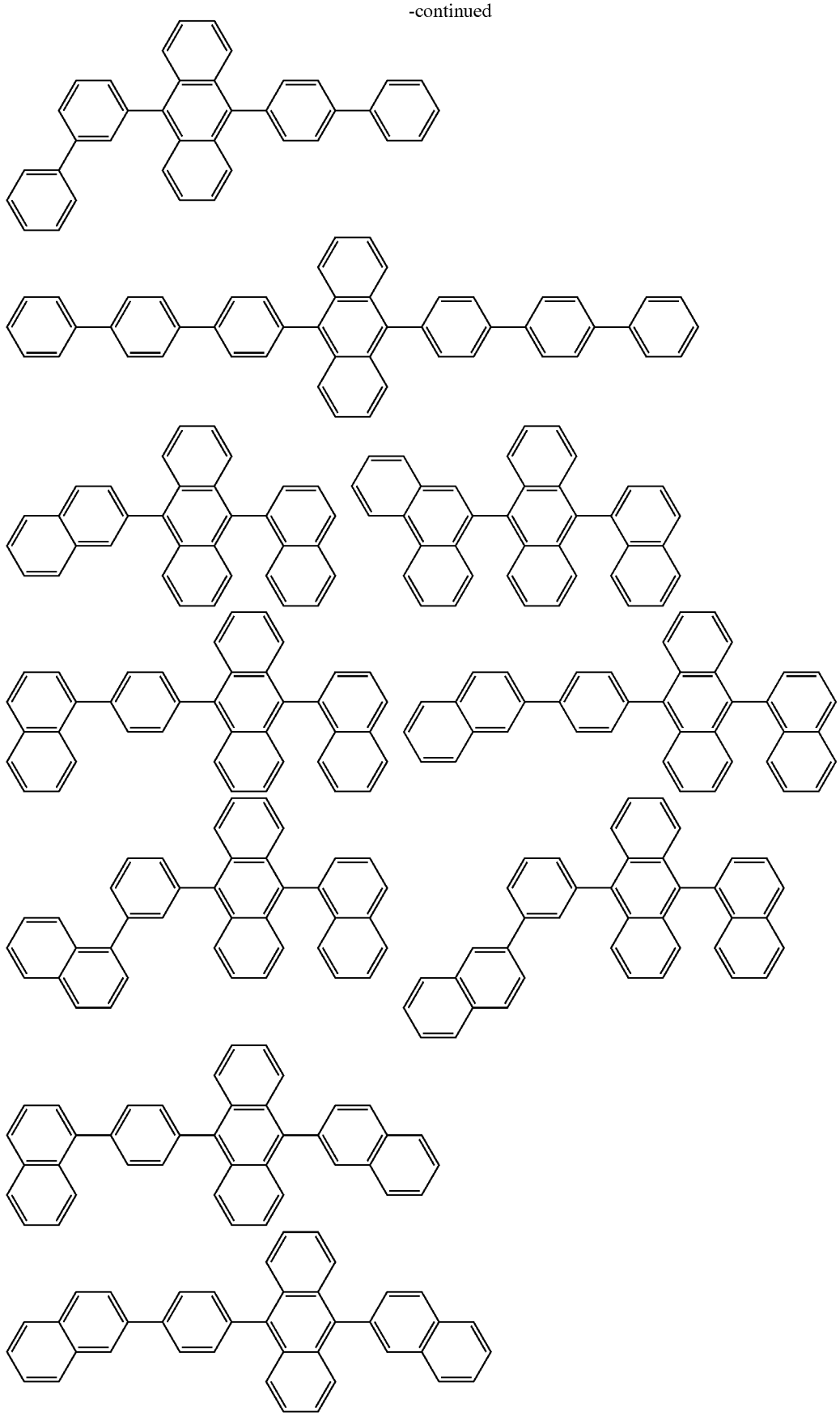

-continued
| 249 | 250 |
|---|---|
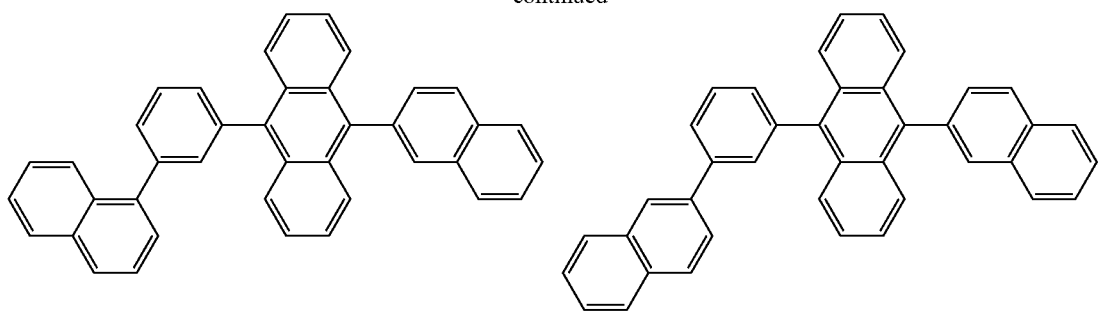
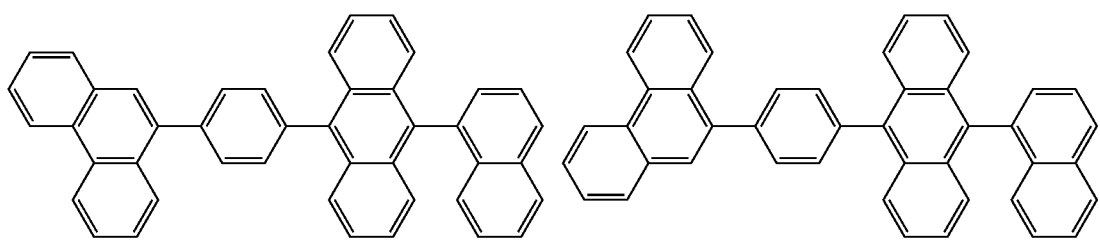
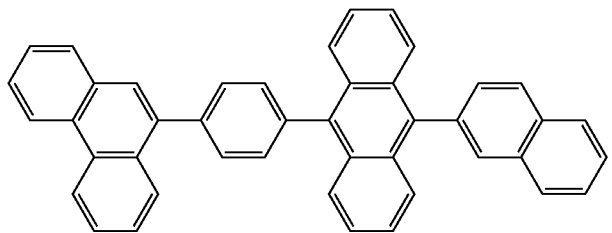
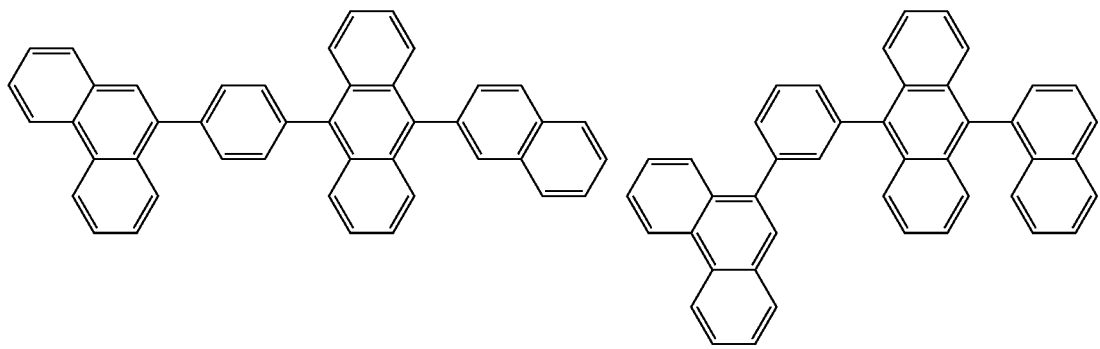
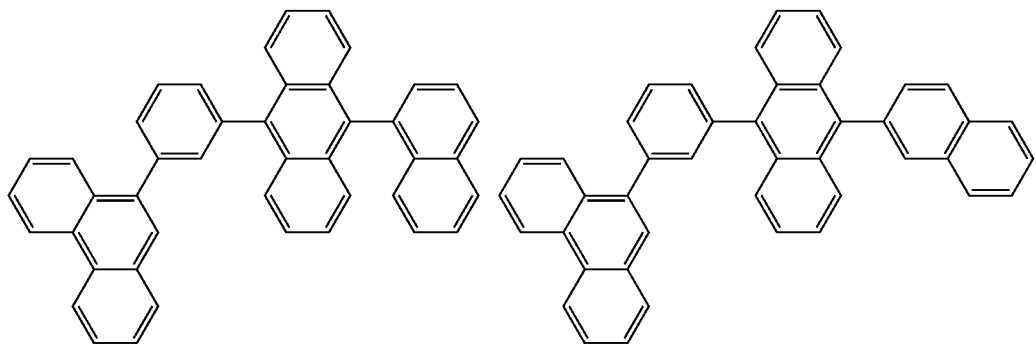

251 252
-continued
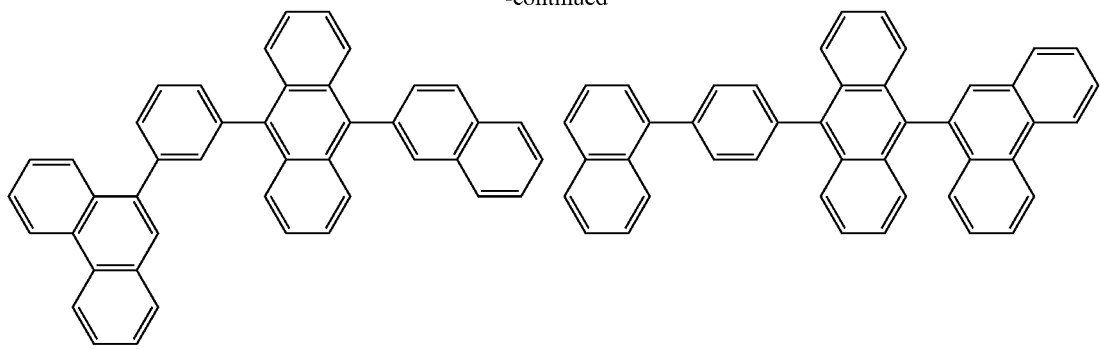
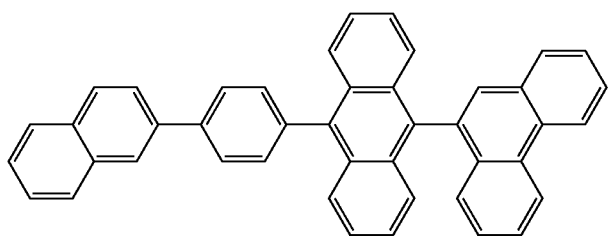
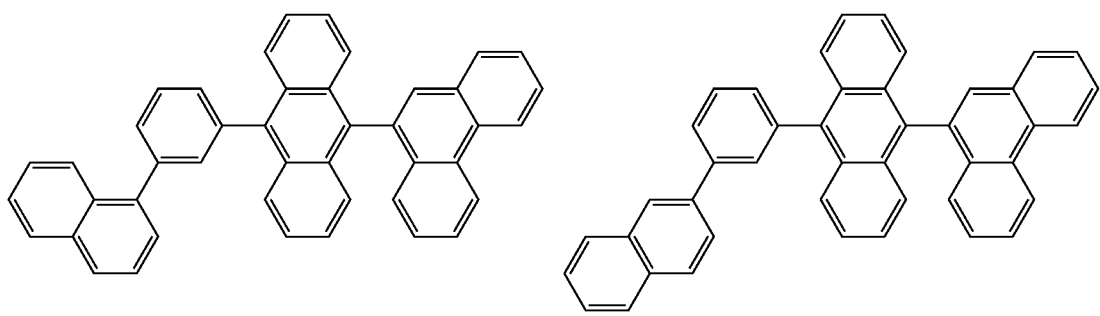
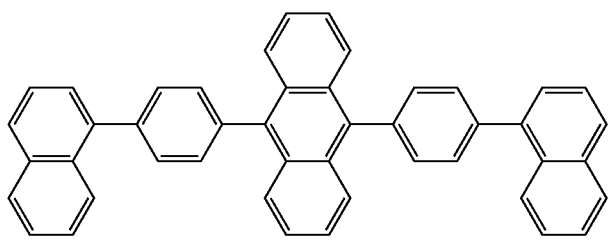
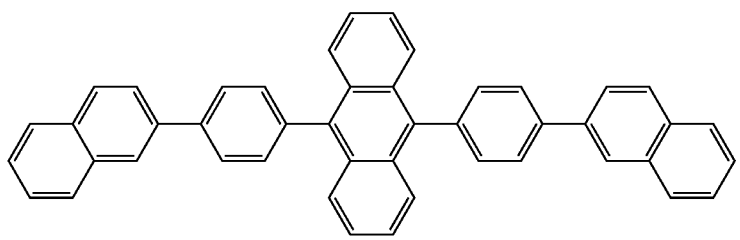
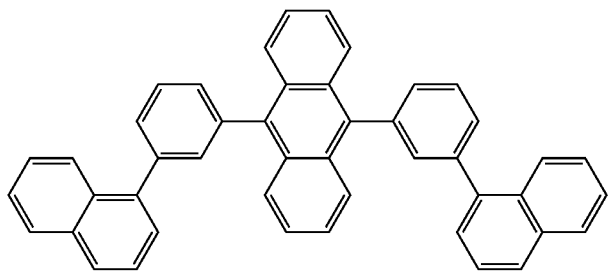

-continued
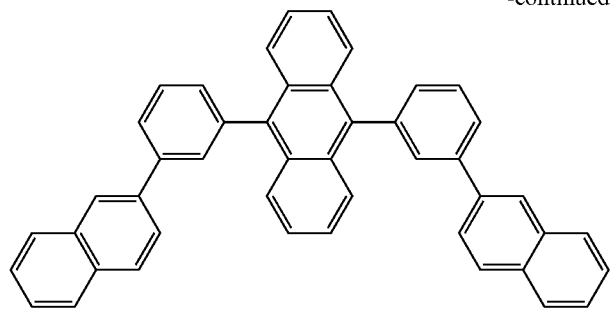
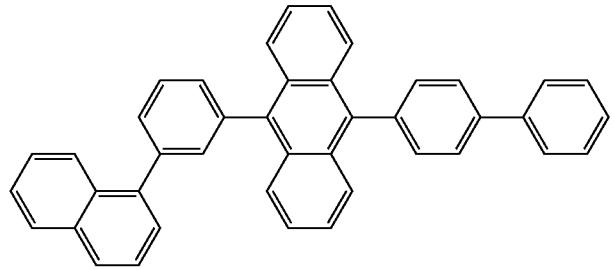
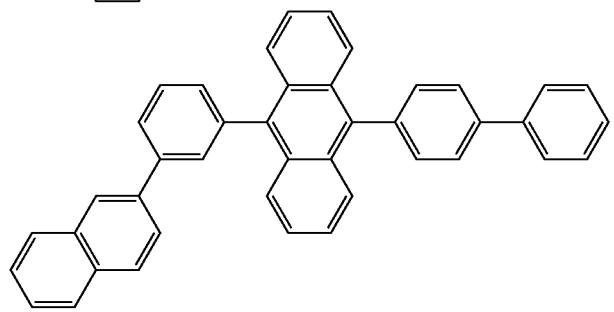
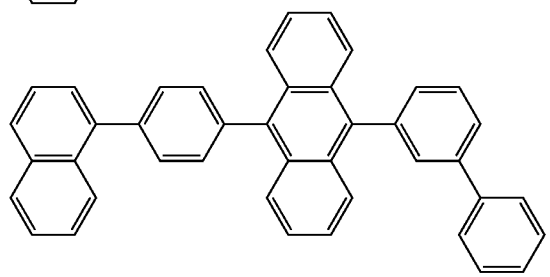
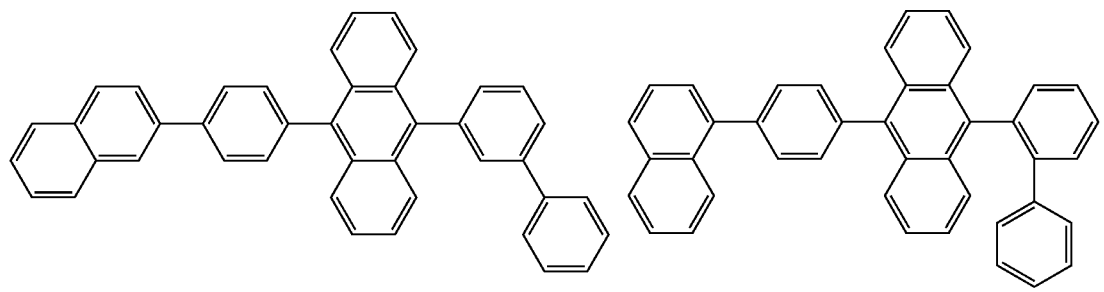
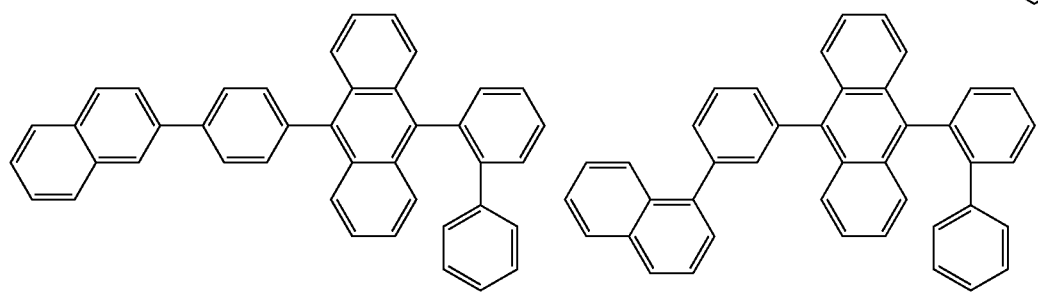

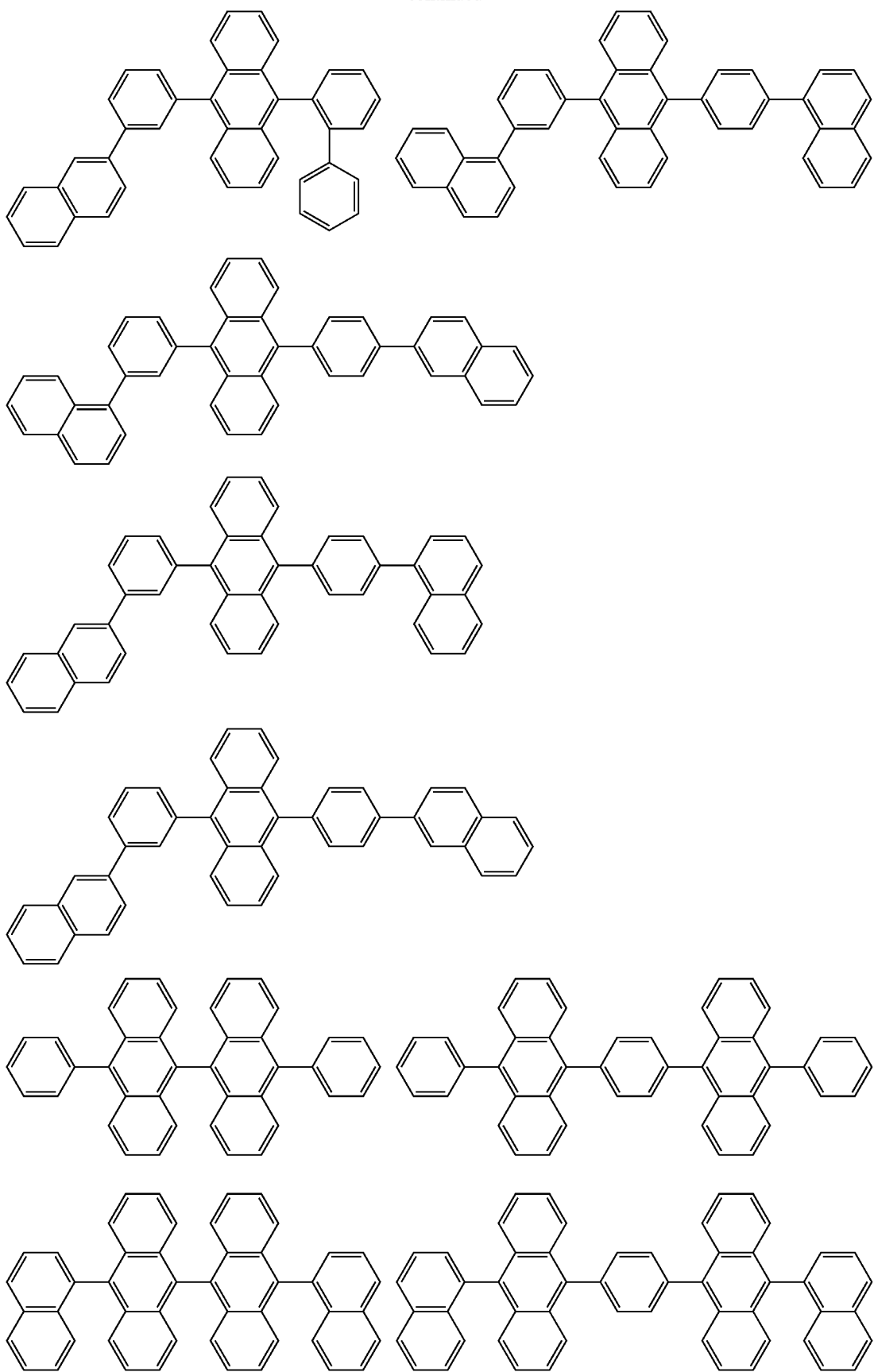
-continued

-continued
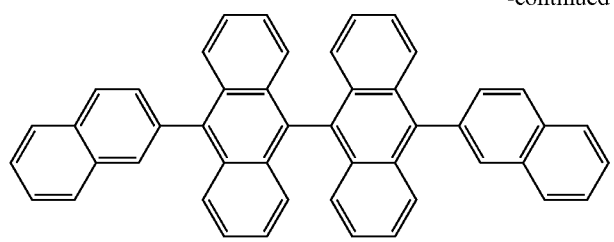
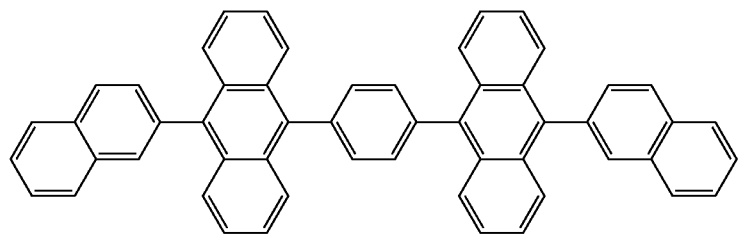
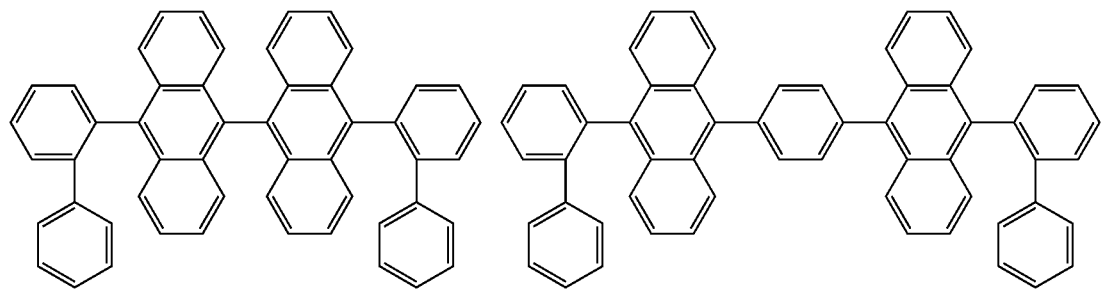
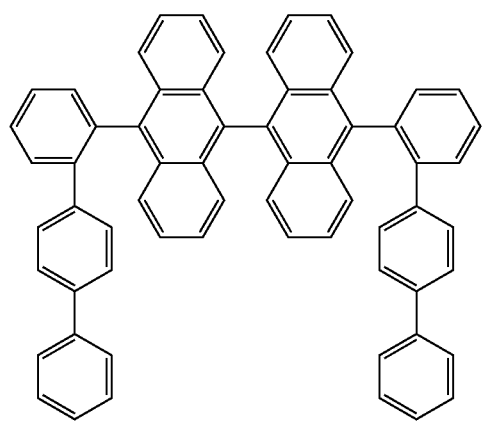
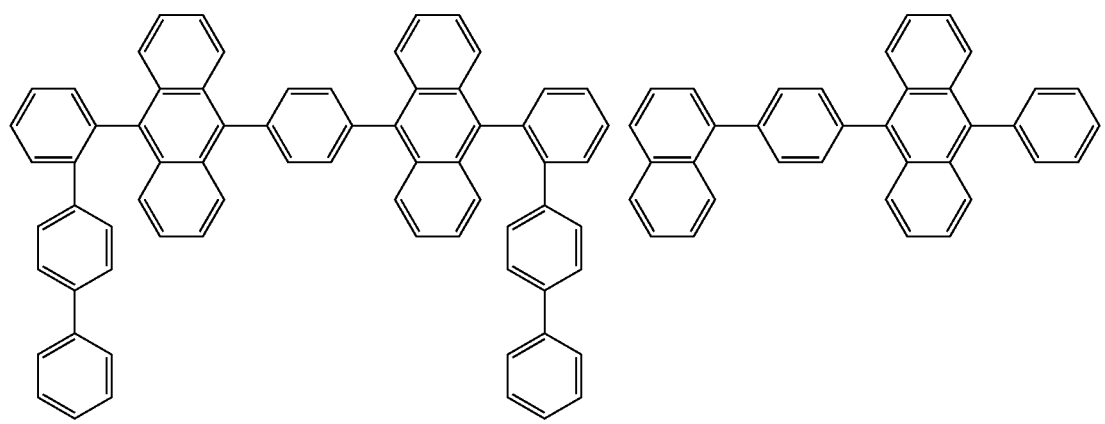

259 260
-continued
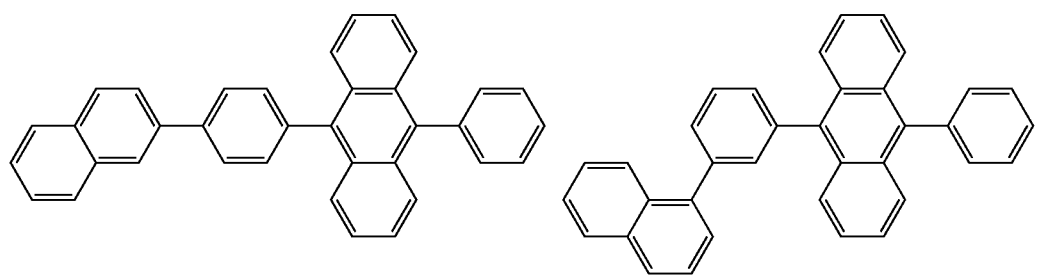
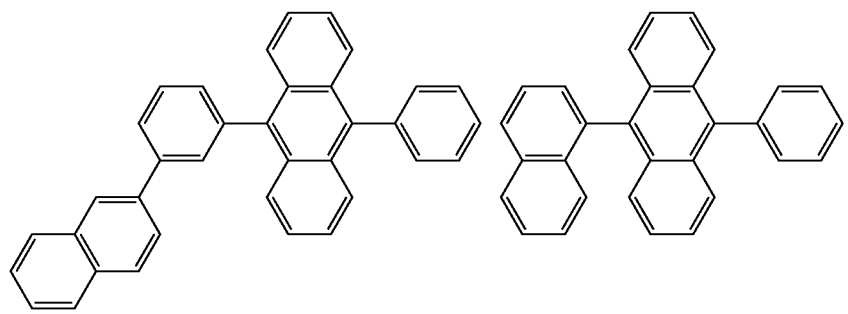
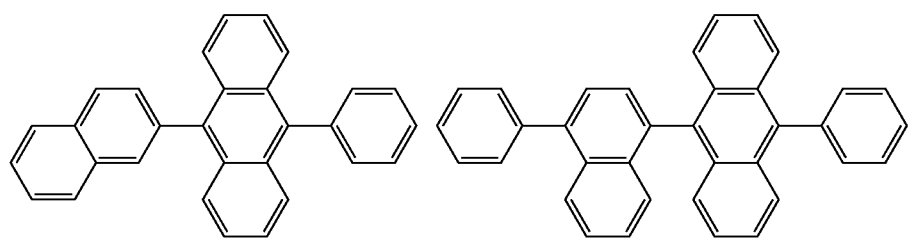
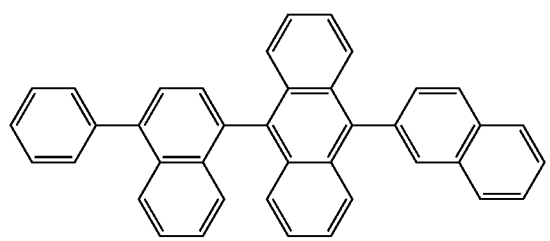

261 262
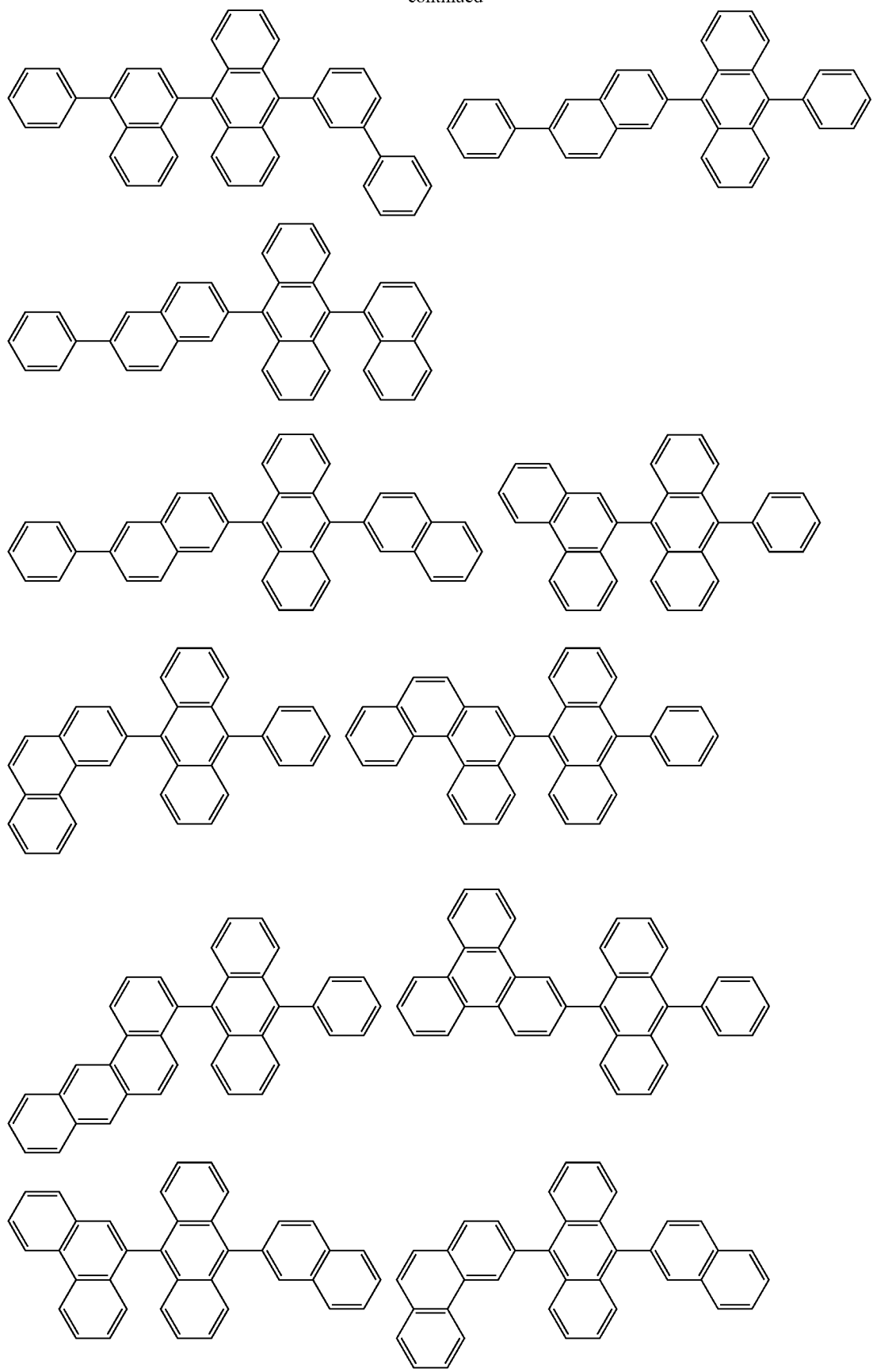

263                                    264
-continued
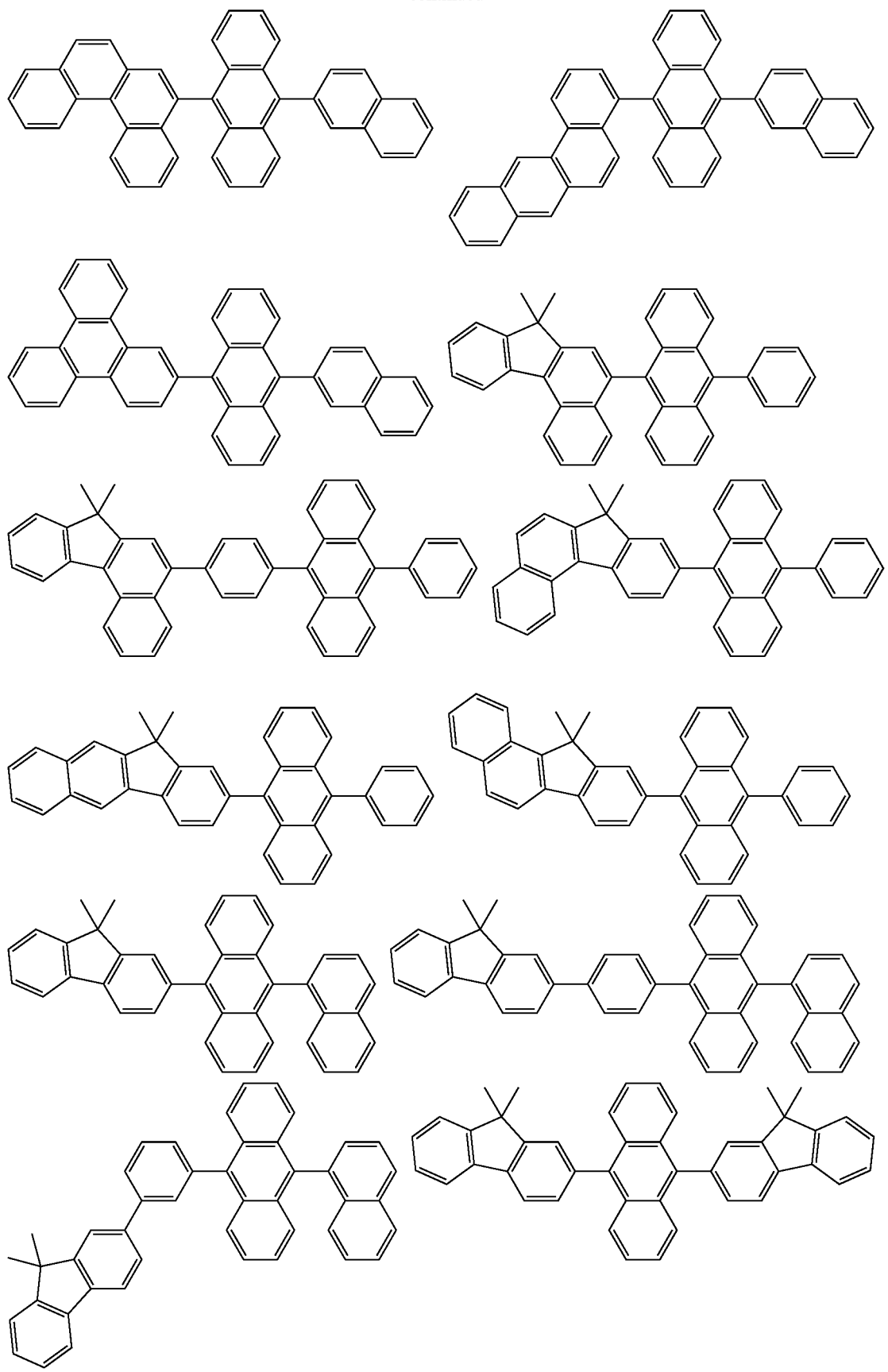

-continued
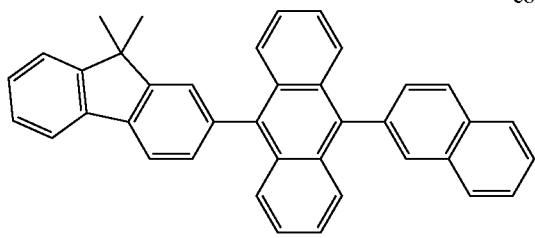
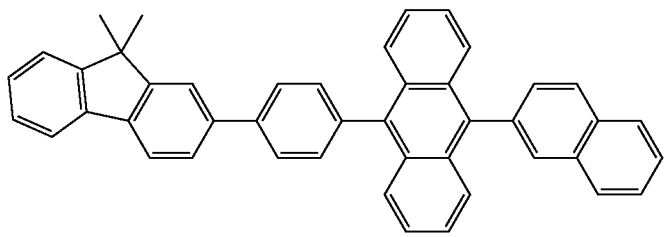
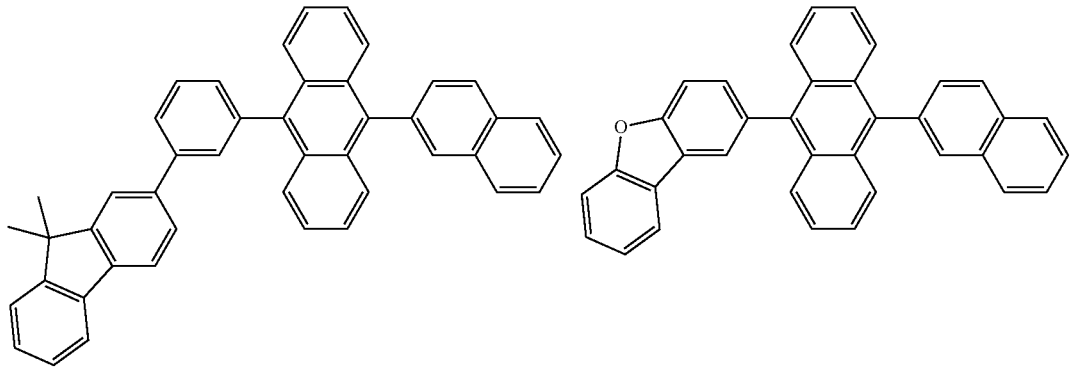
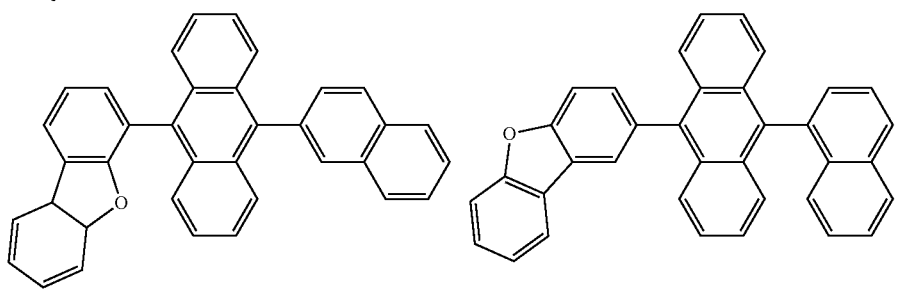
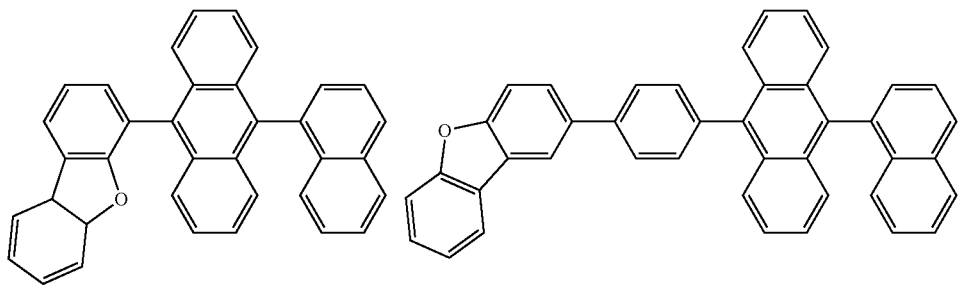
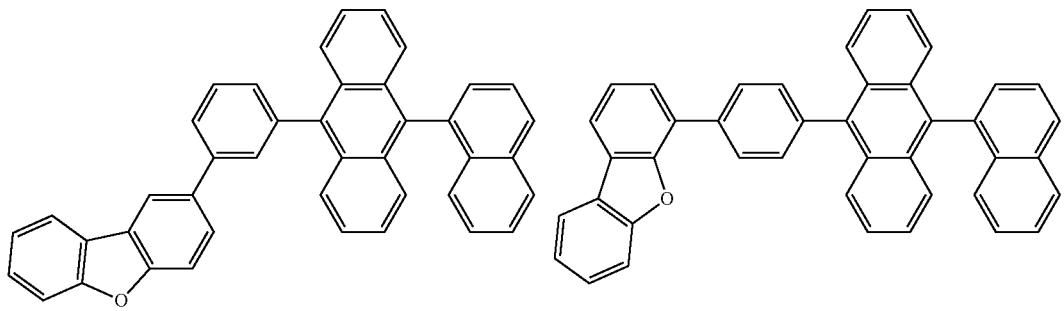

-continued
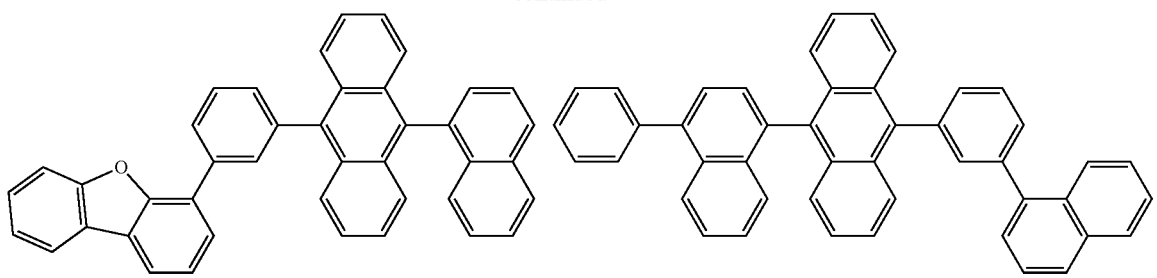
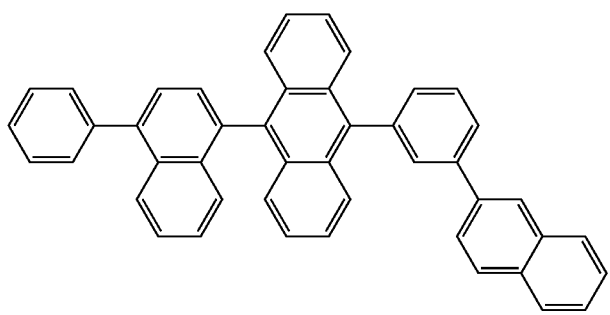
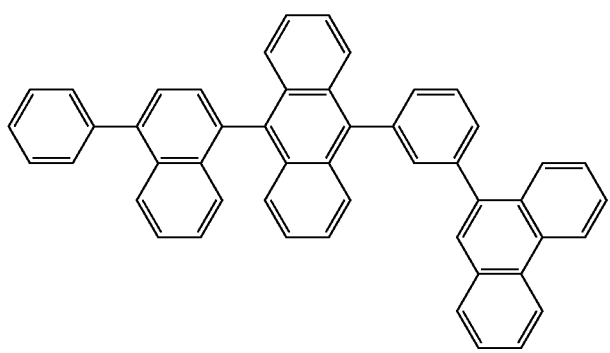
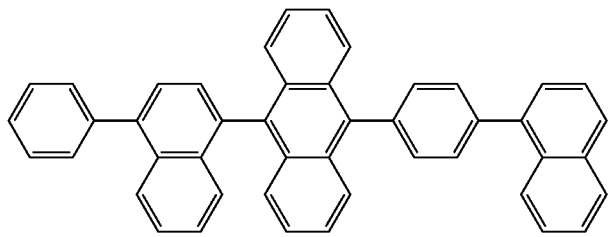
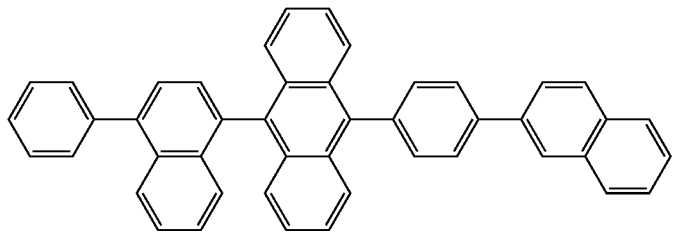
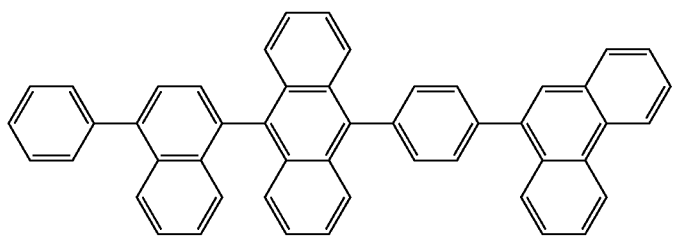

-continued
| 269 | 270 |
|---|---|
| 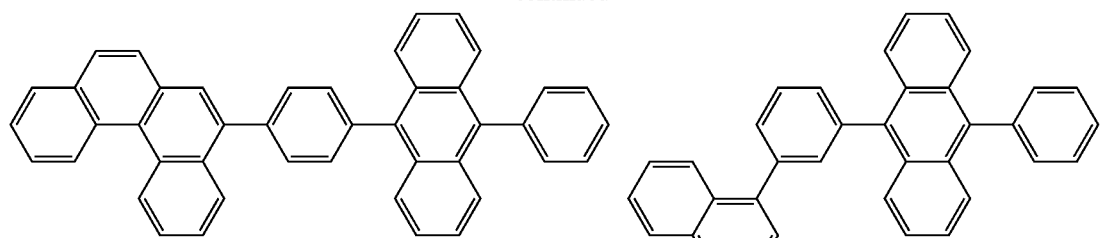 | 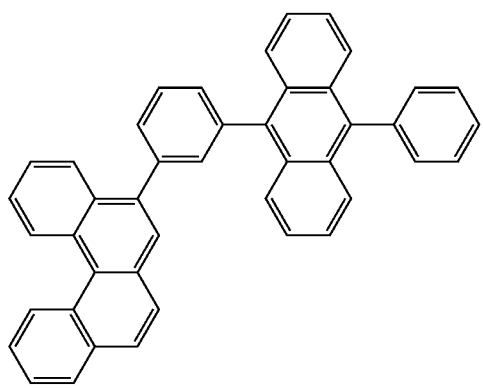 |
| 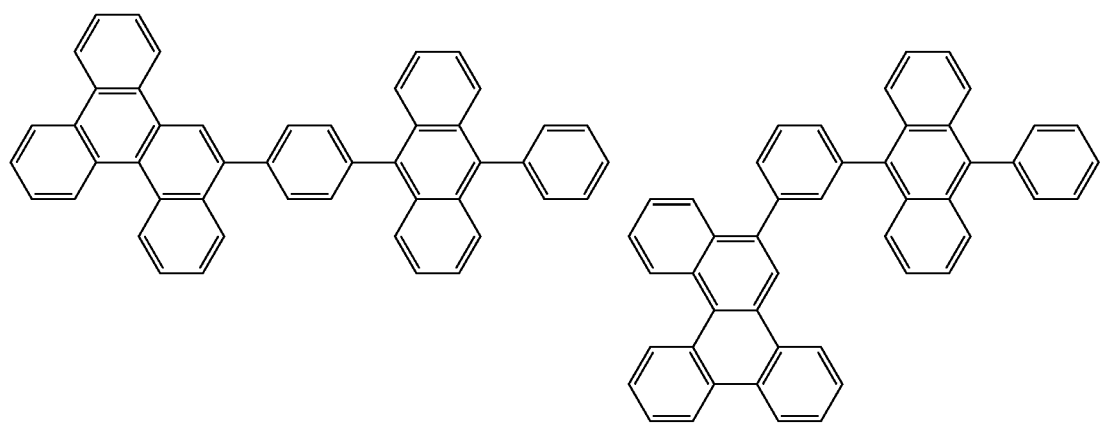 | |
| 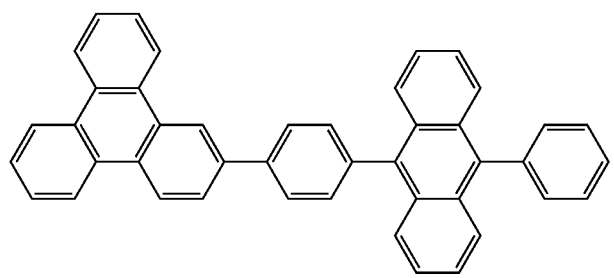 | |
| 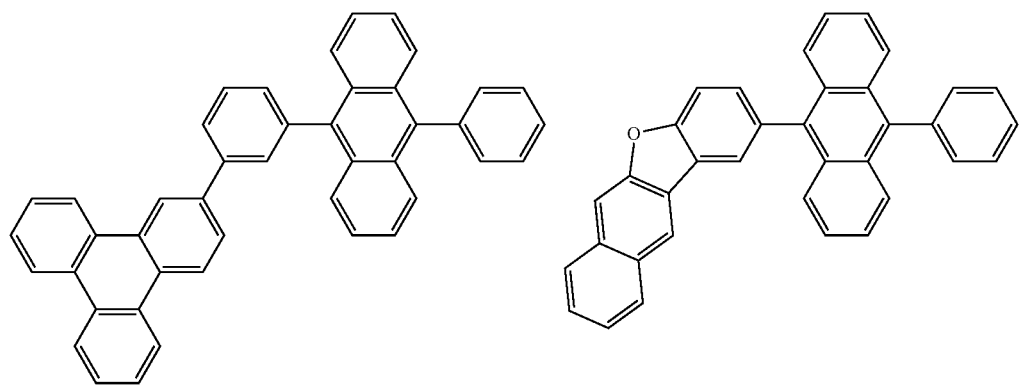 | |

271
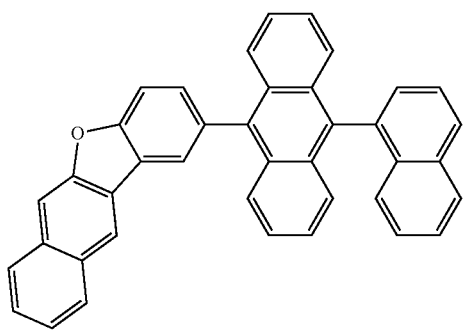
272
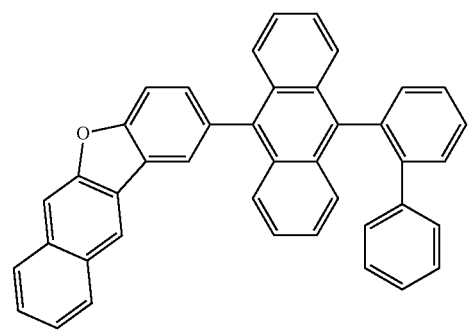
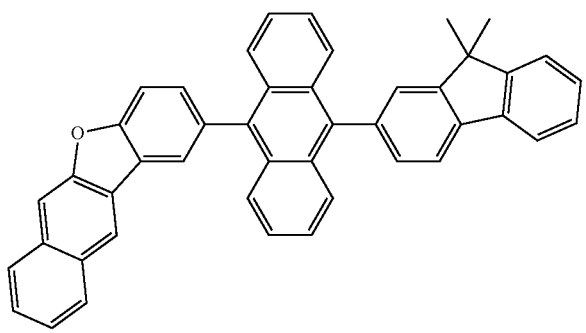
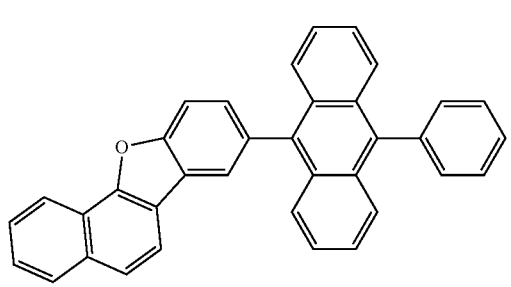
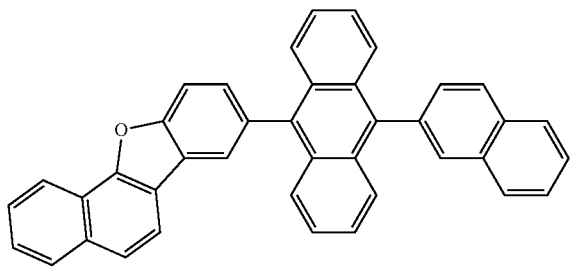
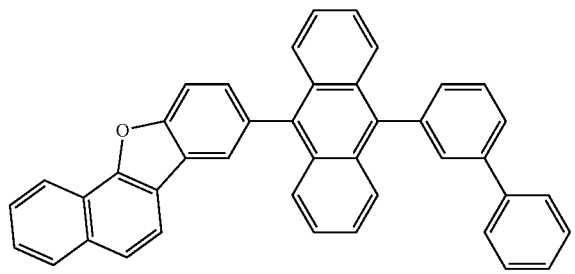
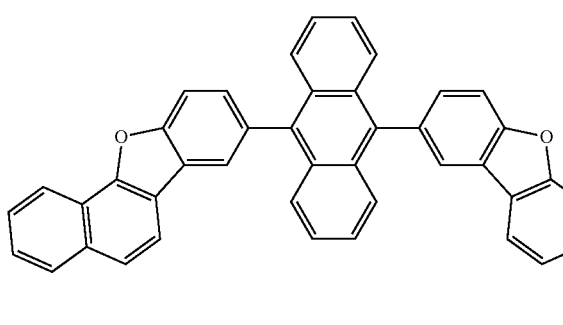
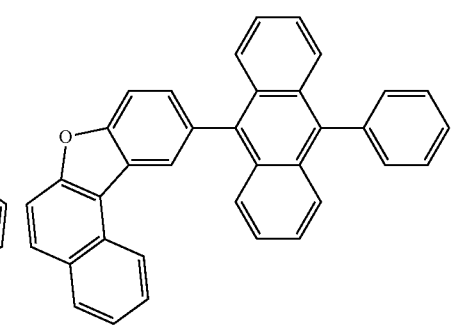
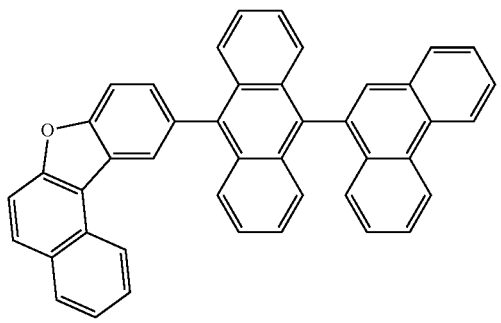
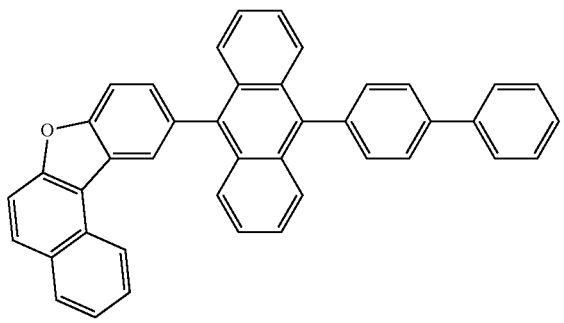

273
-continued
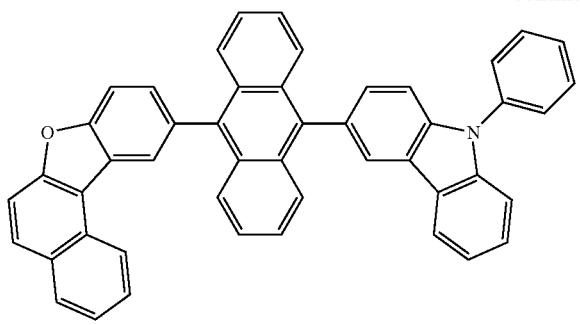
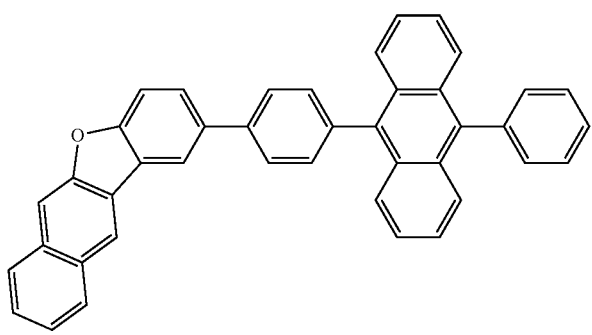
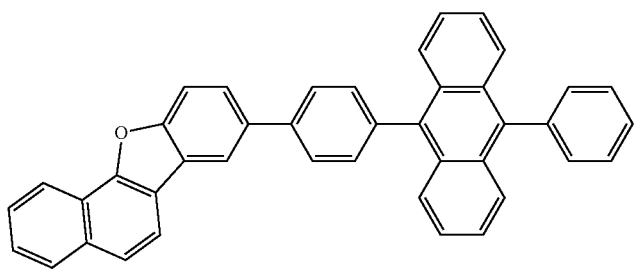
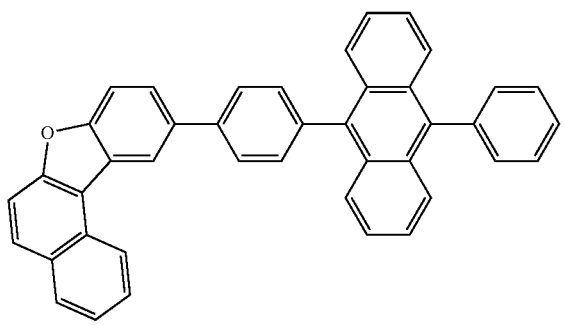
274
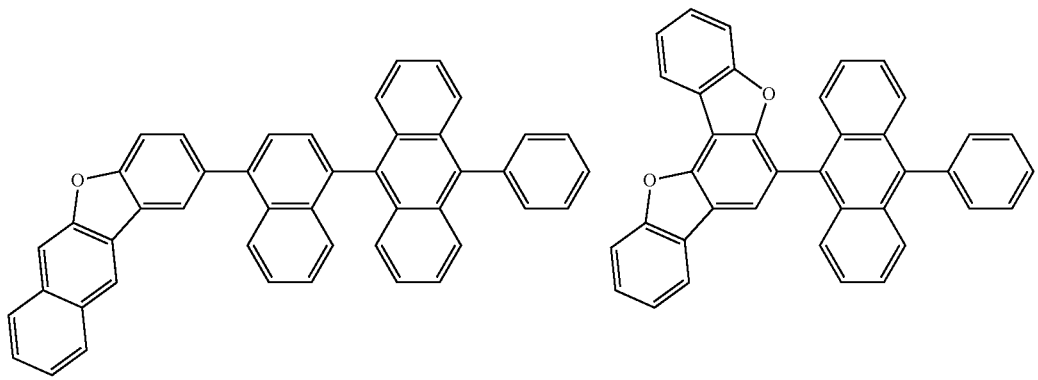

275 276
-continued
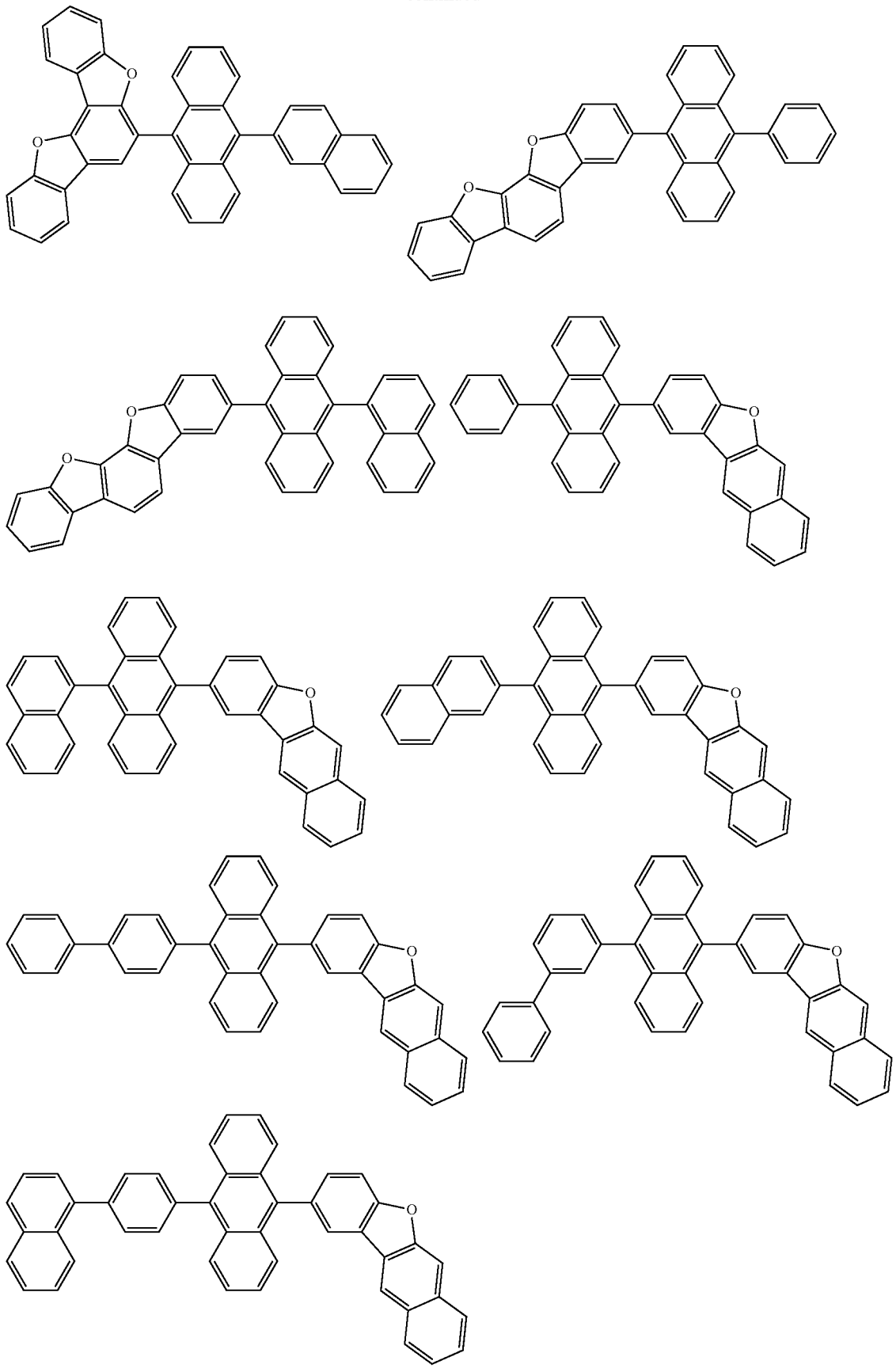

-continued
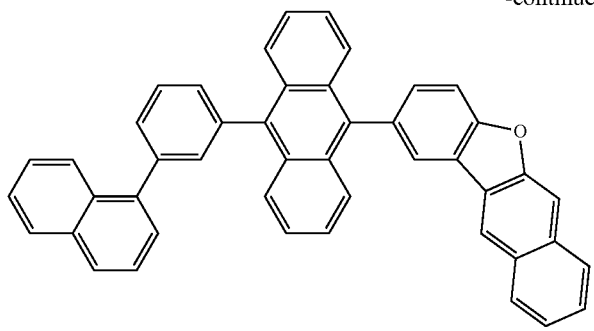
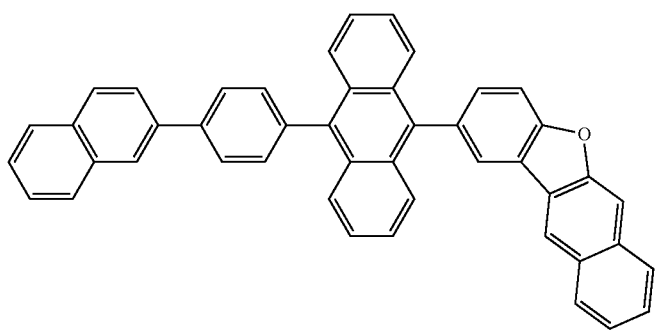
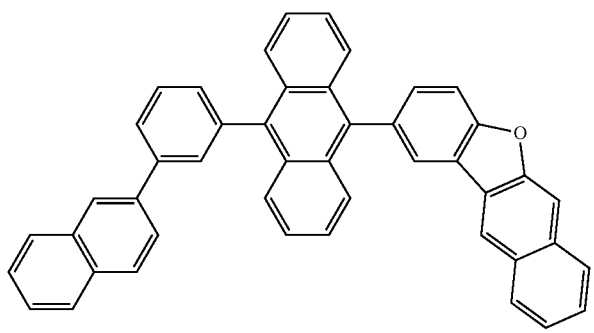
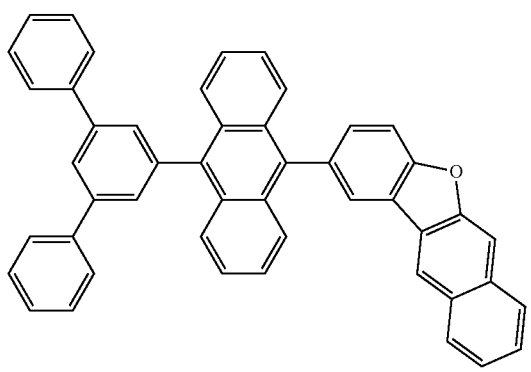
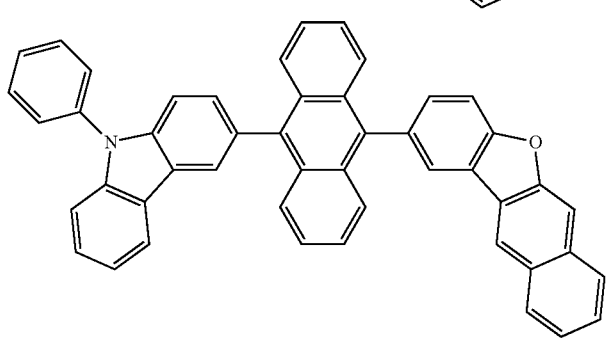

-continued
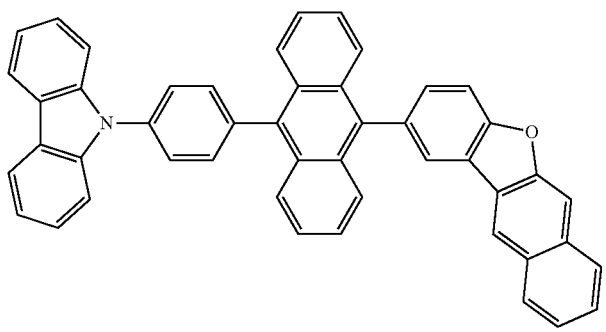
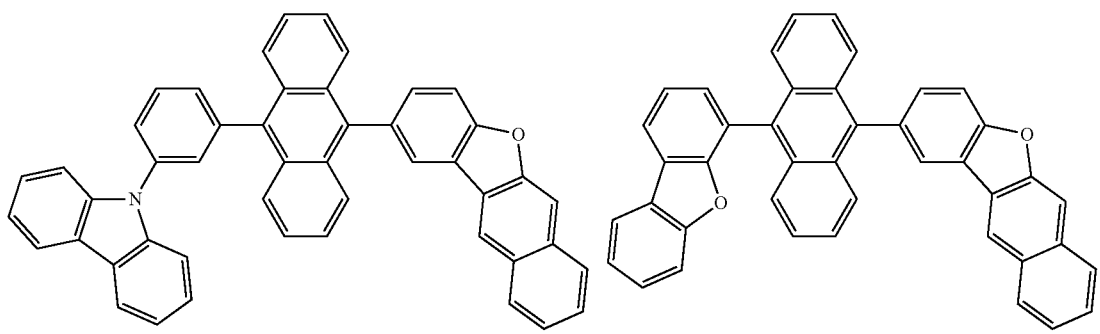
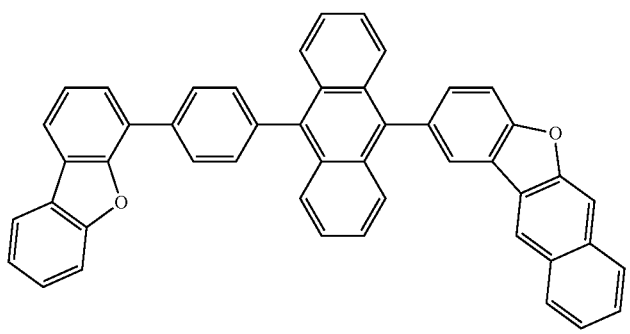
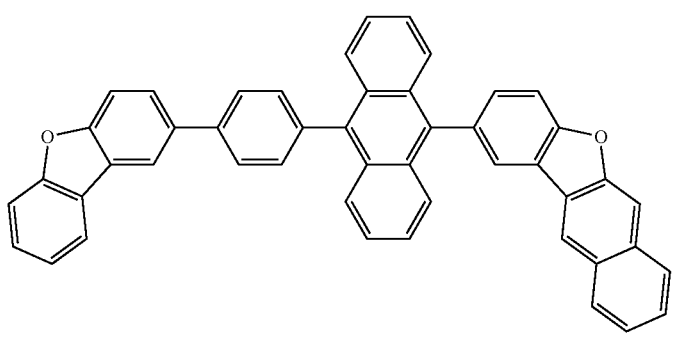
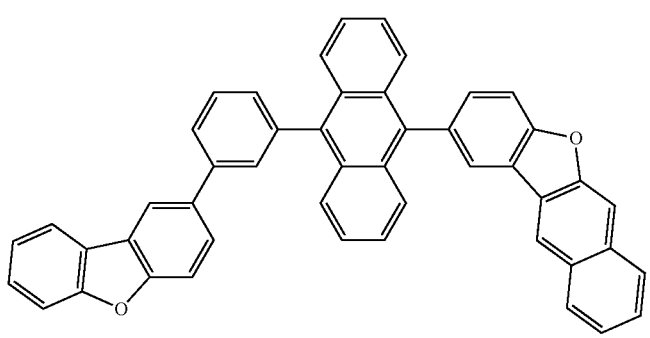

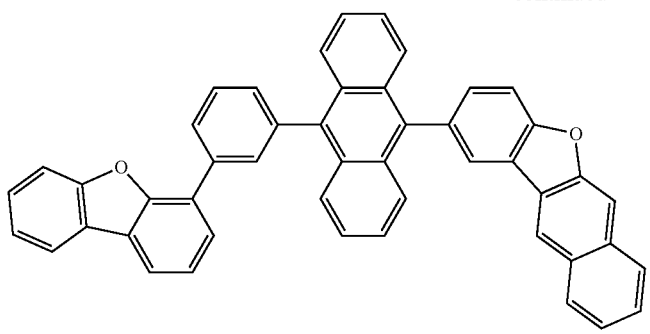
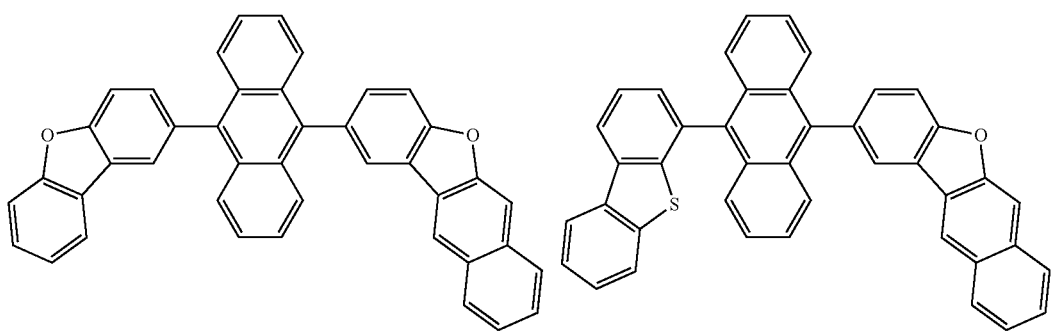
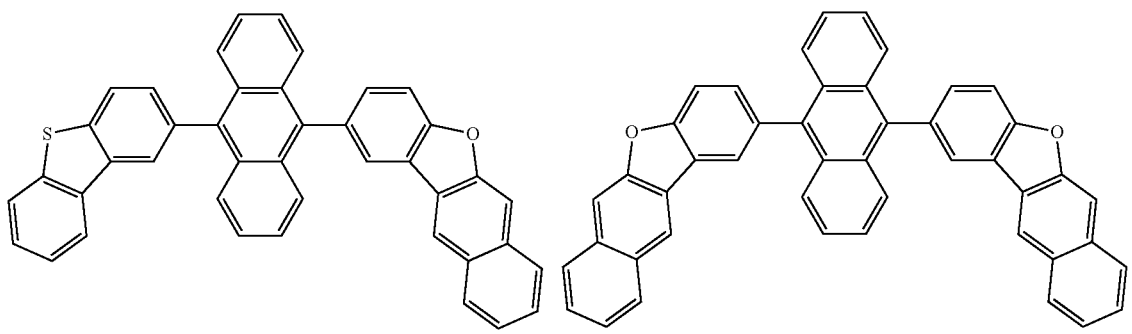
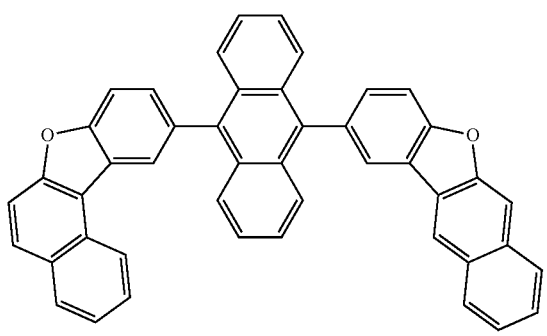
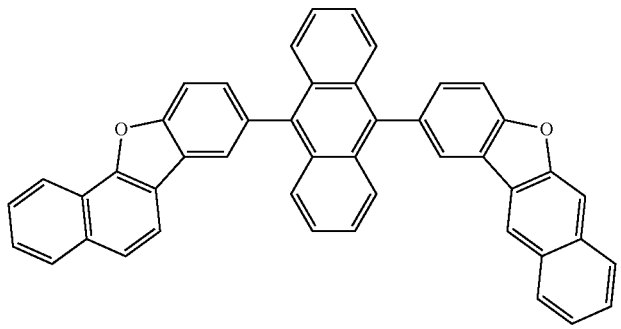

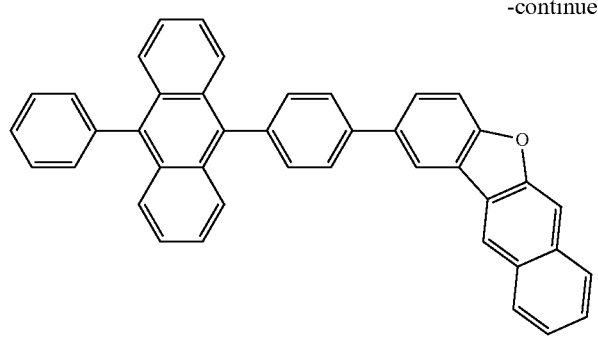
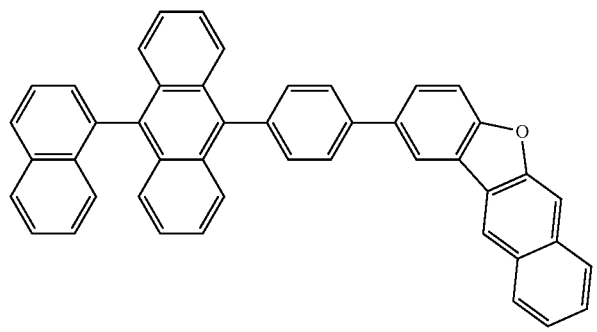
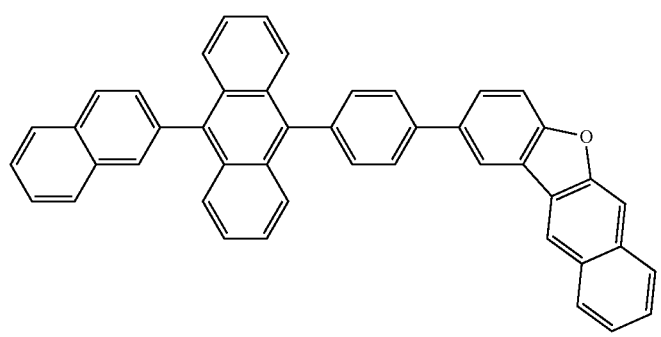
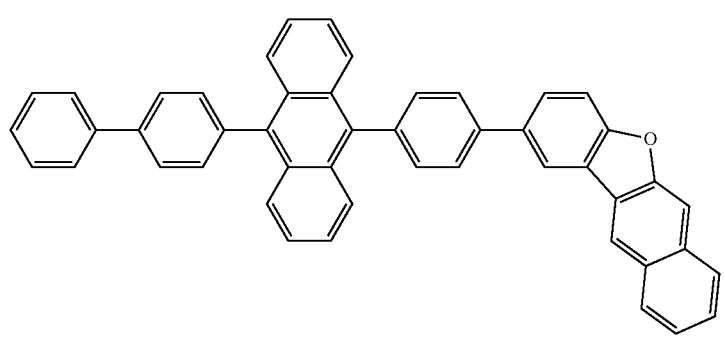
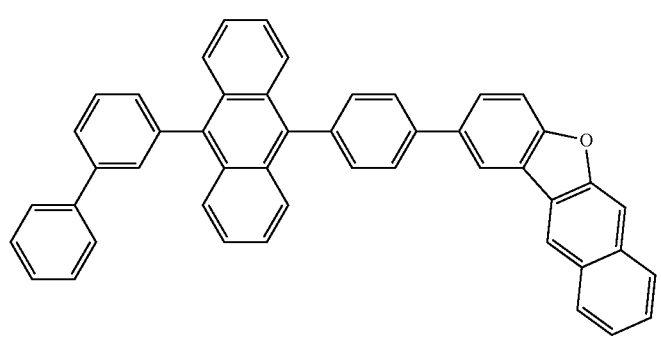

-continued
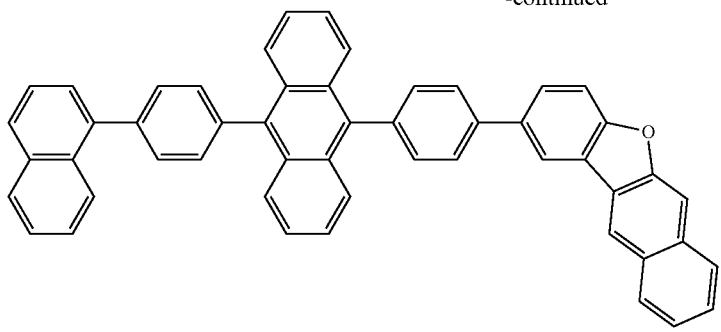
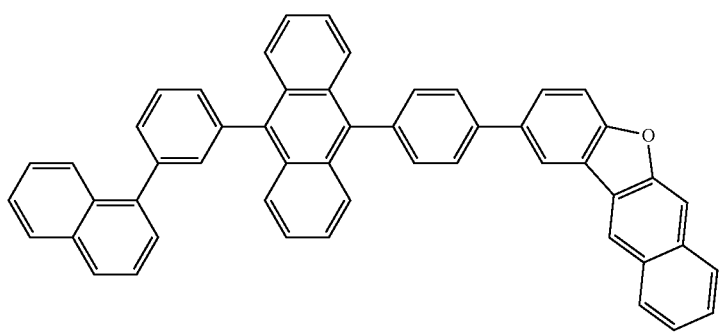
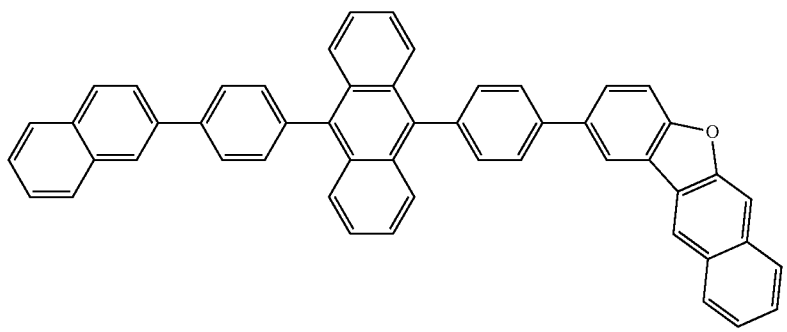
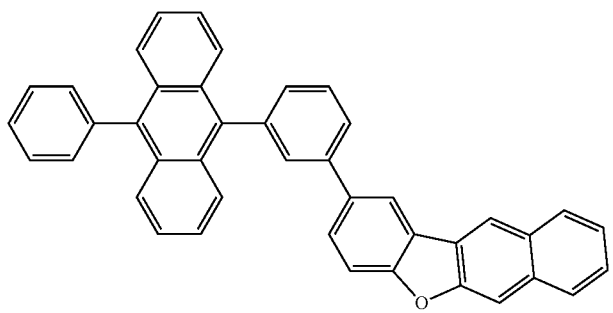
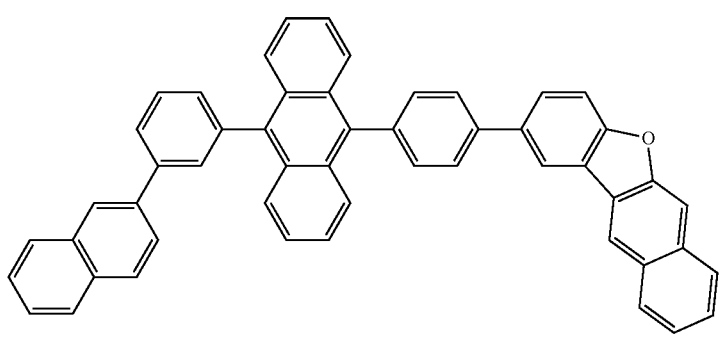

-continued
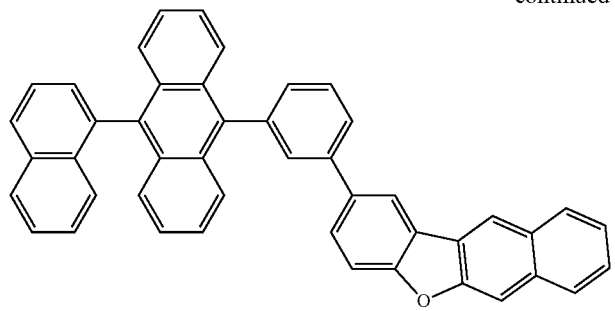
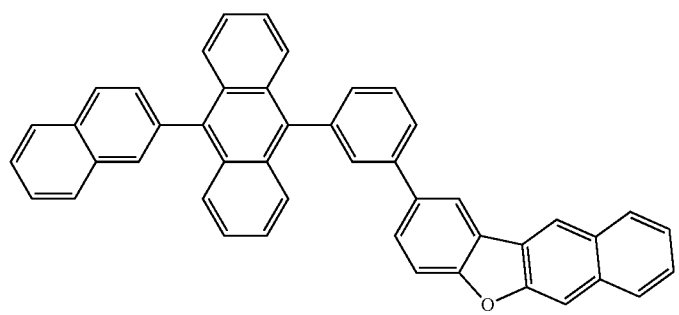
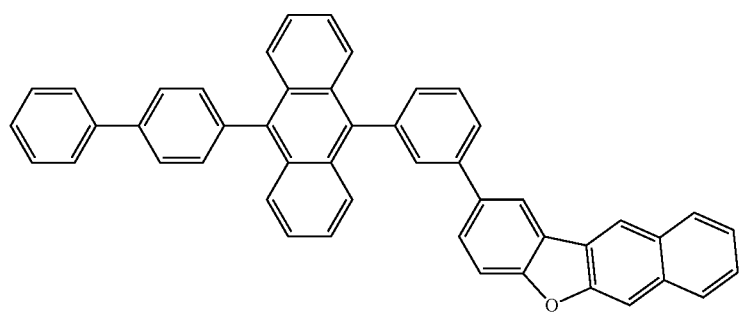
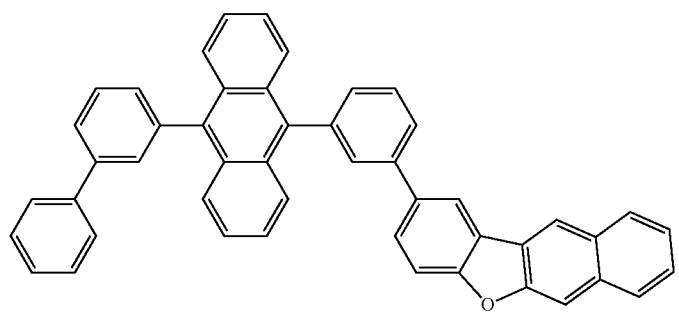
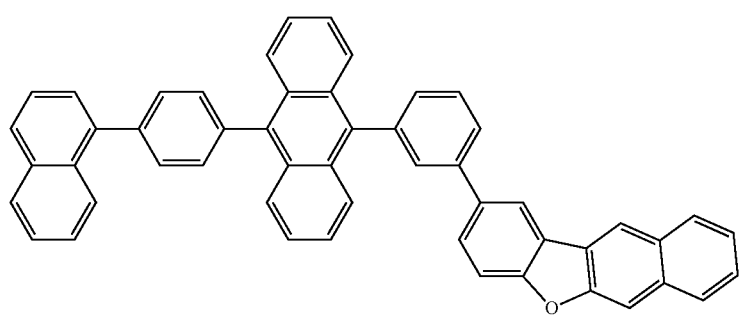

-continued
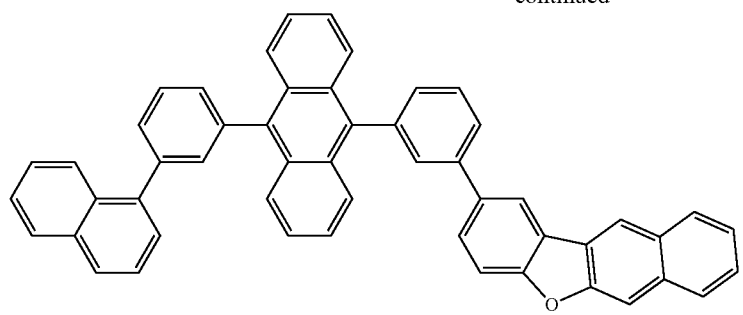
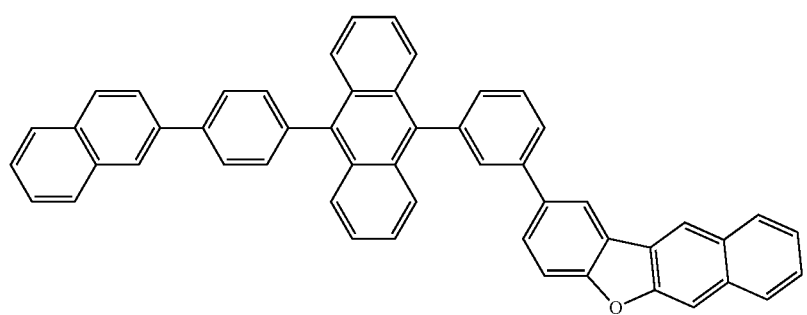
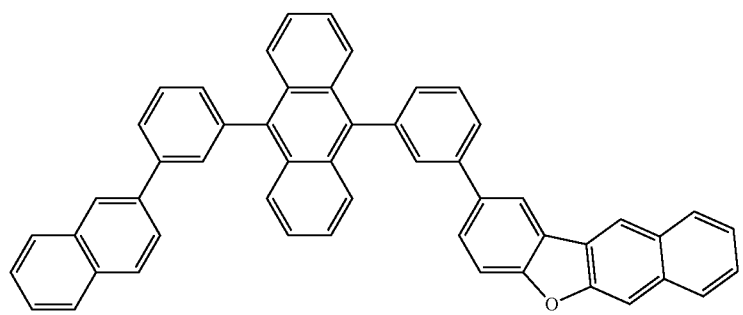
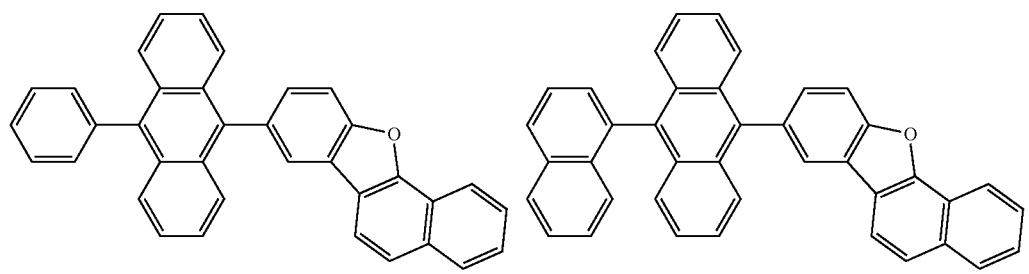
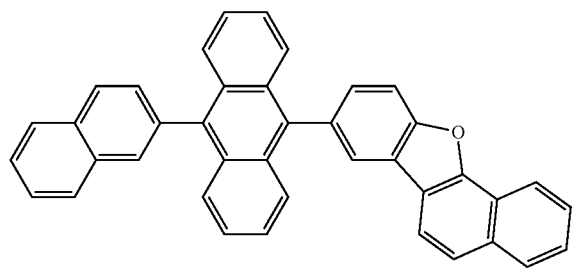

-continued
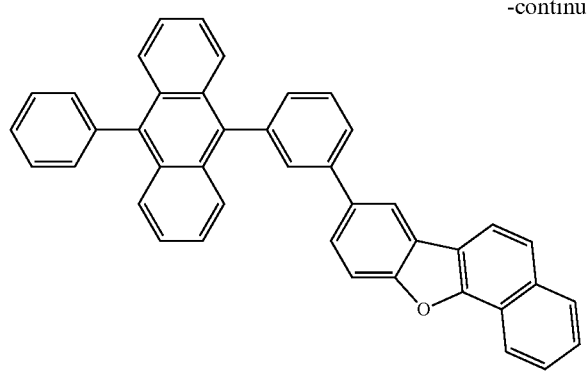
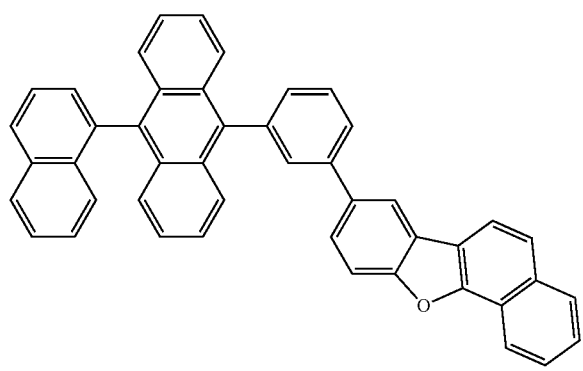
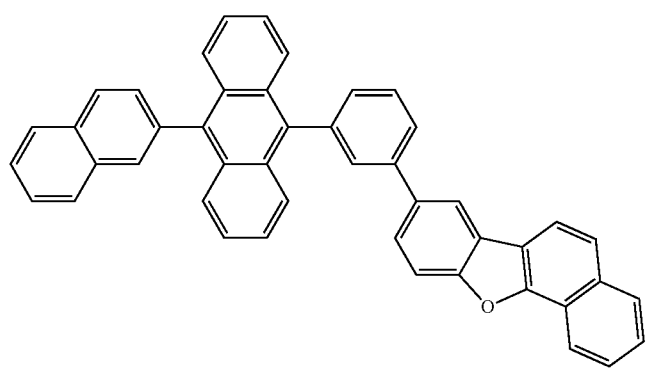
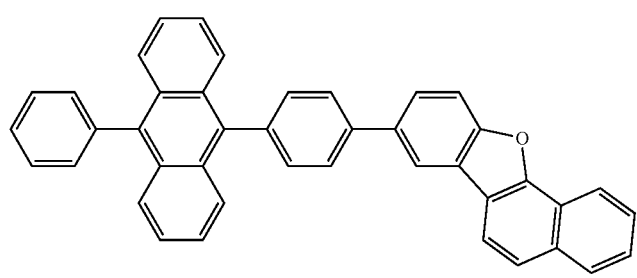
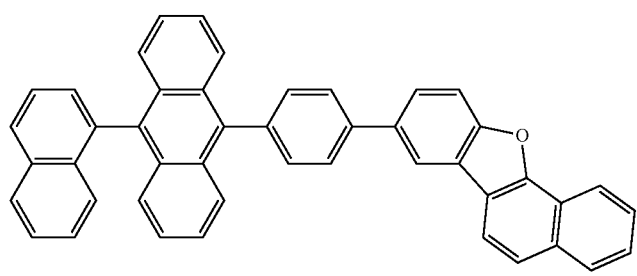

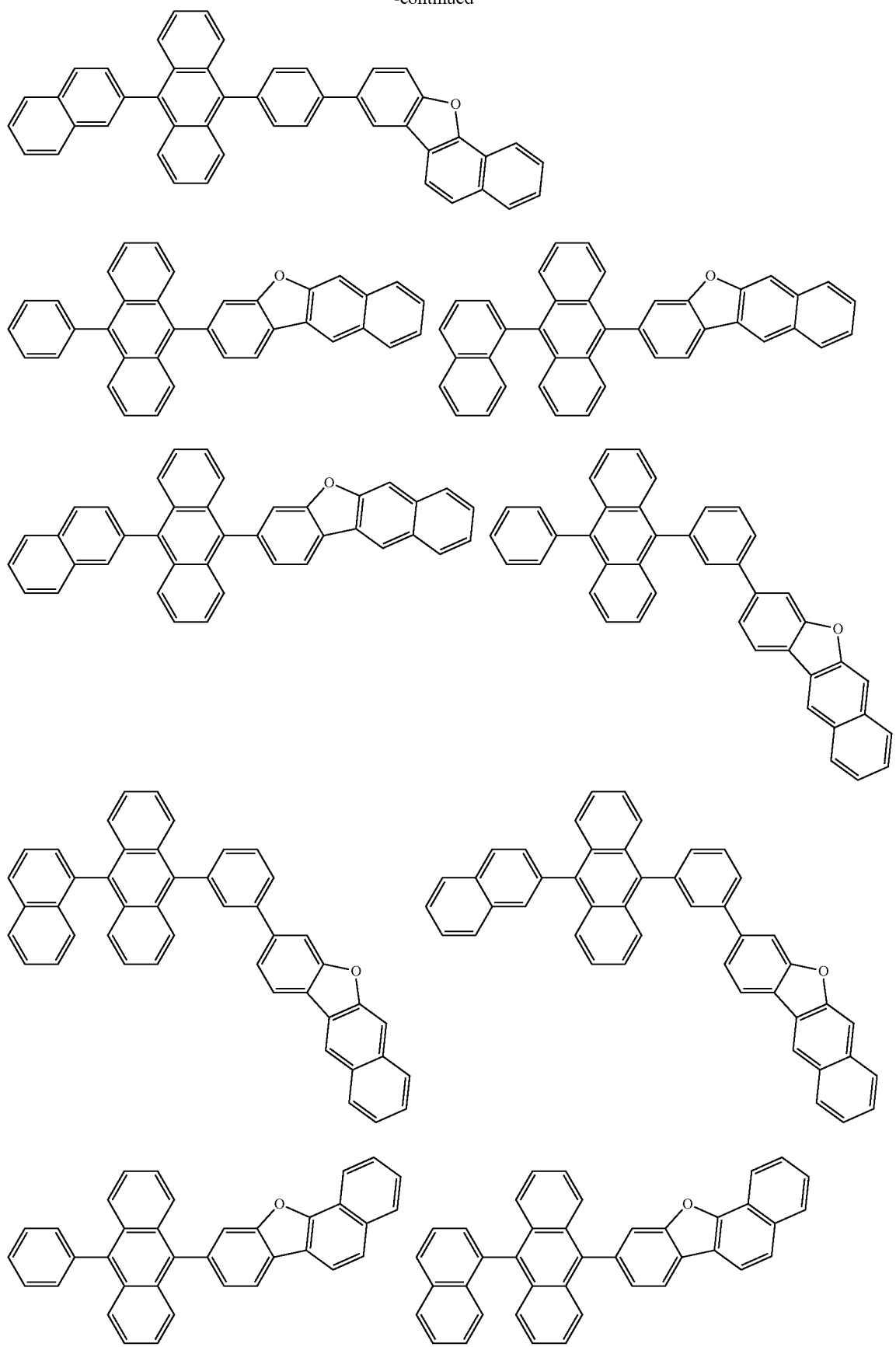

-continued
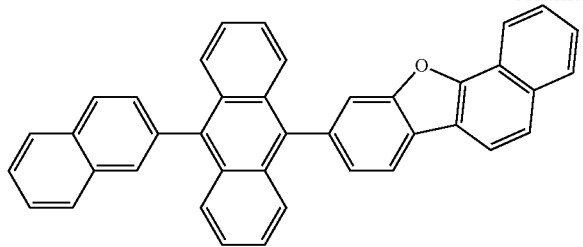
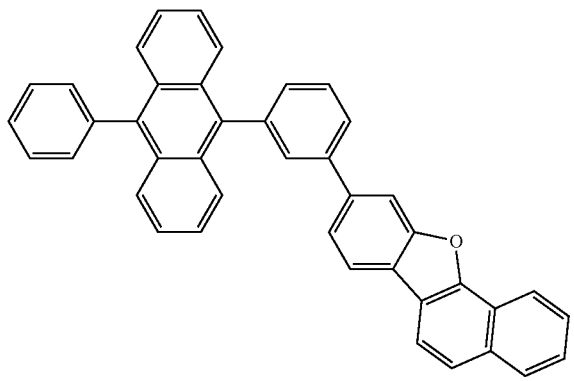 [SMILES: c1cc(-c2ccc3c(c2)oc2c4ccccc4ccc32)cc(-c2c3ccccc3c(-c3cccc4ccccc34)c3ccccc23)c1]
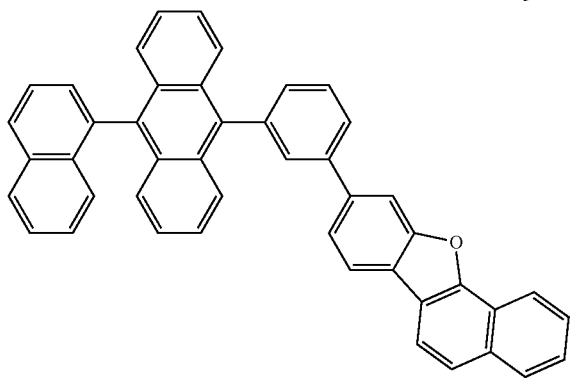
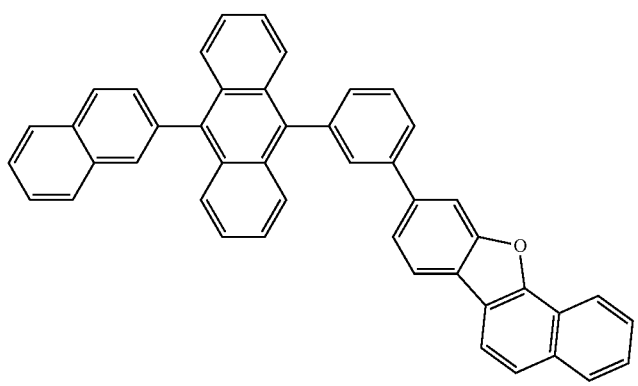
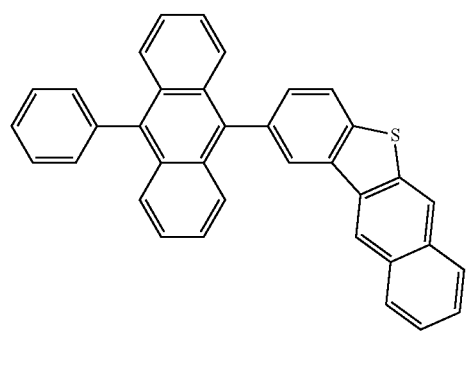
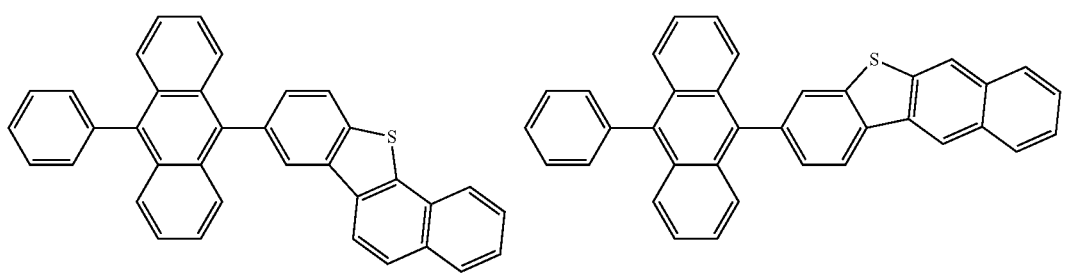

297 298
-continued
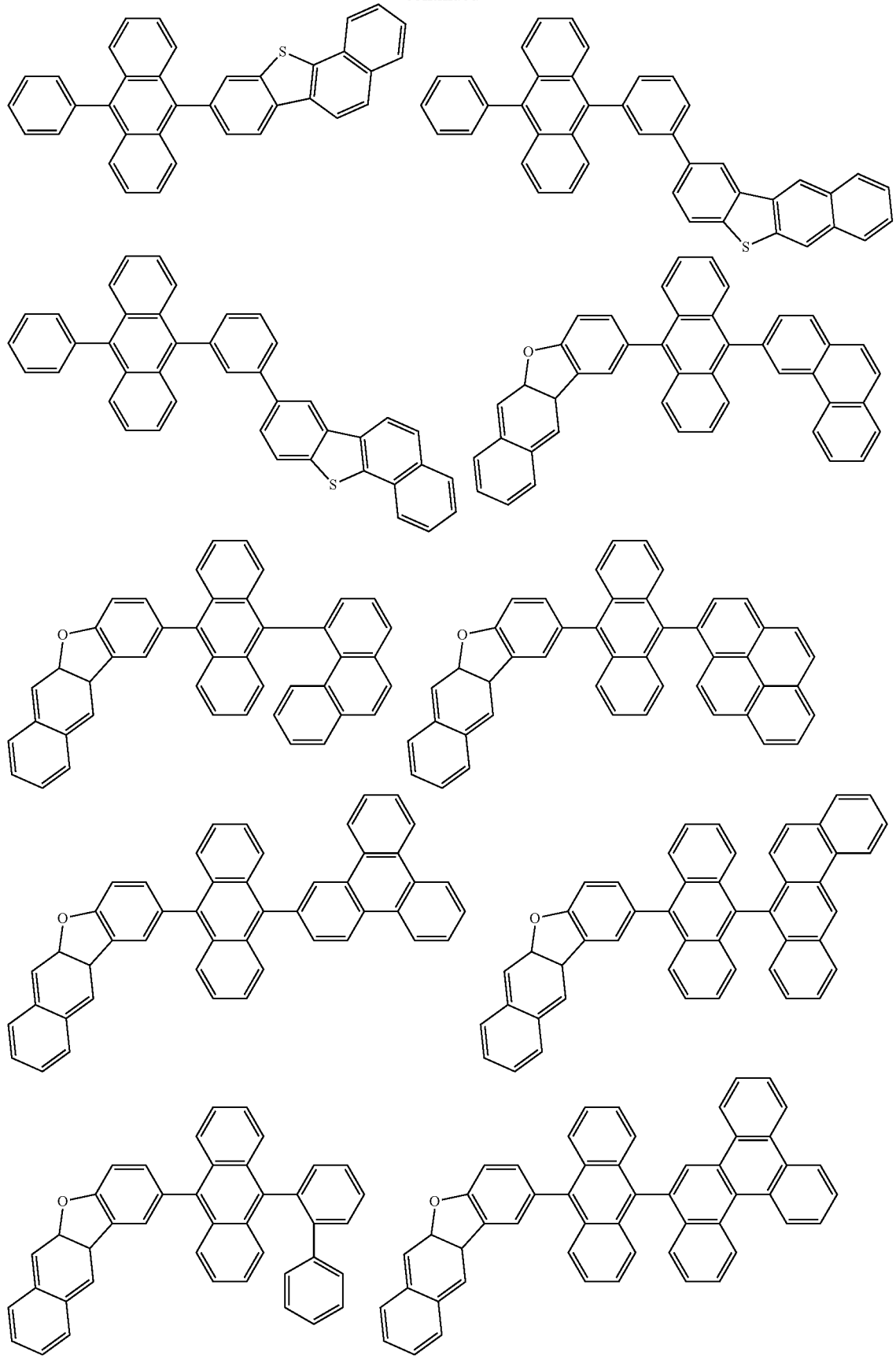

-continued
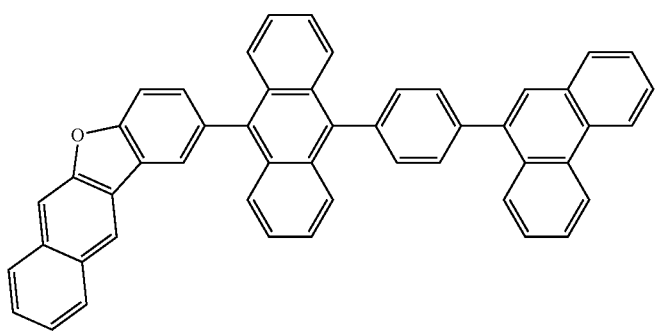
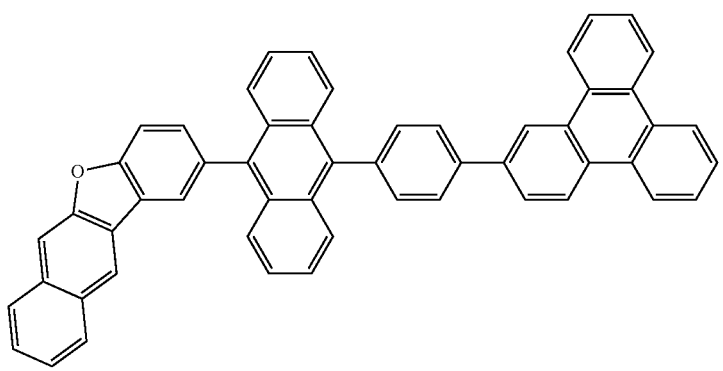
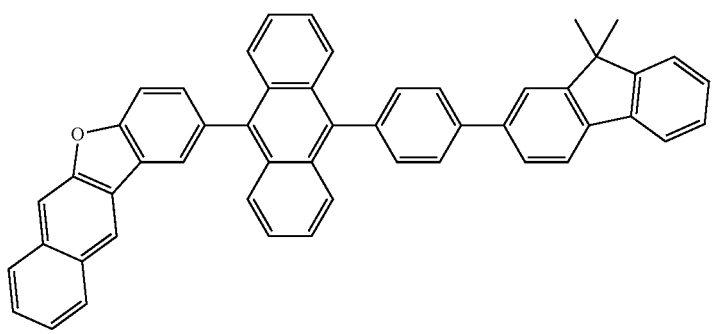
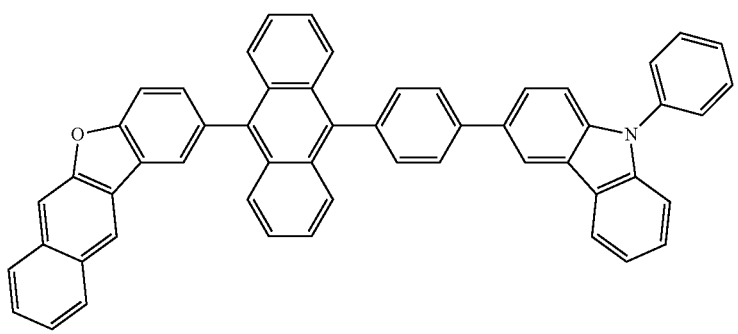
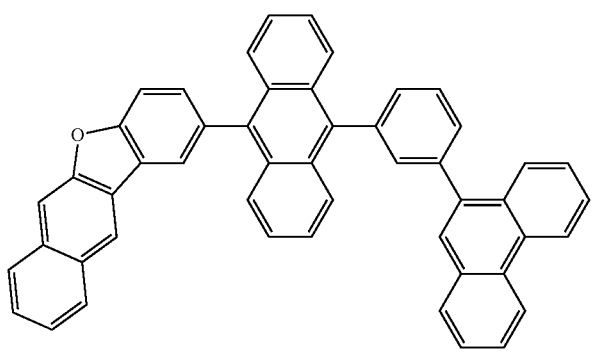

-continued
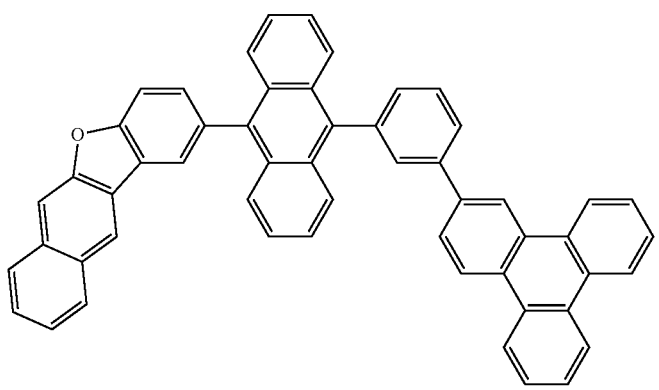
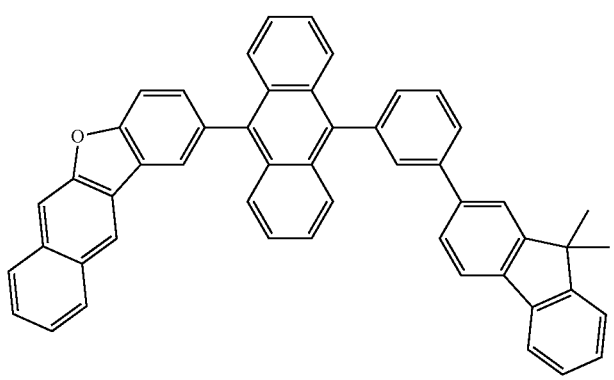
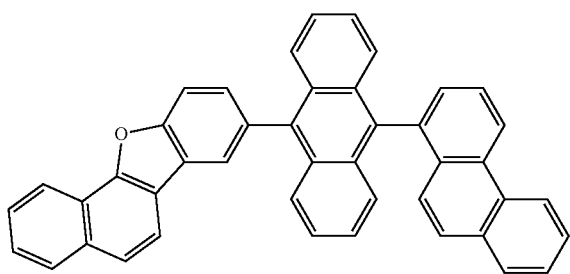
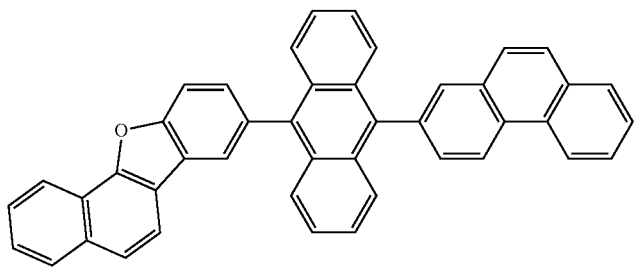
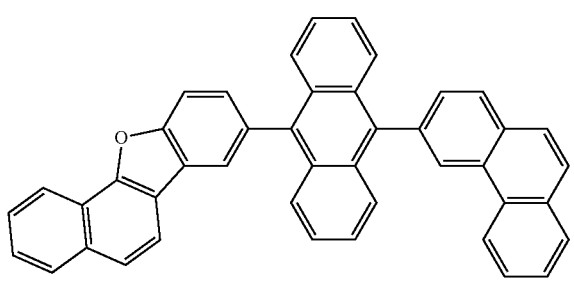

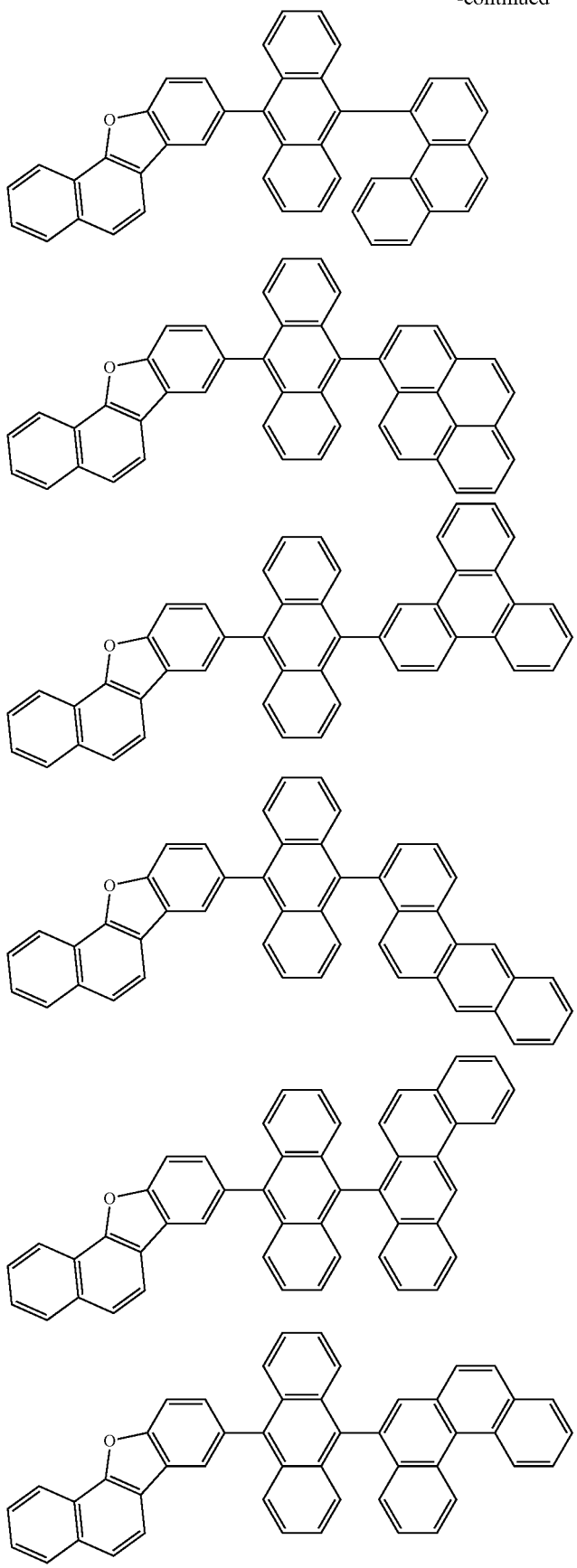

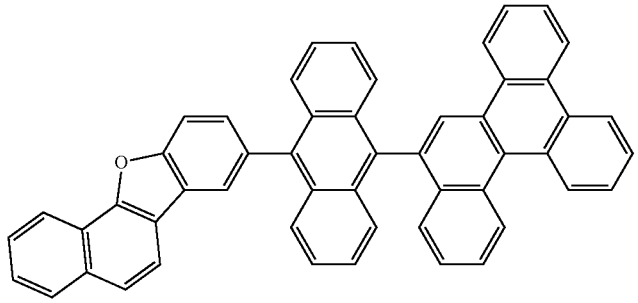
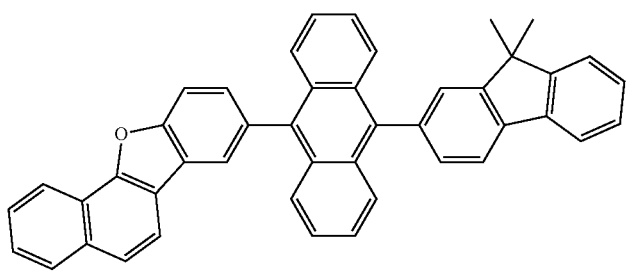
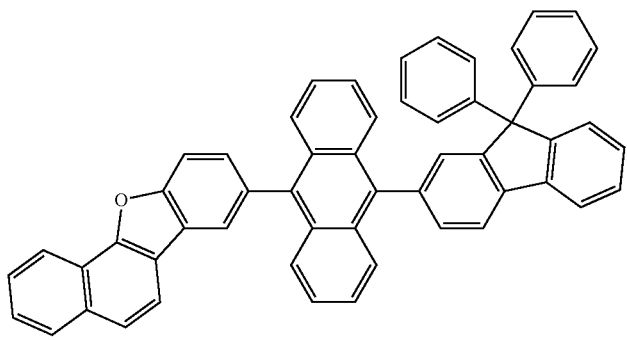
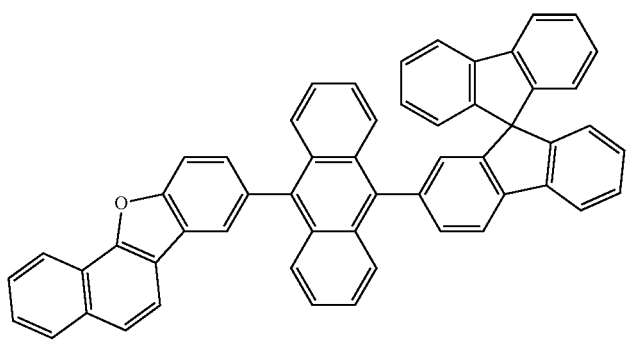
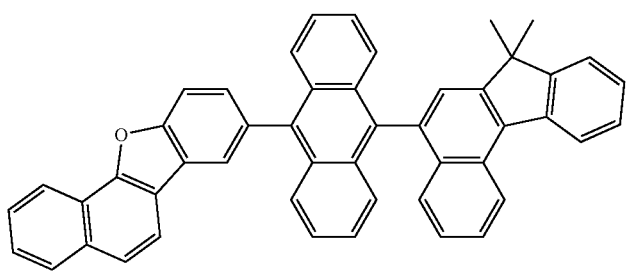

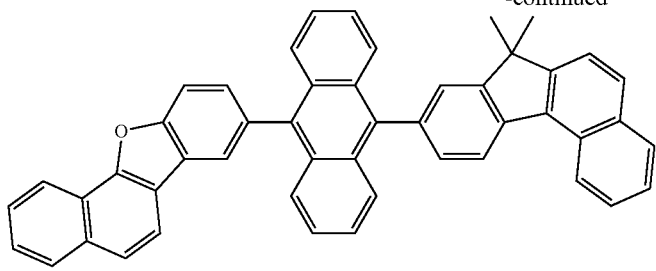
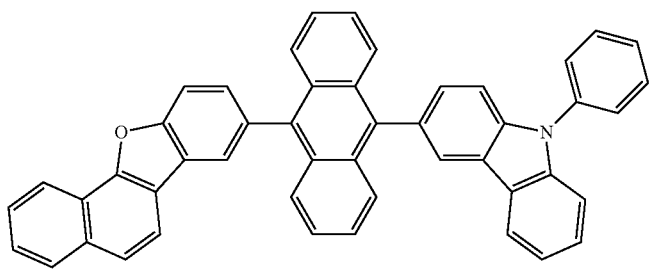
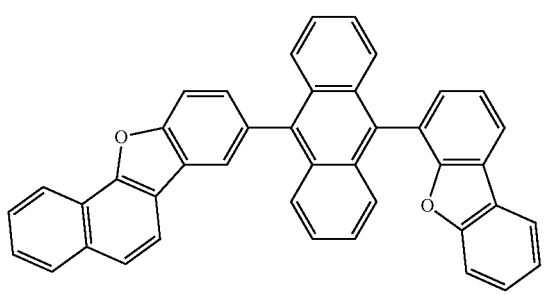
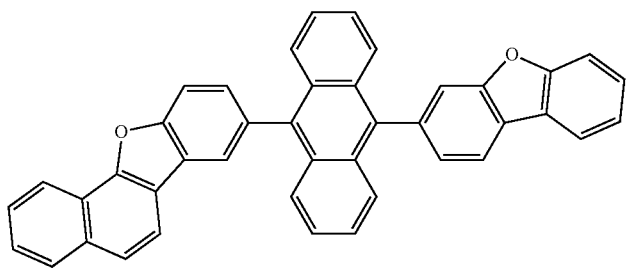
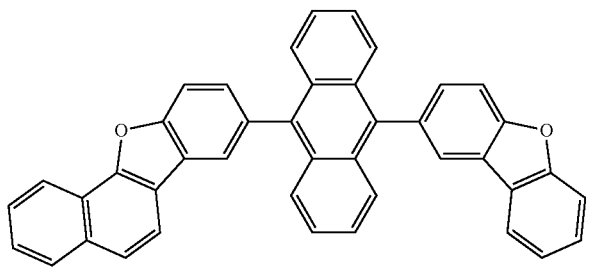
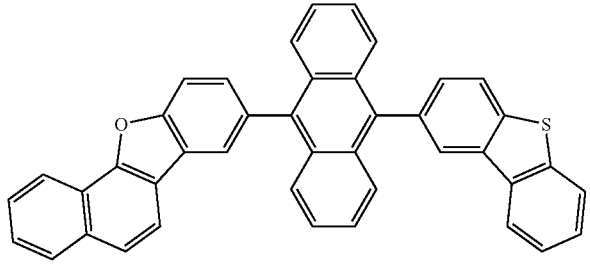

-continued
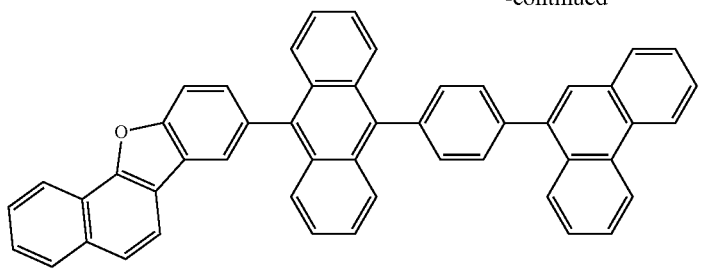
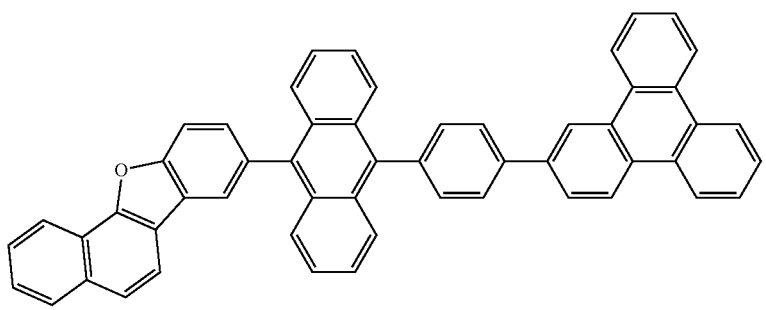
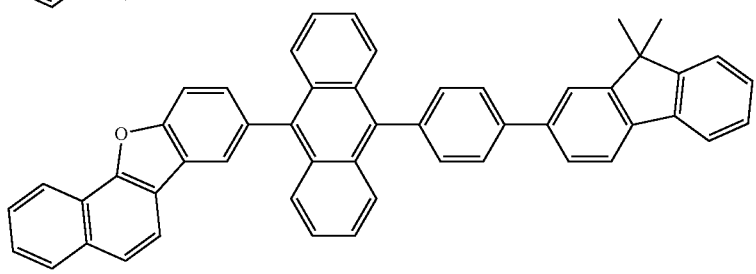
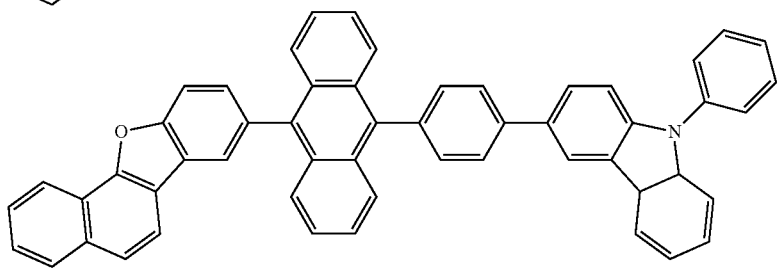
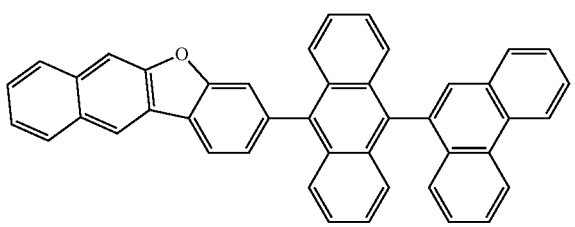
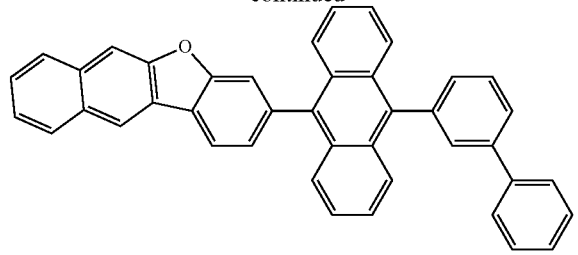
-continued
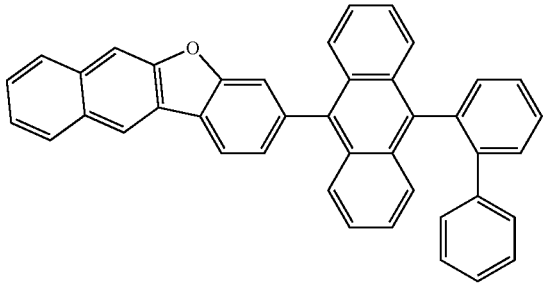
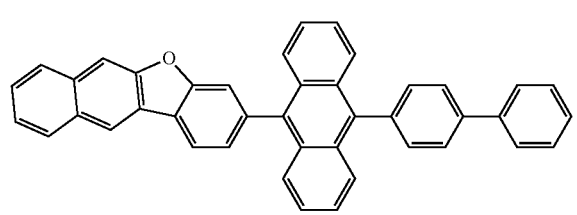

311
-continued
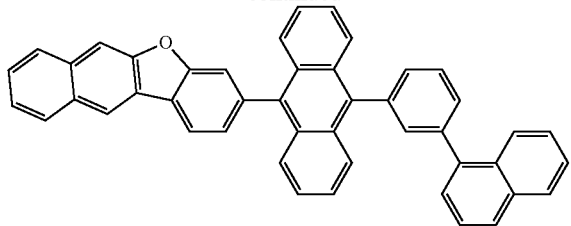
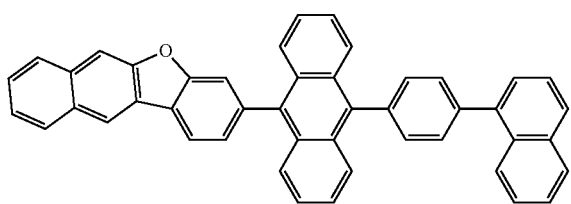
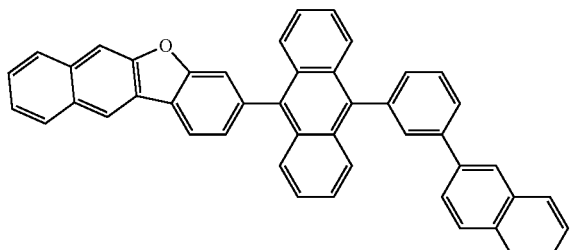
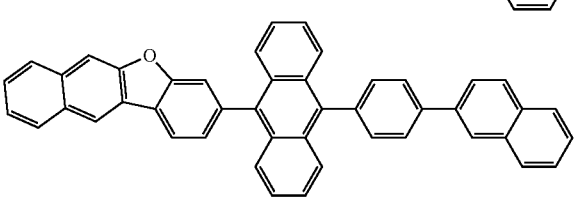
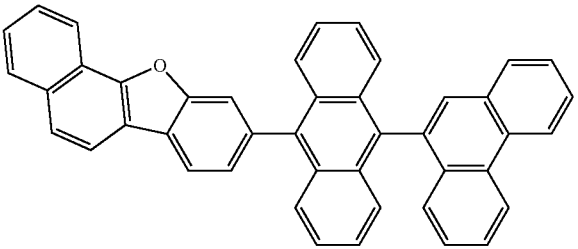
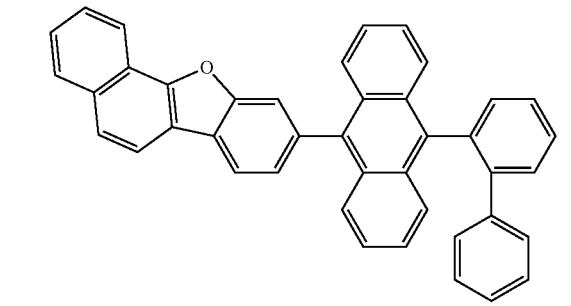
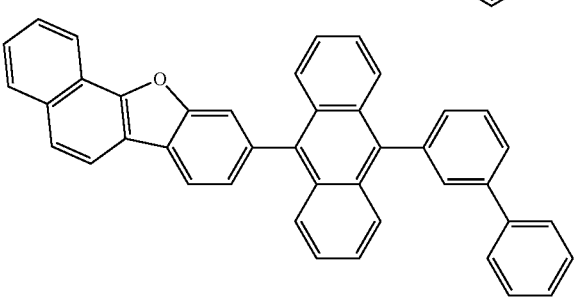
312
-continued
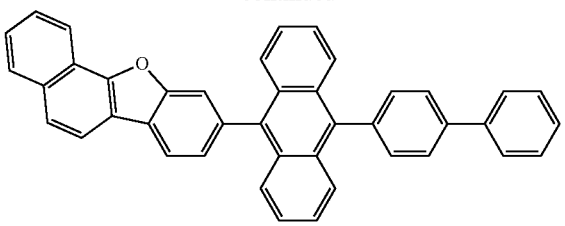
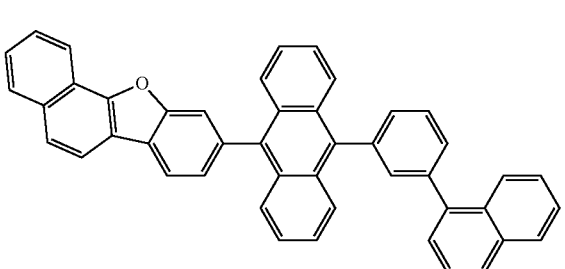
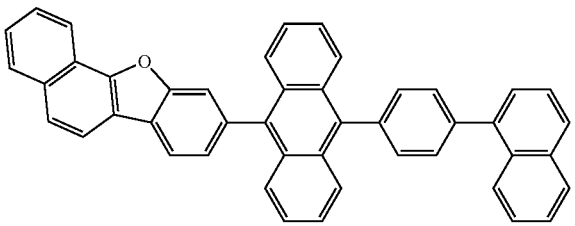
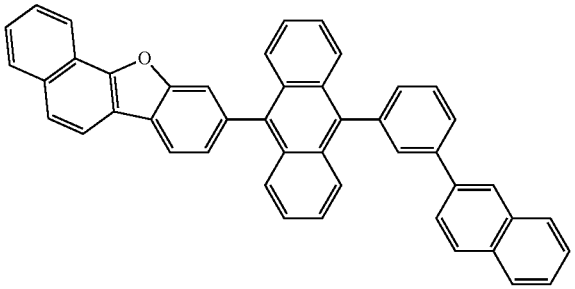
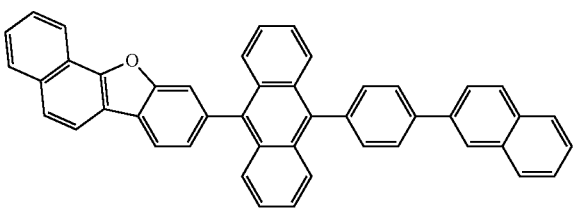

313
-continued
314
-continued
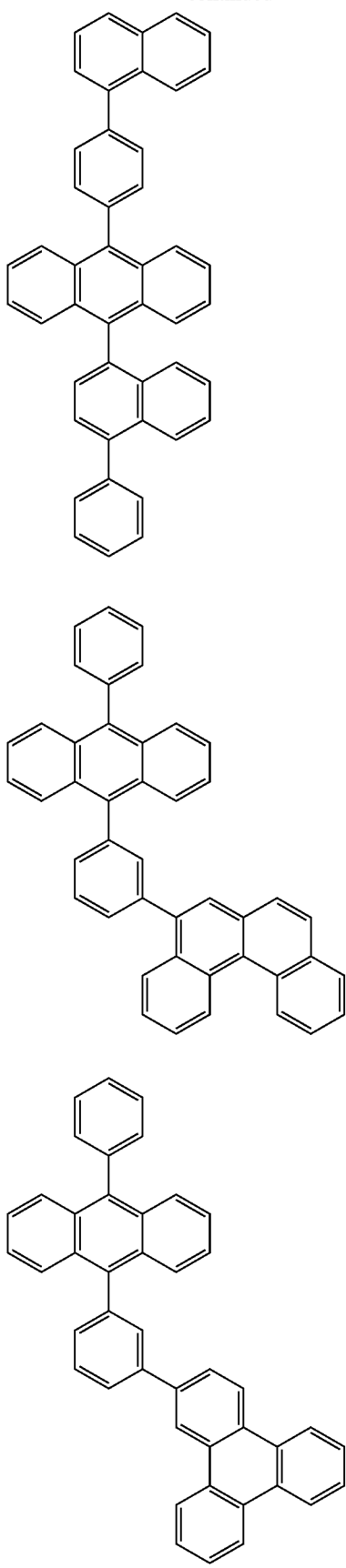

315
-continued
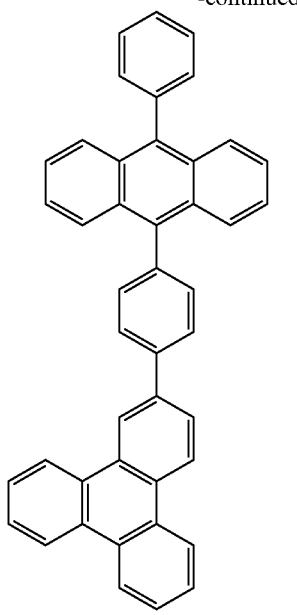
316
-continued
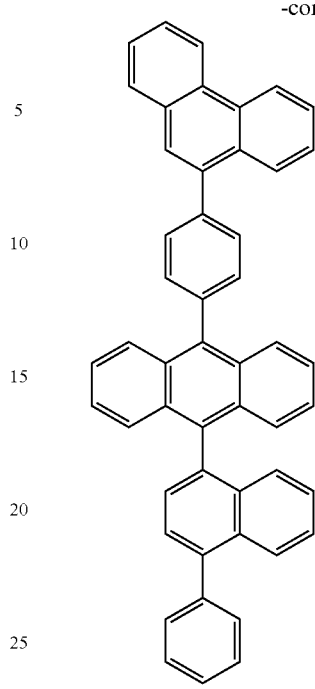
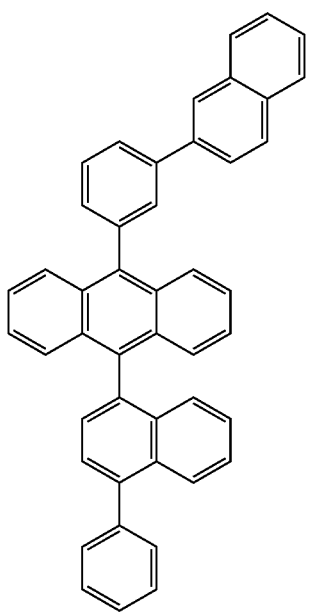
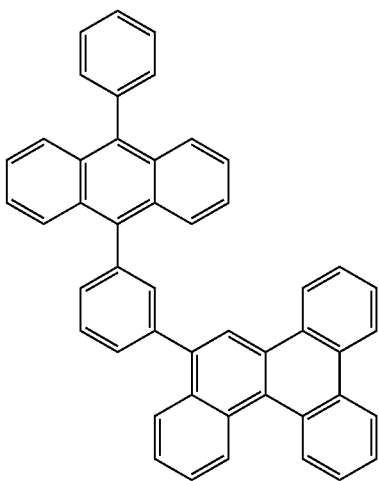

317
-continued
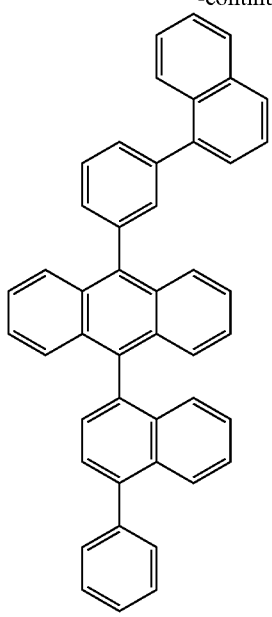
318
-continued
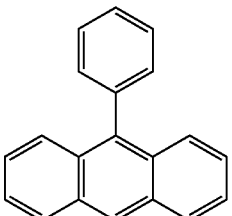
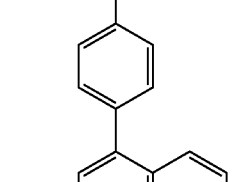
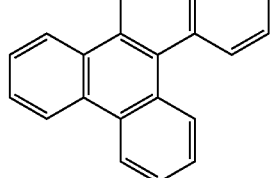
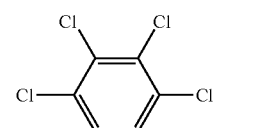
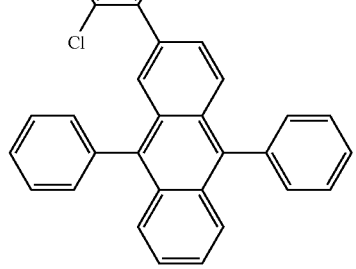
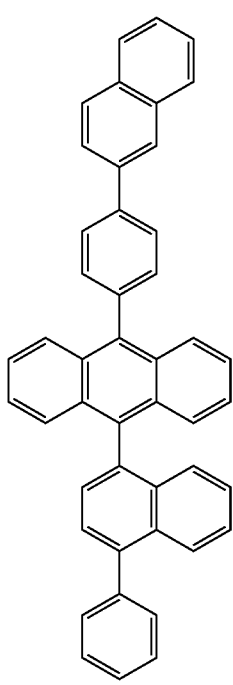
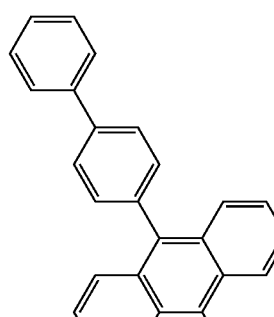
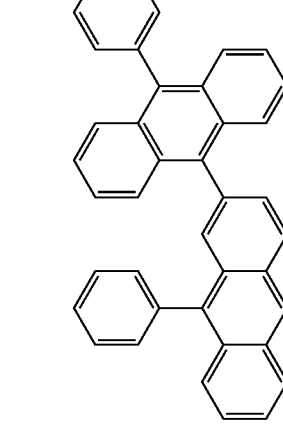

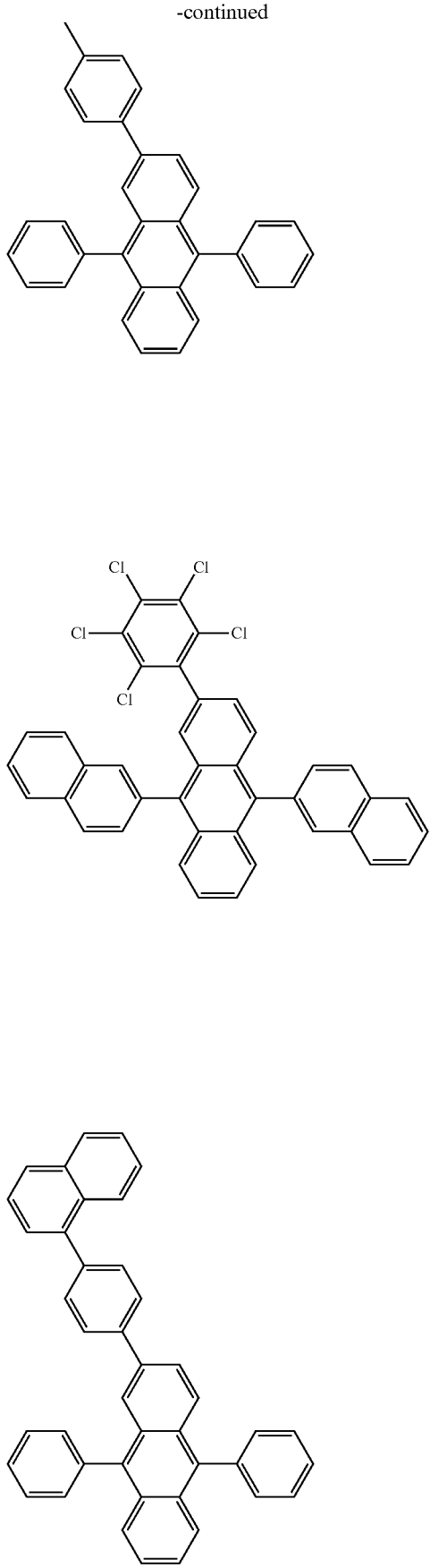

321
-continued
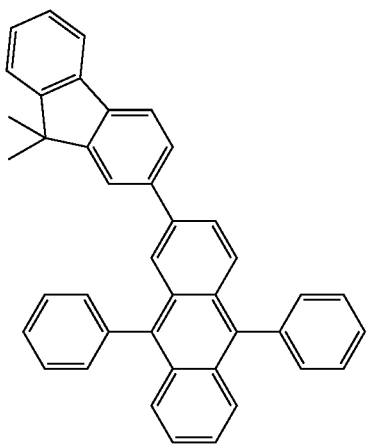
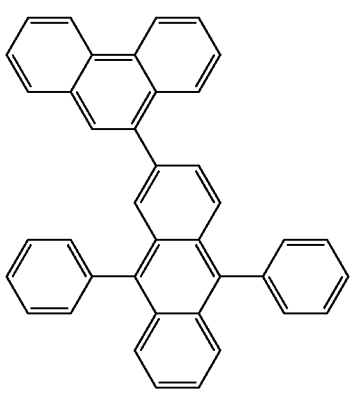
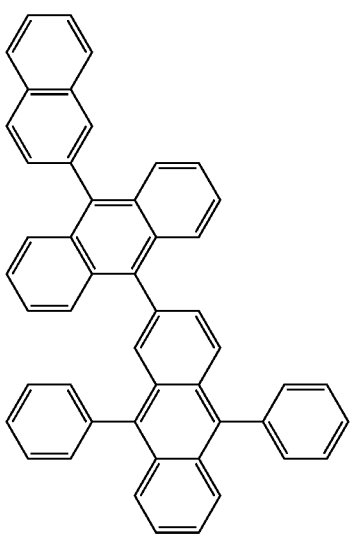
322
-continued
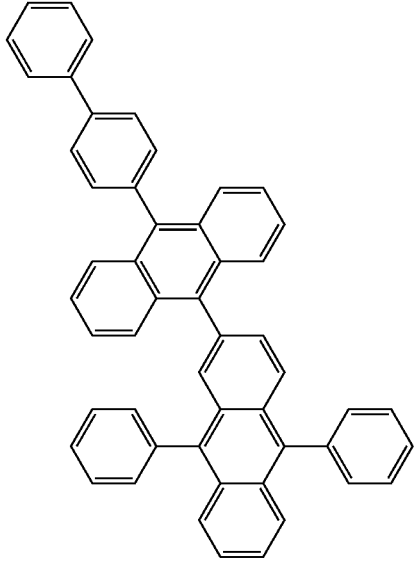
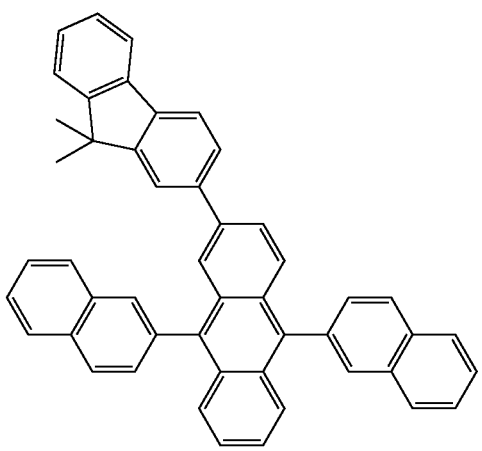
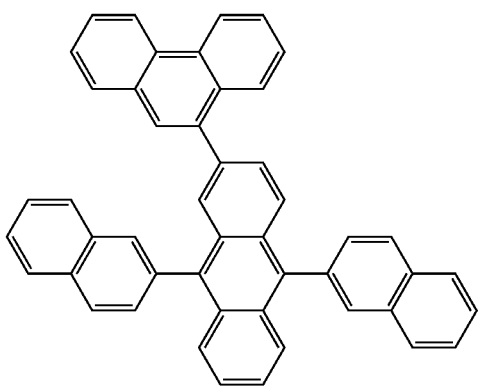

323
-continued
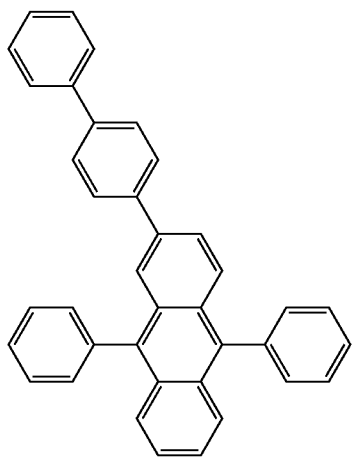
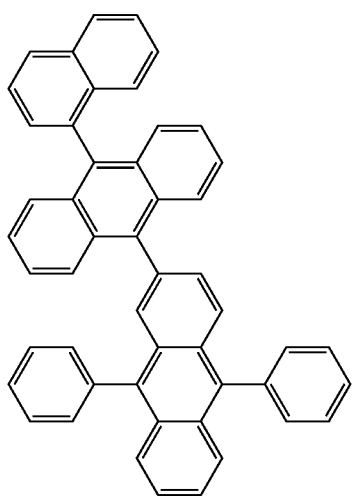
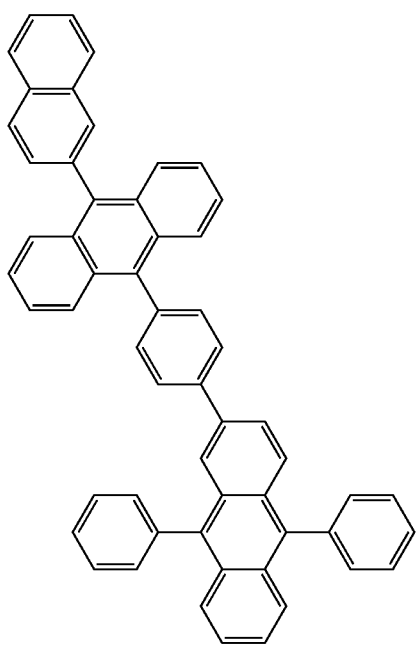
324
-continued
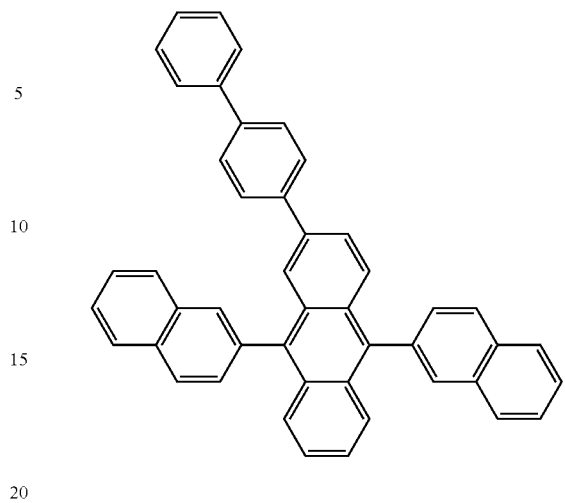
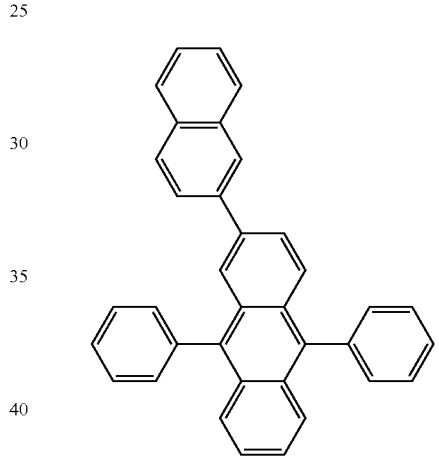
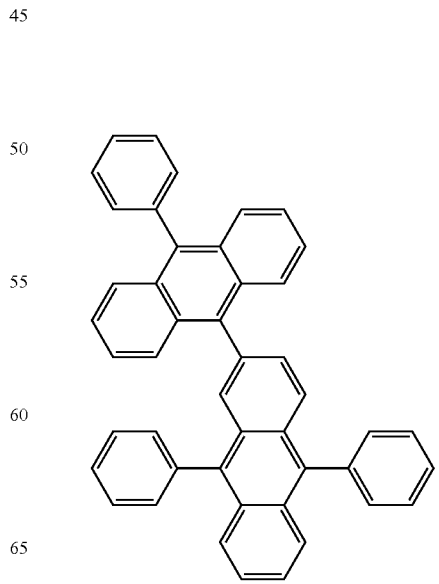

325
-continued
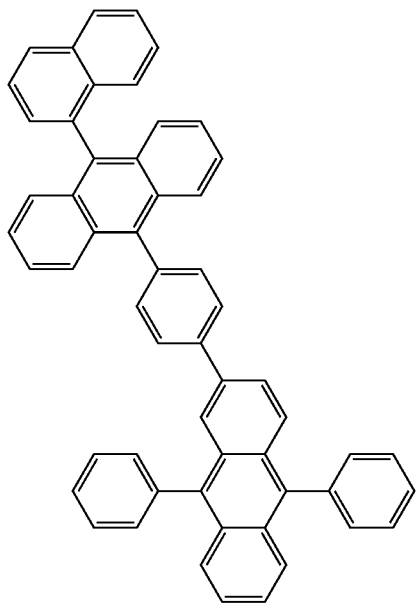
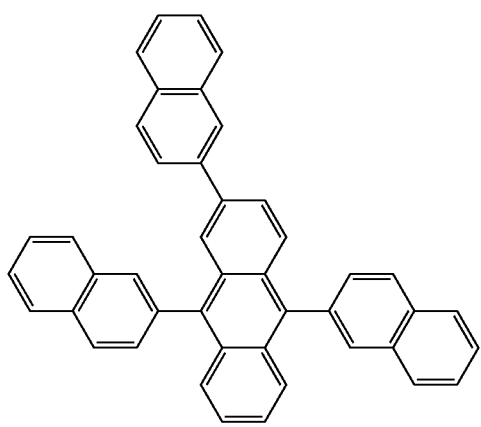
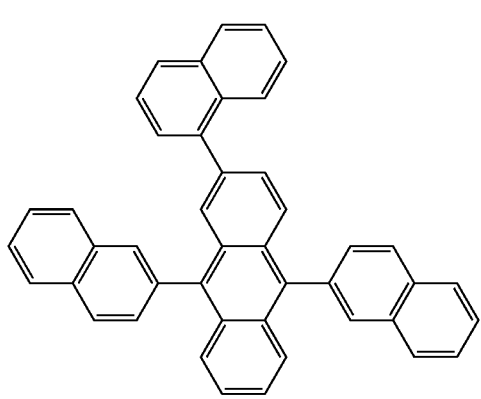
326
-continued
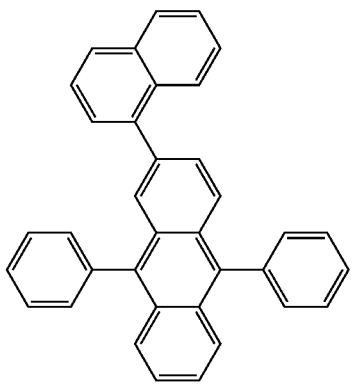
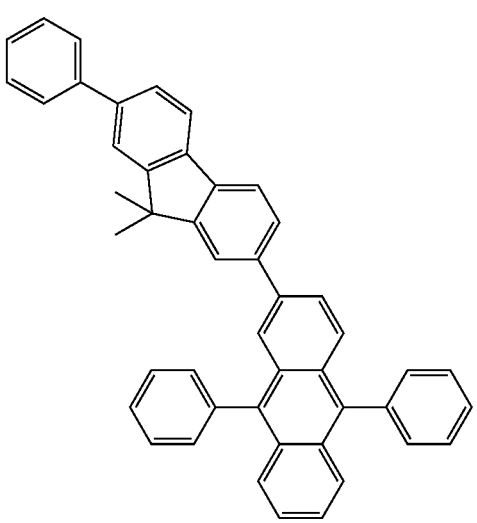
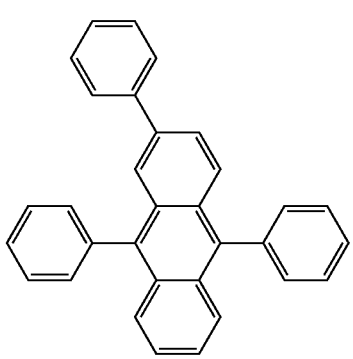

327
-continued
328
-continued
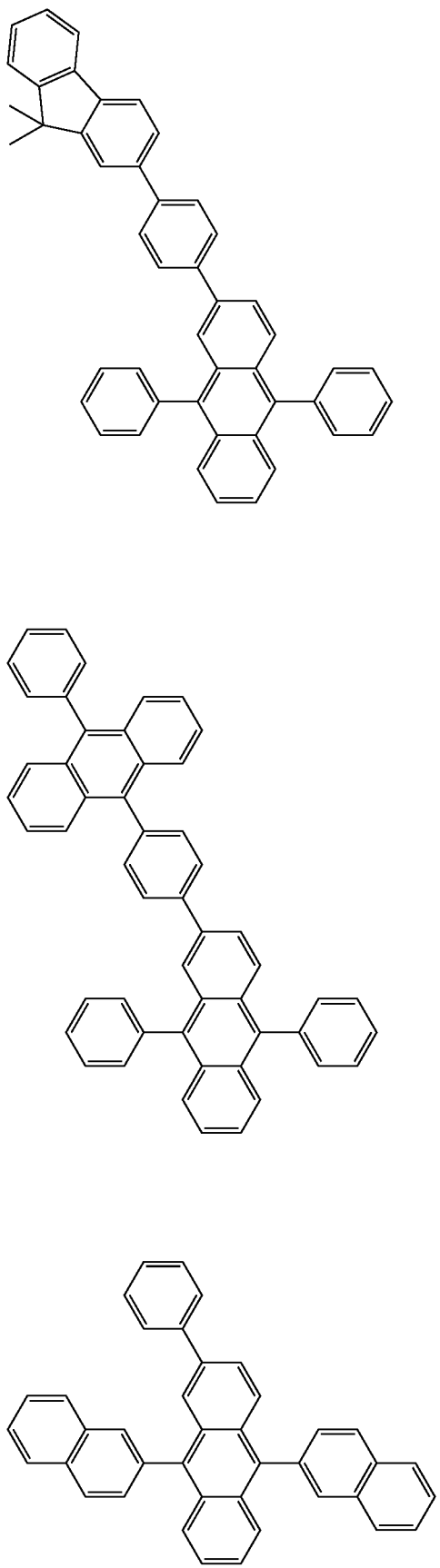
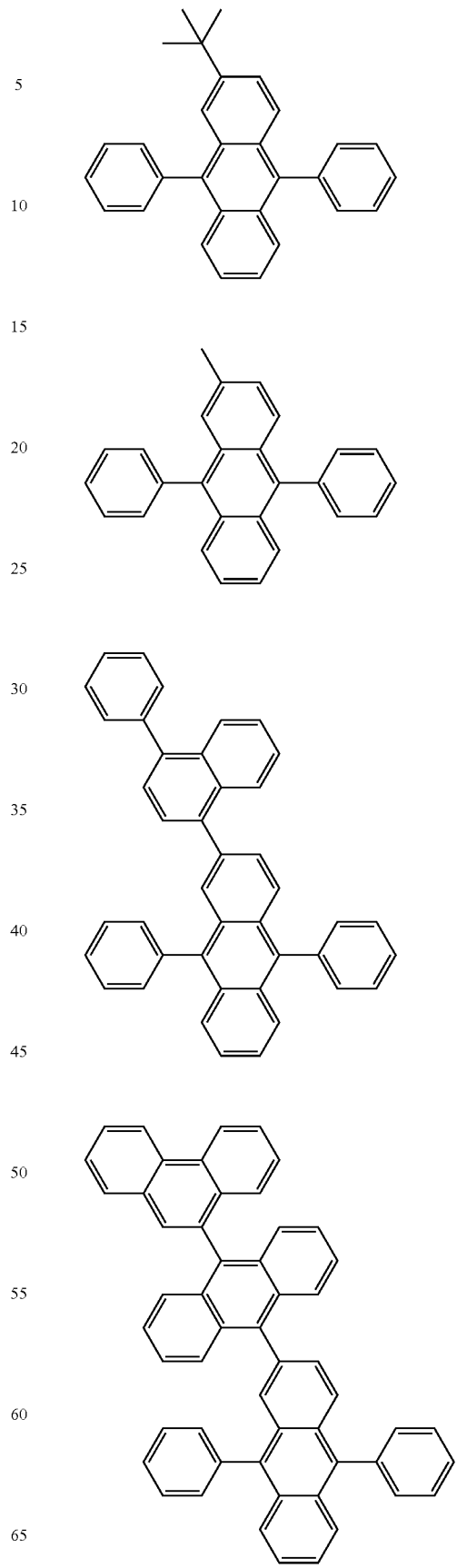

329
-continued
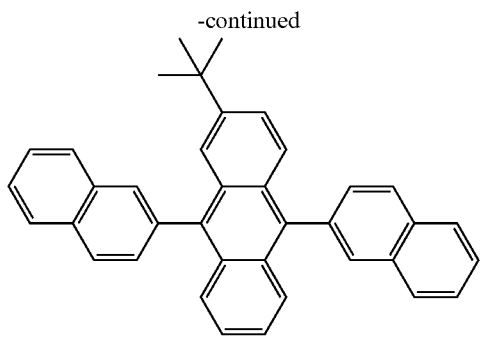
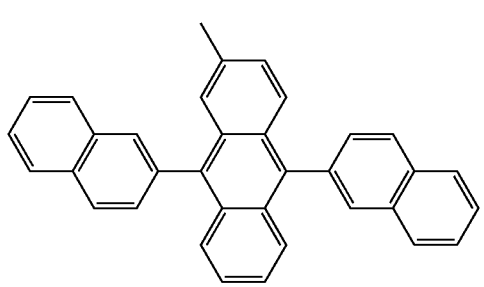
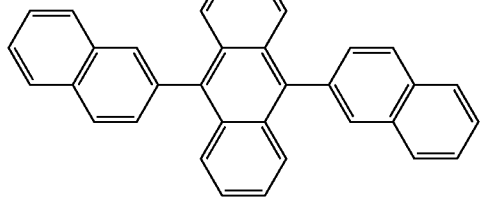
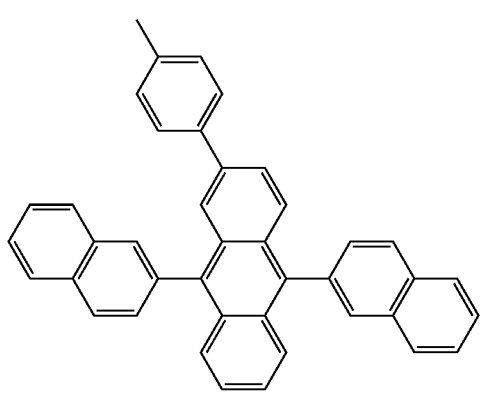
330
-continued
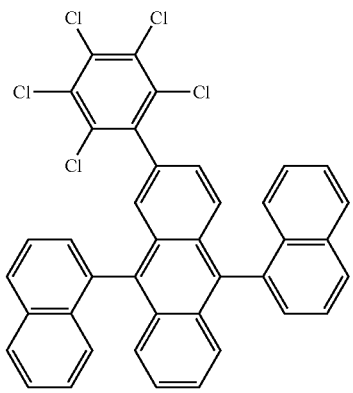
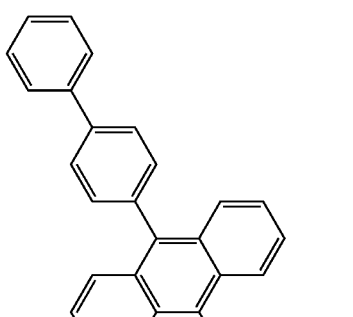
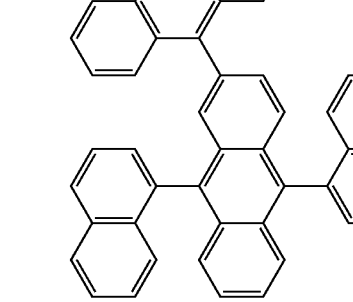
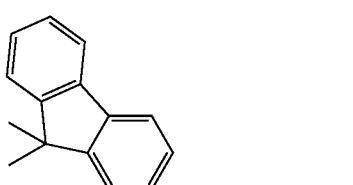
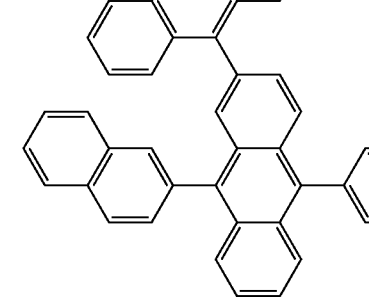

331
-continued
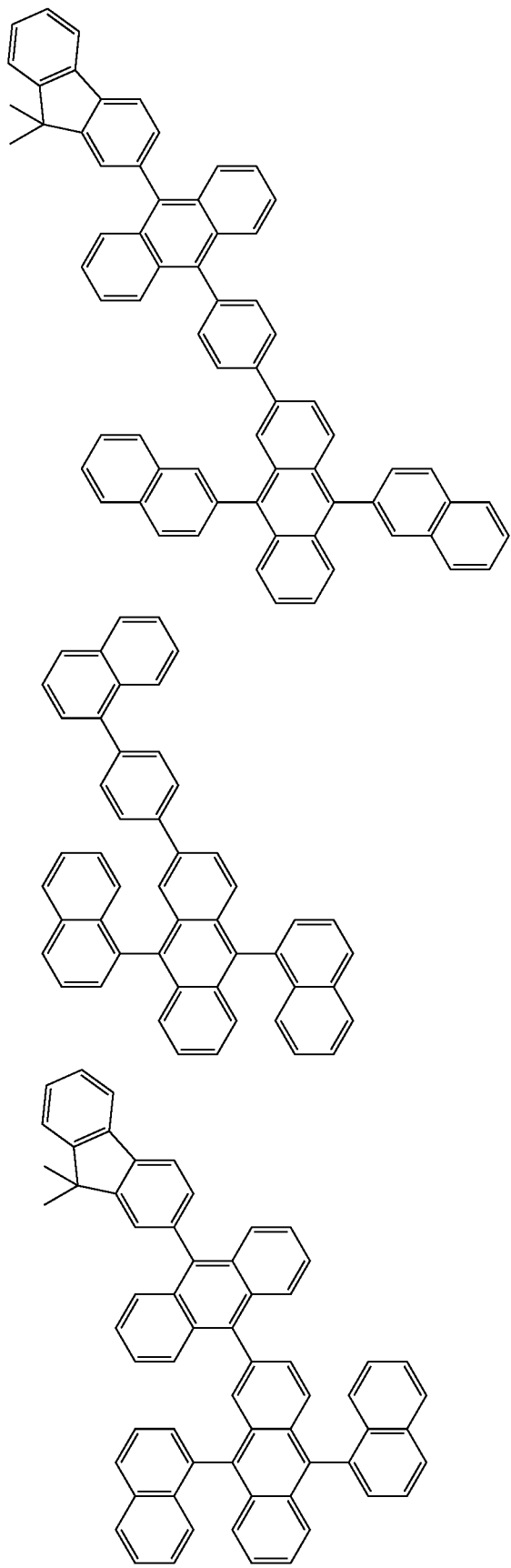
332
-continued
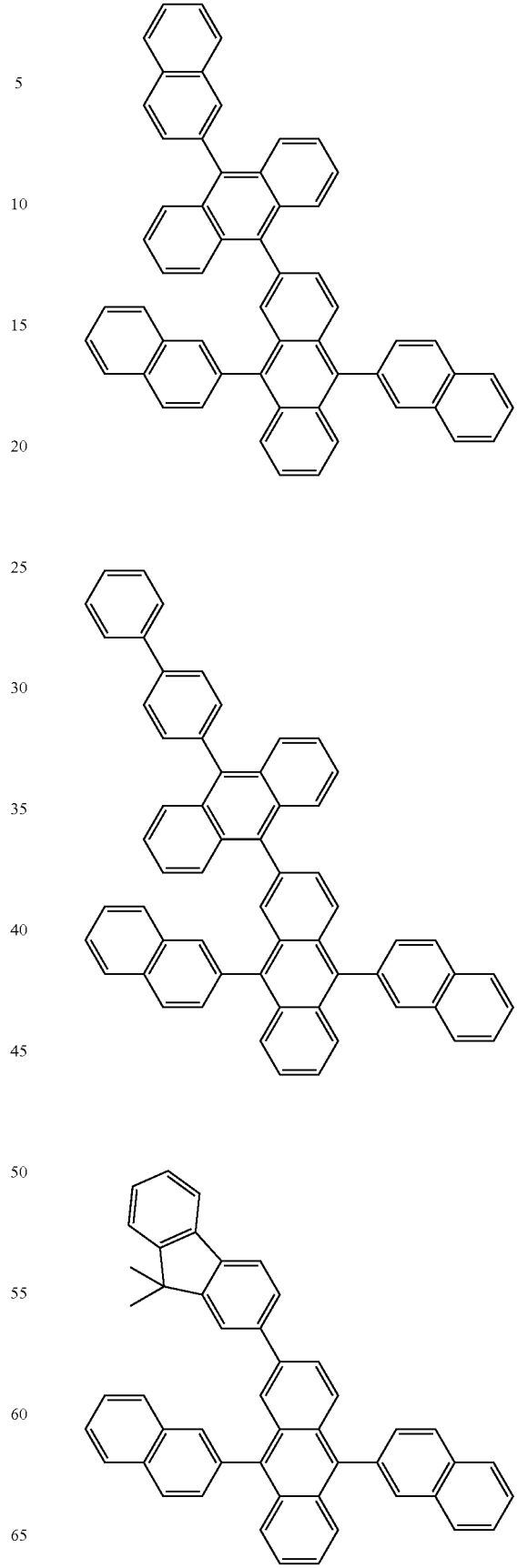

333
-continued
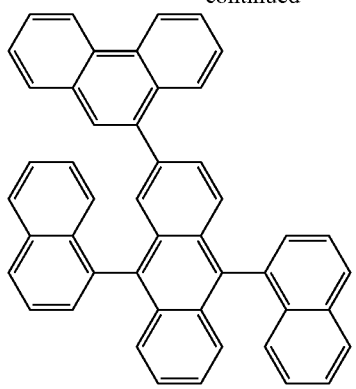
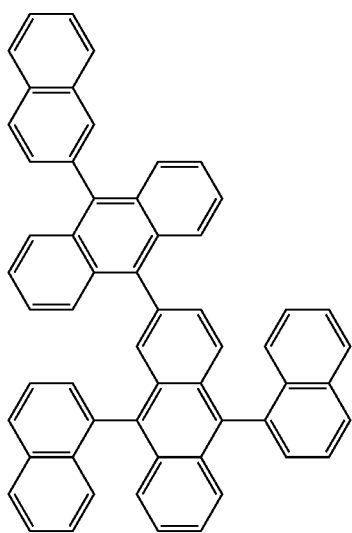
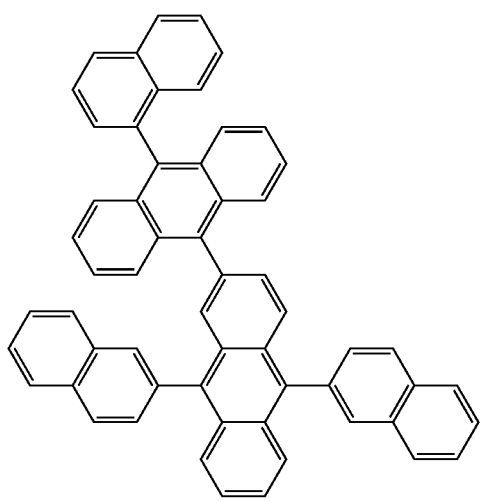
334
-continued
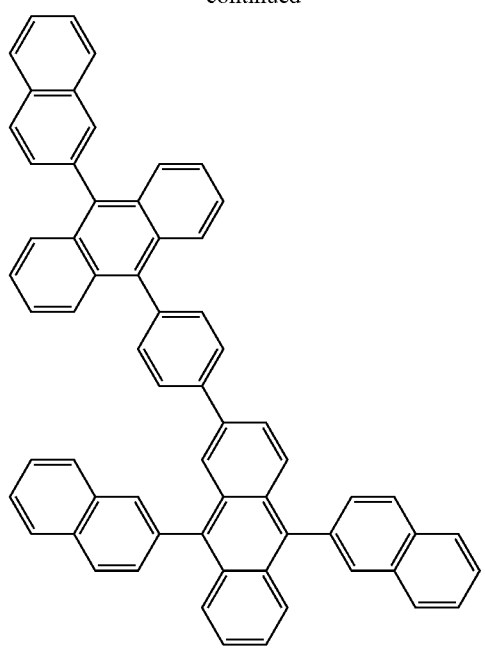
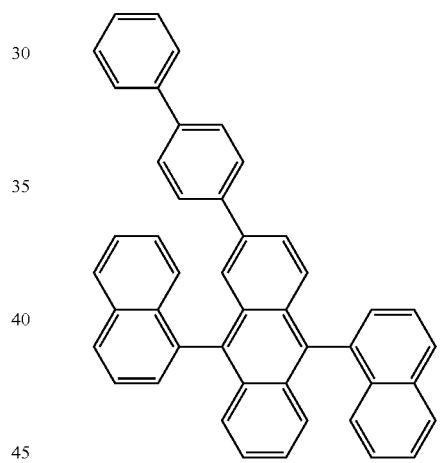
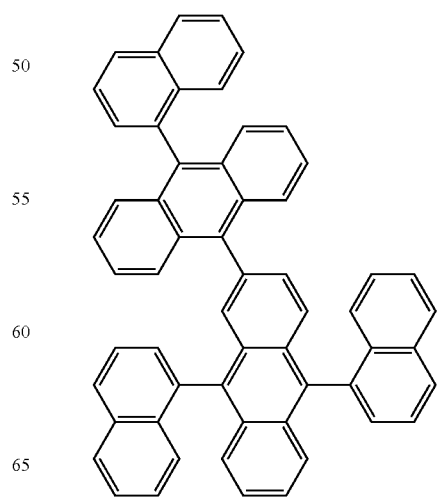

335
-continued
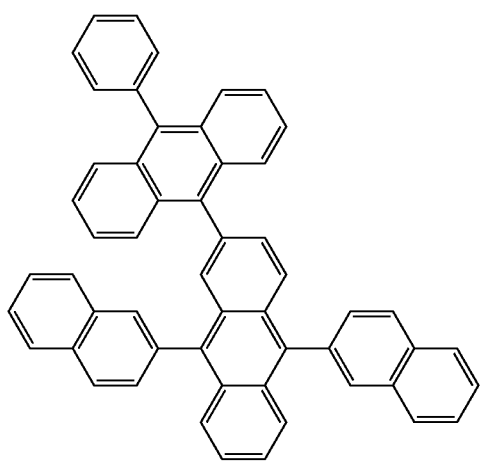
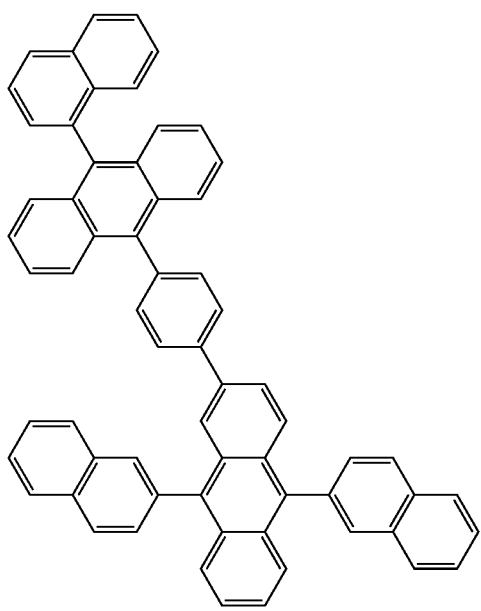
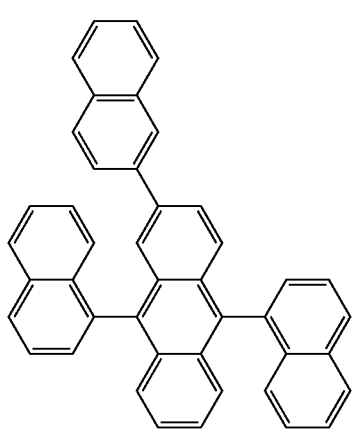
336
-continued
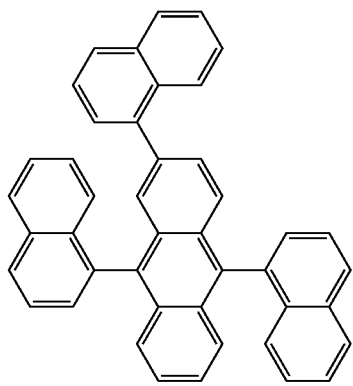
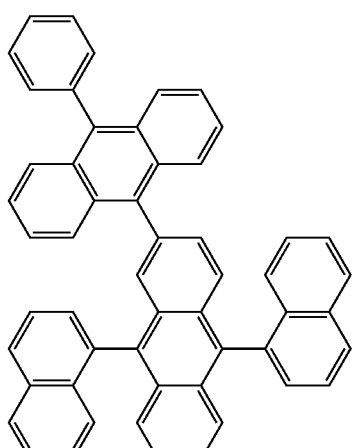
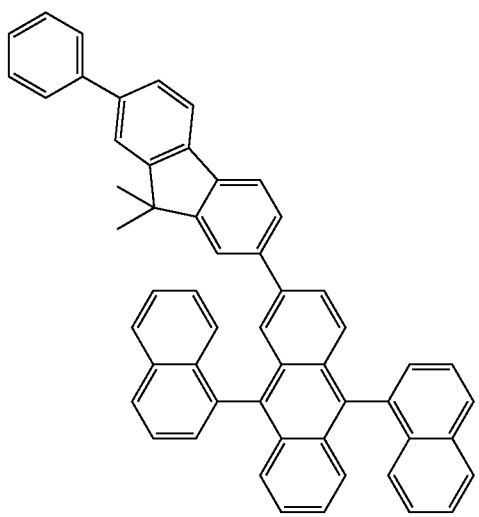

337
-continued
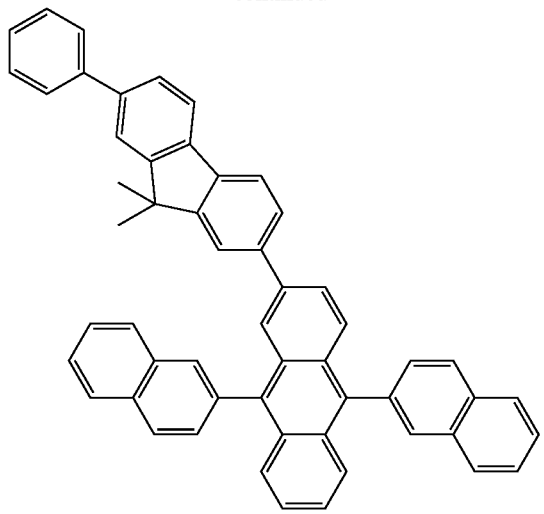
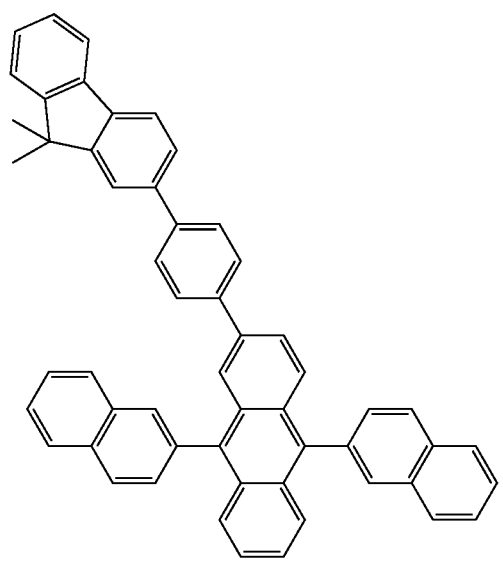
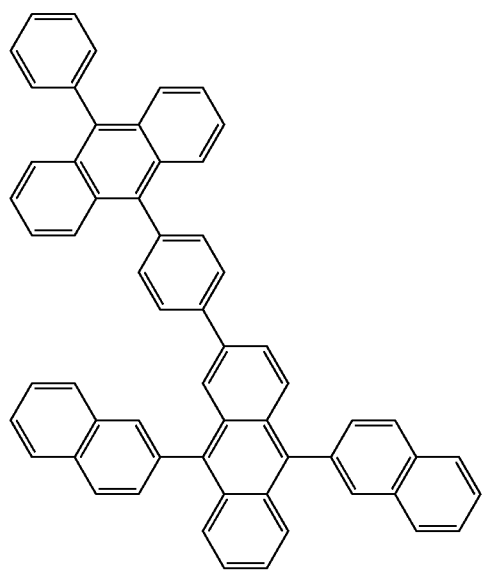
338
-continued
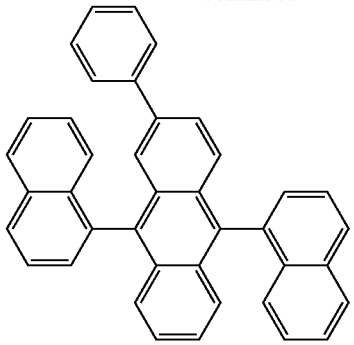
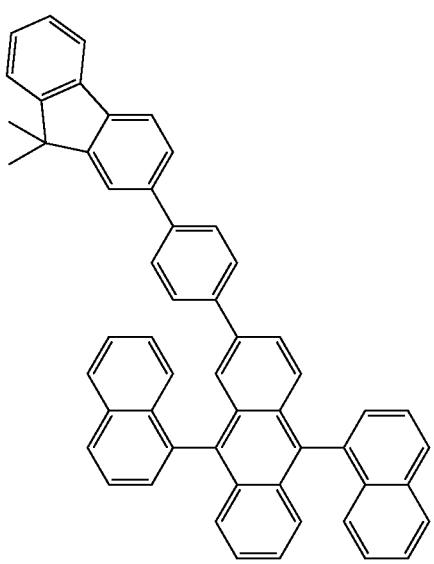
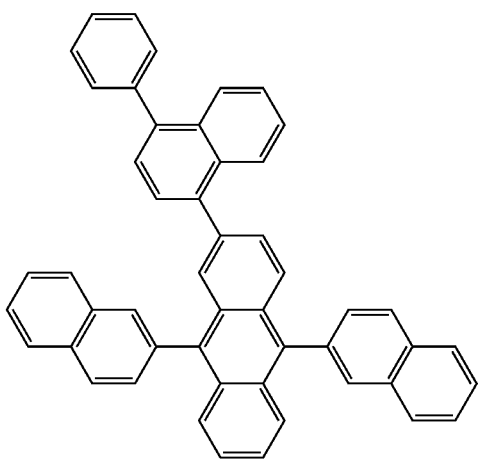

339
-continued
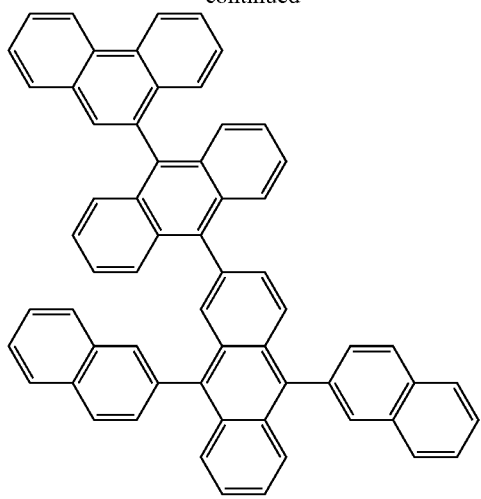
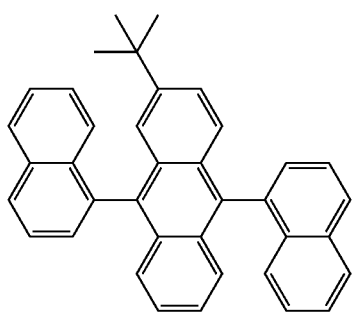
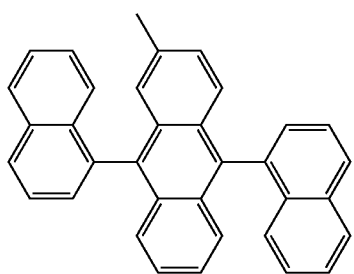
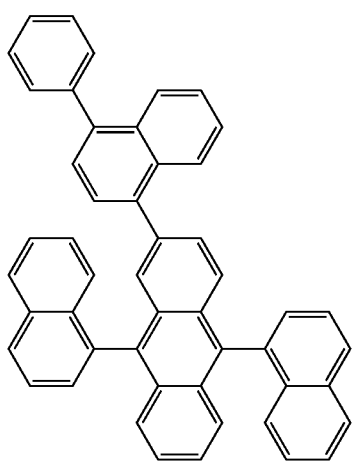
340
-continued
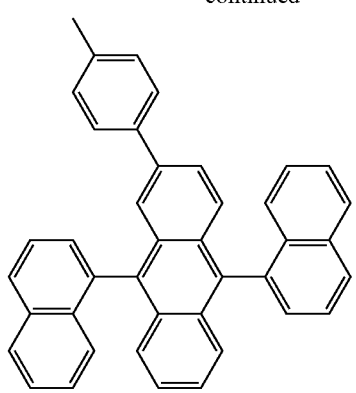
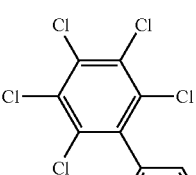
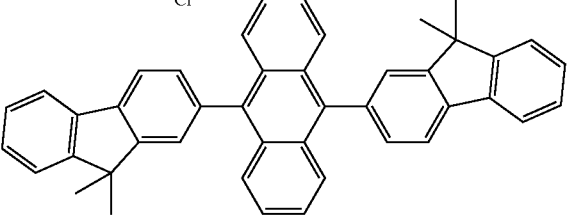
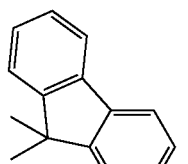
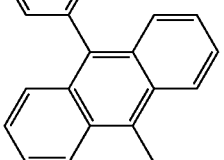
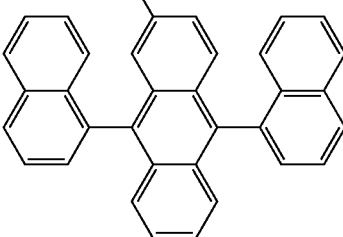

341
-continued
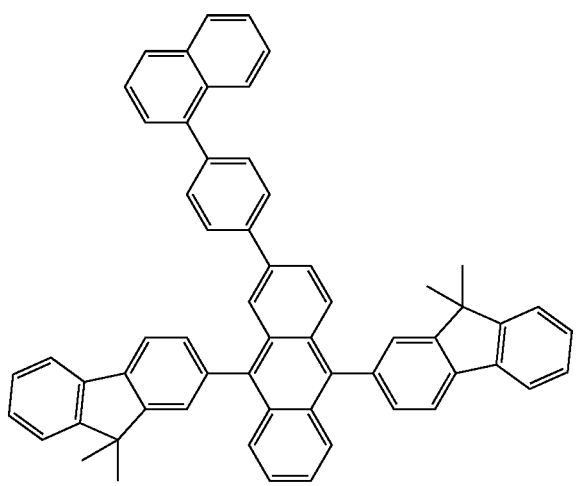
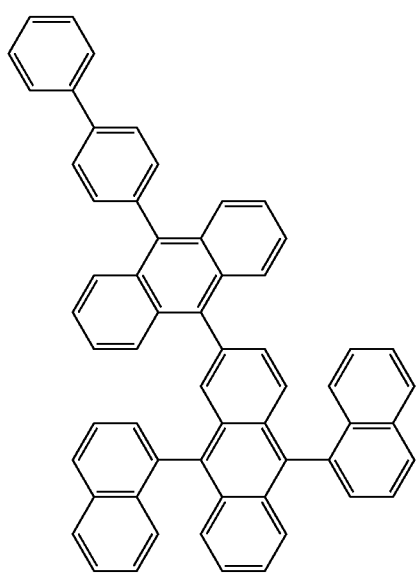
342
-continued
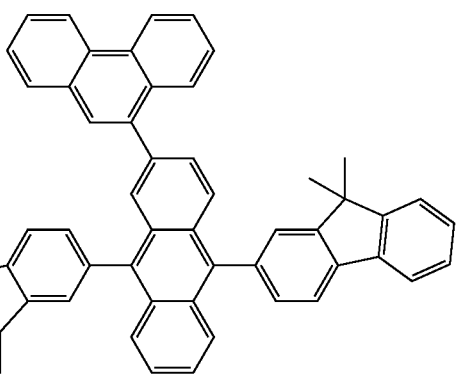
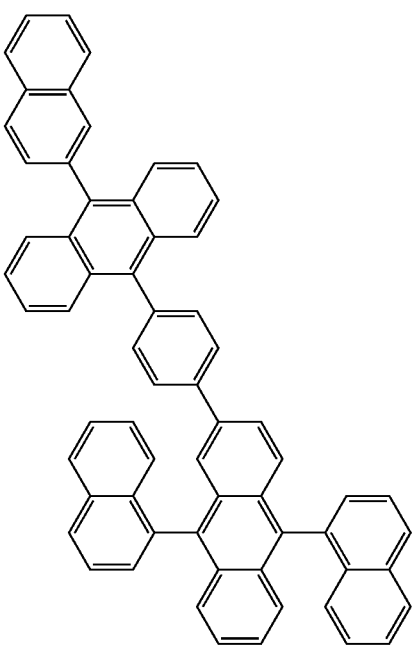
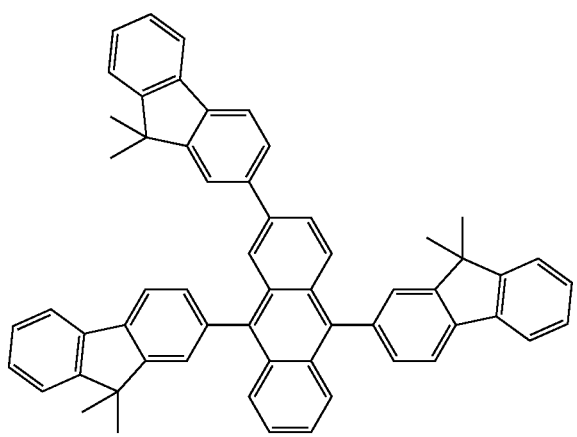
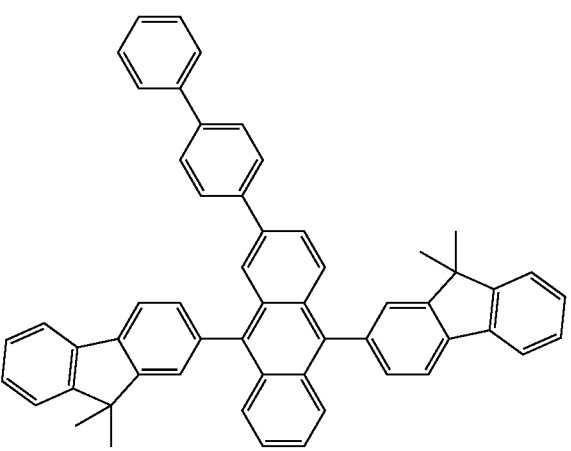

343
344
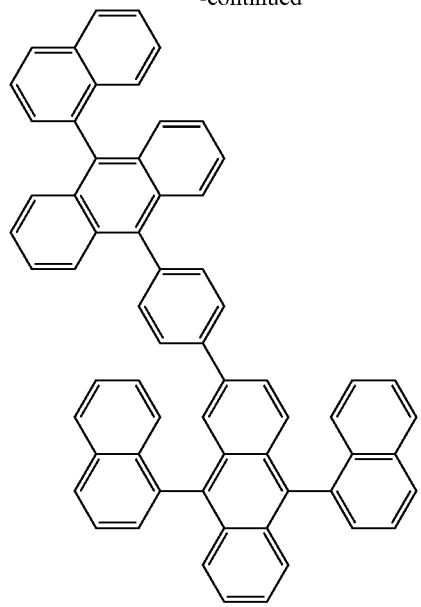
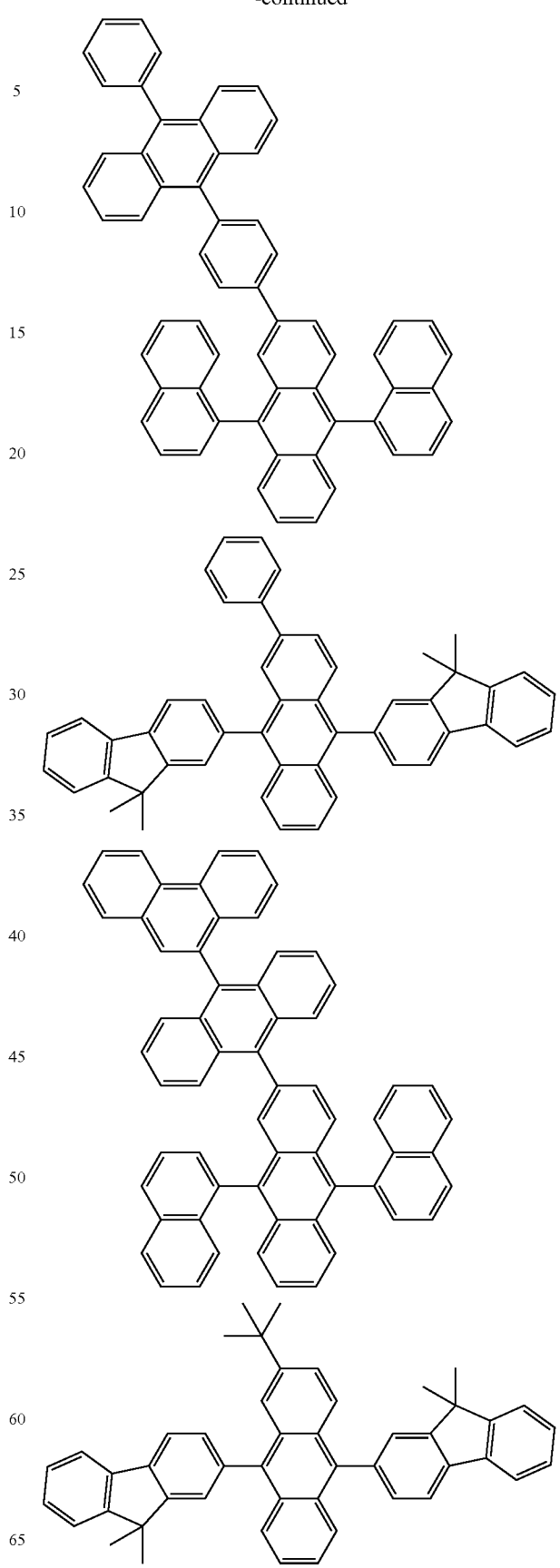

345
-continued
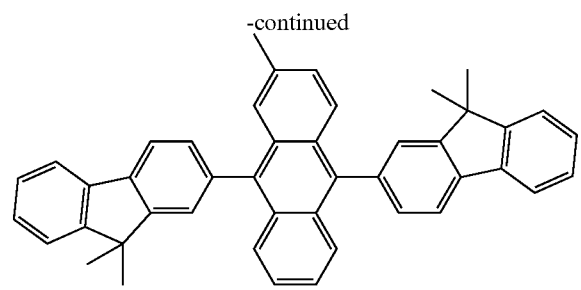
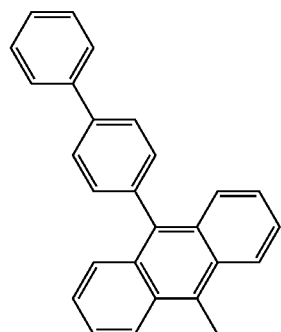
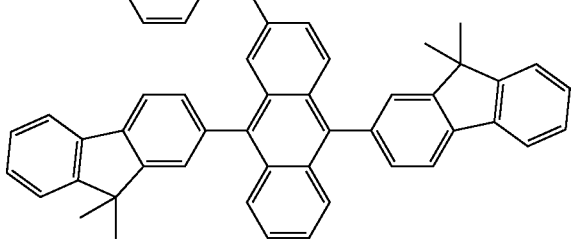
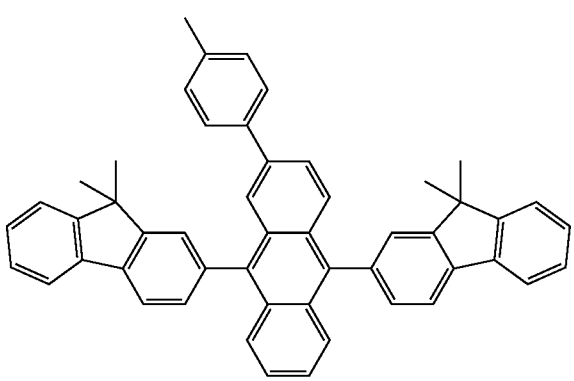
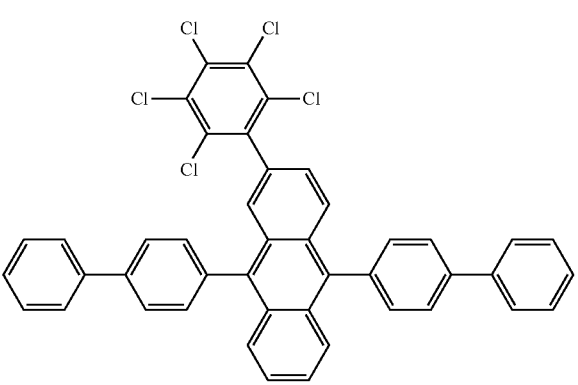
346
-continued
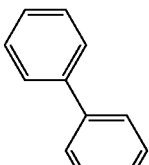
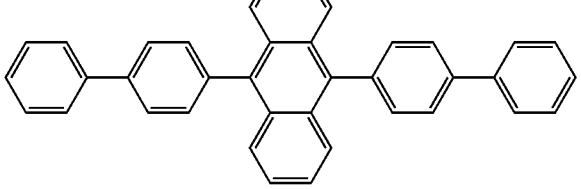
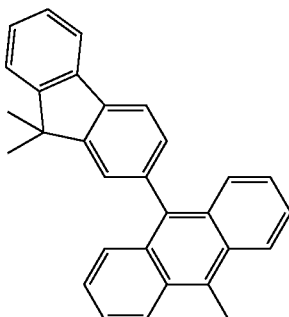
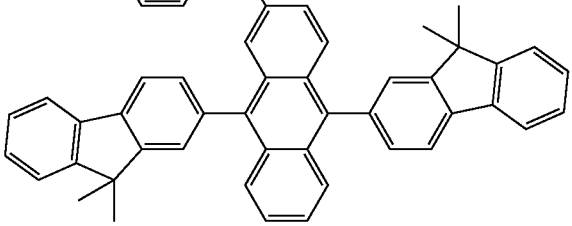
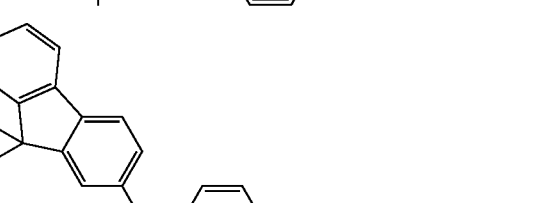
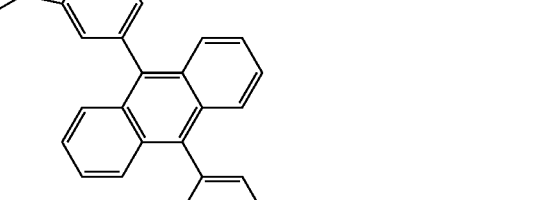
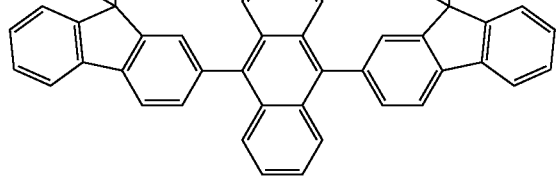

347
-continued
348
-continued
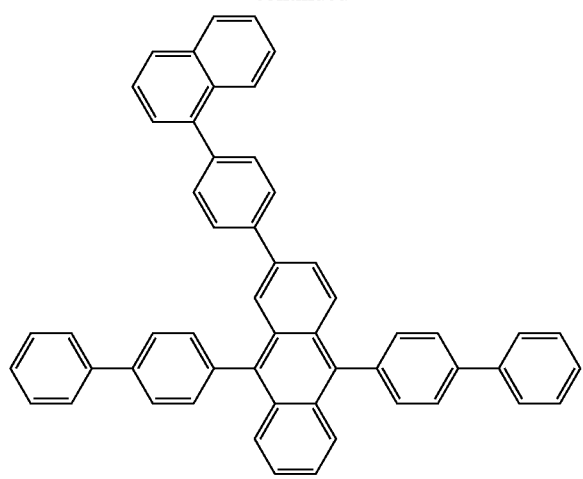
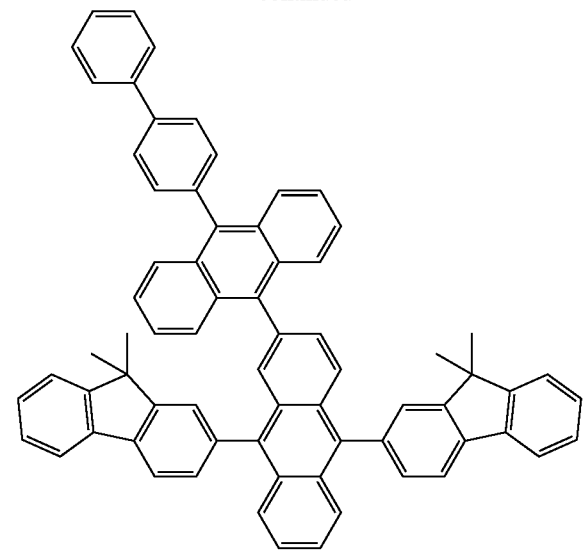
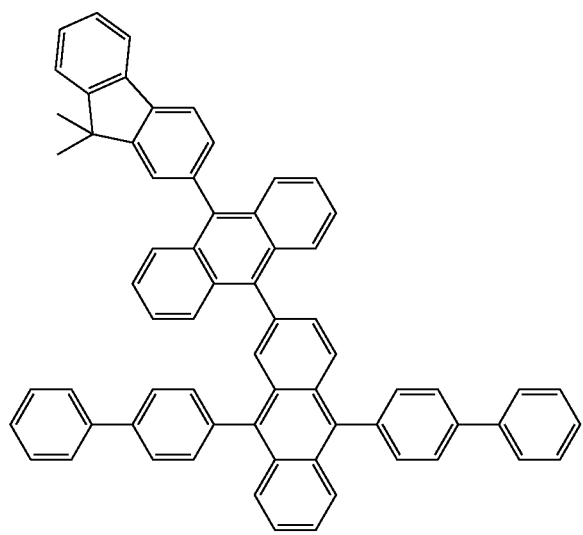
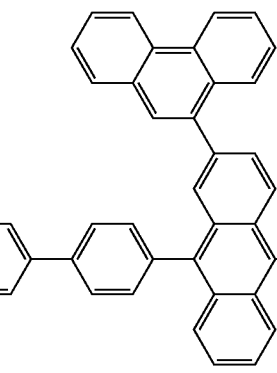
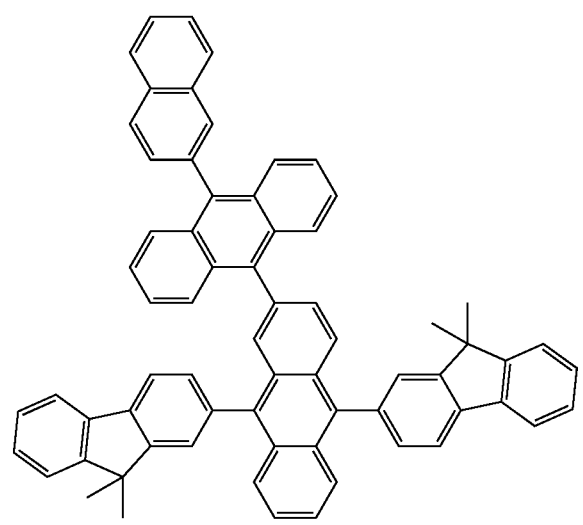

349
-continued
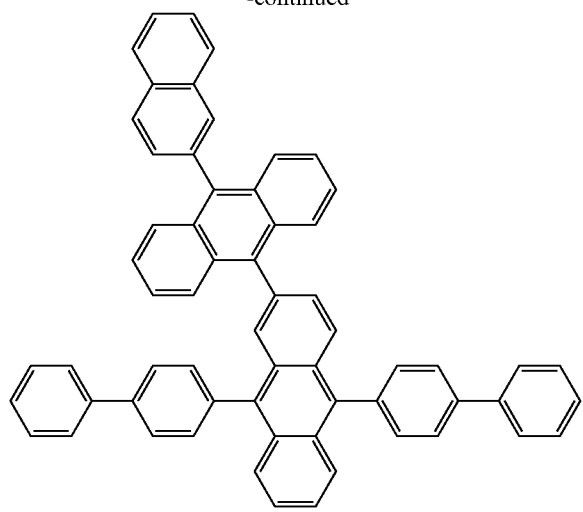
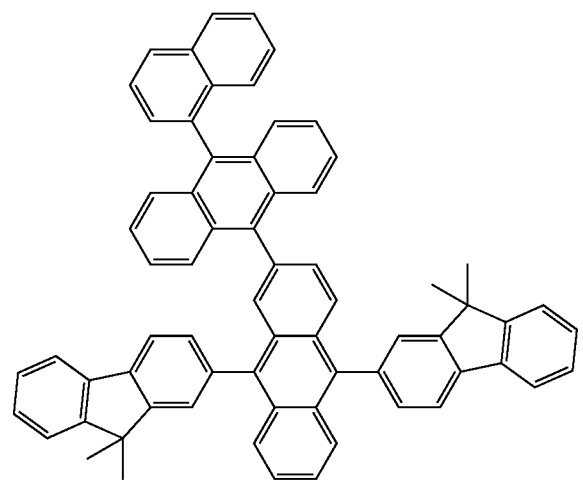
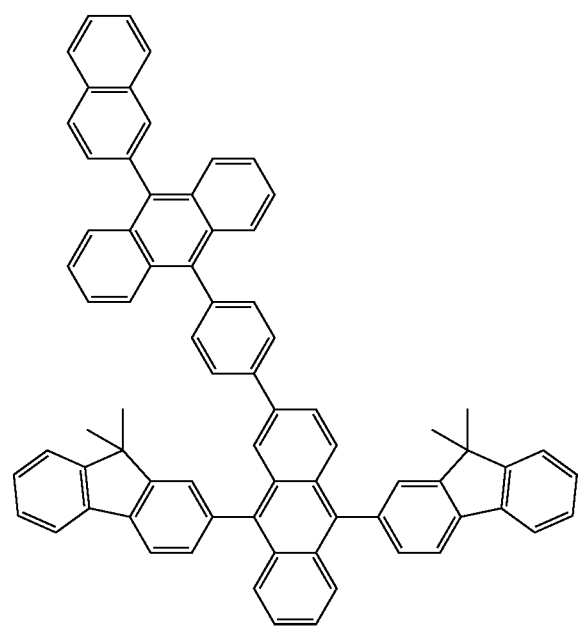
350
-continued
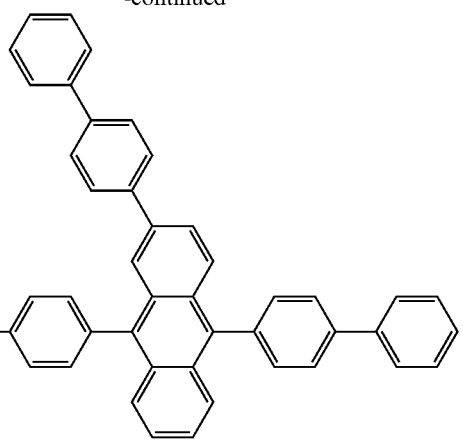
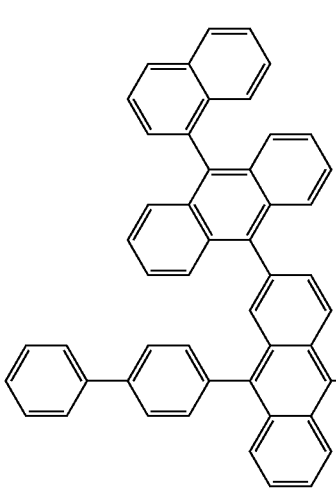
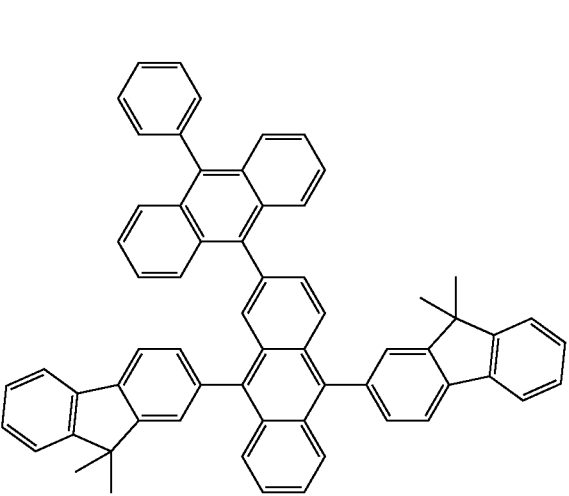

351
-continued
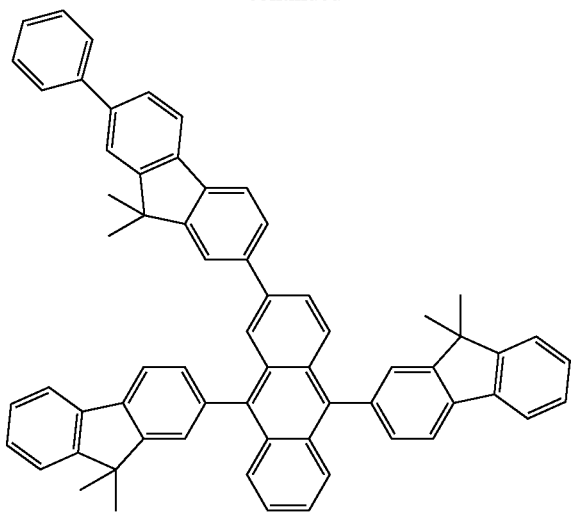
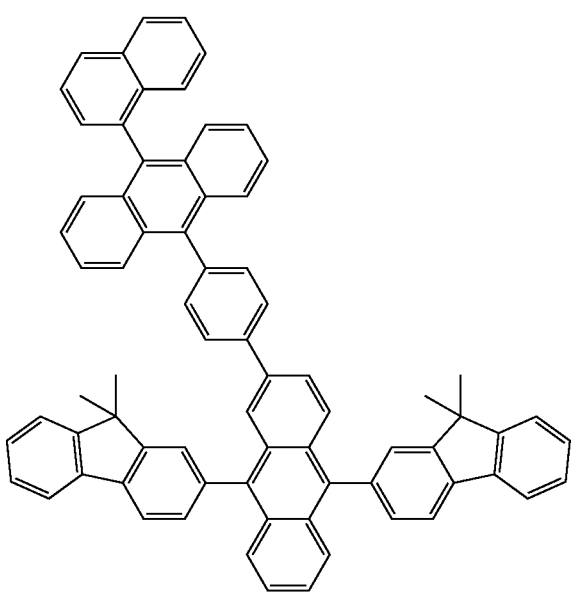
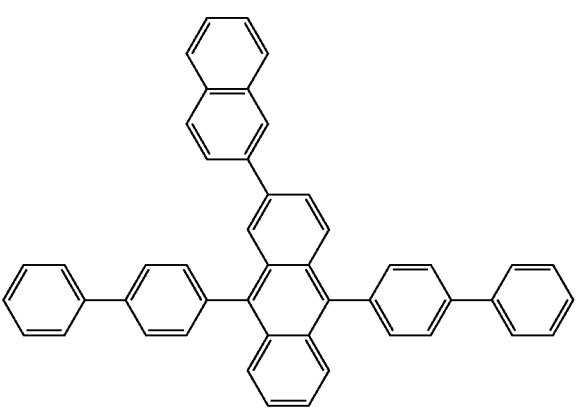
352
-continued
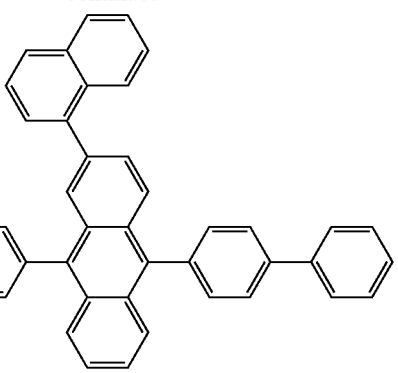
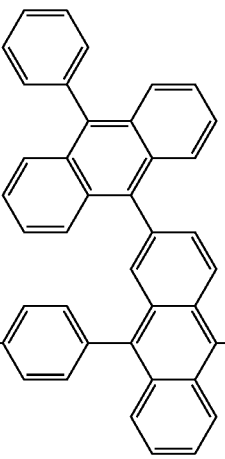
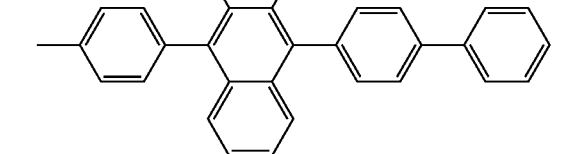
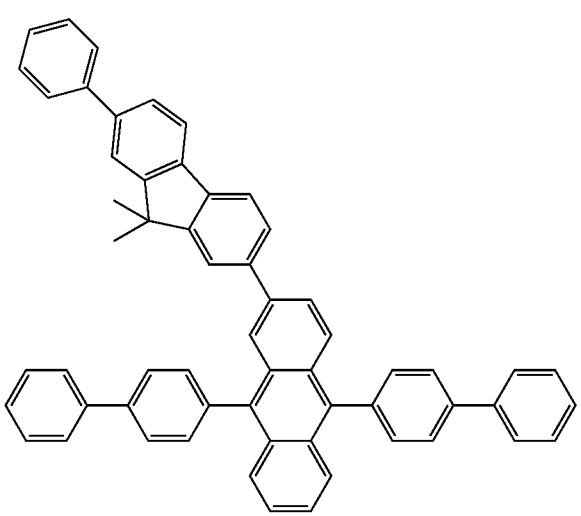

353
-continued
354
-continued
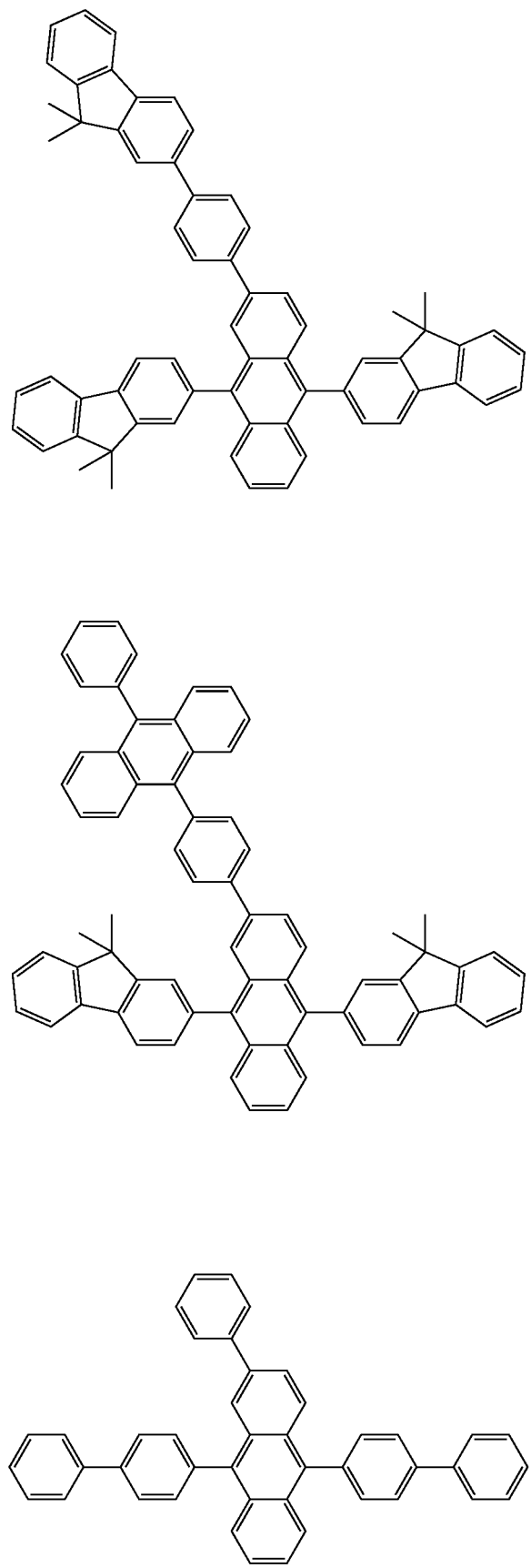
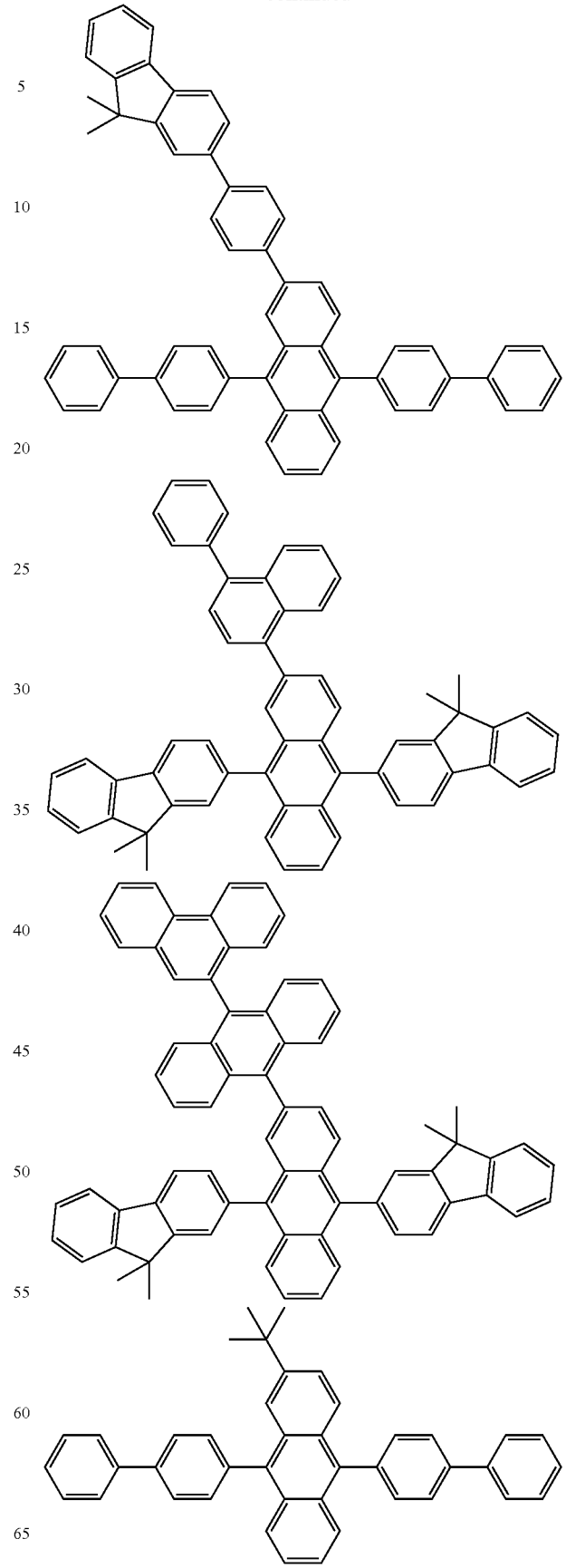

355
-continued
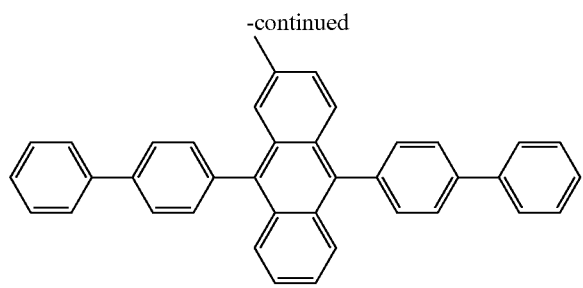
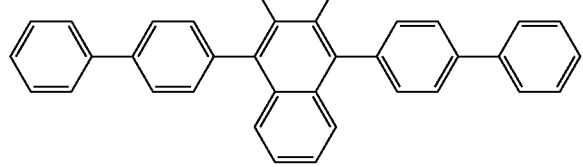
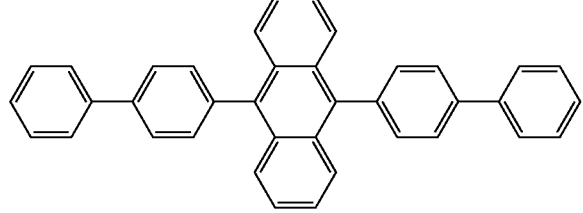
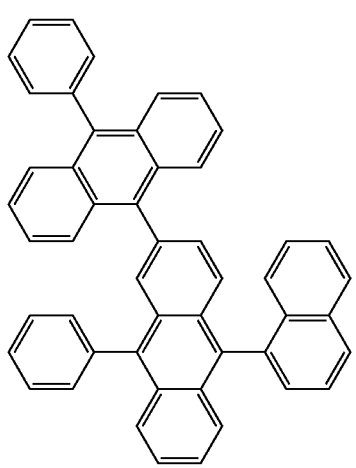
356
-continued
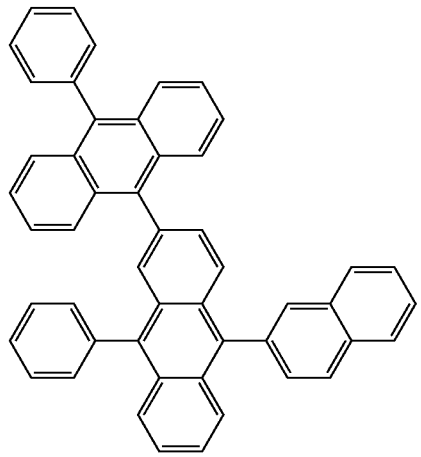
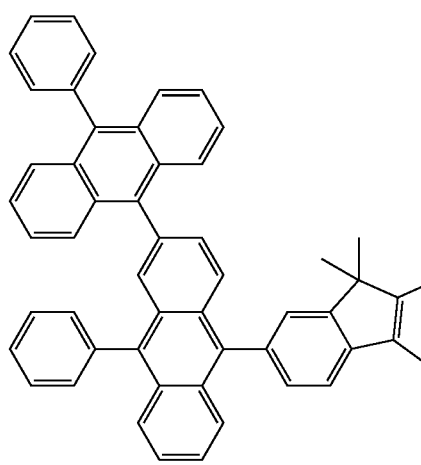
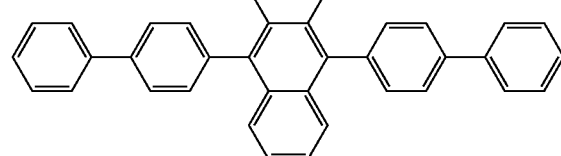

357
-continued
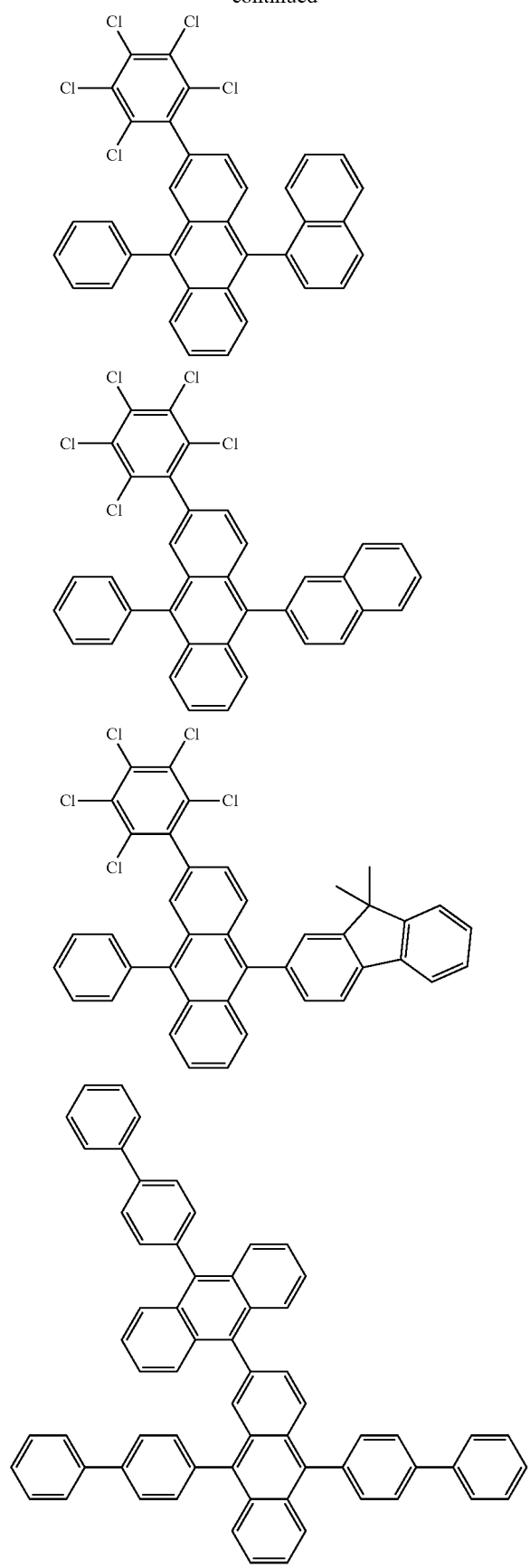
358
-continued
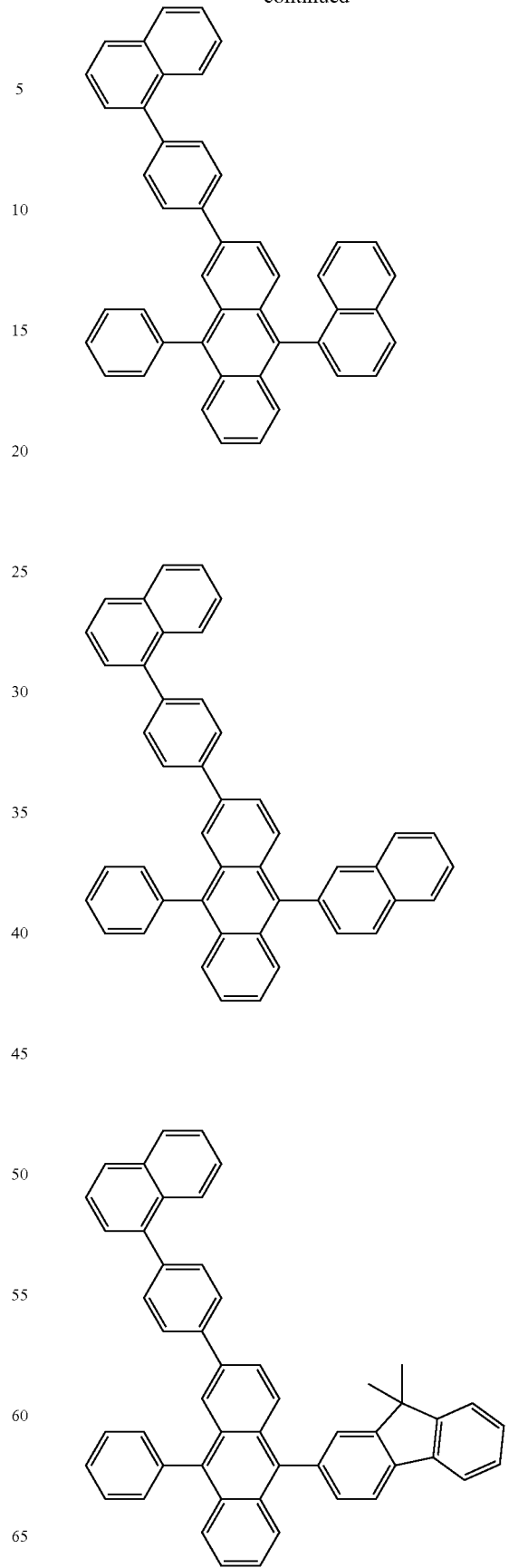

359
-continued
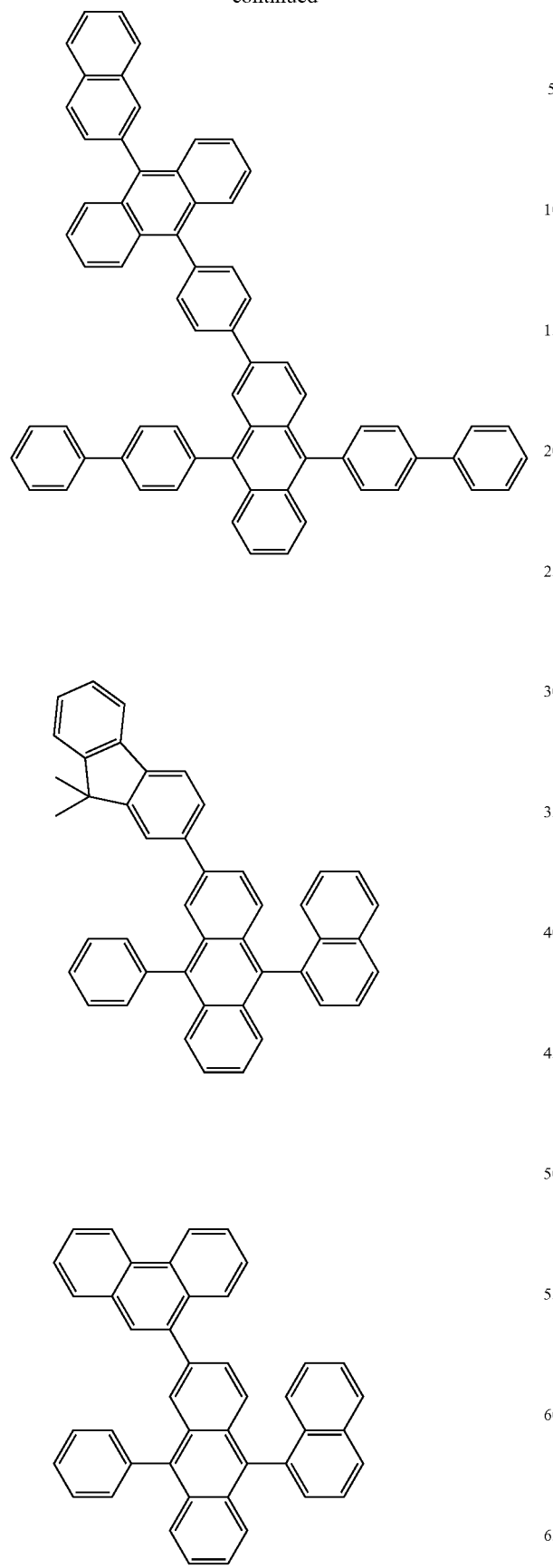
360
-continued
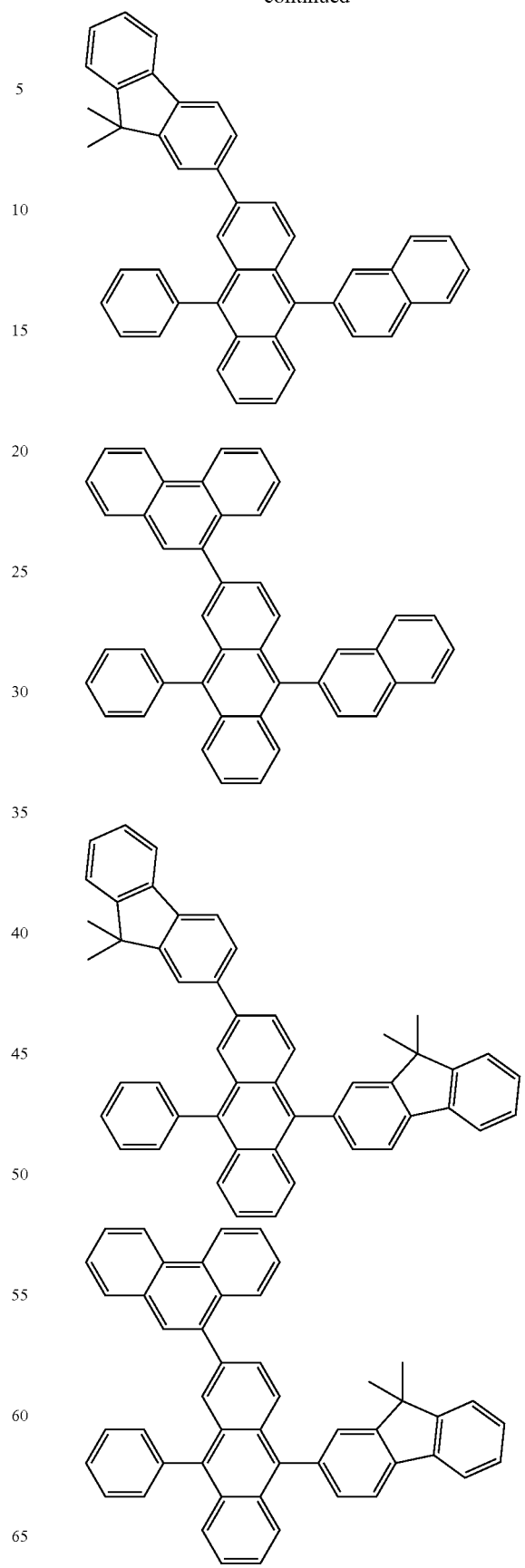

361
-continued
362
-continued
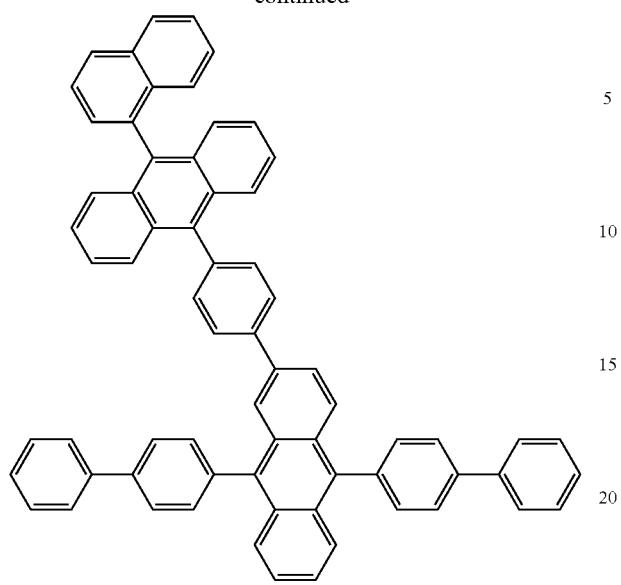
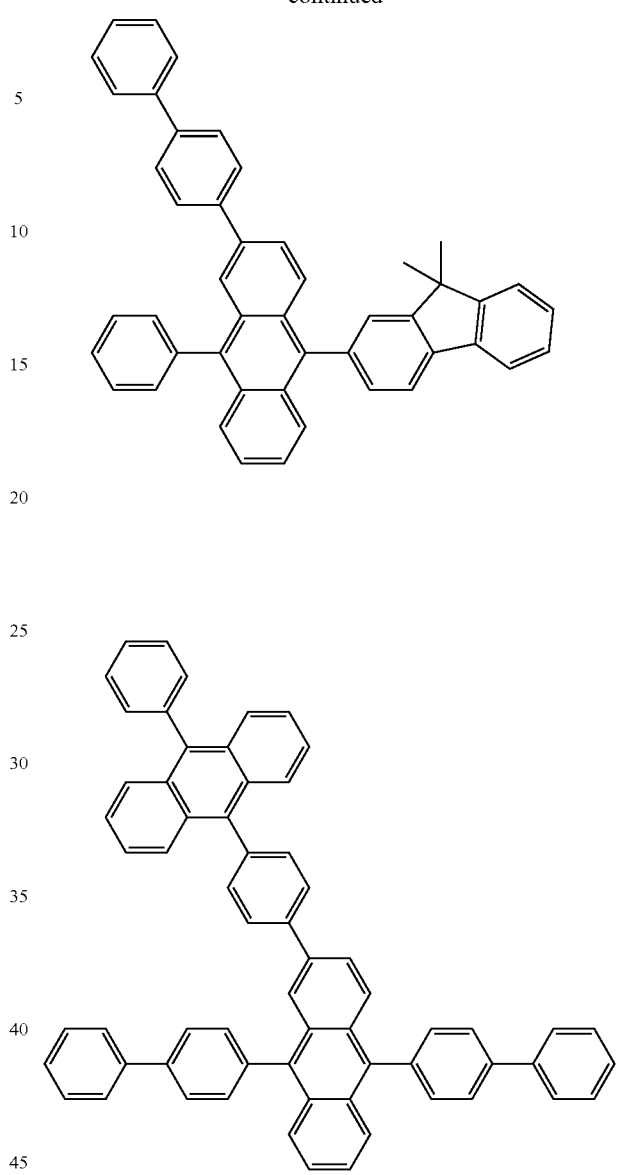
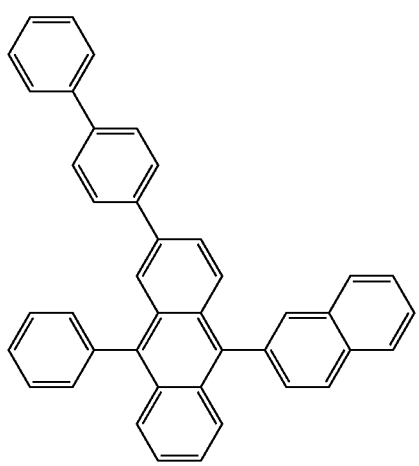
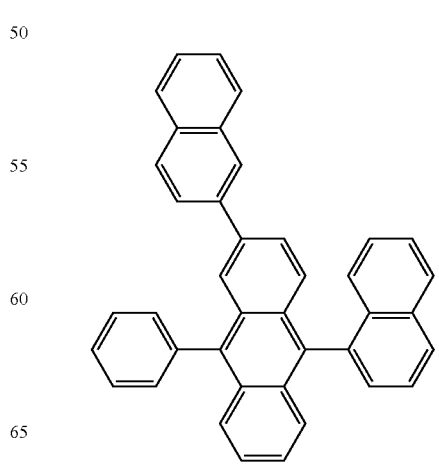

-continued
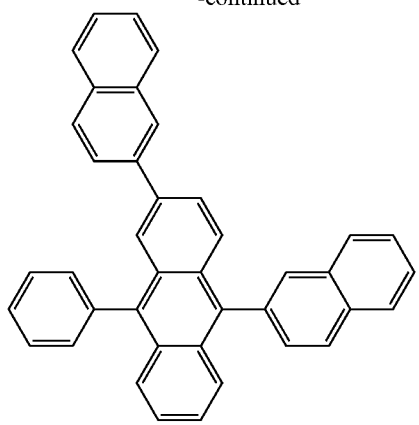
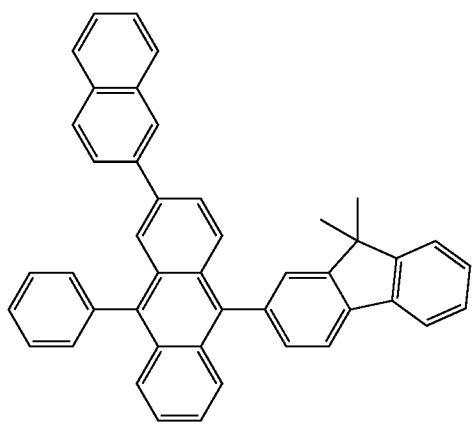
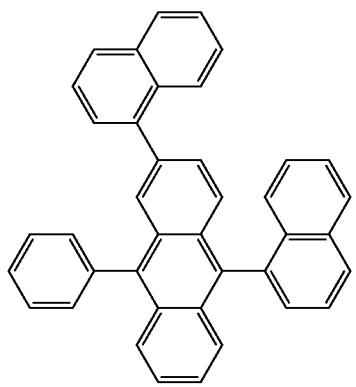
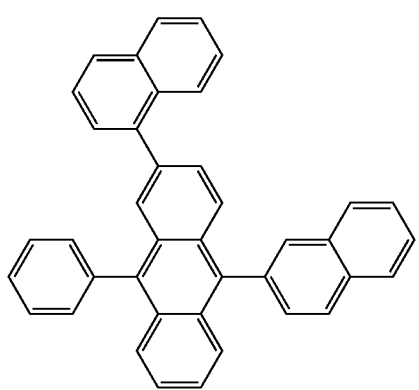
-continued
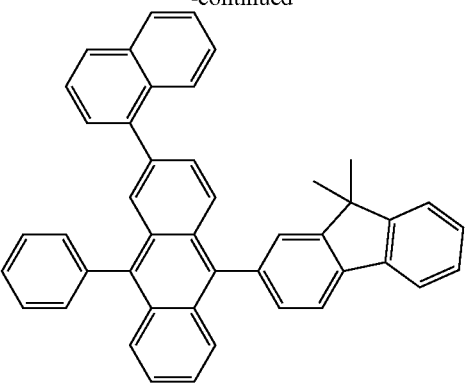
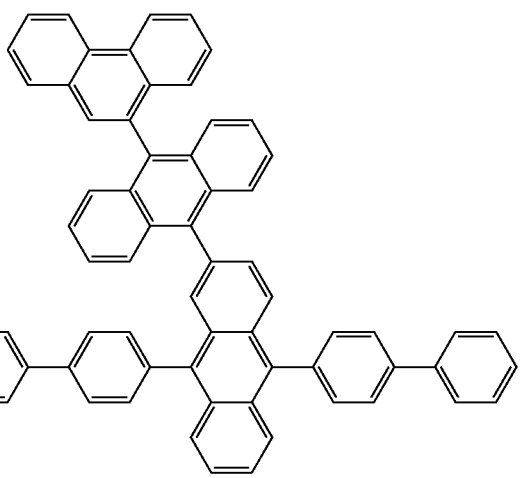
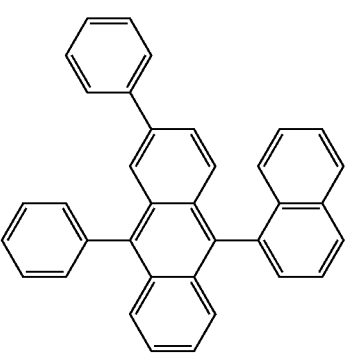
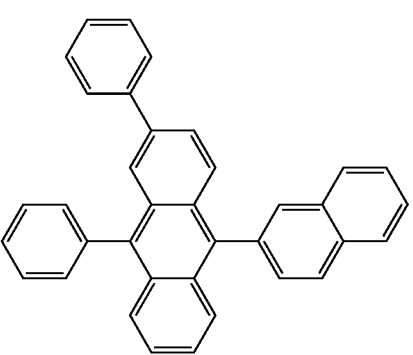

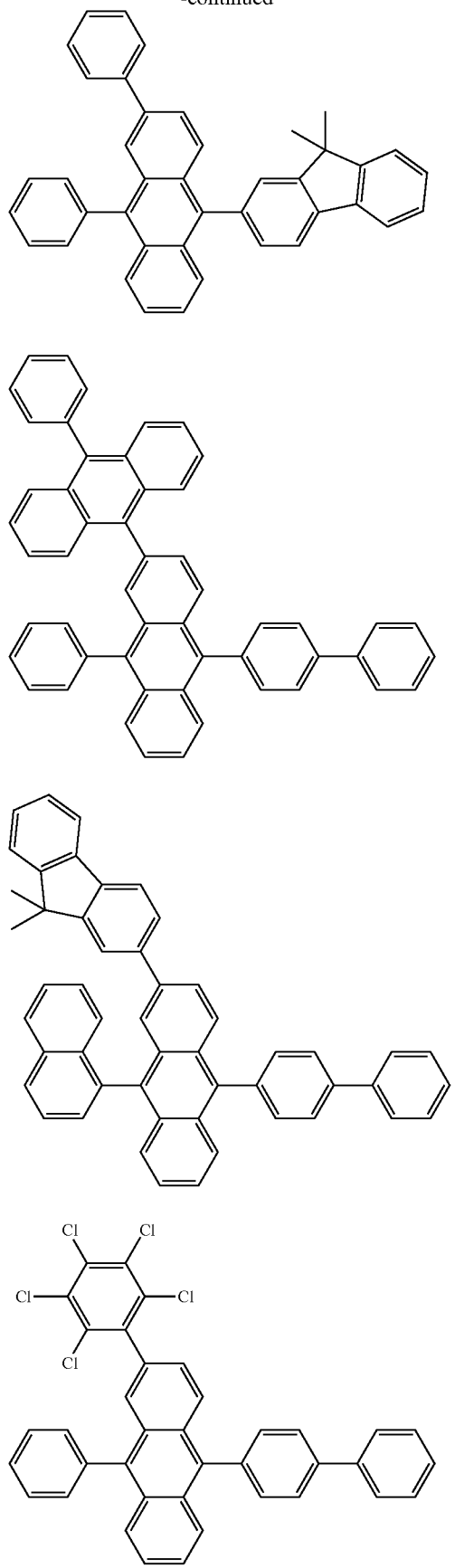

367
-continued
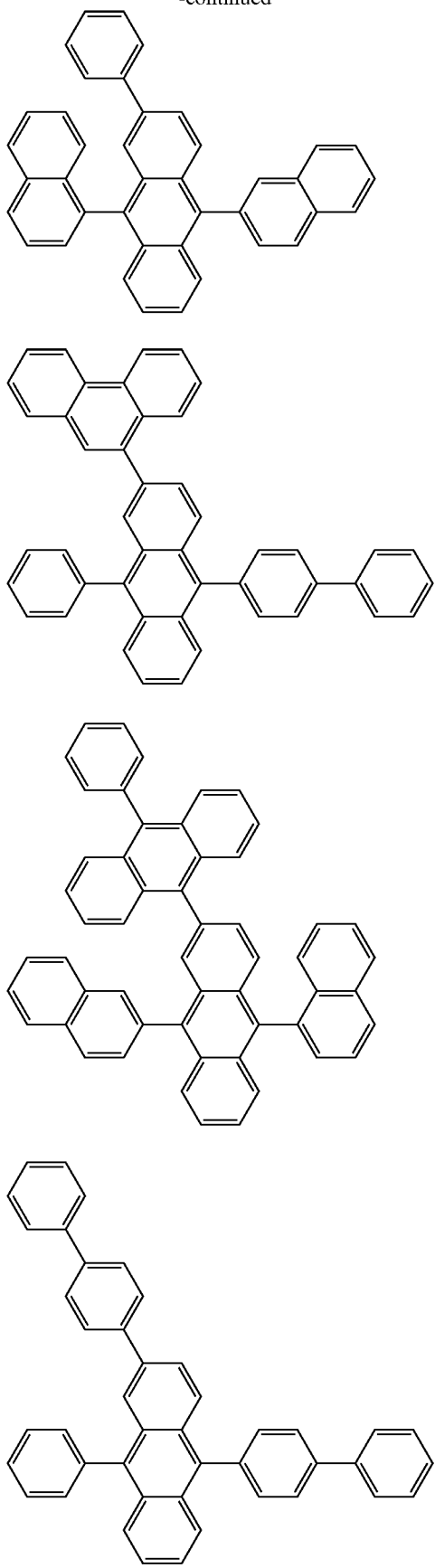
368
-continued
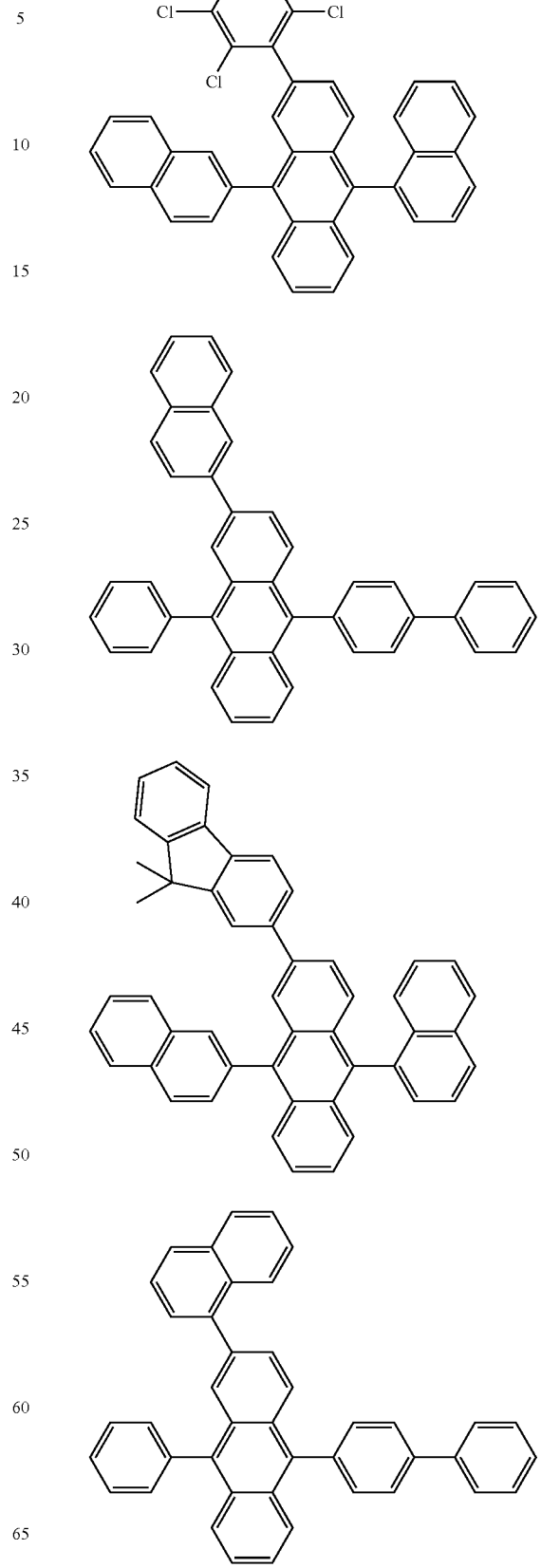

369
-continued
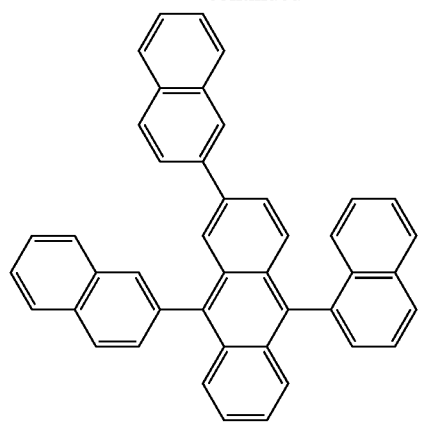
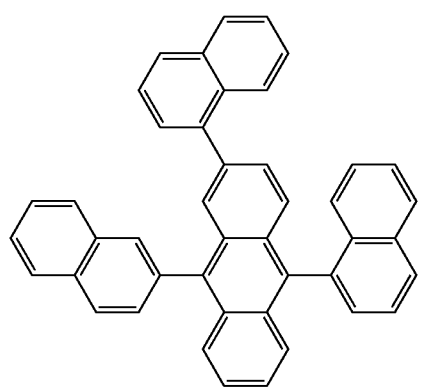
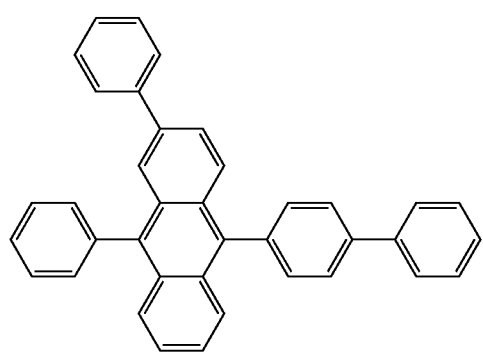
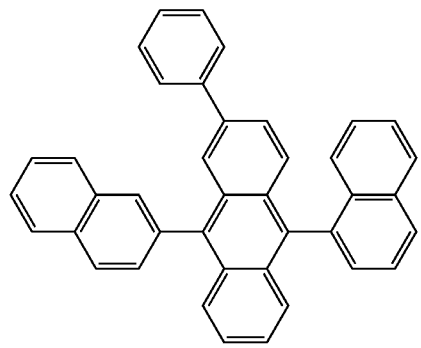
370
-continued
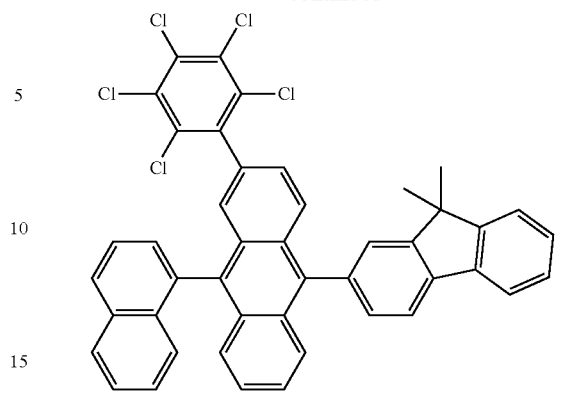
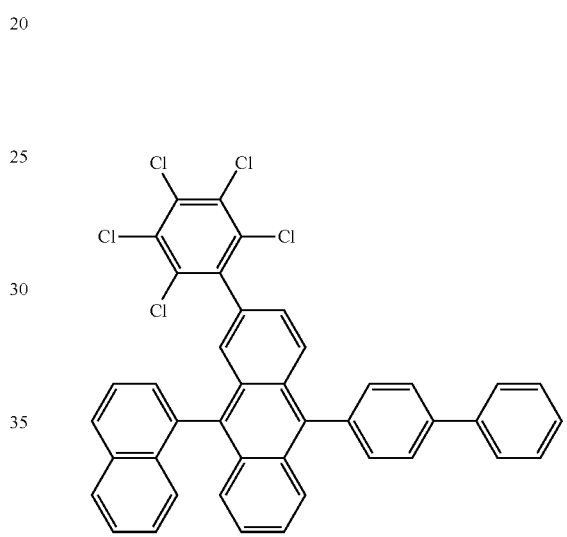
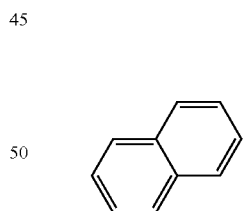
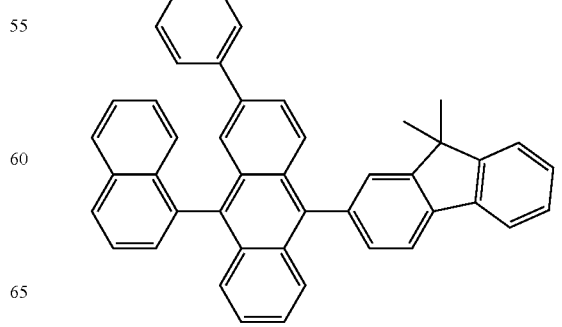

371
-continued
372
-continued
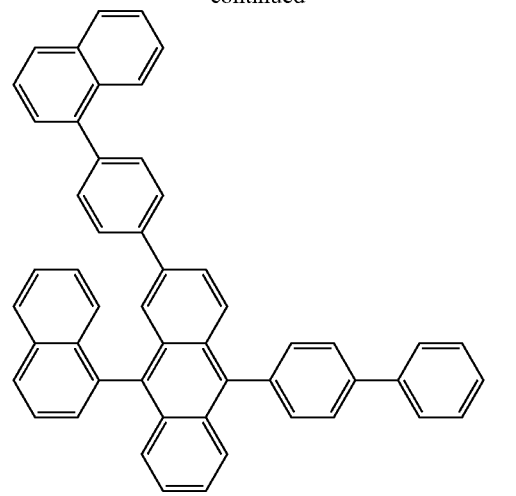
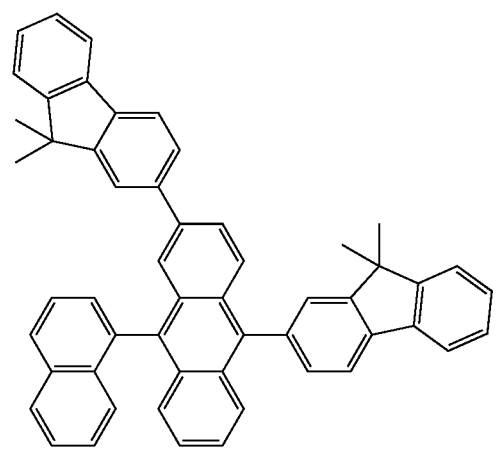
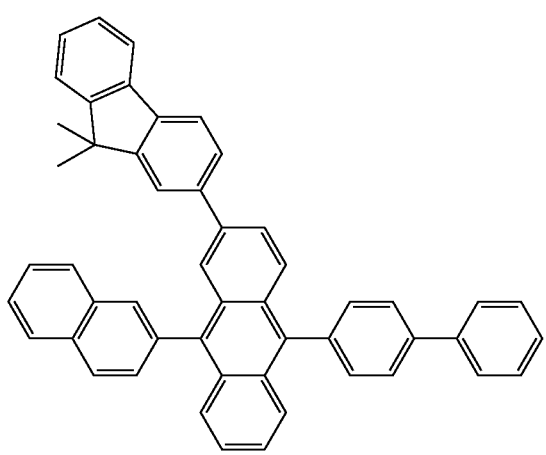
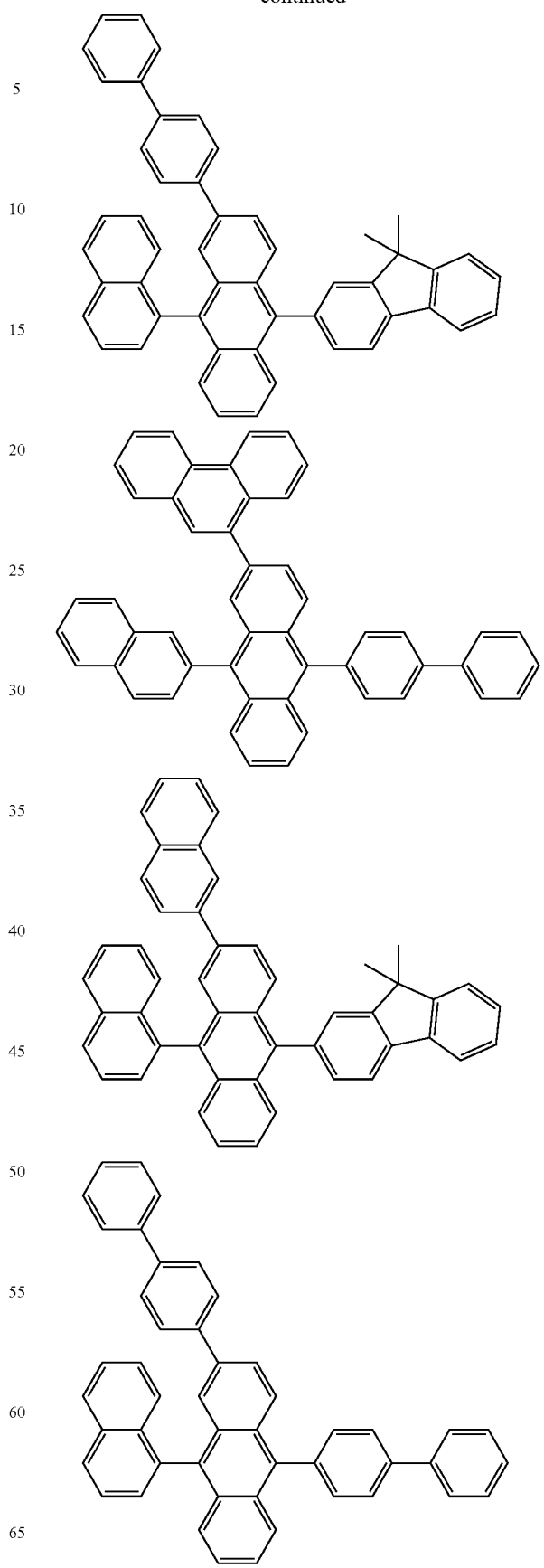

373
-continued
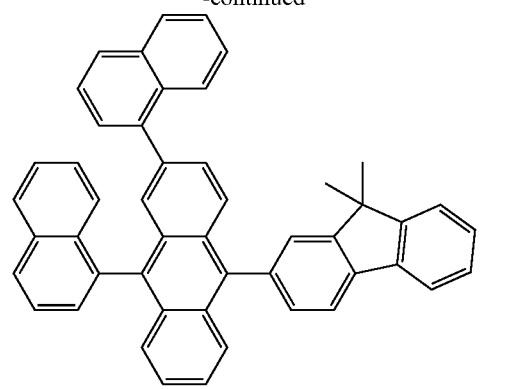
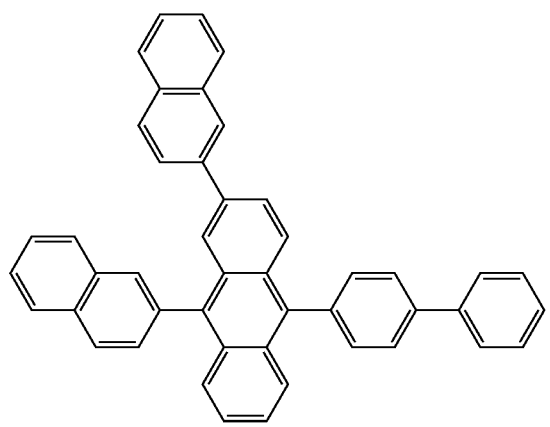
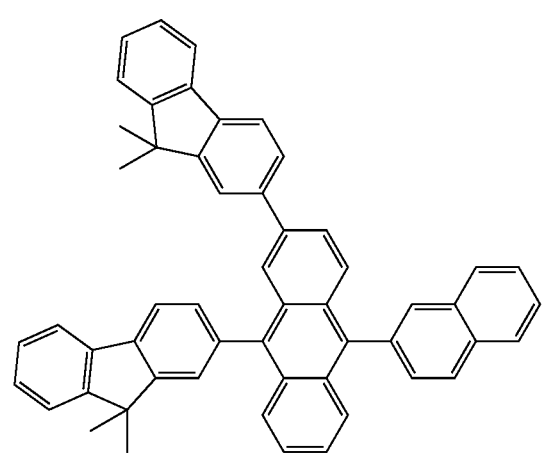
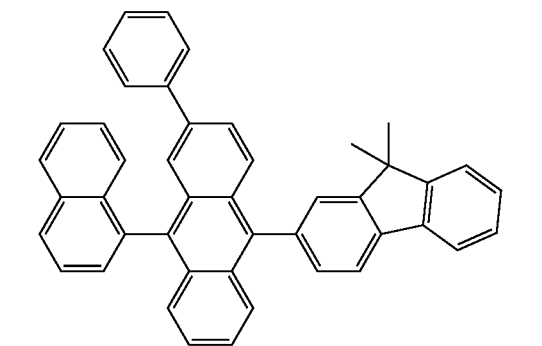
374
-continued
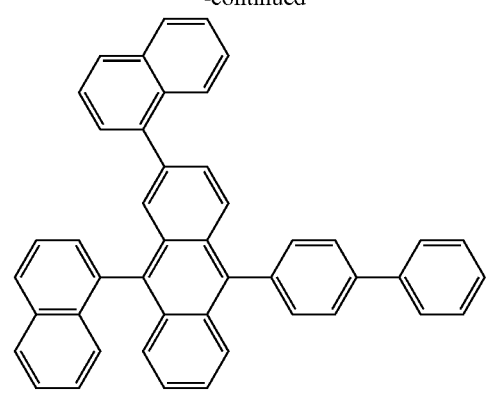
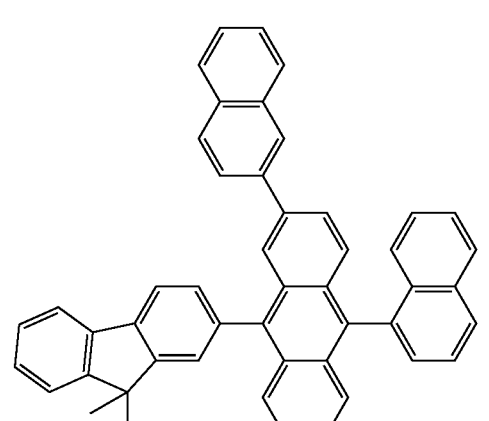
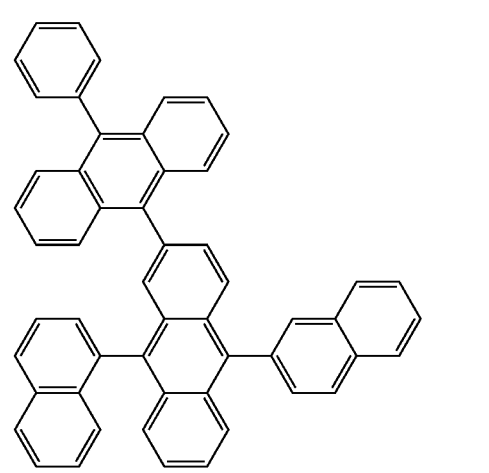
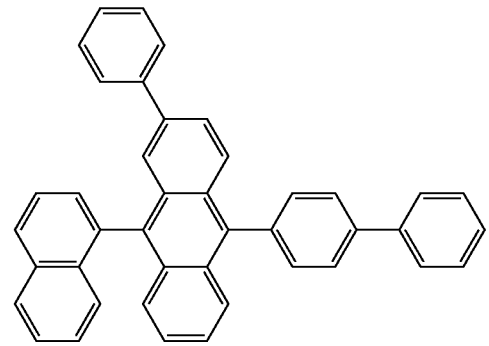

375
-continued
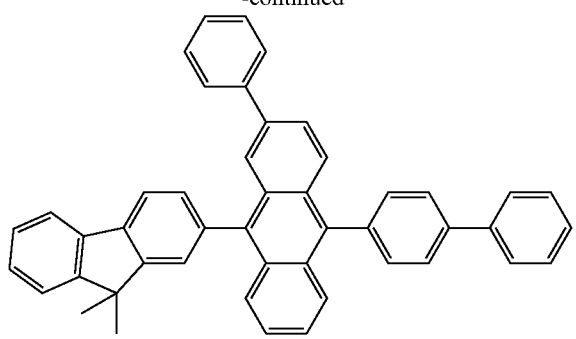
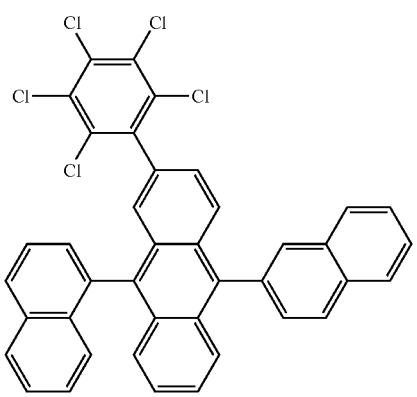
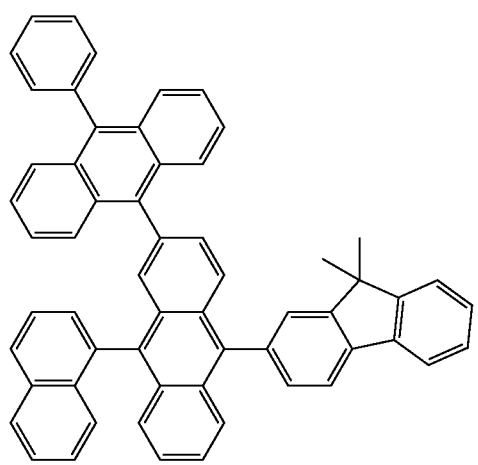
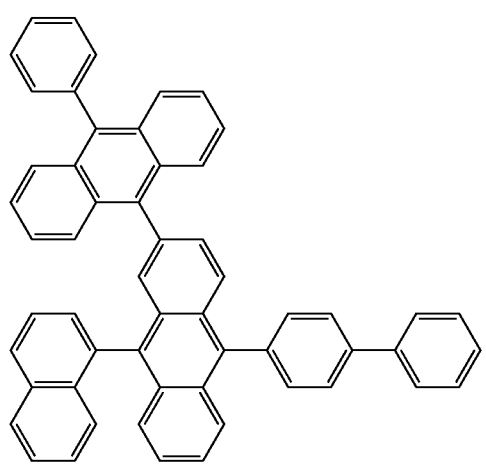
376
-continued
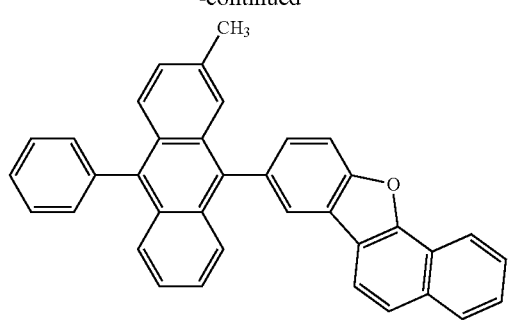
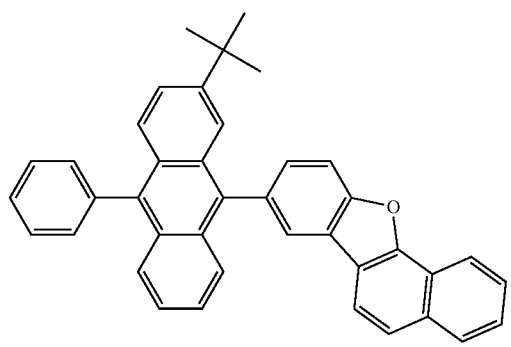
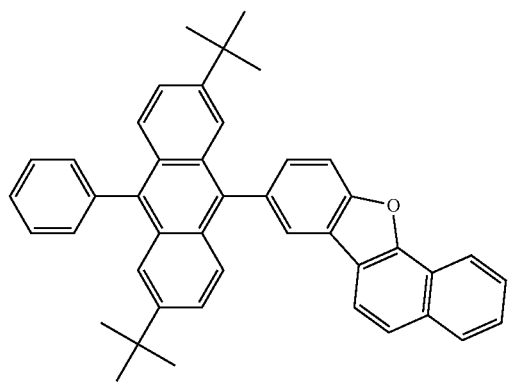
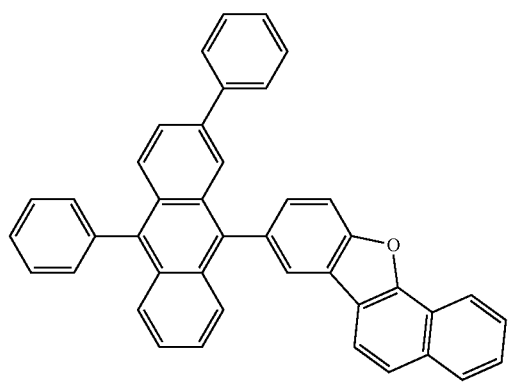

377
-continued
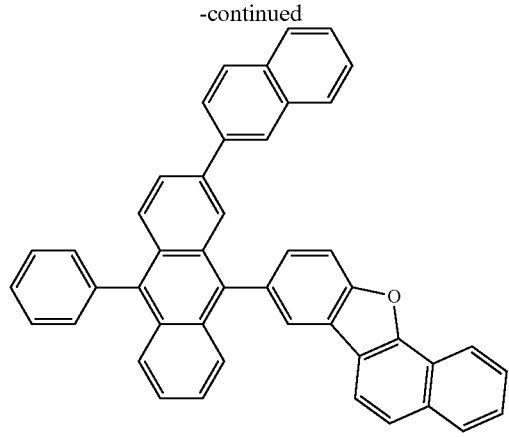
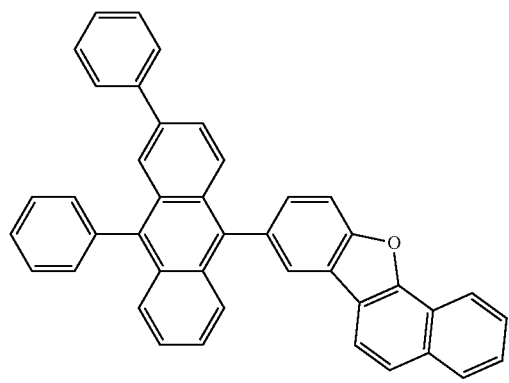
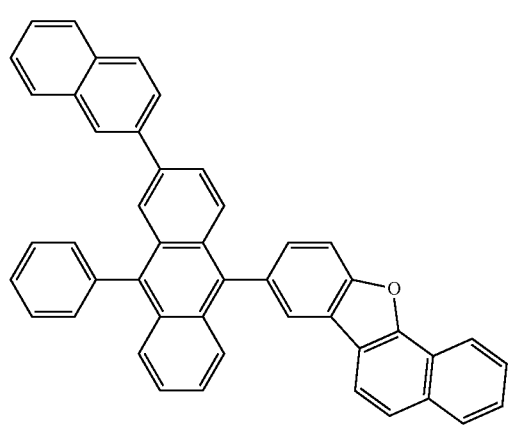
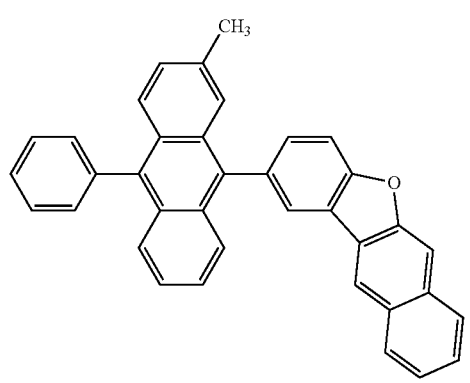
378
-continued
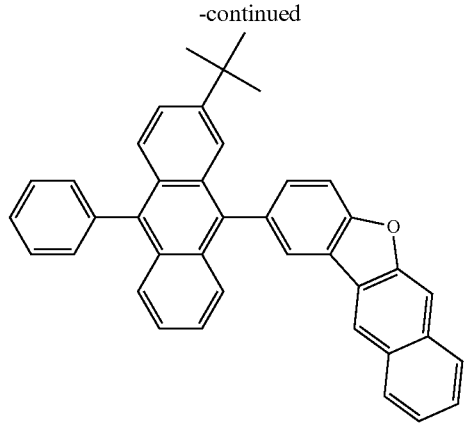
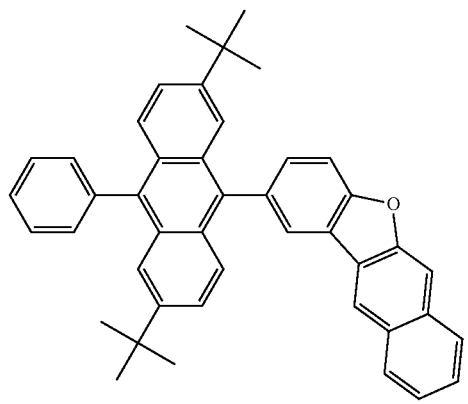
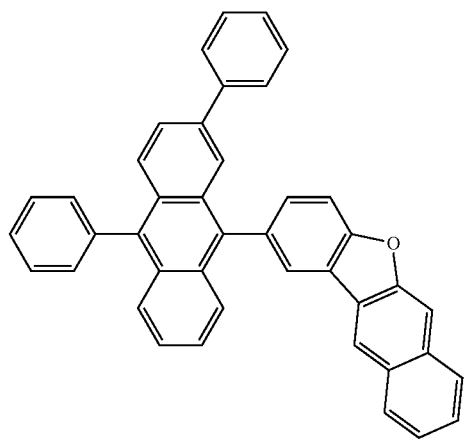
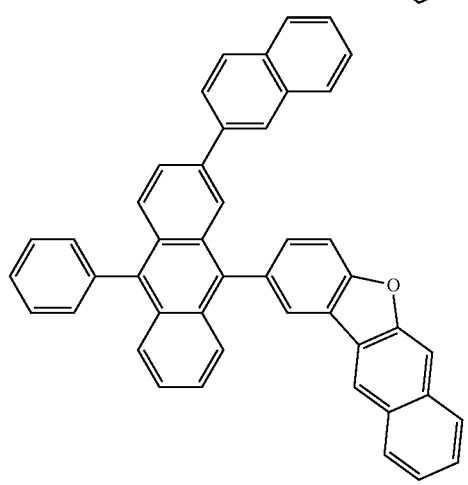

-continued

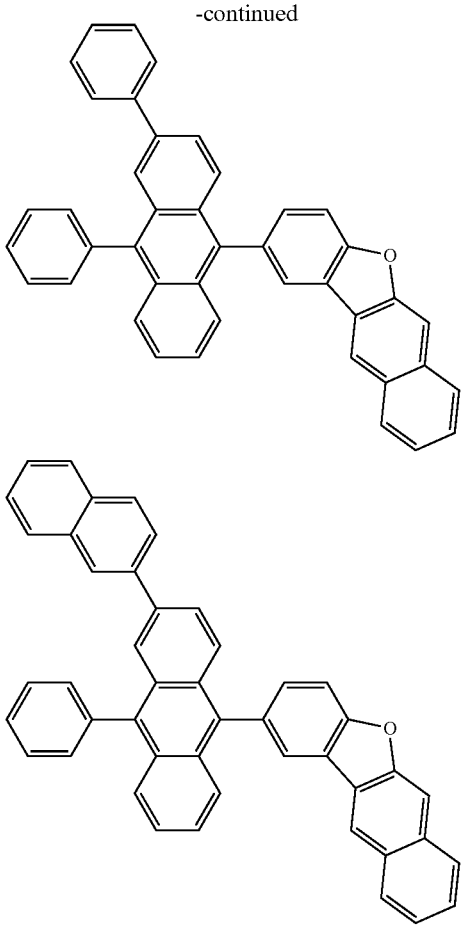

Electron-donating Dopant

The organic EL device of the invention preferably comprises an electron donating dopant at an interfacial region between the cathode and the emitting unit. With such a construction, the organic EL device has an improved luminance and an elongated lifetime. The electron-donating dopant comprises a metal having a work function of 3.8 eV or less and examples thereof include at least one selected from alkali metal, alkali metal complex, alkali metal compound, alkaline earth metal, alkaline earth metal complex, alkaline earth metal compound, rare earth metal, rare earth metal complex, and rare earth metal compound.

Examples of the alkali metal include Na (work function: 2.36 eV), K (work function: 2.28 eV), Rb (work function: 2.16 eV), and Cs (work function: 1.95 eV), with those having a work function of 2.9 eV or less being particularly preferred. Examples of the alkaline earth metal include Ca (work function: 2.9 eV), Sr (work function: 2.0 to 2.5 eV), and Ba (work function: 2.52 eV), with those having a work function of 2.9 eV or less being particularly preferred. Examples of the rare earth metal include Sc, Y, Ce, Tb, and Yb, with those having a work function of 2.9 eV or less being particularly preferred.

Examples of the alkali metal compound include alkali oxide, such as $Li_2O$, $Cs_2O$, $K_2O$, and alkali halide, such as LiF, NaF, CsF, and KF, with LiF, $Li_2O$, and NaF being preferred. Examples of the alkaline earth metal compound include BaO, SrO, CaO, and mixture thereof, such as $Ba_xSr_{1-x}O$ (0<x<1) and $Ba_xCA^1_{-x}O$ (0<x<1), with BaO, SrO, and CaO being preferred. Examples of the rare earth metal compound include $YbF_3$, $ScF_3$, $ScO_3$, $Y_2O_3$, $Ce_2O_3$, $GdF_3$, and $TbF_3$, with $YbF_3$, $ScF_3$, and $TbF_3$ being preferred.

Examples of the alkali metal complex, alkaline earth metal complex, and rare earth metal are not particularly limited as long as containing at least one metal ion selected from an alkali metal ion, an alkaline earth metal ion, and a rare earth metal ion, respectively. The ligand is preferably, but not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfulborane, bipyridyl, phenanthroline, phthalocyanine, porphyrin, cyclopentadiene, β-diketones, azomethines, and derivative thereof.

The electron-donating dopant material is added to the interfacial region preferably into a form of layer or island, which is formed by co-depositing the electron-donating dopant material with an organic compound (light emitting material, electron injecting material) for forming the interfacial region by a resistance heating deposition method, thereby dispersing the electron-donating dopant material into the organic material. The disperse concentration expressed by the ratio of organic material: electron-donating dopant material is 100:1 to 1:100 by mole.

When the electron-donating dopant material is formed into a form of layer, a light emitting material or an electron injecting material is formed into an interfacial organic layer, and then, the electron-donating dopant material alone is deposited by a resistance heating deposition method into a layer having a thickness of preferably 0.1 to 15 nm. When the electron-donating dopant material is formed into a form of island, a light emitting material or an electron injecting material is made into an interfacial island, and then, the electron-donating dopant material alone is deposited by a resistance heating deposition method into a form of island having a thickness of preferably 0.05 to 1 nm.

The molar ratio of the main component and the electron-donating dopant in the organic EL device of the invention is preferably 5:1 to 1:5.

Electron Transporting Layer

The electron transporting layer is an organic layer disposed between the light emitting layer and the cathode and transports electrons from the cathode to the light emitting layer. If two or more electron transporting layers are provided, the organic layer closer to the cathode may be called an electron injecting layer in some cases. The electron injecting layer injects electrons from the cathode to the organic layer unit efficiently.

An aromatic heterocyclic compound having one or more heteroatoms in its molecule is preferably used as an electron transporting material used in the electron transporting layer, and a nitrogen-containing ring derivative is particularly preferred. In addition, the nitrogen-containing ring derivative is preferably an aromatic ring compound having a nitrogen-containing, 6- or 5-membered ring, or a fused aromatic ring compound having a nitrogen-containing, 6- or 5-membered ring.

The nitrogen-containing ring derivative is preferably, for example, a metal chelate complex of a nitrogen-containing ring represented by formula (A):

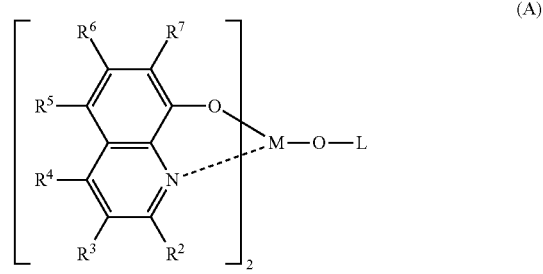

(A)

wherein each of $R^2$ to $R^7$ independently represents a hydrogen atom, a halogen atom, a hydroxyl group, an amino group, a hydrocarbon group having 1 to 40, preferably 1 to 20, more preferably 1 to 10, and still more preferably 1 to 6 carbon atoms, an alkoxy group having 1 to 40, preferably 1 to 20, more preferably 1 to 10, and still more preferably 1 to 6 carbon atoms, an aryloxy group having 6 to 40, preferably 6 to 20, and more preferably 6 to 12 ring carbon atoms, an alkoxycarbonyl group having 2 to 40, preferably 2 to 20, more preferably 2 to 10, and still more preferably 2 to 5 carbon atoms, or an aromatic heterocyclic group having 9 to 40, preferably 9 to 30, and more preferably 9 to 20 ring atoms, each optionally having a substituent.

M is aluminum (Al), gallium (Ga), or indium (In), with In being preferred.

L is a group represented by formula (A') or (A"):

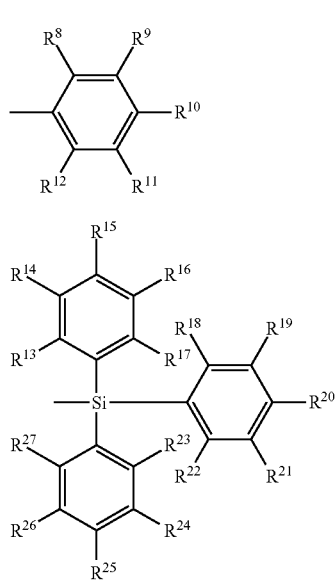

Each $R^8$ to $R^{12}$ in formula (A') independently represents a hydrogen atom or a substituted or unsubstituted hydrocarbon group having 1 to 40, preferably 1 to 20, more preferably 1 to 10, and still more preferably 1 to 6 carbon atoms. Two adjacent groups may form a ring structure. Each of $R^{13}$ to $R^{27}$ in formula (A") independently represents a hydrogen atom or a substituted or unsubstituted hydrocarbon group having 1 to 40, preferably 1 to 20, more preferably 1 to 10, and still more preferably 1 to 6 carbon atoms. Two adjacent groups may form a ring structure.

Examples of the hydrocarbon group having 1 to 40 carbon atoms for $R^8$ to $R^{12}$ and $R^{13}$ to $R^{27}$ in formulae (A') and (A") are the same as those described above with respect to $R^2$ to $R^7$ of formula (A).

Examples of the divalent group formed by two adjacent groups of $R^8$ to $R^{12}$ and $R^{13}$ to $R^{27}$ which completes the ring structure include a tetramethylene group, a pentamethylene group, a hexamethylene group, a diphenylmethane-2,2'-diyl group, a diphenylethane-3,3'-diyl group, and a diphenylpropane-4,4'-diyl group.

The electron transporting compound for use in the electron transporting layer is preferably a metal complex including 8-hydroxyquinoline or its derivative, an oxadiazole derivative, or a nitrogen-containing heterocyclic derivative.

The electron transporting compound is preferably good in the thin film-forming property. Examples of the electron transporting compound are shown below.

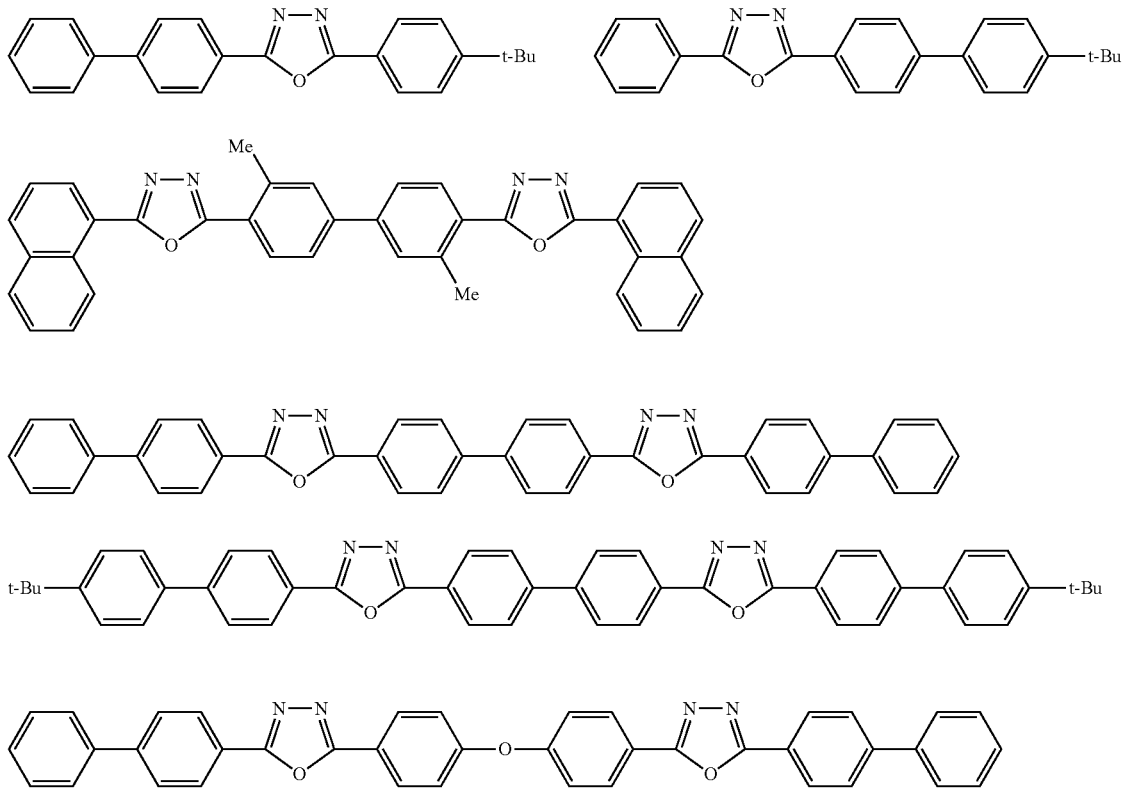

Example of the nitrogen-containing heterocyclic derivative for use as the electron transporting compound also includes a nitrogen-containing compound other than the metal complex, for example, a compound having a nitrogen-containing heterocyclic group selected from the following formulae is preferred.

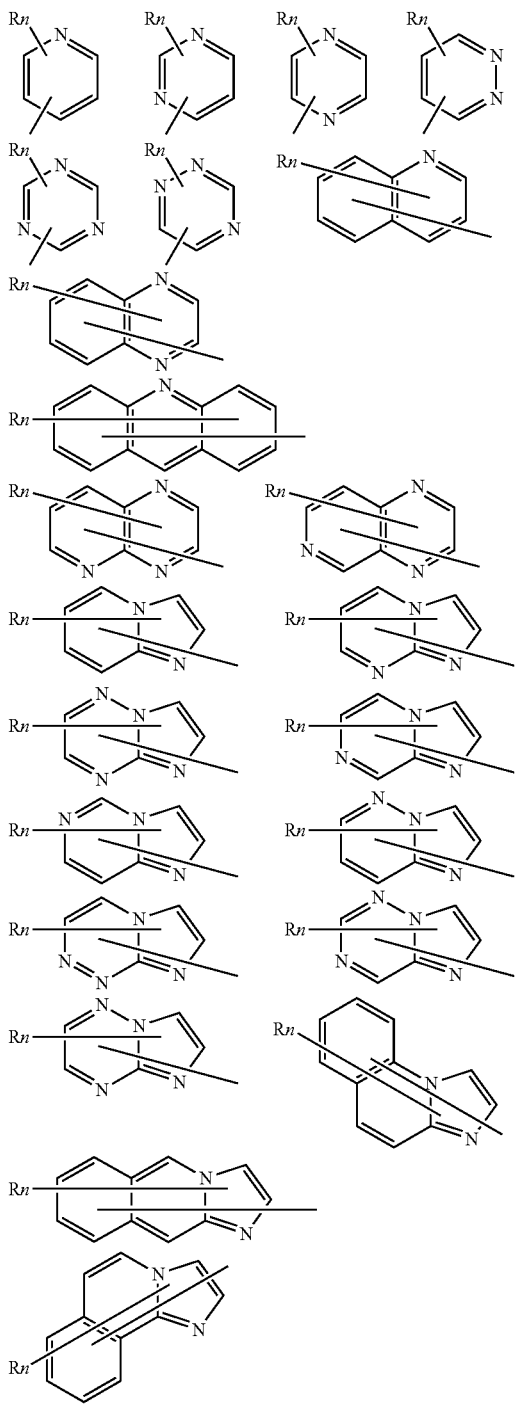

wherein R is an aromatic hydrocarbon group or a fused aromatic hydrocarbon group each having 6 to 40 carbon atoms, an aromatic heterocyclic group or a fused aromatic heterocyclic group each having 3 to 40 carbon atoms, an alkyl group having 1 to 20 carbon atoms, or an alkoxy group having 1 to 20 carbon atoms; and n is an integer of 0 to 5. If n is an integer of 2 or more, groups R may be the same or different.

The electron transporting layer in the organic EL device of the invention preferably comprises at least one compound selected from the nitrogen-containing heterocyclic derivatives represented by formulae (60) to (62):

 (60)

 (61)

 (62)

wherein:
$Z^{11}$, $Z^{12}$, and $Z^{13}$ each independently represent a nitrogen atom or a carbon atom;

$R^A$ and $R^B$ each independently represent a substituted or unsubstituted aryl group having 6 to 50, preferably 6 to 30, more preferably 6 to 20, and still more preferably 6 to 12 ring carbon atoms, a substituted or unsubstituted heterocyclic group having 5 to 50, preferably 5 to 30, more preferably 5 to 20, and still more preferably 5 to 12 ring atoms, a substituted or unsubstituted alkyl group having 1 to 20, preferably 1 to 10, and more preferably 1 to 6 carbon atoms, a substituted or unsubstituted haloalkyl group having 1 to 20, preferably 1 to 10, and more preferably 1 to 6 carbon atoms, or a substituted or unsubstituted alkoxyl group having 1 to 20, preferably 1 to 10, and more preferably 1 to 6 carbon atoms;

n is an integer of 0 to 5, when n is an integer of 2 or more, groups $R^A$ may be the same or different, and adjacent two groups $R^A$ may bond to each other to form a substituted or unsubstituted hydrocarbon ring;

$Ar^{11}$ represents a substituted or unsubstituted aryl group having 6 to 50, preferably 6 to 30, more preferably 6 to 20, and still more preferably 6 to 12 ring carbon atoms or a substituted or unsubstituted heterocyclic group having 5 to 50, preferably 5 to 30, more preferably 5 to 20, and still more preferably 5 to 12 ring atoms;

$Ar^{12}$ represents a hydrogen atom, a substituted or unsubstituted alkyl group having 1 to 20, preferably 1 to 10, and more preferably 1 to 6 carbon atoms, a substituted or unsubstituted haloalkyl group having 1 to 20, preferably 1 to 10, and more preferably 1 to 6 carbon atoms, a substituted or unsubstituted alkoxyl group having 1 to 20, preferably 1 to 10, and more preferably 1 to 6 carbon atoms, a substituted or unsubstituted aryl group having 6 to 50, preferably 6 to 30, more preferably 6 to 20, and still more preferably 6 to 12 ring carbon atoms, or a substituted or unsubstituted heteroaryl group having 5 to 50, preferably 5 to 30, more preferably 5 to 20, and still more preferably 5 to 12 ring atoms;

provided that one of $Ar^{11}$ and $Ar^{12}$ is a substituted or unsubstituted fused aromatic hydrocarbon group having 10 to 50, preferably 10 to 30, more preferably 10 to 20, and still more preferably 10 to 14 ring carbon atoms or a substituted or unsubstituted fused aromatic heterocyclic group having 9 to 50, preferably 9 to 30, more preferably 9 to 20, and still more preferably 9 to 14 ring atoms;

$Ar^{13}$ represents a substituted or unsubstituted arylene group having 6 to 50, preferably 6 to 30, more preferably 6 to 20, and still more preferably 6 to 12 ring carbon atoms or a substituted or unsubstituted heteroarylene group having 5 to 50, preferably 5 to 30, more preferably 5 to 20, and still more preferably 5 to 12 ring atoms; and $L^{11}$, $L^{12}$, and $L^{13}$ each independently represent a single bond, a substituted or unsubstituted arylene group having 6 to 50, preferably 6 to 30, more preferably 6 to 20, and still more preferably 6 to 12 ring carbon atoms or a substituted or unsubstituted divalent fused aromatic heterocyclic group having 9 to 50, preferably 9 to 30, more preferably 9 to 20, and still more preferably 9 to 14 ring atoms.

Examples of the nitrogen-containing heterocyclic derivative represented by formulae (60) to (62) are shown below.

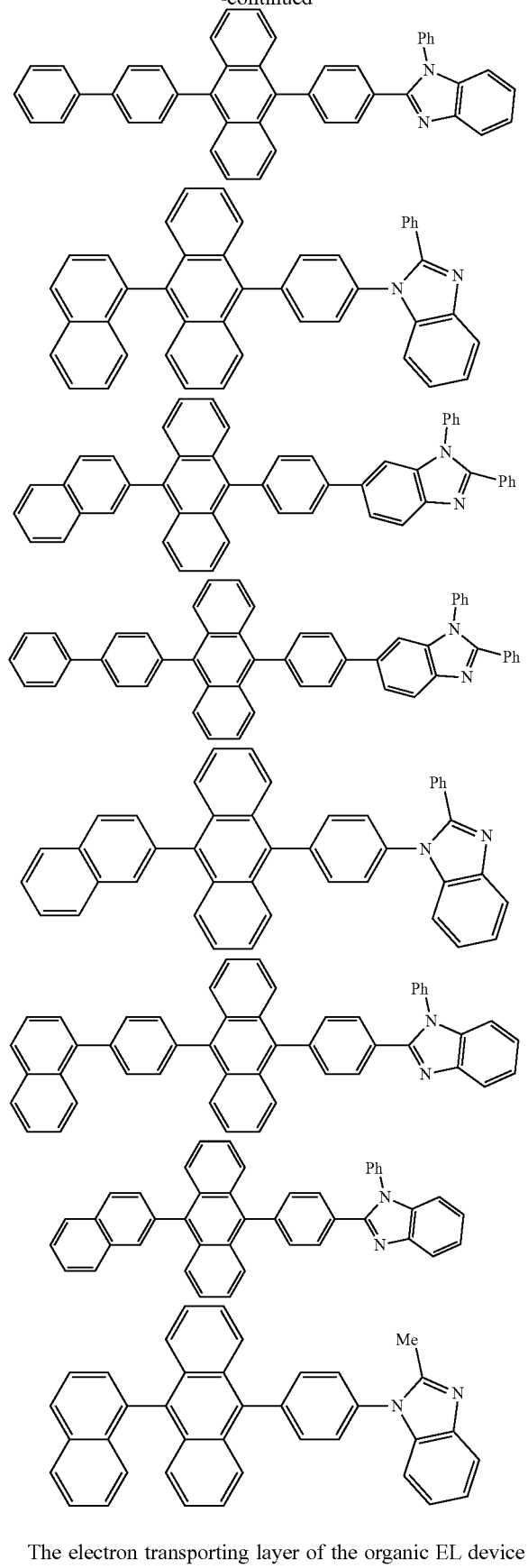

The electron transporting layer of the organic EL device of the invention may be made into two-layered structure of a first electron transporting layer (anode side) and a second electron transporting layer (cathode side).

The thickness of the electron transporting layer is preferably 1 to 100 nm, although not particularly limited thereto. If the electron transporting layer is of a two-layered structure of a first electron transporting layer (anode side) and a second electron transporting layer (cathode side), the thickness is preferably 5 to 60 nm and more preferably 10 to 40 nm for the first electron transporting layer, and preferably 1 to 20 nm and more preferably 1 to 10 nm for the second electron transporting layer.

Preferred example of the material for an electron injecting layer optionally formed adjacent to the electron transporting layer include, in addition to the nitrogen-containing ring derivative, an inorganic compound, such as an insulating material and a semiconductor. The electron injecting layer formed by the insulating material or the semiconductor effectively prevents the leak of electric current to enhance the electron injecting properties.

The insulating material is preferably at least one metal compound selected from the group consisting of an alkali metal chalcogenide, an alkaline earth metal chalcogenide, an alkali metal halide and an alkaline earth metal halide. The alkali metal chalcogenide, etc. mentioned above are preferred because the electron injecting properties of the electron injecting layer are further enhanced. Example of preferred alkali metal chalcogenide includes $Li_2O$, $K_2O$, $Na_2S$, $Na_2Se$ and $Na_2O$, and example of preferred alkaline earth metal chalcogenide includes CaO, BaO, SrO, BeO, BaS and CaSe. Example of preferred alkali metal halide includes LiF, NaF, KF, LiCl, KCl and NaCl. Example of the alkaline earth metal halide includes a fluoride, such as $CaF_2$, $BaF_2$, $SrF_2$, $MgF_2$ and $BeF_2$, and a halide other than the fluoride.

Example of the semiconductor includes an oxide, a nitride or an oxynitride of at least one element selected from the group consisting of Ba, Ca, Sr, Yb, Al, Ga, In, Li, Na, Cd, Mg, Si, Ta, Sb and Zn. The semiconductor may be used alone or in combination of two or more. The inorganic compound in the electron injecting layer preferably forms a microcrystalline or amorphous insulating thin film. If the electron injecting layer is formed from such an insulating thin film, the pixel defects, such as dark spots, can be decreased because a more uniform thin film is formed. Example of such an inorganic compound includes the alkali metal chalcogenide, the alkaline earth metal chalcogenide, the alkali metal halide and the alkaline earth metal halide.

The thickness of the layer of the insulating material or the semiconductor is preferably about 0.1 to 15 nm. The electron injecting layer preferably contains the electron-donating dopant mentioned above.

Hole Transporting Layer

The hole transporting layer is an organic layer formed between the light emitting layer and the anode and transports holes from the anode to the light emitting layer. When the hole transporting layer is formed by two or more layers, the layer closer to the anode may be defined as a hole injecting layer in some cases. The hole injecting layer injects holes from the anode to the organic layer unit efficiently.

An aromatic amine compound, for example, the aromatic amine derivative represented by formula (I) is preferably used as a material for the hole transporting layer:

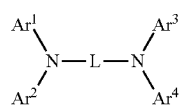
(I)

wherein:

each of $Ar^1$ to $Ar^4$ represents a substituted or unsubstituted aromatic hydrocarbon group having 6 to 50, preferably 6 to 30, more preferably 6 to 20, and still more preferably 6 to 12 ring carbon atoms, a substituted or unsubstituted fused aromatic hydrocarbon group having 6 to 50, preferably 6 to 30, more preferably 6 to 20, and still more preferably 6 to 12 ring carbon atoms, a substituted or unsubstituted aromatic heterocyclic group having 5 to 50, preferably 5 to 30, more preferably 5 to 20, and still more preferably 5 to 12 ring carbon atoms, a substituted or unsubstituted fused aromatic heterocyclic group having 5 to 50, preferably 5 to 30, more preferably 5 to 20, and still more preferably 5 to 12 ring atoms, or a group wherein the aromatic hydrocarbon group or the fused aromatic hydrocarbon group is bonded to the aromatic heterocyclic group or the fused aromatic heterocyclic group;

$Ar^1$ and $Ar^2$ or $Ar^3$ and $Ar^4$ may form a ring; and

L represents a substituted or unsubstituted aromatic hydrocarbon group having 6 to 50, preferably 6 to 30, more preferably 6 to 20, and still more preferably 6 to 12 ring carbon atoms, a substituted or unsubstituted fused aromatic hydrocarbon group having 6 to 50, preferably 6 to 30, more preferably 6 to 20, and still more preferably 6 to 12 ring carbon atoms, a substituted or unsubstituted aromatic heterocyclic group having 5 to 50, preferably 5 to 30, more preferably 5 to 20, and still more preferably 5 to 12 ring carbon atoms, or a substituted or unsubstituted fused aromatic heterocyclic group having 5 to 50, preferably 5 to 30, more preferably 5 to 20, and still more preferably 5 to 12 ring atoms.

Examples of the compound represented by formula (I) are shown below.

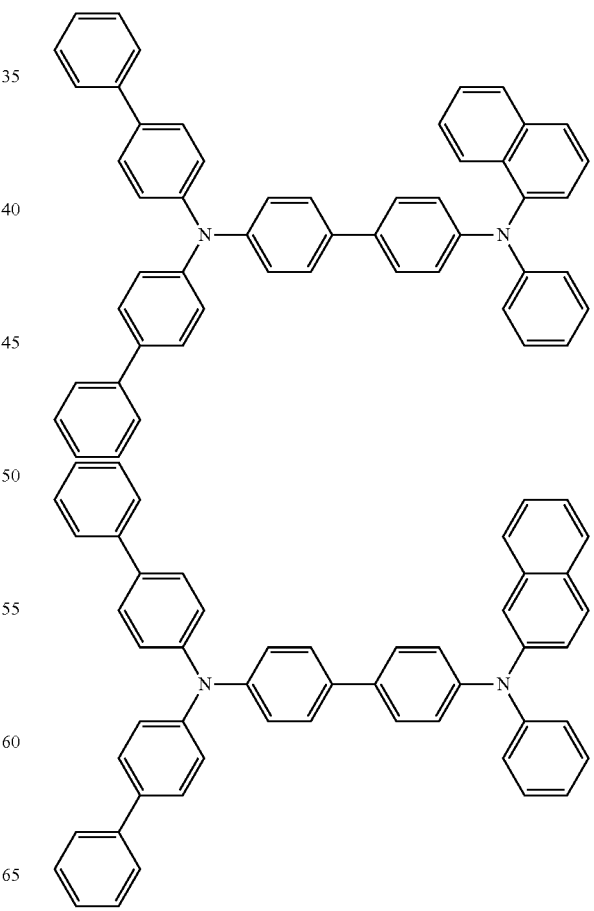

389
-continued
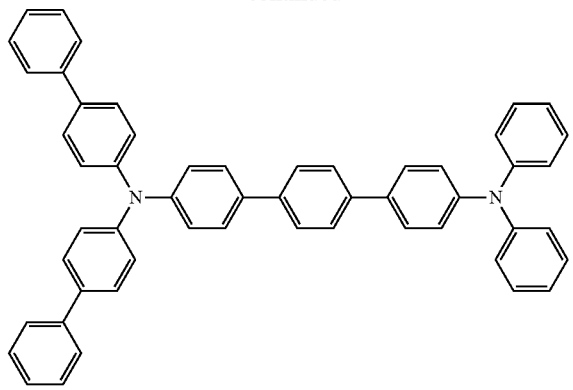
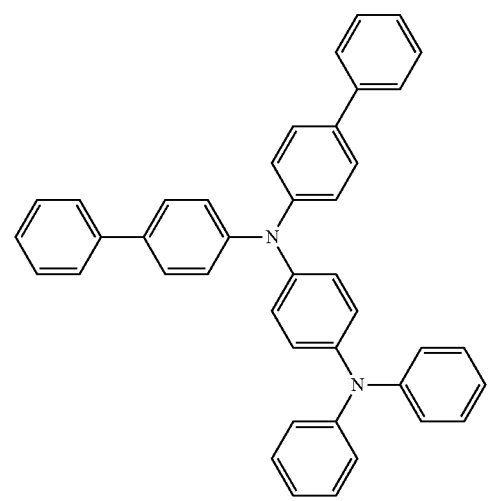
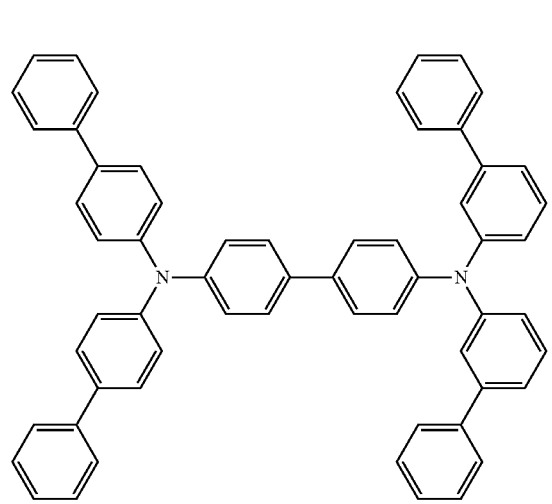
390
-continued
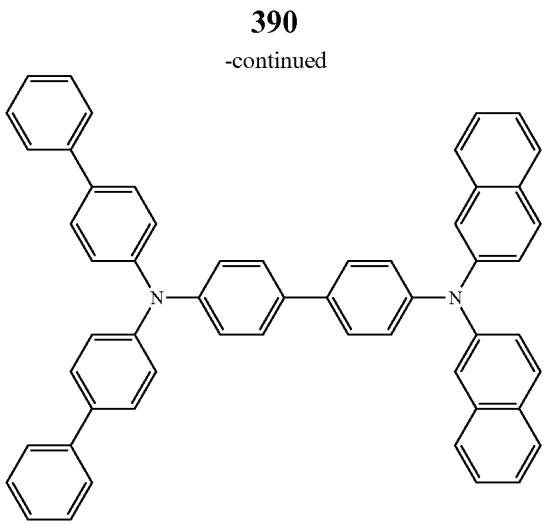
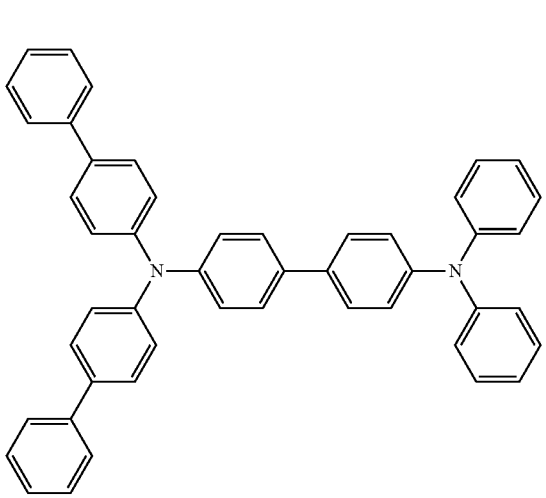
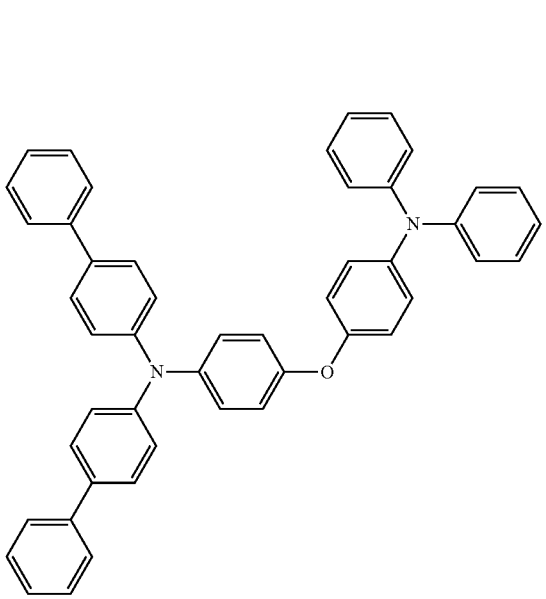

391
-continued
392
-continued
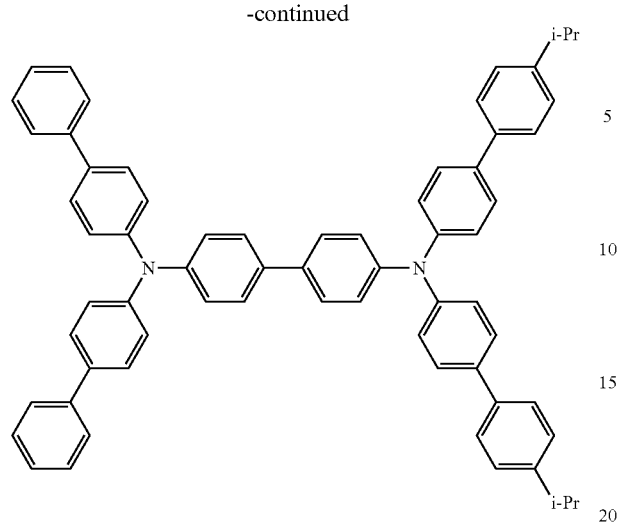
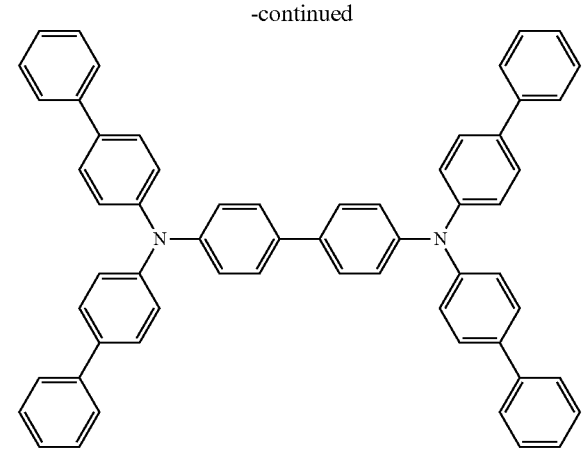
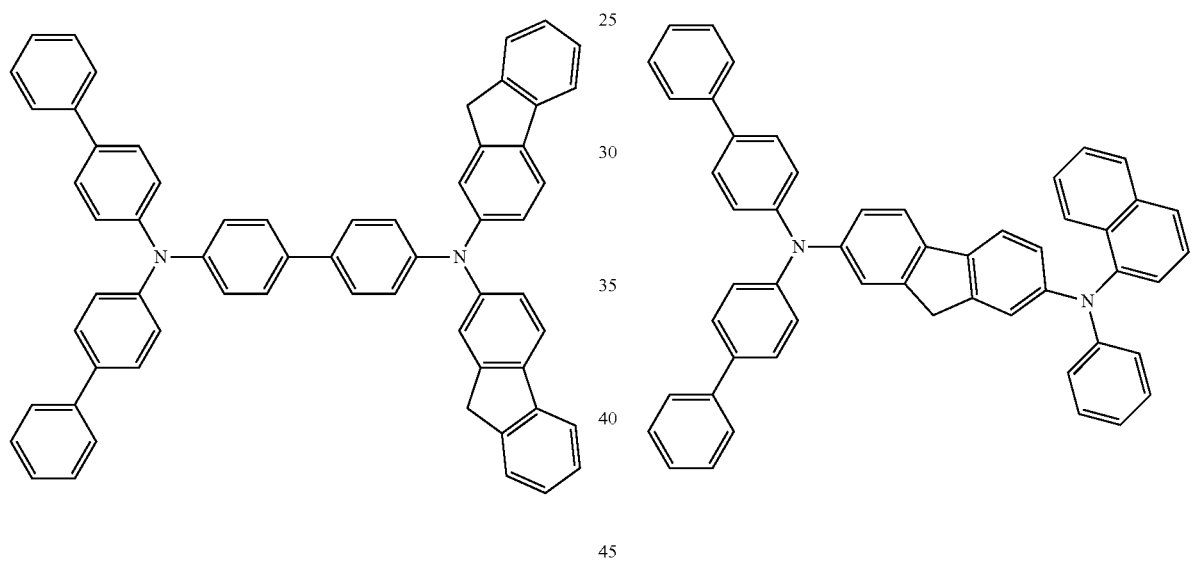
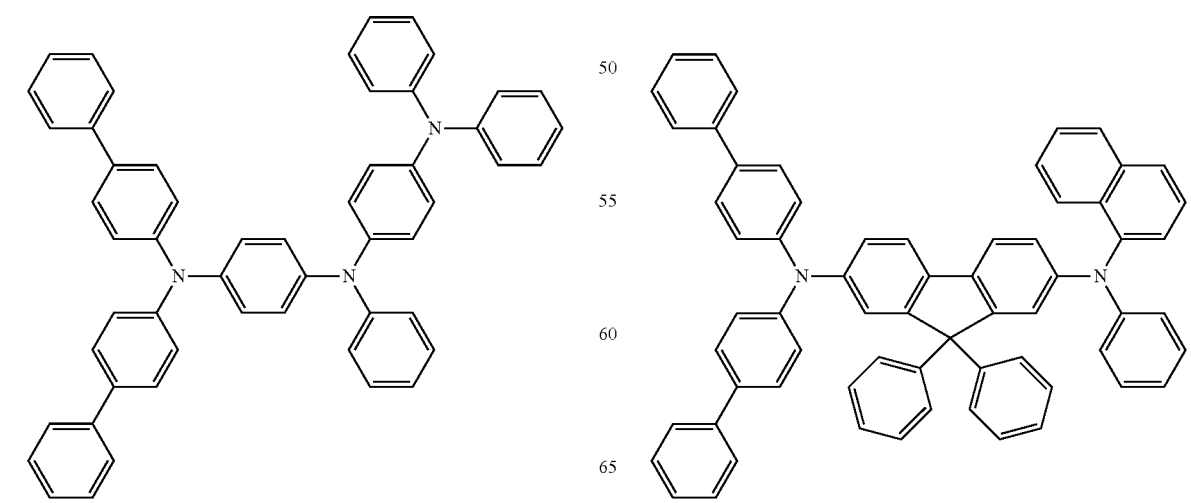

393
-continued
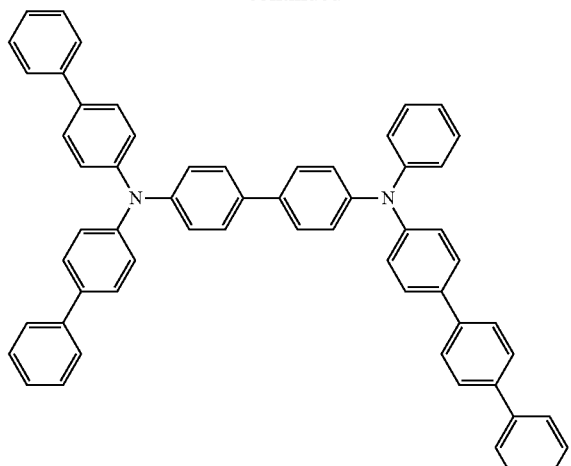
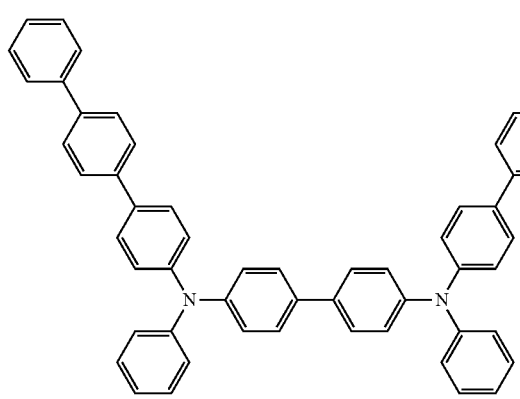
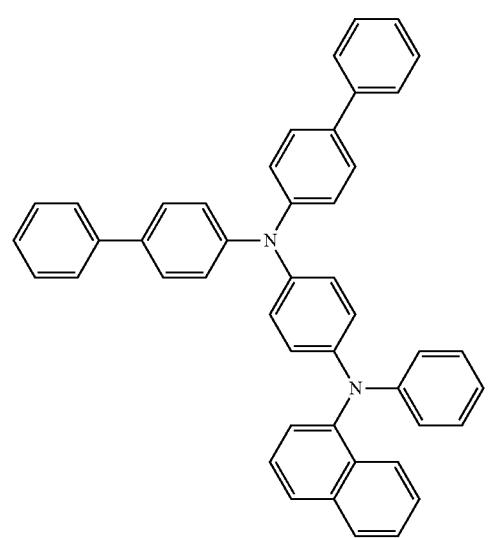
394
-continued
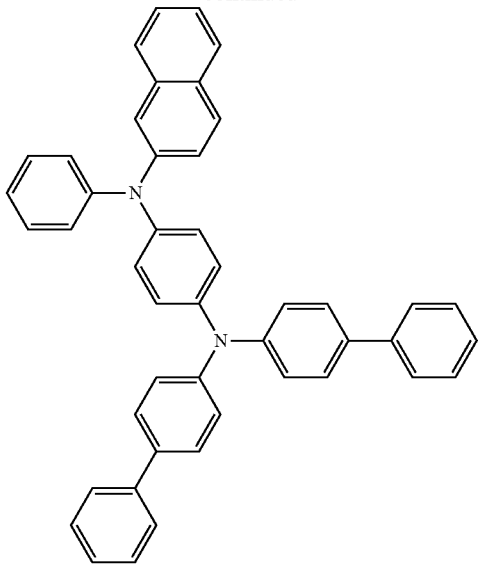
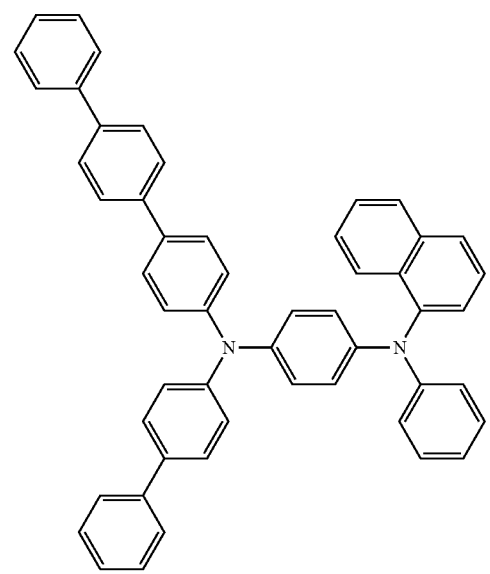
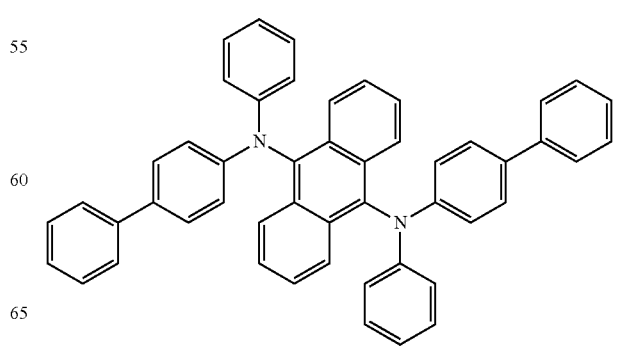

395
-continued
396
-continued
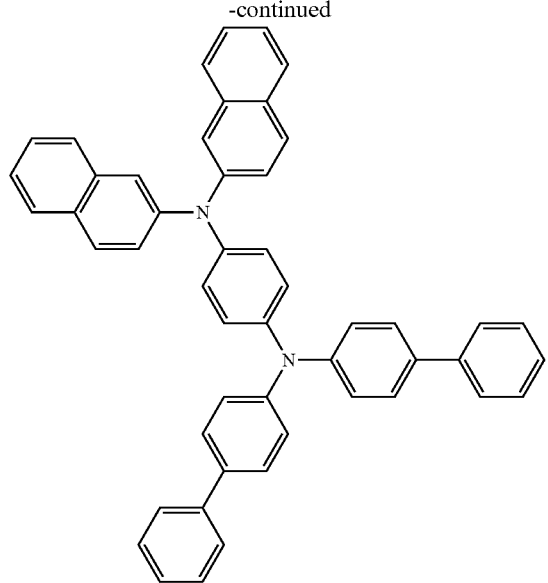
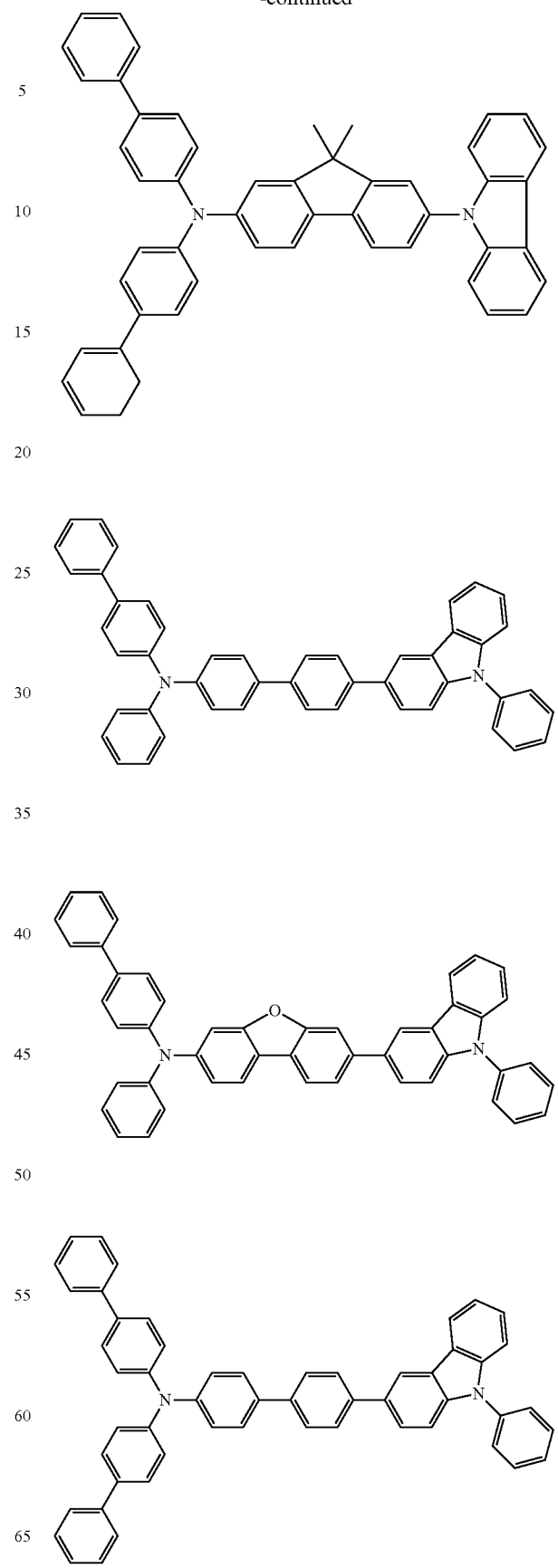

397
-continued
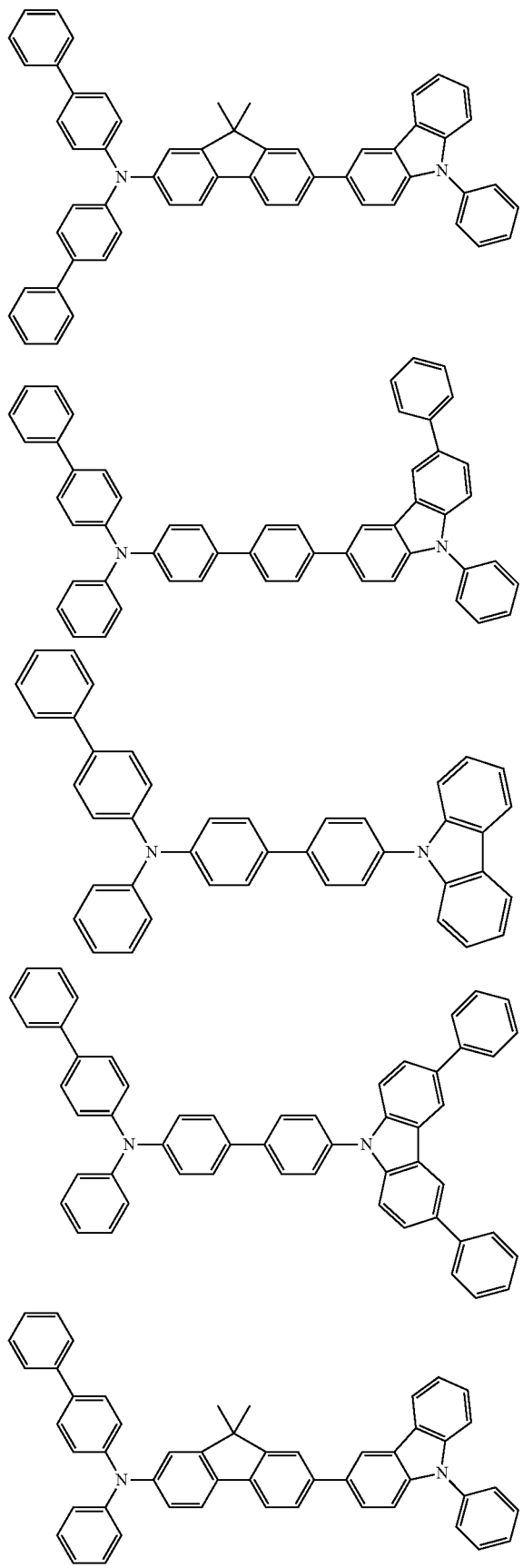
398
-continued
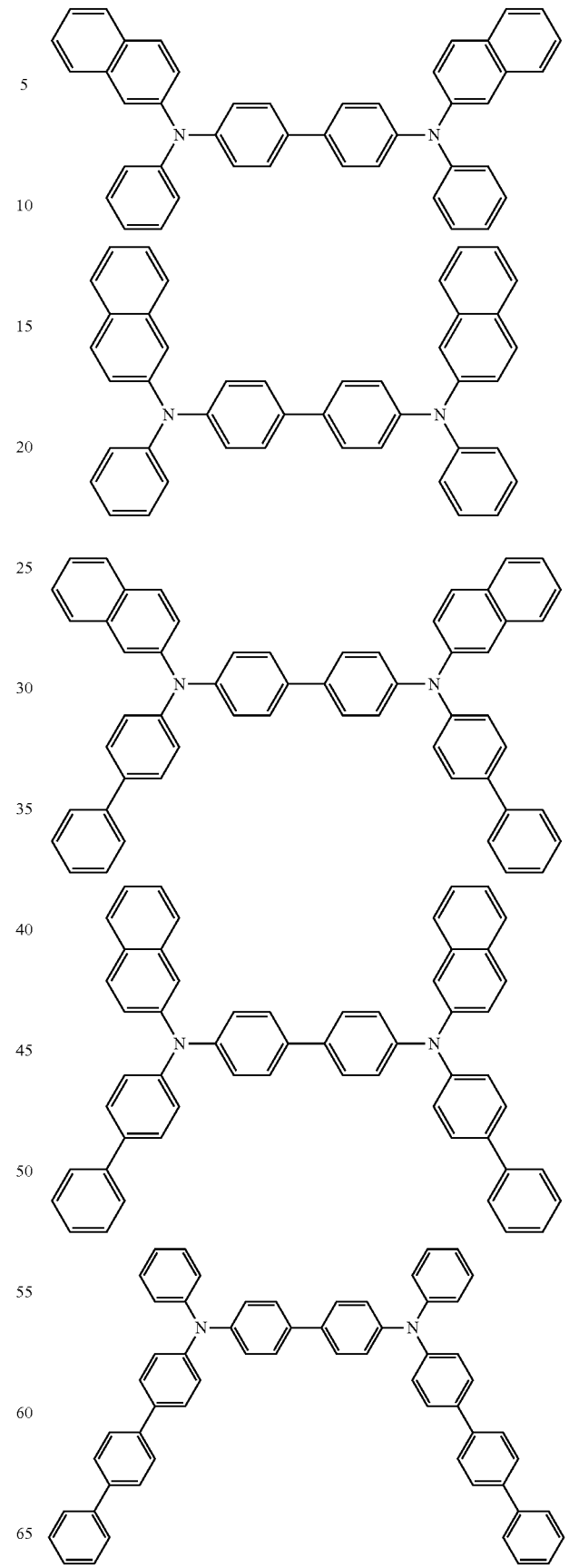

399
-continued
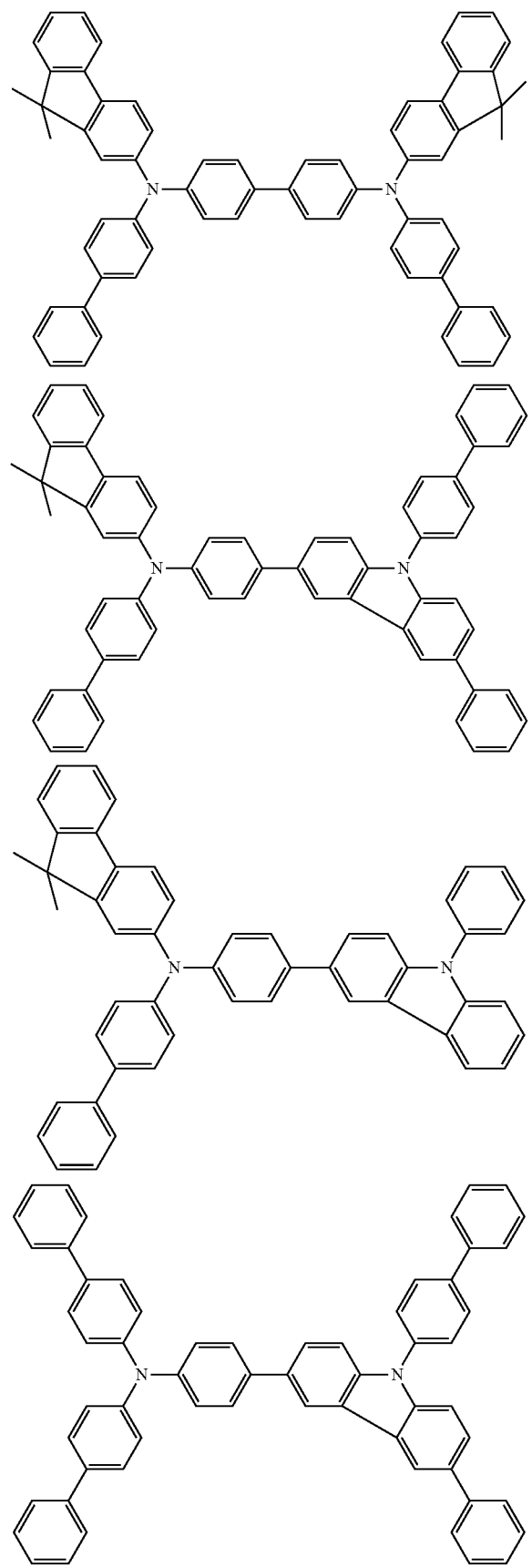
400
-continued
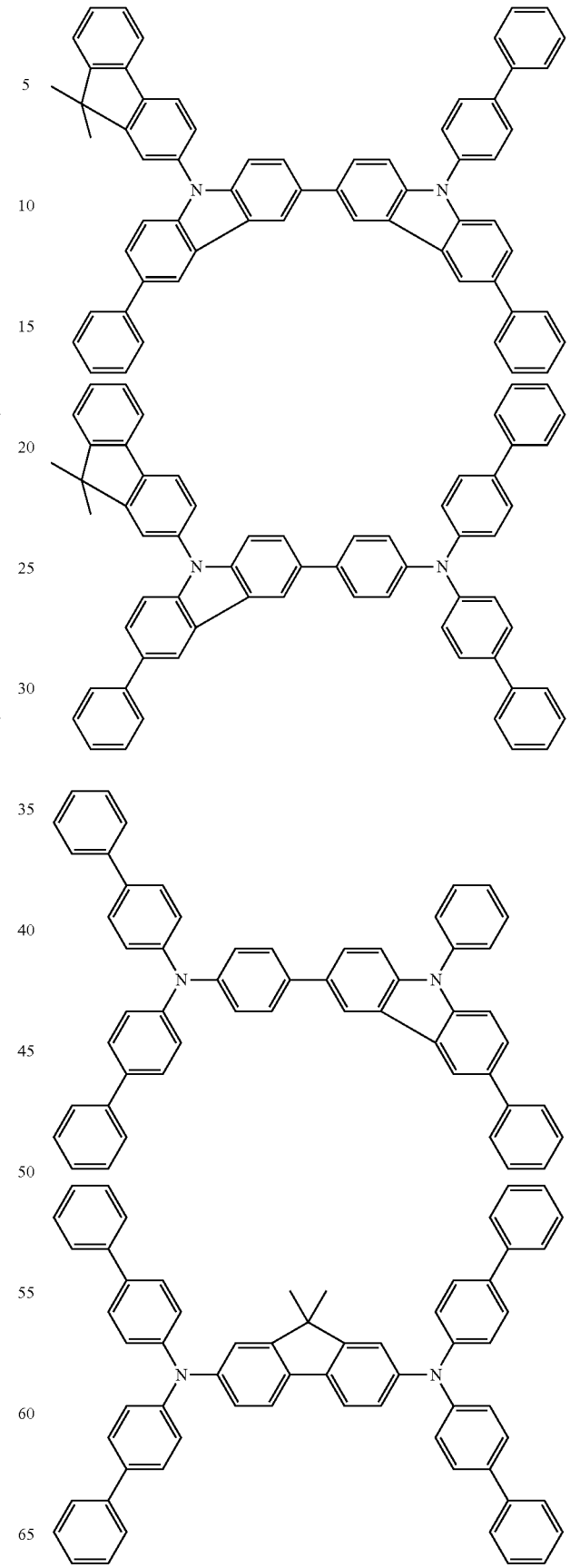

401
-continued
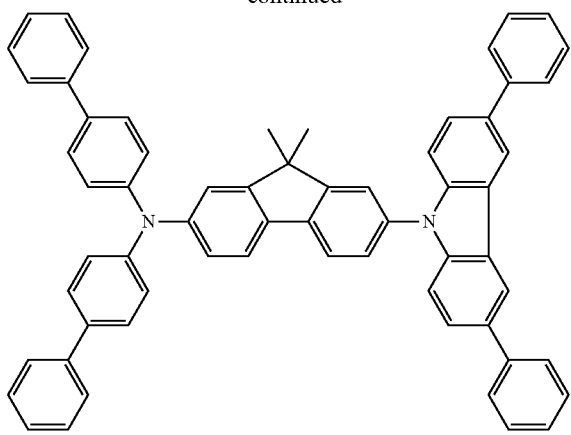
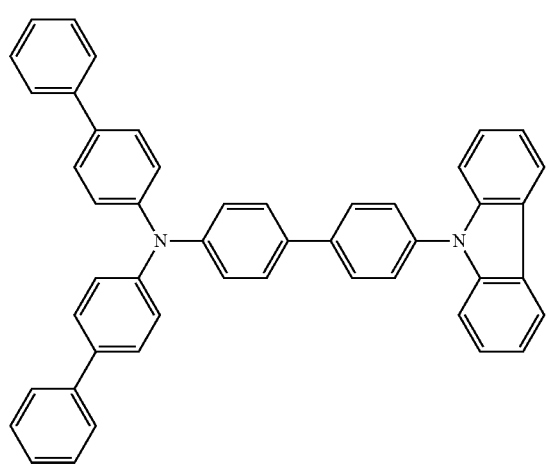
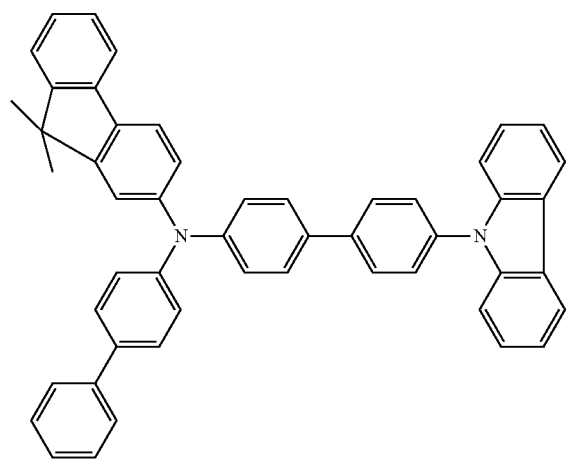
402
-continued
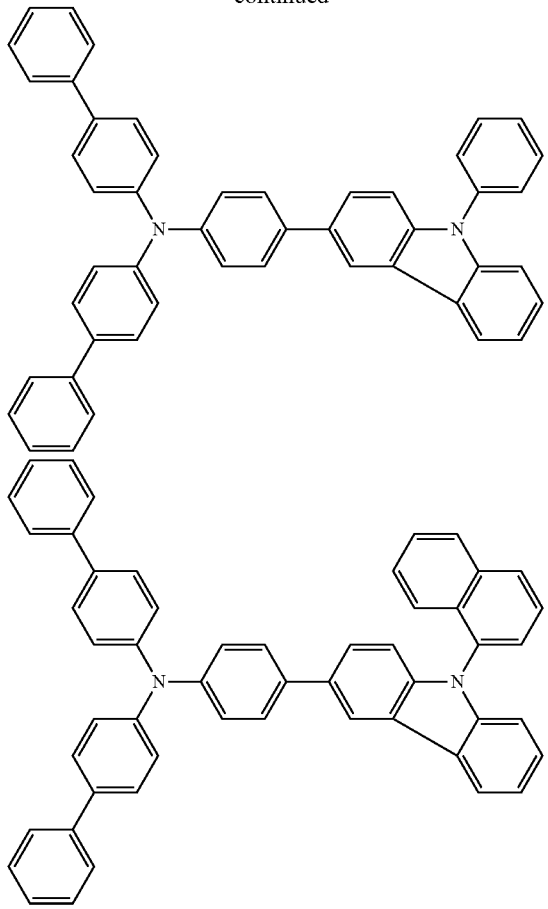
An aromatic amine represented by formula (II) is also preferably used to form the hole transporting layer:
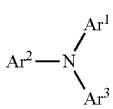
(II)
wherein $Ar^1$ to $Ar^3$ are the same as defined with respect to $Ar^1$ to $Ar^4$ of formula (I). Examples of the compound represented by formula (II) are shown below, although not limited thereto.
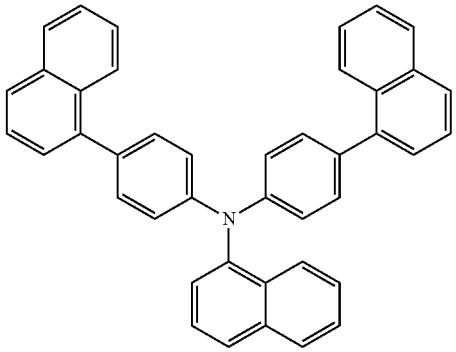

403
-continued
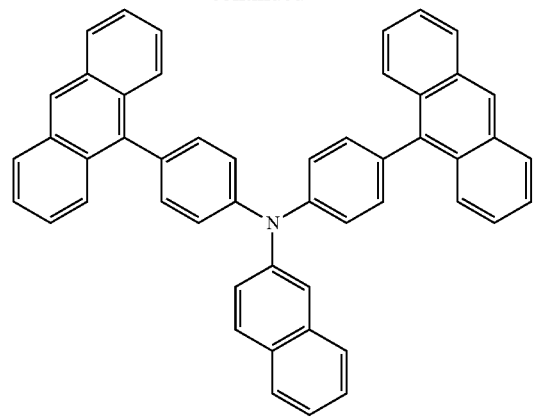
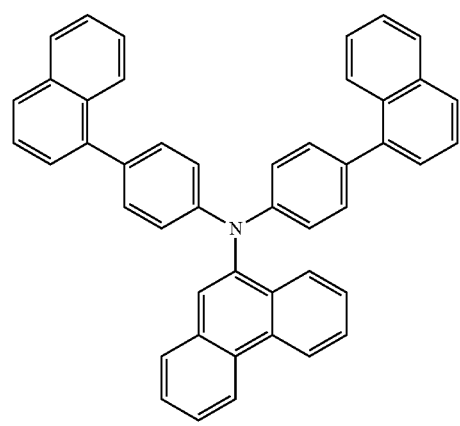
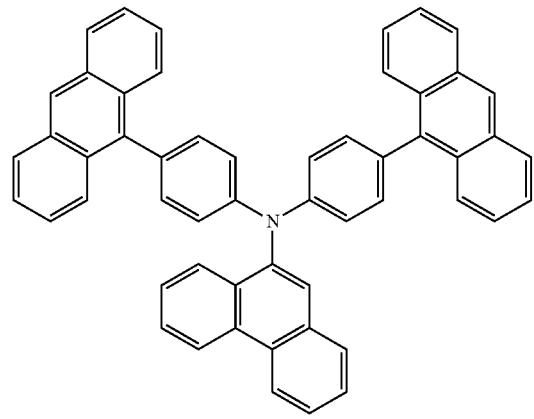
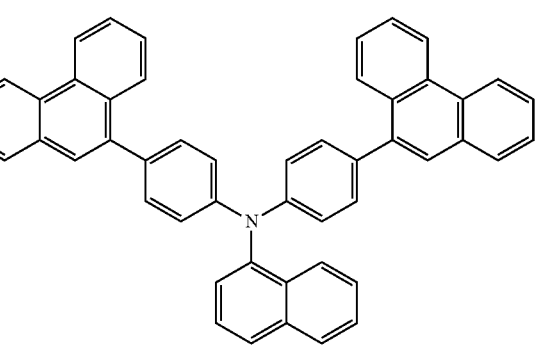
404
-continued
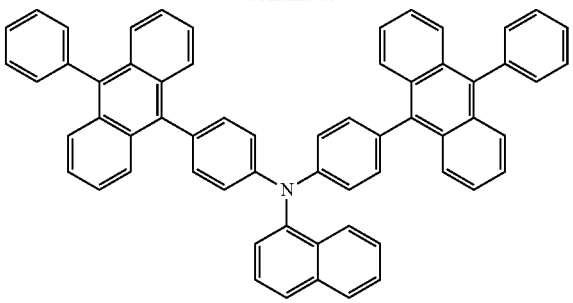
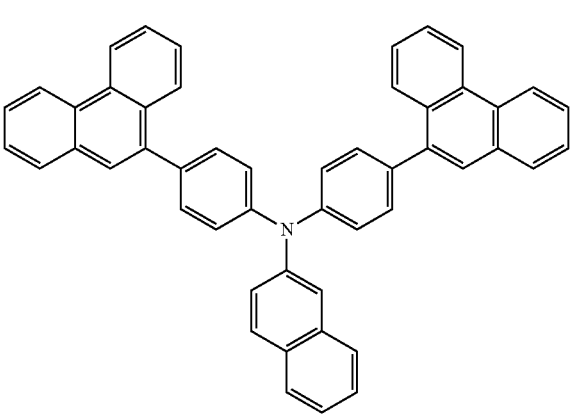
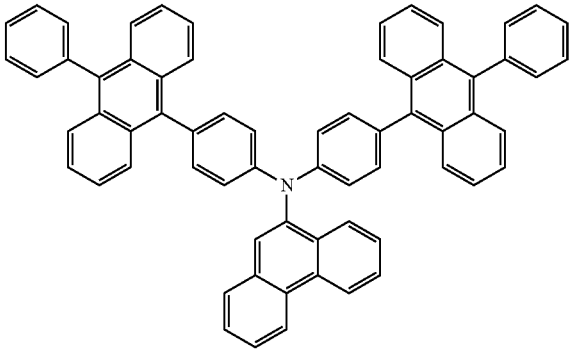
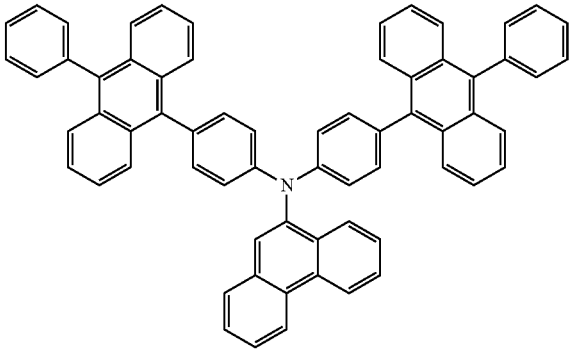

405
-continued
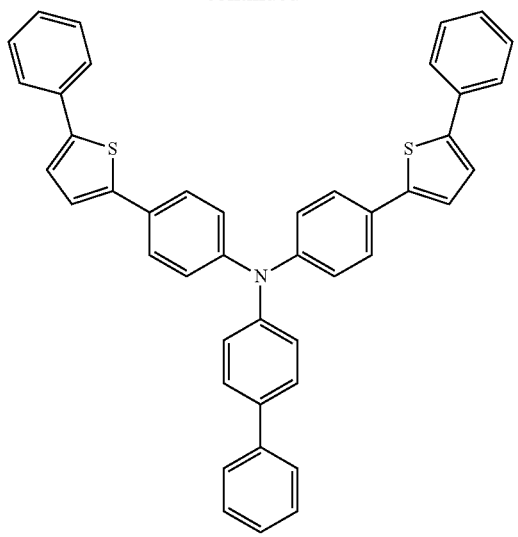
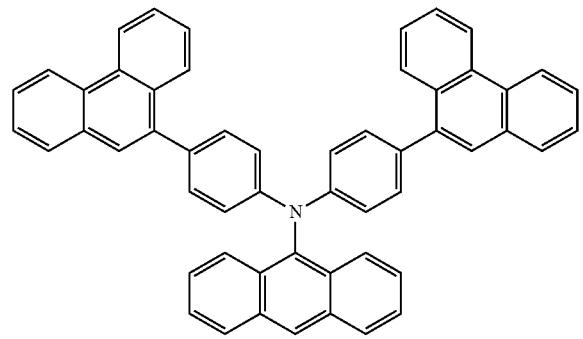
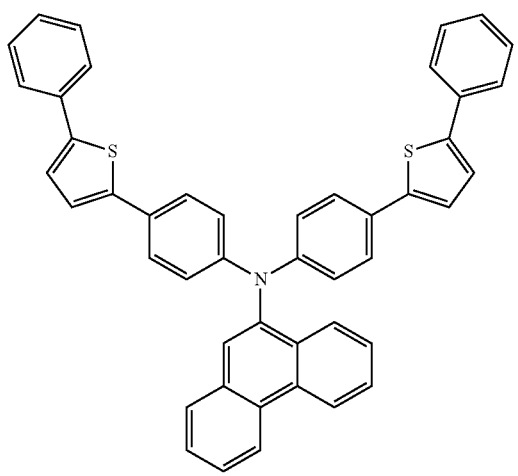
406
-continued
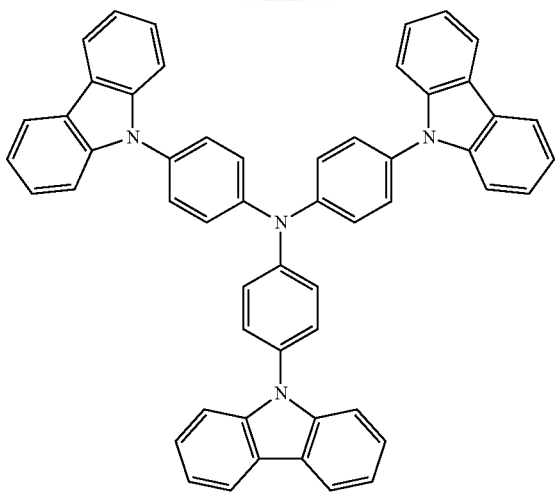
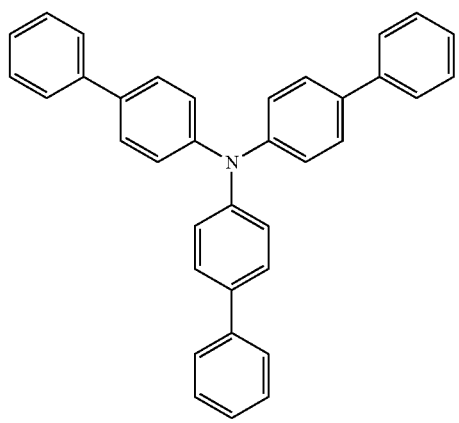
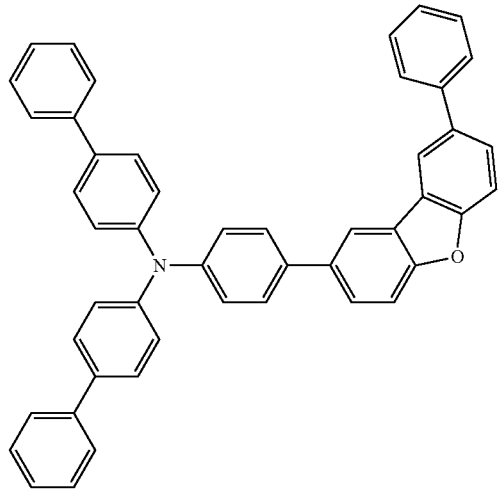

407
-continued
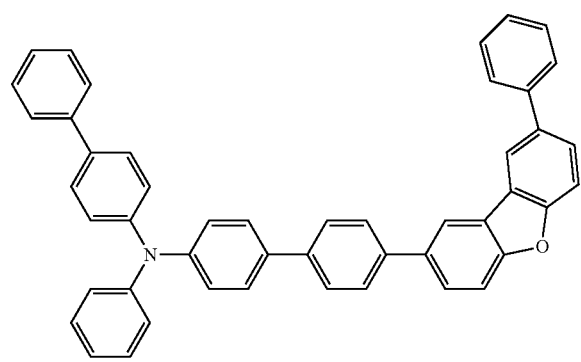
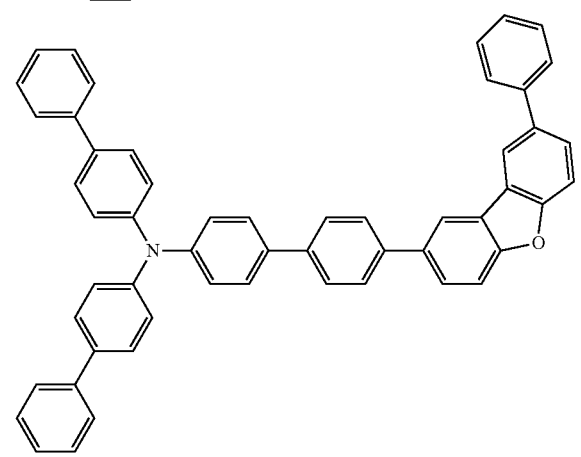
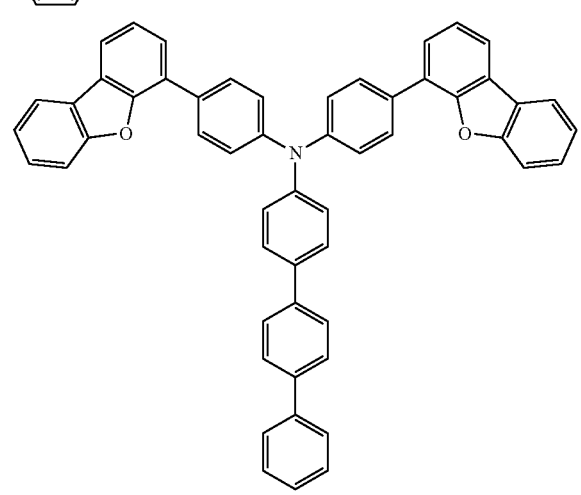
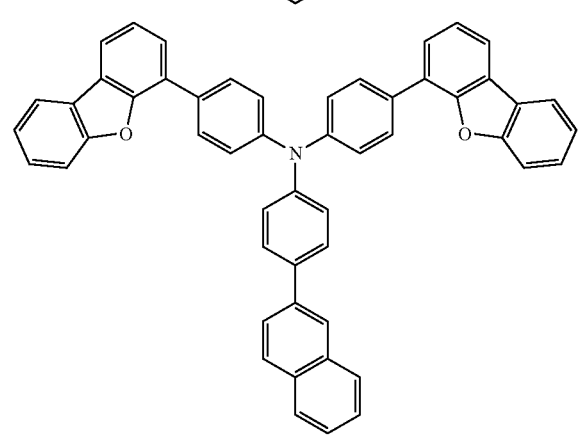
408
-continued
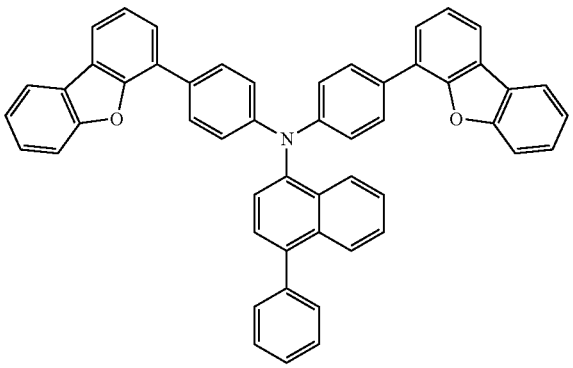
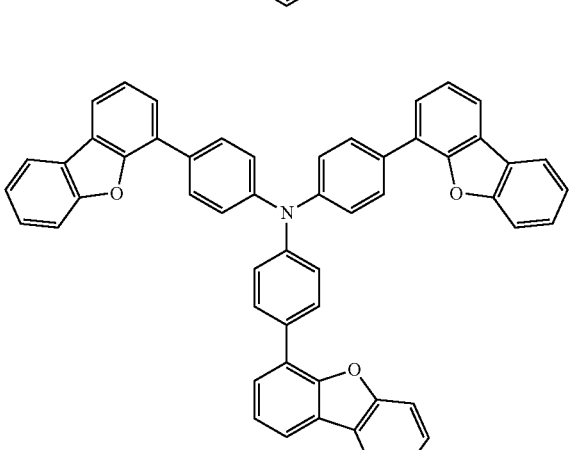
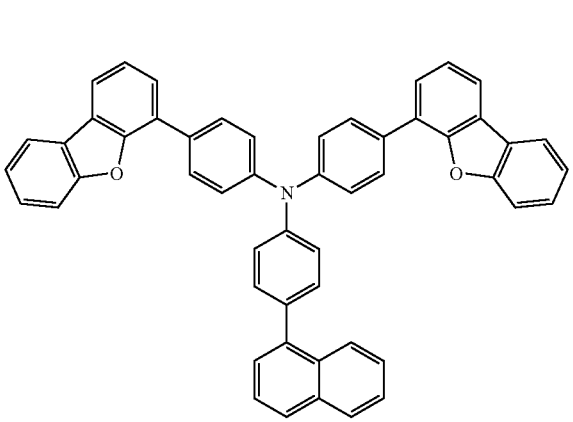
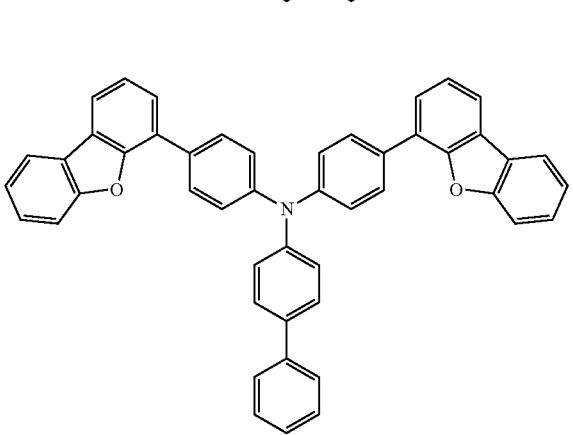

-continued

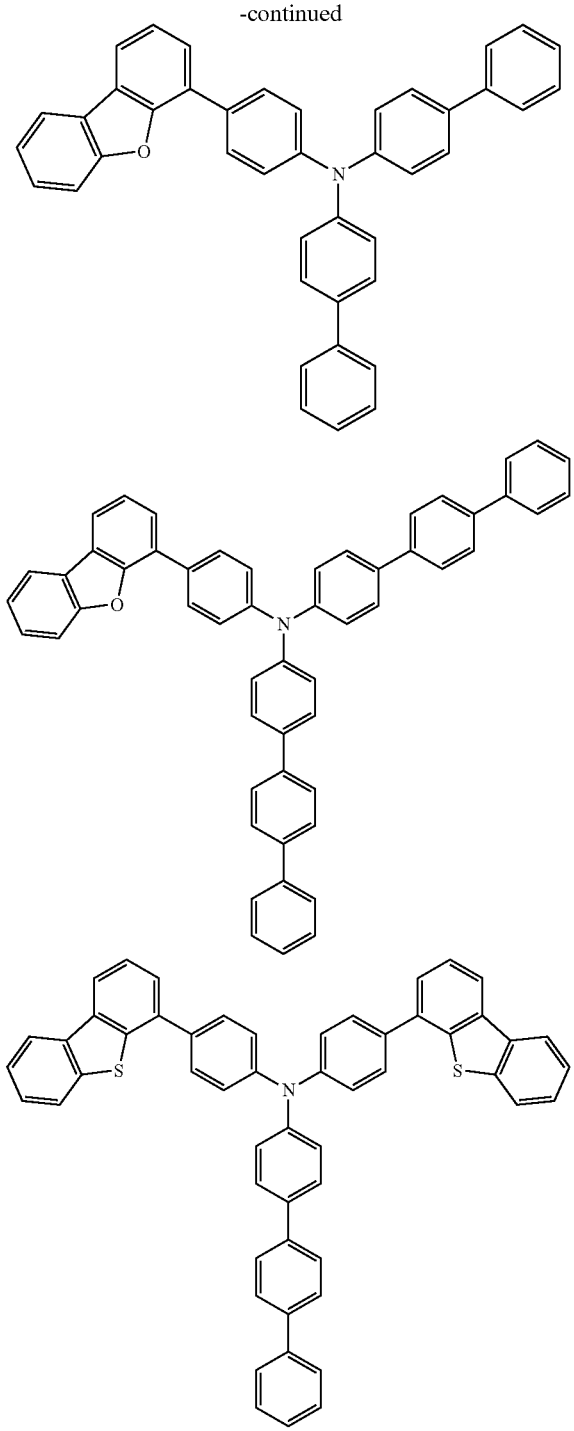

The hole transporting layer of the organic EL device of the invention may be made into two-layered structure of a first hole transporting layer (anode side) and a second hole transporting layer (cathode side).

The thickness of the hole transporting layer is preferably 10 to 200 nm, although not particularly limited thereto. If the hole transporting layer is of a two-layered structure of a first hole transporting layer (anode side) and a second hole transporting layer (cathode side), the thickness is preferably 50 to 150 nm and more preferably 50 to 110 nm for the first hole transporting layer, and preferably 5 to 50 nm and more preferably 5 to 30 nm for the second hole transporting layer.

The organic EL device of the invention may have a layer comprising an acceptor material which is disposed in contact with the anode side of the hole transporting layer or the first hole transporting layer. With such a layer, it is expected that the driving voltage is lowered and the production cost is reduced.

The acceptor material is preferably a compound represented by the following formula.

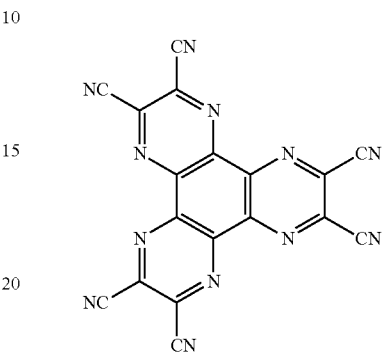

The thickness of the layer comprising the acceptor material is preferably 5 to 20 nm, although not particularly limited thereto.

N/P Doping

The carrier injecting properties of the hole transporting layer and the electron transporting layer can be controlled, as described in JP 3695714B, by the doping (n) with a donor material or the doping (p) with an acceptor material.

A typical example of the n-doping is an electron transporting material doped with a metal, such as Li and Cs, and a typical example of the p-doping is a hole transporting material doped with an acceptor material, such as $F_4TCNQ$.

Space Layer

For example, in an organic EL device wherein a fluorescent emitting layer and a phosphorescent emitting layer are laminated, a space layer is disposed between the fluorescent emitting layer and the phosphorescent emitting layer to prevent the diffusion of excitons generated in the phosphorescent emitting layer to the fluorescent emitting layer or to control the carrier balance. The space layer may be disposed between two or more phosphorescent emitting layers.

Since the space layer is disposed between the light emitting layers, a material combining the electron transporting ability and the hole transporting ability is preferably used for forming the space layer. To prevent the diffusion of triplet energy in the adjacent phosphorescent emitting layer, the triplet energy of the material for the space layer is preferably 2.6 eV or more. The materials described with respect to the hole transporting layer are usable as the material for the space layer.

Blocking Layer

The organic EL device of the invention preferably comprises a blocking layer, such as an electron blocking layer, a hole blocking layer, and a triplet blocking layer, which is disposed adjacent to the light emitting layer.

The electron blocking layer is a layer for preventing the diffusion of electrons from the light emitting layer to the hole transporting layer and disposed between the light emitting layer and the hole transporting layer.

The hole blocking layer is a layer for preventing the diffusion of holes from the light emitting layer to the electron transporting layer and disposed between the light emitting layer and the electron transporting layer.

The triplet blocking layer prevents the diffusion of triplet excitons generated in the light emitting layer to adjacent layers and confines the triplet excitons in the light emitting layer, thereby preventing the energy of the triplet excitons from being deactivated on the molecules other than the emitting dopant, i.e., on the molecules in the electron transporting layer.

The electron mobility of the electron injecting layer is preferably $10^{-6}$ cm$^2$/Vs or more at an electric field strength of 0.04 to 0.5 MV/cm. Within the above range, the injection of electrons from the cathode to the electron transporting layer is promoted and the injection of electrons to the adjacent blocking layer and light emitting layer is also promoted, thereby enabling to drive a device at lower voltage.

Electronic Device

The organic EL device comprising the compound of the invention is of high performance and is usable in electronic device, for example, as display parts, such as organic EL panel module, display devices of television sets, mobile phones, personal computer, etc., and light emitting sources of lighting equipment and vehicle lighting equipment.

EXAMPLES

The present invention will be described below in more detail with reference to the examples. However, it should be noted that the scope of the invention is not limited thereto.

Synthesis Example 1

Synthesis of Compound 2

(1) Synthesis of Intermediate 1

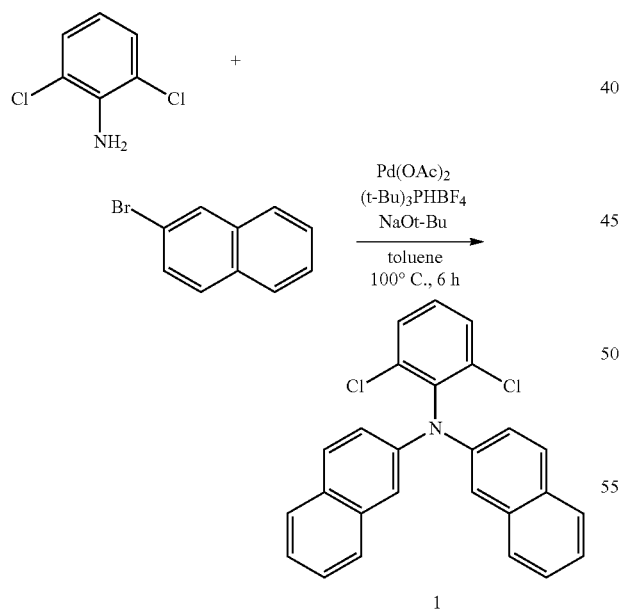

Under an argon atmosphere, a solution of 1.0 g of 2,6-dichloroaniline (6.17 mmol), 2.68 g of 2-bromonaphthalene (13.0 mmol), 28 mg of palladium acetate (0.123 mmol), 72 mg of tri-t-butylphosphine tetrafluoroborate (0.247 mmol), and 1.78 g of sodium t-butoxide (18.5 mmol) in 15 mL of toluene was stirred at 100° C. for 6 h. After the reaction, water was added to the reaction mixture, which was then extracted with dichloromethane. The collected organic layer was concentrated, and the obtained solid was purified by column chromatography to obtain 1.8 g of white solid, which was identified as the target intermediate 1 by a mass spectroscopic analysis of m/e=414 to the molecular weight of 414.32 (yield: 71%).

(2) Synthesis of Compound 2

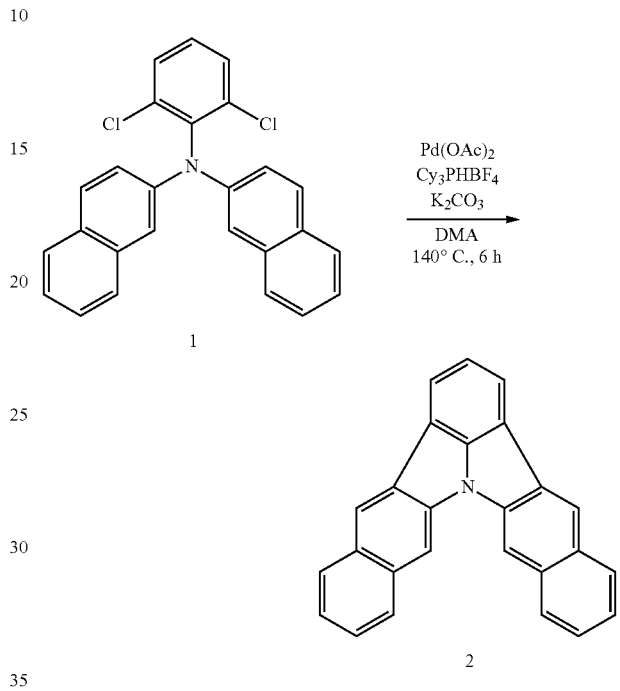

Under an argon atmosphere, a solution of 100 mg of intermediate 1 (0.241 mmol), 2.7 mg of palladium acetate (0.0121 mmol), 9.0 mg of tricyclohexylphosphine tetrafluoroborate (0.0241 mmol), and 133 mg of potassium carbonate (0.964 mmol) in 3 mL of dimethylacetamide was heated at 140° C. for 6 h. After the reaction, water was added to the reaction mixture, which was then extracted with dichloromethane. The collected organic layer was concentrated, and the obtained solid was purified by flash column chromatography to obtain 32 mg of a yellow solid, which was identified as the target compound 2 by a mass spectroscopic analysis of m/e=341 to the molecular weight of 341.40 (yield: 39%).

Synthesis Example 2

Synthesis of Compound 5

(1) Synthesis of Intermediate 3

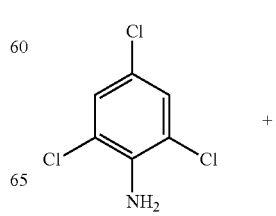

-continued

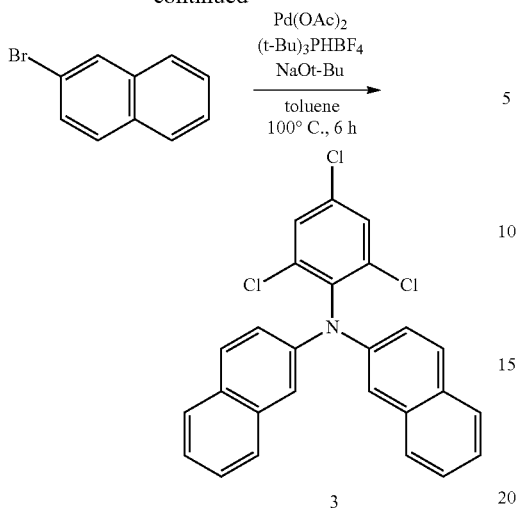

Under an argon atmosphere, a solution of 1.0 g of 2,4,6-trichloroaniline (5.09 mmol), 2.21 g of 2-bromonaphthalene (10.7 mmol), 22 mg of palladium acetate (0.102 mmol), 59 mg of tri-t-butylphosphine tetrafluoroborate (0.204 mmol), and 1.38 g of sodium t-butoxide (15.3 mmol) in 15 mL of toluene was stirred at 100° C. for 6 h. After the reaction, water was added to the reaction mixture, which was then extracted with dichloromethane. The collected organic layer was concentrated, and the obtained solid was purified by column chromatography to obtain 1.5 g of white solid, which was identified as the target intermediate 3 by a mass spectroscopic analysis of m/e=448 to the molecular weight of 448.77 (yield: 66%).

(2) Synthesis of Intermediate 4

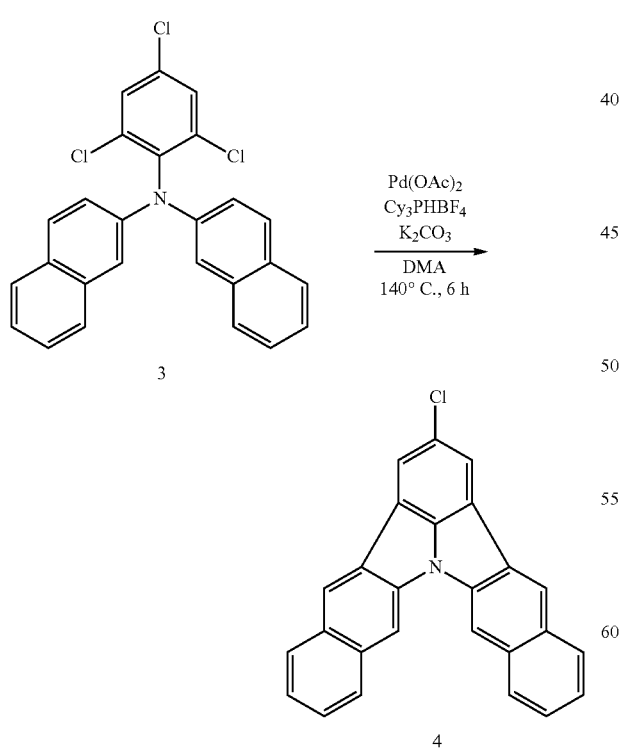

Under an argon atmosphere, a solution of 100 mg of the intermediate 3 (0.223 mmol), 2.5 mg of palladium acetate (0.0111 mmol), 6.4 mg of tricyclohexylphosphine tetrafluoroborate (0.0222 mmol), 92 mg of potassium carbonate (0.669 mmol) in 3 mL of dimethylacetamide was heated at 140° C. for 6 h. After the reaction, water was added to the reaction mixture, which was then extracted with dichloromethane. The collected organic layer was concentrated, and the obtained solid was purified by flash column chromatography to obtain 26 mg of a yellow solid, which was identified as the target intermediate 4 by a mass spectroscopic analysis of m/e=375 to the molecular weight of 375.85 (yield: 30%).

(3) Synthesis of Compound 5

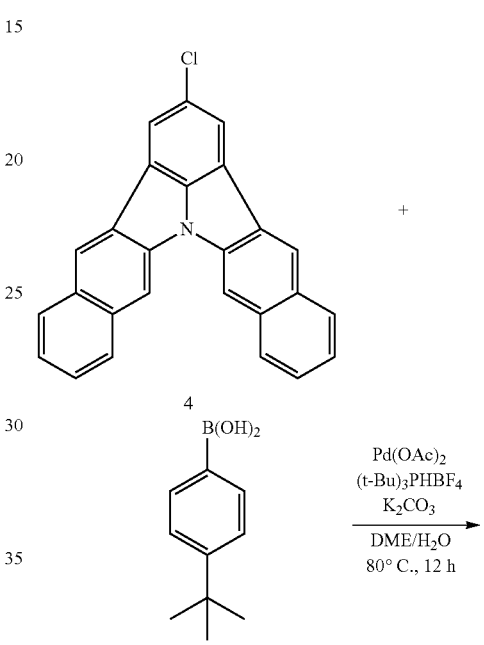

Under an argon atmosphere, a mixture of 20 mg of the intermediate 4 (0.0532 mmol), 9.3 mg of 4-tert-butylphenylboronic acid (0.0639 mmol), 1.2 mg of palladium acetate (0.00532 mmol), 3.1 mg of tri-t-butylphosphine tetrafluoroborate (0.0106 mmol), and 14.7 mg of potassium carbonate (0.106 mmol) in 2 mL of dimethoxyethane and 0.5 mL of water was stirred at 80° C. for 12 h. After the reaction, water was added to the reaction mixture, which was then extracted with dichloromethane. The collected organic layer was concentrated, and the obtained solid was purified by column chromatography to obtain 16 mg of a yellow solid, which was identified as the target compound 5 by a mass spectroscopic analysis of m/e=473 to the molecular weight of 473.61 (yield: 64%).

Synthesis Example 3

Synthesis of Compound 7 of potassium phosphate (3.99 mmol) in 2 mL of toluene was stirred at 160° C. for 7 min. After the reaction, the precipitated solid was collected by filtration and washed with toluene and methanol to obtain 167 mg of a yellow solid, which was identified as the target compound 7 by a mass spectroscopic analysis of m/e=493 to the molecular weight of 493.6 (yield: 83%).

Synthesis Example 4

Synthesis of Compound 9

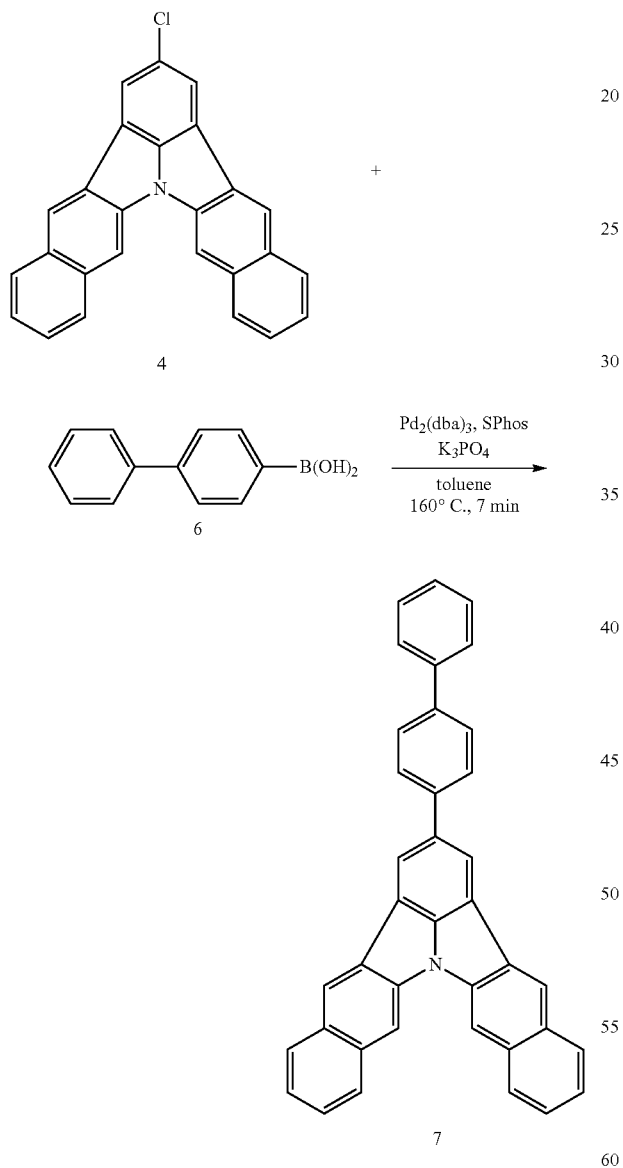

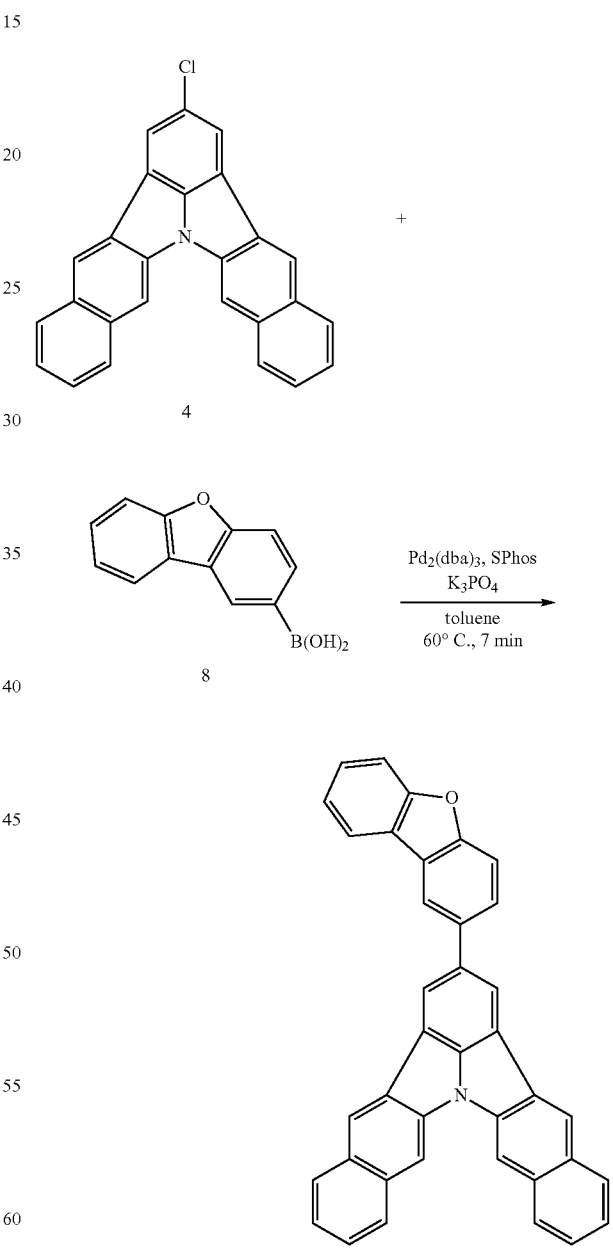

Under an argon atmosphere, a mixture of 150 mg of the intermediate 4 (0.399 mmol), 395 mg of boronic acid 6 (1.995 mmol), 15 mg of tris(dibenzylideneacetone) dipalladium(0) (0.016 mmol), 26 mg of 2-dicyclohexylphosphino-2',6'-dimethoxybiphenyl (SPhos) (0.064 mmol), and 847 mg Under an argon atmosphere, a mixture of 150 mg of the intermediate 4 (0.399 mmol), 423 mg of boronic acid 8 (1.995 mmol), 15 mg of tris(dibenzylideneacetone) dipalladium(0) (0.016 mmol), 26 mg of SPhos (0.064 mmol), and 847 mg of potassium phosphate (3.99 mmol) in 2 mL of toluene was stirred at 160° C. for 7 min. After the reaction, the precipitated solid was collected by filtration and washed with toluene and methanol to obtain 188 mg of a yellow solid, which was identified as the target compound 9 by a mass spectroscopic analysis of m/e=507 to the molecular weight of 507.58 (yield: 93%).

Synthesis Example 5

Synthesis of Compound 11

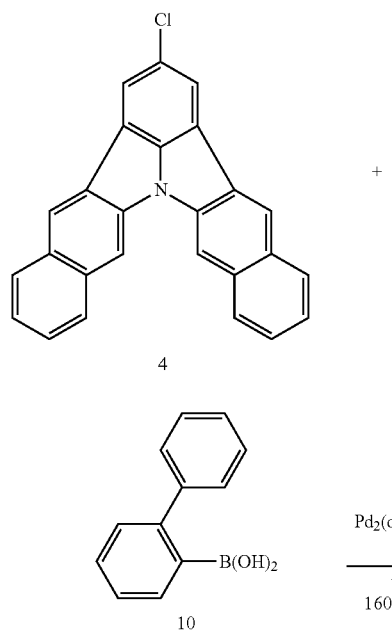

-continued

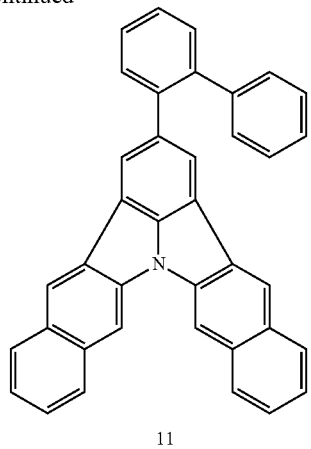

11

Under an argon atmosphere, a mixture of 150 mg of the intermediate 4 (0.399 mmol), 395 mg of boronic acid 10 (1.995 mmol), 15 mg of tris(dibenzylideneacetone) dipalladium (0.016 mmol), 26 mg of SPhos (0.064 mmol), and 847 mg of potassium phosphate (3.99 mmol) in 2 mL of toluene was stirred at 160° C. for 5 min. After the reaction, the precipitated solid was collected by filtration and washed with toluene and methanol to obtain 142 mg of a yellow solid, which was identified as the target compound 11 by a mass spectroscopic analysis of m/e=493 to the molecular weight of 493.6 (yield: 72%).

Synthesis Example 6

Synthesis of Compound 17

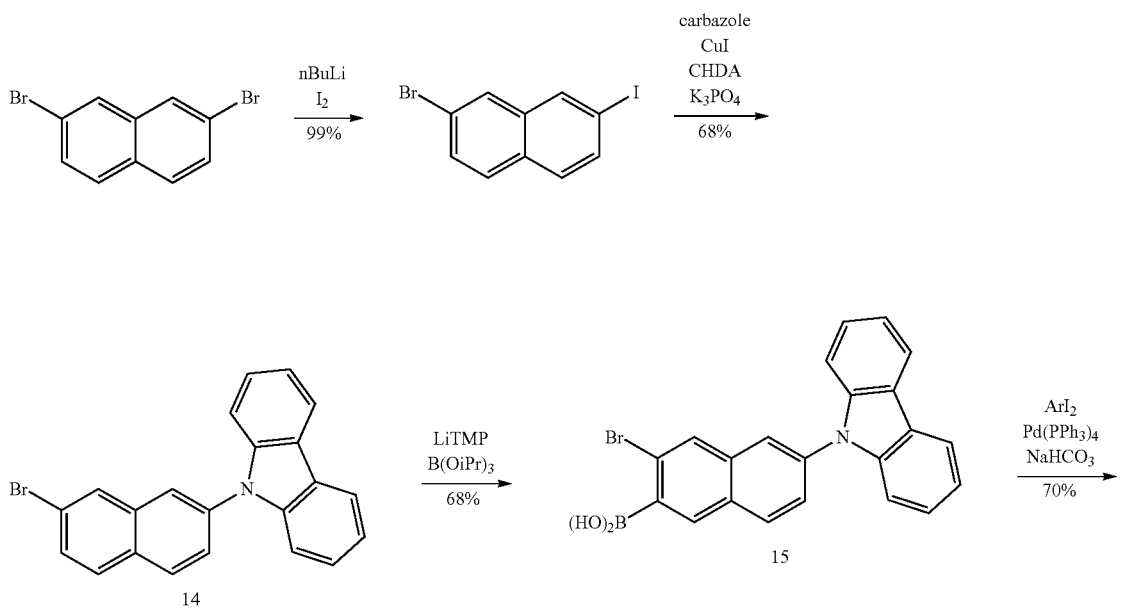

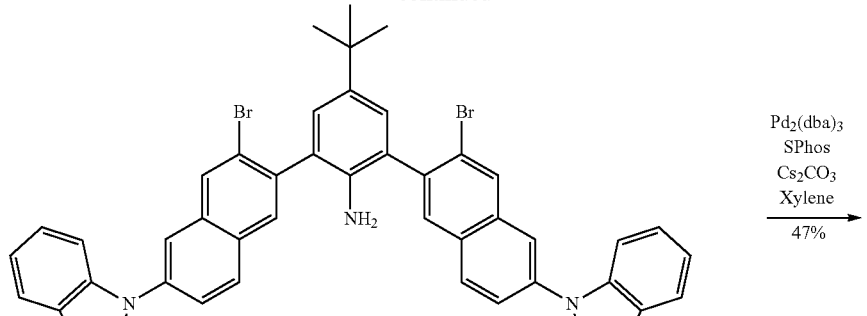

16

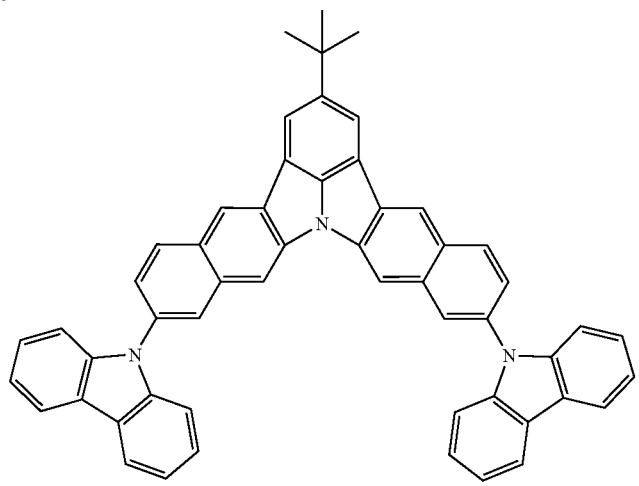

17

(1) Synthesis of 2-bromo-7-iodonaphthalene

Under an argon atmosphere, a solution of 5.0 g of 2,7-dibromonaphthalene (17 mmol) in a mixed solvent of 80 mL of anhydrous tetrahydrofuran and 40 mL of anhydrous toluene was cooled in a dry ice/acetone bath to −48° C. After adding 10.6 mL of a n-butyllithium/hexane solution (1.64 mol/L, 17 mmol), the resultant solution was stirred at −45° C. for 20 min and then at −72° C. for 30 min. After adding 4.9 g of a tetrahydrofuran solution of iodine (19 mmol), the reaction mixture was stirred at −72° C. for one hour and then at room temperature for 2.5 h. The reaction mixture was deactivated by 60 mL of a 10% by mass aqueous solution of sodium sulfite and then extracted with 150 mL of toluene. The organic layer was washed with 30 mL of a saturated saline and dried over magnesium sulfate. After evaporating off the solvent, the residue was dried under reduced pressure to obtain 5.66 g of a pale yellow solid, which was identified as the target 2-bromo-7-iodonaphthalene by a mass spectroscopic analysis of m/e=339 to the molecular weight of 339 (yield: 99%).

(2) Synthesis of Intermediate 14

Under an argon atmosphere, into a suspension of 2.55 g of 9H-carbazole (15 mmol), 5.7 g of 2-bromo-7-iodonaphthalene (17 mmol), 30 mg of copper iodide (0.16 mmol), and 7.5 g of potassium phosphate (35 mmol) in 20 mL of anhydrous 1,4-dioxane, 0.19 mL of trans-1,2-diaminocyclohexane (1.6 mmol) was added. The resultant mixture was refluxed for 10 h. After the reaction, 200 mL of toluene was added and the inorganic matter was removed by filtration. The filtrate was concentrated and the obtained 6.5 g of a brown solid was purified by a column chromatography to obtain 3.8 g of a white acicular crystal, which was identified as the target intermediate 14 by a mass spectroscopic analysis of m/e=332 to the molecular weight of 332 (yield: 68%).

(3) Synthesis of Intermediate 15

Under an argon atmosphere, a solution of 2.9 g of 2,2,6,6-tetramethylpiperidine (20.6 mmol) in 30 mL of anhydrous tetrahydrofuran was cooled to −43° C. in a dry ice/acetone bath. After adding 2.5 mL of a n-butyllithium/hexane solution (1.64 mol/L, 20.5 mmol), the solution was stirred at −36° C. for 20 min and then cooled to −70° C. After adding 7 mL of triisopropoxyborane (30 mmol) dropwise and then adding 20 mL of a tetrahydrofuran solution of 3.8 g of the intermediate 14 (10.2 mmol), the solution was stirred for 10 h in a cooling bath. After the reaction, 100 mL of a 5% by mass hydrochloric acid was added. The solution was stirred at room temperature for 30 min and then extracted with 150 mL of ethyl acetate. The organic layer was washed with 30 mL of a saturated saline and dried over magnesium sulfate, and then the solvent was evaporated off. The obtained 4.9 g of a yellow amorphous solid was purified by a column chromatography to obtain 2.9 g of a yellow solid, which was identified as the target intermediate 15 by a mass spectroscopic analysis of m/e=415 to the molecular weight of 415 (yield: 68%).

(4) Synthesis of Intermediate 16

Under an argon atmosphere, into a suspension of 1.27 g of 2,6-diiodo-4-tert-butylaniline (3.2 mmol), 2.9 g of the intermediate 15 (7.0 mmol), 0.36 g of tetrakis(triphenylphosphine) palladium (0.31 mmol), and 2.1 g of sodium hydrogen carbonate (25 mmol) in 40 mL of 1,2-dimethoxyethane, 21 mL of water was added. The resultant mixture was refluxed for 11 h. After the reaction, the reaction mixture was extracted with 200 mL of dichloromethane, the organic layer was dried over magnesium sulfate, and the solvent was evaporated off. The obtained 3.5 g of a yellow amorphous solid was purified by a column chromatography to obtain 2.0 g of a white solid, which was identified as the target intermediate 16 by a mass spectroscopic analysis of m/e=887 to the molecular weight of 887 (yield: 70%).

(5) Synthesis of Compound 17

Under an argon atmosphere, a suspension of 1.0 g of the intermediate 16 (1.1 mmol), 41 mg of tris(dibenzylideneacetone) dipalladium(0) (45 μmol), 5 mg of SPhos (0.18 mmol), and 2.2 g of cesium carbonate (6.7 mmol) in 100 mL of anhydrous xylene was refluxed for 10 h. After the reaction, the reaction mixture was filtered. The collected matter was washed with water and methanol and then dried under reduced pressure. The obtained 0.427 g of a pale green solid was purified by a column chromatography to obtain 0.37 g of a yellow solid, which was identified as the target compound 17 by a mass spectroscopic analysis of m/e=727 to the molecular weight of 727 (yield: 47%).

Synthesis Example 7

Synthesis of Compound 22

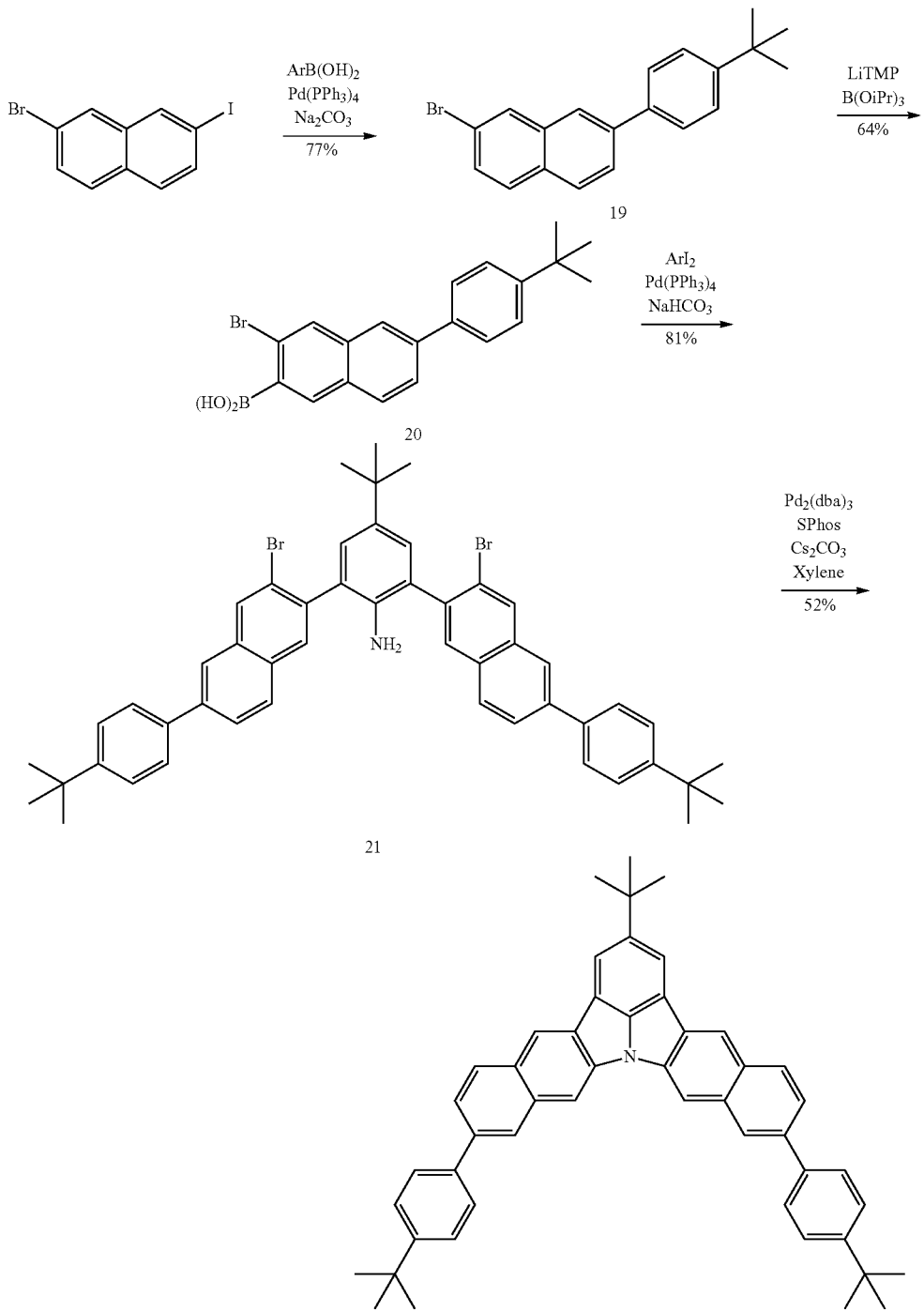

(1) Synthesis of Intermediate 19

Under an argon atmosphere, into a solution of 3.0 g of 4-tert-butylphenylboronic acid (17 mmol), 5.66 g of 2-bromo-7-iodonaphthalene (17 mmol), and 0.35 g of tetrakis(triphenylphosphine) palladium (0.30 mmol) in 45 mL of 1,2-dimethoxyethane, 23 mL of a 2 M aqueous solution of sodium carbonate (45 mmol) was added. The resultant solution was refluxed for 11 h. After the reaction, the reaction mixture was extracted with 150 mL of toluene. The organic layer was washed with 30 mL of a saturated saline and dried over magnesium sulfate, and then the solvent was evaporated off. The obtained brown solid (9.2 g) was purified by a column chromatography to obtain 4.45 g of a white solid, which was identified as the target intermediate 19 by a mass spectroscopic analysis of m/e=338 to the molecular weight of 338 (yield: 77%).

(2) Synthesis of Intermediate 20

Under an argon atmosphere, a solution of 2.8 g of 2,2,6,6-tetramethylpiperidine (20 mmol) in 30 mL of anhydrous tetrahydrofuran was cooled to −40° C. in a dry ice/acetone bath. After adding 12 mL of a n-butyllithium/hexane solution (1.64 mol/L, 20 mmol), the solution was stirred at −54° C. for 20 min. After the reaction, the solution was cooled to −65° C. and then 6 mL of triisopropoxyborane (26 mmol) was added dropwise and 20 mL of a tetrahydrofuran solution of 4.45 g of the intermediate 19 (13 mmol) was added. The resultant solution was stirred for 10 h in a cooling bath. After the reaction, 70 mL of a 5% by mass hydrochloric acid was added, and then stirred at room temperature for 30 min and extracted with 200 mL of ethyl acetate. The organic layer was washed with 30 mL of a saturated saline and dried over magnesium sulfate, and then the solvent was evaporated off. The obtained 5.5 g of a yellow amorphous solid was purified by a column chromatography to obtain 3.19 g of a white solid, which was identified as the target intermediate 20 by a mass spectroscopic analysis of m/e=382 to the molecular weight of 382 (yield: 64%).

(3) Synthesis of Intermediate 21

Under an argon atmosphere, into a suspension of 3.19 g of the intermediate 20 (8.3 mmol), 1.5 g of 2,6-diiodo-4-tert-butylaniline (3.7 mmol), 0.43 g of tetrakis(triphenylphosphine) palladium (0.37 mmol), and 2.5 g of sodium hydrogen carbonate (30 mmol) in 50 mL of 1,2-dimethoxyethane, 25 mL of water was added. The resultant mixture was refluxed for 11 h. The reaction mixture was extracted with 200 mL of dichloromethane. The organic layer was dried over magnesium sulfate and then the solvent was evaporated off. The obtained 4.14 g of a yellow amorphous solid was purified by a column chromatography to obtain 2.47 g of a white solid, which was identified as the target intermediate 21 by a mass spectroscopic analysis of m/e=821 to the molecular weight of 821 (yield: 81%).

(4) Synthesis of Compound 22

Under an argon atmosphere, a suspension of 2.47 g of the intermediate 21 (3.0 mmol), 0.11 g of tris(dibenzylideneacetone) dipalladium(0) (0.12 mmol), 0.20 g of SPhos (0.49 mmol), and 5.9 g of cesium carbonate (18 mmol) in 250 mL of anhydrous xylene was refluxed for 11 h. After the reaction, the reaction mixture was filtered and the collected matter was successively washed with water and methanol and then dried under reduced pressure. The obtained 1.88 g of a pale yellow acicular crystal was purified by a column chromatography to obtain 1.03 g of a yellow solid, which was identified as the target compound 22 by a mass spectroscopic analysis of m/e=661 to the molecular weight of 661 (yield: 52%).

Synthesis Example 8

Synthesis of Compound 30

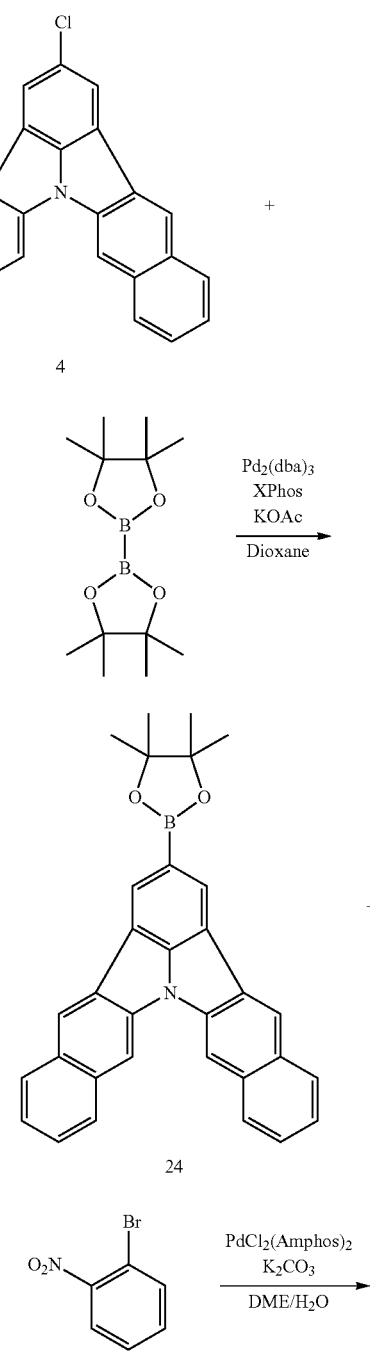

-continued

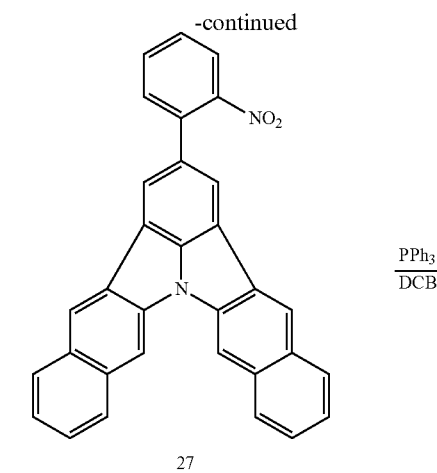

27

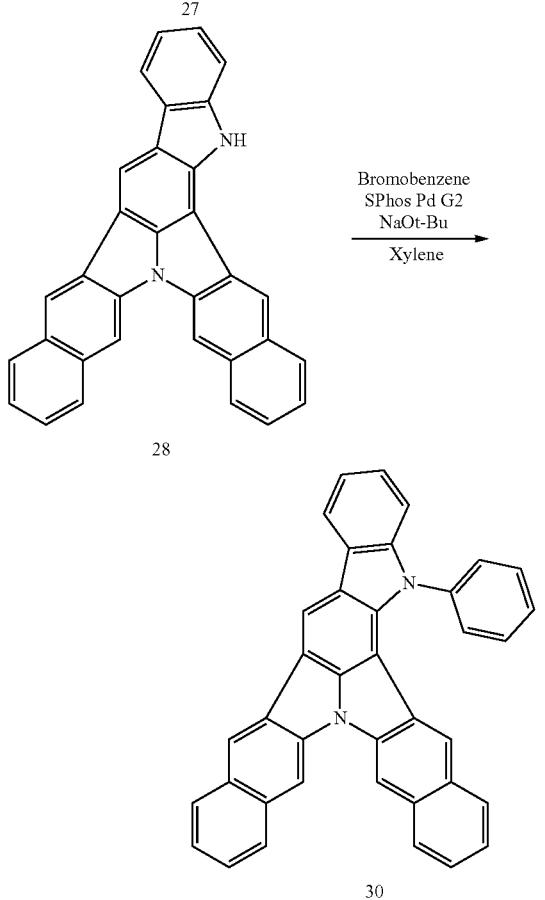

(1) Synthesis of Intermediate 24

Under an argon atmosphere, a solution of 1.00 g of the intermediate 4 (2.66 mmol), 1.15 g of bispinacolatodiboron (4.52 mmol), 0.43 g of tris(dibenzylideneacetone) dipalladium(0) (0.37 mmol), 101 mg of 2-dicyclohexylphosphino-2',4',6'-triisopropylbiphenyl (0.213 mmol), and 0.522 g of potassium acetate (5.32 mmol) in 120 mL of dioxane was refluxed for 20 h. After the reaction, water was added and then stirred. The precipitate was collected by filtration and washed with methanol. The obtained solid was purified by a column chromatography to obtain 0.67 g of a yellowish brown solid, which was identified as the target intermediate 24 by a mass spectroscopic analysis of m/e=467 to the molecular weight of 467.36 (yield: 54%).

(2) Synthesis of Intermediate 27

Under an argon atmosphere, into a solution of 30 mg of the intermediate 24 (0.064 mmol), 13 mg of 1-bromo-2-nitrobenzene (0.064 mmol), 0.909 mg of bis(di-tert-butyl(4-dimethylaminophenyl)phosphine) dichloropalladium(II) (PdCl$_2$(Amphos)$_2$: compound 26) (0.00128 mmol) in 3 mL of 1,2-dimethoxyethane, 0.1 mL of a 2 M aqueous solution of sodium carbonate was added. The resultant solution was refluxed for 24 h. The precipitate was collected by hot filtration and washed with methanol and toluene to obtain 13 mg of an orange solid, which was identified as the target intermediate by a mass spectroscopic analysis of m/e=462 to the molecular weight of 462.50 (yield: 43%).

(3) Synthesis of Intermediate 28

Under an argon atmosphere, a solution of 13 mg of the intermediate 27 (0.028 mmol) and 37 mg of triphenylphosphine (0.14 mmol) in 1 mL of 1,2-dichlorobenzene was refluxed for 50 h. After the reaction, methanol was added and the precipitate was collected by filtration to obtain 4 mg of a brown solid, which was identified as the target intermediate 28 by a mass spectroscopic analysis of m/e=430 to the molecular weight of 430.50 (yield: 33%).

(4) Synthesis of Compound 30

Under an argon atmosphere, a solution of 4 mg of the intermediate 28 (0.01 mmol), 8 mg of bromobenzene (0.05 mmol), 7 mg of chloro(2-dicyclohexylphosphino-2',6'-dimethoxy-1,1'-biphenyl)[2-(2'-amino-1,1'-biphenyl)] palladium (II) (SPhos Pd G2) (0.01 mmol), and 3 mg of sodium t-butoxide (0.03 mmol) in xylene (2 mL of) was refluxed for 8 h. After the reaction, chlorobenzene was added to the reaction mixture which was then heated. After adding silica gel, the reaction mixture was filtered through celite and the collected solid was washed with hexane to obtain 1 mg of a yellow solid, which was identified as the target compound 30 by a mass spectroscopic analysis of m/e=506 to the molecular weight of 506.59 (yield: 20%).

Synthesis Example 9

Synthesis of Compound 34

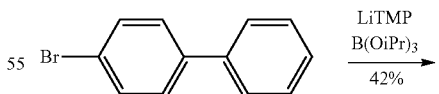

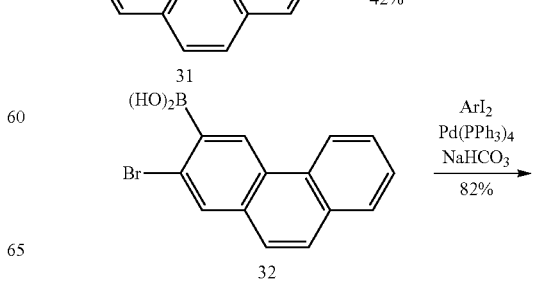

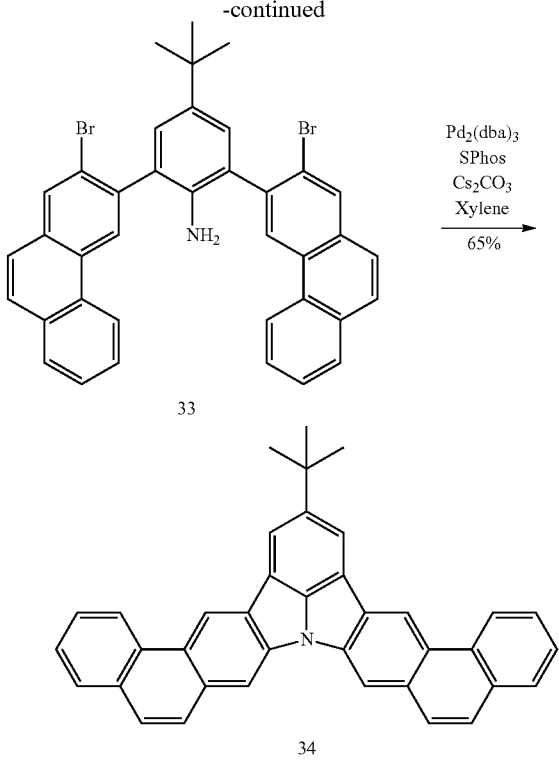

(1) Synthesis of Intermediate 32

Under an argon atmosphere, a solution of 4.1 g of 2,2,6,6-tetramethylpiperidine (29 mmol) in 45 mL of anhydrous tetrahydrofuran was cooled to −48° C. in a dry ice/acetone bath. After adding 18 mL of a n-butyllithium/hexane solution (1.64 mol/L, 18 mmol), the solution was stirred at −48° C. for 20 min and cooled to −65° C., and then 9 mL of triisopropoxyborane (39 mmol) was added dropwise. After 5 min, 20 mL of a tetrahydrofuran solution of 5.0 g of 2-bromophenanthrene (19 mmol) was added and the solution was stirred for 10 h in a cooling bath. After the reaction, 70 mL of a 5% by mass hydrochloric acid was added. The solution was stirred at room temperature (25° C.) for 30 min and then extracted with 200 mL of ethyl acetate. The organic layer was washed with 30 mL of a saturated saline and dried over magnesium sulfate. After evaporating off the solvent, the residue was dried under reduced pressure. The obtained 5.97 g of a pale yellow solid was purified by a column chromatography to obtain 2.4 g of a white solid, which was identified as the target intermediate 32 by a mass spectroscopic analysis of m/e=300 to the molecular weight of 300 (yield: 42%).

(2) Synthesis of Intermediate 33

Under an argon atmosphere, into a suspension of 24 g of the compound 32 (8.0 mmol), 1.45 g of 2,6-diiodo-4-tert-butylaniline (3.6 mmol), 0.42 g of tetrakis(triphenylphosphine) palladium (0.36 mmol), and 2.4 g of sodium hydrogen carbonate (29 mmol) in 50 mL of 1,2-dimethoxyethane, 25 mL of water was added. The resultant mixture was refluxed for 10 h. The reaction mixture was diluted with 150 mL of water, and the solid was collected by filtration, washed successively with water and methanol, and then dried under reduced pressure. The obtained 2.8 g of a yellow solid was purified by a column chromatography to obtain 1.95 g of a white solid, which was identified as the target intermediate 33 by a mass spectroscopic analysis of m/e=657 to the molecular weight of 657 (yield: 82%).

(3) Synthesis of Compound 34

Under an argon atmosphere, a suspension of 1.95 g of the intermediate 33 (3.0 mmol), 0.11 g of tris(dibenzylideneacetone) dipalladium(0) (0.12 mmol), 0.20 g of SPhos (0.49 mmol), and 5.9 g of cesium carbonate (18 mmol) in 250 mL of anhydrous xylene was refluxed for 10 h. After the reaction, the solid collected by filtration was washed successively with water and methanol and then dried under reduce pressure. The obtained 0.99 g of a dark yellowish green solid was purified by a column chromatography to obtain 0.97 g of a yellow plate crystal, which was identified as the target compound 34 by a mass spectroscopic analysis of m/e=497 to the molecular weight of 497 (yield: 65%).

Synthesis Example 10

Synthesis of Compound 38

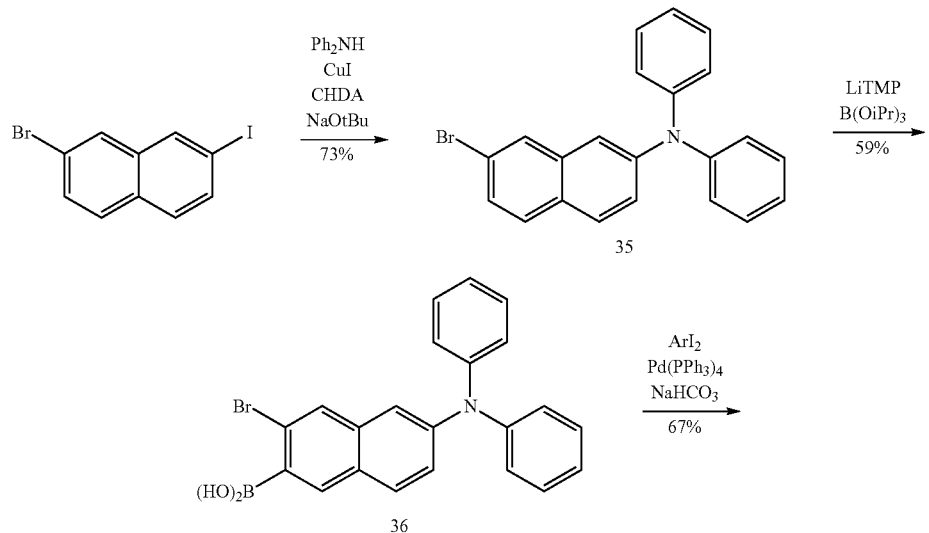

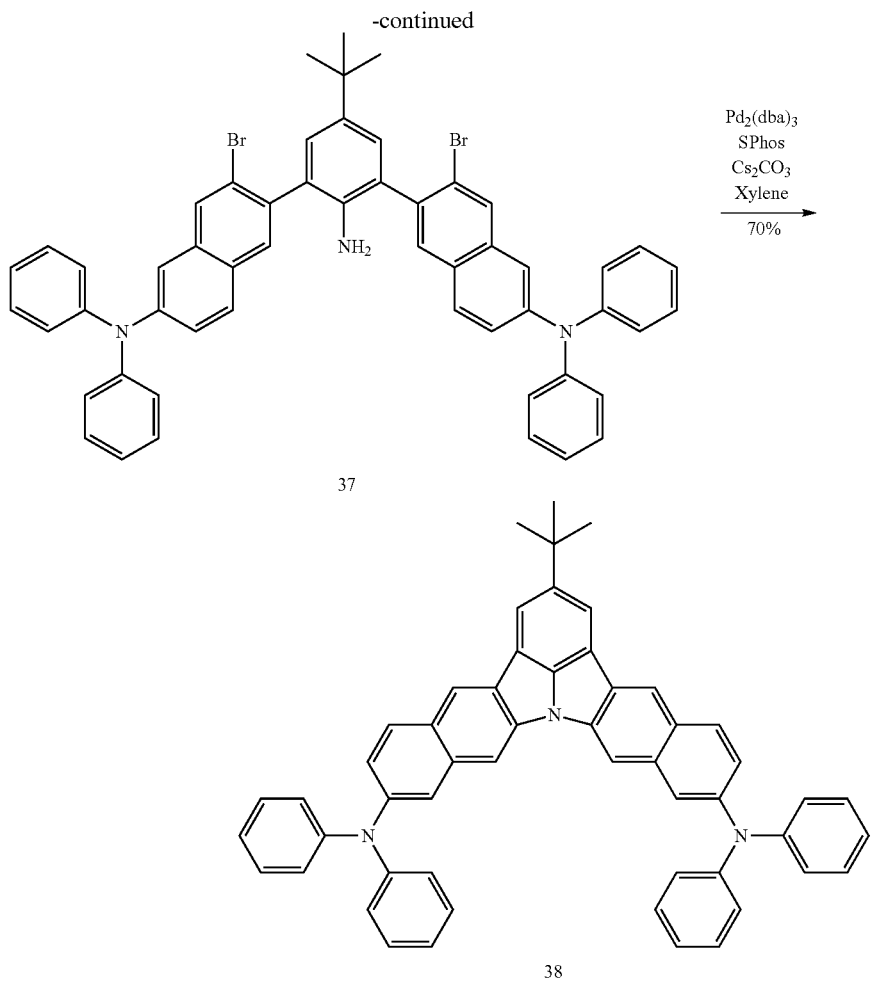

(1) Synthesis of Intermediate 35

Under an argon atmosphere, into a suspension of 2.83 g of 2-bromo-7-iodonaphthalene (16.7 mmol), 5.57 g of diphenylamine (16.7 mmol), 30 mg of copper iodide (0.16 mmol), and 2.2 g of sodium t-butoxide (23 mmol) in 20 mL of anhydrous 1,4-dioxane, 0.19 mL of trans-1,2-diaminocyclohexane (1.6 mmol) was added. The resultant mixture was stirred at 110° C. for 10 h. The reaction mixture was filtered through a silica pad. The filtrate was washed with 100 mL of toluene, the solvent was evaporated off, and the residue was dried under reduced pressure. The obtained 6.7 g of a deep brown oil was purified by a column chromatography to obtain 4.56 g of a white solid, which was identified as the target intermediate 35 by a mass spectroscopic analysis of m/e=373 to the molecular weight of 373 (yield: 68%).

(2) Synthesis of Intermediate 36

Under an argon atmosphere, a solution of 3.4 g of 2,2,6,6-tetramethylpiperidine (24 mmol) in 35 mL of anhydrous tetrahydrofuran was cooled to −30° C. in a dry ice/acetone bath. After adding 14.7 mL of a n-butyllithium/hexane solution (1.64 mol/L, 24 mmol), the solution was stirred at −20° C. for 20 min and cooled to −75° C., and then 8.3 mL of triisopropoxyborane (36 mmol) was added dropwise to the solution. After 5 min, 20 mL of a tetrahydrofuran solution of 4.5 g of the intermediate 35 (12 mmol) was added and the solution was stirred for 10 h in a cooling bath. After the reaction, 100 mL of a 5% by mass hydrochloric acid was added. The resultant solution was stirred at room temperature for 30 min and extracted with 150 mL of ethyl acetate. The organic layer was washed with 30 mL of a saturated saline and dried over magnesium sulfate, and then the solvent was evaporated off. The obtained 5.8 g of a reddish brown amorphous solid was purified by a column chromatography to obtain 2.94 g of a pale yellow solid, which was identified as the target intermediate 36 by a mass spectroscopic analysis of m/e=417 to the molecular weight of 417 (yield: 59%).

(3) Synthesis of Intermediate 37

Under an argon atmosphere, into a suspension of 1.28 g of 2,6-diiodo-4-tert-butylaniline (3.19 mmol), 2.94 g of the intermediate 36 (7.0 mmol), 0.37 g of tetrakis(triphenylphosphine) palladium (0.32 mmol), and 2.1 g of sodium hydrogen carbonate (25 mmol) in 45 mL of 1,2-dimethoxyethane, 22 mL of water was added. The resultant mixture was refluxed for 11 h. After the reaction, the reaction mixture was extracted with 150 mL of dichloromethane. The organic layer was dried over magnesium sulfate and then the solvent was evaporated off. The obtained 3.8 g of a yellow amorphous solid was purified by a column chromatography to obtain 1.92 g of a yellow solid, which was identified as the target intermediate 37 by a mass spectroscopic analysis of m/e=891 to the molecular weight of 891 (yield: 67%).

(4) Synthesis of Compound 38

Under an argon atmosphere, a suspension of 1.92 g of the intermediate 37 (2.1 mmol), 0.14 g of tris(dibenzylideneacetone) dipalladium(0) (0.34 mmol), and 4.1 g of cesium carbonate (12.6 mmol) in 200 mL of anhydrous xylene was refluxed for 11 h. After the reaction, the reaction mixture was filtered, the solvent was evaporated off, and the residue was dried under reduced pressure. The obtained yellow solid was purified by a column chromatography to obtain 1.6 g of a yellow solid. The obtained solid was recrystallized from 40 mL of toluene to obtain 1.07 g of a yellow acicular crystal, which was identified as the target compound 38 by a mass spectroscopic analysis of m/e=731 to the molecular weight of 731 (yield: 70%).

Example 1

The compound 2 obtained in Synthesis Example 1 showed an absorption peak at 423 nm when measured by Spectrophotometer U-3310 manufactured by Hitachi High-Tech Science Corporation. By exciting with light at 349 nm, the compound 2 showed a fluorescent peak at 432 nm when measured by Fluorescent Spectrophotometer F-7000 manufactured by Hitachi High-Tech Science Corporation.

The half width was measured in the following manner.

The compound 2 was dissolved in toluene to prepare a fluorescence specimen (5 µmol/mL). The fluorescence intensity was measured by irradiating the fluorescence specimen in a quartz cell with an excitation light at room temperature (300 K) while changing the wavelength, thereby obtaining a photoluminescence spectrum with a vertical coordinate of fluorescence intensity and a horizontal coordinate of wavelength. The emitted fluorescence was measured by using Fluorescent Spectrophotometer F-7000 manufactured by Hitachi High-Tech Science Corporation.

Figure 2:
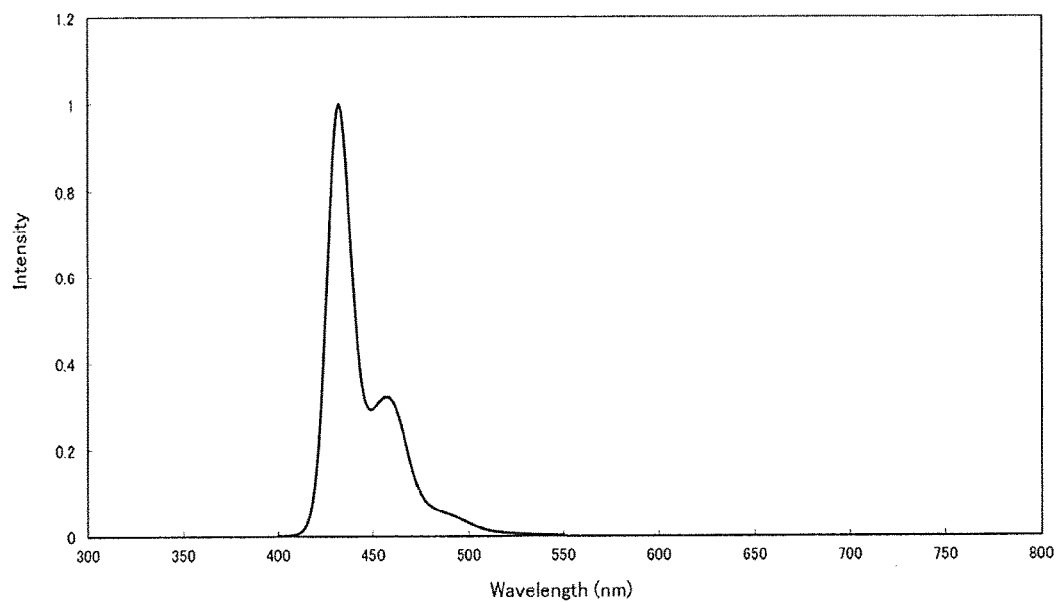
FIG. 2 is a chart showing a photoluminescence spectrum of the compound 2 of Example 1.

The half width (nm) of the compound 2 was determined from the obtained photoluminescence spectrum, which is shown in FIG. 2. The half width of the compound 2 was 16 nm.

PLQY was measured in the following manner.

A toluene solution (5 µmol/mL) of the compound 2 was measured for PLQY by using an absolute PL quantum yield spectrometer (Quantaurus-QY manufactured by Hamamatsu Photonics K.K.), obtaining a result of 83%.

The singlet energy EgS was measured in the following manner.

A toluene solution (20 µmol/mL) of the compound 2 was measured for an absorption spectrum by using Spectrophotometer U-3310 manufactured by Hitachi High-Tech Science Corporation. On the obtained absorption spectrum with a vertical coordinate of absorbance and a horizontal coordinate of wavelength, a line tangent to the falling portion of the peak at the longest wavelength of the spectrum was drawn, and the wavelength $\lambda_{edge}$ (nm) at the intersection of the tangent line and the horizontal coordinate was determined. The value of wavelength was converted to the value of energy by the following equation to determine EgS:

$$EgS \text{ (eV)} = 1239.85/\lambda_{edge}.$$

The line tangent to the falling portion of the absorption spectrum at the longer wavelength side of the spectrum was drawn in following manner. When moving along the spectrum curve from its maximum value at the longest wavelength towards the longer wavelength side, the slope of the tangent line drawn at each point of the curve decreases as the curve falls down, i.e., as the value of the vertical coordinate decreases, then increases and repeatedly decreases. The tangent line with the minimum slope drawn at the longest wavelength side was taken as the tangent line for determining EgS.

Figure 3:
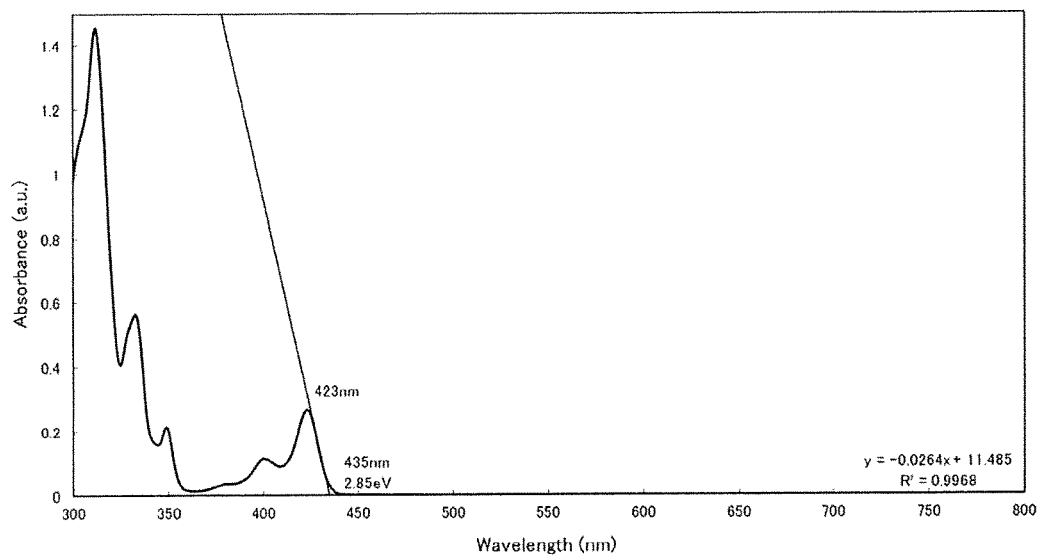
FIG. 3 is a chart showing an absorption spectrum of the compound 2 of Example 1.

The singlet energy (S1) of the compound 2 determined in the manner as describe above was 2.85 eV. The absorption spectrum of the compound 2 is shown in FIG. 3.

Examples 2 to 9

The compounds 7, 9, 11, 17, 22, 30, 34, and 38 obtained in Synthesis Examples 3 to 10 were measured for the wavelength (λ) of fluorescent peak, the half width, PLQY, and the singlet energy (S1) in the same manner as in Example 1.

Comparative Example 1

The wavelength of fluorescent peak, the half width, PLQY, and the singlet energy of the comparative compound 1, each of which was determined in the same manner as in Example 1, were 375 nm, 24 nm, 40%, and 3.30 eV, respectively.

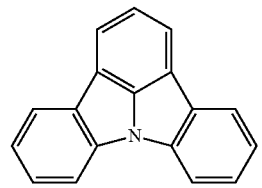

Comparative compound 1

Comparative Example 2

The wavelength of fluorescent peak, the half width, PLQY, and the singlet energy of the comparative compound 2, each of which was determined in the same manner as in Example 1, were 406 nm, 17 nm, 60% and, 3.02 eV, respectively.

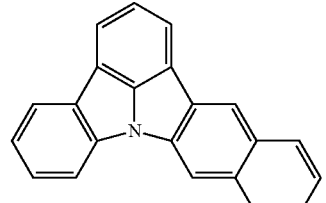

Comparative compound 2

Comparative Example 3

The wavelength of fluorescent peak, the half width, PLQY, and the singlet energy of the comparative compound 3 (pyrene derivative), each of which was determined in the same manner as in Example 1, were 455 nm, 35 nm, 90%, and 2.75 eV, respectively.

Comparative compound 3

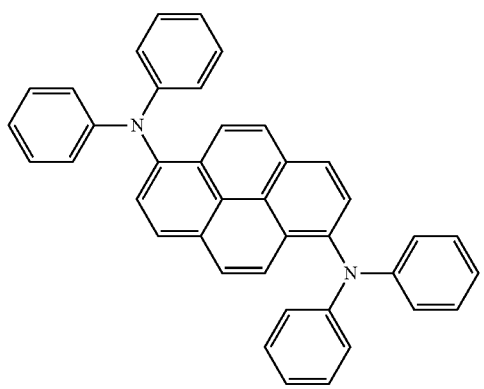

The results of the measurements in the examples and the comparative examples are collectively shown in Table 1.

TABLE 1

|   |   | λ (nm) | Half width (nm) | PLQY (%) | S1 (eV) |
|---|---|---|---|---|---|
| Examples | | | | | |
| 1 | Compound 2 | 432 | 16 | 83 | 2.85 |
| 2 | Compound 7 | 442 | 17 | 75 | 2.79 |
| 3 | Compound 9 | 442 | 18 | 77 | 2.79 |
| 4 | Compound 11 | 439 | 16 | 79 | 2.81 |
| 5 | Compound 17 | 436 | 15 | 83 | 2.83 |
| 6 | Compound 22 | 444 | 17 | 84 | 2.78 |
| 7 | Compound 30 | 435 | 16 | 80 | 2.83 |
| 8 | Compound 34 | 426 | 15 | 72 | 2.89 |
| 9 | Compound 38 | 440 | 15 | 83 | 2.81 |
| Comparative Examples | | | | | |
| 1 | Comparative compound 1 | 375 | 24 | 40 | 3.30 |
| 2 | Comparative compound 2 | 406 | 17 | 60 | 3.02 |
| 3 | Comparative compound 3 | 455 | 35 | 90 | 2.75 |

As evidenced from the above, the compounds 2, 7, 9, 11, 17, 22, 30, 34, and 38 of the invention gave a spectrum with a narrow half width, a high color purity, and a sharp shape, as compared with the comparative compounds 1 and 3. In addition, the compound 2, as compared with the comparative compounds 1 and 2, showed an extremely high PLQY although not having a substituent. Further, the compounds 2, 7, 9, 11, 17, 22, 30, 34, and 38 emitted a deep blue light of 426 to 444 nm, although the comparative compounds 1 and 2 gave spectra having the fluorescent peaks outside the visible light region, i.e., at 375 nm and 406 nm, respectively.

Production of Organic EL Device

Each organic EL device was produced in the following manner.

Device Example 1

A glass substrate of 25 mm×75 mm×1.1 mm thick having an ITO transparent electrode (anode) (product of Geomatec Company) was cleaned by ultrasonic cleaning in isopropyl alcohol for 5 min and then UV-ozone cleaning for 30 min. The thickness of ITO film was 130 nm.

The cleaned glass substrate was mounted to a substrate holder of a vacuum vapor deposition apparatus. The compound HI-1 was vapor-deposited on the surface having the transparent electrode line so as to cover the transparent electrode to form a hole injecting layer with a thickness of 5 nm.

On the hole injecting layer, the compound HT-1 was vapor-deposited to form a first hole transporting layer with a thickness of 80 nm.

Then, the compound HT-2 was vapor-deposited on the first hole transporting layer to form a second hole transporting layer with a thickness of 10 nm.

Successively thereafter, the compound BH-1 and the compound 2 (dopant material) were vapor co-deposited on the second hole transporting layer to form a light emitting layer with a thickness of 25 nm. The concentration of the compound 2 (dopant material) in the light emitting layer was 4% by mass.

Successively thereafter, the compound ET-1 was vapor-deposited on the light emitting layer to form a first electron transporting layer with a thickness of 10 nm.

Successively thereafter, the compound ET-2 was vapor-deposited on the first electron transporting layer to form a second electron transporting layer with a thickness of 15 nm.

Further, lithium fluoride (LiF) was vapor-deposited on the second electron transporting layer to form an electron injecting electrode with a thickness of 1 nm.

Then, metallic aluminum (Al) was vapor-deposited on the electron injecting electrode to form a metal cathode with a thickness of 80 nm.

The structure of the obtained organic EL device was: ITO (130)/HI-1 (5)/HT-1 (80)/HT-2 (10)/BH-1:Compound 2 (25, 4% by mass)/ET-1 (10)/ET-2 (15)/LiF (1)/Al (80).

Each numeral in parenthesis is the thickness of each layer (unit of measure: nm). The same applies below.

Device Example 2

An organic EL device was produced in the same manner as in Device Example 1 except for using the compound 5 in the light emitting layer in place of the compound 2 (dopant material).

The structure of the obtained organic EL device was: ITO (130)/HI-1 (5)/HT-1 (80)/HT-2 (10)/BH-1:Compound 5 (25, 4% by mass)/ET-1 (10)/ET-2 (15)/LiF (1)/Al (80).

Device Example 3

An organic EL device was produced in the same manner as in Device Example 1 except for using BH-2 in the light emitting layer in place of BH-1 (host material).

The structure of the obtained organic EL device was: ITO (130)/HI-1 (5)/HT-1 (80)/HT-2 (10)/BH-2:Compound 2 (25, 4% by mass)/ET-1 (10)/ET-2 (15)/LiF (1)/Al (80).

Device Example 4

An organic EL device was produced in the same manner as in Device Example 2 except for using BH-2 in the light emitting layer in place of BH-1 (host material).

The structure of the obtained organic EL device was: ITO (130)/HI-1 (5)/HT-1 (80)/HT-2 (10)/BH-2:Compound 5 (25, 4% by mass)/ET-1 (10)/ET-2 (15)/LiF (1)/Al (80).

Device Example 5

An organic EL device was produced in the same manner as in Device Example 2 except for changing the concentration of the Compound 5 (dopant material) in the light emitting layer to 2% by mass.

The structure of the obtained organic EL device was:
ITO (130)/HI-1 (5)/HT-1 (80)/HT-2 (10)/BH-2:Compound 5 (25, 2% by mass)/ET-1 (10)/ET-2 (15)/LiF (1)/Al (80).

The organic EL device emitted blue light with a main peak wavelength of 449 nm.

Device Example 6

An organic EL device was produced in the same manner as in Device Example 5 except for using BH-2 in the light emitting layer in place of BH-1 (host material).
The structure of the obtained organic EL device was:
ITO (130)/HI-1 (5)/HT-1 (80)/HT-2 (10)/BH-2:Compound 5 (25, 2% by mass)/ET-1 (10)/ET-2 (15)/LiF (1)/Al (80).

Device Example 7

An organic EL device was produced in the same manner as in Device Example 5 except for using BH-5 in the light emitting layer in place of BH-1 (host material).
The structure of the obtained organic EL device was:
ITO (130)/HI-1 (5)/HT-1 (80)/HT-2 (10)/BH-5:Compound 5 (25, 2% by mass)/ET-1 (10)/ET-2 (15)/LiF (1)/Al (80).

Device Example 8

An organic EL device was produced in the same manner as in Device Example 5 except for using BH-6 in the light emitting layer in place of BH-1 (host material).
The structure of the obtained organic EL device was:
ITO (130)/HI-1 (5)/HT-1 (80)/HT-2 (10)/BH-6:Compound 5 (25, 2% by mass)/ET-1 (10)/ET-2 (15)/LiF (1)/Al (80).

Device Example 9

An organic EL device was produced in the same manner as in Device Example 5 except for using BH-7 in the light emitting layer in place of BH-1 (host material).
The structure of the obtained organic EL device was:
ITO (130)/HI-1 (5)/HT-1 (80)/HT-2 (10)/BH-7:Compound 5 (25, 2% by mass)/ET-1 (10)/ET-2 (15)/LiF (1)/Al (80).

Device Example 10

An organic EL device was produced in the same manner as in Device Example 5 except for using BH-8 in the light emitting layer in place of BH-1 (host material).
The structure of the obtained organic EL device was:
ITO (130)/HI-1 (5)/HT-1 (80)/HT-2 (10)/BH-8:Compound 5 (25, 2% by mass)/ET-1 (10)/ET-2 (15)/LiF (1)/Al (80).

Device Example 11

An organic EL device was produced in the same manner as in Device Example 5 except for using BH-9 in the light emitting layer in place of BH-1 (host material).
The structure of the obtained organic EL device was:
ITO (130)/HI-1 (5)/HT-1 (80)/HT-2 (10)/BH-9:Compound 5 (25, 2% by mass)/ET-1 (10)/ET-2 (15)/LiF (1)/Al (80).

Device Example 12

An organic EL device was produced in the same manner as in Device Example 5 except for using BH-10 in the light emitting layer in place of BH-1 (host material).
The structure of the obtained organic EL device was:
ITO (130)/HI-1 (5)/HT-1 (80)/HT-2 (10)/BH-10:Compound 5 (25, 2% by mass)/ET-1 (10)/ET-2 (15)/LiF (1)/Al (80).

Device Example 13

An organic EL device was produced in the same manner as in Device Example 5 except for using BH-11 in the light emitting layer in place of BH-1 (host material).
The structure of the obtained organic EL device was:
ITO (130)/HI-1 (5)/HT-1 (80)/HT-2 (10)/BH-11:Compound 5 (25, 2% by mass)/ET-1 (10)/ET-2 (15)/LiF (1)/Al (80).

Device Example 14

An organic EL device was produced in the same manner as in Device Example 5 except for using BH-12 in the light emitting layer in place of BH-1 (host material).
The structure of the obtained organic EL device was:
ITO (130)/HI-1 (5)/HT-1 (80)/HT-2 (10)/BH-12:Compound 5 (25, 2% by mass)/ET-1 (10)/ET-2 (15)/LiF (1)/Al (80).

Device Example 15

An organic EL device was produced in the same manner as in Device Example 5 except for using BH-13 in the light emitting layer in place of BH-1 (host material).
The structure of the obtained organic EL device was:
ITO (130)/HI-1 (5)/HT-1 (80)/HT-2 (10)/BH-13:Compound 5 (25, 2% by mass)/ET-1 (10)/ET-2 (15)/LiF (1)/Al (80).

Device Example 16

An organic EL device was produced in the same manner as in Device Example 5 except for using BH-14 in the light emitting layer in place of BH-1 (host material).
The structure of the obtained organic EL device was:
ITO (130)/HI-1 (5)/HT-1 (80)/HT-2 (10)/BH-14:Compound 5 (25, 2% by mass)/ET-1 (10)/ET-2 (15)/LiF (1)/Al (80).

Device Example 17

An organic EL device was produced in the same manner as in Device Example 1 except for using the compound 7 in the light emitting layer in place of the compound 2 (dopant material).
The structure of the obtained organic EL device was:
ITO (130)/HI-1 (5)/HT-1 (80)/HT-2 (10)/BH-1:Compound 7 (25, 4% by mass)/ET-1 (10)/ET-2 (15)/LiF (1)/Al (80).

Device Example 18

An organic EL device was produced in the same manner as in Device Example 1 except for using the compound 9 in the light emitting layer in place of the compound 2 (dopant material).
The structure of the obtained organic EL device was:
ITO (130)/HI-1 (5)/HT-1 (80)/HT-2 (10)/BH-1:Compound 9 (25, 4% by mass)/ET-1 (10)/ET-2 (15)/LiF (1)/Al (80).

Device Example 19

An organic EL device was produced in the same manner as in Device Example 1 except for using the compound 11 in the light emitting layer in place of the compound 2 (dopant material).

The structure of the obtained organic EL device was:
ITO (130)/HI-1 (5)/HT-1 (80)/HT-2 (10)/BH-1:Compound 11 (25, 4% by mass)/ET-1 (10)/ET-2 (15)/LiF (1)/Al (80).

Device Example 20

An organic EL device was produced in the same manner as in Device Example 1 except for using the compound 17 in the light emitting layer in place of the compound 2 (dopant material).
The structure of the obtained organic EL device was:
ITO (130)/HI-1 (5)/HT-1 (80)/HT-2 (10)/BH-1:Compound 17 (25, 4% by mass)/ET-1 (10)/ET-2 (15)/LiF (1)/Al (80).

Device Example 21

An organic EL device was produced in the same manner as in Device Example 1 except for using the compound 22 in the light emitting layer in place of the compound 2 (dopant material).
The structure of the obtained organic EL device was:
ITO (130)/HI-1 (5)/HT-1 (80)/HT-2 (10)/BH-1:Compound 22 (25, 4% by mass)/ET-1 (10)/ET-2 (15)/LiF (1)/Al (80).

Device Example 22

An organic EL device was produced in the same manner as in Device Example 3 except for using the compound 17 in the light emitting layer in place of the compound 2 (dopant material).
The structure of the obtained organic EL device was:
ITO (130)/HI-1 (5)/HT-1 (80)/HT-2 (10)/BH-2:Compound 17 (25, 4% by mass)/ET-1 (10)/ET-2 (15)/LiF (1)/Al (80).

Device Example 23

An organic EL device was produced in the same manner as in Device Example 3 except for using the compound 22 in the light emitting layer in place of the compound 2 (dopant material).
The structure of the obtained organic EL device was:
ITO (130)/HI-1 (5)/HT-1 (80)/HT-2 (10)/BH-2:Compound 22 (25, 4% by mass)/ET-1 (10)/ET-2 (15)/LiF (1)/Al (80).

Device Example 24

An organic EL device was produced in the same manner as in Device Example 20 except for using BH-15 in the light emitting layer in place of BH-1 (host material).
The structure of the obtained organic EL device was:
ITO (130)/HI-1 (5)/HT-1 (80)/HT-2 (10)/BH-15:Compound 17 (25, 4% by mass)/ET-1 (10)/ET-2 (15)/LiF (1)/Al (80).

Device Example 25

An organic EL device was produced in the same manner as in Device Example 21 except for using BH-15 in the light emitting layer in place of BH-1 (host material).
The structure of the obtained organic EL device was:
ITO (130)/HI-1 (5)/HT-1 (80)/HT-2 (10)/BH-15:Compound 22 (25, 4% by mass)/ET-1 (10)/ET-2 (15)/LiF (1)/Al (80).

Device Example 26

An organic EL device was produced in the same manner as in Device Example 20 except for using BH-16 in the light emitting layer in place of BH-1 (host material).
The structure of the obtained organic EL device was:
ITO (130)/HI-1 (5)/HT-1 (80)/HT-2 (10)/BH-16:Compound 17 (25, 4% by mass)/ET-1 (10)/ET-2 (15)/LiF (1)/Al (80).

Device Example 27

An organic EL device was produced in the same manner as in Device Example 21 except for using BH-16 in the light emitting layer in place of BH-1 (host material).
The structure of the obtained organic EL device was:
ITO (130)/HI-1 (5)/HT-1 (80)/HT-2 (10)/BH-16:Compound 22 (25, 4% by mass)/ET-1 (10)/ET-2 (15)/LiF (1)/Al (80).

Device Example 28

An organic EL device was produced in the same manner as in Device Example 5 except for using the compound 7 in the light emitting layer in place of the compound 5 (dopant material).
The structure of the obtained organic EL device was:
ITO (130)/HI-1 (5)/HT-1 (80)/HT-2 (10)/BH-1:Compound 7 (25, 2% by mass)/ET-1 (10)/ET-2 (15)/LiF (1)/Al (80).

Device Example 29

An organic EL device was produced in the same manner as in Device Example 5 except for using the compound 9 in the light emitting layer in place of the compound 5 (dopant material).
The structure of the obtained organic EL device was:
ITO (130)/HI-1 (5)/HT-1 (80)/HT-2 (10)/BH-1:Compound 9 (25, 2% by mass)/ET-1 (10)/ET-2 (15)/LiF (1)/Al (80)

Device Example 30

An organic EL device was produced in the same manner as in Device Example 5 except for using the compound 11 in the light emitting layer in place of the compound 5 (dopant material).
The structure of the obtained organic EL device was:
ITO (130)/HI-1 (5)/HT-1 (80)/HT-2 (10)/BH-1:Compound 11 (25, 2% by mass)/ET-1 (10)/ET-2 (15)/LiF (1)/Al (80).

Device Example 31

An organic EL device was produced in the same manner as in Device Example 5 except for using the compound 17 in the light emitting layer in place of the compound 5 (dopant material).
The structure of the obtained organic EL device was:
ITO (130)/HI-1 (5)/HT-1 (80)/HT-2 (10)/BH-1:Compound 17 (25, 2% by mass)/ET-1 (10)/ET-2 (15)/LiF (1)/Al (80).

Device Example 32

An organic EL device was produced in the same manner as in Device Example 5 except for using the compound 22 in the light emitting layer in place of the compound 5 (dopant material).
The structure of the obtained organic EL device was:
ITO (130)/HI-1 (5)/HT-1 (80)/HT-2 (10)/BH-1:Compound 22 (25, 2% by mass)/ET-1 (10)/ET-2 (15)/LiF (1)/Al (80).

Device Example 33

An organic EL device was produced in the same manner as in Device Example 6 except for using the compound 17 in the light emitting layer in place of the compound 5 (dopant material).

The structure of the obtained organic EL device was:
ITO (130)/HI-1 (5)/HT-1 (80)/HT-2 (10)/BH-2:Compound 17 (25, 2% by mass)/ET-1 (10)/ET-2 (15)/LiF (1)/Al (80).

Device Example 34

An organic EL device was produced in the same manner as in Device Example 6 except for using the compound 22 in the light emitting layer in place of the compound 5 (dopant material).
The structure of the obtained organic EL device was:
ITO (130)/HI-1 (5)/HT-1 (80)/HT-2 (10)/BH-2:Compound 22 (25, 2% by mass)/ET-1 (10)/ET-2 (15)/LiF (1)/Al (80).

Device Example 35

An organic EL device was produced in the same manner as in Device Example 31 except for using BH-15 in the light emitting layer in place of BH-1 (host material).
The structure of the obtained organic EL device was:
ITO (130)/HI-1 (5)/HT-1 (80)/HT-2 (10)/BH-15:Compound 17 (25, 2% by mass)/ET-1 (10)/ET-2 (15)/LiF (1)/Al (80).

Device Example 36

An organic EL device was produced in the same manner as in Device Example 32 except for using BH-15 in the light emitting layer in place of BH-1 (host material).
The structure of the obtained organic EL device was:
ITO (130)/HI-1 (5)/HT-1 (80)/HT-2 (10)/BH-15:Compound 22 (25, 2% by mass)/ET-1 (10)/ET-2 (15)/LiF (1)/Al (80).

Device Example 37

An organic EL device was produced in the same manner as in Device Example 31 except for using BH-16 in the light emitting layer in place of BH-1 (host material).
The structure of the obtained organic EL device was:
ITO (130)/HI-1 (5)/HT-1 (80)/HT-2 (10)/BH-16:Compound 17 (25, 2% by mass)/ET-1 (10)/ET-2 (15)/LiF (1)/Al (80).

Device Example 38

An organic EL device was produced in the same manner as in Device Example 32 except for using BH-16 in the light emitting layer in place of BH-1 (host material).
The structure of the obtained organic EL device was:
ITO (130)/HI-1 (5)/HT-1 (80)/HT-2 (10)/BH-16:Compound 22 (25, 2% by mass)/ET-1 (10)/ET-2 (15)/LiF (1)/Al (80).

Device Comparative Example 1

An organic EL device was produced in the same manner as in Device Example 5 except for using the comparative compound 3 in the light emitting layer in place of the compound 5 (dopant material).
The structure of the obtained organic EL device was:
ITO (130)/HI-1 (5)/HT-1 (80)/HT-2 (10)/BH-1:Comparative compound 3 (25, 2% by mass)/ET-1 (10)/ET-2 (15)/LiF (1)/Al (80).

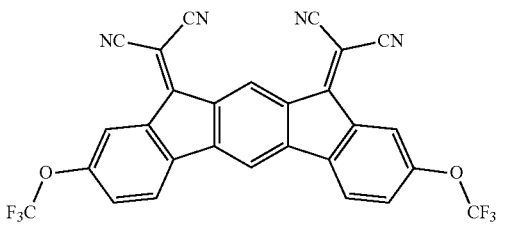

HI-1

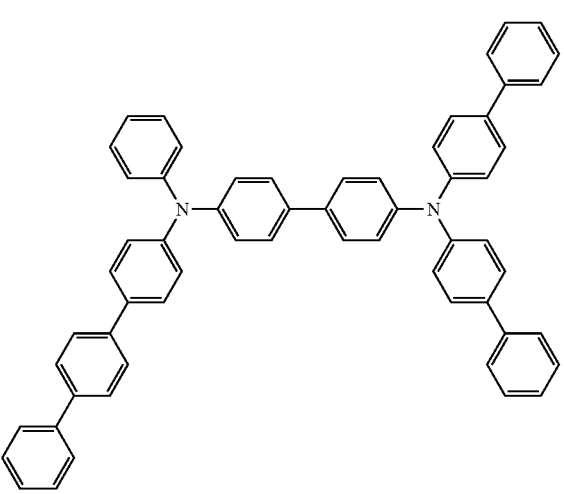

HT-1

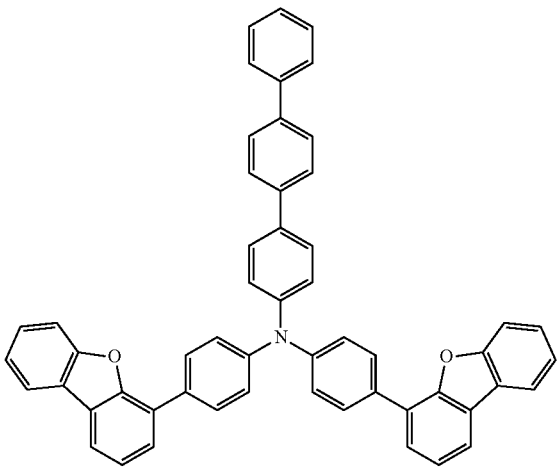

HT-2

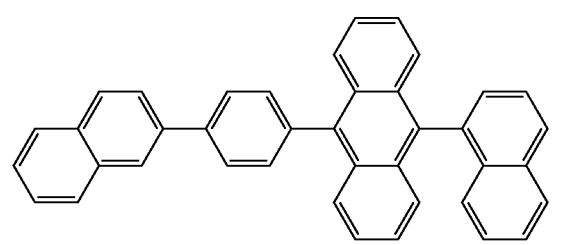

BH-1

BH-2
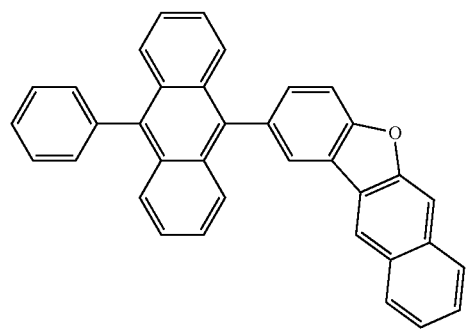
BH-5
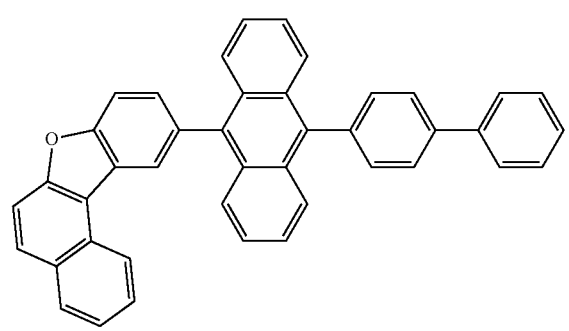
BH-6
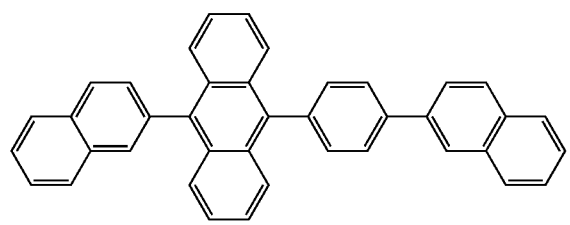
BH-7
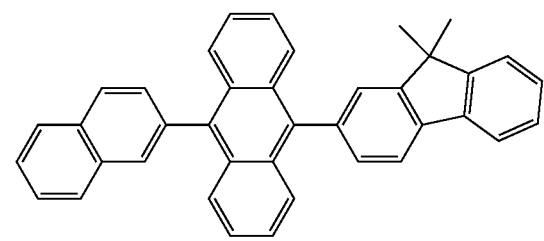
BH-8
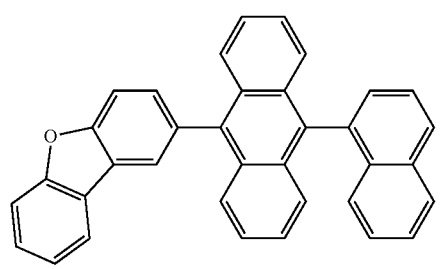
BH-9
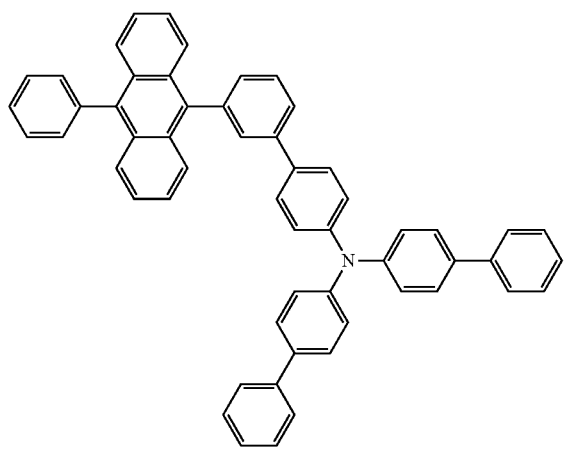
BH-10
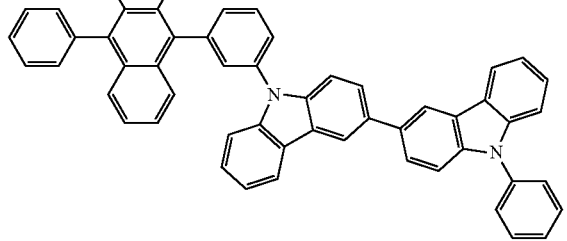
BH-11
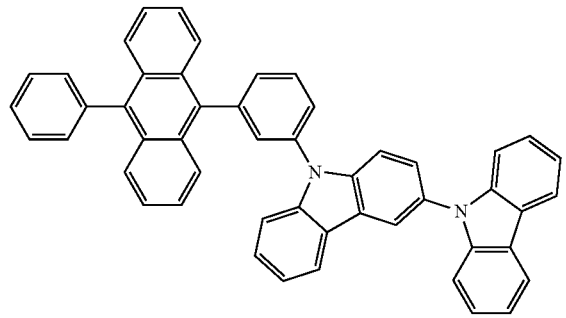
BH-12
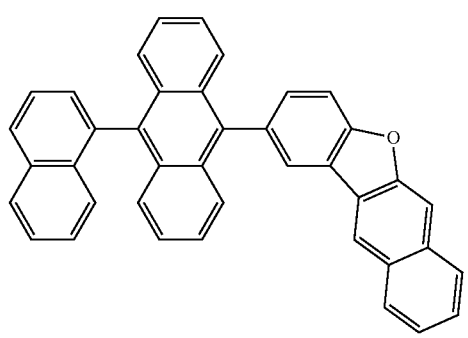

BH-13

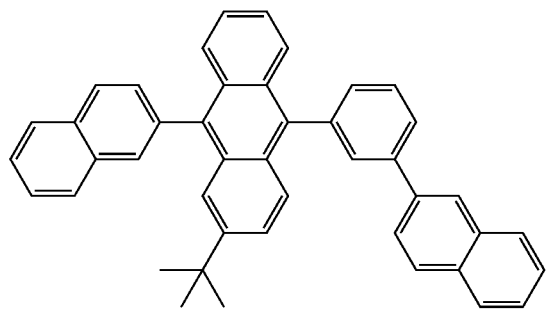

BH-14

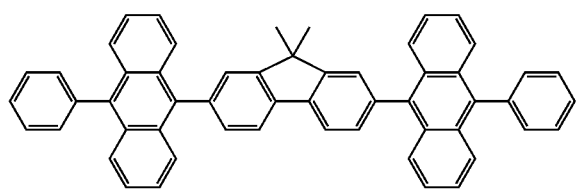

BH-15

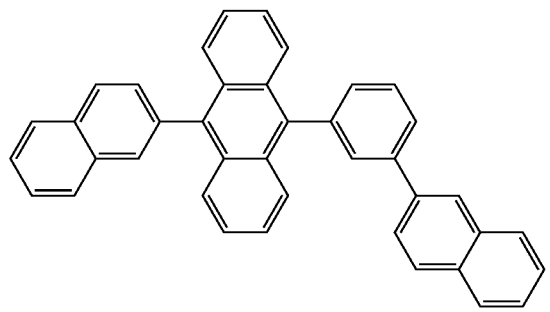

BH-16

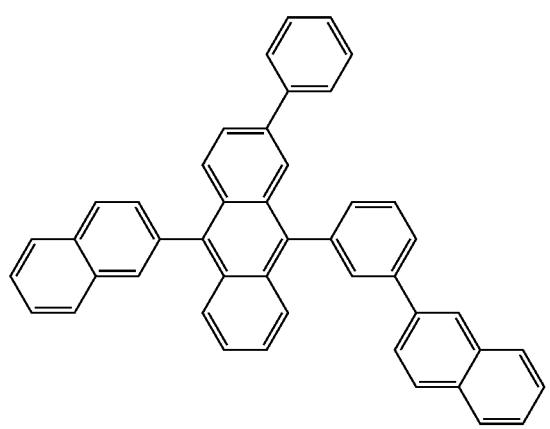

ET-1

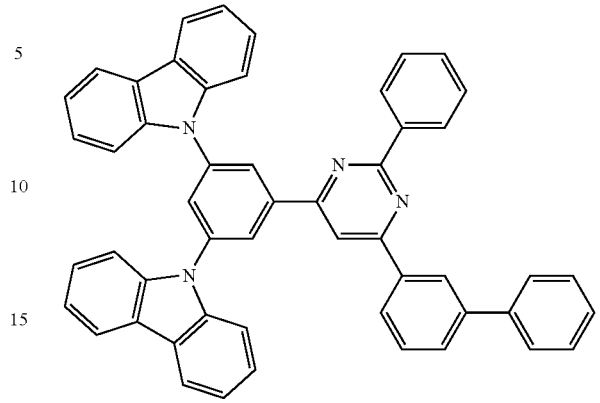

ET-2

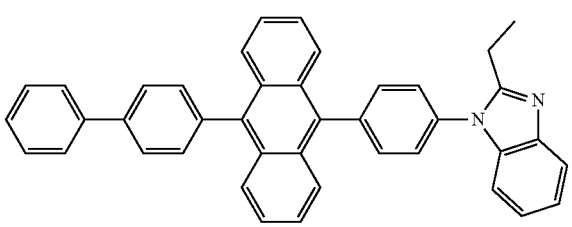

Evaluation of Organic EL Device

The organic EL devices thus obtained were evaluated for the following properties. The evaluated results are shown in the following Table 2.

Driving Voltage

The voltage (unit of measure: V) applied to the organic EL device to obtain a current density of 10 mA/cm$^2$ was measured.

Main Peak Wavelength

The main peak wavelength λp (unit of measure: nm) was measured by applying the voltage to the organic EL devise to obtain a current density of 10 mA/cm$^2$ by using a spectroradiometer CS-1000 manufactured by Konica Minolta.

TABLE 2

| Device examples | Dopant material | Content by mass (% by mass) | Host material | Voltage (V) | λp (nm) |
|---|---|---|---|---|---|
| 1 | Compound 2 | (4) | BH-1 | 3.8 | 441 |
| 2 | Compound 5 | (4) | BH-1 | 3.7 | 449 |
| 3 | Compound 2 | (4) | BH-2 | 3.4 | 441 |
| 4 | Compound 5 | (4) | BH-2 | 3.4 | 450 |
| 5 | Compound 5 | (2) | BH-1 | 3.7 | 449 |
| 6 | Compound 5 | (2) | BH-2 | 3.4 | 448 |
| 7 | Compound 5 | (2) | BH-5 | 3.4 | 449 |
| 8 | Compound 5 | (2) | BH-6 | 3.6 | 449 |
| 9 | Compound 5 | (2) | BH-7 | 3.4 | 448 |
| 10 | Compound 5 | (2) | BH-8 | 3.8 | 448 |
| 11 | Compound 5 | (2) | BH-9 | 3.3 | 446 |
| 12 | Compound 5 | (2) | BH-10 | 3.4 | 450 |
| 13 | Compound 5 | (2) | BH-11 | 3.5 | 447 |
| 14 | Compound 5 | (2) | BH-12 | 3.5 | 449 |
| 15 | Compound 5 | (2) | BH-13 | 3.7 | 449 |
| 16 | Compound 5 | (2) | BH-14 | 3.5 | 448 |
| 17 | Compound 7 | (4) | BH-1 | 3.7 | 451 |
| 18 | Compound 9 | (4) | BH-1 | 3.7 | 452 |
| 19 | Compound 11 | (4) | BH-1 | 3.7 | 447 |
| 20 | Compound 17 | (4) | BH-1 | 3.6 | 442 |
| 21 | Compound 22 | (4) | BH-1 | 3.7 | 453 |

TABLE 2-continued

| Device examples | Dopant material | Content by mass (% by mass) | Host material | Voltage (V) | λp (nm) |
|---|---|---|---|---|---|
| 22 | Compound 17 | (4) | BH-2 | 3.3 | 443 |
| 23 | Compound 22 | (4) | BH-2 | 3.3 | 453 |
| 24 | Compound 17 | (4) | BH-15 | 3.8 | 442 |
| 25 | Compound 22 | (4) | BH-15 | 3.8 | 453 |
| 26 | Compound 17 | (4) | BH-16 | 3.4 | 444 |
| 27 | Compound 22 | (4) | BH-16 | 3.5 | 454 |
| 28 | Compound 7 | (2) | BH-1 | 3.7 | 450 |
| 29 | Compound 9 | (2) | BH-1 | 3.7 | 450 |
| 30 | Compound 11 | (2) | BH-1 | 3.7 | 446 |
| 31 | Compound 17 | (2) | BH-1 | 3.7 | 442 |
| 32 | Compound 22 | (2) | BH-1 | 3.7 | 451 |
| 33 | Compound 17 | (2) | BH-2 | 3.3 | 442 |
| 34 | Compound 22 | (2) | BH-2 | 3.3 | 451 |
| 35 | Compound 17 | (2) | BH-15 | 3.8 | 442 |
| 36 | Compound 22 | (2) | BH-15 | 3.9 | 451 |
| 37 | Compound 17 | (2) | BH-16 | 3.5 | 444 |
| 38 | Compound 22 | (2) | BH-16 | 3.5 | 453 |
| Device comparative examples 1 | Comparative compound 3 | (2) | BH-1 | 4.0 | 466 |

All the produced organic EL devices emitted blue light. Each of the organic EL devices of Device Examples 1 to 38 wherein the compound of formula (1) was used was operated at lower driving voltage as compared with the organic EL device of Device Comparative Example 1 wherein the comparative compound 3 was used, because the compound of formula (1) transported holes more easily than the comparative compound 3.

REFERENCE SIGNS LIST

1: Organic electroluminescence device
2: Substrate
3: Anode
4: Cathode
5: Light emitting layer
6: Hole injecting layer/hole transporting layer
7: Electron injecting layer/electron transporting layer
10: Emission layer

The invention claimed is:
1. A compound represented by formula (1):

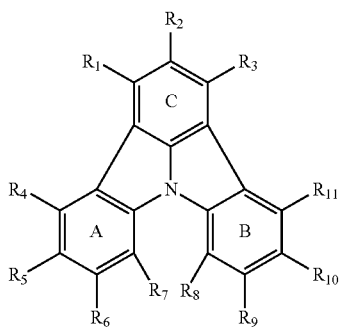

(1)

wherein:
three or more pairs $R_n$ and $R_{n+1}$ selected from the group consisting of $R_1$ and $R_2$, $R_2$ and $R_3$, $R_4$ and $R_5$, $R_5$ and $R_6$, $R_6$ and $R_7$, $R_8$ and $R_9$, $R_9$ and $R_{10}$, and $R_{10}$ and $R_{11}$, wherein n is an integer selected from 1, 2, 4 to 6, and 8 to 10, are bonded to each other to form a ring structure together with two ring atoms to which $R_n$ and $R_{n+1}$ are bonded, wherein the ring structure has 3 or more atoms comprising a carbon atom, an oxygen atom, a sulfur atom, a nitrogen atom, or mixtures thereof;

the ring structure optionally comprises at least one substituent independently selected from the group consisting of a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by —Si($R_{101}$)($R_{102}$)($R_{103}$), a group represented by —N($R_{104}$)($R_{105}$), a substituted or unsubstituted aryl group having 6 to 50 ring carbon atoms, and a substituted or unsubstituted heteroaryl group having 5 to 50 ring atoms;

when a pair of $R_1$ and $R_2$ form one of the ring structure, or a pair of $R_2$ and $R_3$ form one of the ring structure, the atoms composing the ring structure do not have a substituent selected from the group consisting of a substituted aryl group and a substituted or unsubstituted heteroaryl group;

substituents may be bonded to each other to form another ring structure;

the 3 or more atoms does not include atoms in the at least one substituent;

provided that a pair of $R_1$ and $R_2$ and a pair of $R_2$ and $R_3$, a pair of $R_4$ and $R_5$ and a pair of $R_5$ and $R_6$, a pair of $R_5$ and $R_6$ and a pair of $R_6$ and $R_7$, a pair of $R_8$ and $R_9$ and a pair of $R_9$ and $R_{10}$, and a pair of $R_9$ and $R_{10}$ and a pair of $R_{10}$ and $R_{11}$ do not form one of the ring structure at the same time;

the three or more pairs $R_n$ and $R_{n+1}$ are selected such that each of three rings of a ring A, a ring B, and a ring C has one of the ring structure;

three or more ring structures on the three rings of the ring A, the ring B, and the ring C may be the same or different;

$R_1$ to $R_{11}$ not forming the ring structure are independently a hydrogen atom, a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by —Si(R$_{101}$)(R$_{102}$)(R$_{103}$), a group represented by —N(R$_{104}$)(R$_{105}$), a substituted or unsubstituted aryl group having 6 to 50 ring carbon atoms, or a substituted or unsubstituted heteroaryl group having 5 to 50 ring atoms; and each of R$_{101}$ to R$_{105}$ is independently a hydrogen atom, a substituted or unsubstituted alkyl group having 1 to 20 carbon atoms, a substituted or unsubstituted cycloalkyl group having 3 to 20 ring carbon atoms, a substituted or unsubstituted aryl group having 6 to 50 ring carbon atoms, or a substituted or unsubstituted heteroaryl group having 5 to 50 ring atoms.

2. The compound according to claim 1, wherein:
the ring structure is represented by any of formulae (2) to (8):

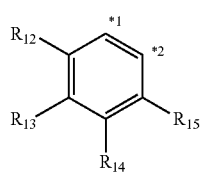
(2)

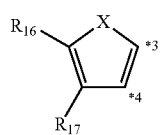
(3)

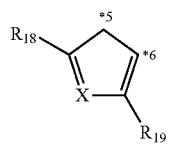
(4)

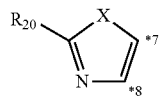
(5)

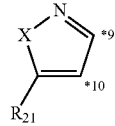
(6)

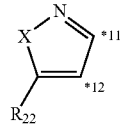
(7)

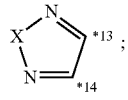
(8)

each of *1 and *2, *3 and *4, *5 and *6, *7 and *8, *9 and *10, *11 and *12, and *13 and *14, represents two ring carbon atoms of the ring structure through which R$_n$ and R$_{n+1}$ are bonded;

R$_n$ may be bonded to either of two ring carbon atoms represented by *1 and *2, *3 and *4, *5 and *6, *7 and *8, *9 and *10, *11 and *12, or *13 and *14;

X is selected from the group consisting of C(R$_{23}$)(R$_{24}$), NR$_{25}$, O, and S;

R$_{12}$ to R$_{25}$ are independently a hydrogen atom, a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by —Si(R$_{101}$)(R$_{102}$)(R$_{103}$), a group represented by —N(R$_{104}$)(R$_{105}$), a substituted or unsubstituted aryl group having 6 to 50 ring carbon atoms, or a substituted or unsubstituted heteroaryl group having 5 to 50 ring atoms;

each of R$_{101}$ to R$_{105}$ is independently a hydrogen atom, a substituted or unsubstituted alkyl group having 1 to 20 carbon atoms, a substituted or unsubstituted cycloalkyl group having 3 to 20 ring carbon atoms, a substituted or unsubstituted aryl group having 6 to 50 ring carbon atoms, or a substituted or unsubstituted heteroaryl group having 5 to 50 ring atoms; and adjacent groups of R$_{12}$ to R$_{17}$ and R$_{23}$ to R$_{24}$ may be bonded to each other to form another ring structure, with the proviso that, when the pair of R$_1$ and R$_2$ of formula (1) form one of the ring structure of formula (3), or the pair of R$_2$ and R$_3$ of formula (1) form one of the ring structure of formula (3), and R$_{16}$ and R$_{17}$ of formula (3) are bonded to each other to form another ring system, R$_{25}$ does not represent a substituted aryl group, a substituted heteroaryl group or unsubstituted heteroaryl group.

3. The compound according to claim 1, wherein:
the ring structure is represented by any of formulae (9) to (11):

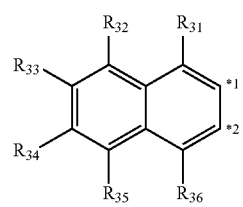
(9)

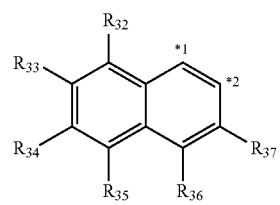
(10)

-continued

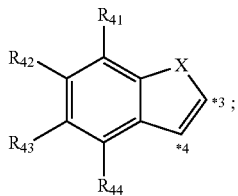
(11)

each of *1 and *2, and *3 and *4 represents two ring carbon atoms to which the three or more pairs $R_n$ and $R_{n+1}$ are bonded;

$R_n$ may be bonded to either of two ring carbon atoms represented by *1 and *2, or *3 and *4;

each of $R_{101}$ to $R_{105}$ is independently a hydrogen atom, a substituted or unsubstituted alkyl group having 1 to 20 carbon atoms, a substituted or unsubstituted cycloalkyl group having 3 to 20 ring carbon atoms, a substituted or unsubstituted aryl group having 6 to 50 ring carbon atoms, or a substituted or unsubstituted heteroaryl group having 5 to 50 ring atoms;

X is selected from the group consisting of $C(R_{23})(R_{24})$, $NR_{25}$, O, and S;

$R_{23}$ to $R_{25}$, $R_{31}$ to $R_{37}$ and $R_{41}$ to $R_{44}$ are independently a hydrogen atom, a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by $—Si(R_{101})(R_{102})(R_{103})$, a group represented by $—N(R_{104})(R_{105})$, a substituted or unsubstituted aryl group having 6 to 50 ring carbon atoms, or a substituted or unsubstituted heteroaryl group having 5 to 50 ring atoms;

adjacent groups of $R_{23}$ to $R_{24}$, $R_{31}$ to $R_{37}$ and $R_{41}$ to $R_{44}$ may be bonded to each other to form another ring structure; and with the proviso that, when the pair of $R_1$ and $R_2$ of formula (1) form one of the ring structure of formula (11), or the pair of $R_2$ and $R_3$ of formula (1) form one of the ring structure of formula (11), $R_{25}$ does not represent a substituted aryl group, a substituted heteroaryl group or unsubstituted heteroaryl group.

4. The compound according to claim 1, wherein:

at least one selected from the group consisting of $R_4$, $R_5$, $R_{10}$, and $R_{11}$ does not form the ring structure and independently represents a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by $—Si(R_{101})(R_{102})(R_{103})$ wherein $R_{101}$ to $R_{103}$ are as defined above, a group represented by $—N(R_{104})(R_{105})$ wherein $R_{104}$ and $R_{105}$ are as defined above, a substituted or unsubstituted aryl group having 6 to 50 ring carbon atoms, or a substituted or unsubstituted heteroaryl group having 5 to 50 ring atoms; and each of $R_{101}$ to $R_{105}$ is independently a hydrogen atom, a substituted or unsubstituted alkyl group having 1 to 20 carbon atoms, a substituted or unsubstituted cycloalkyl group having 3 to 20 ring carbon atoms, a substituted or unsubstituted aryl group having 6 to 50 ring carbon atoms, or a substituted or unsubstituted heteroaryl group having 5 to 50 ring atoms.

5. The compound according to claim 1, wherein:

the substituent of the ring structure is independently a substituted or unsubstituted alkyl group having 1 to 20 carbon atoms, a group represented by $—N(R_{104})(R_{105})$ a substituted or unsubstituted aryl group having 6 to 50 ring carbon atoms, a substituted or unsubstituted heteroaryl group having 5 to 50 ring atoms, or any of the following groups:

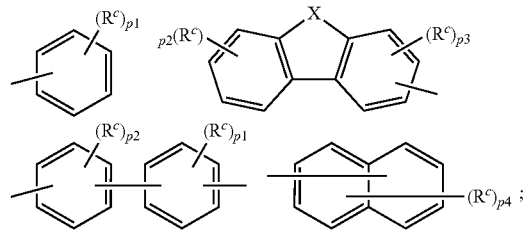

each of $R_{101}$ to $R_{105}$ is independently a hydrogen atom, a substituted or unsubstituted alkyl group having 1 to 20 carbon atoms, a substituted or unsubstituted cycloalkyl group having 3 to 20 ring carbon atoms, a substituted or unsubstituted aryl group having 6 to 50 ring carbon atoms, or a substituted or unsubstituted heteroaryl group having 5 to 50 ring atoms;

X is selected from the group consisting of $C(R_{23})(R_{24})$, $NR_{25}$, O, and S;

$R_{23}$ to $R_{25}$ and $R^c$ are independently a hydrogen atom, a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by —Si(R$_{101}$)(R$_{102}$)(R$_{103}$), a group represented by —N(R$_{104}$)(R$_{105}$), a substituted or unsubstituted aryl group having 6 to 50 ring carbon atoms, or a substituted or unsubstituted heteroaryl group having 5 to 50 ring atoms;

adjacent groups of R$_{23}$ to R$_{24}$ and R$^c$ may be bonded to each other to form another ring structure;

p1 is an integer of 0 to 5;
p2 is an integer of 0 to 4;
p3 is an integer of 0 to 3; and
p4 is an integer of 0 to 7, with the proviso that, when a pair of R$_1$ and R$_2$ of formula (1) form one of the ring structure, or a pair of R$_2$ and R$_3$ of formula (1) form one of the ring structure, the atoms composing the ring structure do not have a substituent selected from the group consisting of a substituted aryl group and a substituted or unsubstituted heteroaryl group.

6. The compound according to claim 5, wherein:

the substituent of the ring structure is independently a substituted or unsubstituted alkyl group having 1 to 20 carbon atoms, a substituted or unsubstituted aryl group having 6 to 50 ring carbon atoms, or any of the following groups:

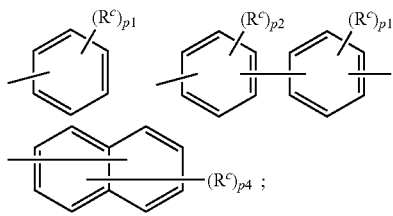

R$^c$ is independently a hydrogen atom, a halogen atom, a cyan group, a substituted or unsubstituted alkyl group having 1 to 20 carbon atoms, a substituted or unsubstituted alkenyl group having 1 to 20 carbon atoms, a substituted or unsubstituted alkenyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by —Si(R$_{101}$)(R$_{102}$)(R$_{103}$), a group represented by —N(R$_{104}$)(R$_{105}$), a substituted or unsubstituted aryl group having 6 to 50 ring carbon atoms, or a substituted or unsubstituted heteroaryl group having 5 to 50 ring atoms;

each of R$_{101}$ to R$_{105}$ is independently a hydrogen atom, a substituted or unsubstituted alkyl group having 1 to 20 carbon atoms, a substituted or unsubstituted cycloalkyl group having 3 to 20 ring carbon atoms, a substituted or unsubstituted aryl group having 6 to 50 ring carbon atoms, or a substituted or unsubstituted heteroaryl group having 5 to 50 ring atoms;

adjacent group of R$^c$ may be bonded to each other to form another ring structure;

p1 is an integer of 0 to 5;
p2 is an integer of 0 to 4;
p4 is an integer of 0 to 7;

with the proviso that, when a pair of R$_1$ and R$_2$ of formula (1) form one of the ring structure, or a pair of R$_2$ and R$_3$ of formula (1) form one of the ring structure, the atoms comprising the ring structure do not have a substituent selected from the group consisting of a substituted aryl group and a substituted or unsubstituted heteroaryl group.

7. The compound according to claim 1, wherein:

the at least one substituent is independently a hydrogen atom, a substituted or unsubstituted alkyl group having 1 to 20 carbon atoms, a group represented by —N(R$_{104}$)(R$_{105}$), a substituted or unsubstituted aryl group having 6 to 50 ring carbon atoms, a substituted or unsubstituted heteroaryl group having 5 to 50 ring atoms, or any of the following groups:

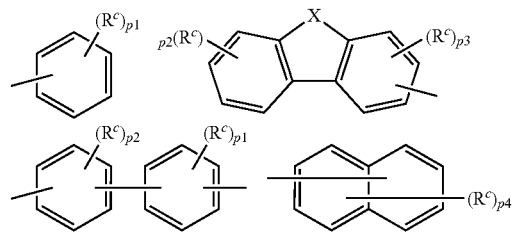

each of R$_{101}$ to R$_{105}$ is independently a hydrogen atom, a substituted or unsubstituted alkyl group having 1 to 20 carbon atoms, a substituted or unsubstituted cycloalkyl group having 3 to 20 ring carbon atoms, a substituted or unsubstituted awl group having 6 to 50 ring carbon atoms, or a substituted or unsubstituted heteroaryl group having 5 to 50 ring atoms;

X is selected from the group consisting of C(R$_{23}$)(R$_{24}$), NR$_{25}$, O, and S;

R$_{23}$ to R$_{25}$ and R$^c$ are independently a hydrogen atom, a halogen atom, a cyano group, a substituted or unsubstituted alkyl group having 1 to 20 carbon atoms, a substituted or unsubstituted alkenyl group having 1 to 20 carbon atoms, a substituted or unsubstituted alkenyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by —Si(R$_{101}$)(R$_{102}$)(R$_{103}$), a group represented by —N(R$_{104}$)(R$_{105}$), a substituted or unsubstituted aryl group having 6 to 50 ring carbon atoms, or a substituted or unsubstituted heteroaryl group having 5 to 50 ring atoms;

adjacent group of R$_{23}$ to R$_{24}$ and R$^c$ may be bonded to each other to form another ring structure;

p1 is an integer of 0 to 5;
p2 is an integer of 0 to 4;
p3 is an integer of 0 to 3; and
p4 is an integer of 0 to 7, with the proviso that, when a pair of $R_1$ and $R_2$ of formula (1) form one of the ring structure, or a pair of $R_2$ and $R_3$ of formula (1) form one of the ring structure, the atoms comprising the ring structure do not have a substituent selected from the group consisting of a substituted aryl group and a substituted or unsubstituted heteroaryl group.

8. The compound according to claim 2, wherein:
$R_{12}$ to $R_{22}$ in formulae (2) to (8) are independently a hydrogen atom, a substituted or unsubstituted alkyl group having 1 to 20 carbon atoms, a group represented by —N($R_{104}$)($R_{105}$), a substituted or unsubstituted aryl group having 6 to 50 ring carbon atoms, a substituted or unsubstituted heteroaryl group having 5 to 50 ring atoms, or any of the following groups:

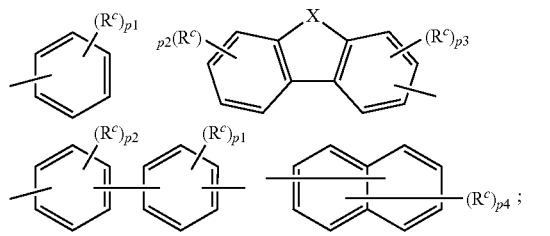

each of $R_{101}$ to $R_{105}$ is independently a hydrogen atom, a substituted or unsubstituted alkyl group having 1 to 20 carbon atoms, a substituted or unsubstituted cycloalkyl group having 3 to 20 ring carbon atoms, a substituted or unsubstituted aryl group having 6 to 50 ring carbon atoms, or a substituted or unsubstituted heteroaryl group having 5 to 50 ring atoms:

X is selected from the group consisting of C($R_{23}$)($R_{24}$), N$R_{25}$, O, and S;

$R_{23}$ to $R_{25}$ and $R^c$ are independently a hydrogen atom, a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by —Si($R_{101}$)($R_{102}$)($R_{103}$), a group represented by —N($R_{104}$)($R_{105}$), a substituted or unsubstituted aryl group having 6 to 50 ring carbon atoms, or a substituted or unsubstituted heteroaryl group having 5 to 50 ring atoms;

adjacent group of $R_{23}$ to $R_{24}$ and $R^c$ may be bonded to each other to form another ring structure;

p1 is an integer of 0 to 5;
p2 is an integer of 0 to 4;
p3 is an integer of 0 to 3; and
p4 is an integer of 0 to 7, with the proviso that, when the pair of $R_1$ and $R_2$ of formula (1) form one of the ring structure of formula (3), or the pair of $R_2$ and $R_3$ of formula (1) form one of the ring structure of formula (3), and $R_{16}$ and $R_{17}$ of formula (3) are bonded to each other to form another ring system, $R_{25}$ does not represent a substituted aryl group, a substituted heteroaryl group or unsubstituted heteroaryl group.

9. The compound according to claim 1, wherein the compound is represented by formula (3-1):

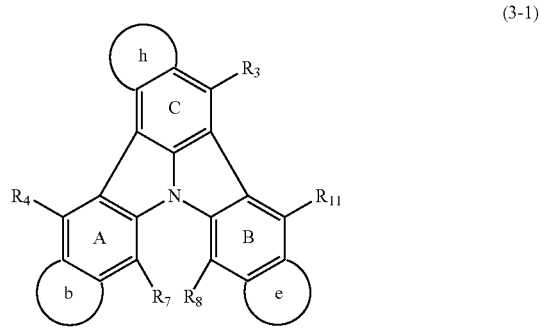

(3-1)

wherein:
each of rings b, e, and h is independently one of the ring structure comprising 3 or more atoms;
the ring structure optionally comprises at least one substituent and substituents may be bonded to each other to form a ring structure;
the at least one substituent of each of the rings b and e is a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by —Si($R_{101}$)($R_{102}$)($R_{103}$), a group represented by —N($R_{104}$)($R_{105}$), a substituted or unsubstituted aryl group having 6 to 50 ring carbon atoms, or a substituted or unsubstituted heteroaryl group having 5 to 50 ring atoms;
the at least one substituent of the ring h is a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by —Si(R₁₀₁)(R₁₀₂)(R₁₀₃), a group represented by —N(R₁₀₄)(R₁₀₅), or an unsubstituted aryl group having 6 to 50 ring carbon atoms;
the atoms composing the ring h do not have a substituent selected from the group consisting of a substituted aryl group and a substituted or unsubstituted heteroaryl group;
substituents of the ring structure may be bonded to each other to form another ring structure:
the 3 or more atoms do not include atoms in the at least one substituents;
R₃, R₄, R₇, R₈ and R₁₁ are independently a halogen atom, a cyano group, a substituted or unsubstituted alkyl group having 1 to 20 carbon atoms, a substituted or unsubstituted alkenyl group having 1 to 20 carbon atoms, a substituted or unsubstituted alkenyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by —Si(R₁₀₁)(R₁₀₂)(R₁₀₃), a group represented by —N(R₁₀₄)(R₁₀₅), a substituted or unsubstituted aryl group having 6 to 50 ring carbon atoms, or a substituted or unsubstituted heteroaryl group having 5 to 50 ring atoms; and
each of R₁₀₁ to R₁₀₅ is independently a hydrogen atom, a substituted or unsubstituted alkyl group having 1 to 20 carbon atoms, a substituted or unsubstituted cycloalkyl group having 3 to 20 ring carbon atoms, a substituted or unsubstituted aryl group having 6 to 50 ring carbon atoms, or a substituted or unsubstituted heteroaryl group having 5 to 50 ring atoms.

10. The compound according to claim 9, wherein:
the at least one substituent of the ring h is a substituted or unsubstituted alkyl group having 1 to 20 carbon atoms, a group represented by —N(R₁₀₄)(R₁₀₅), or a substituted aryl group having 6 to 50 ring carbon atoms;
the at least one substituent of the rings b, e and h is independently a substituted or unsubstituted alkyl group having 1 to 20 carbon atoms, a group represented by —N(R₁₀₄)(R₁₀₅), a substituted or unsubstituted aryl group having 6 to 50 ring carbon atoms, a substituted or unsubstituted heteroaryl group having 5 to 50 ring atoms, or any of the following groups:

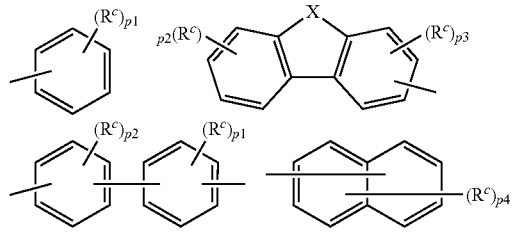

wherein:
X is selected from the group consisting of C(R₂₃)(R₂₄), NR₂₅, O, and S;
R₂₃ to R₂₅ and Rᶜ are independently a hydrogen atom, a halogen atom, a cyano group, a substituted or unsubstituted alkyl group having 1 to 20 carbon atoms, a substituted or unsubstituted alkene group having 1 to 20 carbon atoms, a substituted or unsubstituted alkynyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkyl group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by —Si(R₁₀₁)(R₁₀₂)(R₁₀₃), a group represented by —N(R₁₀₄)(R₁₀₅), a substituted or unsubstituted aryl group having 6 to 50 ring carbon atoms, or a substituted or unsubstituted heteroaryl group having 5 to 50 ring atoms;
adjacent group of R₂₃ to R₂₄ and Rᶜ may be bonded to each other to form another ring structure;
p1 is an integer of 0 to 5;
p2 is an integer of 0 to 4;
p3 is an integer of 0 to 3;
p4 is an integer of 0 to 7; and
the atoms composing the ring h do not have a substituent selected from the group consisting of a substituted aryl group and a substituted or unsubstituted heteroaryl group.

11. The compound according to claim 1, wherein the compound is represented by formula (5-1):

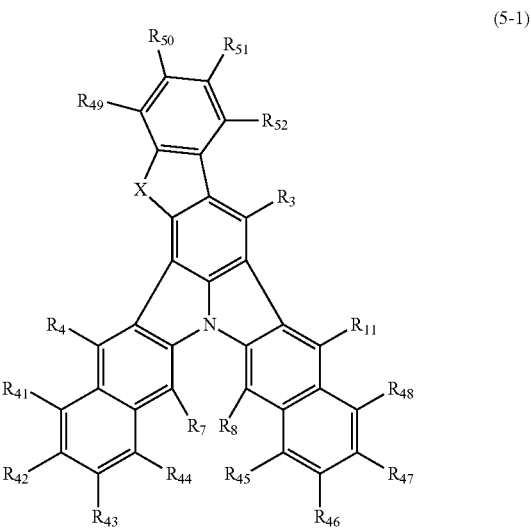

wherein:
X is selected from C(R₂₃)(R₂₄), NR₂₅, O, and S; and
R₃, R₄, R₇, R₈, R₁₁, R₄₁ to R₅₂, and R₂₃ to R₂₅ are independently a hydrogen atom, a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by —Si($R_{101}$)($R_{102}$)($R_{103}$), a group represented by —N($R_{104}$)($R_{105}$), a substituted or unsubstituted aryl group having 6 to 50 ring carbon atoms, or a substituted or unsubstituted heteroaryl group having 5 to 50 ring atoms;

$R_{25}$ does not represent a substituted aryl group, a substituted heteroaryl group or an unsubstituted heteroaryl group;

each of $R_{101}$ to $R_{105}$ is independently a hydrogen atom, a substituted or unsubstituted alkyl group having 1 to 20 carbon atoms, a substituted or unsubstituted cycloalkyl group having 3 to 20 ring carbon atoms, a substituted or unsubstituted aryl group having 6 to 50 ring carbon atoms, or a substituted or unsubstituted heteroaryl group having 5 to 50 ring atoms: and adjacent groups of $R_{23}$ to $R_{24}$ and $R_{41}$ to $R_{52}$ may be bonded to each other to form another ring structure.

12. The compound according to claim 11, wherein $R_{25}$ is an unsubstituted aryl group having 6 to 50 ring carbon atoms.

13. A material for organic electroluminescence devices, the material comprising the compound according to claim 1.

14. The material for organic electroluminescence devices according to claim 13, wherein the material is a dopant material for organic electroluminescence devices.

15. An organic electroluminescence device, comprising an organic thin film layer between a cathode and an anode, wherein the organic thin film layer comprises one or more layers and at least one light emitting layer, and at least one layer of the organic thin film layer comprises the compound according to claim 1.

16. The organic electroluminescence device according to claim 15, wherein the light emitting layer comprises the compound.

17. The organic electroluminescence device according to claim 16, wherein the light emitting layer comprises the compound in an amount of 0.1 to 30% by mass.

18. The organic electroluminescence device according to claim 15, wherein the at least one layer comprises the compound and an anthracene derivative.

19. The organic electroluminescence device according to claim 15, wherein the at least one layer comprises the compound and an anthracene derivative represented by formula (20):

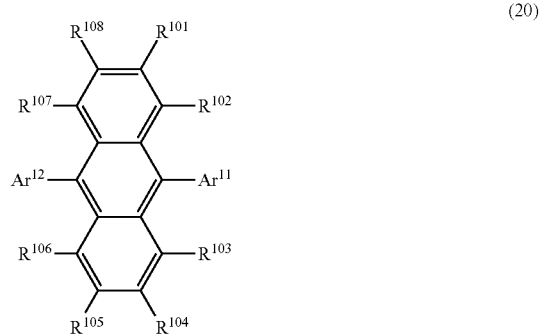

(20)

wherein:
each of $Ar^{11}$ and $Ar^{12}$ is independently a substituted or unsubstituted single ring group having 5 to 50 ring atoms or a substituted or unsubstituted fused ring group having 8 to 50 ring atoms;

each of $R^{101}$ to $R^{108}$ is independently selected from a hydrogen atom, a substituted or unsubstituted single ring group having 5 to 50 ring atoms, a substituted or unsubstituted fused ring group having 8 to 50 ring atoms, a group comprising the single ring group and the fused ring group, a substituted or unsubstituted alkyl group having 1 to 50 carbon atoms, a substituted or unsubstituted cycloalkyl group having 3 to 50 ring carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 ring carbon atoms, a substituted or unsubstituted silyl group, a halogen atom, and a cyano group.

20. An electronic device comprising the organic electroluminescence device according to claim 15.

* * * * *

UNITED STATES PATENT AND TRADEMARK OFFICE
CERTIFICATE OF CORRECTION

PATENT NO. : 10,230,058 B2
APPLICATION NO. : 15/912123
DATED : March 12, 2019
INVENTOR(S) : Royota Takahashi et al.

It is certified that error appears in the above-identified patent and that said Letters Patent is hereby corrected as shown below:

In the Claims

Column 447, Line 35:

""     (4)

Should read:

     (4)

--     --

Column 447, Line 50:

""     (7)

Should read:

     (7)

--     --

Signed and Sealed this
Sixth Day of August, 2019

Andrei Iancu
*Director of the United States Patent and Trademark Office*

CERTIFICATE OF CORRECTION (continued)
U.S. Pat. No. 10,230,058 B2

Column 447, Line 55:

"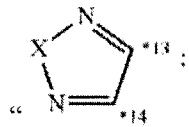 (8)"

Should read:

-- (8);--

Column 449, Line 5:

"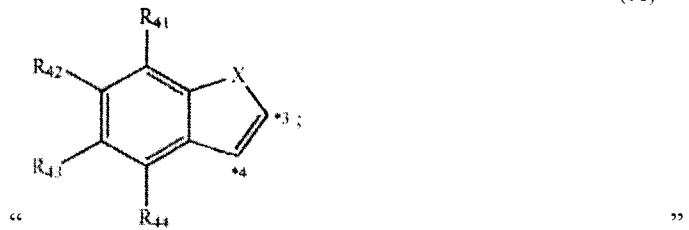 (11)"

Should read:

--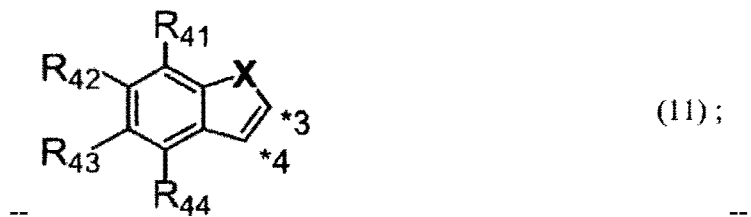 (11);--

Column 451, Line 47:
"unsubstituted fluoralkvl group having 1 to 20 carbon"
Should read:
--unsubstituted fluoralkyl group having 1 to 20 carbon--

Column 452, Line 45:
"20 carbon atoms, a substituted or unsubstituted alkenyl"
Should read:
--20 carbon atoms, a substituted or unsubstituted alkynyl--

Column 455, Line 11:
"one substituents"
Should read:
--one substituent--

CERTIFICATE OF CORRECTION (continued)
U.S. Pat. No. 10,230,058 B2

Column 456, Line 2:
"atoms, a substituted or unsubstituted alkene group"
Should read:
--atoms, a substituted or unsubstituted alkenyl group--

Column 457, Line 23:
"group having 5 to 50 ring atoms: and"
Should read:
--group having 5 to 50 ring atoms; and--

Column 451, Line 38:
"cyan group, a substituted or unsubstituted alkyl group"
Should read:
--cyano group, a substituted or unsubstituted alkyl group--

Column 451, Line 42:
"substituted or unsubstituted alkenyl group having 1 to"
Should read:
--substituted or unsubstituted alkynyl group having 1 to--

Column 452, Line 36:
"or unsubstituted awl group having 6 to 50 ring carbon"
Should read:
--or unsubstituted aryl group having 6 to 50 ring carbon--

Column 456, Line 10:
"stituted or unsubstituted fluoroalkyl group having 1"
Should read:
--stituted or unsubstituted fluoroalkoxy group having 1--